US007285631B2

(12) United States Patent
Bejanin et al.

(10) Patent No.: US 7,285,631 B2
(45) Date of Patent: Oct. 23, 2007

(54) HUMAN CDNAS AND PROTEINS AND USES THEREOF

(75) Inventors: Stephane Bejanin, Paris (FR); Hiroaki Tanaka, Antony (FR)

(73) Assignee: Serono Genetics Institute S.A., Evry (FR)

( * ) Notice: Subject to any disclaimer, the term of this patent is extended or adjusted under 35 U.S.C. 154(b) by 502 days.

(21) Appl. No.: 10/485,231

(22) PCT Filed: Oct. 15, 2001

(86) PCT No.: PCT/IB01/02321

§ 371 (c)(1),
(2), (4) Date: Jul. 2, 2004

(87) PCT Pub. No.: WO03/014151

PCT Pub. Date: Feb. 20, 2003

(65) Prior Publication Data

US 2005/0119171 A1 Jun. 2, 2005

Related U.S. Application Data

(60) Provisional application No. 60/326,470, filed on Oct. 1, 2001, provisional application No. 60/318,204, filed on Sep. 7, 2001, provisional application No. 60/314,734, filed on Aug. 24, 2001, provisional application No. 60/311,305, filed on Aug. 10, 2001.

(51) Int. Cl.
*C07K 14/435* (2006.01)

(52) U.S. Cl. .................................................... 530/350

(58) Field of Classification Search .................... None
See application file for complete search history.

(56) References Cited

U.S. PATENT DOCUMENTS

| | | | | |
|---|---|---|---|---|
| 4,902,505 | A | 2/1990 | Pardridge et al. | 424/85.7 |
| 4,987,084 | A | 1/1991 | Tedder et al. | 436/63 |
| 5,229,494 | A | 7/1993 | Evans et al. | 530/350 |
| 5,445,942 | A | 8/1995 | Rabin et al. | 435/18 |
| 5,595,721 | A | 1/1997 | Kaminski et al. | 424/1.49 |
| 5,599,400 | A | 2/1997 | Mao et al. | 134/25.2 |
| 5,641,670 | A | 6/1997 | Treco et al. | 435/325 |
| 5,693,496 | A | 12/1997 | Alves et al. | 435/69.3 |
| 5,714,459 | A | 2/1998 | O'Brien et al. | 514/2 |
| 5,762,926 | A | 6/1998 | Gage et al. | 424/93.21 |
| 5,840,688 | A | 11/1998 | Tso | 514/12 |
| 5,932,536 | A | 8/1999 | Wright et al. | 514/2 |
| 5,948,756 | A | 9/1999 | Barenholz et al. | 514/12 |
| 5,952,034 | A | 9/1999 | Buchanan et al. | 426/656 |
| 5,989,545 | A | 11/1999 | Foster et al. | 424/183.1 |
| 6,004,554 | A | 12/1999 | Thorpe et al. | 424/178.1 |
| 6,027,935 | A | 2/2000 | Purchio et al. | 435/325 |
| 6,074,844 | A | 6/2000 | Hillman et al. | 435/69.1 |
| 6,090,631 | A | 7/2000 | Catterall et al. | 436/501 |
| 6,099,857 | A | 8/2000 | Gross | 424/450 |
| 6,110,747 | A | 8/2000 | Blaschuk et al. | 436/512 |
| 6,113,951 | A | 9/2000 | Buchanan et al. | 426/18 |
| 6,117,454 | A | 9/2000 | Kreuter et al. | 424/490 |
| 6,153,192 | A | 11/2000 | Kopetzki et al. | 424/184.1 |
| 6,169,074 | B1 | 1/2001 | Montal et al. | 514/12 |
| 6,180,602 | B1 | 1/2001 | Kato et al. | 514/12 |
| 6,190,723 | B1 | 2/2001 | Buchanan et al. | 426/656 |
| 6,191,154 | B1 | 2/2001 | Landreth et al. | 514/369 |
| 6,197,940 | B1 | 3/2001 | Klinefelter | 530/350 |
| 6,268,487 | B1 | 7/2001 | Kutzko et al. | 530/414 |
| 2003/0118997 | A1 | 6/2003 | Bejanin et al. | 435/6 |

FOREIGN PATENT DOCUMENTS

| | | | |
|---|---|---|---|
| EP | 1033401 | A2 | 9/2000 |
| WO | WO97/07198 | A2 | 2/1997 |
| WO | WO98/14581 | A1 | 4/1998 |
| WO | WO98/56818 | A1 | 12/1998 |
| WO | WO99/02171 | A1 | 1/1999 |
| WO | WO99/24565 | A1 | 5/1999 |
| WO | WO99/38963 | A1 | 8/1999 |
| WO | WO 00/55632 | A1 | 9/2000 |
| WO | WO 01/51618 | A2 | 7/2001 |

OTHER PUBLICATIONS

Albertin, G. et al., "Cerebellin stimulates the secretory activity of the rat adrenal gland: in vitro and in vivo studies", *Neuropeptides* (2000), 34:7-11; INIST CNRS.

Biber, K. et al., Ischemia-Induced Neuronal Expression of the Microglia Attracting Chemokine Secondary Lymphoid-Tissue Chemokine (SLC), *GLIA* (2001), 34:121-133; INIST CNRS.

Braun, S. et al., "The CC Chemokine CKβ/ELC/Exodus 3 Mediates Tumor Rejection of Murine Breast Cancer Cells Through NK Cells", *J. Immunol* (2000), 164:4025-31; The American Association of Immunologists.

Brem, H. et al. "Interstitial chemotherapy with drug polymer implants for the treatment of recurrent gliomas", *J. Neurosurg.* (1991), 74:441-446; INIST CNRS.

Bronson, R. et al., "Sperm antibodies: their role in infertility", *Fertil and Steril* (1984), 42:171-83; The American Fertility Society.

Bunn Jr., P. et al., "Imaging of T-Cell Lymphoma by Radiolabelled Monoclonal Antibody", *Lancet* (1984), 2:1219-21.

Cella, M. et al., "A Novel Inhibitory Receptor (ILT3) Expressed on Monocytes, Macrophages, and Dendritic Cells Involved in Antigen Processing", *J. Exp. Med.* (1997), 185(10):1743-1751; The Rockefeller University Press.

Chee, M. et al., "Accessing Genetic Information with High-Density DNA Arrays", *Science* (1996), 274:610-614.

Dialynas, D. et al., Preconditioning with fetal cord blood facilities engraftment of primary childhood T-cell acute lymphoblastic leukemia in immunodeficient mice, *Blood* (2001), 97(10):3218-25; The American Society of Hematology.

(Continued)

*Primary Examiner*—James Martinell
(74) *Attorney, Agent, or Firm*—Saliwanchik, Lloyd & Saliwanchik

(57) ABSTRACT

The invention concerns GENSET polynucleotides and polypeptides. Such GENSET products may be used as reagents in forensic analyses, as chromosome markers, as tissue/cell/organelle-specific markers, in the production of expression vectors. In addition, they may be used in screening and diagnosis assays for abnormal GENSET expression and/or biological activity and for screening compounds that may be used in the treatment of GENSET-related disorders.

6 Claims, No Drawings

OTHER PUBLICATIONS

Dieu-Nosjean, M.-C., et al., "Regulation of the dendritic cell trafficking: a process that involves the participation of selective chemokines", *J. Leukoc. Biol.* (1999); 66:252-62; INIST CNRS.
Gosling, J. et al., "Cutting Edge: Identification of a Novel Chemokine Receptor That Binds Dendritic Cell- and T Cell-Active Chemokines Including ELC, SLC, and TECK", *J. Immunol.* (2000), 164:2851-6; The American Association of Immunologist.
Gunn, M. et al., "Mice Lacking Expression of Secondary Lymphoid Organ Chemokine Have Defects in Lymphocyte Homing and Denkritic Cell Localization", *J. Exp. Med.* (1999), 189(3):451-460.
Gunn, M. et al., "A chemokine expressed in lymphoid high endothelial venules promotes the adhesion and chemotaxis of naïve T lymphocytes", *Proc. Natl. Acad. Sci. USA* (1998), 95:258-263.
Hiraiwa, M. et al., "Binding and transport of gangliosides by prosaposin", *Proc. Natl. Acad. Sci. USA* (1992), 89:11254-11258.
Hjelmström, P. et al., "Lypmhoid Tissue Homing Chemokines Are Expressed in Chronic Inflammation", *American Journal of Pathology* (2000), 156(4):1133-8.
Kaneda, Y. et al., "Increased Expression of DNA Cointroduced with Nuclear Protein in Adult Rat Liver", *Science* (1989), 243:375-8.
Kennedy, J.H. et al., "Protein-Protein Coupling Reactions and the Applications of Protein Conjugates", *Clin. Chim. Acta* (1976), 70:1-31; Elsevier Scientific Publishing Company, Amsterdam, Holland.
Kim, C. et al., "SLC/Exodus2/6Ckine/TCA4 induces chemotaxis of hemopoietic progenitor cells: differential activity of ligands of CCR7, CXCR3, or CXCR4 in chemotaxis vs. suppression of progenitor proliferation", *J. Leukoc. Biol.* (1999), 66:455-61.
Kirk, C. et al., "T Cell-dependent Antitumor Immunity Mediated by Secondary Lymphoid Tissue Chemokine: Augmentation of Dendritic Cell-based Immunotherapy", *Cancer Research* (1999), 61:2062-70.
Loechel. F. et al., "Human ADAM 12 (Meltrin α) Is an Active Metalloprotease", *J. Biol. Chem.* (1998), 273:16993-7; The American Society for Biochemistry and Molecular Biology, Inc.
Loeffen, J. et al., "The human NADH:ubiquinone oxidoreductase NDUFS5 (15kDa) subunit: cDNA cloning, chromosomal localization, tissue distribution and the absence of mutations in isolated complex I-deficient patients", *J. Inher. Metab. Dis.* (1999), 22:19-28; SSIEM and Kluwer Academic Publishers, Holland.
Machens, H.-G. et al., "Bioartificial Skin", *Cells Tissues Organs* (2000), 167:88-94; INIST CNRS.
Marg, A. et al., "Neurotractin, A Novel Neurite Outgrowth-promoting Ig-like Protein that Interacts with CEPU-1 and LAMP", *J. Cell Biol.* (1999), 145:865-876; The Rockefeller University Press.
Medley, Q., et al., "Characterization of GMP-17, a granule membrane protein that moves to the plasma membrane of natural killer cells following target cell recognition", *Proc. Natl. Acad. Sci. USA* (1996), 93:685-689.
Melton, R., et al., "Antibody-Enzyme Conjugates for Cancer Therapy", *J. Natl. Cancer Inst.* (1996) 88(3/4):153-65; INIST CNRS.
Miyachi, K. et al., "Autoantibody to a Nuclear Antigen in Proliferating Cells", *J. Immunol.* (1978), 121(6):2228-34; The Williams & Wilkins Co.
Morimoto, S. et al., "Distribution of saposin proteins (sphingolipid activator proteins) in lysosomal storage and other diseases", *Proc. Natl. Acad. Sci. USA* (1990), 87:3493-3497.
Mulligan, R. "The Basic Science of Gene Therapy", *Science* (1993), 260:926-32.
Murphy, P. et al., "International Union of Pharmacology. XXII. Nomenclature for Chemokine Receptors", *Pharmacological Reviews* (2000), 52(1):145-176.
Nagira, M. et al., "Molecular Cloning of a Novel Human CC Chemokine Secondary Lymphoid-Tissue Chemokine That is a Potent Chemoattractant for Lymphocytes and Mapped to Chromosome 9p13", *J. Biol. Chem.* (1997), 272(31):19518-24.
Nagira, M. et al., "Enhanced HIV-1 Replication by Chemokines Constitutively Expressed in Secondary Lymphoid Tissues", *Virology* (1999), 264:422-426, INIST CNRS.
Nomura, T. et al., "Enhancement of Anti-Tumor Immunity by Tumor Cells Transfected with the Secondary Lymphoid Tissue Chemokine EBI-1-Ligand Chemokine and Stromal Cell-Derived Factor-1α Chemokine Genes", *Int. J. Cancer* (2001), 91:597-606; INIST CNRS.
Patel, D. et al., "Chemokines Have Diverse Abilities to Form Solid Phase Gradients", *Clinical Immunology* (2001), 99(1):43-52; Academic Press.
Ramsden, C.A. et al., "A new disorder of hyaluronan metabolism associated with generalized folding and thickening of the skin", *J. Pediatr.* (2000), 136(1):62-68.
Rao, C.N. et al., "Prokaryotic Expression, Purification, and Reconstitution of Biological Activities (Antiprotease, Antitumor, and Heparin-Binding) for Tissue Factor Pathway Inhibitor-2", *Biochem. Biophys. Res. Commun.* (2000), 276:1286-94; Academic Press.
Reape, T. et al., "Expression and Cellular Localization of the CC Chemokines PARC and ELC in Human Atherosclerotic Plaques", *Am. J. Pathol.* (1999), 154(2), 365; American Society for Investigative Pathology.
Satoh, F. et al., "Cerebellin and cerebellin mRNA in the human brain, adrenal glands and the tumor tissues of adrenal tumour, ganglioneuroblastoma and neuroblastoma", *J. Endocrinol.* (1997), 154:27-34; Journal of Endocrinology, Ltd., Great Britain.
Schuurs, A.H.W.M. et al., "Enzyme-Immunoassay", *Clin. Chim. Acta* (1977), 81:1-40; Elsevier/North-Holland Biomedical Press.
Sharma, S. et al., "Secondary Lymphoid Tissue Chemokine Mediates T Cell-Dependent Anitumor Responses In Vivo", *J. Immunol.* (1979), 164:4558-63; The American Association of Immunologists.
Simpson, D.W., et al., "A Rapid, Inexpensive and Easily Quantified Assay for Phagocytosis and Microbicidal Activity of Macrophages and Neutrophils", *J. Immunol. Methods* (1979), 29:221-226; Elsevier/North-Holland Biomedical Press.
Swanson, M. et al., "IFN-y Production by Th1 Cells Generated from Naïve $CD4^+$ T Cells Exposed to Norepinephrine", *J. Immunol.* (2001), 166:232-240; The American Association of Immunologists.
Ulmer, J. et al., "Heterologous Protection Against Influenza by Injection of DNA Encoding a Viral Protein", *Science* (1993), 259:1745-9.
Urade, Y. et al., "Precerebellin is a cerebellum-specific protein with similarity to the globular domain of complement C1q B chain", *Proc. Natl. Acad. Sci. USA* (1991), 88:1069-1073.
Wikstrand, C., et al., "Monoclonal antibody therapy of human gliomas: Current status and future approaches", *Cancer Metastasis Rev.* (1999), 18:451-64; Kluwer Academic Press, Holland.
Wolfsberg, T., et al., "ADAMs in Fertilization and Development", *Development Biology* (1996), 180:389-401; Academic Press, Inc.
Yoshida, H., et al., "Identification of the *cis*-Acting Endoplasmic Reticulum Stress Response Element Responsible for Transcriptional Induction of Mammalian Glucose-regulated Proteins", *J. Bio. Chem.* (1998), 273:33-741; The American Society for Biochemistry and Molecular Biology, Inc.
Accession No. AAF36777, Database GENBANK, Colonna, M. et al.
Accession No. AAG45834, Database GENBANK, Nakano, H. et al.
Accession No. AB035356, Database GENPEPT, Homo sapiens mRNA for neurexin l-alpha protein, complete cds., Dec. 2, 1999.
Accession No. AF020352, Database GENPEPT, Homo sapiens NADH:ubiquinone oxidoreductase 15 kDa IP subunit mRNA, nuclear gene encoding mitochondrial protein, complete cds; subunit of Mitochondrial Complex I., May 12, 1999.
Accession No. CAA50710, Database GENPEPT, Larsen, F. et al.
Accession No. O00585, Database SWISSPROT, Hromas, R. et al.
Accession No. O09006, Database SWISSPROT, Hromas, R. et al.
Accession No. O43506, Database SWISSPROT, Hooft van Huijsduijnen, R.
Accession No. O75926 Database SWISSPROT, Liu, B.
Accession No. P01011, Database SWISSPROT, Chandra, T. et al.
Accession No. P02760, Database SWISSPROT, Vetr, H. et al.
Accession No. P07602, Database SWISSPROT, Rorman, E.G. et al.
Accession No. P09110, Database SWISSPROT, Bout, A. et al.
Accession No. P11049, Database SWISSPROT, Classon, B.J. et al.
Accession No. P12004, Database SWISSPROT, Almendral, J.M.
Accession No. P19827, Database GENPEPT, Bost, F. et al.

Accession No. P31607, Database GENPEPT, Rouault, J. et al.
Accession No. U42068, Database GENPEPT, "Human liver endoplasmic reticulum P58 mRNA, complete cds; protein disulfide isomerase isoform", Jan. 5, 1996.
Accession No. U82979, Database GENPEPT, Human immunoglobulin-like3 mRNA, complete cds; ILT3; member of the immunoglobulin-superfamily, Jun. 13, 1997.
Accession No. P41217, Database SWISSPROT, McCaughan, G.W. et al.
Accession No. P48307, Database SWISSPROT, Miyagi, Y. et al.
Accession No. Q13449, Database SWISSPROT, Pimenta, A.F. et al.
Accession No. Q16617, Database SWISSPROT, Turman, M.A. et al.
Accession No. Q9Y531, Database SPTREMBL, Peck, A., Submitted (Jun. 1999) to the EMBL/GenBank/DDBJ databases.
Database GENESEQP, Accession No. AAR99844; "Human natural killer cell, cell surface mol. NKG7", Feb. 11, 1997 (first entry).
Turman, et al., "Characterization of a novel gene (NKG7) on human chromosome 19 that is expressed in natural killer cells and T cells", *Hum. Immunol.* (1993), 36:34-40.
Austin, et al., "Intraepidermal lymphocytes in psoriatic lesions are activated GMP-17(TIA-1)+CD8+CD3+CTLs as determined by phenotypic analysis", *J. Cutan Pathol.* (1998), 25:79-88.
Chuang, L. S.-H. et al. "Human DNA-(Cytosine-5) Methyltransferase-PCNA Complex as a Target for $p21^{WAF1}$" *Science*, Sep. 26, 1997, pp. 1996-2000, vol. 277.
Gulbis, J. M. et al. "Structure of the C-Terminal Region of $p21^{WAF1/CIP1}$ Complexed with Human PCNA" *Cell*, Oct. 18, 1996, pp. 297-306, vol. 87.
Jacobs, K. A. et al. "A genetic selection for isolating cDNAs encoding secreted proteins" *Gene*, 1997, pp. 289-296, vol. 198.
Klein, R. D. et al. "Selection for genes encoding secreted proteins and receptors" *Proc. Natl. Acad. Sci. USA*, Jul. 1996, pp. 7108-7113, vol. 93.
Travali, S. et al. "Structure of the Human Gene for the Proliferating Cell Nuclear Antigen" *The Journal of Biological Chemistry*, May 5, 1989, pp. 7466-7472, vol. 264, No. 13.

HUMAN CDNAS AND PROTEINS AND USES THEREOF

CROSS-REFERENCE TO RELATED APPLICATIONS

This application is the U.S. national stage application of International patent application No. PCT/IB01/02321, filed Oct. 15, 2001, which claims the benefit of U.S. Provisional Patent Application No. 60/326,470, filed Oct. 1, 2001; U.S. Provisional Patent Application No. 60/318,204, filed Sep. 7, 2001; U.S. Provisional Patent Application No. 60/314,734, filed Aug. 24, 2001; and U.S. Provisional Patent Application No. 60/311,305, filed Aug. 10, 2001;

The Sequence Listing for this application is on duplicate compact discs labeled "Copy 1" and "Copy 2." Copy 1 and Copy 2 each contain only one file named "seq-list-replace.txt" which was created on May 4, 2007, and is 216 KB. The entire contents of each of the computer discs are incorporated herein by reference in their entireties.

FIELD OF THE INVENTION

The present invention is directed to GENSET polynucleotides and polypeptides, and fragments, derivatives, and variants thereof. The present invention also relates to recombinant vectors including the polynucleotides of the present invention, particularly recombinant vectors comprising a GENSET gene regulatory region or a sequence encoding a GENSET polypeptide, and to host cells containing the polynucleotides of the invention. The invention further relates to antibodies that specifically bind to the polypeptides of the invention and to methods for producing such antibodies and fragments thereof. The invention also provides for methods of detecting the presence of the polynucleotides and polypeptides of the present invention in a sample, methods of diagnosis and screening of abnormal GENSET polypeptide expression and/or biological activity, methods of screening compounds for their ability to modulate the activity or expression of the GENSET polypeptides, and uses of such compounds.

BACKGROUND OF THE INVENTION cDNAs encoding secreted proteins or fragments thereof represent a particularly valuable source of therapeutic agents. Thus, there is a need for the identification and characterization of secreted proteins and the nucleic acids encoding them.

In addition to being therapeutically useful themselves, secretory proteins include short peptides, called signal peptides, at their amino termini which direct their secretion. These signal peptides are encoded by the signal sequences located at the 5' ends of the coding sequences of genes encoding secreted proteins. Because these signal peptides will direct the extracellular secretion of any protein to which they are operably linked, the signal sequences may be exploited to direct the efficient secretion of any protein by operably linking the signal sequences to a gene encoding the protein for which secretion is desired. In addition, fragments of the signal peptides called membrane-translocating sequences may also be used to direct the intracellular import of a peptide or protein of interest. This may prove beneficial in gene therapy strategies in which it is desired to deliver a particular gene product to cells other than the cells in which it is produced. Signal sequences encoding signal peptides also find application in simplifying protein purification techniques. In such applications, the extracellular secretion of the desired protein greatly facilitates purification by reducing the number of undesired proteins from which the desired protein must be selected. Thus, there exists a need to identify and characterize the 5' fragments of the genes for secretory proteins which encode signal peptides.

Sequences coding for secreted proteins may also find application as therapeutics or diagnostics. In particular, such sequences may be used to determine whether an individual is likely to express a detectable phenotype, such as a disease, as a consequence of a mutation in the coding sequence for a secreted protein. In instances where the individual is at risk of suffering from a disease or other undesirable phenotype as a result of a mutation in such a coding sequence, the undesirable phenotype may be corrected by introducing a normal coding sequence using gene therapy. Alternatively, if the undesirable phenotype results from overexpression of the protein encoded by the coding sequence, expression of the protein may be reduced using antisense or triple helix based strategies.

The secreted human polypeptides encoded by the coding sequences may also be used as therapeutics by administering them directly to an individual having a condition, such as a disease, resulting from a mutation in the sequence encoding the polypeptide. In such an instance, the condition can be cured or ameliorated by administering the polypeptide to the individual.

In addition, the secreted human polypeptides or fragments thereof may be used to generate antibodies useful in determining the tissue type or species of origin of a biological sample. The antibodies may also be used to determine the cellular localization of the secreted human polypeptides or the cellular localization of polypeptides which have been fused to the human polypeptides. In addition, the antibodies may also be used in immunoaffinity chromatography techniques to isolate, purify, or enrich the human polypeptide or a target polypeptide which has been fused to the human polypeptide.

SUMMARY OF THE INVENTION

The present invention provides a purified or isolated polynucleotide comprising, consisting of, or consisting essentially of a nucleotide sequence selected from the group consisting of: (a) the sequences of the odd SEQ ID NOs:1-23; (b) the sequences of clone inserts of the deposited clone pool; (c) the coding sequences of the odd SEQ ID NOs:1-23; (d) the coding sequences of the clone inserts of the deposited clone pool; (e) the sequences encoding one of the polypeptides of the even SEQ ID NOs:2-24; (f) the sequences encoding one of the polypeptides encoded by the clone inserts of the deposited clone pool; (g) the genomic sequences coding for the GENSET polypeptides; (h) the 5' transcriptional regulatory regions of GENSET genes; (i) the 3' transcriptional regulatory regions of GENSET genes; (j) the polynucleotides comprising the nucleotide sequence of any combination of (g)-(i); (k) the variant polynucleotides of any of the polynucleotides of (a)-(j); (l) the polynucleotides comprising a nucleotide sequence of (a)-(k), wherein the polynucleotide is single stranded, double stranded, or a portion is single stranded and a portion is double stranded; (m) the polynucleotides comprising a nucleotide sequence complementary to any of the single stranded polynucleotides of (l). The invention further provides for fragments of the nucleic acids and polypeptides of (a)-(m) described above.

Further embodiments of the invention include purified or isolated polynucleotides that comprise, consist of, or consist essentially of a nucleotide sequence at least 70% identical, more preferably at least 75%, and even more preferably at least 80%, 85%, 90%, 95%, 96%, 97%, 98%, or 99% identical, to any of the nucleotide sequences in (a)-(m) above, e.g. over a region of contiguous nucleotides at least about any one integer between 10 and the last integer representing the last integer representing the last nucleotide of a specified sequence of the sequence listing, or a polynucleotide which hybridizes under stringent hybridization conditions to a polynucleotide of the present invention including (a) through (m) above.

The present invention also relates to recombinant vectors, which include the purified or isolated polynucleotides of the present invention, and to host cells recombinant for the polynucleotides of the present invention, as well as to methods of making such vectors and host cells. The present invention further relates to the use of these recombinant vectors and recombinant host cells in the production of GENSET polypeptides. The present invention further relates to a polynucleotide of the present invention operably linked to a regulatory sequence including promoters, enhancers, etc.

The invention further provides a purified or isolated polypeptide comprising, consisting of, or consisting essentially of an amino acid sequence selected from the group consisting of: (a) the full length polypeptides of even SEQ ID NOs:2-24; (b) the full length polypeptides encoded by the clone inserts of the deposited clone pool; (c) the epitope-bearing fragments of the polypeptides of even SEQ ID NOs:2-24; (d) the epitope-bearing fragments of the polypeptides encoded by the clone inserts contained in the deposited clone pool; (e) the domains of the polypeptides of even SEQ ID NOs:2-24; (f) the domains of the polypeptides encoded by the clone inserts contained in the deposited clone pool; (g) the signal peptides of the polypeptides of even SEQ ID NOs:2-24 or encoded by the human cDNAs of the deposited clone pool; (h) the mature polypeptides of even SEQ ID NOs:2-24 or encoded by the human cDNAs of the deposited clone pool; and (i) the allelic variant polypeptides of any of the polypeptides of (a)-(h). The invention further provides for fragments of the polypeptides of (a)-(i) above, such as those having biological activity or comprising biologically functional domain(s).

The present invention further includes polypeptides with an amino acid sequence with at least 70% similarity, and more preferably at least 75%, 80%, 85%, 90%, 95%, 96%, 97%, 98%, or 99% similarity to those polypeptides described in (a)-(i), or fragments thereof, as well as polypeptides having an amino acid sequence at least 70% identical, more preferably at least 75% identical, and still more preferably 80%, 85%, 90%, 95%, 96%, 97%, 98%, or 99% identical to those polypeptides described in (a)-(i), or fragments thereof, e.g. over a region of amino acids at least any one integer between 6 and the last integer representing the last amino acid of a specified polypeptide sequence of the sequence listing. The invention further relates to methods of making the polypeptides of the present invention.

The present invention further relates to transgenic plants or animals, wherein said transgenic plant or animal is transgenic for a polynucleotide of the present invention and expresses a polypeptide of the present invention.

The invention further relates to antibodies that specifically bind to GENSET polypeptides of the present invention and fragments thereof as well as to methods for producing such antibodies and fragments thereof.

The invention also provides kits, uses and methods for detecting GENSET gene expression and/or biological activity in a biological sample. One such method involves assaying for the expression of a GENSET polynucleotide in a biological sample using the polymerase chain reaction (PCR) to amplify and detect GENSET polynucleotides or Southern and Northern blot hybridization to detect GENSET genomic DNA, cDNA or mRNA. Alternatively, a method of detecting GENSET gene expression in a test sample can be accomplished using a compound which binds to a GENSET polypeptide of the present invention or a portion of a GENSET polypeptide.

The present invention also relates to diagnostic methods and uses of GENSET polynucleotides and polypeptides for identifying individuals or non-human animals having elevated or reduced levels of GENSET gene products, which individuals are likely to benefit from therapies to suppress or enhance GENSET gene expression, respectively, and to methods of identifying individuals or non-human animals at increased risk for developing, or at present having, certain diseases/disorders associated with GENSET polypeptide expression or biological activity.

The present invention also relates to kits, uses and methods of screening compounds for their ability to modulate (e.g. increase or inhibit) the activity or expression of GENSET polypeptides including compounds that interact with GENSET gene regulatory sequences and compounds that interact directly or indirectly with a GENSET polypeptide. Uses of such compounds are also within the scope of the present invention.

The present invention also relates to pharmaceutical or physiologically acceptable compositions comprising, an active agent, the polypeptides, polynucleotides or antibodies of the present invention, as well as, typically, a physiologically acceptable carrier.

The present invention also relates to computer systems containing cDNA codes and polypeptide codes of sequences of the invention and to computer-related methods of comparing sequences, identifying homology or features using GENSET polypeptides or GENSET polynucleotide sequences of the invention.

In another aspect, the present invention provides an isolated polynucleotide, the polynucleotide comprising a nucleic acid sequence encoding a polypeptide of the present invention including the polypeptide of (a) through (i) above.

In another aspect, the present invention provides a non-human transgenic animal comprising the host cell.

In another aspect, the present invention provides a method of making a GENSET polypeptide, the method comprising a) providing a population of host cells comprising a herein-described polynucleotide and b) culturing the population of host cells under conditions conducive to the production of the polypeptide within said host cells.

In one embodiment, the method further comprises purifying the polypeptide from the population of host cells.

In another aspect, the present invention provides a method of making a GENSET polypeptide, the method comprising a) providing a population of cells comprising a polynucleotide encoding a herein-described polypeptide; b) culturing the population of cells under conditions conducive to the production of the polypeptide within the cells; and c) purifying the polypeptide from the population of cells.

In another aspect, the present invention provides a biologically active polypeptide encoded by any of the herein-described polynucleotides.

In one embodiment, the polypeptide is selectively recognized by an antibody raised against an antigenic polypeptide, or an antigenic fragment thereof, the antigenic polypeptide comprising any one of the sequences shown as even SEQ ID NOs:2-24 or any one of the sequences of polypeptides encoded by the human cDNAs of the deposited clone pool.

In another aspect, the present invention provides an antibody that specifically binds to any of the herein-described polypeptides and methods of binding antibody to said polypeptide.

In another aspect, the present invention provides a method of determining whether a GENSET gene is expressed within a mammal, the method comprising the steps of: a) providing a biological sample from said mammal; b) contacting said biological sample with either of: (i) a polynucleotide that hybridizes under stringent conditions to any of the herein-described polynucleotides; or (ii) a polypeptide that specifically binds to any of the herein-described polypeptides; and c) detecting the presence or absence of hybridization between the polynucleotide and an RNA species within the sample, or the presence or absence of binding of the polypeptide to a protein within the sample; wherein a detection of the hybridization or of the binding indicates that the GENSET gene is expressed within the mammal.

In one embodiment, the polynucleotide is a primer, and the hybridization is detected by detecting the presence of an amplification product comprising the sequence of the primer. In another embodiment, the polypeptide is an antibody.

In another aspect, the present invention provides a method of determining whether a mammal has an elevated or reduced level of GENSET gene expression, the method comprising the steps of: a) providing a biological sample from the mammal; and b) comparing the amount of any of the herein-described polypeptides, or of an RNA species encoding the polypeptide, within the biological sample with a level detected in or expected from a control sample; wherein an increased amount of the polypeptide or the RNA species within the biological sample compared to the level detected in or expected from the control sample indicates that the mammal has an elevated level of the GENSET gene expression, and wherein a decreased amount of the polypeptide or the RNA species within the biological sample compared to the level detected in or expected from the control sample indicates that the mammal has a reduced level of the GENSET gene expression.

In another aspect, the present invention provides a method of identifying a candidate modulator of a GENSET polypeptide, the method comprising: a) contacting any of the herein-described polypeptides with a test compound; and b) determining whether the compound specifically binds to the polypeptide; wherein a detection that the compound specifically binds to the polypeptide indicates or inhibits or activates of a specified biological activity that the compound is a candidate modulator of the GENSET polypeptide.

BRIEF DESCRIPTION OF TABLES

Table I provides the Applicants' internal designation number (Clone ID_Clone Name) which corresponds to each sequence identification number (SEQ ID NO) of the Sequence Listing, and indicates whether the sequence is a nucleic acid sequence (DNA) or a polypeptide sequence (PRT). Further provided is information regarding the name of the corresponding nucleic acid or polypeptide sequence, and information regarding the deposit of biological material. It should be appreciated that biological materials have been deposited with reference to their corresponding Clone ID, Clone Name, or both Clone ID_Clone Name.

Table II provides the positions of the nucleotides of the corresponding SEQ ID NOs of the Sequence Listing which comprise the open reading frame (ORF), signal peptide, mature peptide, polyadenylation signal, and the polyA tail of the polynucleotides of the invention.

Table III provides the positions of the amino acid of the corresponding SEQ ID NOs. of the Sequence Listing which comprise the positions of immunogenic epitopes of the polypeptides of the invention, which are useful in antibody generation.

BRIEF DESCRIPTION OF SEQUENCES

Sequences are presented in the accompanying Sequence Listing.

Odd SEQ ID NOs:1-23 are the nucleotide sequences of cDNAs, with open reading frames as indicated. When appropriate, the potential polyadenylation site and polyadenylation signal are also indicated.

Even SEQ ID NOs:2-24 are the amino acid sequences of proteins encoded by the cDNAs of odd SEQ ID NOs:1-23.

In accordance with the regulations relating to Sequence Listings, the following codes have been used in the Sequence Listing to describes nucleotide sequences. The code "r" in the sequences indicates that the nucleotide may be a guanine or an adenine. The code "y" in the sequences indicates that the nucleotide may be a thymine or a cytosine. The code "m" in the sequences indicates that the nucleotide may be an adenine or a cytosine. The code "k" in the sequences indicates that, the nucleotide may be a guanine or a thymine. The code "s" in the sequences indicates that the nucleotide may be a guanine or a cytosine. The code "w" in the sequences indicates that the nucleotide may be an adenine or a thymine. In addition, all instances of the symbol "n" in the nucleic acid sequences mean that the nucleotide can be adenine, guanine, cytosine or thymine.

In some instances, the polypeptide sequences in the Sequence Listing contain the symbol "Xaa." These "Xaa" symbols indicate either (1) a residue which cannot be identified because of nucleotide sequence ambiguity or (2) a stop codon in the determined sequence where applicants believe one should not exist (if the sequence were determined more accurately). In some instances, several possible identities of the unknown amino acids may be suggested by the genetic code.

In the case of secreted proteins, it should be noted that, in accordance with the regulations governing Sequence Listings, in the appended Sequence Listing the encoded protein (i.e. the protein containing the signal peptide and the mature protein or fragment thereof) extends from an amino acid residue having a negative number through a positively numbered amino acid residue. Thus, the first amino acid of the mature protein resulting from cleavage of the signal peptide is designated as amino acid number 1, and the first amino acid of the signal peptide is designated with the appropriate negative number.

In the case that a polynucleotide or polypeptide sequence described in the specification for SEQ ID NOs:1-24 is in conflict with the corresponding sequence provided in the Sequence listing, the sequences provided in the Sequence listing controls.

It should be appreciated that the polynucleotide and polypeptide sequences of SEQ ID NO:1-24 of the Sequence Listing are hereby incorporated by reference in their entireties.

DETAILED DESCRIPTION OF THE INVENTION AND PREFERRED EMBODIMENTS

Definitions.

Before describing the invention in greater detail, the following definitions are set forth to illustrate and define the meaning and scope of the terms used to describe the invention herein.

The term "GENSET gene," when used herein, encompasses genomic, mRNA and cDNA sequences encoding a GENSET polypeptide, including the 5' and 3' untranslated regions of said sequences.

The term "GENSET polypeptide biological activity" or "GENSET biological activity" is intended for polypeptides exhibiting any activity similar, but not necessarily identical, to an activity of a GENSET polypeptide of the invention. The GENSET polypeptide biological activity of a given polypeptide may be assessed using any suitable biological assay, a number of which are known to those skilled in the art. In contrast, the term "biological activity" refers to any activity that any polypeptide may have.

The term "corresponding mRNA" refers to mRNA which was or can be a template for cDNA synthesis for producing a cDNA of the present invention.

The term "corresponding genomic DNA" refers to genomic DNA which encodes an mRNA of interest, e.g. corresponding to a cDNA of the invention, which genomic DNA includes the sequence of one of the strands of the mRNA, in which thymidine residues in the sequence of the genomic DNA (or cDNA) are replaced by uracil residues in the mRNA.

The term "deposited clone pool" is used herein to refer to the pool of clones deposited with the ATCC or other depositary authority.

The term "heterologous", when used herein in reference to a polypeptide or polynucleotide, is intended to designate any polynucleotide or polypeptide other than a particular GENSET polynucleotide or GENSET polypeptide of the invention, respectively.

"Providing" with respect to, e.g. a biological sample, population of cells, etc. indicates that the sample, population of cells, etc. is somehow used in a method or procedure. Significantly, "providing" a biological sample or population of cells does not require that the sample or cells are specifically isolated or obtained for the purposes of the invention, but can instead refer, for example, to the use of a biological sample obtained by another individual, for another purpose.

An "amplification product" refers to a product of any amplification reaction, e.g. PCR, RT-PCR, LCR, etc.

A "modulator" of a protein or other compound refers to any agent that has a functional effect on the protein, including physical binding to the protein, alterations of the quantity or quality of expression of the protein, altering any measurable or detectable activity, property, or behavior of the protein, or in any way interacts with the protein or compound. "A test compound" can be any molecule that is evaluated for its ability to modulate a protein or other compound.

An antibody or other compound that specifically binds to a polypeptide or polynucleotide of the invention is also said to "selectively recognize" the polypeptide or polynucleotide.

The term "isolated" with respect to a molecule requires that the molecule be removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment. Specifically excluded from the definition of "isolated" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified polynucleotide makes up less than 5% (may also be specified as 10%, 25%, 50%, or 75%) of the number of nucleic acid inserts in the vector molecules. Further specifically excluded are whole cell genomic DNA or whole cell RNA preparations (including said whole cell preparations which are mechanically sheared or enzymatically digested). Further specifically excluded are the above whole cell preparations as either an in vitro preparation or as a heterogeneous mixture separated by electrophoresis (including blot transfers of the same) wherein the polynucleotide of the invention has not further been separated from the heterologous polynucleotides in the electrophoresis medium (e.g., further separating by excising a single band from a heterogeneous band population in an agarose gel or nylon blot).

The term "purified" does not require absolute purity; rather, it is intended as a relative definition. Purification of starting material or natural material to at least one order of magnitude, preferably two or three orders, and more preferably four or five orders of magnitude is expressly contemplated. The term "purified" is further used herein to describe a polypeptide or polynucleotide of the invention which has been separated from other compounds including, but not limited to, polypeptides or polynucleotides, carbohydrates, lipids, etc. The term "purified" may be used to specify the separation of monomeric polypeptides of the invention from oligomeric forms such as homo- or heterodimers, trimers, etc. The term "purified" may also be used to specify the separation of covalently closed (i.e. circular) polynucleotides from linear polynucleotides. A substantially pure polypeptide or polynucleotide typically comprises about 50%, preferably 60 to 90% weight/weight of a polypeptide or polynucleotide sample, respectively, more usually about 95%, and preferably is over about 99% pure but, may be specified as any integer of percent between 50 and 100. Polypeptide and polynucleotide purity, or homogeneity, is indicated by a number of means well known in the art, such as agarose or polyacrylamide gel electrophoresis of a sample, or using HPLC. As an alternative embodiment, purification of the polypeptides and polynucleotides of the present invention may be expressed as "at least" a percent purity relative to heterologous polypeptides and polynucleotides (DNA, RNA or both). As a preferred embodiment, the polypeptides and polynucleotides of the present invention are at least; 10%, 20%, 30%, 40%, 50%, 60%, 70%, 80%, 90%, 95%, 96%, 96%, 98%, 99%, or 100% pure relative to heterologous polypeptides and polynucleotides, respectively. As a further preferred embodiment the polypeptides and polynucleotides have a purity ranging from any number, to the thousandth position, between 90% and 100% (e.g., a polypeptide or polynucleotide at least 99.995% pure) relative to either heterologous polypeptides or polynucleotides, respectively, or as a weight/weight ratio relative to all compounds and molecules other than those existing in the carrier. Each number representing a percent purity, to the thousandth position, may be claimed as individual species of purity.

As used interchangeably herein, the terms "nucleic acid molecule(s)", "oligonucleotide(s)", and "polynucleotide(s)" include RNA or DNA (either single or double stranded, coding, complementary or antisense), or RNA/DNA hybrid sequences of more than one nucleotide in either single chain or duplex form (although each of the above species may be particularly specified). The term "nucleotide" is used herein as an adjective to describe molecules comprising RNA, DNA, or RNA/DNA hybrid sequences of any length in single-stranded or duplex form. More precisely, the expression "nucleotide sequence" encompasses the nucleic material itself and is thus not restricted to the sequence information (i.e. the succession of letters chosen among the four base letters) that biochemically characterizes a specific DNA or RNA molecule. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotides" which comprise at least one modification such as (a) an alternative linking group, (b) an analogous form of purine, (c) an analogous form of pyrimidine, or (d) an analogous sugar (see, e.g., WO 95/04064). Preferred modifications of the present invention include, but are not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v) ybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil and 2,6-diaminopurine. The polynucleotide sequences of the invention may be prepared by any known method, including synthetic, recombinant, ex vivo generation, or a combination thereof, as well as utilizing any purification methods known in the art (for teachings regarding the preparation of modified oligos and nucleotides, see, e.g., U.S. Pat. Nos. 5,378,825; 5,386,023; 5,489,677; 5,602,240; and 5,610,289, 5,264,562 and 5,264,564, 5,223,618, 5,508, 270, 4,469,863, 5,610,289 or 5,625,050, 5,256,775 or 5,366, 878, PCT applications WO 94/17093 and WO 94/02499, U.S. Pat. Nos. 5,476,925, 5,023,243, 5,130,302 and 5,177, 198).

The term "upstream" is used herein to refer to a location which is toward the 5' end of the polynucleotide from a specific reference point.

The terms "complementary" or "complement thereof" are used herein to refer to the sequences of polynucleotides which is capable of forming Watson & Crick base pairing with another specified polynucleotide throughout the entirety of the complementary region. For the purpose of the present invention, a first polynucleotide is deemed to be complementary to a second polynucleotide when each base in the first polynucleotide is paired with its complementary base. Complementary bases are, generally, A and T (or A and U), or C and G. "Complement" is used herein as a synonym from "complementary polynucleotide", "complementary nucleic acid" and "complementary nucleotide sequence". These terms are applied to pairs of polynucleotides based solely upon their sequences and not any particular set of conditions under which the two polynucleotides would actually bind. Unless otherwise stated, all complementary polynucleotides are fully complementary on the whole length of the considered polynucleotide.

The terms "polypeptide" and "protein", used interchangeably herein, refer to a polymer of amino acids without regard to the length of the polymer; thus, peptides, oligopeptides, and proteins are included within the definition of polypeptide. This term also does not specify or exclude chemical or post-expression modifications of the polypeptides of the invention, although chemical or post-expression modifications of these polypeptides may be included or excluded as specific embodiments. Therefore, for example, modifications to polypeptides that include the covalent attachment of glycosyl groups, acetyl groups, phosphate groups, lipid groups and the like are expressly encompassed by the term polypeptide. Further, polypeptides with these modifications may be specified as individual species to be included or excluded from the present invention. The natural or other chemical modifications, such as those listed in examples above can occur anywhere in a polypeptide, including the peptide backbone, the amino acid side-chains and the amino or carboxyl termini, and may be present in the same or varying degrees at several sites in a given polypeptide. Also, a given polypeptide may contain many types of modifications. Polypeptides may be branched, for example, as a result of ubiquitination, and they may be cyclic, with or without branching. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, for instance Creighton, (1993), Posttranslational Covalent Modification of Proteins, W.H. Freeman and Company, New York B. C. Johnson, Ed., Academic Press, New York 1-12; Seifter, et al., (1990) Meth Enzymol 182:626-646; Rattan et al., (1992) Ann N Y Acad Sci 663:48-62). Also included within the definition are polypeptides which contain one or more analogs of an amino acid (including, for example, non-naturally occurring amino acids, amino acids which only occur naturally in an unrelated biological system, modified amino acids from mammalian systems, etc.), polypeptides with substituted linkages, as well as other modifications known in the art, both naturally occurring and non-naturally occurring.

As used herein, the terms "recombinant polynucleotide" and "polynucleotide construct" are used interchangeably to refer to linear or circular, purified or isolated polynucleotides that have been artificially designed and which comprise at least two nucleotide sequences that are not found as contiguous nucleotide sequences in their initial natural environment. In particular, these terms mean that the polynucleotide or cDNA is adjacent to "backbone" nucleic acid to which it is not adjacent in its natural environment. Additionally, to be "enriched" the cDNAs will represent 5% or more of the number of nucleic acid inserts in a population of nucleic acid backbone molecules. Backbone molecules according to the present invention include nucleic acids such as expression vectors, self-replicating nucleic acids, viruses, integrating nucleic acids, and other vectors or nucleic acids used to maintain or manipulate a nucleic acid insert of interest. Preferably, the enriched cDNAs represent 15% or more of the number of nucleic acid inserts in the population of recombinant backbone molecules. More preferably, the enriched cDNAs represent 50% or more of the number of nucleic acid inserts in the population of recombinant backbone molecules. In a highly preferred embodiment, the enriched cDNAs represent 90% or more (including any number between 90 and 100%, to the thousandth position, e.g., 99.5%) of the number of nucleic acid inserts in the population of recombinant backbone molecules.

The term "recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide.

As used herein, the term "operably linked" refers to a linkage of polynucleotide elements in a functional relationship. A sequence which is "operably linked" to a regulatory sequence such as a promoter means that said regulatory element is in the correct location and orientation in relation to the nucleic acid to control RNA polymerase initiation and expression of the nucleic acid of interest. For instance, a promoter or enhancer is operably linked to a coding sequence if it affects the transcription of the coding sequence.

The term "domain" refers to an amino acid fragment with specific biological properties. This term encompasses all known structural and linear biological motifs. Examples of such motifs include but are not limited to leucine zippers, helix-turn-helix motifs, glycosylation sites, ubiquitination sites, alpha helices, and beta sheets, signal peptides which direct the secretion of proteins, sites for post-translational modification, enzymatic active sites, substrate binding sites, and enzymatic cleavage sites.

Although each of these terms has a distinct meaning, the terms "comprising", "consisting of" and "consisting essentially of" may be interchanged for one another throughout the instant application. The term "having" has the same meaning as "comprising" and may be replaced with either the term "consisting of" or "consisting essentially of".

Unless otherwise specified in the application, nucleotides and amino acids of polynucleotides and polypeptides, respectively, of the present invention are contiguous and not interrupted by heterologous sequences.

As used herein, the term "tumor" refers to an abnormal mass or population of cells that result from excessive cell division, whether malignant or benign, and all pre-cancerous and cancerous cells and tissues. A "tumor" is further defined as two or more physically associated neoplastic cells. The term "transformed cells," "malignant cells" or "cancer" are interchangeable and refer to cells that have undergone malignant transformation, and also includes lymphocytes that have undergone blast transformation. Transformed cells have a greater ability to cause tumors when injected into animals, can typically proliferate without requiring adhesion to a substratum, and also lack contact inhibition. The term "cancer" or "neoplastic disease" encompasses any type of cancer, in any tissue, and includes, but is not limited to, carcinomas, lymphomas, blastomas, sarcomas, and leukemias.

The terms "inducing" or "inducing" with respect to a cellular process, e.g., apoptosis, refers to increasing or decreasing the number of cells that undergo the process, or the rate by which cells undergo the process, in a given cell population. Preferably the increase or decrease is at least 1.25, 1.5, 2, 5, 10, 50, 100, 500 or 1000 fold increase or decrease as compared to normal, untreated or negative control cells.

A "therapeutically effective amount", in reference to the treatment of a disease or condition, refers to an amount of a compound that is capable of having any detectable, positive effect on any symptom, aspect, or characteristics of the disease or condition.

The terms "killing" or "inducing cytotoxicity" as used herein refer to inducing cell death by either apoptosis and/or necrosis, whereby embodiments of the invention include only apoptosis, only necrosis and both apoptosis and necrosis.

The terms "preventing" and "suppressing" as used herein refer to administering a compound prior to the onset of clinical symptoms of a disease or condition so as to prevent a physical manifestation of the disease or condition. The term "prophylaxis" is distinct from "treatment" and encompasses "preventing" and "suppressing". Herein, "protection" includes "prophylaxis". Protection need not be absolute to be useful.

The term "treating" as used herein refers to administering a compound after the onset of clinical symptoms. The term "in need of treatment" as used herein refers to a judgment made by a caregiver that an individual or animal requires or will benefit from treatment. This judgment is made based on a variety of factors that are in the realm of a caregiver's expertise, but that include the knowledge that the individual or animal is ill, or will be ill, as the result of a condition that is treatable by a compound of the invention.

The term "individual" or "patient" as used herein refers to any animal, including mammals, preferably mice, rats, other rodents, rabbits, dogs, cats, swine, cattle, sheep, horses, or primates, and most preferably humans. The term may specify male or female or both, or exclude male or female.

As used herein, the term "non-human animal" refers to any non-human animal, including insects, birds, rodents and more usually mammals. Preferred non-human animals include: primates; farm animals such as swine, goats, sheep, donkeys, cattle, horses, chickens, rabbits; and rodents, preferably rats or mice. As used herein, the term "animal" is used to refer to any species in the animal kingdom, preferably vertebrates, including birds and fish, and more preferably a mammal. Both the terms "animal" and "mammal" expressly embrace human subjects unless preceded with the term "non-human".

As used herein, the terms "physiologically acceptable," "pharmaceutically acceptable," and "pharmaceutical" are interchangeable.

Identity Between Nucleic Acids or Polypeptides

The terms "percentage of sequence identity" and "percentage homology" are used interchangeably herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Identity or similarity is evaluated using any of the variety of sequence comparison algorithms and programs known in the art. Such algorithms and programs include, but are by no means limited to, TBLASTN, BLASTP, FASTA, TFASTA, CLUSTALW, FASTDB (Pearson and Lipman, (1988), PNAS 85(8):2444-2448; Altschul et al., (1990), J. Mol. Biol. 215(3):403-410; Thompson et al. (1994), Nucleic Acids Res. 22(2):4673-4680; Higgins et al., (1996), Meth. Enzymol. 266:383-402; Altschul et al., (1993), Nature Genetics 3:266-272; Brutlag et al. (1990) Comp. App. Biosci. 6:237-24).

In a particularly preferred embodiment, protein and nucleic acid sequence identities are evaluated using the Basic Local Alignment Search Tool ("BLAST") which is well known in the art (e.g., Karlin and Altschul, (1990), PNAS 87:2267-2268; Altschul et al., (1997), Nuc. Acids Res. 25:3389-3402). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) BLASTN compares a query protein sequence against a nucleotide sequence database translated in all six reading frames (both strands); and (5) BLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., (1992), Science 256:1443-1445; Henikoff and Henikoff, (1993), Proteins 17:49-61). Less preferably, the PAM or PAM250 matrices may also be used (see, e.g., Schwartz and Dayhoff, (1978), eds., Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (see, e.g., Karlin and Altschul, 1990). The BLAST programs may be used with the default parameters or with modified parameters provided by the user.

Another preferred method for determining the best overall match between a query nucleotide or amino acid sequence (a sequence of the present invention) and a subject sequence, also referred to as a global sequence alignment, can be determined using the FASTDB computer program based on the algorithm of Brutlag et al. (1990). In a sequence alignment the query and subject sequences are both DNA or amino acid sequences. An RNA sequence can also be compared by first converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. If the subject sequence is shorter than the query sequence because of 5' or 3' deletions (for nucleotide sequences) or N- or C-terminal deletions (for amino acid sequences), not because of internal deletions, a manual correction must be made to the results, because the FASTDB program does not account for terminal truncations of a subject sequence when calculating percent identity. The manual correction involves determining the percent of the total query sequence that is not aligned because of a truncation in the subject sequence, and subtracting this percentage from the percent identity calculated by the FASTDB program. This corrected score is what is used for the purposes of the present invention. No other manual corrections are made for the purposes of the present invention.

Polynucleotides of the Invention

Many of the methods described in the present specification rely on the use of common molecular biological techniques. A number of such techniques are taught, generally, in "Molecular Cloning; A Laboratory Manual", 2d ed., Cole Spring Harbor Laboratory Press, Sambrook, et al., eds., 1989, and "Methods in Enzymology; Guide to Molecular Cloning Techniques", Academic Press, Berger and Kimmel eds., 1987.

The present invention concerns GENSET genomic and cDNA sequences. The present invention encompasses GENSET genes, polynucleotides comprising GENSET genomic and cDNA sequences, as well as fragments and variants thereof. These polynucleotides may be purified, isolated, or recombinant.

Also encompassed by the present invention are allelic variants, orthologs, splice variants, and/or species homologues of the GENSET genes. Procedures known in the art can be used to obtain full-length genes and cDNAs, allelic variants, splice variants, full-length coding portions, orthologs, and/or species homologues of genes and cDNAs corresponding to a nucleotide sequence selected from the group consisting of sequences of odd SEQ ID NOs:1-23 and sequences of clone inserts of the deposited clone pool, using information from the sequences disclosed herein or the clone pool deposited with the ATCC. For example, allelic variants, orthologs and/or species homologues may be isolated and identified by making suitable probes or primers from the sequences provided herein and screening a suitable nucleic acid source for allelic variants and/or the desired homologue using any technique known to those skilled in the art including those described into the section entitled "To find similar sequences".

In a specific embodiment, the polynucleotides of the invention are at least 15, 30, 50, 100, 125, 500, or 1000 continuous nucleotides. In another embodiment, the polynucleotides are less than or equal to 300 kb, 200 kb, 100 kb, 50 kb, 10 kb, 7.5 kb, 5 kb, 2.5 kb, 2 kb, 1.5 kb, or 1 kb in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 75, 50, 25, 20, 15, 10, 5, 4, 3, 2, or 1 naturally occurring genomic flanking gene(s).

Deposited Clone Pool of the Invention

Expression of GENSET genes has been shown to lead to the production of at least one mRNA species per GENSET gene, which cDNA sequence is set forth in the appended Sequence Listing as odd SEQ ID NOs:1-23. The cDNAs corresponding to these GENSET mRNA species were cloned either in the vector pBluescriptII $SK^-$ (Stratagene) or in a vector called pPT. Cells containing the cloned cDNAs of the present invention are maintained in permanent deposit by the inventors at Genset, S. A., 24 Rue Royale, 75008 Paris, France. Table I provides Genset's internal designation number assigned to each SEQ ID NO., and indicates whether the sequence is a nucleic acid sequence (DNA) or a protein (PRT) sequence. Each cDNA can be removed from the Bluescript vector in which it was inserted by performing a NotI Pst I double digestion, or from the pPT vector by performing a MunI HindIII double digestion, to produce the appropriate fragment for each clone, provided the cDNA sequence does not contain any of the corresponding restriction sites within its sequence. Alternatively, other restriction enzymes of the multicloning site of the vector may be used to recover the desired insert as indicated by the manufacturer.

Pools of cells containing GENSET genes as described in the Sequence Listing, from which the cells containing a particular polynucleotide is obtainable, were or will be also deposited with the American Tissue Culture Collection (ATCC), 10801 University Boulevard, Manassas, Va. 20110-2209, United States. Each cDNA clone has been transfected into separate bacterial cells (*E-coli*) for these composite deposits.

Bacterial cells containing a particular clone can be obtained from the composit deposit using standard methods, e.g., by plating a culture of the composit deposit, transferring the lysed colonies to a filter, and hybridizing the filter with a labelled probe such as an oligonucleotide probe specific for the clone of interest. Alternatively, individual cDNA inserts can be recovered from the pool of bacteria using PCR with primers designed at both ends of the cDNA insertion, including primers designed in the multicloning site of the vector.

cDNA Sequences of the Invention

Structural parameters of each of the cDNAs of the present invention are presented in the appended Sequence Listing. Accordingly, the coding sequence (CDS) or open reading frame (ORF) of each cDNA of the invention refers to the nucleotide sequence beginning with the first nucleotide of the start codon and ending with the nucleotide immediately 5' to the first nucleotide of the stop codon. Similarly, the 5' untranslated region (or 5'UTR) of each cDNA of the invention refers to the nucleotide sequence starting at nucleotide 1 and ending at the nucleotide immediately 5' to the first nucleotide of the start codon. The 3' untranslated region (or 3'UTR) of each cDNA of the invention refers to the nucleotide sequence starting at the first nucleotide of the stop codon and ending at the last nucleotide of the cDNA.

Coding Sequences

Another object of the invention is an isolated, purified or recombinant polynucleotide comprising the coding sequence of a sequence selected from the group consisting of the polynucleotide sequences of the appended Sequence Listing, those of human cDNA clone inserts of the deposited clone pool and variants thereof.

It will be appreciated that should the extent of the coding sequence differ from that indicated in the appended sequence listing as a result of a sequencing error, reverse transcription or amplification error, mRNA splicing, post-translational modification of the encoded protein, enzymatic cleavage of the encoded protein, or other biological factors, one skilled in the art would be readily able to identify the extent of the coding sequences in the polynucleotide sequences of the Sequence Listing, those of the human cDNA inserts of the deposited clone pool, and allelic variants thereof. Accordingly, the scope of any claims herein relating to nucleic acids containing the coding sequence of one of the polynucleotide sequences of the Sequence Listing and those of the cDNA inserts of the deposited clone pool is not to be construed as excluding any readily identifiable variations from or equivalents to the coding sequences described in the appended sequence listing. Equivalents include any alterations in a nucleotide coding sequence that does not result in an amino acid change, or that results in a conservative amino acid substitution, as defined below, in the polypeptide encoded by the nucleotide sequence. Similarly, should the extent of the polypeptides differ from those indicated in the appended Sequence Listing as a result of any of the preceding factors, the scope of claims relating to polypeptides comprising the amino acid sequence of the polypeptide sequences of the appended Sequence Listing is not to be construed as excluding any readily identifiable variations from or equivalents to the sequences described in the appended sequence listing.

The above disclosed polynucleotides that contain the coding sequence of the GENSET genes may be expressed in a desired host cell or a desired host organism, when this polynucleotide is placed under the control of suitable expression signals. The expression signals may be either the expression signals contained in the regulatory regions in the GENSET genes of the invention or, in contrast, the signals may be exogenous regulatory nucleic sequences. Such a polynucleotide, when placed under the suitable expression signals, may also be inserted in a vector for its expression and/or amplification.

Further included in the present invention are polynucleotides encoding the polypeptides of the present invention that are fused in frame to the coding sequences for additional heterologous amino acid sequences. Also included in the present invention are nucleic acids encoding polypeptides of the present invention together with additional, non-coding sequences, including, but not limited to, non-coding 5' and 3' sequences, vector sequence, sequences used for purification, probing, or priming. For example, heterologous sequences include transcribed, untranslated sequences that may play a role in transcription and mRNA processing, such as ribosome binding and stability of mRNA. The heterologous sequences may alternatively comprise additional coding sequences that provide additional functionalities, e.g. a hexahistidine or HA tag).

Regulatory Sequences of the Invention

As mentioned, the genomic sequence of GENSET genes contain regulatory sequences in the non-coding 5'-flanking region and possibly in the non-coding 3'-flanking region that border the GENSET polypeptide coding regions containing the exons of these genes.

Polynucleotides derived from GENSET polynucleotide 5' and 3' regulatory regions are useful in order to detect the presence of at least a copy of a genomic nucleotide sequence of the GENSET gene or a fragment thereof in a test sample.

Preferred Regulatory Sequences

Polynucleotides carrying the regulatory elements located at the 5' end and at the 3' end of GENSET polypeptide coding regions may be advantageously used to control the processing, localization, stability, maturation and transcriptional and translational activity of a heterologous polynucleotide of interest, e.g; the regulatory polynucleotides may be part of a recombinant expression vector that may be used to express a coding sequence in a desired host cell or host organism (for a review on UTRs see Decker and Parker, (1995) Curr. Opin. Cell. Biol. 7(3):368-92, Derrigo et al., (2000) Int. J. Mol. Med. 5(2):111-23). In particular, 3' UTRs may be used in order to control the stability of heterologous mRNAs in recombinant vectors using any methods known to those skilled in the art including Makrides (1999) Protein Expr Purif 1999 November;17(2):183-202), U.S. Pat. Nos. 5,925,564; 5,807,707 and 5,756,264.

The present invention also concerns a purified or isolated nucleic acid comprising a polynucleotide which is selected from the group consisting of the 5' and 3' GENSET polynucleotide regulatory regions, sequences complementary thereto, regulatory active fragments and variants thereof, and those that hybridize under stringent hybridization conditions therewith. Further included are nucleic acids comprising a nucleotide sequence having at least 95% identity with any of the herein-described GENSET 5' or 3' regulatory sequences, as well as 5'- or 3'-UTRs of the polynucleotide sequences of the appended Sequence Listing, of human cDNA clone inserts of the deposited clone pool, sequences complementary thereto, regulatory active fragments and allelic variants thereof. Fragments of 5' and 3' regulatory regions may have a length corresponding to any one integer between 20 and 20,000 nucleotides in length.

For the purpose of the invention, a nucleic acid or polynucleotide is "functional" as a "regulatory region" for expressing a recombinant polypeptide or a recombinant polynucleotide if said regulatory polynucleotide contains nucleotide sequences which contain transcriptional and translational regulatory information, and such sequences are "operably linked" to nucleotide sequences which encode the desired polypeptide or the desired polynucleotide.

The invention also comprises a nucleic acid molecule encoding a desired polypeptide or a nucleic acid molecule of interest, wherein said nucleic acid molecule is operably linked to any of the herein-described regulatory sequences. The desired polypeptide may be of various nature or origin, encompassing proteins of prokaryotic viral or eukaryotic origin. Also encompassed are eukaryotic proteins such as intracellular proteins, such as "house keeping" proteins, membrane-bound proteins, such as mitochondrial membrane-bound proteins and cell surface receptors, and secreted proteins such as endogenous mediators such as cytokines. The desired polypeptide may be a heterologous polypeptide or a GENSET polypeptide.

Polynucleotide Variants

The invention also relates to variants of the polynucleotides described herein and fragments thereof. "Variants" of polynucleotides, as the term is used herein, are polynucleotides that differ from a reference polynucleotide. Generally, differences are limited so that the nucleotide sequences of the reference and the variant are closely similar overall and, in many regions, identical. The present invention encompasses both allelic variants and degenerate variants.

Allelic Variant

A variant of a polynucleotide may be a naturally occurring variant such as a naturally occurring allelic variant, or it may be a variant that is not known to occur naturally. By an "allelic variant" is intended one of several alternate forms of a gene occupying a given locus on a chromosome of an organism (see Lewin, (1989), PNAS 86:9832-8935). Diploid organisms may be homozygous or heterozygous for an allelic form. Non-naturally occurring variants of the polynucleotide may be made by art-known mutagenesis techniques, including those applied to polynucleotides, cells or organisms.

Degenerate Variant

In addition to the isolated polynucleotides of the present invention, and fragments thereof, the invention further includes polynucleotides which comprise a sequence substantially different from those described above but which, due to the degeneracy of the genetic code, still encode a GENSET polypeptide of the present invention. These polynucleotide variants are referred to as "degenerate variants" throughout the instant application. That is, all possible polynucleotide sequences that encode the GENSET polypeptides of the present invention are contemplated. This includes the genetic code and species-specific codon preferences known in the art.

Nucleotide changes present in a variant polynucleotide may be silent, which means that they do not alter the amino acids encoded by the polynucleotide. However, nucleotide changes may also result in amino acid substitutions, additions, deletions, fusions and truncations in the polypeptide encoded by the reference sequence. The substitutions, deletions or additions may involve one or more nucleotides. The variants may be altered in coding or non-coding regions or both. Alterations in the coding regions may produce conservative or non-conservative amino acid substitutions, deletions or additions. In the context of the present invention, preferred embodiments are those in which the polynucleotide variants encode polypeptides which retain substantially the same biological properties or activities as the GENSET protein. More preferred polynucleotide variants are those containing conservative substitutions.

Similar Polynucleotides

Other embodiments of the present invention provide a purified, isolated or recombinant polynucleotide which is at least 80%, 85%, 90%, 95%, 96%, 97%, 98% or 99% identical to a polynucleotide of the present invention. Although similar polynucleotides encoding polypeptides with GENSET biological activity are preferred, the presence of GENSET biological activity in an encoded protein is not necessary because even where a particular nucleic acid molecule does not encode a polypeptide having activity, one of skill in the art would still know how to use the nucleic acid molecule, for instance, as a hybridization probe or primer. Uses of the nucleic acid molecules of the present invention that do not encode a polypeptide having GENSET activity include, inter alia, isolating a GENSET gene or al lelic variants thereof from a DNA library, and detecting GENSET mRNA expression in biological samples suspected of containing GENSET mRNA or DNA, e.g., by Northern Blot or PCR analysis.

Hybridizing Polynucleotides

In another aspect, the invention provides an isolated or purified nucleic acid molecule comprising a polynucleotide which hybridizes under stringent hybridization conditions to any polynucleotide of the present. Such hybridizing polynucleotides may be of at least any one integer between 10 and 10,000 nucleotides in length.

Of course, a polynucleotide which hybridizes only to polyA+ sequences (such as any 3' terminal polyA+ tract of a cDNA shown in the sequence listing), or to a 5' complementary stretch of T (or U) residues, would not be included in the definition of "polynucleotide," since such a polynucleotide would hybridize to any nucleic acid molecule containing a poly(A) stretch or the complement thereof (e.g., practically any double-stranded cDNA clone generated using oligo dT as a primer).

Complementary Polynucleotides

The invention further provides isolated nucleic acid molecules having a nucleotide sequence fully complementary to any polynucleotide of the invention.

Polynucleotide Fragments

The present invention is further directed to portions or fragments of the polynucleotides of the present invention. Uses for the polynucleotide fragments of the present invention include probes, primers, molecular weight markers and for expressing the polypeptide fragments of the present invention. Fragments include portions of polynucleotides selected from the group consisting of a) polynucleotide sequences of the Sequence Listing, b) genomic GENSET sequences, c) polynucleotides encoding a polypeptide of the present invention, d) sequences of human cDNA clone inserts of the deposited clone pool, and e) polynucleotides encoding the polypeptides encoded by the human cDNA clone inserts of the deposited clone pool. Particularly included in the present invention is a purified or isolated polynucleotide comprising at least 8, 10, 12, 15, 18, 20, 25, 28, 30, 35, 40, 50, 75, 100, 150, 200, 300, 400, 500, 800, 1000, 1500, or 2000 consecutive nucleotides of a polynucleotide of the present invention. Further, polynucleotides are provided comprising at least X nucleotides, wherein "X" is defined as any integer between 8 and the integer representing the 3' most nucleotide position as set forth in the sequence listing or elsewhere herein.

Further included as preferred polynucleotides of the-present invention are polynucleotide fragments that are specified in terms of their 5' and 3' position. Where the 5' and 3' positions are represented by the position numbers set forth in the appended sequence listing wherein the 5' most nucleotide is 1 and the 3' most nucleotide is the last nucleotide for a particular SEQ ID No., all polynucleotide fragments corresponding to every combination of a 5' and 3' nucleotide position that a polynucleotide fragment of the present invention, at least 8 contiguous nucleotides in length, could occupy on a polynucleotide of the invention are specifically considered. These species of polynucleotide fragments may alternatively be described by the formula "a to b"; where "a" equals the 5' most nucleotide position and "b" equals the 3' most nucleotide position of the polynucleotide; and further where "a" equals an integer between 1 and the number of nucleotides of the polynucleotide sequence of the present invention minus 8, and where "b" equals an integer between 9 and the number of nucleotides of the polynucleotide sequence of the present invention; and where "a" is an integer smaller then "b" by at least 8. All of the polynucleotide fragments described in either of these ways can be immediately envisaged and are therefore not individually listed solely for the purpose of not unnecessarily lengthening the specification. Any of these polynucleotide fragments may also be specifically excluded from the present invention. Any number of fragments specified by 5' and 3' positions or by size in nucleotides, as described above, may be excluded. Preferred excluded fragments include those having substantial homology to repeated sequences including Alu, L1, THE and MER repeats, SSTR sequences or satellite, micro-satellite, and telomeric repeats.

Other preferred fragments of the invention are polynucleotides comprising polynucleotide sequences encoding domains of polypeptides. Such fragments may be used to obtain other polynucleotides encoding polypeptides having similar domains using hybridization or RT-PCR techniques. Alternatively, these fragments may be used to express a polypeptide domain which may have a specific biological property.

Another object of the invention is an isolated, purified or recombinant polynucleotide encoding a polypeptide consisting of, consisting essentially of, or comprising a contiguous span of at least (any integer between 5 and 1,000 consecutive amino acids in length more preferably at least) 5, 6, 8, 10, 12, 15, 20, 25, 30, 35, 40, 50, 60, 75, 100, 150 or 200 consecutive amino acids. The present invention further encompasses any combination of the polynucleotide fragments listed in this section.

Oligonucleotide Primers and Probes

The present invention also encompasses fragments of GENSET polynucleotides for use as primers and probes. Polynucleotides derived from the GENSET genomic and cDNA sequences are useful in order to detect the presence of at least a copy of a GENSET polynucleotide or fragment, complement, or variant thereof in a test sample.

Structural Definition

Any polynucleotide of the invention may be used as a primer or probe. Particularly preferred probes and primers of the invention include isolated, purified, or recombinant polynucleotides comprising a contiguous span of at least 12, 15, 18, 20, 25, 30, 35,40, 50, 60, 70, 80, 90, 100, 150, 200, 500, or 1000 nucleotides of a polynucleotide of the present invention.

For amplification purposes, pairs of primers with approximately the same Tm are preferable. Primers may be designed using methods known in the art. Amplification techniques that can be used in the context of the present invention include, but are not limited to, the ligase chain reaction (LCR) described in EP-A-320 308, WO 9320227 and EP-A-439 182, the polymerase chain reaction (PCR, RT-PCR) and techniques such as the nucleic acid sequence based amplification NASBA) described in Guatelli et al., (1990) PNAS 35:273-286 and in Compton (1991) Nature 350(6313):91-92, Q-beta amplification as described in European Patent Application No 4544610, strand displacement amplification as described in Walker, et al. (1996), Clin. Chem. 42:9-13 and EP A 684 315 and, target mediated amplification as described in WO 9322461.

The probes of the present invention are useful for a number of purposes, including for Southern hybridization to genomic DNA, to detect PCR amplification products, to detect mismatches in a GENSET gene or mRNA, and in in situ hybridization. Any of the polynucleotides, primers and probes of the present invention can be conveniently immobilized on any type of solid support, such as latex particles, microparticles, magnetic beads, non-magnetic beads (including polystyrene beads), membranes (including nitrocellulose strips), plastic tubes, walls of microtiter wells, glass or silicon chips, sheep (or other suitable animal's) red blood cells and duracytes. Suitable methods for immobilizing nucleic acids on solid phases include ionic, hydrophobic, covalent interactions and the like. A solid support, as used herein, refers to any material which is insoluble, or can be made insoluble by a subsequent reaction. The solid support can be chosen for its intrinsic ability to attract and immobilize the capture reagent, or alternatively may retain an additional receptor which has the ability to attract and immobilize the capture reagent. The polynucleotides of the invention can be attached to or immobilized on a solid support individually or in groups of at least 2, 5, 8, 10, 12, 15, 20, or 25 distinct polynucleotides of the invention to a single solid support. In addition, polynucleotides other than those of the invention may be attached to the same solid support as one or more polynucleotides of the invention.

Oligonucleotide Array

A substrate comprising a plurality of oligonucleotide primers or probes of the invention may be used either for detecting or amplifying targeted sequences in GENSET genes, may be used for detecting mutations in the coding or in the non-coding sequences of GENSET genes, and may also be used to determine GENSET gene expression in different contexts such as in different tissues, at different stages of a process (embryo development, disease treatment), and in patients versus healthy individuals as described elsewhere in the application.

As used herein, the term "array" means a one dimensional, two dimensional, or multidimensional arrangement of nucleic acids of sufficient length to permit specific detection of gene expression. For example, the array may contain a plurality of nucleic acids derived from genes whose expression levels are to be assessed. The array may include any of the herein-described GENSET genomic DNA, a GENSET cDNA, sequences complementary thereto or fragments thereof. Preferably, the fragments are at least 12, 15, 18, 20, 25, 30,35, 40, 50, or 100 nucleotides in length.

Any polynucleotide provided herein may be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention, including Genechips™ (see, e.g., U.S. Pat. No. 5,143,854; PCT publications WO 90/15070 and 92/10092, Fodor et al., (1991) Science 251: 767-777). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip (see, e.g., U.S. Pat. Nos. 5,143,854 and 5,412,087, and in PCT Publications WO 90/15070, WO 92/10092 and WO 95/11995). Further presentation strategies known in the art may be used, such as those disclosed in WO 94/12305, WO 94/11530, WO 97/29212 and WO 97/31256.

Consequently, the invention concerns an array of nucleic acid molecules comprising at least one, two, or five polynucleotides of the invention, particularly probes or primers as described herein.

Methods of Making the Polynucleotides of the Invention

The present invention also comprises methods of making the polynucleotides of the invention. Polynucleotides of the invention may be synthesized either enzymatically using techniques well known to those skilled in the art including amplification or hybridization-based methods as described herein, or chemically.

A variety of chemical methods of synthesizing nucleic acids are known to those skilled in the art. In many of these methods, synthesis is conducted on a solid support. Alternatively, polynucleotides may be prepared as described in U.S. Pat. No. 5,049. In some embodiments, several polynucleotides prepared as described above are ligated together to generate longer polynucleotides having a desired sequence.

Polypeptides of the Invention

The term "GENSET polypeptides" is used herein to embrace all of the proteins and polypeptides of the present invention. The present invention encompasses GENSET polypeptides, including recombinant, isolated or purified GENSET polypeptides consisting of: (a) the full length polypeptides of even SEQ ID NOs:2-24; (b) the full length polypeptides encoded by the clone inserts of the deposited clone pool; (c) the epitope-bearing fragments of the polypeptides of even SEQ ID NOs:2-24; (d) the epitope-bearing fragments of the polypeptides encoded by the clone inserts contained in the deposited clone pool; (e) the domains of the polypeptides of even SEQ ID NOs:2-24; (f) the domains of the polypeptides encoded by the clone inserts contained in the deposited clone pool; (g) the signal peptides of the polypeptides of even SEQ ID NOs:2-24 or encoded by the human cDNAs of the deposited clone pool; (h) the mature polypeptides of even SEQ ID NOs:2-24 or encoded by the human cDNAs of the deposited clone pool; and (i) the allelic variant polypeptides of any of the polypeptides of (a)-(f). Other objects of the invention are polypeptides encoded by the polynucleotides of the invention as well as fusion polypeptides comprising such polypeptides.

Polypeptide Variants

The present invention further provides for GENSET polypeptides encoded by allelic and splice variants, orthologs, and/or species homologues. Procedures known in the art can be used to obtain, allelic variants, splice variants, orthologs, and/or species homologues of polynucleotides encoding polypeptides of the Sequence Listing and polypeptides encoded by the clone inserts of the deposited clone pool, using information from the sequences disclosed herein or the clones deposited with the ATCC.

The polypeptides of the present invention also include polypeptides having an amino acid sequence at least 50% identical, more preferably at least 60% identical, and still more preferably 70%, 80%, 90%, 95%, 96%, 97%, 98% or 99% identical to a polypeptide of the present invention. By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, (indels) or substituted with another amino acid.

Further polypeptides of the present invention include polypeptides which have at least 90% similarity, more preferably at least 95% similarity, and still more preferably at least 96%, 97%, 98% or 99% similarity to those described above. "Similarity" is calculated exactly as described above for "identity", except that for the purposes of the calculation a matching amino acid can be either identical or an amino acid representing an "equivalent" change, as defined below.

These alterations of the reference sequence may occur at the amino or carboxy terminal positions of the reference amino acid sequence or anywhere between those terminal positions, interspersed either individually among residues in the reference sequence or in one or more contiguous groups within the reference sequence. The variant polypeptides described herein are included in the present invention regardless of whether they have their normal biological activity, as one of skill in the art would recognize that variant polypeptides lacking biological activity would still be useful, for instance, as a vaccine, to generate antibodies, as epitope tags, in epitope mapping, as molecular weight markers on SDS-PAGE gels or on molecular sieve gel filtration columns.

Preparation of the Polypeptides of the Invention

The polypeptides of the present invention can be prepared in any suitable manner known in the art. Such polypeptides include isolated naturally occurring polypeptides, recombinantly produced polypeptides, synthetically produced polypeptides, or polypeptides produced by a combination of these methods. The polypeptides of the present invention are preferably provided in an isolated form, and may be partially or preferably substantially purified.

Isolation

From Natural Sources

The GENSET proteins of the invention may be isolated from natural sources, including bodily fluids, tissues and cells, whether directly isolated or cultured cells, of humans or non-human animals. Methods for extracting and purifying natural proteins are known in the art, and include the use of detergents or chaotropic agents to disrupt particles followed by differential extraction and separation of the polypeptides by ion exchange chromatography, affinity chromatography, sedimentation according to density, and gel electrophoresis. See, e.g., "Methods in Enzymology, Academic Press, 1993" for a variety of methods for purifying proteins. Polypeptides of the invention also can be purified from natural sources using antibodies directed against the polypeptides of the invention, using standard methods.

From Recombinant Sources

Preferably, the GENSET polypeptides of the invention are recombinantly produced using routine expression methods known in the art. The polynucleotide encoding the desired polypeptide is operably linked to a promoter into an expression vector suitable for any convenient host. Both eukaryotic and prokaryotic host systems are used in forming recombinant polypeptides. The polypeptide is then isolated from lysed cells or from the culture medium and purified to the extent needed for its intended use. Any polynucleotide of the present invention may be used to express GENSET polypeptides.

Consequently, a further embodiment of the present invention is a method of making a polypeptide of the present invention, said method comprising the steps of providing a GENSET polynucleotide (e.g. a polynucleotide encoding a GENSET polypeptide), inserting the polynucleotide in an expression vector such that the cDNA is operably linked to a promoter; and introducing the expression vector into a host cell whereby said host cell produces said polypeptide. In one aspect of this embodiment, the method further comprises the step of isolating the polypeptide. Any suitable expression vector and system (e.g. cell-based system such as 3T3 cells) may be used, according to methods well known in the art.

In one embodiment, the entire coding sequence of a GENSET cDNA and the 3'UTR through the polyA signal of the cDNA is operably linked to a promoter in the expression vector.

In another embodiment, an additional nucleotide sequence is included which codes for secretory or leader sequences, pro-sequences, sequences which aid in purification, such as multiple histidine residues, or an additional sequence for stability during recombinant production.

Alternatively, the GENSET polypeptide to be expressed may also be a product of transgenic animals, i.e., as a component of the milk of transgenic cows, goats, pigs or sheep which are characterized by somatic or germ cells containing a nucleotide sequence encoding the protein of interest.

Any standard method may be used to recover a GENSET polypeptide expressed using these methods, including differential extraction, ammonium sulfate or ethanol precipitation, acid extraction, anion or cation exchange chromatography, phosphocellulose chromatography, hydrophobic interaction chromatography, antibody-based methods, affinity chromatography, hydroxylapatite chromatography, HPLC, immunochromatography, and lectin chromatography.

Depending upon the host employed in a recombinant production procedure, the polypeptides of the present invention may be glycosylated or may be non-glycosylated, and may also include an initial modified methionine residue, in some cases as a result of host-mediated processes. In addition, polypeptides of the present invention may or may not contain the amino terminal methionine.

From Chemical Synthesis

In addition, polypeptides of the invention, especially short protein fragments, can be chemically synthesized using techniques known in the art (See, e.g., Creighton (1983), Proteins: Structures and Molecular Principles, W.H. Freeman & Co. 2nd Ed., T. E., New York; and Hunkapiller et al., (1984) *Nature.* 310(5973):105-11). For example, a polypeptide corresponding to a fragment of a polypeptide sequence of the invention can be synthesized by use of a peptide synthesizer. Alternatively, the methods described in U.S. Pat. No. 5,049,656, may be used.

Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoroamino acids, designer amino acids such as b-methyl amino acids, Ca-methyl amino acids, Na-methyl amino acids, and amino acid analogs in general. Furthermore, the amino acid can be D (dextrorotary) or L (levorotary).

Modifications

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see, e.g., U.S. Pat. No. 4,179,337). The chemical moieties for derivatization may be selected from water soluble polymers (branched or unbranched) such as polyethylene glycol (preferably between 1 and 100 kD), ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties. The chemical moiety may be attached using any method, e.g. via a free amino, carboxyl, or sulfhydryl group (see, e.g., EP 0 401 384, or Malik et al., (1992), Exp. Hematol. 20:1028-1035).

Multimerization

The polypeptides of the invention may be in monomers or multimers (i.e., dimers, trimers, tetramers and higher multimers). Accordingly, the present invention relates to monomers and multimers of the polypeptides of the invention, their preparation, and compositions containing them.

Multimers encompassed by the invention may be homomers or heteromers. As used herein, the term "homomer" refers to a multimer containing only polypeptides with the same amino acid sequence (although a small amount of variation is allowed), and "heteromer" refers to a multimer containing one or more heterologous polypeptides.

Multimers of the invention may be the result of hydrophobic, hydrophilic, ionic and/or covalent associations and/or may be indirectly linked. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by cross-linking between cysteine residues located within the polypeptide sequences. Any of these associations may involve one or more amino acid residues contained in an amino acid provided in the sequence listing or in a heterologous polypeptide sequence of a fusion protein, e.g., in an Fc fusion protein, osteoprotegerin fusion protein, peptide linker fusion protein, Flag® fusion protein, or leucine zipper fusion protein of the invention (see, e.g., U.S. Pat. No. 5,478,925, WO 98/49305, or U.S. Pat. No. 5,073,627, Landschulz et al., (1988), Science. 240:1759, WO 94/10308, Hoppe et al., (1994), FEBS Letters. 344:191 and in U.S. patent application Ser. No. 08/446,922). Other methods of making multimers include the addition of cysteine or biotin to the C-terminus or N-terminus of the polypeptide using techniques known in the art, or by generating liposomes containing the polypeptide components desired to be contained in the multimer of the invention (see, e.g., U.S. Pat. No. 5,478,925 for numerous methods of multimerization).

Multimers of the invention may be generated using chemical or genetic engineering techniques known in the art.

Mutated Polypeptides

To improve or alter the characteristics of GENSET polypeptides of the present invention, recombinant DNA technology can be used to create novel mutant proteins or muteins including single or multiple amino acid substitutions, deletions, additions, or fusion proteins. Such modified polypeptides can show, e.g., increased/decreased biological activity or increased/decreased stability. In addition, they may be purified in higher yields and show better solubility than the corresponding natural polypeptide, at least under certain purification and storage conditions.

N— and C-Terminal Deletions

It is known in the art that one or more amino acids may be deleted from the N-terminus or C-terminus without substantial loss of biological function. (See, e.g., Ron et al., (1993), Biol Chem., 268 2984-2988 ; Dobeli, et al. 1988.) Accordingly, the present invention provides polypeptides having one or more residues deleted from the amino and/or carboxy terminus.

Other Mutations

The invention includes numerous variations of the GENSET polypeptides which show substantial GENSET polypeptide activity. Such mutants include deletions, insertions, inversions, repeats, and substitutions selected according to general rules known in the art so as to have little effect on activity.

There are two main approaches for studying the tolerance of an amino acid sequence to change (see, Bowie et al., (1994), *Science.* 247:1306-1310). The first method relies on the process of evolution, in which mutations are either accepted or rejected by natural selection. The second approach uses genetic engineering to introduce amino acid changes at specific positions of a cloned gene and selections or screens to identify sequences that maintain functionality.

Examples of this include site-directed mutagenesis or alanine-scanning mutagenesis (see, e.g., Cunningham et al. (1989), Science 244:1081-1085). These studies have revealed that proteins are surprisingly tolerant of amino acid substitutions.

Typically seen as conservative substitutions are the replacements, one for another, among the aliphatic amino acids Ala, Val, Leu and Phe; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Thus, the polypeptide of the present invention may be, for example, one in which one or more of the amino acid residues are substituted with a conserved or non-conserved amino acid residue (preferably a conserved amino acid residue). Such substituted amino acid residue may or may not be one encoded by the genetic code, and may include a substituent group.

As indicated, changes are preferably of a minor nature, such as conservative amino acid substitutions that do not significantly affect the folding or activity of the protein. The following groups of amino acids represent equivalent changes: (1) Ala, Pro, Gly, Glu, Asp, Gin, Asn, Ser, Thr; (2) Cys, Ser, Tyr, Thr; (3) Val, Ile, Leu, Met, Ala, Phe; (4) Lys, Arg, His; (5) Phe, Tyr, Trp, His.

Furthermore, GENSET polypeptides of the present invention may include one or more amino acid substitutions that mimic modified amino acids. An example of this type of substitution includes replacing amino acids that are capable of being phosphorylated (e.g., serine, threonine, or tyrosine) with a negatively charged amino acid that resembles the negative charge of the phosphorylated amino acid (e.g., aspartic acid or glutamic acid). Also included is substitution of amino acids that are capable of being modified by hydrophobic groups (e.g., arginine) with amino acids carrying bulky hydrophobic side chains, such as tryptophan or phenylalanine. Therefore, a specific embodiment of the invention includes GENSET polypeptides that include one or more amino acid substitutions that mimic modified amino acids at positions where amino acids that are capable of being modified are normally positioned. Furthermore, any GENSET polypeptide amino acid capable of being modified may be excluded from substitution with a modification-mimicking amino acid.

A specific embodiment of a modified GENSET peptide molecule of interest according to the present invention, includes, but is not limited to, a peptide molecule which is resistant to proteolysis, is a peptide in which the —CONH— peptide bond is modified and replaced by a (CH2NH) reduced bond, a (NHCO) retro inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH— bond.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (see, e.g., Pinckard et al., (1967), Clin. Exp. Immunol 2:331-340; Robbins et al., (1987), Diabetes. 36:838-845; and Cleland et al., (1993) Crit. Rev. Ther. Drug Carr. Syst. 10:307-377).

A further embodiment of the invention relates to a polypeptide which comprises the amino acid sequence of a GENSET polypeptide having an amino acid sequence which contains at least any one integer from 1 to 50 of conservative amino acid substitutions. Any conservative substitution or combination of substitutions may also be excluded.

Polypeptide Fragments

Structural Definition

The present invention is further directed to fragments of the polypeptides of the present invention. More specifically, the present invention embodies purified, isolated, and recombinant polypeptides comprising at least any one integer between 6 and 1000 (or the length of the polypeptides amino acid residues minus 1 if the length is less than 1000) of consecutive amino acid residues. Preferably, the fragments are at least 6, preferably at least 8 to 10, more preferably 12, 15, 20, 25, 30, 35, 40, 50, 60, 75, 100, 125, 150, 175, 200, 225, 250, 275, or 300 consecutive amino acids of a polypeptide of the present invention.

In addition to the above polypeptide fragments, further preferred sub-genuses of polypeptides comprise at least X amino acids, wherein "X" is defined as any integer between 6 and the integer representing the C-terminal amino acid of the polypeptide of the present invention including the polypeptide sequences of the sequence listing below. Further included are species of polypeptide fragments at least 6 amino acids in length, as described above, that are further specified in terms of their N-terminal and C-terminal positions. However, included in the present invention as individual species are all polypeptide fragments, at least 6 amino acids in length, as described above, and may be particularly specified by a N-terminal and C-terminal position. That is, every combination of a N-terminal and C-terminal position that a fragment at least 6 contiguous amino acid residues in length could occupy, on any given amino acid sequence of the sequence listing or of the present invention is included in the present invention Further preferred polypeptide fragments comprising amino acids of the sequences of the EVEN numbered SEQ ID NOs. of the Sequence listing, and polynucleotides encoding the same, are selected from the group consisting of amino acids starting at position one and continuing to any position selected from the group consisting of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134,135, 136,137, 138, 139, 140, 141, 142, 143, 144, 145, 146, 147, 148, 149, 150, 151, 152, 153, 154,155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, and 786, wherein the numbering of amino acids comprising any one fragment is consistent with the polypeptide sequence of any one EVEN numbered SEQ ID of the Sequence listing.

Further preferred polypeptide fragments comprising amino acids of the sequences of the EVEN numbered SEQ ID NOs. of the Sequence listing, and polynucleotides encoding the same, are selected from the group consisting of amino acids ending at the terminal amino acid of the protein (e.g. position 787) and beginning at any position selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, and 782, wherein the numbering of amino acids comprising any one fragment is consistent with the polypeptide sequence of any one EVEN numbered SEQ ID of the Sequence listing.

Further preferred polypeptide fragments of the EVEN numbered SEQ ID NOs. of the Sequence listing, and polynucleotides encoding the same, are selected from the group consisting of fragments comprising any 50 or 100 consecutive amino acids starting from an amino acid position selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, and 738, wherein the numbering of amino acids comprising any one fragment is consistent with the polypeptide sequence of any one EVEN numbered SEQ ID of the Sequence listing.

These specific embodiments, and other polypeptide and polynucleotide fragment embodiments described herein may be modified as being "at least", "equal to", "equal to or less than", "less than", "at least _____but not greater than _____" or "from _____to _____" a specified size or specified N-terminal and/or C-terminal positions. It is noted that all ranges used to describe any embodiment of the present invention are inclusive unless specifically set forth otherwise.

The above species of polypeptide fragments of the present invention may alternatively be described by the formula "a to b"; where "a" equals the N-terminal most amino acid position and "b" equals the C-terminal most amino acid position of the polynucleotide; and further where "a" equals an integer between 1 and the number of amino acids of the polypeptide sequence of the present invention minus 6, and where "b" equals an integer between 7 and the number of amino acids of the polypeptide sequence of the present invention; and where "a" is an integer smaller then "b" by at least 6.

The above polypeptide fragments of the present invention can be immediately envisaged using the above description and are therefore not individually listed solely for the purpose of not unnecessarily lengthening the specification. Moreover, the above fragments need not have a GENSET biological activity, although polypeptides having these activities are preferred embodiments of the invention, since even inactive fragments are useful, for example, in immunoassays, in epitope mapping, epitope tagging, as vaccines, as molecular weight markers, and to generate antibodies to a particular portion of the polypeptide.

The present invention also provides for the exclusion in any polypeptide of any one or more of the above-described fragments, e.g., one or more individual fragments specified by N-terminal and C-terminal positions or of any fragments specified by size in amino acid residues as described above.

Functional Definition

Domains

Preferred polynucleotide fragments of the invention comprise domains of polypeptides of the invention. Such domains may eventually comprise linear or structural motifs and signatures including, but not limited to, leucine zippers, helix-turn-helix motifs, post-translational modification sites such as glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites. Such domains may present a particular biological activity such as DNA or RNA-binding, secretion of proteins, transcription regulation, enzymatic activity, substrate binding activity, etc.

In a preferred embodiment, domains comprise a number of amino acids that is any integer between 6 and 1000. Domains may be synthesized using any methods known to those skilled in the art, including those disclosed herein. Methods for determining the amino acids which make up a domain with a particular biological activity include mutagenesis studies and assays to determine the biological activity to be tested, as well as bioinformatic methods for recognizing domains, motifs, or signatures, e.g., in a database such as Prosite (Hofmann et al., (1999) Nucl. Acids Res. 27:215-219; Bucher and Bairoch (1994) Proceedings 2nd International Conference on Intelligent Systems for Molecular Biology. Altman et al, Eds., pp53-61, AAAIPress, Menlo Park), Pfam (Sonnhammer, et al., (1997) Proteins. 28(3):405-20; Henikoffet al., (2000) Electrophoresis 21(9): 1700-6; Bateman et al., (2000) Nucleic Acids Res. 28(1): 263-6), Blocks, Print, Prodom, Sbase, Smart, Dali/FSSP, HSSP, CATH, SCOP, COG. For a review on available databases, see issue 1 of volume 28 of Nucleic Acid Research (2000).

Epitopes and Antibody Fusions:

A preferred embodiment of the present invention is directed to epitope-bearing polypeptides and epitope-bearing polypeptide fragments. These epitopes may be "antigenic epitopes" or both an "antigenic epitope" and an "immunogenic epitope". An "immunogenic epitope" is defined as a part of a protein that elicits an antibody response in vivo when the polypeptide is the immunogen. On the other hand, a region of polypeptide to which an antibody binds is defined as an "antigenic determinant" or "antigenic epitope." The number of immunogenic epitopes of a protein generally is less than the number of antigenic epitopes (see, e.g., Geysen et al., (1984), PNAS 81:3998-4002). It is particularly noted that although a particular epitope may not be immunogenic, it is nonetheless useful since antibodies can be made to both immunogenic and antigenic epitopes. The present epitopes may be linear (i.e., composed of a contiguous sequence of amino acids repeated along the polypeptide chain) or nonlinear (also called "conformational", i.e., composed of amino acids brought into proximity as a result of the folding of the polypeptide chain).

An epitope can comprise as few as 3 amino acids in a spatial conformation, which is unique to the epitope. Generally an epitope consists of at least 6 such amino acids, and more often at least 8-10 such amino acids. In preferred embodiment, antigenic epitopes comprise a number of amino acids that is any integer between 3 and 50. Fragments which function as epitopes may be produced by any conventional means (see, e.g., Houghten (1985), PNAS 82:5131-5135), also further described in U.S. Pat. No. 4,631,21. Methods for determining the amino acids which make up an epitope include x-ray crystallography, 2-dimensional nuclear magnetic resonance, and epitope mapping, e.g., the Pepscan method described by Geysen, et al. (1984); WO 84/03564; and WO 84/03506. Nonlinear epitopes are determined by methods such as protein footprinting (U.S. Pat. No. 5,691,448). Another example is the algorithm of Jameson and Wolf, (1988), Comp. Appl. Biosci. 4:181-186. The Jameson-Wolf antigenic analysis, for example, may be performed using the computer program PROTEAN, using default parameters (Version 4.0 Windows, DNASTAR, Inc., 1228 South Park Street Madison, Wis.). Epitopes may also be identified in vivo by testing for an antigenic response using standard methods.

All fragments of the polypeptides of the present invention, at least 6, 8, 10, 12, 15, 20, 25, 30, 35, 40, 50, 60, 75, 100, 125, 150, 175, 200, 225, 250, 275, or 300 amino acids residues in length, are included in the present invention as being useful as antigenic linear epitopes. Polypeptides of the present invention that are not specifically described as immunogenic are not considered non-antigenic as they may be antigenic in vivo. The epitope-bearing fragments of the present invention preferably comprise 6 to 50 amino acids (i.e. any integer between 6 and 50, inclusive) of a polypeptide of the present invention. Any number of epitope-bearing fragments of the present invention may also be excluded.

Nonlinear epitopes comprise more than one noncontiguous polypeptide sequence of at least one amino acid each. Such epitopes result from noncontiguous polypeptides brought into proximity by secondary, tertiary, or quaternary structural features. Preferred polypeptides providing nonlinear epitopes are formed by a contiguous surface of natively folded protein and are thus at least 10 amino acids in length, further preferably 12, 15, 20, 25, 30, 35, 40, 50, 60, 75, 100, 125, 150, 175, 200, 225, 250, 275, or 300 amino acids of a polypeptide of the present invention. Additionally, nonlinear epitopes may be formed by synthetic peptides that mimic an antigenic site or contiguous surface normally presented on a protein in the native conformation.

Immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention are used to induce antibodies according to methods well known in the art including, but not limited to, in vivo immunization, in vitro immunization, and phage display methods (see, e.g., Sutcliffe, et al., supra; Wilson, et al., supra, and Bittle, et al., supra). If in vivo immunization is used, animals may be immunized with free peptide; however, anti-peptide antibody titer may be boosted by coupling of the peptide to a macromolecular carrier using standard methods, such as keyhole limpet hemacyanin (KLH) or tetanus toxoid. Animals such as rabbits, rats and mice are immunized with either free or carrier-coupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of anti-peptide antibody, which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo (see, e.g., EPA 0,394,827; and Traunecker et al., (1988), Nature. 331:84-86; Fountoulakis et al., (1995) Biochem. 270:3958-3964). Additional fusion proteins of the invention may be generated through the techniques of gene-shuffling, motif-shuffling, exon-shuffling, or codon-shuffling (collectively referred to as "DNA shuffling"; see, for example, U.S. Pat. Nos. 5,605,793; 5,811,238; 5,834,252; 5,837,458; and Patten, et al. (1997), Curr Opinion Biotechnol. 8:724-733; Harayama (1998), Trends Biotechnol. 16(2): 76-82; Hansson et al., (1999), J. Mol. Biol. 287:265-276; and Lorenzo and Blasco (1998) Biotechniques. 24(2):308-313). The present invention further encompasses any combination of the polypeptide fragments listed in this section.

Antibodies

Definitions

The present invention further relates to antibodies and T-cell antigen receptors (TCR), which specifically bind the polypeptides, and more specifically, the epitopes of the polypeptides of the present invention. The antibodies of the present invention include IgG (including IgG1, IgG2, IgG3, and IgG4), IgA (including IgA1 and IgA2), IgD, IgE, or IgM, and IgY. The term "antibody" (Ab) refers to a polypeptide or group of polypeptides which are comprised of at least one binding domain, where a binding domain is formed from the folding of variable domains of an antibody molecule to form three-dimensional binding spaces with an internal surface shape and charge distribution complementary to the features of an antigenic determinant of an antigen, which allows an immunological reaction with the antigen. As used herein, the term "antibody" is meant to include whole antibodies, including single-chain whole antibodies, and antigen binding fragments thereof. In a preferred embodiment the antibodies are human antigen binding antibody fragments of the present invention include, but are not limited to, Fab, Fab' F(ab)2 and F(ab')2, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH1, CH2, and CH3 domains. Also included in the invention are any combinations of variable region(s) and hinge region, CH1, CH2, and CH3 domains. The present invention further includes chimeric, humanized, and human monoclonal and polyclonal antibodies, which specifically bind the polypeptides of the present invention. The present invention further includes antibodies that are anti-idiotypic to the antibodies of the present invention.

The antibodies of the present invention may be monospecific, bispecific, and trispecific or have greater multispecificity. Multispecific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, et al., (1991), J. Immunol. 147:60-69; U.S. Pat. Nos. 5,573,920, 4,474,893, 5,601,819, 4,714,681, 4,925,648; Kostelny et al., (1992), J. Immunol. 148:1547-1553.

Antibodies of the present invention may be described or specified in terms of the epitope(s) or epitope-bearing portion(s) of a polypeptide of the present invention, which are recognized or specifically bound by the antibody. The antibodies may specifically bind a complete protein encoded by a nucleic acid of the present invention, or a fragment thereof. Antibodies which specifically bind any epitope or polypeptide of the present invention may also be excluded as individual species.

Thus, another embodiment of the present invention is a purified or isolated antibody capable of specifically binding to any of the polypeptides of the present invention. In one aspect of this embodiment, the antibody is capable of binding to a linear epitope-containing polypeptide comprising at least 6 consecutive amino acids, preferably at least 8 to 10 consecutive amino acids, more preferably at least 12, 15, 20, 25, 30, 40, 50, or 100 consecutive amino acids of a polypeptides of the present invention. In another aspect of this embodiment, the antibody is capable of binding to a nonlinear epitope-containing polypeptide comprising 10 amino acids in length, further preferably 12, 15, 20, 25, 30, 35, 40, 50, 60, 75, or 100 amino acids, further preferably, a contiguous surface of the native conformation of a polypeptide of the present application.

Antibodies of the present invention may also be described or specified in terms of their cross-reactivity. Antibodies that do not specifically bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein, e.g., using FASTDB and the parameters set forth herein) to a polypeptide of the present invention are also included in the present invention. Further included in the present invention are antibodies, which only bind polypeptides encoded by polynucleotides, which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $\times10^{-12}$M, $10^{-12}$M, $5\times10^{-13}$M, $10^{-13}$M, $5\times10^{-14}$M, $10^{-14}$M, and $10^{-15}$M.

The invention also concerns a purified or isolated antibody capable of specifically binding to a mutated GENSET protein or to a fragment or variant thereof comprising an epitope of the mutated GENSET protein.

Preparation of Antibodies

The antibodies of the present invention may be prepared by any suitable method known in the art. For example, a polypeptide of the present invention or an antigenic fragment thereof can be administered to an animal in order to induce the production of sera containing "polyclonal antibodies". As used herein, the term "monoclonal antibody" is not limited to antibodies produced through hybridoma technology but it rather refers to an antibody that is derived from a single clone, including eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art (see, e.g., Harlow and Lane, (1988) Antibodies A Laboratory Manual. Cold Spring Harbor Laboratory. pp. 53-242; Hammerling (1981), Monoclonal Antibodies and T-Cell Hybridomas, Elsevier, N.Y. 563-681; Kohler and Milstein, (1975) Nature 256:495; Davis, et al., Basic Methods in Molecular Biology, ed., Elsevier Press, NY (1986), Section 21-2).).

Briefly, a mouse is repetitively inoculated with a few micrograms of the GENSET protein, or a portion thereof, over a period of a few weeks. The mouse is then sacrificed, and the antibody producing cells of the spleen isolated. The spleen cells are fused by means of polyethylene glycol with mouse myeloma cells, and antibody-producing clones are identified (see, e.g., Engvall, (1980) Meth. Enzymol. 70:419). Selected positive clones can be expanded and their monoclonal antibody product harvested for use.

Further, Fab and F(ab')2 fragments may be produced, for example, from hybridoma-produced antibodies by proteolytic cleavage, using enzymes such as papain (to produce Fab fragments) or pepsin (to produce F(ab')2 fragments Polyclonal antiserum containing antibodies to heterogeneous epitopes in the GENSET protein or a portion thereof can be prepared by immunizing suitable non-human animals (e.g., mouse, rat, rabbit, goat, or horse) with the GENSET protein or a portion thereof, which can be unmodified or modified to enhance immunogenicity (see, e.g., Vaitukaitis et al., (1971) J. Clin. Endocrinol. Metab. 33:988-991; Ouchterlony et al., (1973) Chap. 19 in: Handbook of Experimental Immunology D. Wier (ed) Blackwell). The protein or fragment is typically introduced into the non-human mammal in the presence of an appropriate adjuvant (e.g. aluminum hydroxide, RIBI, etc.). Serum from the immunized animal is collected, treated and tested according to known procedures. If the serum contains polyclonal antibodies to undesired epitopes, the polyclonal antibodies can be purified by immunoaffinity chromatography. Affinity of the antisera for the antigen is determined using standard methods.

Alternatively, antibodies of the present invention can be produced through the application of recombinant DNA technology or through synthetic chemistry using methods known in the art. In phage display methods, for example, functional antibody domains are displayed on the surface of a phage particle, which carries polynucleotide sequences encoding them, and phage with a desired binding property are selected from a repertoire or combinatorial antibody library (e.g. human or murine) by selecting directly with antigen, typically antigen bound or captured to a solid surface or bead (see, e.g., Brinkman et al., (1995) J. Immunol Methods, 182:41-50; Ames et al., (1995), J. Immunol. Meth., 184:177-186.; Kettleborough et al., (1994), Eur. L Immunol., 24:952-958; Persic et al., (1997), Gene, 1879-81; Burton et al. (1994), Adv. Immunol., 57:191-280; PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403, 484, 5,580,717, 5,427,908, 5,750,753, 5,821,047, 5,571,698, 5,427,908, 5,516,637, 5,780,225, 5,658,727 and 5,733,743). After phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria (see, e.g., WO 92/22324; Mullinax et al., (1992), BioTechniques. 12(6):864-869; and Sawai et al., (1995), AJRI 34:26-34; and Better et al., (1988), *Science.* 240:1041-1043).

Further teaching regarding the preparation of single-chain Fvs and antibodies is provided in U.S. Pat. Nos. 4,946,778 and 5,258,498; Huston et al., (1991), Meth. Enymol. 203: 46_88; Shu, et al., (1993), PNAS 90:7995-7999; and Skerra, et al., (1988), and Science 240:1038-1040. For some uses, including in vivo use of antibodies in humans and in vitro detection assays, it may be preferable to use chimeric, shuffled, humanized, or human antibodies (see e.g., Morrison, (1985); Oi et al., (1986), BioTechniques 4:214; Gillies et al., (1989), J. Immunol Methods. 125:191-202; and U.S. Pat. Nos. 5,807,715; EP 0 239 400; WO 91/09967; U.S. Pat. Nos. 5,530,101; and 5,585,089, EP 0 592 106; EP 0 519 596; Padlan (1991), Molec. Immunol. 28(4/5):489498; Studnicka et al., (1994), Protein Engineering. 7(6):805-814; Roguska et al., (1994), PNAS 91:969-973, U.S. Pat. Nos. 5,565,332, 4,444,887, 4,716,111, 5,545,806, and 5,814,318; WO 98/46645; WO 98/50433; WO 98/24893; WO 96/34096; WO 96/33735; and WO 91/10741).

Further included in the present invention are antibodies recombinantly fused or chemically conjugated (including both covalent and non-covalent conjugations) to any heterologous molecule, such as a polypeptide of the present invention, another polypeptide, a label useful for detection assays, or an effector molecule such as a drug or toxin (see, e.g., WO 92/08495; WO 91/14438; WO 89/12624; U.S. Pat. No. 5,314,995; and EP 0 396 387). Fused antibodies may also be used to target the polypeptides of the present invention to particular cell types, either in vitro or in vivo, by fusing or conjugating the polypeptides of the present invention to antibodies specific for particular cell surface receptors, and may also be used in vitro immunoassays and purification methods using methods known in the art (see e.g., Harbor, et al. supra; WO 93/21232; EP 0 439 095; Naramura et al, (1994), Immunol. Lett. 39:91-99; U.S. Pat. No. 5,474,981; Gillies et al., (1992), PNAS 89:1428-1432; Fell et al., (1991), J. Immunol. 146:2446-2452).

The present invention further includes compositions comprising the polypeptides of the present invention fused or conjugated to antibody domains other than the variable regions. For example, the polypeptides of the present invention may be fused or conjugated to an antibody Fc region, or portion thereof, and/or the hinge region, CH1 domain, CH2 domain, or CH3 domain or portions thereof, as well as to portions of IgA or IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi et al., (1991), PNAS 88:10535-10539; Zheng, et al. (1995), J. Immunol. 154:5590-5600; and Vil, et al. (1992), PNAS 89:11337-11341.

Non-human animals or mammals, whether wild-type or transgenic, which express a different species of GENSET polypeptide than the one to which antibody binding is desired, and animals which do not express a GENSET polypeptide (i.e. a GENSET knock out animal as described herein) are particularly useful for preparing antibodies, as such animals will recognize all or most of the exposed regions of a GENSET protein as foreign antigens, and therefore produce antibodies with a wider array of GENSET epitopes. Moreover, smaller polypeptides with only 10 to 30 amino acids may be useful in obtaining specific binding to any one of the GENSET proteins. In addition, the humoral immune system of animals which produce a species of GENSET that resembles the antigenic sequence will preferentially recognize the differences between the animal's native GENSET species and the antigen sequence, and produce antibodies to these unique sites in the antigen sequence. Such a technique will be particularly useful in obtaining antibodies that specifically bind to any one of the GENSET proteins.

A preferred embodiment of the invention is a method of specifically binding an antibody or antibody fragment to a GENSET polypeptide. This method comprises the step of contacting a GENSET polypeptide-specific antibody or fragment thereof with a GENSET polypeptide under antibody-binding conditions. Further included is a method of specifically binding an antibody or antibody fragment to an epitope, domain, or fragment of a GENSET polypeptide. This method may be used to, for example, detect, purify, or modify the activity of GENSET polypeptides, as discussed herein.

Antibodies of the invention can be used to assay protein levels in a test sample or biological sample using methods known to those of skill in the art. Antibody-based methods useful for detecting protein include immunoassays, such as the enzyme linked immunosorbent assay (ELISA) and radioimmunoassay (RIA). Suitable antibody assay labels are known in the art and include enzyme labels, such as glucose oxidase, horseradish peroxidase, and alkaline phosphatase; radioisotopes, such as iodine (125I, 121I), carbon (14C), sulfur (35S), tritium (3H), indium (121In), and technetium (99Tc); luminescent labels, such luminol, isolumino, theromatic acridinium ester, imidazole, acridinium salt, oxalate ester, luciferin, luciferase, and aequorin; and fluorescent labels, such as fluorescein isothiocyanate, rhodamine, phycoerythrin, phycocyanin, allophycocyanin, o-phthaldehyde, and fluorescamine.

Uses of Polynucleotides

Uses of Polynucleotides as Reagents

The polynucleotides of the present invention may be used as reagents in isolation procedures, diagnostic assays, and forensic procedures. For example, sequences from the GENSET polynucleotides of the invention may be detectably labeled and used as probes to isolate other sequences capable of hybridizing to them. In addition, sequences from the GENSET polynucleotides of the invention may be used to design PCR primers to be used in isolation, diagnostic, or forensic procedures.

To Find Corresponding Genomic DNA Sequences

The GENSET cDNAs of the invention may also be used to clone sequences located in the vicinity, preferably upstream of the cDNAs of the invention on the corresponding genomic DNA. Such sequences may be capable of regulating gene expression, including promoter sequences, enhancer sequences, and other sequences which influence transcription or translation levels.

Use of cDNAs or Fragments Thereof to Clone Upstream Sequences from Genomic DNA

Sequences derived from polynucleotides of the inventions may be used to isolate the promoters of the corresponding genes using chromosome walking techniques (e.g., using the GenomeWalker™ kit from Clontech). Once the upstream genomic sequences have been cloned and sequenced, prospective promoters and transcription start sites within the upstream sequences may be identified by comparing the sequences upstream of the polynucleotides of the inventions with databases containing known transcription start sites, transcription factor binding sites, or promoter sequences.

In addition, promoters in the upstream sequences may be identified using promoter reporter vectors, e.g., by placing a reporter gene (e.g., secreted alkaline phosphatase, luciferase, beta-galactosidase, or green fluorescent protein) under the control of regulatory active polynucleotide fragments or variants of the GENSET promoter region located upstream of the first exon of the GENSET gene. A large number of suitable promoter reporter vectors are known in the art. The promoters and other regulatory sequences located upstream of the polynucleotides of the inventions may be used to design expression vectors capable of directing the expression of an inserted gene in a desired spatial, temporal, developmental, or quantitative manner.

To Find Similar Sequences

Polynucleotides of the invention may be used to isolate and/or purify nucleic acids similar thereto using any methods well known to those skilled in the art including the techniques based on hybridization or on amplification described in this section. These methods may be used to obtain the genomic DNAs which encode the mRNAs from which the GENSET cDNAs are derived, mRNAs corresponding to GENSET cDNAs, or nucleic acids which are homologous to GENSET cDNAs or fragments thereof, such as variants, species homologues or orthologs.

Hybridization-Based Methods

Techniques for identifying cDNA clones in a cDNA library which hybridize to a given probe sequence are disclosed in Sambrook et al., (1989) Molecular Cloning: A Laboratory Manual. (2ed., Cold Spring Harbor Laboratory, Cold Spring Harbor, New York), and in Hames and Higgins (1985) Nucleic Acid Hybridization: A Practical Approach (Hames and Higgins Ed., IRL Press, Oxford). The same techniques may be used to isolate genomic DNAs.

A probe comprising at least 10 consecutive nucleotides from a GENSET cDNA or fragment thereof, is labeled using standard methods with a detectable label such as a radioisotope or a fluorescent molecule. The cDNAs or genomic DNAs in the library are transferred to a nitrocellulose or nylon filter and denatured. After blocking of nonspecific sites, the filter is incubated with the labeled probe for an amount of time sufficient to allow binding of the probe to cDNAs or genomic DNAs containing a sequence capable of hybridizing thereto.

By varying the stringency of the hybridization conditions used to identify cDNAs or genomic DNAs which hybridize to the detectable probe, cDNAs or genomic DNAs having different levels of identity to the probe can be identified and isolated as described below.

Stringent Conditions

"Stringent hybridization conditions" are defined as conditions in which only nucleic acids having a high level of identity to the probe are able to hybridize to said probe. These conditions may be calculated as follows:

For probes between 14 and 70 nucleotides in length the melting temperature (Tm) is calculated using the formula: Tm=81.5+16.6(log(Na+))+0.41(fraction G+C)−(600/N) where N is the length of the probe.

If the hybridization is carried out in a solution containing formamide, the melting temperature may be calculated using the equation: Tm=8 1.5+16.6(log(Na+))+0.41 (fraction G+C)−(0.63% formamide)−(600/N) where N is the length of the probe.

Prehybridization may be carried out in 6×SSC, 5× Denhardt's reagent, 0.5% SDS, 100 μg denatured fragmented salmon sperm DNA or 6×SSC, 5× Denhardt's reagent, 0.5% SDS, 100 μg denatured fragmented salmon sperm DNA, 50% formamide (see, e.g., Sambrook et al., 1986).

Hybridization is conducted according to standard methods. For probes over 200 nucleotides in length, the hybridization may be carried out at 15-25° C. below the Tm. For shorter probes, such as oligonucleotide probes, the hybridization may be conducted at 15-25° C. below the Tm. Preferably, for hybridizations in 6×SSC, the hybridization is conducted at approximately 68° C. Preferably, for hybridizations in 50% formamide containing solutions, the hybridization is conducted at approximately 42° C.

Following hybridization, the filter is washed in 2×SSC, 0.1% SDS at room temperature for 15 minutes. The filter is then washed with 0.1×SSC, 0.5% SDS at room temperature for 30 minutes to 1 hour. Thereafter, the solution is washed at the hybridization temperature in 0.1×SSC, 0.5% SDS. A final wash is conducted in 0.1×SSC at room temperature.

Nucleic acids which have hybridized to the probe are identified by autoradiography or other conventional techniques.

Low and Moderate Conditions

Changes in the stringency of hybridization and signal detection are primarily accomplished through the manipulation of formamide concentration (lower percentages of formamide result in lowered stringency); salt conditions, or temperature. The above procedure may thus be modified to identify nucleic acids having decreasing levels of identity to the probe sequence. For example, the hybridization temperature may be decreased in increments of 5° C. from 68° C. to 42° C. in a hybridization buffer having a sodium concentration of approximately 1 M. Following hybridization, the filter may be washed with 2×SSC, 0.5% SDS at the temperature of hybridization. These conditions are considered to be "moderate" conditions above 50° C. and "low" conditions below 50° C. Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of identity to the probe.

Following hybridization, the filter may be washed with 6×SSC, 0.5% SDS at 50° C. These conditions are considered to be "moderate" conditions above 25% formamide and "low" conditions below 25% formamide. cDNAs or genomic DNAs which have hybridized to the probe are identified by autoradiography or other conventional techniques.

Note that variations in the above conditions may be accomplished through the inclusion and/or substitution of alternate blocking reagents (e.g. Denhardt's reagent, BLOTTO, heparin, denatured salmon sperm DNA, etc.) used to suppress background in hybridization experiments.

PCR-Based Methods

In addition to the above described methods, other protocols are available to obtain homologous cDNAs using GENSET cDNA of the present invention or fragment thereof, as described below.

cDNAs may be prepared by obtaining mRNA from the tissue, cell, or organism of interest, e.g., using mRNA preparation procedures utilizing polyA selection procedures or other techniques known to those skilled in the art. A first primer capable of hybridizing to the polyA tail of the mRNA (e.g. an oligo(T) primer) is hybridized to the mRNA, and a reverse transcription reaction is performed to generate a first cDNA strand (see, e.g., Current Protocols in Molecular Biology, John Wiley and Sons, Inc. 1997 and Sambrook, et al., 1989). Typically, such oligo(T) primers comprise an additional sequence upstream of the poly(dT) stretch which facilitates subsequent manipulation of the DNA, such as a restriction site-containing sequence.

The first cDNA strand is then hybridized to a second primer containing at least 10 consecutive nucleotides of a polynucleotide of the invention. Often, the second primer used contains sequences located upstream of the translation initiation site. The second primer is extended to generate a second cDNA strand complementary to the first cDNA strand. Alternatively, RT-PCR may be performed as described above using primers from both ends of the cDNA to be obtained. See, e.g., *Current Protocols in Molecular Biology*, John Wiley & Sons, Inc. 1997 and Sambrook, et al., 1989.

Other Protocols

Alternatively, other procedures may be used for obtaining homologous cDNAs. In one approach, cDNAs are prepared from mRNA and cloned into double stranded phagemids using standard methods. The cDNA library in the double stranded phagemids is then rendered single stranded, a biotinylated oligonucleotide comprising the sequence of a fragment of a known GENSET cDNA, genomic DNA or fragment thereof is hybridized to the single stranded phagemids. Hybrids between the biotinylated oligonucleotide and phagemids are isolated and the corresponding phagemids are released from the beads and converted into double stranded DNA using a primer specific for the GENSET cDNA or fragment used to design the biotinylated oligonucleotide. Alternatively, protocols such as the Gene Trapper kit (Gibco BRL), may be used.

As a Chromosome Marker

GENSET polynucleotides may be mapped to their chromosomal locations using any methods or techniques known to those skilled in the art including radiation hybrid (RH) mapping (See, e.g., Benham et al. (1989) *Genomics* 4:509-517 and Cox et al., (1990) Science 250:245-250; and Schuler et al., (1996) Science 274:540-546), PCR-based mapping, and Fluorescence in situ hybridization (FISH) mapping, as described below.

Mapping of cDNAs to Human Chromosomes Using PCR Techniques

GENSET cDNAs and genomic DNAs may be assigned to human chromosomes using PCR based methodologies. In such approaches, oligonucleotide primer pairs are designed from the cDNA sequence, and PCR is used to screen a series of somatic cell hybrid cell lines containing defined sets of human chromosomes. Only those somatic cell hybrids with chromosomes containing the human gene corresponding to the GENSET cDNA or genomic DNA will yield an amplified fragment, and the single human chromosome present in all cell hybrids that give rise to an amplified fragment is the chromosome containing that GENSET cDNA or genomic DNA (see, e.g., Ledbetter et al., (1990) Genomics 6:475481).

Mapping of cDNAs to Chromosomes Using Fluorescence in situ Hybridization

Fluorescence in situ hybridization (FISH) allows the GENSET cDNA or genomic DNA to be mapped to a particular location on a given chromosome. The chromosomes to be used for fluorescence in situ hybridization techniques may be obtained from a variety of sources including cell cultures, tissues, or whole blood (see, e.g., Cherif et al., (1990) PNAS 87:6639-6643).

Use of cDNAs to Construct or Expand Chromosome Maps

Once the GENSET cDNAs or genomic DNAs have been assigned to particular chromosomes, they may be utilized to construct a high resolution map of the chromosomes on which they are located or to identify the chromosomes in a sample.

Chromosome mapping involves assigning a given unique sequence to a particular chromosome as described above. Once the unique sequence has been mapped to a given chromosome, it is ordered relative to other unique sequences located on the same chromosome (see, e.g., Nagaraja et al., (1997) Genome Res. March 1997;7(3):210-22).

Identification of Genes Associated with Hereditary Diseases or Drug Response

In another embodiment, any particular GENSET cDNA or genomic DNA may be used as a test probe to associate that GENSET cDNA or genomic DNA with a particular phenotypic characteristic.

In one embodiment, GENSET cDNAs or genomic DNAs are mapped to a particular location on a human chromosome using standard techniques and the location is searched in Mendelian Inheritance in Man (V. McKusick, Mendelian Inheritance in Man; available on line through Johns Hopkins University Welch Medical Library). Often, this search reveals the region of the human chromosome which contains the GENSET cDNA or genomic DNA to be a very gene rich region containing several known genes and several diseases or phenotypes for which genes have not been identified. The gene corresponding to this GENSET cDNA or genomic DNA thus becomes an immediate candidate for each of these genetic diseases.

Genomic DNA, mRNA or cDNA from patients with these diseases or phenotypes may then be screened, e.g. using PCR primers from the GENSET cDNA or genomic DNA, or by sequencing, for differences in the expression, size, or sequence of the GENSET cDNA or genomic DNAs in patients relative to in disease-free individuals. Any detected difference indicates a role for the GENSET gene in the disease or phenotype.

Uses of Polynucleotides in Recombinant Vectors

The present invention also relates to recombinant vectors including the isolated polynucleotides of the present invention, and to host cells recombinant for a polynucleotide of the invention, such as the above vectors, as well as to methods of making such vectors and host cells and for using them for production of GENSET polypeptides by recombinant techniques.

Recombinant Vectors

The term "vector" is used herein to designate either a circular or a linear DNA or RNA molecule, which is either double-stranded or single-stranded, and which comprises at least one polynucleotide of interest that is sought to be transferred in a cell host or in a unicellular or multicellular host organism.

In one preferred embodiment, the present invention provides expression vectors comprising either a regulatory polynucleotide or a coding nucleic acid of the invention, or both. Expression vectors may be used to express a GENSET polypeptide for purification, as well as for constructing transgenic animals and also for gene therapy (including in vivo and ex vivo methods). The encoded protein may be transiently expressed in a host organism or cell or stably expressed in the host organism or cell. The encoded protein may have any of the activities described herein. The encoded protein may be a protein which the host organism lacks or, alternatively, the encoded protein may augment the existing levels of the protein in the host organism.

Some of the elements which can be found in the vectors of the present invention are described in further detail in the following sections.

General Features of the Expression Vectors of the Invention

Typical expression vectors of the present invention comprise a transcriptional unit comprising an assembly of a genetic element or elements having a regulatory role in gene expression, for example a promoter and a structural or coding sequence which is transcribed into mRNA and eventually translated into a polypeptide, said structural or coding sequence being operably linked to the regulatory elements described above, and appropriate transcription initiation and termination sequences. Additional features may include enhancers, a leader sequence enabling extracellular secretion of translated protein by a host cell, origins of replication, selectable markers permitting transformation of the host cell, ribosome binding sites, polyadenylation signals, splice donor and acceptor sites, transcriptional termination sequences, and 5'-flanking non-transcribed sequences.

Regulatory Elements

The suitable promoter regions used in the expression vectors according to the present invention are chosen taking into account the cell host in which the heterologous gene has to be expressed.

A suitable promoter may be heterologous with respect to the nucleic acid for which it controls the expression or alternatively can be endogenous to the native polynucleotide containing the coding sequence to be expressed. Promoter regions can be selected from any desired gene using, for example, CAT (chloramphenicol transferase) vectors and more preferably pKK232-8 and pCM7 vectors. Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., (1983) Mol. Cell. Biol. 3:2156-2165; O'Reilly et al. (1992), "Baculovirus Expression Vectors: A Laboratory Manual", W. H. Freeman and Co., New York), the lambda PR promoter or also the trc promoter.

Eukaryotic promoters include CMV immediate early, HSV thymidine kinase, early and late SV40, LTRs from retrovirus, and mouse metallothionein-L. Selection of a convenient vector and promoter is well within the level of ordinary skill in the art.

Selectable Markers

Selectable markers confer an identifiable change to the cell permitting easy identification of cells containing the expression construct. The selectable marker genes for selection of transformed host cells are preferably dihydrofolate reductase or neomycin resistance for eukaryotic cell culture, TRP1 for *S. cerevisiae* or tetracycline, rifampicin or ampicillin resistance in *E. Coli*, or levan saccharase for mycobacteria, this latter marker being a negative selection marker.

Preferred Vectors

The present recombinant vectors may be any sort of vector, including, but not limited to, YACs (Yeast Artificial Chromosome), BACs (Bacterial Artificial Chromosome), phage, phagemids, cosmids, plasmids, and linear DNA.

Bacterial Vectors

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, for example, pKK223-3 (Pharmacia, Uppsala, Sweden), pGEM1(Promega Biotec, Madison, Wis., USA), pQE70, pQE60, pQE-9 (Qiagen), pbs, pD 10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

Bacteriophage Vectors

The P1 bacteriophage vector may contain large inserts ranging from about 80 to about 100 kb. The construction of P1 bacteriophage vectors is well known in the art (see, e.g., Sternberg (1992) Trends Genet. 8:1-16, Sternberg (1994) Mamm. Genome. 5:397404, Linton et al., (1993) J. Clin. Invest. 92:3029-3037, McCormick et al., (1994) Genet. Anal. Tech. Appl. 11:158-164.

Viral Vectors

Any viral vector can be used to carry out the herein-described methods. In one specific embodiment, the vector is derived from an adenovirus, e.g., human adenovirus type 2 or 5 (see, e.g., Feldman et al. (1996) Medecine/Sciences, 12:47-55, Ohno et al., (1994) Science 265:781-784, French patent application No. FR-93.05954).

Adeno-associated viral vectors are also preferred for the herein-described methods.

Particularly preferred retroviruses for the preparation or construction of retroviral in vitro or in vitro gene delivery vehicles of the present invention include retroviruses selected from the group consisting of Mink-Cell Focus Inducing Virus, Murine Sarcoma Virus, Reticuloendotheliosis virus and Rous Sarcoma virus. Particularly preferred Murine Leukemia Viruses include the 4070A and the 1504A viruses, Abelson (ATCC No VR-999), Friend (ATCC No VR-245), Gross (ATCC No VR-590), Rauscher (ATCC No VR-998) and Moloney Murine Leukemia Virus (ATCC No VR-190; PCT Application No WO 94/24298). Particularly preferred Rous Sarcoma Viruses include Bryan high titer (ATCC Nos VR-334, VR-657, VR-726, VR-659 and VR-728). Other preferred retroviral vectors are those described in Roth et al., (1996) Nature Medicine, 2(9):985-991, WO 93/25234, WO 94/06920, Roux et al. (1989), PNAS 86:9079-9083, Julan et al. (1992), J. Gen. Virol. 73:3251-3255, and Neda et al. (1991), J. Biol. Chem. 266:14143-14146.

BAC Vectors

The bacterial artificial chromosome (BAC) cloning system (Shizuya et al. (1992), PNAS 89:8794-8797), has been developed to stably maintain large fragments of genomic DNA (100-300 kb) in *E. coli*. A preferred BAC vector comprises a pBeloBAC11 vector that has been described by Kim U-J. et al. (1996), Genomics 34:213-218. BAC vectors, and the construction thereof, are well known in the art, and any suitable Baculovirus Another specific suitable host vector system is the pVL1392/1393 baculovirus transfer vector (Pharmingen) that is used to transfect the SF9 cell line (ATCC No. CRL 1711) which is derived from *Spodoptera frugiperda*. Other suitable vectors for the expression of the GENSET polypeptide of the present invention in a baculovirus expression system include those described by Chai et al. (1993), Biotechnol. Appl. Biochem. 18:259-273; Vlasak, et al. (1983), Eur. J. Biochem. 135:123-126, and Lenhard et al., (1996) Gene. 169:187-190.

Delivery of the Recombinant Vectors

To effect expression of the polynucleotides and polynucleotide constructs of the invention, the constructs must be delivered into a cell. This delivery may be accomplished in vitro, as in laboratory procedures for transforming cell lines, or in vivo or ex vivo, as in the treatment of certain diseases states.

One mechanism is viral infection, where the expression construct is encapsulated in an infectious viral particle (see, U.S. Pat. No. 5,968,821). The expression construct, preferably a recombinant viral vector as discussed herein, is used to transduce packaging cells, which then produce infectious viral particles including the expression construct. The particles are then used to transduce eukaryotic cells (see, Miller, A. D. (1990) Blood 76:271; U.S. Pat. No. 6,228,844).

Replication defective retrovirus comprising a GENSET polynucleotide may be packaged into virions, which can then be used to infect a target cell through the use of a helper virus by standard techniques (see, e.g., Current Protocols in Molecular Biology, Ausubel, F. M. et al. (eds.) Greene Publishing Associates, (1989)). Any of a large number of retroviruses can be used and are well known in the art (see, e.g., Eglitis, et al. (1985) Science 230:1395-1398; Danos and Mulligan (1988) PNAS 85:6460-6464; Wilson, et al. (1988) PNAS 85:3014-3018; Armnentano, et al. (1990) PNAS 87:6141-6145; Huber, et al. (1991) PNAS 88:8039-8043; Ferry, et al. (1991) PNAS 88:8377-8381; Chowdhury, et al. (1991) Science 254:1802-1805; van Beusechem, et al. (1992) PNAS 89:7640-7644; Kay, et al. (1992) Human Gene Therapy 3:641-647; Dai, et al. (1992) PNAS 89:10892-10895; Hwu, et al. (1993) J. Immunol. 150:4104-4115).

Another viral gene delivery system useful in the present invention utilizes adenovirus-derived vectors. The genome of an adenovirus can be manipulated such that it encodes a gene product of interest, but is inactivated in terms of its ability to replicate in a normal lytic viral life cycle (see, e.g., Berkner, et al. (1988) BioTechniques 6:616; Rosenfeld, et al. (1991) Science 252:431-434; and Rosenfeld, et al. (1992) Cell 68:143-155). Any standard adenoviral vector may be used in the present invention (see, e.g., Jones, et al. (1979) Cell 16:683; Graham, et al. in Methods in Molecular Biology, E. J. Murray, Ed. (Humana, Clifton, N.J., 1991) vol. 7. pp.109-127).

Yet another viral vector system useful for delivery of polynucleotides is the adeno-associated virus (AAV). Adeno-associated virus is a naturally occurring defective virus that requires another virus, such as an adenovirus or a herpes virus, as a helper virus for efficient replication and a productive life cycle (see Muzyczka, et al., Curr. Top. Micro. Immunol. (1992) 158:97-129). Any standard AAV vector may be used in the present invention (see, e.g., Flotte et al., (1992) Am. J. Respir. Cell Mol. Biol. 7:349-356; Am. J. Respir. Cell. Mol. Biol. 7:349-356; Samulski et al. (1989) J. Virol. 63:3822-3828; and McLaughlin et al. (1989) J. Virol. 62:1963-1973, Tratschin, et al. (1985) Mol. Cell. Biol. 5:3251-3260, Hermonat, et al. (1984) PNAS 81:6466-6470; Tratschin, et al. (1985) Mol. Cell. Biol. 4:2072-2081; Wondisford, et al. (1988) Mol. Endocrinol. 2:32-39; Tratschin, et al. (1984) J. Virol. 51:611-619; and Flotte, et al. (1993) J. Biol. Chem. 268:3781-3790).

Other viral vector systems that may have application in gene therapy have been derived from herpes virus, vaccinia virus, and several RNA viruses. In particular, herpes virus vectors may provide a unique strategy for persistence of inserted gene expression in cells of the central nervous system and ocular tissue (Pepose, et al. (1994) Invest Ophthalmol Vis Sci 35:2662-2666).

Several non-viral methods for the transfer of polynucleotides into cells, e.g., mammalian cells, in vivo, in vitro, or ex vivo, are also contemplated by the present invention, and include, without being limited to, calcium phosphate precipitation (Graham et al., (1973) Virol. 52:456-457; Chen et al. (1987) Mol. Cell. Biol. 7:2745-2752); DEAE-dextran (Gopal (1985) Mol. Cell. Biol., 5:1188-1190); electroporation (Tur-Kaspa et al. (1986) Mol. Cell. Biol. 6:716-718; Potter et al., (1984) PNAS 81(22):7161-7165); direct microinjection (Harland et al., (1985) J. Cell. Biol. 101:1094-1095); DNA-loaded liposomes (Nicolau et al., (1982) Biochim. Biophys. Acta. 721:185-190; Fraley et al., (1979) PNAS 76:3348-3352); and receptor-mediated transfection. (Wu and Wu (1987), J. Biol. Chem. 262:4429-4432; and Wu and Wu (1988), Biochemistry 27:887-892).

One specific embodiment for a method for delivering a protein or peptide to the interior of a cell of a vertebrate in vivo or in vitro comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect (see, e.g., WO 90/11092, WO 95/11307, Tascon et al. (1996), Nature Medicine 2(8):888-892, and Huygen et al., (1996) Nature Medicine 2(8):893-898). Naked polynucleotides of the invention may also be introduced into cells using particle bombardment (biolistic), e.g., DNA-coated microprojectiles accelerated to a high velocity allowing them to pierce cell membranes and enter cells without killing them (Klein et al., (1987) Nature 327:70-73).

Liposomal preparations for use in the present invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Feigner, et al., PNAS (1987) 84:7413-7416); mRNA (Malone, et al., PNAS (1989) 86:6077-6081); and purified transcription factors (Debs et al., J. Biol. Chem. (1990) 265: 10189-10192), in functional form. Any of a large number of cationic liposomes can be used. N[1-2,3-dioleyloxy)propyll-N,N,N-triethylammonium (DOTMA) liposomes are particularly useful and are available under the trademark Lipofectin, from GIBCO BRL, Grand Island, N.Y. Other commercially available liposomes include transfectace (DDAB/DOPE) and DOTAP/DOPE (Boehringer).

Similarly, anionic and neutral liposomes are readily available, such as from AvantiPolar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolarnine (DOPE), among others. These materials can also be mixed with the DOTMA and DOTAP starting materials in appropriate ratios. Methods for making liposomes using these materials are well known in the art, as are various combinations of liposomes.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art (Straubinger, et al., Methods of Immunology (1983), 101:512-527; U.S. Pat. No. 5,965,421). Generally, the ratio of DNA to liposomes will be from about 10:1 to about 1:10 (with about 5:1 to about 1:5 or about 3:1 to about 1:3 being preferred). Additionally, liposomes may be targeted to specific cell types by embedding a targeting moiety such as a member of a receptor-receptor ligand pair into the lipid envelope of the vesicle (see, e.g., U.S. Pat. Nos. 6,177,433, 6,110,490, and P.C.T No. WO9704748).

The amount of vector to be injected to the desired host organism varies according to the site of injection. As an indicative dose, it will be injected between 0.1 and 100 μg of the vector in an animal body, preferably a mammal body, for example a mouse body.

Secretion Vectors

Some of the GENSET cDNAs or genomic DNAs of the invention may also be used to construct secretion vectors capable of directing the secretion of the proteins encoded by genes inserted in the vectors. Such secretion vectors may facilitate the purification or enrichment of the proteins encoded by genes inserted therein by reducing the number of background proteins from which the desired protein must be purified or enriched. Exemplary secretion vectors are described below.

The secretion vectors of the present invention comprise a promoter capable of directing gene expression in the host cell, tissue, or organism of interest, a cloning site for inserting a coding sequence, and a signal sequence from a polynucleotide of the invention is operably linked to the promoter such that the mRNA transcribed from the promoter will direct the translation of the signal peptide. The host cell, tissue, or organism may be any cell, tissue, or organism which recognizes the signal peptide encoded by the signal sequence in the GENSET cDNA or genomic DNA. Suitable hosts include mammalian cells, tissues or organisms, avian cells, tissues, or organisms, insect cells, tissues or organisms, or yeast. The signal sequences may also be inserted into vectors designed for gene therapy.

The secretion vector may be DNA or RNA and may integrate into the chromosome of the host, be stably maintained as an extrachromosomal replicon in the host, be an artificial chromosome, or be transiently present in the host. Preferably, the secretion vector is maintained in multiple copies in each host cell.

Cell Hosts

Another object of the invention comprises a host cell that has been transformed or transfected with one of the polynucleotides described herein, and in particular a polynucleotide either comprising a GENSET polypeptide-encoding polynucleotide regulatory sequence or the polynucleotide coding for a GENSET polypeptide. Also included are host cells that are transformed (prokaryotic cells), transfected (eukaryotic cells), or transduced with a recombinant vector such as one of those described above. Preferred host cells used as recipients for the expression vectors of the invention include prokaryotic host cells such as *Escherichia coli* strains (I.E.DH5-α strain), *Bacillus subtilis, Salmonella typhimurium*, and strains from species like *Pseudomonas, Streptomyces* and *Staphylococcus*, as well as eukaryotic host cells such as HeLa cells, Cv 1 cells, COS cells, Sf-9 cells, C127 cells, 3T3, CHO, human kidney 293, and BHK cells.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides (see, e.g., U.S. Pat. No. 5,641,670; WO 96/29411; WO 94/12650; Koller, et al., (1989); and Zijlstra, et al. (1989); U.S. Pat. Nos. 6,054,288; 6,048,729; 6,048,724; 6,048,524; 5,994,127; 5,968,502; 5,965,125; 5,869,239; 5,817,789; 5,783,385; 5,733,761; 5,641,670; 5,580,734; and in WO96/29411, WO 94/12650; and Koller, et al., (1994).

GENSET gene expression in mammalian cells, preferably human cells, may be rendered defective, or alternatively may be altered by replacing endogenous GENSET polypeptide-encoding genes in the genome of an animal cell by a GENSET polypeptide-encoding polynucleotide according to the invention. These genetic alterations may be generated by homologous recombination using previously described specific polynucleotide constructs.

Mammal zygotes, such as murine zygotes may be used as cell hosts. For example, murine zygotes may undergo microinjection with a purified DNA molecule of interest. In addition, any one of the polynucleotides of the invention may be introduced in an embryonic stem (ES) cell line, preferably a mouse ES cell line. ES cells, and methods of their isolation and maintenance, are well known in the art, and are described, inter alia, in Abbondanzo et al., (1993), Meth. Enzymol., Academic Press, New York, pp 803-823, Robertson, (1987), Embryo-derived stem cell lines; In: E. J. Robertson Ed. Teratocarcinomas and embryonic stem cells: a practical approach. IRL Press, Oxford, pp. 71, and Pease and William, (1990), Exp. Cell. Res. 190: 209-211.

Transgenic Animals

The terms "transgenic animals" or "host animals" are used herein to designate animals that have their genome genetically and artificially manipulated so as to include one of the nucleic acids according to the invention. The cells affected may be somatic, germ cells, or both. Preferred animals are non-human mammals and include those belonging to a genus selected from *Mus* (e.g. mice), *Rattus* (e.g. rats) and *Oryctogalus* (e.g. rabbits). In one embodiment, the invention encompasses non-human host mammals and animals comprising a recombinant vector of the invention or a GENSET gene disrupted by homologous recombination with a knock out vector. Thus, the present invention also concerns a transgenic animal containing a nucleic acid, a recombinant expression vector, or a recombinant host cell according to the invention. A further object of the invention comprises recombinant host cells obtained from a transgenic animal described herein.

Such transgenic animals may be good experimental models in order to study the diverse pathologies related to the increase or decrease of the expression of a given GENSET gene. The transgenic animals may also be used to express a desired polypeptide of interest under the control of the regulatory polynucleotides of the GENSET gene, leading to high yields in the synthesis of this protein of interest, or to tissue-specific expression of the gene.

In one embodiment, transgenic animals of the present invention are produced by inserting a recombinant polynucleotide of the invention into an embryonic or ES stem cell line (see, e.g., Thomas, et al. (1987) Cell 51:503-512; Mansour et al., (1988) Nature 336:348-352), and isolating, cloning and injecting positive cells into blastocysts, which are then inserted into a female host animal and allowed to grow to term. For more details regarding the production of transgenic animals, and specifically transgenic mice, see U.S. Pat. Nos. 4,873,191; 5,464,764; 5,789,215, Bradley (1987; In: E. J. Robertson (Ed.), Teratocarcinomas and embryonic stem cells: A practical approach. IRL Press, Oxford, pp.113, Wood, et al. (1993), PNAS, 90: 4582-4585, Nagy et al., (1993), PNAS 90: 8424-8428.

In another embodiment, transgenic animals are produced by microinjecting polynucleotides into a fertilized oocyte. Methods for culturing fertilized oocytes to the pre-implantation stage are described, e.g., by Gordon, et al. ((1984) Methods in Enzymology, 101, 414); Hogan, et al. ((1986) in Manipulating the mouse embryo, A Laboratory Manual. Cold Spring Harbor Laboratory Press, Cold Spring Harbor, N.Y (for the mouse embryo)); Hammer, et al. ((1985) Nature, 315, 680 (for rabbit and porcine embryos)); Gandolfi, et al. ((1987) J. Reprod. Fert. 81, 23-28); Rexroad, et al. ((1988) J. Anim. Sci. 66, 947-953) (for ovine embryos)); and Eyestone, et al. ((1989) J. Reprod. Fert. 85, 715-720); Camous et al. ((1984) J. Reprod. Fert. 72, 779-785); and Heyman, et al. ((1987) Theriogenology 27, 5968 (for bovine embryos)). Pre-implantation embryos are then transferred to an appropriate female by standard methods to permit the birth of a transgenic or chimeric animal, depending upon the stage of development when the transgene is introduced.

In a preferred embodiment of the present invention, transgenic mammals are generated that secrete recombinant GENSET polypeptides in their milk. Preferably, expression in the mammary gland is accomplished by operably linking the polynucleotide encoding the GENSET polypeptide to a mammary gland specific promoter (e.g., from a casein or lactoglobulin gene) and, optionally, other regulatory elements. Promoter and other regulatory sequences, vectors, and other relevant teachings are provided, e.g., by Clark (1998) J Mammary Gland Biol Neoplasia 3:337-50; Jost, et al. (1999) Nat. Biotechnol 17:16041; U.S. Pat. Nos. 5,994,616; 6,140,552; 6,013,857; Sohn, et al. (1999) DNA Cell Biol. 18:845-52; Kim, et al. (1999) J. Biochem. (Japan) 126:320-5; Soulier, et al. (1999) Euro. J. Biochem. 260:533-9; Zhang, et al. (1997) Chin. J. Biotech. 13:271-6; Rijnkels, et al. (1998) Transgen. Res. 7:5-14; Korhonen, et al. (1997) Euro. J. Biochem. 245:482-9; Uusi-Oukari, et al. (1997) Transgen. Res. 6:75-84; Hitchin, et al. (1996) Prot. Expr. Purif. 7:247-52; Platenburg, et al. (1994) Transgen. Res. 3:99-108; Heng-Cherl, et al. (1993) Animal Biotech. 4:89-107; and Christa, et al. (2000) Euro. J. Biochem. 267:1665-71.

In another embodiment, the polypeptides of the invention can be produced in milk by introducing polynucleotides encoding the polypeptides into somatic cells of the mammary gland in vivo, e.g. mammary secreting epithelial cells. For example, plasmid DNA can be infused through the nipple canal, e.g. in association with DEAE-dextran (see, e.g., Hens, et al. (2000) Biochim. Biophys. Acta 1523:161-171), in association with a ligand that can lead to receptor-mediated endocytosis of the construct (see, e.g., Sobolev, et al. (1998) 273:7928-33), or in a viral vector such as a retroviral vector, e.g. the Gibbon ape leukemia virus (see, e.g., Archer, et al. (1994) PNAS 91:6840-6844). In any of these embodiments, the polynucleotide may be operably linked to a mammary gland specific promoter, as described above, or, alternatively, any strongly expressing promoter such as CMV or MoMLV LTR.

The polynucleotides used in such embodiments can either encode a full-length GENSET protein or a GENSET fragment. Typically, the encoded polypeptide will include a signal sequence to ensure the secretion of the protein into the milk.

Uses of Polypeptides of the Invention

Protein of SEQ ID NO:2 (Internal Designation Clone 243525_116-119-1-0-G6-F)

The cDNA of Clone 243525_116-119-1-0-G6-F (SEQ ID NO:1) encodes protein PCNAlt of SEQ ID NO:2, comprising the amino acid sequence:

MPSGEFARICRDLSHIGDAVVISCAKDGVKFSASGELGNGNIKLSQTSNVDKEEEAVTIEM NEPVQLTFALRYLNFFTKATPLSSTVTLSMSADVPLVVEYKIADMGHLKYYLAP KIEDEEG S. Accordingly, it will be appreciated that all characteristics and uses of polypeptides of SEQ ID NO:2 described throughout the present application also pertain to the polypeptides encoded by the human cDNA included in Clone 243525_116-119-1-0-G6-F. In addition, it will be appreciated that all characteristics and uses of the polynucleotides of SEQ ID NO:1 described throughout the present application also pertain to the nucleic acids comprising the human cDNA in Clone 243525_116-119-1-0-G6-F. A preferred embodiment of the invention is directed toward the compositions of SEQ ID NO:1, SEQ ID NO:2, and Clone 243525_116-119-1-0-G6-F. Also preferred are polypeptide fragments having a biological activity as described herein and the polynucleotides encoding the fragments.

The cDNA of SEQ ID NO:1 is a splice variant of the human proliferating cell nuclear antigen (PCNA), encoding a 123 amino-acid protein of SEQ ID NO:2 named PCNAlt. The protein of SEQ ID:2 comprises the PCNA C-terminal domain.

Mammalian PCNA is so named because of its initial discovery as a cell cycle-dependent antigen (Miyachi et al, 1978). PCNA plays a critical role in several biological processes that appear disparate but have in common a role in DNA metabolism. PCNAlt is a highly conserved essential component of the DNA replication machinery. The subcellular distribution of PCNAlt changes through the cell cycle, localizing to sites of DNA replication in S-phase of cell cycle. PCNA]t is a nuclear protein required for leading strand DNA synthesis by DNA polymerase delta, which is part of the essential pathway for DNA replication. Consistent with its essential role in DNA replication, the expression of PCNAlt is very low in quiescent and senescent cells but increases after stimulation by serum or by various growth factors. In addition, PCNAlt and polymerase delta also play essential roles in the repair of damaged DNA. PCNAlt levels are elevated in response to DNA damage in vivo, the protein relocalizes to sites of DNA repair following damage. A direct role of PCNAlt in nucleotide excision repair has been demonstrated. Co-ordination of these two roles of PCNAlt is thus essential for the maintenance of genetic integrity. In addition, PCNAlt can interact with a variety of cellular proteins involved in cell cycle regulation and check point control, such as cyclins and cyclin-dependent kinases.

In one embodiment, the protein of the invention or part thereof is used to quantify in vitro the amount of cell proliferation in a biological sample. PCNAlt is thus used in assays and diagnostic kits for the quantification of cell proliferation in tissue samples such as a tissue section or in cell cultures. The method comprises the steps of contacting a biological sample with a detectably labeled compound capable of selectively binding PCNAlt polypeptides or polynucleotides. For example, a polyclonal or monoclonal antibody, a PCNAlt-binding fragment thereof, or a nucleic acid probe may be used. Preferably, antibody used in this embodiment is directed against nonlinear epitopes of PCNAlt. Preferably, the antibody used in this embodiment specifically binds to PCNAlt polypeptides and not to PCNA polypeptides. Detection can be carried out directly or indirectly with known immunohistological or immunofluorescence techniques. Reagents contained in a kit according to the invention can be directly labeled with generally known molecules, including, but not limited to, enzymes such as alkaline phosphatase and peroxidase and fluorescent dyes such as FITC, rhodamine, and Texas-Red. However, labeling can also occur indirectly by using primary antibodies labeled with molecules such as biotin or digoxigenin which are then detected with a secondary reagent.

In another embodiment, the current invention provides a method of effectively blocking proliferation or inhibiting the growth of a cell in vivo or in vitro. Preferably, the present invention can be used to stop unrestrained cell proliferation and to eliminate as many tumor cells as possible. More preferably, it is used to inhibit cell proliferation independent of Gadd45 and p21 control. The method will be performed by administering an antisense oligonucleotide directed against PCNAlt into the cell. Such a method comprises the step of introducing a polynucleotide construct comprising an antisense oligonucleotide directed against PCNAlt to a cell. One strategy for delivering antisense oligonucleotides to targeted cells involves encapsulation or incorporation of the therapeutic bioactive molecules in liposomes, such as cationic liposomes. These liposomes are known to provide a shield against nucleotide degradation in vivo and can be targeted to specific areas of the body at which point they slowly release their contents. Alternatively, a polynucleotide construct comprising plasmid DNA operably linked to the antisense oligonucleotide could be used. The nucleotide sequences are administered in vivo in a suitable buffer or carrier solution known to those of skill in the art.

Any compound that inhibits or significantly decreases the expression of PCNAlt polypeptides can also be used to inhibit replication within one or more cells of the sample. Such compounds can be identified by screening for test substances that decrease PCNAlt expression This method of screening comprises the steps of contacting a cell with a test substance and comparing PCNAlt expression in the cell after exposure to the test substance to that of an unexposed control cell. In addition, any compound that inhibits or significantly decreases the activity of PCNAlt polypeptides can also be used to inhibit replication within one or more cells of the sample. Such compounds can be identified by screening for test substances that decrease PCNAlt activity comprising the steps of contacting a cell with a test substance and comparing PCNAlt activity on the cell replication after exposure to the test substance to that of an unexposed control cell. For example, inhibitor compounds can represent molecules which disrupt the interaction between PCNAlt and their cellular targets involved in cell progression.

Alternatively, in another embodiment, the present invention provides a method of effectively stimulating DNA replication in cells. The level or activity of PCNAlt can be increased in cells to stimulate DNA replication, thereby inducing cell proliferation. Preferably, PCNAlt is used to increase cell proliferation independent of Gadd45 and p21 control. PCNAlt levels may be increased by introducing PCNAlt polynucleotides or polypeptides into a cell in an amount sufficient to specifically stimulate DNA replication of one or more cells within the sample. Preferably, such methods can be performed in vitro to increase proliferation of cells in culture. For example, it can be used to maintain cell proliferation under serum starvation conditions that is required for some in vitro experiments. On the other hand, an increased level of PCNAlt is also used to decrease cell proliferation specifically dependent on Gadd45 or p21 control. Whatever the case, the level of PCNAlt can be increased in cells in any of a number of ways. For instance, purified PCNAlt protein may be introduced to the cells by microinjection or by liposome or micelle-mediated transport. Such liposomal or micellar microcapsule may optionally be combined with a cell type-specific target, such as an antibody or receptor ligand. Alternatively, PCNAlt polynucleotides may be introduced to a cell by methods common to the art such as transfection, electroporation, or viral transduction. The vectors mentioned above may also be used to introduce PCNAlt polynucleotides to a cell.

The present invention also provides animal models generated by modulating the expression or activity of the present protein in one or more tissues of the animal. Preferably, PCNAlt expression can be selectively activated or inactivated in a particular cell type using a conditional expression system. These animals can be generated with any inducible method of targeting inactivation of PCNAlt. Such animals are useful for a number of purposes, because they represent an in vivo assay method for testing the efficacy of PCNAlt inactivation as a candidate strategy potentially useful for the treatment of various pathophysiological aspects of diseases specifically related to an excess of cell proliferation including the cancers listed herein. Such models are also extremely useful in the assessment of combinatory therapies, i.e. PCNAlt inactivation in addition to one or other compounds of interest. Malignancy conditions to be tested can be induced by any method well known in the art such as chemicals, expression of various oncogenes by transgenesis for example, genotoxic agents (UV, gamma irradiation), etc.

In another embodiment, the current invention is used to diagnose diseases or disorders associated with unrestrained cell proliferation and in particular in various cancers. Aberrant PCNAlt expression or localization is a significant prognostic indicator, and is preferably used as a prognostic factor for the clinical course of various cancers. More preferably, it can be measured in case of tumors linked to p53 inactivation. In one such embodiment, the present invention can also provide indicators that are suitable to estimate the efficacy or responsiveness to a form of chemotherapy. The method of detection may preferably occur directly on a section of the sample. The sample material can be present for example as a biopsy, a tissue homogenate, a fine-needle aspirate or tumor resection or can be performed by flow cytometry. The method comprises the steps of contacting a tissue sample obtained from an individual suspected of suffering from the disease or condition or at risk of developing the disease or condition, with a detectably labeled compound capable of selectively binding PCNAlt polypeptides or nucleic acids. For example, a polyclonal or monoclonal antibody or PCNAlt-binding fragment thereof or a nucleic acid probe may be used. Preferably, the antibodies used in one such embodiment are directed against nonlinear epitopes of PCNAlt. Preferably, the antibodies specifically bind to PCNAlt polypeptides and not to PCNA polypeptides. Detection can be carried out directly or indirectly with known immunohistological and immunofluorescent techniques. Reagents contained in a kit according to the invention can be directly labeled with generally known molecules, including, but not limited to enzymes such as alkaline phosphatase and peroxidase and fluorescent dyes such as FITC, rhodamine, and Texas-Red. However, labeling can also occur indirectly by using secondary antibodies labeled with molecules such as biotin, digoxigenin or the like and are then detected with a secondary reagent. PCNAlt immunoreactivity can be regarded as indicative of neoplasia but preferably with at least one other marker. The second marker index to be detected is selected from the group comprising a marker for transformed cells, protein being overexpressed in a neoplastic cell, or a protein expressed in a form normally not present in the cell. For example, the procedure can be adapted for double immunostaining of PCNAlt together with alpha-actin, bromodeoxyuridine, keratin, type IV collagen and vimentin. In addition, the protein representing the second marker may preferably represent a tissue specific marker. Thus, a kit may contain an antibody directed against PCNAlt and antibodies against one or more of the markers mentioned above. The condition of an individual can be monitored continuously and the quantified amount of this particular protein measured in the pathological sample can be compared with the amount quantified in a biological sample of a normal individual or with previous samples from the same individual. The determination of all indices mentioned above can occur at the same time, sequentially or after one another.

In one other embodiment, the present invention is useful in diagnosing patients with an excess amount of PCNAlt and monitor PCNAlt expression in such conditions. Preferably, the present invention provides a method to diagnose and the monitor diseases such as systemic lupus erythematosis disease and malignant lymphomas. The method comprises the steps of contacting a tissue sample obtained from an individual suspected of suffering from the disease or condition or at risk of developing such a disease or condition, with a detectably labeled compound capable of selectively binding PCNAlt polypeptides or nucleic acids. For example, a polyclonal or monoclonal antibody or a PCNAlt-binding fragment thereof or a nucleic acid probe may be used. Preferably, the antibodies used in one such embodiment are directed against nonlinear epitopes of PCNAlt. Preferably, the antibodies specifically bind to PCNAlt polypeptides and not to PCNA polypeptides. Thus, the amount of PCNAlt can be monitored and quantified in a subject in the pathological sample and be compared with the amount quantified in a biological sample of a normal individual.

A further embodiment of the present invention is to provide novel methods and compositions useful for the treatment or prevention of diseases and conditions related to excessive cell proliferation and preferably with malignancy conditions. Such methods comprise the administration of a therapeutically-effective amount of antisense PCNAlt oligonucleotides to mammals suffering from the disease or condition, where "effective amount" is meant a concentration of antisense oligonucleotides capable of significantly reducing cell proliferation. The compositions of the invention are preferably delivered to an individual in a pharmaceutically acceptable carrier, such as a saline solution or other physiological buffer suitable for administration to a patient. The particular amount of the compositions of the invention that will be administered to the mammal for any particular condition will depend on the clinical condition of the patient, and other factors such as the weight, age, and route of delivery. Such compositions can be administered by any suitable route. For treatment purposes, the composition can also be incorporate into liposomes, such as cationic liposomes to deliver the therapeutic bioactive molecules to targeted cells. These compositions can comprise antisense oligonucleotides directed against PCNAlt, and, optionally, one or more other compounds of interest. This co-administration may be by simultaneous administration or by separate or sequential administrations. All of these additional components may be either obtained from natural sources or produced by recombinant genetic engineering techniques and/or chemical modification.

Protein of SEQ ID NO:4 (Internal Destination Clone 643144_181-17-2-0-A12-F)

The cDNA of Clone 643144_181-17-2-0-A12-F (SEQ ID NO:3) encodes Lectir of SEQ ID NO:4, comprising the amino acid sequence:

```
MQDEDGYITLNIKTRKPALVSVGSASSSWWRVMALILLILCVGMVVGLVALGIWSVMQR
NYLQDENENRTGTLQQLAKRFCQYVVKQSELKGTFKGHKCSPCDTNWRYYGDSCYGFF
RHNLTWEESKQYCTDMNATLLKIDNRNIVEYIKARTHLIRWVGLSRQKSNEVWKWEDGS
VISENMFEFLEDGKGNMNCAYFHNGKMHPTFCENKHYLMCERKAGMTKVDQLP.
```

Accordingly, it will be appreciated that all characteristics and uses of the polypeptides of SEQ ID NO:4 described throughout the present application also pertain to the polypeptides encoded by the human cDNA included in Clone 643144_181-17-2-0-A12-F. In addition, it will be appreciated that all characteristics and uses of the polynucleotides of SEQ ID NO:3 described throughout the present application also pertain to the nucleic acids comprising the human cDNA in Clone 643144_181-17-2-0-A12-F. A preferred embodiment of the invention is directed toward the compositions of SEQ ID NO:4, SEQ ID NO:3, and Clone 643144_181-17-2-0-A12-F.

Lectir is a polymorphic variant of the C-type Lectin-like receptor 2 (GenBank accession number AAF36777). Lectir possesses an anchor signal, a transmembrane domain (VMALILLILCVGMVVGLVALGIW) (SEQ ID NO:53), a lectin C-type domain (QYCTDMNATLLKIDNRNIVEY-IKARTHLIRWVGLSRQKSNEVWKWEDGS-VJSENMFFFL EDGKGNMNCAYFHNGKMHPTFCEN-KHYLMCE) (SEQ ID NO:54) and an extracellular link domain (RHNLTWEESKQYCTDMNATL) (SEQ ID NO:55V Lectir is homologous to the oxidized LDL receptor (LOX-1). Lectir is expressed in myeloid cells such as monocytes, dendritic cells and granulocytes.

Lectir is involved in antigen capture and phagocytosis of apoptotic bodies. Phagocytosis of aged and apoptotic cells is an essential process to protect normal healthy cells from the harmful contents and debris of dying cells. Apoptosis is accompanied by the clustering of intracellular autoantigens, which are selectively-cleaved and phosphorylated, and by the exposure of anionic phospholipids such as phosphatidylserine. Modified lipoproteins (e.g., oxidized lipoproteins) play a crucial role in apoptosis signaling. Lectins and C-type lectin like receptors are expressed both by cells undergoing apoptosis and by phagocytic cells. Lectir is a phagocytic receptor that binds to phospholipids, captures apoptotic bodies and directs them from the extracellular space to a specialized processing compartment of myeloid cells.

An embodiment of the invention is directed to compositions comprising an antibody directed against a Lectir polypeptide or against a Lectir polypeptide fragment. Preferably, the antibody specifically binds to the Lectir polypeptide and not to the C-type Lectin-like receptor-2 polypeptide. An additional preferred embodiment of the invention is a method of binding Leclir polypeptides with a Leclir-specific antibody or Leclir-binding fragment thereof. This method comprises the step of contacting a Leclir polypeptide with a Leclir-binding antibody or Leclir-binding fragment thereof under conditions that allow binding. This method may be applied to detection and purification of Leclir, as well as targeting Leclir-expressing cells. These aspects are discussed in detail herein.

A preferred aspect of the invention is a host cell recombinant for polynucleotides encoding a Leclir polypeptide or a biologically active fragment thereof. An additional preferred aspect is a host cell recombinant for polynucleotides capable of directing Leclir expression. Preferably, the polynucleotides capable of directing Leclir expression are located in the 5' regulatory region of the Leclir gene. Further preferably, these polynucleotides are located within 500 base pairs of the Leclir coding region. These polynucleotides preferably comprise a promoter sequence.

An embodiment of the present invention includes methods of purifying Lectir polypeptides. This method comprises the steps of: i) obtaining a cell capable of expressing a Lectir polypeptide; ii) growing said cell under conditions suitable to produce said polypeptide; and iii) purifying said polypeptide. An example of this method comprises the steps of: i) transfecting a mammalian host cell with a recombinant expression vector comprising a polynucleotide of the present invention, and ii) purifying the produced protein. Leclir purification of the protein can be done following any technique well-known to those skilled in the art. Preferably, a Leclir-binding antibody or an antigen binding fragment thereof may be bound to a chromatographic support to form an affinity chromatography column. Preferably, the antibodies are those described above.

An embodiment of the present invention relates to methods of using the polypeptides and the polynucleotides of the present invention to enhance phagocytosis of accumulating apoptotic cells. Any compositions and methods containing, e.g., Lectir polypeptide or part thereof, a polynucleotide encoding the protein, or a compound that increases the expression or activity of Lectir can be used.

In a preferred embodiment, a Lectir polypeptide is used in a method to enhance phagocytosis of apoptotic cells. This method comprises the step of introducing Lectir polypeptide to a cell. Preferred cells are phagocytic cells, such as dendritic cells and macrophages. Lectir polypeptides may be introduced by introducing a polynucleotide construct comprising polynucleotides that encode Lectir polypeptides or a biologically active fragment thereof to a cell. This method may be directed to the removal of apoptotic cells from a sample of cells to be cultured. Additionally, this method may be applied to reduce the severity of diseases that result from cellular accumulation such as rheumatoid arthritis, systemic lupus erythematosis, psoriatic arthritis, asthma, bronchitis, sarcoidosis, and pulmonary fibrosis. This method may also be applied when treating a patient with apoptosis-inducing drugs such as, e.g., cisplatin and carboplatin, for reducing cellular accumulation of apoptotic cells. Notably, apoptosis-inducing drugs are widely used for treating tumor proliferation.

In another embodiment, the methods of the present invention relate to the administration of a recombinant expression vector comprising one of the polynucleotides of the invention to a patient suffering from a disease associated with accumulation of apoptotic cells. Preferred expression vectors include viral vectors, especially adenoviral and lentiviral vectors.

In still another embodiment, genetic modification of a cell with a vector comprising one of the polynucleotides of the invention may be accomplished using one or more techniques well known in the gene therapy field. For example, one of the methods described in Mulligan (Mulligan, Science, 260:926-32 (1993)), which disclosure is hereby incorporated by reference in its entirety, can be used.

In still another embodiment, the compositions of the present invention comprise a substance that increases Lectir expression. Additionally, the methods of the present invention relate to methods of screening test substances that increase Lectir expression. These methods comprise the steps of: i) contacting a cell with a test substance; and ii) comparing Lectir expression in the cell after exposure to the test substance to that of an unexposed control cell. Preferably, the test substance modifies the expression of Lectir in monocytes, dendritic cells and/or granulocytes while not in other cell types.

Another embodiment of the present invention is directed to compositions comprising substances that increase Lectir phagocytic activity. Additionally, the methods of the present invention relate to methods of screening test substances that increase Lectir expression. These methods comprise the steps of: i) contacting a cell with a test substance; and ii) comparing Lectir activity in the cell after exposure to the test substance to that of an unexposed control cell. Preferably, the test substance modifies Lectir activity in monocytes, dendritic cells and/or granulocytes while not in other cell types. Several methods, including but not limited to the method described by Simpson et al. (J Immunol Methods 29:221-6 (1979)), which disclosure is hereby incorporated by reference in its entirety, are available for quantifying phagocytic activity. Such a method can also be used for verifying in vitro effectiveness of compositions and methods of the present invention to enhance phagocytosis.

In a preferred embodiment, Lectir polypeptides or a substance that increases Lectir expression or Lectir activity can be processed in accordance with conventional methods of pharmacy to produce medicinal agents for administration to patients. Thus, the pharmaceutical composition comprising Lectir or part thereof or a substance that increases Lectir expression may be made up in a solid form (e.g. granules for oral administration, powders for inhalation) or in a liquid form (e.g. solutions for oral administration or for injection). Effective doses of the compositions of the present invention for treating a patient suffering from disorders associated with accumulation of apoptotic cells can be determined according to the relevant techniques.

Another embodiment of the present invention relates to methods of using an antibody directed against Lectir polypeptides for purifying myeloid cells. Preferred antibodies are those described above. Such a method for myeloid cells comprises the steps of: i) labeling an Lectir-specific antibody with a molecule that can be used to provide a detectable signal, ii) running a body fluid through a sorting apparatus (e.g., a fluorescence-activated cell sorter or a magnetic activated cell-sorting apparatus, containing the labeled anti-Lectir antibody). Myeloid cells, which include monocytes, granulocytes, and megakaryocytes monitor for the presence of foreign bodies, provide protection against neoplastic cells, scavenge foreign materials, and produce platelets. A highly purified population of myeloid cells is necessary for a variety of in vitro experiments and in vivo indications. For example, myeloid cells find use in i) enriching the hematopoietic system of a host deficient in any class of myeloid cells; and ii) detecting diseases associated with myeloid cell dysfunction.

Protein of SEQ ID NO:6 (Internal Designation Clone 212950.cREC_116-075-2-0-H1-F)

The cDNA of Clone 212950.cREC_116-075-2-0-H1-F (SEQ ID NO:5) encodes vlADAM20 of SEQ ID NO:6, comprising the amino acid sequence:

```
MVQLHQDTDPQIPKGQPCTLNSSEGGARPAVPHTLFSSALDRWLHNDSFIMAVGEPLVHI
RVTLLLLWFGMFLSISGHSQARPSQYFTSPEVVIPLKVISRGRGAKAPGWLSYSLRFGGQR
YIVHMRVNKLLFAAHLPVFTYTEQHALLQDQPFIQDDCYYHGYVEGVPESLVALSTCSGG
FLGMLQINDLVYEIKPISVSATFEHLVYKIDSDDTQFPPMRCGLTEEKLIAHQMELQLSYNFT
LKQSSFVGWWTHQRFVELVVVVDNIRYLFSQSNATTVQHEVFNVVNIVDSFYHPLEVDVI
LTGIDIWTASNPLPTSGDLDNVLEDFSIWKNYNLNNRLQHDVAHLFIKDTQGMKLGVAYV
KGICQNPFNTGVDVFEDNRLVVFAITLGHELGHNLGMQHDTQWCVCELQWCIMHAYRK
VTTKFSNCSYAQYWDSTISSGLCIQPPPYPGNIFRLKYCGNLVVEEGEECDCGTIRQCAKDP
CCLLNCTLHPGAACAFGICCKDCKFLPSGTLCRQQVGECDLPEWCNGTSHQCPDDVYVQ
DGISCNVNAFCYEKTCNNHDIQCKEIFGQDARSASQSCYQEINTQGNRFGHCGIVGTTYVK
CWTPDIMCGRVQCENVGVIPNLIEHSTVQQFHLNDTTCWGTDYHLGMAIPDIGEVKDGTV
CGPEKICIRKKCASMVHLSQACQPKTCNMRGICNNKQHCHCNHEWAPPYCKDKGYGGSA
DSGPPPKNNMEGLNVMGKLRYLSLLCLLPLVAFLLFCLHVLFKKRTKSKEDEEG.
```

Accordingly, it will be appreciated that all characteristics and uses of the polypeptides of SEQ ID NO:6 described throughout the present application also pertain to the polypeptides encoded by the human cDNA included in Clone 212950.cREC_116-075-2-0-H1-F. In addition, it will be appreciated that all characteristics and uses of the polynucleotides of SEQ ID NO:5 described throughout the present application also pertain to the nucleic acids comprising the human cDNA in Clone 212950.cREC_116-075-2-0-H1-F. A preferred embodiment of the invention is directed toward the compositions of SEQ ID NO:6, SEQ ID NO:5, and Clone 212950.cREC_116-075-2-0-H1-F.

Preferred vlADAM20 polypeptides for uses in the methods described below include the polypeptides comprising the amino sequence of: MVQLHQDTDPQIPKGQPCTLNSSEGGAR PAVPHTLFSSALDRWLHNDSFI (SEQ ID NO:56).

```
MVQLHQDTDPQIPKGQPCTLNSSEGGARPAVPHTLFSSALDRWLHNDSFI.
```

Also preferred are the polypeptide fragments having a biological activity of proteolytically processing sperm surface proteins and the polynucleotides encoding the fragments.

vlADAM20 is a sperm protein that is a member of the ADAM family, and that displays all structural elements that are characteristic of this family. Notably, vlADAM20 displays a catalytic site of an active $Zn^{2+}$ metalloprotease (HELGHNLGMQHD) (SEQ ID NO:57), one disintegrin consensus sequence (EEGEECDCG) (SEQ ID NO:58) and one transmembrane domain. The ADAM family of proteins contains a disintegrin and metalloproteinase domain. Members of this family are cell surface proteins with a unique structure possessing both potential adhesion and protease domains. Although all ADAMs have the same domain organization, members of the ADAM do not all display the same functions. The functions displayed by members of the ADAM family are regulated by processes that include alternative splicing, differential gene expression, dimerization, and proteolytic processing. ADAMs are involved in diverse biological processes such as spermatogenesis, fertilization, myoblast fusion and neuron proliferation (Wolfsberg et al, Dev Biol. 180:389-401 (1996)).

vlADAM20 is a novel membrane-anchored sperm surface protease that is involved in spermatogenesis. vlADAM20 is involved in remodeling the developing sperm surface, i.e., proteolytically processing other sperm surface proteins.

An embodiment of the invention is directed to a composition comprising a vlADAM20 polypeptide sequence of SEQ ID NO:6.

A further embodiment of the invention is directed to a composition comprising a vlADAM20 polypeptide fragment having biological activity of proteolytically processing sperm surface proteins.

A further embodiment of the invention is directed to a composition comprising a polynucleotide sequence of SEQ ID NO:5 encoding a vlADAM20 polypeptide.

A further embodiment of the invention is directed to a composition comprising a polynucleotide sequence encoding a vlADAM20 polypeptide fragment having biological activity of proteolytically processing sperm surface proteins.

A further embodiment of the invention is directed to an antibody or an antigen-binding fragment that binds to a vlADAM20 polypeptide or against a vlADAM20 polypeptide fragment. Preferably, the antibody specifically binds to the vlADAM20 polypeptide and not to the ADAM20 polypeptide. Preferably, the antibody or antigen-binding fragment recognizes an epitope comprising one or more of the 50 amino-acids located at the amino-terminal extremity of vlADAM20, wherein one or more of these amino-acids are required for antibody binding. Even more preferably, the antibody recognizes the QLHQDTDPQIPKGQPCT (SEQ ID NO:59) amino-acid sequence or the LNSSEGGAR (SEQ ID NO:60) amino-acid sequence. As used herein, the term anti-vlADAM20 antibody includes both intact molecules as well as active fragments thereof, such as those capable of binding antigens.

The present invention also relates to a method of binding an anti-vlADAM20 antibody to a vlADAM20 polypeptide comprising the step of: contacting a vlADAM20 polypeptide with said antibody or antigen-binding fragment thereof under conditions that allow binding to take place. Such conditions are well known to those skilled in the art. Additionally, the present invention also relates to a method of binding an anti-vlADAM20 antibody or antigen-binding fragment thereof to a cell expressing a vlADAM20 polypeptide or fragment thereof comprising the step of: contacting a cell expressing a vlADAM20 polypeptide or part thereof with said antibody or antigen-binding fragment under conditions that allow binding to take place. Preferably, the antibody or fragment used in these methods is vlADAM20-specific, as discussed above. Such methods are for example useful for purifying testis cells as further described herein.

Another embodiment of the present invention relates to methods of using compositions comprising an antibody directed against vlADAM20 polypeptides for purifying testis cells. Preferably, such compositions comprise the preferred antibodies described above. Such a method for purifying testis cells comprises the steps of: i) labeling by standard methods of the anti-vlADAM20 antibody with a molecule that can be used to provide a detectable signal, ii) running a biopsied testis sample or mammalian cells through a sorting apparatus, e.g. a fluorescence-activated cell sorter or a magnetic activated cell-sorting apparatus, containing the labeled anti-vlADAM20 antibody. Purifying testis cells are useful for in vitro analysis and diagnosis of various diseases associated with testis including, but not limited to, testicular cancer, testicular intraepithelial neoplasia, testicular microlithiasis and sterility.

An embodiment of the present invention relates to a method of producing vlADAM20 polypeptides comprising the steps of: i) transfecting a host cell with a recombinant expression vector comprising a polynucleotide of the present invention; and optionally ii) purifying the produced protein. The purification of the protein can be done following any technique well known to those skilled in the art. Preferably, an antibody directed against vlADAM20 or part thereof may be bound to a chromatographic support to form an affinity chromatography column. Even more preferably, the antibody recognizes the 50 amino-terminal amino acids of vlADAM20. Alternatively, vlADAM20 polypeptides may be produced by a method comprising the step of: i) transfecting a host cell with a polynucleotide capable of directing vlADAM20 expression. Preferably, the polynucleotides capable of directing vlADAM20 expression are located in the 5' regulatory region of the vlADAM20 gene. Further preferably, these polynucleotides are located within 500 base pairs of the vlADAM20 coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties.

In an embodiment, a vlADAM20 polypeptide or a biologically active fragment thereof can be used in a “cocktail” of proteases that is able to digest a wide range of proteins. Such protease cocktails are useful in laboratory assays to degrade undesirable proteins in a sample, for example for removing proteins in a DNA preparation or for removing enzymes after any enzymatic reaction.

In another embodiment, vlADAM20 or a biologically active fragment thereof can be used in combination with a detergent for the removal of stains having a protein component, similar to the use of proteases described in U.S. Pat. No. 5,599,400, which disclosure is incorporated by reference in its entirety. The composition can contain known detergent constituents such as, e.g. surfactants, foam enhancers and fillers. The detergent preferably contains between 0.001% to 10% vlADAM20 polypeptides. vlADAM20 polypeptides can be included in a detergent composition or can be combined with other constituents at the time of use as an additive. The detergent additive can be formulated as a liquid, powder, granulate or slurry.

Still another embodiment relates to compositions and methods for using vlADAM20 polypeptides as a contraceptive immunogen. It was shown that men and women who spontaneously produce anti-sperm antibodies are infertile but otherwise healthy (Bronson et al, Fertil Steril. 42:171-83 (1984)). Such a method comprises the step of: administering to an individual a vlADAM20 polypeptide as described in U.S. Pat. No. 6,197,940, which disclosure is hereby incorporated in its entirety, in an effective amount to reduce the fertility of that individual via generation of antibodies to vlADAM20. Preferably, immunogenic vlADAM20 polypeptides are used in such compositions. The administered amount of immunogenic vlADAM20 polypeptides depends upon factors such as route of administration, species, and the use of booster administration. For example, a dose of about 0.1 to 100 micrograms of vlADAM20 polypeptides per kg of body weight may be used. Compositions of the present invention may be prepared as both human and veterinary vaccine formulations. Contraceptive vaccines can be produced by combining vlADAM20 polypeptides with a pharmaceutically suitable carrier and with an adjuvant that contains non-specific stimulators of the immune system such as, e.g., immunogenic fragments of *Bordatella pertussis.*

Compositions of the present invention may be made up in a solid form (e.g. granules for oral administration) or in a liquid form (e.g. solutions for oral administration or for injection). Compositions of the present invention are included in the carrier in an amount that is effective to reduce the fertility of the subject being treated. Compositions of the present invention may also comprise other contraceptive molecules. For example, a female contraceptive vaccine comprising vlADAM20 polypeptides may also comprise PH30 beta chain proteins that are described in U.S. Pat. No. 5,693,496, which disclosure is incorporated hereby by reference in its entirety, and a male contraceptive vaccine may also comprise SP-22 polypeptides that are described in U.S. Pat. No. 6,197,940, which disclosure is incorporated hereby by reference in its entirety.

A further embodiment of the present invention is directed to substances that decrease vlADAM20 expression, and to a method of screening for such substances comprising the steps of: i) contacting a cell with a test substance, ii) comparing vlADAM20 expression in an exposed cell to that of an unexposed control cell, iii) quantifying said expression levels, and iv) determining the ratio of vlADAM20 expression in an exposed cell relative to the expression in an unexposed cell. Preferably, vlADAM20 expression is studied in testis cells. Preferably, compositions comprising substances that decrease vlADAM20 expression can be administered to male individuals for contraceptive purposes.

A further embodiment of the present invention is directed to substances that decrease vlADAM20 activity, and to a method of screening for such substances comprising the steps of: i) contacting a cell with a test substance, ii) comparing vlADAM20 proteolytic activity in an exposed cell to that of an unexposed control cell, iii) quantifying said expression levels, and iv) determining the ratio of vlADAM20 proteolytic activity in an exposed cell relative to the expression in an unexposed cell. Preferably, vlADAM20 expression is studied in testis cells. vlADAM20 proteolytic activity can for example be measured by the alpha 2M complex formation assay as described by Frosty Loechel et al (J Biol Chem 273:16993-7 (1998)). Preferably, compositions comprising substances that decrease vlADAM20 expression can be administered to male individuals for contraceptive purposes.

As used herein, the term antagonist includes substances that that decrease vlADAM20 expression, substances that decrease vlADAM20 activity, and antibodies or antigen-binding fragments that inhibit the activity of vlADAM20.

Another embodiment of the present invention relates to methods of using compositions comprising a vlADAM20 antagonist for blocking vlADAM20 proteolytic activity. Preferably, the antagonist is one of the preferred antibodies described above. Such compositions can be administered to a cell, a tissue sample or an individual. Preferably, such compositions are administered to male individuals for blocking spermatogenesis in contraceptive purposes.

Still another embodiment of the present invention relates to methods of using compositions comprising an anti-vlADAM20 antibody for agglutinating and immobilizing sperm. Preferably, such compositions comprise the preferred antibodies described above. Such compositions can be administered to, e.g., a cell, a tissue sample or a patient. Preferably, such compositions are administered to female individuals for blocking fertilization in contraceptive purposes.

Protein of SEQ ED NO:8 (Internal Designation Clone 1000849866_181-44-3-0-A9-F)

The cDNA of SEQ ID NO:7 of clone 1000849866_181-44-3-0-A9-F encodes Lipoglobulin of SEQ ID NO:8, comprising the sequence: MRSLGALLLLLSACLAVSAG-PVPTPPDNIQVQENFNISRIYGKWYNLAIGSTCPW LKKIMD RMTVSTLVLGEGATEAEISMTSTR-WRKGVCEETSGAYEKTDTDGKFLYHKSKWNITMES YVVHTNYDEYAIFLTKKFSRHHGPTI-TAKLYGRAPQLRETLLQDFRVVAQGVGIPEDSIFT MADRGECVPGEQEPEPILIPRVRRAAT-PRRGRIRGWATGN. Accordingly, it will be appreciated that all characteristics and uses of the polypeptide of SEQ ID NO:8 described throughout the present application also pertains to the polypeptide encoded by the human cDNA included in clone 1000849866_181-44-3-0-A9-F. In addition, it will be appreciated that all characteristics and uses of the polynucleotides of SEQ ID NO:7 described throughout the present application also pertains to the polypeptide encoded by the nucleic acids comprising the human cDNA in clone 1000849866_181-44-3-0-A9-F. A preferred embodiment also pertain toward the composition of SEQ ID NO:7, SEQ ID NO:8 and clone 1000849866_181-44-3-0-A9-F. Also preferred are polypeptides fragments having a biological activity as described herein and the polynucleotides encoding the fragments.

The protein of SEQ ID NO:8 is a splice variant of the sequence of Alpha 1 Microglobulin (swissprot accession number P02760). The 221 amino acid lipoglobulin protein displays a lipocalin motif and belongs to the lipocalin superfamily. These extra-cellular proteins bind and transport small hydrophobic ligands such as steroids, bilins, retinoids, and lipids. Lipocalins function in a variety of processes including nutrient transport, cell growth regulation, immune response and prostaglandin synthesis.

Lipoglobulin is a plasma glycoprotein. The protein carries a set of chromophores which gives the protein a yellow-brown color and an extremely heterogeneous charge. Lipoglobulin can associate covalently with many plasma proteins like factor IX Zutphen, Factor XII Tenri and several protein C mutants. Lipoglobulin is translated in the liver cell and secreted to the blood. Lipoglobulin is found in many physiological fluids including plasma, urine, and cerebrospinal fluid. The protein appears not only as a free monomer but also in complexes with IgA and albumin. Lipoglobulin is also involved in anti-inflammatory and immunosuppressive activities. Lipoglobulin is one of the positive acute-phase proteins, in that circulating levels of lipoglobulin increase in response to stress and inflammatory stimulation. Lipoglobulin accumulates at sites of inflammation where it inhibits platelet and neutrophil activation and inhibits phagocytosis. The immunomodulatory properties of lipoglobulin are due to glycosylation. Lipoglobulin is 40% carbohydrate, making it unusually acidic and soluble. The glycosylation pattern of lipoglobulin changes during acute-phase response, and deglycosylated lipoglobulin has no immunosuppressive activity. Lipocalins are used as diagnostic and prognostic markers in a variety of disease states. The plasma level of Lipoglobulin can be monitored during pregnancy and in diagnosis and prognosis of conditions including cancer chemotherapy, renal dysfunction, myocardial infarction, arthritis, and multiple sclerosis.

An additional preferred embodiment of the invention is a method of binding lipoglobulin polypeptides with a lipoglobulin-specific antibody or lipoglobulin-binding fragment thereof. This method comprises the step of contacting a lipoglobulin polypeptide with a lipoglobulin-binding antibody or lipoglobulin-binding fragment thereof under conditions that allow binding. This method may be applied to detection and purification of lipoglobulin. These aspects are discussed in detail herein.

An embodiment of the present invention relates to compositions comprising Lipoglobulin polypeptides. The method of producing Lipoglobulin polypeptides comprises the steps of: i) transfecting a host cell with a recombinant expression vector comprising a polynucleotide of the present invention, and ii) purifying the produced protein. The purification of the protein can be done following any technique well known to those skilled in the art. Preferably, an antibody directed against Lipoglobulin or part thereof, preferably, an antibody directed against the C-terminal sequence of Lipoglobulin polypeptide, may be bound to a chromatographic support to form an affinity chromatography column.

In another embodiment, the invention provides methods and compositions for detecting the level of Lipoglobulin mRNA expression. Quantification of mRNA levels of Lipoglobulin may be useful for the diagnosis or prognosis of diseases associated with an altered expression of the protein of the invention. Conditions, diseases or disorders associated with altered expression include, but are not limited to, certain cancers, cystic fibrosis, ulcer, clotting disorders such as hemophelia, inflammation and immune based disorders, acquired immunodeficiency syndrome (AIDS), autoimmune disorders such as arthritis, fertility disorders, and hypothyroidism.

Assays for the detection and quantification of the mRNA of the protein of the invention are well known in the art (see, for example, Maniatis, Fitsch and Sambrook, Molecular Cloning; A Laboratory Manual (1982), or Current Protocols in Molecular Biology, Ausubel, F. M. et al. (Eds), Wiley & Sons, Inc.). For example, the nucleic acid molecule or probe may be labeled by standard methods and added to a biological sample from a patient under conditions of formation of hybridization complexes. After an incubation period, the sample is washed and the amount of label (or signal) associated with hybridization is quantified and compared with a standard value. If the amount of label in the patient sample is significantly altered in comparison to the standard value, then the presence of the associated condition, disease or disorder is indicated. Such assays may also be used to evaluate the efficacy of a particular therapeutic treatment regimen in animal studies and in clinical trial and to monitor the treatment of an individual patient. Once the presence of a condition is established and a treatment protocol is initiated, diagnostics assays may be repeated on a regular basis to determine if the level of expression in the patient begins to approximate that which is observed in a normal subject. The results obtained from successive assays may be used to show the efficacy of treatment over a period ranging from several days to months.

In another embodiment, the Lipoglobulin polypeptide or fragment thereof may be used to diagnose, disorders characterized by the presence of substrates, for example, Factor IX Zutphen, Factor XII Tenri and several protein C mutants. Such disorders include but are not limited to, factor XII deficiency and haemophilia B. In such a method, the Lipoglobulin polypeptide or fragment thereof is used in assays and diagnostic kits for the identification and/or quantification of substrates such as Factor IX Zutphen, Factor XII Tenri, and protein C mutants in a biological sample.

In another embodiment, the invention relates to methods and compositions for detecting and quantifying the level of the protein of the invention present in a particular biological sample. These methods are useful for the diagnosis or prognosis of diseases associated with altered levels of the protein of the invention. Diagnostic assays to detect the protein of the invention may comprise a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract.

Detection and quantification of Lipoglobulin polypeptides using either specific polyclonal or monoclonal antibodies are known in the art. Examples of such techniques include enzyme-linked immunoabsorbent assays (ELISAs), radioimmunoassays (RIAs), and fluorescence activated cell sorting (FACS). Example of an antibody is described in U.S. Pat. No. 6,153,192, which disclosure is incorporated by reference in its entirety.

In one embodiment, Lipoglobulin or a preferred fragment may be administered to a subject to treat or prevent a condition associated with altered expression or activity of the protein of the invention. Examples of such conditions include, but are not limited to, those described above.

In another embodiment, a pharmaceutical composition comprising a substantially purified Lipoglobulin polypeptide in conjunction with a pharmaceutical carrier may be administered to a subject to treat or prevent a condition associated with altered expression or activity of the endogenous protein including, but not limited to, those provided above.

In another embodiment, a substance which modulates the activity of Lipoglobulin may be administered to a subject to treat or prevent a condition associated with altered half life, expression, or activity of Lipoglobulin polypeptides including, but not limited to, those listed above. In one aspect, an antibody which specifically binds Lipoglobulin may be used as a targeting and delivery mechanism for bringing a pharmaceutical agent to cells that express Lipoglobulin (i.e., hepatocytes). In an additional embodiment, a vector capable of expressing Lipoglobulin or a preferred fragment may be administered to a subject to treat or prevent a condition associated with altered half life, expression, or activity of the protein of the invention including but not limited to, those listed above.

In a still further embodiment, a vector of expressing the polynucleotide encoding Lipoglobulin or a fragment thereof may be administered to a subject to treat or prevent a condition associated with altered half life, expression, or activity of the protein of the invention including but not limited to, those described above.

In another embodiment, the invention relates to a method of screening for compounds that bind a Lipoglobulin polypeptide or fragment thereof. Such method comprises the step of labeling the ligand molecule to be tested with a detectable label, such as a fluorescent, radioactive, or enzymatic tag, placing the ligand molecule to be tested in contact with Lipoglobulin polypeptide, or a fragment thereof under conditions which permit specific binding to occur, removing of non-specifically bound molecules, and detecting bound molecules using appropriate means. In a preferred embodiment, the proteins of the invention or part thereof may be used to identify and/or quantify substrates using any techniques known to those skilled in the art. To find substrates, the proteins of the invention, or part thereof, or derivative thereof, may be used for screening libraries of compounds in any of a variety of drug screening techniques. The fragment employed in such screening may be free in solution, affixed to a solid support, borne on a cell surface, or located intracellularly. The formation of binding complexes, between the proteins of the invention, or part thereof, or derivative thereof, and the agent being tested, may be measured by methods well known to those skilled in the art such as the BIAcore (Upsala, Sweden). Antagonists or inhibitors of the proteins of the invention may be produced using methods which are generally known in the art, including the screening of libraries of pharmaceutical agents to identify those which specifically bind the protein of the invention. Another technique for drug screening which may be used provides for high throughput screening of compounds having suitable binding affinity to the protein of the invention. For example, antagonists of Lipoglobulin polypeptide will prevent the inhibition of platelets and neutrophils by Lipoglobulin polypeptides.

Protein of SEQ ID NO:10 (Internal Designation Clone 164341_117-001-5-0-E2-F)

The cDNA of clone 164341_117-001-5-0-E2-F (SEQ ID NO:9) encodes peroxisomal beta ketothiolase (PBK) of SEQ ID NO:10, comprising the amino acid sequence: MQRLQVVLGHLRGPADSGWMPQAAPCLS-GAPQASAADVVVVHGRRTAICRAGR GGFKDTTP-DELLSAVMTAVLKDVNL-RPEQLGDICVGNVLQPGAGAIMARIAQFLSDIPETV PLSTVNRQCSSGLQAVASIAGWSPCP-WLTEGTLEILLRA. Accordingly, it will be appreciated that all characteristics and uses of the polypeptides of SEQ ID NO:10 described throughout the present application also pertain to the polypeptides encoded by the human cDNA included in Clone 164341_117-001-5-0-E2-F. In addition, it will be appreciated that all characteristics and uses of the polynucleotides of SEQ ID NO:9 described throughout the present application also pertain to the nucleic acids comprising the human cDNA in Clone 164341_117-001-5-0-E2-F. A preferred embodiment of the invention is directed toward the compositions of SEQ ID NO:9, SEQ ID NO:10, and clone 164341_117-001-5-0-E2-F. Also preferred are polypeptide fragments having a biological activity as described herein and the polynucleotides encoding the fragments.

The protein of SEQ ID NO:10, PBK, is a splice variant of the sequence of 3-Ketoacyl-CoA Thiolase protein (swissprot accession number P09110). The 153 amino acid protein of PBK displays one membrane-spanning segment: CSS-GLQAVASIAGWSPCPWLT (SEQ ID NO:61). Accordingly, some embodiments of the present invention relate to polypeptides comprising the transmembrane domain. Finally, the protein of the invention displays a thiolase domain spanning the sequence: APQASAADVVVVHGR-RTAICRAGRGGFKDTTPDELLSAVMTAVLKDVNLRPE QLGDICVGNVLQPGAGAIMARAQFLSDI-PETVPLSTVNRQCSSGLQAVASIAGWSPCPWL TEGTLEIL (SEQ ID NO:62). Accordingly, a preferred embodiment of the present invention comprises the amino acids of the thiolase domain and polynucleotides encoding the same.

Living organisms are exposed to a number of different fatty acids and their various derivatives arising either via endogenous synthesis or from exogenous sources. These hydrophobic compounds can have specific metabolic, structural or endocrine functions before elimination, which can involve metabolism to $CO_2$ or to more polar lipid metabolites allowing their excretion. Quantitatively, one of the major pathways metabolizing fatty acids is beta-oxidation and PKB is involved in this pathway.

PBK is a ketoacyl-CoA thiolase involved in the formation of an acyl-enzyme intermediate and as such, plays a role in fatty acid metabolism, cellular vesicle transport and maintenance of the cytoarchitecture, cellular proteolysis, endocytosis, signal transduction, lysosomal storage, cell proliferation and differentiation, immune and inflammatory response. The enzyme's substrates are compounds preferably containing an ester bond, preferably a thiol ester bond, more preferably an acyl thioester bond.

PBK mediates lipid homeostasis in target organs like liver, adipose tissue and is regulated by peroxisome proliferator activated receptors (PPAR alpha and PPAR gamma). Deficiency of PBK leads to very low peroxisomal beta-oxidation activity and the accumulation of very-long-chain fatty acids and intermediates in the biosynthesis of bile acids. Such peroxisomal disorders are peroxisome-deficient Zellweger syndrome and Rhizomelic Chondrodysplasia Punctata.

An additional preferred embodiment of the invention is a method of binding PBK polypeptides with a PBK-specific antibody or PBK-binding fragment thereof. This method comprises the step of contacting a PBK polypeptide with a PBK-binding antibody or PBK-binding fragment thereof under conditions that allow binding. This method may be applied to detection and purification of PBK, as well as modification of PBK function. These aspects are discussed in detail herein.

A preferred aspect of the invention is a host cell recombinant for polynucleotides encoding a PBK polypeptide or a biologically active fragment thereof. An additional preferred aspect is a host cell recombinant for polynucleotides capable of directing PBK expression. Preferably, the polynucleotides capable of directing PBK expression are located in the 5' regulatory region of the PBK gene. Further preferably, these polynucleotides are located within 500 base pairs of the PBK coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. PBK protein produced by said host cell may be used for in vitro detection and purification methods as well as diagnosis and in vivo applications.

In one embodiment, the hydrolytic activity of the protein of the invention or part thereof may be assayed using any of the assays known to those skilled in the art including those described in U.S. Pat. No. 5,445,942, which disclosure is hereby incorporated in its entirety.

Another embodiment of the invention relates to compositions and methods using the protein of the invention or part thereof to label peroxisomes, in order to visualize any change in number, topology or morphology of this organelle, for example in association with beta-oxidation peroxisomal disorders such as, but not limited to Zellweger syndrome, Pseudo Zellweger, Rhizomelic Chondrodysplasia Punctata, X-linked adrenoleukodystrophy (ALD), neonatal adrenoleukodystrophy, pseudoneonatal adrenoleukodystrophy, acyl-coA deficiency, bifunctional enzyme deficiency, Refsum's disease, DHAP acyl transferase deficiency, hyperpipecolatemia and acatalasemia.

For example, the protein may be rendered easily detectable by inserting the cDNA encoding the protein of the invention into a eukaryotic expression vector in frame with a sequence encoding a tag sequence. Eukaryotic cells expressing the tagged protein of the invention may also be used for the in vitro screening of drugs or genes capable of treating any beta-oxidation peroxisomal disorders.

An embodiment of the invention provides for a method of screening test substances for modulators of PBK expression.

This method comprises the steps of: i) contacting a cell with a test substance; and ii) comparing PBK expression in the cell after exposure to the test substance to that of an unexposed control cell. PBK expression is determined by methods common to the art or included herein, by detecting PBK polynucleotides or polypeptides. An example of this method comprises the steps of: i) culturing two equivalent cell samples; ii) adding a test substance to one of the cultures and not the other; iii) harvesting both cultures at a specified time; iv) purifying the mRNA from each sample of cells; v) comparing the level of PBK mRNA in each sample by Northern blot, RTPCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) comparing the level of PBK polypeptides in each sample by Western blot, immunohistochemistry, or another method common to the art. The invention provides for design and use of specific antibodies and antibody fragments, as discussed herein.

Agents which modulate the expression or activity of the PBK of the subject invention include, but are not limited to antisense oligonucleotides, riboymes, drugs, and antibodies. These agents may be made and used according to methods well known in the art. Also, agents which increase PBK expression are hypolipidemic compounds. Moreover, the protein of the invention, or biologically active fragments thereof, may be used in screening assays for therapeutic compounds. A variety of drug screening techniques may be employed. In this aspect of the invention, the protein or biologically active fragment thereof, may be free in solution, affixed to a solid support, recombinantly expressed on, or chemically attached to, a cell surface, or located intracellularly. The formation of binding complexes, between the protein of the invention, or biologically active fragments thereof, and the compound being tested, may be measured by methods well known to those skilled in the art, like, but not limited to, the BIAcore (Upsala, Sweden). Another technique for drug screening which may be used provides for high throughput screening of compounds having suitable binding affinity to the protein of the invention as described in published PCT application WO84/03564, and incorporated herein by reference in its entirety.

Another embodiment of the subject invention provides compositions and methods of selectively increasing the activity of the protein of the invention. Activation of PBK allows for the successful treatment and/or management of diseases or biochemical abnormalities associated with PBK activity. Agonists, able to increase the expression or the activity of the protein of the invention, are useful in the treatment of diseases associated with decreased peroximal beta-oxidation of fatty acids, for example, Pseudo Zellweger syndrome and Rhizomelic Chondrodysplasia Punctata (RCDP). Preferred agonists include hypolipidemic compounds. Each hypolipidemic compound may additionally be excluded individually or as a group.

In another embodiment, the present invention includes the use of PBK polypeptides, or fragments having a desired biological activity to treat or ameliorate a condition in an individual. For example, the condition may be Pseudo-Zellweger syndrome or Rhizomelic Chondrodysplasia Punctata (RCDP). In such embodiments, a PBK polypeptide or a fragment thereof, is administered to an individual in whom it is desired to increase any of the activities of PBK. A PBK polypeptide or fragment thereof may be administered directly to the individual or, alternatively, a nucleic acid encoding the a PBK polypeptide or a fragment thereof may be administered to the individual. For example, a polynucleotide encoding a PBK polypeptide or a fragment is comprised in a recombinant expression vector which can be administered to a patient suffering from Pseudo-Zellweger syndrome or Rhizomelic Chondrodysplasia Punctata (RCDP). Preferred expression vectors include viral vectors, especially adenoviral and lentiviral vectors. Alternatively, an agent which increases the activity of PBK polypeptides may be administered to the individual. Preferred agonists are hypolipidemic compounds. Specific hypolipidemic compounds may additionally be excluded individually or as a group.

In such a method, an agent that increases PBK activity can be processed in accordance with conventional methods of pharmacy to produce medicinal agents for administration to patients. Thus, the pharmaceutical composition comprising an agent that increases PBK activity may be made up in a solid form (e.g. granules for oral administration, powders for inhalation) or in a liquid form (e.g. solutions for oral administration or for injection). Effective doses of the compositions of the present invention for treating a patient suffering from disorders like, but not limited to, Pseudo-Zellweger syndrome or Rhizomelic Chondrodysplasia Punctata (RCDP), can be determined according to the relevant techniques. Additional agents may be identified by contacting a PBK polypeptide or a cell or preparation containing a PBK polypeptide with a test agent and assaying whether the test agent increases the activity of the protein. For example, the test agent may be a chemical compound or a polypeptide or peptide.

In one embodiment, the subject method utilizes eukaryotic or prokaryotic host cells which are stably transformed with recombinant nucleic acids expressing the PBK polypeptide or biologically active fragments thereof. The transformed cells may be viable or fixed. Drugs or compounds which are candidates for the activation of the protein of the invention, or biologically active fragments thereof, are screened against such transformed cells in binding assays well known to those skilled in the art. Alternatively, assays such as those taught in Geysen H. N., WO Application 84/03564, published on Sep. 13, 1984, and incorporated herein by reference in its entirety, may be used to screen for peptide compounds which demonstrate binding affinity for, or the ability to activate, PBK polypeptides or biologically active fragments thereof.

Another embodiment of the invention relates to composition and methods using polynucleotide sequences encoding the protein of the invention or part thereof to establish transgenic model animals (*D. melanogaster, M. musculus*), by any method familiar to those skilled in the art. By modulating in vivo the expression of the transgene with drugs or modifier genes (activator or suppressor genes), animal models can be developed that mimic human peroxisome-associated disorders such as Zellweger syndrome, Rhizomelic Chondrodysplasia Punctata, X-linked adrenoleukodystrophy (ALD), acyl-coA deficiency, bifunctional enzyme deficiency, Refsum's disease, DHAP acyl transferase deficiency and acatalasemia. These animal models would thus allow the identification of potential therapeutic agents for treatment of the disorders. In addition, recombinant cell lines derived from these transgenic animals may be used for similar approaches ex vivo.

In another embodiment, the invention relates to methods and compositions for detecting and quantifying the level of the protein of the invention present in a particular biological sample. These methods are useful for the diagnosis or prognosis of diseases associated with altered levels of the protein of the invention like, but not limited to, pseudo-Zellweger syndrome. Diagnostic assays to detect the protein of the invention may comprise a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract.

Assays for the quantification of the protein PBK may be performed according to methods well known in the art. Typically, these assays comprise contacting the sample with a ligand of the protein of the invention or an antibody (polyclonal or monoclonal) which recognizes the protein of the invention or a fragment thereof, and detecting the complex formed between the protein of the invention present in the sample and the ligand or antibody. Fragments of the ligands and antibodies may also be used in the binding assays, provided these fragments are capable of specifically interacting with the protein of the subject invention. Further, the ligands and antibodies which bind to the protein of the invention may be labeled according to methods known in the art. Labels which are useful in the subject invention include, but are not limited to, enzymes labels, radioisotopic labels, paramagnetic labels, and chemiluminescent labels. Typical techniques are described by Kennedy, J. H., et al. (1976) *Clin. Chim. Acta* 70:1-31, which disclosure is hereby incorporated by reference in its entirety; and Schurs, A. H. et al. (1977) *Clin. Chim. Acta* 81: 1-40, which disclosure is hereby incorporated by reference in its entirety). For example, PBK will be detected in fibroblasts of control individuals but not of Zellweger patients by immunoblot.

In another embodiment, an array of oligonucleotides probes comprising the nucleotides encoding PBK polypeptidesor fragments thereof can be constructed to conduct efficient screening of e.g., genetic mutations. A microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents (see for example: Chee, M. et al., Science, 274:610-614 (1996), which disclosure is hereby incorporated by reference in its entirety). Genetic variants, mutations, and polymorphisms of PBK gene are related to peroxisomal beta-oxidation disorders such as Rhizomelic Chondrodysplasia Punctata.

Protein of SEQ ID NO:12 (Internal Designation Clone 1000837037_228-43-2-0-C3-F)

The cDNA of Clone $1000837037_{13}$ 228-43-2-0-C3-F (SEQ ID NO: 11) encodes myeloidin of SEQ ID NO: 12, comprising the amino acid sequence: MPFSHLSTYS-LVWVMAAVVLCTAQVQVVTQDEREQLYT-TASLKCSLQNAQEALIVTW QKKKAVSPENMVTF-SENHGVVIQPAYKDKINITQLGLQNSTITFWNITLED EGCYMCLFN TFGFGKISGTACLTVYVQPIVSLHYKF-SEDHLNITCSATARPAPMVFWKVPRSGIENSTVT LSHPNGTTSVTSILHIKDPKN-QVGKEVICQVLHLGTVTDFKQTVNKGY-WFSVPLLLSIVSL VILLVLISILLYWKRFIRNQDREP. Accordingly, it will be appreciated that all characteristics and uses of the polypeptides of SEQ ID NO: 12 described throughout the present application also pertain to the polypeptides encoded by the human cDNA included in Clone $1000837037_{13}$ 228-43-2-0-C3-F. In addition, it will be appreciated that all characteristics and uses of the polynucleotides of SEQ ID NO: 11 described throughout the present application also pertain to the nucleic acids comprising the human cDNA included in Clone $1000837037_{13}$ 228-43-2-0-C3-F. A preferred embodiment of the invention is directed toward the compositions of SEQ IDNO:12, SEQ IDNO:l 1, and Clone $1000837037_{13}$ 228-43-2-0-C3-F. Preferred myeloidin polypeptides for uses in the methods described below include the polypeptides comprising the amino sequence of: QVQVVTQDEREQLYTTASLKCS-LQNAQEALIVTWQKKKAVSPENMVTFSENHGVVIQ PAYKDKINITQLGLQNSTITFWNITLE-DEGCYMCLFNTFGFGKISGTACLTVYVQPIVSLH YKFSEDHLNITCSATARPAPMVF-WKVPRSGIENSTVTLSHPNGTTSVTSILHIKDPKNQV GKEVICQVLHLGTVTDFKQTVNKGYWFS-VPLLLSIVSLVILLVLISILLYWKRHRNQDREP (SEQ ID NO: 127). Also preferred are polypeptide fragments having a biological activity as described herein and the polynucleotides encoding the fragments The protein of the present invention, myeloidin, is a novel splice variant of the brain OX-2 protein (Genbank accession number P412 17). Myeloidin is 262 amino acids long. OX-2 is 274 amino-acids long and differs from myeloidin at both the amino-terminal and the carboxyl-terminal extremities. Another known splice variant of OX-2, my033, is 269 amino acids long and differs from myeloidin at the amino-terminal extremity. Myeloidin displays a signal peptide (MPFSHL-STYSLVWVMAAVVLCTA) (SEQ ID NO:63), one transmembrane domain (VPLLLSIVSLVILLVLISILLYW) (SEQ ID NO:64) and two immunoglobulin (Ig) domains (TASLKCS-LQNAQEALIVTWQKKKAVSPENMVTF-SENHGVVIQPAYKDKINITQLGLQNS TITFWNITLE-DEGCYMCLF (SEQ ID NO:65) and EDHLNITCSATARPAPMVFWKVPRSGIEN STVTLSH-PNGTTSVTSILHIKDPKNQVGKEVICQV (SEQ ID NO :66)). Myeloidin is expressed by a wide variety of cells, including those of the central nervous system (CNS).

Myeloidin is a cell surface protein that delivers an inhibitory signal for myeloid lineage cells. Myeloidin binds to a receptor specifically located on myeloid lineage cells. In peculiar, myeloidin delivers an inhibitory signal to brain microglial cells. Microglial cells regulate the regenerative state and remodeling of the brain by producing a variety of cytotoxic and neurotrophic molecules when activated. More generally, myeloidin is involved in immune suppression by inhibiting cytotoxic cells.

An embodiment of the invention is directed to a composition comprising a myeloidin polypeptide sequence of SEQ ID NO:12.

A further embodiment of the invention is directed to a composition comprising a myeloidin polypeptide fragment having biological activity of delivering an inhibitory signal for myeloid lineage cells.

A further embodiment of the invention is directed to a composition comprising a polynucleotide sequence of SEQ ID NO:11 encoding a myeloidin polypeptide.

A further embodiment of the invention is directed to a composition comprising a polynucleotide sequence encoding a myeloidin polypeptide fragment having biological activity of delivering an inhibitory signal for myeloid lineage cells.

A further embodiment of the invention is directed to a composition comprising an antibody recognizing a myeloidin polypeptide sequence of SEQ ID NO:12 or a myeloidin polypeptide fragment having same biological activity. Preferably, the antibody binds to myeloidin but not to OX-2 or to my033. As further used herein, an anti-myeloidin antibody refers to an antibody that specifically binds either to a myeloidin polypeptide or to a myeloidin polypeptide fragment having the same biological activity. An anti-myeloidin antibodies may be an entire molecule or an antigen binding fragment thereof.

The present invention also relates to a method of binding an anti-myeloidin antibody to a myeloidin polypeptide comprising the step of: contacting a myeloidin polypeptide with said antibody under conditions that allow binding to take place. Such conditions are well known to those skilled in the art. Additionally, the present invention also relates to a method of binding an anti-myeloidin antibody to a cell expressing a myeloidin polypeptide or fragment thereof comprising the step of: contacting a cell expressing a myeloidin polypeptide or part thereof with said antibody under conditions that allow binding to take place. Such methods of binding an anti-myeloidin antibody to a myeloidin polypeptide are for example useful for purifying myeloidin polypeptides.

Another embodiment relates to a method of producing myeloidin polypeptides comprising the steps of: i) transfecting a host cell with a recombinant expression vector comprising a polynucleotide of the present invention, and optionally ii) purifying the produced protein. The purification of the protein can be done following any technique well-known to those skilled in the art. Preferably, an anti-myeloidin may be bound to a chromatographic support to form an affinity chromatography column. Alternatively, myeloidin polypeptides may be produced by a method comprising the step of: i) transfecting a host cell with a polynucleotide capable of directing myeloidin expression. Preferably, the polynucleotides capable of directing myeloidin expression are located in the 5' regulatory region of the myeloidin gene. Further preferably, these polynucleotides are located within 500 base pairs of the myeloidin coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties.

An additional aspect of the previous embodiment relates to methods of producing myeloidin in vivo in a mammal. Preferred such method is a method of genetically modifying donor cells by gene transfer of myeloidin polynucleotides for grafting the cells into the central nervous as described in U.S. Pat. No. 5,762,926, which disclosure is incorporated by reference in its entirety. Preferably, donor cells are neurons or fibroblasts. Most preferably, such methods are applied to a mammal suffering from neurodegenerative disorders. Preferred mammals are mice and humans.

One embodiment of the present invention is directed to methods of isolating or purifying microglial cells using myeloidin polypeptides. The study and use of isolated microglial cells and purified microglial cell populations (including, for example, characterizing the interaction these cells in vitro or in vivo with drugs and drug candidates) provides information useful in treating neurological disorders. One method for obtaining a cell population enriched in microglial cells comprises the steps of: i) contacting a preparation comprising microglial cells with a myeloidin polypeptide, wherein myeloidin is immobilized on a matrix prior to or after contacting; and ii) removing non-adherent cells, thereby producing cell population enriched in microglial cells. For example, the matrix may be plastic and the myeloidin polypeptide may be immobilized by adsorption. Another method for isolating or purifying microglial cell populations using compositions comprising using an myeloidin polypeptide comprises the steps of: i) labeling by standard methods the myeloidin polypeptide with a molecule that can be used to provide a detectable signal, ii) contacting the labeled myeloidin polypeptide with a cell under conditions that allow protein binding, and iii) sorting the cell based on the presence or absence of the detectable signal. Sorting and detection are preferably accomplished by a sorting apparatus, e.g. a fluorescence-activated cell sorter or a magnetic activated cell-sorting apparatus. Preferably, the preparations comprising microglial cells are prepared from brain (e.g., from rat or mouse brain) and may be from a normal mammal or from a mammal with a neurological disorder. Preparation of cell suspension tissue containing microglia can be performed according to any method well-known to those skilled in the art, e.g., the methods described in PCT application WO 01/51618, which disclosure is hereby incorporated by reference in its entirety.

Another preferred embodiment relates to methods of screening for substances that increase or decrease myeloidin expression comprising the steps of: i) contacting a cell with a test substance; and ii) comparing myeloidin expression in the cell after exposure to the test substance to that of an unexposed control cell. Preferably, the test substance modifies the expression of myeloidin in a specific cell type while not in others. Most preferably, the test substance modifies myeloidin expression specifically in neural cells.

A further embodiment of the present invention is directed to substances that increase or deacrease myeloidin activity and to a method of screening for such substances comprising the steps of: i) contacting a cell with a test substance, ii) determining myeloidin activity, iii) comparing myeloidin activity in the cell after exposure to that of an unexposed control cell, and iv) determining the ratio of myeloidin activity in an exposed cell relative to the activity in an unexposed cell. Preferably, myeloidin activity is studied in a neural cell. Myeloidin activity can be determined by studying microglial-mediated activation of astrocytes, i.e., to determine its ability to prevent a reactive astrocyte morphology in culture. Myeloidin activity can also be determined by measuring cytokine production as described in PCT application WO 99/24565, which disclosure is hereby incorporated by reference in its entirety.

As further used herein, substances that increase myeloidin expression or myeloidin activity are defined as myeloidin agonists. As further used herein, substances that decrease myeloidin expression or myeloidin activity are defined as myeloidin antagonists. The term antagonist comprises anti-myeloidin antibodies that inhibit the biological activity of myeloidin polypeptides.

An embodiment of the present invention relates to methods of using myeloidin antagonists of the present invention to induce or to enhance activation of myeloid lineage cells. Such methods comprise the step of: contacting a cell, a tissue, or an individual with a composition comprising a myeloidin antagonist and optionally a pharmaceutical carrier. In a preferred embodiment, such methods for activating myeloid lineage cells are directed toward brain microglial cells. Such methods can be used to destroy invading microorganisms, to promote neuroregeneration, or to remove potentially deleterious debris and promote tissue repair consecutively to brain injury. Infections that can be treated or reduced in severity by activating microglial cells include but are not limited to brain abscess due to, e.g., *Aspergillus* CNS infections, meningitis due to, e.g., *Cryptococcus* CNS infections, neuropsychiatric disorders associated with streptococcal infection (PANDAS), and influenza virus-associated encephalopathy.

Another embodiment of the present invention relates to methods of using the polypeptides and the polynucleotides of the present invention to prevent or to reduce activation of myeloid lineage cells. Such methods comprise the step of: contacting a cell, a tissue, or an individual with a composition comprising a myeloidin polypeptide or a myeloidin agonist, and optionally a pharmaceutical carrier. In a preferred embodiment, such methods for preventing or reducing myeloid lineage cell activation are directed toward brain microglial cells. Such methods can be used to treat or to reduce in severity neural inflammation, and more specifically neurodegenerative disorders and pathological inflammations consecutive to brain injury. Neurodegenerative disorders associated with neural inflammation include but are not limited to stroke, Parkinson's disease, Alzheimer's disease, cerebellum-type Creutzfeldt-Jakob disease, and Huntington's disease.

In another preferred embodiment, such methods for preventing or reducing myeloid lineage cell activation are directed for preventing or treating inflammation associated with autoimmune diseases. Autoimmune diseases that may be treated or prevented according to the present invention include, but are not limited to, multiple sclerosis, type 1 insulin-dependant diabetes mellitus, and rheumatoid arthritis.

Effectiveness of compositions and methods of the present invention to modulate microglial activity can be verified in vitro by studying the effects of the compositions of the present invention on the morphology of astrocytes. Effectiveness of compositions and methods of the present invention to treat a given disease associated with microglial activation can be verified using models that depend upon the disease that is treated. For example, one model described in U.S. Pat. No. 6,191,154, which disclosure is hereby incorporated by reference in its entirety, can be used as a tissue model for the sequence of events following trauma in the nervous system.

The quantity of myeloidin polypeptides, anti-myeloidin antibodies, myeloidin agonists or myeloidin antagonists that is administered for treating a patient suffering from diseases described above can be determined according to the particular application and the potency of the active component. For preparing pharmaceutical compositions from the compounds of the present invention, pharmaceutically acceptable carriers can be in any suitable form (e.g., solids, liquids, gels). The present invention contemplates a variety of techniques for administration of the therapeutic compositions. Suitable routes include, but are not limited to, oral, rectal, or transdermal administration, and intradermal, subcutaneous or intravenous injections. Indeed, it is not intended that the present invention is limited to any particular administration route. The assessment of the clinical features and the design of an appropriate therapeutic regimen for the individual patient are ultimately the responsibility of the prescribing physician. Furthermore, the compositions of the invention may be administered alone or in combination with other known agents treating the disorders treated above.

Protein of SEQ ID NO:14 (Internal Designation Clone 101005_105-020-4-0-H11-F)

The cDNA of Clone 101005_105-020-4-0-H11-F (SEQ ID NO:13) encodes protein vACT of SEQ ID NO:14, comprising the amino acid sequence: MERMLPLLTLGL-LAAGFCPAVLCHPNSPLDEENLTQEN-QDRGTHVDLGLASANVDFALSLY KQLVLKAPDKN-VIFSPLSISTALAFLSLGAHNTMTEILKGLKFNLT ETSEAEIHQSFQHLLRTL NQSSDELQLSMGNAM-FVKEQLSLLDRFTEDAKRLYGSEAFATD-FQDSAAAKKLINDYVKN GTRGKITDLIKDLDSQTM-MVLVNYIFFKAKWEMPFDPQDTHQSRFYLSK KKWVMVPMMSL HHLTIPYFRDEELSCTVVELKYTG-NASALFILPDQDKMEEV EAMLLPETLKRWRDSLE-FREIG ELYLPKFSISRDYNLNDILLQLGIEE-AFTSKADLSGITGARNLAVSQVVHKAVLDVFEEGTEA SAATAVKITLLSALVETRTWRFNRP-FLMIIVPTDTQNIFFMSKVTNPKQA. Accordingly, it will be appreciated that all characteristics and uses of polypeptides of SEQ ID NO:14 described throughout the present application also pertain to the polypeptides encoded by the human cDNA in Clone 101005_105-020-4-0-H11-F. In addition, it will be appreciated that all characteristics and uses of the polynucleotides of SEQ ID NO:13 described throughout the present application also pertain to the nucleic acids comprising the human cDNA in Clone 101005_105-020-4-0-H11-F. A preferred embodiment of the invention is directed toward the compositions of SEQ ID NO:13, SEQ ID NO:14, and Clone 101005_105-020-4-0-H11-F. Also preferred are polypeptide fragments having a biological activity as described herein and the polynucleotides encoding the fragments.

The cDNA of SEQ ID NO:13 is a novel polymorphic variant of the human alpha 1 anti-chymotrypsin (ACT) protein named vACT, encoded by a gene located on chromosome 14, specifically at position 14q31-q32.3. The cDNA of SEQ ID NO:13 encodes a 423 amino-acid protein of SEQ ID NO:14.

Proteases are key components of a broad range of biological pathways and can be classified into four groups according to their catalytic mechanisms: the serine, cysteine (thiol), aspartic (carboxyl), and metalloproteases. Chymotrypsin is a member of a family of enzymes known as serine proteases, so named because they have an unusually reactive serine residue at their active sites. vACT belongs to the serpin serine protease inhibitor family. Serpins are irreversible suicide inhibitors of proteases that have a central role in regulating proteolysis in diverse physiological processes such as blood coagulation, fibrinolysis, complement activation, angiogenesis, apoptosis, inflammation, neoplasia and viral pathogenesis. vACT neutralizes chymotrypsin by binding to its active site and forming a stable complex. vACT is predominantly synthesized in the liver and specifically inactivates neutrophil cathepsin G, mast cell chymase and pancreatic chymotrypsin. vACT is also an acute phase protein since the plasma concentration of vACT increases within several hours during the inflammatory response. Synthesis of vACT is tightly regulated by the net balance of neutrophil cathepsin G and vACT at sites of inflammation/tissue injury. Alterations of a serpin which affect its functional levels may result in pathology and cause specific clinical syndromes. For example, individuals with vACT deficiency are susceptible to premature development of lung and liver diseases. In addition, changes in the balance between serine proteases and vACT may lead to pathological states similar to those associated with some neurodegenerative diseases such as Alzheimer's disease.

An embodiment of the invention is directed to a composition comprising a vACT polypeptide sequence of SEQ ID NO:14.

A further embodiment of the invention is directed to a composition comprising a vACT polypeptide fragment having biological activity.

A further embodiment of the invention is directed to a composition comprising a polynucleotide sequence of SEQ ID NO:13 encoding a vACT polypeptide.

A further embodiment of the invention is directed to a composition comprising a polynucleotide sequence encoding a vACT polypeptide fragment having biological activity.

In an embodiment, a vACT polypeptide or fragment thereof may be used to inhibit contaminating proteases in a sample. This method comprises the step of adding a protease-inhibiting amount of vACT polypeptide to biological samples, under conditions that allow vACT activity to prevent degradation of protein samples. Preferred biological samples are cell cultures. Such a composition can be used alone or as a "cocktail" with other protease inhibitors. The advantage of using a cocktail of protease inhibitors is that one is able to inhibit a wide range of proteases without knowing the specificity of any of the proteases. Using a cocktail of protease inhibitors also protects a protein sample from a wide range of proteases which may contaminate a protein sample in the future from a vast number of sources. For example, vACT polypeptides or fragments thereof are added to samples where proteolytic degradation by contaminating proteases is undesirable. Such protease inhibitor cocktails are widely used in assays to inhibit proteases susceptible of degrading a protein of interest for which the assay is to be performed. Alternatively, vACT or part thereof may be bound to a chromatographic support, either alone or in combination with other protease inhibitor, using techniques well known in the art, to form an affinity chromatography column. A sample containing the undesirable protease is run through the column to remove the protease. Alternatively, the same methods may be used to identify new target proteases of vACT.

In another preferred embodiment, vACT polypeptides or fragments thereof may be used as an anti-microbial agent useful to inhibit exogenous proteases implicated in a number of infectious diseases including, but not limited to, bacterial and parasite-borne infections. For example, vACT inhibits growth of all strains of group A streptococci, including antibiotic-resistant strains. Accordingly, the present invention can be used to retard or inhibit the growth of certain microbes either in vitro or in vivo. Such methods comprise the step of delivering an amount of vACT polypeptide able to inhibit serine proteases, including by administering purified protein or transfecting cells with a polynucleotide encoding the protein. In vitro, this method comprises the step of contacting an effective amount of vACT polypeptide with a biological sample. Preferred biological samples are cell cultures. In vivo, this method comprises the step of contacting an effective amount of vACT polypeptide with a desired site in an individual. Preferred individuals are those at risk of microbial infection.

In a further embodiment, the present invention provides a method of producing a recombinant serpin capable of effectively modulating serine protease activity. Despite the availability of human alpha 1 anti-chymotrypsin and vACT from serum, quantities large enough for therapeutic uses have been unobtainable, due in large part to the limited availability of human serum. Consequently, there is a great need for other sources of alpha 1 anti-chymotrypsin and vACT to fill the needs created by therapeutic uses. In one preferred embodiment, a milk animal can be used to produce vACT in the milk, thereby generating a significant amount of this particular protein after purification. The protein of the invention may be purified using any techniques known to those skilled in the art including those disclosed in the U.S. Pat. No. 6,268,487, which disclosure is hereby incorporated by reference in its entirety. Any type of animal that produces enough milk can be used in this aim such as, but not limited to, sheep, goat, and cow. These animals can be generated with any method of targeting overexpression of vACT in the milk. Also in this embodiment, the protein of the invention can be produced in host cells that have been transfected with an appropriate expression vector comprising a nucleic acid sequence coding for vACT. The host cells are cultured under conditions whereby the nucleic acid sequence coding for this particular protein is expressed. After a suitable amount of time for the product to accumulate, the protein is purified from the host cells or medium surrounding the cells. Introduction of an expression vector incorporating a nucleic acid sequence coding for vACT into a host cell can be performed in a variety of ways, such as but not limited to calcium or lithium chloride treatment, electroporation, and lipofection.

The present invention also provides animal models generated by modulating the expression or activity of the present protein in one or more tissues of the animal. Such animals are useful for a number of purposes, because they represent an in vivo assay method for testing candidate molecules potentially useful for the treatment of various pathophysiological aspects of diseases specifically related to the activity of vACT. Study of the phenotype of such models can also allow the identification of additional human equivalent diseases caused by or linked with vACT deficiency. These animals can be generated with any method of targeting overexpression or inactivation of vACT. Such models are extremely useful, e.g. in the assessment of candidate therapies and drugs for the treatment of inflammatory diseases and conditions.

A further embodiment of the present invention is to provide novel methods and compositions useful for the treatment of diseases and conditions exhibiting excessive activity of serine proteases and preferably chymotrypsin. vACT or part thereof may be used to inhibit proteases implicated in a number of diseases where cellular proteolysis occurs. Such diseases, characterized by tissue degradation, include, but are not limited to, blood coagulation-related diseases, tumor invasion, infection, and inflammation. More preferably, the present invention is applied in the treatment of diseases associated with an excess level of cathepsin G, mast cells chymase or pancreatic chymotrypsin including but not limited to, chronic emphysema of the lungs, liver diseases, pancreatitis, cardiovascular diseases, and allergic reactions. The methods and compositions are also useful for treatment of Alzheimer's and Parkinson's diseases. Such methods comprise the administration of a therapeutically-effective amount of vACT to mammals suffering from the disease or condition, where "effective amount" is meant a concentration of vACT capable of significantly decrease the activity of serine proteases. The compositions of the invention are preferably delivered to an individual in combination with a physiologically acceptable carrier, such as a saline solution or other physiologically buffer suitable for administration to a patient. For treatment of skin inflammation, the compositions of the invention may be applied to the affected area in combination with a physiologically acceptable ointment or cream. The particular amount of the compositions of the invention that will be administered to the mammal for any particular condition will depend on the clinical condition of the patient, and other factors such as the weight, age, and route of delivery. Such compositions can be administered by any suitable route including, but not limited to, intravenous, intramuscular, intraperitoneal, subcutaneous routes, and topically to an affected area of the skin or by absorption through epithelial or mucocutaneous linings such as nasal, oral, vaginal, rectal. For treatment purposes, the compositions may be administrated using any of the gene therapy methods known in the art to deliver the therapeutic bioactive molecules to targeted cells. These compositions can comprise the protein of the invention, and, optionally, one or more other types of protease inhibitors, or any other compound of interest. This co-administration may be by simultaneous administration or by separate or sequential administrations. All of these additional components may be either obtained from natural sources or produced by recombinant genetic engineering techniques and/or chemical modification.

An additional preferred embodiment of the invention is a method of binding vACT polypeptides with a vACT-specific antibody or vACT-binding fragment thereof. This method comprises the step of contacting a vACT polypeptide with a vACT-binding antibody or vACT-binding fragment thereof under conditions that allow binding. This method may be applied to detection and purification of vACT, as well as modifying vACT function. These aspects are discussed in detail herein.

In other embodiment, the current invention is used to diagnose diseases or disorders associated with altered expression or activity of the present protein. In particular, it is useful in diagnosing patients with abnormally low levels of vACT expression, which results in uncontrolled activity of target proteases. Examples of such diseases and disorders include, but are not limited to, lung and liver diseases, chronic obstructive pulmonary disease (COPD), inflammatory disorders associated with an excess level of cathepsin G, and Alzheimer's and Parkinson's diseases. The method includes the steps of: i) contacting a fluid or tissue sample with a compound capable of selectively binding vACT polypeptide or nucleic acids, and ii) detecting the level, or any other detectable property of vACT in the sample. Preferably, a difference in the level or other property in the sample relative to in a control sample indicates the presence of the disease or disorder, or of a propensity for developing the disease or disorder. Preferably, the fluid or tissue sample is obtained from an individual suspected of suffering from the disease or condition, or at risk of developing the disease or condition. For example, a polyclonal or monoclonal antibody or any immunologically active fragment thereof or a nucleic acid probe may be used. Preferably, the antibodies used in one such embodiment are specifically directed against the variant vACT polypeptides and do not recognize alpha 1 anti-chymotrypsin polypeptides. Detection can be carried out directly or indirectly with known immunohistological and immunofluorescing processes. For this, the reagents contained in the kit according to the invention can be directly labeled with generally known molecules, including, but not limited to, enzymes such as alkaline phosphatase and peroxidase and fluorescent dyes such as FITC, rhodamine, and Texas-Red. However, labeling can also occur indirectly by using secondary antibodies labeled with molecules such as biotin, digoxigenin or the like and are then detected with a secondary reagent. Also in this embodiment, diagnosis of such conditions may be facilitated by the identification of the variant vACT using well known PCR or RT-PCR techniques and in particular in with "real-time" PCR system. Alternatively, using such a method, the present invention provides a tool to correlate modulations in the expression of vACT with certain pathologies. Thus, the present invention provides a novel candidate gene for such conditions.

Since the regulation of serine proteases by their inhibitors are critical for the control of tissue destruction in the diseases described above, in a further embodiment, the present protein or part thereof provides an assay for the monitoring of markers in vivo for characterization of disease states. The invention thus includes test kits useful for the quantification of the amount of vACT in a biological sample. The kits comprise at least one immunological binding partner, e.g. a monoclonal or polyclonal antibody specific for vACT and coupled to detectable markers. Preferably, the antibodies used in one such embodiment specifically bind vACT polypeptides and not alpha 1 anti-chymotrypsin polypeptides. In this embodiment, the application of such assays can be used to monitor the progress of therapy administered to treat these or other conditions. Further, the assays can be used as a measure of toxicity, or during clinical testing of new drugs to assess the impact on tissue degradation. Thus the assays may be applied in any situation wherein the present invention can be used as an index of the condition, treatment, or effect of substances directly administered to the subject or to which the subject is exposed in the environment. Thus, the condition of a patient can be monitored continuously and the quantified amount of such proteins measured in the pathological sample can be compared with the amount quantified in a biological sample of a normal individual or with the previous analysis of the same patient. In this embodiment, this marker can be measured effectively in plasma, serum or blood, by any suitable method, including immunoassays. It can also preferably be measured in tissues and fluids recovered from inflammatory sites.

Protein of SEQ ID NO:16 (Internal Designation 500743419_188-281-3-0-H5-F)

The cDNA of 500743419_188-281-3-0-H5-F (SEQ ID NO:15) encodes protein claudinyn-5 of SEQ ID NO:16, comprising the amino acid sequence: MGSAALEILGLVLCLVGWGGLILACGLPMWQVTAFLDHNIVTAQTTWKGLWMSCVVQS TGHMQCKVYDSVLALSTEVQAARALTVSAVLLAFVALFVTLAGAQCT TCVAPGPAKARV ALTGGVLYLFCGLLALVPLCWFANIVVREFYDPSVPVSQKYELGAALYIGWAATALLMV GGCLLCCGAWVCTGRPDLSFPVKYSAPRRPTATGDNDKKNYV. Accordingly, it will be appreciated that all characteristics and uses of polypeptides of SEQ ID NO:16 described throughout the present application also pertain to the polypeptides encoded by the nucleic acids included in 500743419_188-281-3-0-H5-F. In addition, it will be appreciated that all characteristics and uses of the polynucleotides of SEQ ID NO:15 described throughout the present application also pertain to the nucleic acids comprising the human cDNA in 500743419_188-281-3-0-H5-F. A preferred embodiment of the invention is directed toward the compositions of SEQ ID NO:15, SEQ ID NO:16, and 500743419_188-281-3-0-H5-F. Also preferred are polypeptide fragments having a biological activity as described herein and the polynucleotides encoding the fragments.

The cDNA of SEQ ID NO:15 is a polymorphic variant of the human claudin-5 protein belonging to the PMP22-Claudin family of proteins characterized by four membrane-spanning segments. Claudinyn-5 is 218 amino acids long and contains four membrane-spanning segments. Claudinyn-5 contains the Claudin family signature and is encoded by a gene located on chromosome 22, specifically at position 22q11.2.

The Claudin family of proteins comprises more than twenty small glycoproteins with four predicted transmembrane domains. Claudinyn-5 is a component of tight junction (TJ) strands that play a role in regulation of cell permeability and polarity. Polarized epithelial and endothelial cells form barriers that separate biological compartments and regulate homeostasis. The TJ is a specialized membrane domain at the most apical region of polarized epithelial and endothelial cells that constitute continuous seals around cells. These seals serve as a physical barrier preventing solutes and water from passing freely through the paracellular space. The TJ also restricts the lateral diffusion of membrane lipids and proteins to maintain the cellular polarity. Many diseases marked by changes in cell barrier permeability are in turn related to alteration in TJ function. For example, the increase in microvascular permeability in tumors, contributing to clinically severe symptoms, appears to be the result of a dysregulation of junctional proteins. Increased TJ permeability of the epithelium, and consequently a decrease in epithelial barrier function, precedes the development of some tumors, including carcinomas and adenomas. The lung epithelium forms a barrier that allergens must cross before they can cause sensitization. The nonspecific disruption of intercellular TJs by allergens increases epithelial permeability, allowing allergens to cross the epithelial barrier. Finally, TJ permeability can also be modified by different bacterial toxins, cytokines, hormones and drugs.

An embodiment of the invention is directed to a composition comprising a claudinyn-5 polypeptide sequence of SEQ ID NO:16.

A further embodiment of the invention is directed to a composition comprising a claudinyn-5 polypeptide fragment having biological activity.

A further embodiment of the invention is directed to a composition comprising a polynucleotide sequence of SEQ ID NO:15 encoding a claudinyn-5 polypeptide.

A further embodiment of the invention is directed to a composition comprising a polynucleotide sequence encoding a claudinyn-5 polypeptide fragment having biological activity.

A further embodiment of the invention is directed to a composition comprising an antibody recognizing a claudinyn-5 polypeptide sequence of SEQ ID NO:16 or a claudinyn-5 polypeptide fragment having biological activity. Preferably, the antibody recognizes a non-linear epitopes, and binds to claudinyn-5 but not to claudin-5.

A preferred aspect of the invention is a host cell recombinant for polynucleotides encoding a claudinyn-5 polypeptide or a biologically active fragment thereof. An additional preferred aspect is a host cell recombinant for polynucleotides capable of directing claudinyn-5 expression. Preferably, the polynucleotides capable of directing claudinyn-5 expression are located in the 5' regulatory region of the claudinyn-5 gene. Further preferably, these polynucleotides are located within 500 base pairs of the claudinyn-5 coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. Claudinyn-5 protein produced by said host cell may be used for in vitro detection and purification methods as well as diagnosis and in vivo applications.

Another embodiment relates to a method of producing claudinyn-5 polypeptides comprising the steps of: i) transfecting a mammalian host cell with a recombinant expression vector comprising a polynucleotide of the present invention, and ii) purifying the produced protein. The purification of the protein can be done following any technique well-known to those skilled in the art. Preferably, an antibody directed against claudinyn-5 or part thereof may be bound to a chromatographic support to form an affinity chromatography column. Even more preferably, the antibodies bind to claudinyn-5 but not to claudin-5.

In another embodiment, the present invention provides for a method to increase the intestinal absorption of hydrophilic drugs by increasing the paracellular permeability for said drugs either in vitro or in vivo. Indeed, the intestinal epithelium is a major barrier to the absorption of hydrophilic drugs. The presence of intercellular junctional complexes, and particularly the TJs, renders the epithelium impervious to hydrophilic drugs, which cannot diffuse across the cells through the lipid bilayer of the cell membranes. The expression of claudinyn-5 can be inhibited or decreased for example using antisense-polynucleotides corresponding to claudinyn-5 to down-regulate expression of said proteins. Methods of designing, synthesizing, and using said antisense polynucleotides are well known to those skilled in the art and are discussed herein. The function of claudinyn-5 in TJ complexes can also be more specifically inhibited using direct or indirect inhibitor molecules or antagonistic antibodies directed against the present protein. Any compound that inhibits or significantly decreases the activity of claudinyn-5 polypeptides can be identified by screening for test substances that decrease claudinyn-5 activity comprising the steps of contacting a cell with a test substance and comparing claudinyn-5 activity in the cell after exposure to the test substance to that of an unexposed control cell. Preferably, claudinyn-5 activity is determined by measuring the permeability of the TJs using, for example, methods discussed in U.S. Pat. No. 6,110,747, which disclosures are hereby incorporated by reference in its entirety. Preferably, such methods are used is to temporally increase epithelial permeability for therapeutic ends including but not limited to increasing the efficiency of drug delivery. More preferably, for in vivo purposes, formulations are those comprising said compositions that are compatible with oral delivery.

In a further embodiment, a claudinyn-5 polypeptide-specific antibody or a fragment thereof can be used as a component of drug delivery vehicles such as colloids or liposomes to specifically target therapeutic agents to epithelial cells. Such methods comprise the step of incorporating a claudinyn-5 polypeptide-specific antibody or a fragment thereof, into liposomes used to specifically target therapeutic agents carried by the liposomes to epithelial cells. Such drug delivery systems can be designed using any techniques known to those skilled in the art. In one such embodiment, claudinyn-5-specific antibodies or fragments thereof can also be directly conjugated (either recombinantly or by using chemically active agents) to chemotherapeutic agents, radioisotopes, or prodrugs and said conjugate subsequently used in therapeutic regimens.

The negative effects of the usual preservation solutions on epithelial and endothelial permeability in organs to be transplanted are generally known, considering the disorganization of TJ proteins. This is responsible for the observed tissue injury and edema. In another embodiment, agonists of the expression of claudinyn-5 can be used to maintain the content and integrity of TJs in organs to be transplanted. Further preferred embodiment is a method of using such agonists as constituents of the preservation solutions in order to improve the quality of said organs to be transplanted. Any compound that stimulates or significantly increases the expression of claudinyn-5 polypeptides can be used in one such embodiment. Such compounds can be identified by screening for test substances that increase claudinyn-5 expression comprising the steps of contacting a cell with a test substance and comparing claudinyn-5 expression in the cell after exposure to the test substance to that of an unexposed control cell. In this embodiment, the activity of claudinyn-5 polypeptides can also be increased to preserve TJ function by administering a compound that causes an increase in the activity of the protein. Such compounds can be identified by screening for test substances that increase claudinyn-5 activity comprising the steps of contacting a cell with a test substance and comparing claudinyn-5 activity in the cell after exposure to the test substance to that of an unexposed control cell. Preferably, claudinyn-5 activity is determined by measuring the permeability of the TJs using methods as mentioned above.

The present invention also provides animal models generated by modulating the expression of the present protein in one or more tissues of the animal. Such animals are useful for a number of purposes, because they represent an in vivo assay method for testing candidate molecules potentially useful for the treatment of various pathophysiological aspects of diseases specifically related to the function of claudinyn-5. Study of the phenotype of such models can also allow the identification of additional human equivalent diseases caused by or linked with claudinyn-5 deficiency. These animals can be generated with any method of targeting overexpression or inactivation of claudinyn-5. Such models are extremely useful, e.g. in the assessment of candidate therapies and drugs for the treatment of inflammatory diseases and conditions.

In other embodiment, the current invention is used to diagnose diseases or disorders associated with altered expression of claudinyn-5. In particular, it is useful in diagnosing patients with deficient amounts of claudinyn-5 which results in uncontrolled cell permeability. Examples of such diseases and disorders include, but are not limited to, Crohn's disease, ulcerative colitis, irritable bowel syndrome, allergic asthma, gliobastoma, colorectal carcinoma, and adenomatous polyps. The method includes the steps of i) contacting a biological sample with a compound capable of selectively binding claudinyn-5 polypeptide or nucleic acids, and ii) detecting the level, or any other detectable property of claudinyn-5 in the sample. Preferably, a difference in the level or other property in the sample relative to in a control sample indicates the presence of the disease or disorder, or of a propensity for developing the disease or disorder. Preferably, the biological sample is obtained from an individual suspected of suffering from the disease or condition, or at risk of developing the disease or condition. Preferably, the biological sample comprises an epithelial cell sample. A polyclonal or monoclonal antibody or any immunologically active fragment specific for claudinyn-5 may be used to detect levels of the protein. Preferably, the antibody or fragment thereof is detectably labeled with, for example, a fluorescent, radioactive, or otherwise detectable compound. Detection can be carried out directly or indirectly with known immunohistological and immunofluorescing processes. For this, the reagents contained in the kit according to the invention can be directly labeled with generally known molecules, including, but not limited to, enzymes such as alkaline phosphatase and peroxidase and fluorescent dyes such as FITC, rhodamine, and Texas-Red. However, labeling can also occur indirectly by using secondary antibodies labeled with molecules such as biotin, digoxigenin or the like and are then detected with a secondary reagent. A method using a nucleic acid probe corresponding to claudinyn-5 can also be used to determine the expression of claudinyn-5 using, for example, well known PCR or RT-PCR techniques and in particular in with "real-time" PCR system.

Alternatively, the present invention provides a tool to correlate modulations in the expression of claudinyn-5 with certain pathologies. Thus, the present invention provides a novel candidate gene for such conditions. Also in this embodiment, the determination of the level of the expression of claudinyn-5 within a biological sample provides an assay for an in vivo marker to classify and/or characterize of disease states. Preferably, such a method is applied to diagnose or classify pathologies such as Crohn's disease, ulcerative colitis, irritable bowel syndrome, allergic asthma, gliobastoma, colorectal carcinoma, and adenomatous polyps. The invention thus includes test kits useful for the quantification of the amount of claudinyn-5 in a biological sample. The kits comprise at least one immunological binding partner, e.g. a monoclonal or polyclonal antibody specific for claudinyn-5 and coupled to detectable markers. Application of such assays can be used to monitor the progress of therapy administered to treat these or other conditions. Thus the assays may be applied in any situation wherein the level of claudinyn-5 expression can be used as an index of the condition, treatment, or effect of substances directly administered to the subject or to which the subject is exposed in the environment. Thus, the condition of a patient can be monitored continuously and the quantified amount of claudinyn-5 polypeptides measured in the pathological sample can be compared with the amount quantified in a biological sample of a normal individual or with the previous analysis of the same patient. In this embodiment, this marker can be measured by any suitable method, including immunoassays. It can also preferably be measured in tissues and fluids recovered from inflammatory sites.

A further embodiment of the present invention is to provide novel methods and compositions useful for the treatment of diseases and conditions associated with impaired TJ function. More preferably, claudinyn-5 polypeptide or fragment thereof can be used to treat diseases associated with an impaired claudinyn-5 related function, including but not limited to, Crohn's disease, ulcerative colitis, irritable bowel syndrome, allergic asthma, gliobastoma, colorectal carcinoma, and adenomatous polyps. Such methods comprise the administration of a therapeutically-effective amount of claudinyn-5 to mammals suffering from the disease or condition, where "effective amount" is meant a concentration of claudinyn-5 capable of significantly restore a physiological TJs function. The compositions may be administrated using any of the methods known in the art or discussed herein for delivering claudinyn-5 polynucleotides to a cell. Any agonists of the expression or the activity of claudinyn-5 polypeptides identified as mentioned above can also be used in this embodiment. Such compositions are preferably delivered to an individual in combination with a physiologically acceptable carrier, such as a saline solution or other physiologically buffer suitable for administration to a patient. The particular amount of the compositions of the invention that will be administered to the mammal for any particular condition will depend on the clinical condition of the patient, and other factors such as the weight, age, and route of delivery. These compositions can optionally comprise, one or more other compound of interest. This co-administration may be by simultaneous administration or by separate or sequential administrations. All of these additional components may be either obtained from natural sources or produced by recombinant genetic engineering techniques and/or chemical modification.

In a further embodiment, the present invention provides a method of producing "bioartificial" epithelia from non-epithelial cells. The "bioartificial" epithelia produced according to the invention provides various clinical applications for the generation of epithelia unable to repair or regenerate themselves. It can be used, for example, for reconstructive surgical procedures, for treating of disorders related to epithelial loss (for hereditary, traumatic or oncological reasons) or for another therapeutic purposes (for example, burn treatments). Further preferred is a method of using the nucleic acid corresponding to claudinyn-5 wherein "bioartificial" epithelial cells are obtained by transfection of said nucleic acid, and consequential remodeling, of the patient's autologous cells not affected by any of the above conditions. The use of autologous cells in the preparation of the "bioartificial" epithelial cells of the invention in methods of treating disorders, conditions, or diseases associated with the loss of epithelial cells reduces or eliminates the risk of tissue rejection typically observed in transplantation methodologies. Methods of bioartificial tissue engineering are generally known to those skilled in the art (Machens H. G. et al., Cells Tissues Organs 167: 88-94 (2000), the disclosure of which is hereby incorporated by reference in its entirety).

Protein of SEQ ID NO:18 (Internal Designation Clone 645730_181-16-1-0-G9-F)

The cDNA of Clone 645730_181-16-1-0-G9-F (SEQ ID NO:17) encodes Benzodiazepine Receptor 3 (BZRP-R3) protein of SEQ ID NO:18, comprising the amino acid sequence:

MRLQGAIFVLLPHLGPILVWLFTRDHMSGWCEGPRMLSWCPFYKVLLLVQTAIYSVVGY
ASYLVWKDLGGGLGWPLALPLGLYADQLTISWTVLVLFFTVHNPGLALLHLLLLYGLVV
STALIWHPINKLAALLLLPYLAWLTVTSALTYHLWRDSLCPVHQPQPTEKSD.

Accordingly, it will be appreciated that all characteristics and uses of the polypeptides of SEQ ID NO:18 described throughout the present application also pertain to the polypeptides encoded by the human cDNA included in Clone 645730_181-16-1-0-G9-F. In addition, it will be appreciated that all characteristics and uses of the polynucleotides of SEQ ID NO:17 described throughout the present application also pertain to the nucleic acids comprising the human cDNA in Clone 645730_181-16-1-0-G9-F. A preferred embodiment of the invention is directed toward the compositions of SEQ ID NO:17, SEQ ID NO:18 and Clone 645730_181-16-1-0-G9-F. Also preferred are polypeptide fragments having a biological activity as described herein and the polynucleotides encoding the fragments.

The protein of SEQ ID NO: 18, BZRP-R3, is a novel polymorphic variant of human peripheral benzodiazepine receptor/isoquinoline binding protein (PBR/IBP) (accession numbers Q9Y53 1). BZRP-R3 displays five transmembrane-spanning segments: LQGAIFVLLPHLGPILVWLFT (SEQ ID NO:67), VLLLVQTAIYSVVGYASYLVW (SEQ ID NO:68), GLYADQLTISWTVLVLFFTVH (SEQ ID NQ:69), GLALLHLLLLYGLVVSTALIW (SEQ ID NO:70), and LAALLLLPYLAWLTVTSALTY (SEQ ID NO:71). Accordingly, some embodiments of the present invention relate to polypeptides comprising the transmembrane domains. Moreover, BZRP-R3 displays a stretch of 11 amino acids (VTSALTYHLWR) (SEQ ID NO:72) that bind cholesterol. Accordingly, a preferred embodiment of the present invention comprises the amino acids of the cholesterol recognition/interaction domain and the polynucleotides encoding the same.

BZRP-R3 is capable of binding benzodiazepine and imidazopyridine derivatives, but is distinct from the GABA neurotransmitter receptor. BZRP-R3 polypeptides are most abundant in steroidogenic cells and are found primarily on outer mitochondrial membranes. BZRP-R3 is associated with a 34-kDa pore-forming, voltage-dependent anion channel protein located on the outer/inner mitochondrial membrane contact sites. Ligands of BZRP-R3, upon binding to the receptor, simulate steroid synthesis in steroidogenic cells in vitro and in vivo. BZRP-R3 stimulates steroid formation by increasing the rate of cholesterol transfer from the outer to the inner mitochondrial membrane.

In addition to its role in mediating cholesterol movement across membranes, BZRP-R3 has been implicated in several other physiological functions, including cell growth and differentiation, chemotaxis, mitochondrial physiology, porphyrin and heme biosynthesis, immune response, and anion transport. In addition, BZRP-R3 agonists are potent anti-apoptotic compounds.

BZRP-R3 is associated with stress and anxiety disorders. BZRP-R3 plays a role in the regulation of several stress systems such as the HPA axis, the sympathetic nervous system, the renin-angiotensin axis, and the neuroendocrine axis. In these systems, acute stress typically leads to increases in BZRP-R3 density, whereas chronic stress typically leads to decreases in BZRP-R3 density. For example, in Generalized Anxiety Disorder (GAD), Panic Disorder (PD), Generalized Social Phobia (GSP), and Post-Traumatic Stress Disorders (PTSD), BZRP-R3 density is typically decreased. BZRP-R3 is expressed glial cells in the brain. Furthermore, BZRP-R3 expression is increased in neurodegenerative disorders and after neurotoxic and traumatic-ischemic brain damage. BZRP-R3 expression is decreased in chronic schizophrenics, suggesting that the decreased density of BZRP-R3 in the brain may be involved in the pathophysiology of schizophrenia. However, BZRP-R3 is higher than normal in autopsied brain tissue from PSE patients (Portal-Systemic Encephalopathy patients).

BZRP-R3 increases mitochondrial activity and prevents apoptosis and is therefore implicated in tumor cell proliferation. BZRP-R3 is preferentially expressed in liver and breast cancers. Further, BZRP-R3 is useful as a tool/marker for detection, diagnosis, prognosis and treatment of cancer.

Many ligands have been described that bind to BZRP-R3 with various affinities. Some benzodiazepines, Ro 5-4864 [4-chlorodiazepam], diazepam and structurally related compounds, are potent and selective PBR ligands. Exogenous ligands also include 2-phenylquinoline carboxamides (PK11195 series), imidazo [1,2-a]pyridine-3-acetamides (Alpidem series), pyridazine, and isoquinilone derivatives. Some endogenous compounds, including porphyrins and diazepam binding inhibitor (DBI), bind to BZRP-R3.

A preferred aspect of the invention is a host cell recombinant for polynucleotides encoding a BZRP-R3 polypeptide or a biologically active fragment thereof. An additional preferred aspect is a host cell recombinant for polynucleotides capable of directing BZRP-R3 expression. Preferably, the polynucleotides capable of directing BZRP-R3 expression are located in the 5' regulatory region of the BZRP-R3 gene. Further preferably, these polynucleotides are located within 500 base pairs of the BZRP-R3 coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. BZRP-R3 protein produced by said host cell may be used for in vitro detection and purification methods as well as diagnosis and in vivo applications.

A preferred embodiment of the invention relates to compositions and methods using the protein of the invention or fragment thereof to label mitochondria in order to visualize any change in number, topology or morphology of this organelle, for example in association with a mitochondria-related human disorder, such as hereditary spastic paraplegia, neuroleptic malignant syndrome (NMS), the Rett syndrome, Alpers disease, or mitochondrial encephalomyopathies. For example, the protein may be rendered easily detectable by inserting the cDNA encoding the protein of the invention into a eukaryotic expression vector in frame with a sequence encoding a tag sequence. Eukaryotic cells expressing the tagged protein of the invention may also be used for the in vitro screening of drugs or genes capable of treating any mitochondria-related disease or conditions.

A preferred embodiment of the invention is a method to detect mitochondria comprising the step of contacting an antibody specific for BZRP-R3 with a cell. Preferably, the cell is fixed or otherwise permeable to antibodies. Preferably, the antibody is labeled with any detectable moiety including, but are not limited to, a fluorescent label, a radioactive atom, a paramagnetic ion, biotin, a chemiluminescent label or a label which can be detected through a secondary enzymatic or binding step. The invention further provides a method of diagnosing mitochondria-related disorders or conditions, such as those listed above, and distinguishing these from other disorders.

In another embodiment, the protein of the invention may be used to target heterologous compounds (polynucleotides) to steroidogenic cells and/or the mitochondria. Such recombinant cDNA may be introduced, for example, using in any vector, viral or non-viral, and viral vectors can be but not limited to retroviral, adenoviral, and adeno-associated vectors. For example, these heterologous polynucleotides may be used to deliver nucleic acids for mitochondrial gene therapy, i.e. to replace a defective mitochondrial gene and/or to inhibit the deleterious expression of a mitochondrial gene.

Another preferred embodiment of the invention is a method of screening for compounds that modulate the expression of BZRP-R3. This method comprises the steps of i) contacting a cell with a test compound and ii) comparing the level of BZRP-R3 polypeptides in a cell after exposure to the test compound to that of an untreated control cell. The level of BZRP-R3 polypeptides may be inferred by detecting mRNA for BZRP-R3 by methods common to the art such as Northern blotting or RT-PCR. The level of BZRP-R3 polypeptides may also be detected by antibody-based methods common to the art such as Western blotting or immunofluorescence. Test compounds that increase BZRP-R3 expression are useful as agonists, as discussed herein. Test compounds that decrease BZRP-R3 expression are useful as antagonists, as discussed herein.

Antagonists of BZRP-R3 include agents which decrease the levels of expressed mRNA encoding the protein of SEQ ID NO:18. These include, but are not limited to, RNAi, one or more ribozymes capable of digesting the protein of the invention, or antisense oligonucleotides capable of hybridizing to mRNA encoding BZRP-R3. Antisense oligonucleotides can be administrated as DNA, RNA, as DNA entrapped in proteoliposomes containing viral envelope receptor proteins [Kanoda, Y. et al. (1989) Science 243: 375, which disclosure is hereby incorporated by reference in its entirety] or as part of a vector which can be expressed in the target cell to provide antisense DNA or RNA. Vectors which are expressed in particular cell types are known in the art. Alternatively, the DNA can be injected along with a carrier. A carrier can be a protein such as a cytokine, for example interleukin 2, or polylysine-glycoprotein carriers. Carrier proteins, vectors, and methods of making and using polylysine carrier systems are known in the art. Alternatively, nucleic acids encoding antisense molecules may be coated onto gold beads and introduced into the skin with, for example, a gene gun [Ulmer, J. B. et al. (1993) Science 259:1745, which disclosure is hereby incorporated by reference in its entirety].

A preferred embodiment of the invention is a method of screening for compounds that bind to BZRP-R3 polypeptides. Such compounds are useful for developing agonists and antagonists of BZRP-R3 activity. This method comprises the steps of: i) contacting a BZRP-R3 polypeptide or fragment thereof with a test compound under conditions that allow binding to occur and ii) detecting binding of said test compound. Binding may be detected by any method common to the art such as competition with a labeled antibody specific for BZRP-R3 or by direct labeling of each test substance. In one example of such a method, a polynucleotide encoding a BZRP-R3 polypeptide or a biologically active fragment thereof is transformed into a eukaryotic or prokaryotic host cell. The transformed cells may be viable or fixed. Drugs or compounds which are candidates for binding BZRP-R3 polypeptides are screened against such transformed cells in binding assays well known to those skilled in the art. Alternatively, assays such as those taught in Geysen H. N., WO Application 84/03564, published on Sep. 13, 1984, and incorporated herein by reference in its entirety, may be used to screen for peptide compounds which demonstrate binding affinity for BZRP-R3 polypeptides or fragments thereof. In another embodiment, competitive drug screening assays using neutralizing antibodies specifically compete with a test compound for binding to BZRP-R3 polypeptides or fragments thereof. Preferred test compounds are those included in the benzodiazepine class, such as diazepam (i.e., valium), triazolobenzodiazepine, and adinazolam, as well as modified versions thereof. Further preferred test compounds are in the imidazopyridine and isoquinilone classes. Each test compound may additionally be excluded individually or as a class.

A variety of drug screening techniques may be employed. In this aspect of the invention, BZRP-R3 polypeptide or fragments thereof, may be free in solution, affixed to a solid support, recombinantly expressed on or chemically attached to a cell surface, or located intracellularly. The formation of binding complexes between BZRP-R3 polypeptides or fragments thereof, and the compound being tested, may then be measured as described.

Another embodiment of the subject invention provides compositions and methods of selectively modulating the activity of the protein of the invention. Modulation of BZRP-R3 allows for the successful prevention, treatment, or management of disorders or biochemical abnormalities associated with BZRP-R3. Agonist compounds are those that increase the amount of BZRP-R3 polypeptides in a cell or increase the biological activity of BZRP-R3. A preferred embodiment of the invention is a method of screening for agonists that bind to BZRP-R3 comprising the steps of: i) screening for test substances that bind to BZRP-R3, as described above and ii) detecting BZRP-R3 biological activity. Preferably, this method is accomplished in an intact cell. Further preferably, the cell is a steroidogenic cell such as a testicular or ovarian cell. Preferably, the biological activity of BZRP-R3 is determined by measuring the concentration of steroid hormones released from the cell before and after exposure to the test substance. Agonists of BZRP-R3 will increase the release of steroid hormones from the cell. Antagonist compounds are those that decrease the amount of BZRP-R3 polypeptides in a cell or decrease the biological activity of BZRP-R3. Another preferred embodiment of the invention is a method of screening for antagonists that bind to BZRP-R3 comprising the steps of: i) screening for test substances that bind to BZRP-R3, as described above and ii) detecting BZRP-R3 biological activity. Preferably, this method is accomplished in an intact cell. Further preferably, the cell is a steroidogenic cell such as a testicular or ovarian cell. Preferably, the biological activity of BZRP-R3 is determined by measuring the concentration of steroid hormones released from the cell before and after exposure to the test substance. Antagonists of BZRP-R3 will decrease the release of steroid hormones from the cell.

Antagonists, able to reduce or inhibit the expression or the activity of the protein of the invention, are useful in the treatment of diseases associated with elevated levels of BZRP-R3, increased cell proliferation or reduced apoptosis, and increased cholesterol transport. Thus, the subject invention provides methods for treating a variety of diseases or disorders, including but not limited to, cancers, especially liver and breast cancer, and portal-systemic encephalopathy. Increased cholesterol transport into the mitochondria of steroidogenic cells results in higher than normal production of steroid hormones such as progesterone, testosterone, and estrogen. Abnormally high levels of steroid hormones lead to disruption of adrenocortical feedback mechanisms and underproduction of trophic hormones from the hypothalamus and pituitary. Inhibition of BZRP-R3 and steroidogenesis may increase levels of trophic hormones such as gonadotropin-releasing hormone.

Alternatively, the subject invention provides a method of treating diseases or disorders associated with decreased levels of BZRP-R3 polypeptides and decreased steroid hormone release with an agonist thereof. Such method comprises the step of contacting a cell with a BZRP-R3 agonist. This method comprises the step of contacting a cell with an agonist of BZRP-R3. Thus, the subject invention provides methods of treating disorders including, but not limited to, schizophrenia, chronic stress, GAD, PD, GSP and PTSD. Other disorders which may be treated by agonists of BZRP-R3 include those associated with decreases in cell proliferation, e.g. developmental retardation. Furthermore, because BZRP-R3 is able to transport cholesterol into cells, BZRP-R3 agonists may also be used to increase cholesterol transport into cells. Diseases associated with cholesterol transport deficiencies include lipoidal adrenal hyperplasia, ovarian cysts, abnormal lipid deposits in steroidogenic cells. Disorders that reflect a requirement for cholesterol for myelin and myelination, include Alzheimer's disease, multiple sclerosis, spinal cord injury, and brain development neuropathy. The methods of treating disorders associated with decreased levels of BZRP-R3 may be practiced by introducing agonists which stimulate the expression or the activity of BZRP-R3.

Additionally, disorders resulting from defective mitochondrial activity may be treated with an agonist to BZRP-R3. Defective mitochondrial activity may alternatively or additionally result in the generation of highly reactive free radicals that have the potential of damaging cells and tissues. These free radicals may include reactive oxygen species (ROS) such as superoxide, peroxynitrite and hydroxyl radicals, and other reactive species that may be toxic to cells and cause apoptosis. For example, oxygen free radical induced lipid peroxidation is a well-established pathogenic mechanism in central nervous system (CNS) injury such as that found in a number of degenerative diseases, and in ischemia (i.e., stroke). Diseases associated with altered mitochondrial function and apoptosis include: Alzheimer's Disease, diabetes mellitus, Parkinson's Disease, Huntington's disease, dystonia, Leber's hereditary optic neuropathy, schizophrenia, mitochondrial encephalopathy, lactic acidosis, and stroke.

A further preferred embodiment includes a method of inhibiting apoptosis of cells in culture. This method comprises the step of contacting a cell in culture with an agonist to BZRP-R3. Such methods are useful for culturing cells that are notoriously undergo apoptosis, such as primary neurons and lymphocytes.

In one embodiment, the level of BZRP-R3 in a cell may be increased by introducing nucleic acids encoding a BZRP-R3 polypeptide or biologically active fragment thereof into a targeted cell type. Vectors useful in such methods are known to those skilled in the art, as are methods of introducing such nucleic acids into target tissues.

Antibodies or other polypeptides capable of reducing or inhibiting the activity of BZRP-R3 may be provided as in isolated and substantially purified form. Alternatively, antibodies or other polypeptides capable of inhibiting or reducing the activity of BZRP-R3 may be recombinantly expressed in the target cell to provide a modulating effect. In addition, compounds which inhibit or reduce the activity of BZRP-R3 may be incorporated into biodegradable polymers being implanted in the vicinity of where drug delivery is desired. For example, biodegradable polymers may be implanted at the site of a tumor or, alternatively, biodegradable polymers containing antagonists/agonists may be implanted to slowly release the compounds systemically. Biodegradable polymers, and their use, are known to those of skill in the art (see, for example, Brem et al. (1991) J. Neurosurg. 74:441-446, which disclosure is hereby incorporated by reference in its entirety).

In another embodiment, the invention provides methods and compositions for detecting the level of expression of the mRNA encoding the protein of the invention. Quantification of mRNA levels of BZRP-R3 may be useful for the diagnosis or prognosis of diseases associated with an altered expression of the protein of the invention. Assays for the detection and quantification of the mRNA encoding BZRP-R3 are well known in the art (see, for example, Maniatis, Fitsch and Sambrook, Molecular Cloning; A Laboratory Manual (1982), or Current Protocols in Molecular Biology, Ausubel, F. M. et al. (Eds), Wiley & Sons, Inc., disclosures of which are hereby incorporated by reference in their entireties).

Polynucleotides probes or primers for the detection of BZRP-R3 mRNA can be designed from the cDNA of SEQ ID NO:17. Methods for designing probes and primers are known in the art. In another embodiment, the subject invention provides diagnostic kits for the detection of the mRNA of the protein of the invention in cells. The kit comprises a package having one or more containers of oligonucleotide primers for detection of the polynucleotides of the invention in PCR assays or one or more containers of polynucleotide probes for the detection of the BZRP-R3 mRNA by in situ hybridization or Northern analysis. Kits may, optionally, include containers of various reagents used in various hybridization assays. The kit may also, optionally, contain one or more of the following items: polymerization enzymes, buffers, instructions, controls, or detection labels. Kits may also, optionally, include containers of reagents mixed together in suitable proportions for performing the hybridization assay methods in accordance with the invention. Reagent containers preferably contain reagents in unit quantities that obviate measuring steps when performing the subject methods.

In another embodiment, the invention relates to methods and compositions for detecting and quantifying the level of the protein of the invention present in a particular biological sample. These methods are useful for the diagnosis or prognosis of diseases associated with altered levels of the protein of the invention. Diagnostic assays to detect the protein of the invention may comprise a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract.

Assays for the quantification of BZRP-R3 polypeptides may be performed according to methods well known in the art. Typically, these assays comprise the steps of: contacting the sample with a ligand of the protein of the invention or an antibody (polyclonal or monoclonal) that specifically recognizes the protein of the invention or a fragment thereof and detecting the complex formed between the protein of the invention present in the sample and the ligand or antibody. Fragments of the ligands and antibodies may also be used in the binding assays, provided these fragments are capable of specifically interacting with BZRP-R3 polypeptides. Further, ligands and antibodies which bind to BZRP-R3 may be labeled according to methods known in the art. Labels which are useful in the subject invention include, but are not limited to, enzymes labels, radioisotopic labels, paramagnetic labels, and chemiluminescent labels. Common techniques are described by Kennedy, J. H., et al. (1976) Clin. Chim. Acta 70:1-31; and Schurs, A. H. et al. (1977) Clin. Chim. Acta 81: 1-40, disclosures of which are hereby incorporated by reference in their entireties.

The subject invention also provides methods and compositions for the identification of metastatic tumor masses. In this aspect of the invention, the polypeptide or antibody that specifically binds a BZRP-R3 polypeptide or fragment thereof may be used as a marker for the identification of the metastatic tumor mass. Metastatic tumors originating from the breast or liver may overexpress BZRP-R3 polypeptides, whereas newly forming tumors, or those originating from other tissues are not expected to bear BZRP-R3.

Protein of SEQ ID NO:20 (Internal Designation Clone 646762_181-21-2-0-A3-F)

The cDNA of Clone 646762_181-21-2-0-A3-F (SEQ ID NO:19) encodes Benzodiazepine Receptor 4 (BZRP-R4) protein of SEQ ID NO:20, comprising the amino acid sequence:

MRLQGAIFVLLPHLGPILVWLFTRDHMS-
GLCEGPRMLSWCPFYKVLLLVQTAIYSVVGYA
SYLVWKDLGGGLGWPLALPLG-
LYAVQLTISWTVLVLFFTVHNPGLA-
LLHLLLLYGLVVS TALIWHPNKLAALLLLPY-
LAWLTVTSALTYHLWRDSLCPVHQPQPTEKSD.

Accordingly, it will be appreciated that all characteristics and uses of the polypeptides of SEQ ID NO:20 described throughout the present application also pertain to the polypeptides encoded by the human cDNA included in Clone 646762_181-21-2-0-A3-F. In addition, it will be appreciated that all characteristics and uses of the polynucleotides of SEQ ID NO:19 described throughout the present application also pertain to the nucleic acids comprising the human cDNA in Clone 646762_181-21-2-0-A3-F. A preferred embodiment of the invention is directed toward the compositions of SEQ ID NO:19, SEQ ID NO:20 and Clone 646762_181-21-2-0-A3-F. Also preferred are polypeptide fragments having a biological activity as described herein and the polynucleotides encoding the fragments.

The protein of SEQ ID NO:20, BZRP-R4, is a novel polymorphic variant of human peripheral benzodiazepine receptor/isoquinoline binding protein (PBR/IBP) (accession numbers Q9Y531). BZRP-R4 displays five transmembrane-spanning segments: LQGAIFVLLPHLGPILVWLFT (SEQ ID NO: 67), VLLLVQTAIYSVVGYASYLVW (SEQ ID NO:68), LYAVQLTISWTVLVLFFTVHIN (SEQ ID NO:73), LALLHLLLLYGLVVSTALIWH (SEQ ID NO:74), and LAALLLLPYLAWLTVTSALTY (SEQ ID NO:71). Accordingly, some embodiments of the present invention relate to polypeptides comprising the transmembrane domains. Moreover, BZRP-R4 displays a stretch of 11 amino acids (VTSALTYHLWR) (SEQ ID NO:72) that bind cholesterol. Accordingly, a preferred embodiment of the present invention comprises the amino acids of the cholesterol recognition/interaction domain and the polynucleotides encoding the same.

BZRP-R4 is capable of binding benzodiazepine and imidazopyridine derivatives, but is distinct from the GABA neurotransmitter receptor. BZRP-R4 polypeptides are most abundant in steroidogenic cells and are found primarily on outer mitochondrial membranes. BZRP-R4 is associated with a 34-kDa pore-forming, voltage-dependent anion channel protein located on the outer/inner mitochondrial membrane contact sites. Ligands of BZRP-R4, upon binding to the receptor, simulate steroid synthesis in steroidogenic cells in vitro and in vivo. BZRP-R4 stimulates steroid formation by increasing the rate of cholesterol transfer from the outer to the inner mitochondrial membrane.

In addition to its role in mediating cholesterol movement across membranes, BZRP-R4 has been implicated in several other physiological functions, including cell growth and differentiation, chemotaxis, mitochondrial physiology, porphyrin and heme biosynthesis, immune response, and anion transport. In addition, BZRP-R4 agonists are potent anti-apoptotic compounds.

BZRP-R4 is associated with stress and anxiety disorders. BZRP-R4 plays a role in the regulation of several stress systems such as the HPA axis, the sympathetic nervous system, the renin-angiotensin axis, and the neuroendocrine axis. In these systems, acute stress typically leads to increases in BZRP-R4 density, whereas chronic stress typically leads to decreases in BZRP-R4 density. For example, in Generalized Anxiety Disorder (GAD), Panic Disorder (PD), Generalized Social Phobia (GSP), and Post-Traumatic Stress Disorders (PTSD), BZRP-R4 density is typically decreased. BZRP-R4 is expressed glial cells in the brain. Furthermore, BZRP-R4 expression is increased in neurodegenerative disorders and after neurotoxic and traumatic-ischemic brain damage. BZRP-R4 expression is decreased in chronic schizophrenics, suggesting that the decreased density of BZRP-R4 in the brain may be involved in the pathophysiology of schizophrenia. However, BZRP-R4 is higher than normal in autopsied brain tissue from PSE patients (Portal-Systemic Encephalopathy patients).

BZRP-R4 increases mitochondrial activity and prevents apoptosis and is therefore implicated in tumor cell proliferation. BZRP-R4 is preferentially expressed in liver and breast cancers. Further, BZRP-R4 is useful as a tool/marker for detection, diagnosis, prognosis and treatment of cancer.

Many ligands have been described that bind to BZRP-R4 with various affinities. Some benzodiazepines, Ro 5-4864 [4-chlorodiazepam], diazepam and structurally related compounds, are potent and selective PBR ligands. Exogenous ligands also include 2-phenylquinoline carboxamides (PK11195 series), imidazo [1,2-a]pyridine-3-acetamides (Alpidem series), pyridazine, and isoquinilone derivatives. Some endogenous compounds, including porphyrins and diazepam binding inhibitor (DBI), bind to BZRP-R4.

A preferred aspect of the invention is a host cell recombinant for polynucleotides encoding a BZRP-R4 polypeptide or a biologically active fragment thereof. An additional preferred aspect is a host cell recombinant for polynucleotides capable of directing BZRP-R4 expression. Preferably, the polynucleotides capable of directing BZRP-R4 expression are located in the 5' regulatory region of the BZRP-R4 gene. Further preferably, these polynucleotides are located within 500 base pairs of the BZRP-R4 coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. BZRP-R4 protein produced by said host cell may be used for in vitro detection and purification methods as well as diagnosis and in vivo applications.

A preferred embodiment of the invention relates to compositions and methods using the protein of the invention or fragment thereof to label mitochondria in order to visualize any change in number, topology or morphology of this organelle, for example in association with a mitochondria-related human disorder, such as hereditary spastic paraplegia, neuroleptic malignant syndrome (NMS), the Rett syndrome, Alpers disease, or mitochondrial encephalomyopathies. For example, the protein may be rendered easily detectable by inserting the cDNA encoding the protein of the invention into a eukaryotic expression vector in frame with a sequence encoding a tag sequence. Eukaryotic cells expressing the tagged protein of the invention may also be used for the in vitro screening of drugs or genes capable of treating any mitochondria-related disease or conditions.

A preferred embodiment of the invention is a method to detect mitochondria comprising the step of contacting an antibody specific for BZRP-R4 with a cell. Preferably, the cell is fixed or otherwise permeable to antibodies. Preferably, the antibody is labeled with any detectable moiety including, but are not limited to, a fluorescent label, a radioactive atom, a paramagnetic ion, biotin, a chemiluminescent label or a label which can be detected through a secondary enzymatic or binding step. The invention further provides a method of diagnosing mitochondria-related disease or conditions, for example, but not limited to, those listed above, and distinguishing such diseases from other diseases.

In another embodiment, the protein of the invention may be used to target heterologous compounds (polynucleotides) to steroidogenic cells and/or the mitochondria. Such recombinant cDNA may be introduced, for example, using in any vector, viral or non-viral, and viral vectors can be but not limited to retroviral, adenoviral, and adeno-associated vectors. For example, these heterologous polynucleotides may be used to deliver nucleic acids for mitochondrial gene therapy, i.e. to replace a defective mitochondrial gene and/or to inhibit the deleterious expression of a mitochondrial gene.

Another preferred embodiment of the invention is a method of screening for compounds that modulate the expression of BZRP-R4. This method comprises the steps of i) contacting a cell with a test compound and ii) comparing the level of BZRP-R4 polypeptides in a cell after exposure to the test compound to that of an untreated control cell. The level of BZRP-R4 polypeptides may be inferred by detecting mRNA for BZRP-R4 by methods common to the art such as Northern blotting or RT-PCR. The level of BZRP-R4 polypeptides may also be detected by antibody-based methods common to the art such as Western blotting or immunofluorescence. Test compounds that increase BZRP-R4 expression are useful as agonists, as discussed herein. Test compounds that decrease BZRP-R4 expression are useful as antagonists, as discussed herein.

Antagonists of BZRP-R4 include agents which decrease the levels of expressed mRNA encoding the protein of SEQ ID NO:20. These include, but are not limited to, RNAi, one or more ribozymes capable of digesting the protein of the invention, or antisense oligonucleotides capable of hybridizing to mRNA encoding BZRP-R4. Antisense oligonucleotides can be administrated as DNA, RNA, as DNA entrapped in proteoliposomes containing viral envelope receptor proteins [Kanoda, Y. et al. (1989) Science 243: 375, which disclosure is hereby incorporated by reference in its entirety] or as part of a vector which can be expressed in the target cell to provide antisense DNA or RNA. Vectors which are expressed in particular cell types are known in the art. Alternatively, the DNA can be injected along with a carrier. A carrier can be a protein such as a cytokine, for example interleukin 2, or polylysine-glycoprotein carriers. Carrier proteins, vectors, and methods of making and using polylysine carrier systems are known in the art. Alternatively, nucleic acids encoding antisense molecules may be coated onto gold beads and introduced into the skin with, for example, a gene gun [Ulmer, J. B. et al. (1993) Science 259:1745, which disclosure is hereby incorporated by reference in its entirety].

A preferred embodiment of the invention is a method of screening for compounds that bind to BZRP-R4 polypeptides. Such compounds are useful for developing agonists and antagonists of BZRP-R4 activity. This method comprises the steps of: i) contacting a BZRP-R4 polypeptide or fragment thereof with a test compound under conditions that allow binding to occur and ii) detecting binding of said test compound. Binding may be detected by any method common to the art such as competition with a labeled antibody specific for BZRP-R4 or by direct labeling of each test substance. In one example of such a method, a polynucleotide encoding a BZRP-R4 polypeptide or a biologically active fragment thereof is transformed into a eukaryotic or prokaryotic host cell. The transformed cells may be viable or fixed. Drugs or compounds which are candidates for binding BZRP-R4 polypeptides are screened against such transformed cells in binding assays well known to those skilled in the art. Alternatively, assays such as those taught in Geysen H. N., WO Application 84/03564, published on Sep.

13, 1984, and incorporated herein by reference in its entirety, may be used to screen for peptide compounds which demonstrate binding affinity for BZRP-R4 polypeptides or fragments thereof. In another embodiment, competitive drug screening assays using neutralizing antibodies specifically compete with a test compound for binding to BZRP-R4 polypeptides or fragments thereof. Preferred test compounds are those included in the benzodiazepine class, such as diazepam (i.e., valium), triazolobenzodiazepine, and adinazolam, as well as modified versions thereof. Further preferred test compounds are in the imidazopyridine and isoquinilone classes. Each test compound may additionally be excluded individually or as a class.

A variety of drug screening techniques may be employed. In this aspect of the invention, BZRP-R4 polypeptide or fragments thereof, may be free in solution, affixed to a solid support, recombinantly expressed on or chemically attached to a cell surface, or located intracellularly. The formation of binding complexes between BZRP-R4 polypeptides or fragments thereof, and the compound being tested, may then be measured as described.

Another embodiment of the subject invention provides compositions and methods of selectively modulating the activity of the protein of the invention. Modulation of BZRP-R4 allows for the successful prevention, treatment, or management of disorders or biochemical abnormalities associated with BZRP-R4. Agonist compounds are those that increase the amount of BZRP-R4 polypeptides in a cell or increase the biological activity of BZRP-R4. A preferred embodiment of the invention is a method of screening for agonists that bind to BZRP-R4 comprising the steps of: i) screening for test substances that bind to BZRP-R4, as described above and ii) detecting BZRP-R4 biological activity. Preferably, this method is accomplished in an intact cell. Further preferably, the cell is a steroidogenic cell such as a testicular or ovarian cell. Preferably, the biological activity of BZRP-R4 is determined by measuring the concentration of steroid hormones released from the cell before and after exposure to the test substance. Agonists of BZRP-R4 will increase the release of steroid hormones from the cell. Antagonist compounds are those that decrease the amount of BZRP-R4 polypeptides in a cell or decrease the biological activity of BZRP-R4. Another preferred embodiment of the invention is a method of screening for antagonists that bind to BZRP-R4 comprising the steps of: i) screening for test substances that bind to BZRP-R4, as described above and ii) detecting BZRP-R4 biological activity. Preferably, this method is accomplished in an intact cell. Further preferably, the cell is a steroidogenic cell such as a testicular or ovarian cell. Preferably, the biological activity of BZRP-R4 is determined by measuring the concentration of steroid hormones released from the cell before and after exposure to the test substance. Antagonists of BZRP-R4 will decrease the release of steroid hormones from the cell.

Antagonists, able to reduce or inhibit the expression or the activity of the protein of the invention, are useful in the treatment of diseases associated with elevated levels of BZRP-R4, increased cell proliferation or reduced apoptosis, and increased cholesterol transport. Thus, the subject invention provides methods for treating a variety of diseases or disorders, including but not limited to cancers, especially liver and breast cancer, and portal-systemic encephalopathy. Increased cholesterol transport into the mitochondria of steroidogenic cells results in higher than normal production of steroid hormones such as progesterone, testosterone, and estrogen. Abnormally high levels of steroid hormones lead to disruption of adrenocortical feedback mechanisms and underproduction of trophic hormones from the hypothalamus and pituitary. Inhibition of BZRP-R4 and steroidogenesis may increase levels of trophic hormones such as gonadotropin-releasing hormone.

Alternatively, the subject invention provides a method of treating diseases or disorders associated with decreased levels of BZRP-R4 polypeptides and decreased steroid hormone release with an agonist thereof. Such method comprises the step of contacting a cell with a BZRP-R4 agonist. This method comprises the step of contacting a cell with an agonist of BZRP-R4. Thus, the subject invention provides methods of treating disorders including, but not limited to, schizophrenia, chronic stress, GAD, PD, GSP and PTSD. Other disorders which may be treated by agonists of BZRP-R4 include those associated with decreases in cell proliferation, e.g. developmental retardation. Furthermore, because BZRP-R4 is able to transport cholesterol into cells, BZRP-R4 agonists may also be used to increase cholesterol transport into cells. Diseases associated with cholesterol transport deficiencies include lipoidal adrenal hyperplasia, ovarian cysts, abnormal lipid deposits in steroidogenic cells. Disorders that reflect a requirement for cholesterol for myelin and myelination, include Alzheimer's disease, multiple sclerosis, spinal cord injury, and brain development neuropathy. The methods of treating disorders associated with decreased levels of BZRP-R4 may be practiced by introducing agonists which stimulate the expression or the activity of BZRP-R4.

Additionally, disorders resulting from defective mitochondrial activity may be treated with an agonist to BZRP-R4. Defective mitochondrial activity may alternatively or additionally result in the generation of highly reactive free radicals that have the potential of damaging cells and tissues. These free radicals may include reactive oxygen species (ROS) such as superoxide, peroxynitrite and hydroxyl radicals, and other reactive species that may be toxic to cells and cause apoptosis. For example, oxygen free radical induced lipid peroxidation is a well-established pathogenic mechanism in central nervous system (CNS) injury such as that found in a number of degenerative diseases, and in ischemia (i.e., stroke). Diseases associated with altered mitochondrial function and apoptosis include: Alzheimer's Disease, diabetes mellitus, Parkinson's Disease, Huntington's disease, dystonia, Leber's hereditary optic neuropathy, schizophrenia, mitochondrial encephalopathy, lactic acidosis, and stroke.

A further preferred embodiment includes a method of inhibiting apoptosis of cells in culture. This method comprises the step of contacting a cell in culture with an agonist to BZRP-R4. Such methods are useful for culturing cells that are notoriously undergo apoptosis, such as primary neurons and lymphocytes.

In one embodiment, the level of BZRP-R4 in a cell may be increased by introducing nucleic acids encoding a BZRP-R4 polypeptide or biologically active fragment thereof into a targeted cell type. Vectors useful in such methods are known to those skilled in the art, as are methods of introducing such nucleic acids into target tissues.

Antibodies or other polypeptides capable of reducing or inhibiting the activity of BZRP-R4 may be provided as in isolated and substantially purified form. Alternatively, antibodies or other polypeptides capable of inhibiting or reducing the activity of BZRP-R4 may be recombinantly expressed in the target cell to provide a modulating effect. In addition, compounds which inhibit or reduce the activity of BZRP-R4 may be incorporated into biodegradable polymers being implanted in the vicinity of where drug delivery is desired. For example, biodegradable polymers may be implanted at the site of a tumor or, alternatively, biodegradable polymers containing antagonists/agonists may be implanted to slowly release the compounds systemically. Biodegradable polymers, and their use, are known to those of skill in the art (see, for example, Brem et al. (1991) J. Neurosurg. 74:441-446, which disclosure is hereby incorporated by reference in its entirety).

In another embodiment, the invention provides methods and compositions for detecting the level of expression of the mRNA encoding the protein of the invention. Quantification of mRNA levels of BZRP-R4 may be useful for the diagnosis or prognosis of diseases associated with an altered expression of the protein of the invention. Assays for the detection and quantification of the mRNA encoding BZRP-R4 are well known in the art (see, for example, Maniatis, Fitsch and Sambrook, Molecular Cloning; A Laboratory Manual (1982), or Current Protocols in Molecular Biology, Ausubel, F. M. et al. (Eds), Wiley & Sons, Inc., disclosures of which are hereby incorporated by reference in their entireties).

Polynucleotides probes or primers for the detection of BZRP-R4 mRNA can be designed from the cDNA of SEQ ID NO:19. Methods for designing probes and primers are known in the art. In another embodiment, the subject invention provides diagnostic kits for the detection of the mRNA of the protein of the invention in cells. The kit comprises a package having one or more containers of oligonucleotide primers for detection of the polynucleotides of the invention in PCR assays or one or more containers of polynucleotide probes for the detection of the BZRP-R4 mRNA by in situ hybridization or Northern analysis. Kits may, optionally, include containers of various reagents used in various hybridization assays. The kit may also, optionally, contain one or more of the following items: polymerization enzymes, buffers, instructions, controls, or detection labels. Kits may also, optionally, include containers of reagents mixed together in suitable proportions for performing the hybridization assay methods in accordance with the invention. Reagent containers preferably contain reagents in unit quantities that obviate measuring steps when performing the subject methods.

In another embodiment, the invention relates to methods and compositions for detecting and quantifying the level of the protein of the invention present in a particular biological sample. These methods are useful for the diagnosis or prognosis of diseases associated with altered levels of the protein of the invention. Diagnostic assays to detect the protein of the invention may comprise a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract.

Assays for the quantification of BZRP-R4 polypeptides may be performed according to methods well known in the art. Typically, these assays comprise the steps of: contacting the sample with a ligand of the protein of the invention or an antibody (polyclonal or monoclonal) that specifically recognizes the protein of the invention or a fragment thereof and detecting the complex formed between the protein of the invention present in the sample and the ligand or antibody. Fragments of the ligands and antibodies may also be used in the binding assays, provided these fragments are capable of specifically interacting with BZRP-R4 polypeptides. Further, ligands and antibodies which bind to BZRP-R4 may be labeled according to methods known in the art. Labels which are useful in the subject invention include, but are not limited to, enzymes labels, radioisotopic labels, paramagnetic labels, and chemiluminescent labels. Typical techniques are described by Kennedy, J. H., et al. (1976) Clin. Chim. Acta 70:1-31; and Schurs, A. H. et al. (1977) Clin. Chim. Acta 81: 140, disclosures of which are hereby incorporated by reference in their entireties.

The subject invention also provides methods and compositions for the identification of metastatic tumor masses. In this aspect of the invention, the polypeptide or antibody that specifically binds a BZRP-R4 polypeptide or fragment thereof may be used as a marker for the identification of the metastatic tumor mass. Metastatic tumors which originated from the breast or liver may overexpress BZRP-R4 polypeptides, whereas newly forming tumors, or those originating from other tissues are not expected to bear BZRP-R4.

Protein of SEQ ID NO:22 (Internal Designation Clone 420594 145-19-4-0-E7-F)

The cDNA of Clone 420594 145-19-4-0-E7-F (SEQ ID NO:21) encodes the 106 amino acid Scolakin protein of SEQ ID NO:22 comprising the amino acid sequence: MPFLDIQKRFGLNIDRWLTIQSCEQPYK-MAGRCHAFEKEWIECAHGIGYTRAEKECKIEYD DFVECLLRQKTMRRAGTIRKQRDK-LIKEGKYTPPPHMGKGEPWP. Accordingly, it will be appreciated that all characteristics and uses of polypeptides of SEQ ID NO:22 described throughout the present application also pertain to the polypeptides encoded by the human cDNA included in Clone 420594 145-19-4-0-E7-F. In addition, it will be appreciated that all characteristics and uses of the polynucleotides of SEQ ID NO:21 described throughout the present application also pertain to the nucleic acids comprising the human cDNA in Clone 420594 145-19-4-0-E7-F. Also preferred are fragments having a biological activity as described therein and the polynucleotides encoding the fragments.

Scolakin, the protein of SEQ ID NO:22, represents a novel variant form of the 15 kilodalton NADH dehydrogenase subunit NDUFS5 (Genbank entry AF020352).

NADH dehydrogenase (NADH:ubiquinone oxidoreductase, complex I) is the first multisubunit inner membrane protein complex in a chain of three complexes that make up the mitochondrial electron transport chain. The mitochondrial electron transport chain is responsible for the transport of electrons from NADH to oxygen and the coupling of this oxidation to the synthesis of ATP (oxidative phosphorylation) which provides the energy source for driving a cell's many energy-requiring reactions. NADH dehydrogenase accomplishes the first step in this process by accepting two electrons from NADH and passing them through a flavin molecule to ubiquinone, which transfers the electrons to the second enzyme complex in the chain. It contains a number of prosthetic groups which are involved in the transfer of electrons, namely, flavin mononucleotide (FMN) and at least six iron-sulphur clusters (binuclear and tetranuclear). NADH dehydrogenase is the largest of the three complexes with an estimated mass of 800 kDa comprising about 41 polypeptides of widely varying size and composition. Seven of these complex I polypeptides are encoded by mitochondrial DNA while the remaining are nuclear gene products that are imported into the mitochondria. The polypeptide composition of NADH dehydrogenase is very similar in a variety of mammalian species including rat, rabbit, cow, and man. In man, deficiency of NADH dehydrogenase is one of the most frequent causes of human encephalomyopathies. Defects and altered expression of this enzyme have also been reported to be associated with other disease conditions, i.e., neurodegenerative diseases and cancer. In addition, NADH dehydrogenase reduction of the quinone moiety in chemotherapeutic agents such as doxorubicin is believed to contribute to the antitumor activity and/or mutagenicity of these drugs. Defects in mitochondrial-encoded subunits of complex I have been described. However a relatively small percentage of human complex I deficiency is associated with mitochondrial DNA mutations which suggests that most of the corresponding mutations affect expression or activity of nuclear-encoded subunits of complex I.

Scolakin, the protein of the invention, belongs to the category of the nuclear-encoded subunits of complex I. This subunit is part of the iron-sulphur protein fraction (IP) during complex I purification and it is believed to participate to the redox reactions catalysed by the iron-sulphur centers of this complex. NDUFS5 contains four cysteine residues that form one of the iron-sulphur centers that function in electron transport. Interestingly, Scolakin contains a fifth cysteine due to a glycine to cysteine substitution at position 23 on SEQ ID NO:22. Scolakin is widely expressed with a relatively higher expression in heart, brain, skeletal muscle, liver, kidney and fetal heart and brain, all tissues with high metabolic activities, which are often clinically affected in complex I-deficient patients. In addition, Scolakin expression is high in cancerous tissues and immortalized cells lines, which also have high metabolic requirements. Scolakin plays a role in myopathies, neurodegenerative diseases and cancer.

An embodiment of the invention is directed to a composition comprising a Scolakin polypeptide sequence of SEQ ID NO:22.

A further embodiment of the invention is directed to a composition comprising a Scolakin polypeptide fragment having biological activity.

A further embodiment of the invention is directed to a composition comprising a polynucleotide sequence of SEQ ID NO:21 encoding a Scolakin polypeptide.

A further embodiment of the invention is directed to a composition comprising a polynucleotide sequence encoding a Scolakin polypeptide fragment having biological activity.

A further embodiment of the invention is directed to a method of screening test substances for modulators of Scolakin expression comprising the steps of: i) contacting a cell with a substance to be tested; and ii) comparing Scolakin expression in the cell after exposure to the test substance to that of an untreated control cell.

In one embodiment, a sequence encoding SEQ ID NO:22 bearing G to T and C to T substitutions at nucleotide positions 152 and 398 of SEQ ID NO:21 corresponding to positions 23 and 105, and resulting in the substitution of a glycine residue by a cysteine at position 23 and an arginine residue by a tryptophane at position 105, respectively, can be used for DNA genotyping. Genotyping this locus could be of interest, e.g., in DNA fingerprinting for paternity studies or forensic analyses. It could also be used for genetic association studies, preferably in pathologies relating to mitochondrial disorders, especially those with isolated complex I deficiency.

In another embodiment, the polynucleotide sequence of the invention can be used in pharmacogenomic applications in order to aid in the choice of the ideal drug (e.g. an agonist or an antagonist of Scolakin), or dosage of a drug, for the treatment of a condition or disease in a patient. For example, in one embodiment, the invention provides a method of genotyping a patient to determine the identity of the nucleotides encoding the amino acids at positions 23 and 105 of Scolakin, and administering to the patient a drug or a dosage of the drug that has been established to be preferentially efficacious in those with cysteine and tryptophane residues at positions 23 and 105, respectively (e.g. because of preferential binding of the drug to the isoform of the protein with cysteine and tryptophane at these positions). In another embodiment, the patient is genotyped for the nucleotides encoding amino acid positions 23 and 105, a drug is not administered, e.g. because side effects are known to be associated with the administration of the drug to individuals with cysteine and tryptophane at positions 23 and 105, respectively.

A preferred aspect of the invention is a host cell recombinant for polynucleotides encoding a Scolakin polypeptide or a biologically active fragment thereof. An additional preferred aspect is a host cell recombinant for polynucleotides capable of directing Scolakin expression. Preferably, the polynucleotides capable of directing Scolakin expression are located in the 5' regulatory region of the Scolakin gene. Further preferably, these polynucleotides are located within 500 base pairs of the Scolakin coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. Scolkin protein produced by said host cell may be used for in vitro detection and purification methods as well as diagnosis and in vivo applications.

Another embodiment relates to methods of producing Scolakin polypeptides. The protein of the invention can be produced in host cells that have been transfected with an appropriate expression vector comprising a nucleic acid sequence coding for the protein of the invention. Introduction into a host cell of such expression vector for Scolakin can be performed in a variety of ways, including but not limited to calcium or lithium chloride treatment, electroporation, or lipofection. Any of a wide variety of expression systems can be used to provide the recombinant proteins. Suitable expression vehicles include, but are not limited to plasmids, viral particles or baculovirus for insect cells. The expression vehicle can be integrated into the host cell genome. Optionally, an inducible expression vector can be used to achieve tight controlled expression of the gene in the host cell. The recombinant protein can be recovered from the host cell and purified by any technique well known to those skilled in the art. Preferably, an antibody directed against the protein of the invention or part thereof can be bound to a chromatographic support to form an affinity chromatography column. Alternatively, Scolakin can be chemically synthesized using solid-phase techniques.

In a further embodiment, the invention provides compositions and methods using Scolakin or fragments thereof to label mitochondria in order to visualize any change in number, topology or morphology of this organelle, for example in association with a mitochondria-related human disorder, such as mitochondrial encephalomyopathies, Alpers disease, hereditary spastic paraplegia, neuroleptic malignant syndrome (NMS) or the Rett syndrome. For example, the protein may be rendered easily detectable by inserting the cDNA encoding the protein of the invention into a eukaryotic expression vector in frame with a sequence encoding a tag sequence. A preferred embodiment of the invention is a method to detect mitochondria comprising the step of contacting a monoclonal or polyclonal antibody specific for Scolakin with a cell. Preferably, the cell is fixed or otherwise permeable to antibodies. Preferably, the antibody is primarily or secondarily linked to a fluorescent, radioactive, or otherwise detectable compound.

In another embodiment, the polynucleotide of SEQ ID NO:21 or fragments thereof may be used to target recombinant DNA molecules to the mitochondria. For instance, a chimeric polynucleotide composed of the polynucleotide sequence of the invention recombinantly or chemically fused to a polynucleotide of therapeutic interest would allow the delivery of the therapeutic polynucleotide specifically to the mitochondria. Such chimeric molecules would be of particular interest in gene therapy to restore or modulate mitochondrial activities for the treatment and/or the prevention of disorders due to mitochondrial dysfunction, including, but not limited to, those mentioned above.

In another embodiment, the invention provides compositions and methods for detecting the level of expression of the mRNA encoding the protein of the invention in a mammal, preferably a human. Quantification of mRNA levels of Scolakin may be useful for the diagnosis of diseases or conditions correlated with abnormal expression of the protein, or to monitor regulation of Scolakin during therapeutic intervention as described herein. Assays for the detection and quantification of mRNA are well known in the art. Preferred method comprises the steps of: isolating RNA from a biological sample of a subject, measuring Scolakin mRNA level by quantitative RT-PCR, and comparing the expression in the subject sample to that of a control sample. Polynucleotide probes or primers used for the detection of Scolakin mRNA by hybridization or PCR amplification may be designed from the polynucleotide of SEQ ID NO:21 by methods well known in the art.

In another embodiment, the invention relates to methods and compositions for detecting Scolakin and quantifying its level of expression in a biological sample. These methods may be useful for the diagnosis of conditions or diseases characterized by altered or abnormal expression of the protein of the invention, or in assays to monitor subjects being treated with Scolakin, agonists or antagonists. A preferred method comprises contacting an antibody which specifically binds to Scolakin with a biological sample from a mammalian subject, preferably human, and determining the level of Scolakin in the subject sample compared to a control level representative of a healthy subject, wherein an altered or abnormal level of Scolakin in the subject sample relative to the control level indicates that the subject has the disease or is at an elevated risk of developing the disease. The antibody used can be either monoclonal or polyclonal and can be labeled directly or indirectly for quantification of immune complexes by methods well known to those skilled in the art, for example by ELISA or radioimmunoassays. Diagnostic assays to detect the protein of the invention may comprise a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract.

Another embodiment of the invention is directed to a method to treat or prevent a defect in mitochondrial complex I of a mammal, preferably a human, comprising administering to said mammal the protein of the invention or fragments thereof or polynucleotides encoding the present protein. Expression vectors derived from retroviruses, adenovirus, herpes, or vaccinia viruses may be used for the delivery of the polynucleotide sequences of the invention to the targeted organ, tissue or cell populations. Many methods for introducing vectors into cells or tissues are available and equally suitable for use either in vivo or ex vivo. For ex vivo therapy, vectors may be introduced into stem cells taken from the subject and clonally propagated for autologous transplant back into the same subject. Delivery by transfection and liposome injections may be achieved using methods which are well known in the art. Pharmaceutical compositions comprising Scolakin polypeptides can be administered alone or in combination with at least one other agent, such as stabilizing compound, which may be administered in any sterile biocompatible carrier. They may be administered by any number of routes including, but not limited to, oral, intravenous, intramuscular, intra-arterial, intramedullary, intrathecal, intraventicularly, transdermal, subcutaneous, intranasal, enteral or rectal means. The compositions may be administered to the subject alone or in combination with other agents, drugs or hormones. Preferably, the diseases associated with defective complex I activity to be treated or prevented using the present method include, but are not limited to, fatal neonatal lactic acidosis, myopathy with exercise intolerance and lactic acidosis, MELAS (mitochondrial myopathy, encephalopathy, lactic acidosis, and stroke-like episodes), MERFF (myoclonus epilepsy, and ragged red fibres), encephalomyopathy of childhood and adult life, Leigh syndrome, Alpers and Parkinson's diseases.

An embodiment of the invention provides for a method of screening test substances for modulators of Scolakin expression. This method comprises the steps of: i) contacting a cell with a test substance; and ii) comparing Scolakin expression in the cell after exposure to the test substance to that of an unexposed control cell. Scolakin expression is determined by methods common to the art or included herein, by detecting Scolakin polynucleotides or polypeptides. An example of this method comprises the steps of: i) culturing two equivalent cell samples; ii) adding a test substance to one of the cultures and not the other; iii) harvesting both cultures at a specified time; iv) purifying the mRNA from each sample of cells; v) comparing the level of Scolakin mRNA in each sample by Northern blot, RT-PCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) comparing the level of Scolakin polypeptides in each sample by enzyme-linked immunoabsorbent assay (ELISA), western blot, radioimmunoassay (RIA), or another method common to the art. The invention provides for design and use of specific antibodies and antibody fragments, as discussed herein. Substances that increase Scolakin expression (agonists or activators) may be used to increase complexe I activity. Substances that decrease Scolakin expression (antagonists or inhibitors) may be used to treat or prevent cancers. Methods utilizing Scolakin agonists and antagonists are included herein.

A preferred embodiment of the invention provides a method of screening for test substances that bind Scolakin polypeptides. This method comprises the steps of: i) contacting a test substance with a Scolakin polypeptide or fragment thereof under conditions that allow binding; and ii) detecting the binding of the test substance by methods common to the art (e.g., competitive antibody-based methods such as coimmunopreciptation and Western blotting). Included in this method are test substances that are conjugated to an antibody, antibody fragment, cell-type specific ligand or a portion thereof.

A further preferred embodiment of the invention provides a method of screening test substances that bind to Scolakin for agonists of Scolakin activity, comprising: i) contacting a cell with the substance to be tested; and ii) comparing Scolakin biological activity after exposure to the test substance to that of an unexposed control cell. Measure of Scolakin biological activity may be assessed indirectly by measuring the enzymatic activity of complex I as described by Loeffen et al. (1999, J. Inher. Metab. Dis. Vol. 22, pp 19-28 which disclosure is hereby incorporated by reference in its entirety), an increased in complex I activity in the test sample compared to the control sample being indicative of an activating effect of the test substance on Scolakin.

A further preferred embodiment of the invention provides a method of screening test substances that bind to Scolakin for antagonists of Scolakin activity. This method comprises the steps of: i) contacting a cell with a test substance; and ii) comparing Scolakin biological activity after exposure to the test substance to that of an unexposed control cell. Detection of Scolakin biological activity may be detected by measuring complex I activity as mentioned above, a decrease in complex I activity in the test sample compared to the control sample being indicative of an inhibitory effect of the test substance on Scolakin activity.

It is yet another object of the invention to provide methods of treating or preventing cancers associated with increased complex I activity. This can be achieved by decreasing Scolakin expression or activity in vivo using antibodies, ribozymes or antisense vectors or oligonucleotides. Alternatively, an antagonist of Scolakin activity or expression isolated as described above can be used, such method comprising the step of administering to a subject an antagonist of Scolakin expression or activity. Scolakin antagonists in a physiologically acceptable solution may be delivered by methods common to the art, such as orally or parenterally. Preferably, the Scolakin antagonist is delivered to a specific cell type, for example, by conjugating the antagonist to a cell-type specific targeting moiety (e.g., a ligand or antibody fragment). This method is useful for prevention and treatment of cancers including, but not limited to, cancers of the heart, ovaries, colon, kidney, bladder, prostate, pancreas, brain, stomach, breast, lung, liver and leukemias.

Protein of SEQ ID NO:24 (Internal Designation Clone 119658_105-067-2-0-H4F_1)

The cDNA of Clone 119658_105-067-2-0-H4-F_1 (SEQ ID NO:23) encodes the Docking Of Vesicles (DOV) protein of SEQ ID NO:24, comprising the amino acid sequence: MASRSSDKDGDSVHTASEVPLTPRTNSP-DGRRSSSDTSKSTYSLTRRISSLESRRPSSPLIDIK PIEFGVLSAKKEPIQPSVLRRTYNPDDY-FRKFEPHLYSLDSNSDDVDSLTDEEILSKYQLGM QHFSTQYDLLHNHLTVRVIEARDLPP-PISHDGSRQDMAHSNPYVKICLLPDQKNSKQTGV KRKTQKPVFEERYTFEIPFLEAQR-RTLLLTVVDFDKFSRHCVIGKVSV-PLCEVDLVKGGHW WKALIPSSQNEVELGELLLSL-NYLPSAGRLNVDVIRAKQLLQTDVSQGSDPFVKIQ LVHGL KLVKTKCKTSFLRGTIDPFYNESFS-FKVPQEELENASLVFTVFGHNMKSSND-FIGRIVIGQYS SGPSETNHWRRMLNTHRTAVEQWH-SLRSRAECDRVSPASLEVT. Accordingly, it will be appreciated that all characteristics and uses of the polypeptides of SEQ ID NO:24 described throughout the present application also pertain to the polypeptides encoded by the human cDNA included in Clone 119658 105-067-2-0-H4-F_1. In addition, it will be appreciated that all characteristics and uses of the polynucleotides of SEQ ID NO:23 described throughout the present application also pertain to the nucleic acids comprising the human cDNA in Clone 119658 105-067-2-0-H4-F_1. A preferred embodiment of the invention is directed toward the compositions of SEQ ID NO:23, SEQ ID NO:24, and Clone 119658 105-067-2-0-H4-F_1. Also preferred are polypeptide fragments having a biological activity as described herein and the polynucleotides encoding the fragments.

The sequence of DOV contains similarities to proteins of the Synaptotagmin family. Like Synaptotagmin, DOV is a vesicular transmembrane protein that participates in vesicle docking and fusion. A calcium-dependent conformational change allows the cytoplasmic portion of DOV to dock with specific proteins on the plasma membrane. Vesicle docking results in release of vesicle contents to the extracellular space. DOV polypeptides are required for neurotransmitter release from a presynaptic neuron in response to an excitatory calcium flux in that cell.

A preferred embodiment of the invention includes a composition comprising a DOV polypeptide sequence of SEQ ID NO:24.

A preferred embodiment of the invention includes a composition comprising a DOV polypeptide fragment having biological activity.

A preferred embodiment of the invention includes a composition comprising a polynucleotide sequence of SEQ ID NO:23 encoding a DOV polypeptide.

A preferred embodiment of the invention includes a composition comprising a polynucleotide sequence encoding a DOV polypeptide fragment having biological activity.

A preferred embodiment of the invention includes an excitation-secretion uncoupling peptide (ESUP).

A preferred embodiment of the invention includes an excitation-secretion uncoupling peptide (ESUP). Preferred DOV ESUPs include the peptide sequences: LLIT-INHLTVRVIEARDL PPPISHDGSRQDMAHSNPYVKJ-CLLPDQKNSKQTGVKRKTQKPVFEERY-FFEIPFLEAQRR TLLLTVVDFDKFSRHCVIGKVS (SEQ ID NO:75); GRLNVDVIRAKQLLQTDVSQGS DPFVKJQLVHGLKLVKTKKTSFLRGTID-PFYNESFSFKVPQEELENASLVFTVFGHNMKSS NDFI-GRIVIG (SEQ ID NO:76); and effective ESUP fragments of said peptides.

A preferred embodiment of the invention provides a method of screening for inhibitors of DOV polypeptides comprising the steps of: contacting a test substance with a cell and detecting DOV biological activity in the exposed cell to that in an unexposed control cell. Preferred cells are neurons.

Preferred antagonists include DOV-specific antibodies and fragments thereof, ESUPs, and small molecules.

A preferred embodiment of the invention provides a method of using inhibitors of DOV polypeptides as anticonvulsants and to prevent pain. These methods comprise the step of administering an effective amount of a DOV inhibitor in a physiologically acceptable composition to an individual in need of treatment.

A preferred embodiment provides a method to purify vesicles comprising the steps of: i) contacting an antibody specific for the cytoplasmic portion of DOV polypeptide with a biological sample under conditions that allow antibody binding and ii) removing contaminating materials not bound to the antibody. Preferably, such antibody is primarily or secondarily attached to an insoluble matrix to enable purification.

A preferred embodiment provides a method to detect vesicles comprising the step of contacting an antibody specific for DOV polypeptide with a biological sample under conditions that allow binding and ii) detecting the antibody. Preferred antibodies are covalently labeled with fluorescent, radioactive, or otherwise detectable compounds.

A preferred embodiment provides a method to detect vesicle extrusion comprising the step of contacting an antibody specific for the vesicular portion of DOV with a cell. Preferred antibodies are covalently labeled with fluorescent, radioactive, or otherwise detectable compounds. Preferred cells are neurons.

A preferred embodiment of the invention provide a method to diagnose a neurological disorder comprising the steps of: obtaining a biological test sample from an individual; detecting the level of DOV expression in the test sample; comparing to the level of DOV expression in the test sample to that of control sample(s). Neurological disorders indicated by this method include: Paroxysmal Kinesigenic Choreoathetosis (PKC), paralysis (partial and complete), and mood disorders (depression, bipolar disorder, and schizophrenia).

A preferred embodiment is a method to restore vesicular docking and fusion abilities to a cell comprising the step of introducing DOV polypeptides to a cell. Preferably, this method is applied to treatment and prevention of PKC, partial and complete paralysis, and mood disorders such as depression, bipolar disorder, and schizophrenia. Preferably, DOV polypeptides are delivered by introducing a polynucleotide construct comprising an expression control element operably linked to polynucleotide encoding a DOV polypeptide to a cell.

A preferred aspect of the invention is a host cell recombinant for polynucleotides encoding a DOV polypeptide or a biologically active fragment thereof. An additional preferred aspect is a host cell recombinant for polynucleotides capable of directing DOV expression. Preferably, the polynucleotides capable of directing DOV expression are located in the 5' regulatory region of the DOV gene. Further preferably, these polynucleotides are located within 500 base pairs of the DOV coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. DOV protein produced by said host cell may be used for in vitro detection and purification methods as well as diagnosis and in vivo applications.

In one aspect, the invention includes a DOV polypeptide composition for use in delivering a second composition, preferably nucleic acids, polypeptides, or small molecules, as therapeutic drugs, to target biological cells either in vitro or in vivo. The second composition may, if desirable, be covalently or non-covalently attached or fused to the DOV polypeptide. The DOV polypeptide composition may further comprise artificial lipids or viral components to facilitate delivery of the second molecule by liposomes or lipid vesicles. Methods for using DOV polypeptides in these methods are known in the art and include U.S. Pat. Nos. 6,074,844 and 6,099,857, which disclosures are hereby incorporated by reference in their entireties. In a preferred embodiment, DOV polypeptides are used to faciliate delivery of a second composition, e.g., liposome-mediated DNA transfection, to cells in culture, preferably neuronal cells.

DOV polypeptides are also useful in methods of inhibiting the release of neurotransmitters by preventing the docking and/or fusing of a presynaptic vesicle to the presynaptic membrane. These polypeptides may be referred to as excitation-secretion uncoupling peptides (ESUPs). Fragments of DOV having this blocking activity can be identified using methods known in the art (See e.g., U.S. Pat. Nos. 6,090,631 and 6,169,074 incorporated by reference in their entireties). ESUPs of the present invention comprise synthetic and purified DOV peptide fragments which correspond in primary structure to peptides which serve as binding domains for the assembly of a ternary protein complex ("docking complex") which is critical to neuronal vesicle docking with the cellular plasma membrane prior to neurotransmitter secretion. For optimal activity, ESUPs of the invention have a minimum length of about 20 amino acids and a maximal length of about 100 amino acids, although they may be larger or smaller. Preferred DOV ESUPs for use in inhibiting the release of neurotransmitters include those comprising the sequence: LLHNHLTVRVIEARDLPPPISHD GSRQDMAHSNPYVKICLLPDQKNSKQTGVKRKTQKPVFEERYTFEIPFLEAQRRTLLLTV VDFDKFSRHCVIGKVS (SEQ ID NO:75); GRLNVDVIRAKQLLQTDVSQGSDPFVKI QLVHGLKLVKTKKTSFLRGTIDPFYNESFSFKVPQEELENASLVFTVFGHNMKSSNDHGR IVIG (SEQ ID NO:76); and effective ESUP fragments of said peptides. DOV ESUPs are preferably covalently linked to a targeting moiety. Preferred targeting moieties comprise a ligand to a cell-surface binding site present on a specific cell type (e.g., neuron) that is capable of functionally interacting with the binding site. Preferred targeting moieties are nerve growth factor and functional derivatives thereof. Alternatively, DOV ESUPs may be expressed in a cell by introducing polynucleotides encoding DOV ESUPs to the cell. Methods of introducing polynucleotides to a cell are known to those skilled in the art, as discussed herein and in U.S. Pat. Nos. 6117454 and 6180602, which disclosures are hereby incorporated by reference in their entireties.

Another embodiment of the invention provides a method of screening for antagonists of DOV polypeptides. This method comprises the steps of: contacting a test substance with a cell and detecting DOV biological activity in the exposed cell to that in an unexposed control cell. Preferred cells are neurons. DOV polypeptides are required for efficient neurotransmitter release. Thus, DOV activity can be determined by detecting the level of neurotransmitter released from exposed cells compared to that from unexposed cells. Such assays are common to the art and include antibody-based assays (e.g., ELISA), binding competition assays (e.g., to a specific neurotransmitter receptor), and colormetric assays. Preferred antagonists include DOV-specific antibodies and fragments thereof, ESUPs, and small molecules.

DOV antagonists may be used to inhibit or treat pain. Peptide antagonists in particular may be used according to U.S. Pat. No. 5,989,545 (disclosure of which is hereby incorporated by reference in its entirety) by substituting the polypeptides of the present invention for neurotoxin. In addition, DOV antagonists of the invention may be used as anticonvulsants. Anticonvulsants effectively reduce infarct size in cases of stroke and are effective therapy for seizures, such as those resulting from epilepsy or exposure to neurotoxins. These methods comprise the step of administering an effective amount of DOV antagonist in a physiologically acceptable composition to an individual in need of treatment.

DOV is a component of vesicles, thus, antibodies to DOV are useful in the detection of vesicles, preferably neuronal vesicles transporting neurotransmitters. DOV-specific antibodies can be used during purification of vesicles. This method comprises the steps of: i) contacting an antibody specific for the cytoplasmic portion of DOV polypeptide with a biological sample under conditions that allow antibody binding and ii) removing contaminating materials not bound to the antibody. Preferably, such antibody is primarily or secondarily attached to an insoluble matrix to enable purification. DOV-specific antibodies may also be used as a marker for vesicles. For example, vesicles can be detected in assays such as immunohistochemistry. The vesicular portion of DOV appears on the surface of the cell following extrusion of vesicle contents at the plasma membrane. Thus, antibodies specific for the vesicular portion of DOV are useful for the detection and monitoring of vesicle extrusion. This method comprises the step of contacting an antibody specific for the vesicular portion of DOV with a cell. Preferred antibodies are detectably labeled, for example, with a fluorescent, luminescent, or radiolabeled compound.

Detection of DOV expression (mRNA or protein) levels or mutated forms of DOV is further useful in the determination or diagnosing of whether someone is at risk of developing or has a neurological disorder, such as Paroxysmal Kinesigenic Choreoathetosis (PKC), paralysis (partial or complete), or mood disorders (e.g., depression, bipolar disorder, schizophrenia). This method comprises the steps of: obtaining a biological test sample from an individual; detecting the level of DOV expression in the test sample; comparing to the level of DOV expression in the test sample to that of control sample(s). A decreased level in expression of DOV, mRNA or protein, as compared to an individual without a neurological disorder indicates the individual has or is as risk of developing the disorder.

DOV polypeptides may further be introduced to a cell that is defective in vesicle docking and fusion. This method comprises the step of introducing DOV polypeptides to a cell such that vesicle docking and fusion are allowed. DOV polypeptides may be introduced to a cell by introducing a polynucleotide construct comprising an expression control element operably linked to the coding sequence of DOV to a cell by methods discussed herein. Preferred cells are neurons. DOV polypeptides are preferably applied to treatment of PKC, paralysis (partial or complete), or mood disorders (e.g., depression, bipolar disorder, schizophrenia).

Protein of SEQ ID NO:26 (Internal Designation Clone 500706437_204-5-2-0-C9-F)

The cDNA of Clone 500706437_204-5-2-0-C9-F (SEQ ID NO:25) encodes placentalin of SEQ ID NO:26, comprising the amino acid sequence: MDPARPLGLSILLLFLTEAA LGDAAQEPTGNNAEICLLPLDYG-PCRALLLRYYYDRYTQSCRQFLYGGCEG-NANNFYTW EACDDLAGG. Accordingly, it will be appreciated that all characteristics and uses of the polypeptides of SEQ ID NO:26 described throughout the present application also pertain to the polypeptides encoded by the nucleic acids comprising the human eDNA in Clone 500706437_204-5-2-0-C9-F. In addition, it will be appreciated that all characteristics and uses of the polynucleotides of SEQ ID NO:25 described throughout the present application also pertain to the nucleic acids included in Clone 500706437_204-5-2-0-C9-F. A preferred embodiment of the invention is directed toward the compositions of SEQ IDNO:26, SEQ IDNO:25, and Clone 500706437_204-5-2-0-C9-F Preferred placentalin polypeptides for uses in the methods described below include the polypeptides comprising the amino sequence of: AQEPTGNNAEICLLPLDYG-PCRALLL RYYYDRYTQSCRQFLYGGCEGNANN-FYTWEACDDLAGG (SEQ ID NO:77). Also preferred are polypeptide fragments having a biological activity as described herein and the polynucleotides encoding the fragments.

The protein of the present invention, placentalin, is a variant of the Tissue Factor Pathway Inhibitor 2 (TFPI-2, GenBank accession number P48307). The 84 amino-terminal amino-acids are identical between TFPI-2 and placentalin, and the 4 carboxyl-terminal amino-acids are unique to placentalin. Placentalin displays one signal peptide (MD-PARPLGLSILLLFLTEAALGDA) (SEQ ID NO:78) and one Kunitz inhibitor domain (CLLPLDYGPCRALLL-RYYYDRYTQSCRQFLYGGCEGNANN-FYTWEACDDLA) (SEQ ID NO:79). Placentalin lacks the main heparin-binding site, located at the carboxyl-terminal extremity of TFPI-2. A wide variety of cell types, including endothelial cells, keratinocytes and fibroblasts, synthesize and secrete placentalin under normal conditions. Moreover, placentalin is highly expressed in umbilical vein endothelial cells and its expression level negatively correlates with malignancy-grade of tumors.

Placentalin is a broad-spectrum serine protease inhibitor that inhibits plasmin, trypsin, plasma kallikrein, factor XIa, tissue factor-factor VIIa complex, chymotrypsin, factor IXa-polylysine and cathepsin G. Placentalin plays a major role both in regulation of extracellular matrix (ECM) degradation and in regulation of the blood coagulation pathway. In peculiar, placentalin strongly inhibits the tissue factor-factor VIIa complex, the cellular initiator of the extrinsic coagulation pathway, and plasmin, thereby inhibiting processing of pro-MMPs (matrix metalloproteases) responsible of ECM degradation. Unlike TFPI-2, placentalin is a circulating variant that is not bound to the heparin molecules of the ECM.

An embodiment of the invention is directed to a composition comprising a placentalin polypeptide sequence of SEQ ID NO:26.

A further embodiment of the invention is directed to a composition comprising a placentalin polypeptide fragment having biological activity of binding or inhibiting a serine protease.

A further embodiment of the invention is directed to a composition comprising a polynucleotide sequence of SEQ ID NO:25 encoding a placentalin polypeptide.

A further embodiment of the invention is directed to a composition comprising a polynucleotide sequence encoding a placentalin polypeptide fragment having biological activity.

A further embodiment of the invention is directed to a composition comprising an antibody recognizing a placentalin polypeptide sequence of SEQ ID NO:26 or a placentalin polypeptide fragment having biological activity. Preferably, the antibody recognizes an epitope comprising one or more of the 4 C-terminal amino-acids of placentalin, and binds to placentalin but not to TFPI-2.

A preferred aspect of the invention is a host cell recombinant for polynucleotides encoding a placentalin polypeptide or a biologically active fragment thereof. An additional preferred aspect is a host cell recombinant for polynucleotides capable of directing placentalin expression. Preferably, the polynucleotides capable of directing placentalin expression are located in the 5' regulatory region of the placentalin gene. Further preferably, these polynucleotides are located within 500 base pairs of the placentalin coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. Placentalin protein produced by said host cell may be used for in vitro detection and purification methods as well as diagnosis and in vivo applications.

Another embodiment relates to a method of producing placentalin polypeptides comprising the steps of: i) transfecting a mammalian host cell with a recombinant expression vector comprising a polynucleotide of the present invention, and ii) purifying the produced protein. The purification of the protein can be done following any technique well-known to those skilled in the art. Preferably, an antibody directed against placentalin or part thereof may be bound to a chromatographic support to form an affinity chromatography column. Even more preferably, the antibody binds to placentalin but not to TFPI-2.

A preferred embodiment of the invention is a method of using placentalin to bind serine proteases. This method comprises the step of contacting a placentalin polypeptide or active fragment thereof with a serine protease under conditions that allow placentalin binding, whereby binding inhibits the activity of said serine protease. Preferred serine proteases include plasmin, trypsin, plasma kallikrein, factor XIa, tissue factor-factor VIIa complex, chymotrypsin, factor IXa-polylysine or cathepsin G. This method may be applied to in vitro uses (e.g., protease purification and detection and prevention of protein degradation) as well as in vivo methods (e.g., inhibition of target protease-dependent pathologies such as blood clots and metastasis).

A preferred embodiment of the invention is a method of purifying serine proteases. This method comprises the steps of: contacting a placentalin polypeptide or protease-binding fragment thereof with a serine protease under conditions that allow binding; removing contaminants; and eluting the serine protease with more stringent conditions. Preferably, the placentalin peptide is immobilized on a solid or semi-solid matrix to facilitate washing of sample to remove contaminants. Preferred serine proteases include plasmin, trypsin, plasma kallikrein, factor XIa, tissue factor-factor VIIa complex, chymotrypsin, factor IXa-polylysine or cathepsin G. These may be purified from common biological fluids such as cell culture media and body fluids (e.g., serum, blood, lymph, or cerebrospinal fluid). Purified proteases are useful in biological assays and techniques such as removal of adherent cells from a culture dish and site-directed peptide design.

A further embodiment of the present invention relates to a method of using placentalin or a protease-binding fragment thereof to remove contaminating proteases from a sample comprising the steps of: i) binding placentalin or part thereof to a chromatographic support, either alone or in combination with other protease inhibitors, and ii) running through the column the sample containing the undesirable protease. The sample may be, e.g., a protein preparation or a sample prepared from bodily fluid. Preferably, the sample is prepared from blood.

An embodiment of the present invention relates to a method of using placentalin or part thereof to inhibit contaminating proteases in a sample. Such method comprises the step of adding a protease-inhibiting amount of placentalin polypeptide to a solution under conditions that allow placentalin activity. Preferably, the placentalin polypeptide is comprised in a "cocktail" of protease inhibitors that is able to inhibit a wide range of proteases without knowing the specificity of any of the proteases. Such protease inhibitor cocktails are widely used in laboratory assays to prevent degradation of any protein sample by contaminating proteases.

A preferred embodiment of the inventions is a method of detecting serine proteases. This method comprises the step of contacting a placentalin polypeptide or active fragment thereof with a serine protease and detecting the presence of said serine protease by detecting placentalin. Preferably, the placentalin polypeptide is detectably labeled with, for example, a fluorescent, luminescent, or radioactive compound. Preferred serine proteases to be detected according to this method include plasmin, trypsin, plasma kallikrein, factor XIa, tissue factor-factor VIIa complex, chymotrypsin, factor IXa-polylysine or cathepsin G. Preferably, serine proteases are detected in common biological fluids such as cell culture media and body fluids. This method may be applied to quantifying the level of serine protease expression in a cell sample or individual. This information may be useful in determination of tumor malignancy or diagnosis of blood coagulation disorders.

An additional preferred embodiment of the invention is a method of binding placentalin polypeptides with a placentalin-specific antibody or placentalin-binding fragment thereof. This method comprises the step of contacting a placentalin polypeptide with a placentalin-binding antibody or placentalin-binding fragment thereof under conditions that allow binding. This method may be applied to detection and purification of placentalin, as well as modifying placentalin function. These aspects are discussed in detail herein.

Another embodiment of the present invention relates to a method of diagnosing the malignancy of a tumor comprising the steps of: i) contacting a biological sample with a compound that specifically binds to placentalin polypeptides or nucleic acids, ii) detecting the level, or any other detectable property, of placentalin in the sample, and iii) comparing the resulting signal with those obtained from control samples indicative of a benign, a low-grade, an intermediate-grade and a high-grade malignant tumor. The level of the signal negatively correlates with the malignancy of the tumor. Preferably, this method is directed to diagnose the malignancy of tumors such as, e.g., gliomas, amelanotic melanomas, prostate tumors and lung tumors.

Still another embodiment of the present invention relates to a method of diagnosing the risk for thrombotic deposition comprising the steps of: i) contacting a biological sample with a compound that specifically binds to placentalin polypeptides or nucleic acids, ii) detecting the level, or any other detectable property, of placentalin in the sample, and iii) comparing the resulting signal with those obtained from control samples indicative of a patient presenting no risk for thrombotic deposition. Preferably, such methods are directed to diagnose hypercoagulable syndromes, e.g., artherosclerosis, ischemia, stroke, myocardial infarction, coronary artery disease.

Preferably, the biological sample is either a body fluid or tissue sample that has been purified or partially purified to ease detection. Particularly preferred compounds that specifically bind to placentalin polypeptides are the antibodies described above. Preferably, the antibodies are labeled and detection of the signal may be carried out using immunohistological and immunofluorescing processes that are well-known to those skilled in the art. Alternatively, the antibodies that specifically bind to placentalin polypeptides are not labeled and detection of the signal occurs indirectly by using labeled secondary antibodies. Particularly preferred compounds that specifically bind to placentalin polynucleotides are polynucleotide sequences that are complementary to SEQ ID NO:25 or part thereof. Detection of the signal may be carried out using PCR, RT-PCR techniques, or quantitative PCR techniques.

Still another embodiment relates to a kit for determining the malignancy of a tumor or the risk for thrombotic deposition. Such kits comprise at least one binding partner specific for placentalin polypeptides or nucleic acids coupled to a detectable marker, control samples, and reagents for performing the reaction for detecting the marker. Preferably, the kit is directed to diagnosing the malignancy of a given tumor, e.g., gliomas, amelanotic melanomas, prostate tumors and lung tumors. Alternatively, the kit is directed to monitor the progress of a therapy administered to treat malignant tumors.

Another preferred embodiment relates to substances that increase placentalin expression and to a method of screening for substances that increase placentalin expression comprising the steps of: i) contacting a cell with a test substance; and ii) comparing placentalin expression in the cell after exposure to the test substance to that of an unexposed control cell. Preferably, the test substance modifies the expression of placentalin in a specific cell type while not in others. Most preferably, the test substance modifies placentalin expression specifically in endothelial cells or in neoplastic cells.

A further embodiment of the present invention is directed to substances that increase placentalin activity and to a method of screening for such substances. This method comprises the steps of: i) contacting a placentalin polypeptide with a test substance, ii) determining placentalin activity, and iii) comparing placentalin activity after exposure to that of an unexposed control sample. Preferably, placentalin activity is studied in an endothelial cell or in a neoplastic cell. Placentalin activity can be monitored by studying plasmin inhibition and/or radiolabeled matrix degradation as described in Rao et al. (Biochem Biophys Res Commun. 276:1286-94 (2000)), which disclosure is incorporated herein in its entirety. Substances that increase placentalin expression or activity are defined as placentalin agonists.

An embodiment of the present invention relates to methods of using the polypeptides and the polynucleotides of the present invention to reduce blood coagulation in a mammal. Any compositions and methods containing a placentalin polypeptide or a placentalin agonist can be used. Preferably, such methods for reducing blood coagulation are directed to treat a patient presenting a risk for thrombotic deposition. Most preferably, such methods are directed to treat a patient suffering from thrombotic diseases and/or hypercoagulable syndromes, e.g., artherosclerosis, acute ischemia, stroke, myocardial infarction, coronary artery disease, and thrombotic complications associated with transplantation. A preferred embodiment is a method to reduce blood coagulation comprising the step of introducing a placentalin polypeptide or a protease-inhibiting fragment thereof in a physiologically acceptable composition to the bloodstream of an individual. Delivery to the bloodstream can be direct (e.g., injection to a vein or artery) or indirect (e.g., inhalant or oral delivery), as discussed in detail herein.

In a further embodiment, the present invention provides a method of promoting wound healing by preventing tissue buildup using compositions comprising a placentalin polypeptide or a placentalin agonist. Such a method comprises the step of: contacting said wound with an effective amount of the composition comprising a placentalin polypeptide or a placentalin agonist, wherein the wound includes, but is not limited to, myocardial infarction, skin wound, arterial wall injury, stents and sutures.

Another embodiment of the present invention relates to methods of using the polypeptides and the agonists of the present invention to prevent or reduce ECM degradation in a mammal. Preferably, such methods for preventing or reducing ECM degradation are directed to protect the ECM from degradation by malignant cells, thus blocking the invasion and spread of malignant tumors. Most preferably, a composition comprising a placentalin polypeptide is administered to an individual suffering from abnormal or undesirable cell proliferation, such as, e.g., tumor growth, endothelial cell proliferation, and angiogenesis related to tumor growth. Tumors that can be treated with the compositions of the present invention include, but are not limited to, gliomas, amelanotic melanomas, prostate tumors and lung tumors.

Still another embodiment of the invention relates to the inhibition and/or attenuation of proteases produced by pathogenic microorganisms. This embodiment relates to a method comprising the step of administering a composition comprising placentalin or a biologically active fragment thereof, or a compound that increases the expression or activity of placentalin, to an individual for preventing and/or treating parasitic infections. Placentalin polypeptides or compounds that increase the expression or activity of placentalin may be administered alone or in combination with other agents. Alternatively, this method may be directed to prevent parasitic infections of mammalian cell cultures. It has been shown that protease inhibitors can prevent dissemination of virus, protozoa, bacteria or fungi in the host organism. Accordingly, the polypeptides of the present invention may be used to prevent or to treat, e.g., coccidiosis, staphylococcal infection, infection by the influenza virus, *P. gingivalis* or *T. denticola*, and invasive pulmonary aspergillosis.

In one embodiment, the pharmaceutical compositions for use in prevention of ECM degradation or inhibition of blood coagulation comprise an effective amount of a placentalin polypeptide, placentalin polynucleotide, or substance that increases placentalin expression or activity in mixture with a pharmaceutically acceptable diluent or carrier. An effective amount of the compositions of the present invention may vary according to factors such as the disease, the disease state, age, sex, and weight of the mammal. Dose regimen may be adjusted to provide the optimum therapeutic response. In a preferred embodiment, a composition comprising a substance that increases placentalin expression or activity and a physiologically acceptable carrier is directly introduced to the bloodstream of an individual by injection.

In a preferred embodiment, a placentalin polypeptide is fused to a targeting molecule specific for the tissue of interest. Preferably, the targeted placentalin polypeptide is comprised in a pharmaceutical composition for use in prevention of ECM degradation associated with tumor growth. Most preferably, the placentalin polypeptide is linked to a ligand or an antibody that recognizes a receptor or an antigen specifically expressed on tumor cells by any technique well-known to those skilled in the art. A large number of tumor-associated antigens have been described in the scientific literature. For example, antigens and techniques described by Wikstrand et al (Cancer Metastasis Rev 18:451-64 (1999)), which disclosure is hereby incorporated by reference in its entirety, may be used. Alternatively, the placentalin polypeptide is linked to a ligand that recognizes the vasculature of a tumor. A preferred method for targeting the placentalin polypeptide to the vasulature of solid tumors is described in U.S. Patent 6,004,554, which disclosure is incorporated by reference in its entirety.

Another embodiment is directed to a method of using placentalin polynucleotides for reducing blood coagulation comprising the steps of: i) constructing a recombinant molecule comprising a nucleic acid sequence encoding a placentalin polypeptide that allows expression of placentalin or part thereof under given physiological conditions, and ii) introducing this recombinant molecules into a cell, a mammal or a human. Recombinant molecules comprising a nucleic acid sequence encoding a placentalin polypeptide may be directly introduced into cells or tissues in vivo using delivery vehicles such as retroviral vectors, adenoviral vectors and DNA virus vectors. They may also be introduced into cells in vivo using physiological techniques such as microinjection and electroporation or chemical methods such as coprecipitation and incorporation of DNA into liposomes. Recombinant molecules may also be delivered in the form of an aerosol or by lavage. The placentalin polynucleotides may also be applied extracellularly such as by direct injection into cells. Preferably, placentalin polynucleotides are introduced into endothelial cells or in blood vessel cells. Most preferably, when placentalin polynucleotides are directed to treating a patient presenting a risk for thrombotic deposition, the method described in PCT application WO 99/02171, which disclosure is incorporated by reference in its entirety, can be used.

Protein of SEQ ID NO:28 (Internal Designation Clone 176355_117-0052-0H11-F)

The cDNA of Clone 176355_117-005-2-0-H11-F (SEQ ID NO:27) encodes NAAR protein of SEQ ID NO:28, comprising the amino acid sequence: MASMAAVLTWALALLSAFSATQARKGFWDYFSQTSGDKGRVEQIHQQKMAREPATLKD SLEQDLNNMNKFLEKLRPLSGSEAPRLPQDPVGMRRQLQEELEEVKA RLQPYMAEAHEL VGWNLEGLRQQLKPYTMDLMEQVALRVQELQEQLRVVGEDTKAQLLGGVDEAWALLQ GLQSRWHHTGRFKELFHPYAESLVSGIGRHVQELHRSVAPHAPASPARLSRC VQVLSRK LTLKAKALHARJQQNLDQLREELSRAFAGTGTEEGAGPDPQMLSEEVRQRLQAFRQDTYL QIAAFTRAIDQETEEVQQQLAPPPPGHSAFAPEFQQTDSGKVLSKLQARLDDLWEDITHSL HDQGHSBLGDP. Accordingly, it will be appreciated that all characteristics and uses of the polypeptides of SEQ ID NO:28 described throughout the present application also pertain to the polypeptides encoded by the human cDNA included in Clone 176355_117-005-2-0-H11-F. In addition, it will be appreciated that all characteristics and uses of the polynucleotides of SEQ ID NO:27 described throughout the present application also pertain to the nucleic acids comprising the human cDNA in Clone 176355_117-005-2-0-HI I-F. A preferred embodiment of the invention is directed toward the compositions of SEQ ID NO:27, SEQ ID NO:28 and Clone 176355_117-005-2-0-H11-F. Also preferred are polypeptide fragments having a biological activity as described herein and the polynucleotides encoding the fragments.

The protein of the invention displays an Apolipoprotein motif:

MAAVLTWALALLSAFSATQARKGFWDYFSQTSGDKGRVEQIHQQKMAREPATLK DSLEQDLNNMNKFLEKLRPLSGSEAPRLPQDPVGMRRQLQEELEEVKARIQPYMAEAHE LVGWNLEGLRQQLKPYTMDLMEQVALRVQELQ EQLRVVGEDTKAQLLG&IDEAWALL QGLQSRVVHHTGRFKELFHPYAESLVSGIGRJ-IVQELHRSVAPHAPASPARLSRCVQVLSR KLTLKAKALHARIQQNLD (SEQ ID NO:80). Accordingly, an embodiment of the present invention comprises the amino acids of the apolipoprotein motif and the polynucleotides encoding the same.

Lipoprotein particles such as HDL and LDL contain characteristic apolipoproteins that are responsible for targeting them to certain tissues and for activating enzymes required for the trafficking of the lipid fraction of the lipoprotein, including cholesterol. NAAR is a member of the apolipoprotein family.

Apolipoproteins are the protein component of lipoprotein particles and are responsible for binding to receptors on cell membranes and directing the lipoprotein particles to their intended site of metabolism. These high molecular weight particles are primarily responsible for lipid transport (triglycerides and cholesterol in the form of cholesteryl esters) through the plasma. Lipoprotein particles include chylomicrons and chylomicrons remnant particles, very low density lipoprotein (VLDL), intermediate density lipoprotein (IDL), low density lipoprotien (LDL), and high density lipoprotein (HDL). Elevated levels of lipoprotein particles have been positively correlated with artherosclerosis and a reduction in plasma lipoprotein concentration is correlated with a reduced risk of artherosclerosis. In addition, individual apolipoproteins have unique functions such as the formation of specific associations with lipoprotein particles of distinct classes. Some apolipoproteins act as ligands controlling the interaction of lipoproteins with cell surface receptors, while others functions as cofactors for essential enzymes in lipid metabolism.

NAAR is associated with the chylomicron and HDL fraction of blood. NAAR synthesis by the small intestine increases markedly after the ingestion of lipid with the result being a marked increase in NAAR output in mesenteric lymph. During secretion from small intestine epithelial cells, the pre-NAAR signal peptide is cleaved. The mature NAAR polypeptide is secreted into the lymph as a major constituent of newly synthesized triglyceride-rich lipoprotein as well as the HDL fraction of blood. NAAR is involved in the biogenesis and/or metabolism of intestinal triglyceride-rich lipoproteins. This increase in biosynthesis and secretion of NAAR by the small intestine is triggered by the formation and secretion of intestinal chylomicrons. NAAR levels are regulated by diet and are up-regulated by high fat meals and down-regulated by leptins. NAAR in mesenteric lymph after a lipid meal suppresses food intake, suggesting that NAAR also acts as a satiety factor that circulates in the blood after fat feeding.

NAAR plays a role in triglyceride-rich lipoprotein metabolism, in reverse cholesterol transport, and in facilitating CETP (Cholesterol Ester Transfer Protein) activity. As a result, NAAR is responsible for part of the inter-individual variability in blood cholesterol response to changes in dietary fat/cholesterol intake. Moreover, NAAR may be effectively used in place of HDL particles to prevent the development of atherosclerosis. Also, NAAR plays a significant role in the pathophysiology of diabetes. Levels of NAAR are correlated with glycemic control in young type I diabetes (IDDM) patients and non-insulin-dependent diabetes melitus (NIDDM) patients.

NAAR plays a major role in lipid metabolism and its related disorders. Diseases involving lipid metabolism include, but are not limited to, obesity, obesity-related disorders such as artherosclerosis, cardiovascular disorders such as coronary heart disease, neurodenegenrative disorders such as Alzheimer's disease or dementia, coronary artery disease, mitochondriocytopathies, hyperlipidemia, familial combined hyperlipidemia (FCHL), hypercholesterolemia, obesity-related artheriosclerosis, obesity-related insulin resistance, obesity related hypertension, microangiopathic lesions resulting from obesity-related Type n diabetes, ocular lesions caused by microangiopathy in obese individuals with type II diabetes, and renal lesions caused by microangiopathy in obese individuals with type II diabetes.

An embodiment of the invention is directed to a composition comprising a NAAR polypeptide sequence of SEQ ID NO:28.

A further embodiment of the invention is directed to a composition comprising a NAAR polypeptide fragment having biological activity.

A further embodiment of the invention is directed to a composition comprising a polynucleotide sequence of SEQ ID NO:27 encoding a NAAR polypeptide.

A further embodiment of the invention is directed to a composition comprising a polynucleotide sequence encoding a NAAR polypeptide fragment having biological activity NAAR polypeptides bind free fatty acids (FFAs), triglycerides, and cholesterol, which are associated with atherosclerosis and lipid metabolism-related diseases. A preferred embodiment of the invention is a method comprising the step of: binding a NAAR polypeptide or fragment thereof with an FFA, triglyceride, or cholesterol molecule under conditions that allow binding of NAAR polypeptide to said molecule. In a preferred embodiment, NAAR polypeptide is used to purify FFAs, triglycerides, and cholesterol. In such method, NAAR polypeptide is preferably covalently or non-covalently attached to a solid matrix and allowed to bind FFAs, triglycerides, and cholesterol using techniques well known in the art. This method comprises the steps of: i) washing the solid matrix to get rid of contaminants, ii) eluting the particle of interest using more stringent conditions.

Additional aspects of this embodiment include methods of using NAAR polypeptide to detect and quantify FFAs, triglycerides, and cholesterol using techniques common in the art. This method comprises the steps of: i) obtaining a biological sample suspected of containing FFAs, triglycerides, or cholesterol; ii) contacting said sample with a NAAR polypeptide or fragment thereof under conditions suitable for binding of NAAR; and detecting the presence or absence of FFAs, triglycerides, and cholesterol by detecting NAAR. Preferably, NAAR polypeptide or fragment thereof is covalently attached to a detectable compound. Alternatively, a detectable NAAR-specific antibody or fragment thereof may be used to detect NAAR. This embodiment is useful, for example, as a diagnostic tool for detecting plasma levels of FFAs, triglycerides, and cholesterol.

In another embodiment, the invention is directed to a method of detecting NAAR polypeptide in a biological sample, said method comprising the steps of: i) contacting a biological sample with an antibody or antibody fragment that specifically binds NAAR polypeptide; and ii) detecting the antigen-antibody complex formed. The antibody or antibody fragment may be monoclonal or polyclonal. In addition, the antibody or antibody fragment may be primarily or secondarily labeled by a detectable compound (e.g., radioactive, fluorescent, luminescent, or enzymatic) common in the art.

In some embodiments, the invention also concerns a diagnostic kit for detecting in vitro the presence of NAAR polypeptide. This kit comprises: a polyclonal or monoclonal antibody or fragment thereof that specifically binds a NAAR polypeptide; and optionally, ii) a reagent allowing the detection of the antigen-antibody complexes formed. Preferably, the antibody or antibody fragment is detectably labeled. Such labels include fluorescent, luminescent, and radioactive compounds, as well as enzymatic substrates. The optional reagent may provide a detectable signal and either bind to the antibody or react with the label on such antibody.

NAAR antibodies may be used to diagnose liver-related disorders (e.g., hepatitis, cirrhosis, hepatoma, and FHP), lipid metabolism related disorders such as diabetes, and atherosclerosis. To detect such disorders, an appropriate biological sample (serum, for example) can be tested to determine the level of NAAR being produced (U.S. Pat. No. 6,027,935, which disclosure is incorporated by reference in its entirety). (U.S. Pat. No. 6,027,935, which disclosure is incorporated by reference in its entirety).

An embodiment of the invention provides for a method of screening test substances for modulators of NAAR expression. This method comprises the steps of: i) contacting a cell with a test substance; and ii) comparing NAAR expression in the cell after exposure to the test substance to that of an unexposed control cell. NAAR expression is determined by methods common to the art or included herein, by detecting NAAR polynucleotides or polypeptides. An example of this method comprises the steps of: i) culturing two equivalent cell samples; ii) adding a test substance to one of the cultures and not the other; iii) harvesting both cultures at a specified time; iv) purifying the mRNA from each sample of cells; v) comparing the level of NAAR mRNA in each sample by Northern blot, RTPCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) comparing the level of NAAR polypeptides in each sample by Western blot, immunohistochemistry, or another method common to the art. The invention provides for design and use of specific antibodies and antibody fragments, as discussed herein.

In another embodiment, a NAAR polypeptide or a fragment thereof, may be used to screen for compounds that activate or inhibit NAAR activity. This method comprises the steps of: i) contacting a NAAR polypeptide or fragment thereof with a test substance and ii) monitoring NAAR activity. NAAR binds to bind FFAs, triglycerides, and cholesterol. Thus, NAAR activity may be monitored upon addition of the test substance by competitive binding assays with FFAs, triglycerides, or cholesterol. In this aspect of the invention, a NAAR polypeptide or fragment thereof may be free in solution, affixed to a solid support, recombinantly expressed on or chemically attached to a cell surface, or located intracellularly. The formation of binding complexes between NAAR polypeptide and the compound being tested, may be measured by methods well known to those skilled in the art, such as the BIAcore (Upsala, Sweden). Another technique provides for high throughput screening of compounds having suitable binding affinity to the protein of the invention as described in published PCT application WO84/03564, and incorporated herein by reference in its entirety. Test substances that decrease NAAR expression or activity are defined as inhibitors or antagonists of NAAR. Test substances that increase NAAR expression or activity are defined as activators or agonists. Agents which modulate the expression or activity of the NAAR of the subject invention include, but are not limited to antisense oligonucleotides, ribozymes, and antibodies. These agents may be made and used according to methods well known in the art.

In another embodiment of the invention, the NAAR polypeptide is used to bind FFAs, triglycerides, and cholesterol in vivo and remove these molecules from the bloodstream. This method comprises the step of: introducing an effective amount of NAAR polypeptide or fragment thereof to the bloodstream of an individual. In this embodiment, the NAAR polypeptide may further be expressed as a fusion protein with a polypeptide signal specifying excretion from the body. A preferred method of delivering NAAR polypeptides or biologically active fragments thereof to an individual includes direct, intravenous injection of said polypeptides or fragments in a physiologically acceptable solution (e.g., pH-buffered isotonic saline solutions, pH-buffered isotonic saline solutions modified by addition of viscous elements such as glycerol). Alternatively, NAAR polynucleotides may be introduced to express NAAR polypeptides in the bloodstream. This method comprises the steps of: i) constructing a recombinant viral vector corresponding to a portion of the genome of an adenovirus capable of infecting a cell operatively linked to the nucleotide sequence of the invention and a regulatory sequence directing its expression; ii) delivery of an effective amount of the recombinant adenoviral vector to an individual with or at risk of atherosclerosis, diabetes, or other lipid metabolism disorders.

NAAR polypeptides, fragments thereof, or NAAR agonists may be used to prevent or treat atherosclerosis or arterial lipoprotein deposits of FFAs, triglycerides, and cholesterol as determined by common medical techniques, such as determining the familial predisposition of the individual for these disorders or actual analysis of the serum lipoprotein levels in the individual. Alternatively, NAAR polypeptides, fragments thereof, or NAAR agonists may be delivered to an individual at risk of or suffering from diabetes or another lipid metabolism disorder.

In another embodiment, a NAAR polypeptide, fragment thereof, or NAAR agonist is used in a physiologically acceptable composition to treat septic shock or conditions associated with elevated serum levels of lipopolysaccharide (U.S. Pat. Nos. 5,932,536and 5,948,756, which disclosures are hereby incorporated by reference in their entireties).

In another embodiment, a NAAR polypeptide, fragment thereof, or NAAR agonist is applied to treatment and prevention of obesity, as NAAR peptides have appetite suppressive activities (U.S. Pat. No. 5,840,688, which disclosure is hereby incorporated by reference in its entirety). This method comprises the step of introducing a NAAR polypeptide, fragment thereof, or NAAR agonist in a physiologically acceptable solution to an individual. Preferably, the individual is overweight or has a body mass index (BMI) of 25 or greater.

Another embodiment of the subject invention provides compositions and methods of selectively modulating the activity of the protein of the invention. Modulation of NAAR activity would allow for the successful treatment and management of liver-related and lipid metabolism associated disorders.

Another embodiment of the invention relates to composition and methods using polynucleotide sequences encoding the protein of the invention or part thereof to establish transgenic model animals (*D. melanogaster, M. musculus*), by any method familiar to those skilled in the art. By modulating in vivo the expression of the transgene with drugs or modifier genes (activator or suppressor genes), animal models can be developed that mimic human hormone-dependent disorders such as cancers. These animal models would thus allow the identification of potential therapeutic agents for treatment of the disorders. In addition, recombinant cell lines derived from these transgenic animals may be used for similar approaches ex vivo.

Protein of SEQ ID NO:30 (Internal Designation Clone 222588_116-094-1-0-H2-F)

The cDNA of Clone 222588_116-094-1-0-H2-F (SEQ ID NO:29) encodes Neurexinal protein of SEQ ID NO:30, comprising the amino acid sequence:

```
MTSGSKCPSTDSGKEEYIATFKGSEYFCYDLSQNPIQSSSDEITLSFKTLQRNGLMLHTGKS
ADYVNLALKNGAVSLVINLGSGAFEALVEPVNGKFNDNAWHDVKVTRNLRQVTISVDGI
LTTTGYTQEDYTMLGSDDFFYVGGSPSTADLPGSPIQHESTFAEDPMFQSQTAQL.
```

Accordingly, it will be appreciated that all characteristics and uses of the polypeptides of SEQ ID NO:30 described throughout the present application also pertain to the polypeptides encoded by the human cDNA included in Clone 222588_116-094-1-0-H2-F. In addition, it will be appreciated that all characteristics and uses of the polynucleotides of SEQ ID NO:29 described throughout the present application also pertain to the nucleic acids comprising the human cDNA in Clone 222588_116-094-1-0-H2-F. A preferred embodiment of the invention is directed toward the compositions of SEQ ID NO:29, SEQ ID NO:30 and Clone 222588_116-094-1-0-H2-F. Also preferred are polypeptide fragments having a biological activity as described herein and the polynucleotides encoding the fragments.

The protein of SEQ ID NO:29, Neurexinal, is a splice variant of Neurexin I-alpha protein (Genbank accession number AB035356). The protein of the invention displays a G-Laminin motif: FKTLQRNGLMLHTGKSADYVNLA-LKNGAVSLVINLGSGAFEALVEPVNGKFNDNAW HDVKVTRNLRQVTISVDG-ILTTTGYTQEDYTMLGSDDFFYVGGSPSTADLP (SEQ ID NO:81). Accordingly, some embodiments of the present invention comprise the amino acids of the G-Laminin motif and the polynucleotides encoding the same.

Neurexins are neuronal cell-surface proteins. In addition to a function as cell-adhesion molecules, neurexins serve as signaling receptors. Ligands for alpha-neurexins, called neuroxophilins, are similar to peptide hormones. Neurexins can also serve as receptors for latrotoxins. Neurexin splice variants contribute to target innervation and the transition from neurite outgrowth to synaptogenesis or during synaptic plasticity and regeneration. Neurexins are associated with mediating neuronal processes and signaling exocytosis. Thus, these proteins play a role in neuronal development, neuronal abnormalities (e.g., seizures), and cancer.

Neurexinal, one neurexin isoform, is expressed in sympathetic neurons during target innervation and relative expression levels of splice variants change during differentiation of individual neurons. Neurexinal is a membrane protein detectable only in neurons. Neurexinal expression peaks postnatally. Neurexinal plays a role as a cell adhesion molecule and a signal transduction receptor.

Several ligands to Neurexinal, with putative functions in signaling and cell adhesion have been identified. Neurexinal binds to alpha-latrotoxin with high affinity only in the presence of Ca2+. Alpha-latrotoxin is a large peptide neurotoxin from black widow spider venom that causes massive neurotransmitter release when applied to nerve terminals. Alpha-latrotoxin inserts into the membrane and forms a transmembrane ion pore after anchoring to either of its nerve terminal receptors. In addition, Neurexophilin binds tightly to Neurexinal and alpha-Neurexin but not beta-Neurexins. Neurexophilin is synthesized at high levels only in inhibitory interneurons and functions as a signaling molecule. Dystroglycan is another physiological ligand for Neurexinal and mediates cell adhesion between brain cells. Dystroglycan, a cell surface protein, links the intracellular cytoskeleton to the extracellular matrix. Impairment of this linkage is instrumental in the pathogenesis of muscular dystrophies.

An embodiment of the invention is directed to a composition comprising a novel Neurexinal polypeptide sequence of SEQ ID NO:30.

A further embodiment of the invention is directed to a composition comprising a Neurexinal polypeptide fragment having biological activity of binding alpha-latrotoxin, neurexophilin, or dystroglycan.

A further embodiment of the invention is directed to a composition comprising a polynucleotide sequence of SEQ ID NO:29 encoding a Neurexinal polypeptide.

A further embodiment of the invention is directed to a composition comprising a polynucleotide sequence encoding a Neurexinal polypeptide fragment having biological activity of binding alpha-latrotoxin, neurexophilin, or dystroglycan.

A preferred aspect of the invention is a host cell recombinant for polynucleotides encoding a Neurexinal polypeptide or a biologically active fragment thereof. An additional preferred aspect is a host cell recombinant for polynucleotides capable of directing Neurexinal expression. Preferably, the polynucleotides capable of directing Neurexinal expression are located in the 5' regulatory region of the Neurexinal gene. Further preferably, these polynucleotides are located within 500 base pairs of the Neurexinal coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. Neurexinal protein produced by said host cell may be used for in vitro detection and purification methods as well as diagnosis and in vivo applications.

Neurexinal polypeptides bind alpha-latrotoxin, neurexophilin and dystroglycan. A preferred embodiment of the invention is a method comprising the step of: binding a Neurexinal polypeptide or fragment thereof with an alpha-latrotoxin, neurexophilin or dystroglycan molecule under conditions that allow binding of Neurexinal polypeptide to said molecule. In a preferred embodiment, Neurexinal polypeptide is used to purify alpha-latrotoxin, neurexophilin or dystroglycan. In such method, Neurexinal polypeptide is preferably covalently or non-covalently attached to a solid matrix and allowed to bind alpha-latrotoxin, neurexophilin or dystroglycan using techniques well known in the art. This method comprises the steps of: i) washing the solid matrix to get rid of contaminants, ii) eluting the particle of interest using more stringent conditions. Additional aspects of this embodiment include methods of using Neurexinal polypeptide to detect and quantify alpha-latrotoxin, neurexophilin and dystroglycan using techniques common in the art. This method comprises the steps of: i) obtaining a biological sample suspected of alpha-latrotoxin, neurexophilin and dystroglycan; ii) contacting said sample with a Neurexinal polypeptide or fragment thereof under conditions suitable for binding of Neurexinal; iii) and detecting the presence or absence of alpha-latrotoxin, neurexophilin and dystroglycan by detecting Neurexinal. Preferably, Neurexinal polypeptide or fragment thereof is covalently attached to a detectable compound. Alternatively, a detectable Neurexinal-specific antibody or fragment thereof may be used to detect Neurexinal. This embodiment is useful, for example, as a diagnostic tool for detecting neuronal levels of alpha-latrotoxin, neurexophilin and dystroglycan. A further aspect of the present invention involves the isolation, purification and characterization of Neurexinal. Specifically, the present invention extends to a novel neuronal receptor which is a regulator of neurotransmitter release, and thus mediates alpha-latrotoxin toxicity in the presence of calcium.

An embodiment of the present invention relates to compositions comprising Neurexinal polypeptides. The method of producing Neurexinal polypeptides comprises the steps of: i) transfecting a mammalian host cell with a recombinant expression vector comprising a polynucleotide of the present invention, and ii) purifying the produced protein. Neurexinal may be isolated according to any technique known in the art or disclosed herein. Preferably, an antibody directed against Neurexinal or a fragment thereof, is bound to a chromatographic support to form an affinity chromatography column.

In another embodiment, the protein of the invention may be used to target heterologous compounds (polypeptides or polynucleotides) to the neurons. For instance, a chimeric protein composed of Neurexinal or a fragment thereof recombinantly or chemically fused to a compound, protein, or polynucleotide of interest would allow specific delivery to cells that express ligands for neurexinal, such as dystroglycan. Dystroglycan is expressed in neurons of the cerebral cortex, hippocampus, olfactory bulb, basal ganglia, thalamus, and hypothalamus. A method of targeting these cell populations would be valuable for treatment of a number of neuronal and mood disorders such as epilepsy, stress disorder, schizophrenia, Huntingtons, Alzheimers and Parkinsons disease. In addition, the hypothalamus of obese individuals often expresses lower than normal levels of leptin receptor. Thus, introduction of leptin receptor contructs or agonists to the hypothalamus with heterologous Neurexinal may be an effective treatment for obesity.

A preferred embodiment of the invention relates to compositions and methods using the protein of the invention or fragment thereof to label neurons in order to visualize any change in number, topology or morphology. Such methods can be used to map neuronal tissue damage associated with stroke; neurodegenerative conditions such as schizophrenia, Alzheimer's disease, epilepsy, stress disorder, Huntington's disease, and Parkinson's disease; and peripheral neuromuscular diseases such as myasthenia gravis and AIDS-related complex. For example, the protein of the invention or a fragment thereof may be used to generate specific antibodies, which would in turn allow the visualization of neurons, by methods well known to those skilled in the art. Preferably, the antibody is labeled with any detectable moiety including, but not limited to, a fluorescent label, a radioactive atom, a paramagnetic ion, biotin, a chemiluminescent label or a label which can be detected through a secondary enzymatic or binding step. In a similar fashion, antibodies raised against Neurexinal may be used to identify particular cell types as Neurexinal is specifically expressed only in neurons. Alternatively, quantitative analysis or detection of the protein of the invention, or of nucleic acids encoding Neurexinal, can be carried out by any other technique known to those skilled in the art. The invention further provides a method of diagnosing neurological disease or conditions, including but not limited to those listed above.

In another embodiment, the invention relates to a method of using compounds that bind a Neurexinal polypeptide or fragment thereof. Such method is directed toward diagnosis of disorders related to abnormal Neurexinal levels including neurodegenerative conditions such as schizophrenia, Alzheimer's disease, epilepsy, stress disorder, Huntington's disease, and Parkinson's disease. This method comprises the step of contacting a compound that specifically binds Neurexinal with a biological sample. Preferred compounds include Neurexinal specific antibodies and antigen binding fragments thereof. Further preferred compounds include those labeled with a detectable label, such as a fluorescent, radioactive, or enzymatic tag. This method may rely on various diagnostic techniques, including immunoassays.

In another embodiment, the present invention includes an assay system which may be prepared in the form of a test kit for the quantitative analysis of the extent of the presence of Neurexinal, or to identify compounds that may mimic or block its activity. The system or test kit comprises: a component that specifically binds Neurexinal and optionally, a means for detecting said component. Preferred components are Neurexinal-specific antibodies and antigen-binding fragments thereof. Preferably, the antibody or fragment is detectably labeled with, for example, a fluorescent, luminescent, or radioactive compound. Alternatively, the Neurexinal binding component may be labeled with a detectably enzymatic substrate and the optional means is the enzyme required for detection.

It is a further object of the present invention to provide a method and associated assay system for screening substances that are effective in either mimicking the activity or combating the adverse effects of Neurexinal in mammals.

A preferred embodiment of the invention is a method of screening for test compounds that increase or decrease Neurexinal expression. This method comprises the steps of: i) contacting a cell with a test substance, ii) detecting and quantifying Neurexinal expression levels, and iii) comparing Neurexinal expression in an exposed cell to that of an unexposed control cell. Preferably, Neurexinal expression is studied in neurons. Methods of detecting Neurexinal expression may be directed either to Neurexinal transcripts (e.g., Northern blotting, in situ hybridization, and other nucleotide detecting methods) or Neurexinal polypeptides (e.g., Western blotting or immunohistological methods). The expression level of Neurexinal can be decreased in a biological sample, for example using antisense molecules.

A preferred embodiment of the invention is a method of screening for compounds that increase or decrease Neurexinal activity. This method comprises the steps of: i) contacting a cell with a test substance, ii) detecting and quantifing Neurexinal activity levels, and iii) comparing Neurexinal activity in an exposed cell to that of an unexposed control cell. Preferably, Neurexinal activity is detected by determining binding of Neurexinal to alpha-latrotoxin, neurexophilin or dystroglycan. Binding may be tested by competitive binding assays with detectably-labeled proteins from the above list.

Neurexinal activators or agonists are defined as compounds that increase Neurexinal activity or expression. Neurexinal inhibitors or antagonists are defined as compounds that decrease Neurexinal activity or expression.

In yet a further embodiment, the invention is drawn to antagonists of the activity of Neurexinal. For example, the antagonist may be used to counteract alpha-latrotoxin and used as an antivenom for black widow spider bites. A Neurexinal antagonist may further be used or to treat disorders associated with abnormally high norepinephrine levels, such as Pheochromocytoma, attention-deficit hyperactivity disorder (ADHD), idiopathic torsion dystonia, and monoamine oxidase A deficiency. A method of using a Neurexinal inhibitor comprises the step of: administering a Neurexinal inhibitor in a physiologically acceptable composition to an individual. Physiologically acceptable compositions and carriers are discussed herein. Appropriate treatment will vary depending on the individual situation and may be determined by one skilled in the art.

Neurexinal activators may be used to modulate and/or reverse the degeneration of nerve terminals, to modulate synaptic transmission, or to treat other pathologies related to abnormally low levels of Neurexinal expression. A method of using a Neurexinal activator comprises the step of: administering a Neurexinal activator in a physiologically acceptably solution to an individual. Physiologically acceptable compositions and carriers are discussed herein. Appropriate treatment will vary depending on the individual situation and may be determined by one skilled in the art.

Protein of SEQ ID NO:32 (Internal Designation Clone 119033_105-066-4-0-F10-F)

The cDNA of Clone 119033_105-066-4-0-F10-F (SEQ ID NO:3 1) encodes NPIASY protein of SEQ ID NO:32, comprising the amino acid sequence: MAAELVEAKNMVMSFRVSDLQMLLGFVGRSKSGLKHELVTRALQLVQFDCTPELFKKIK ELYETRYAKKNSEPAPQPHRPLDPLTMHSTYDRAGAVPRT PLAGPNIDYPVLYGKYLNGL GRLPAKTLKPEVRLVKLPFFNMLDELLKPTELVPQNNEKLQESPCIFALTPRQVELIRNSRE LQPGVKAVQVVLRICYSDTSCPQEDQYPPNIAVKVNHSYCSVPGYYPSNK PGVEPKRPCR PINLTHLMYLSSATNRITVTWGNYGKSYSVALYLVRQLTSSELLQRLKTIGVKHPELCKAL VKEKLRLDPDSEIATTGVRVSLICPLVKMRLSVPCRAETCAHLQCFDAVFYLQMNEKKPT WMCPVCDKPAPYDQLIIDGLLSKILSECEDADEIEYLVDGSWCPIRAEKELSCSPQGAILVL GPSDANGLLPAPSVNGSGALGSTGGGGPVGSMENGKPGADVVDLTLDSSSSSEDEEEEEE EEEDEDEEGPRPKRRCPFQKGLVPAC. Accordingly, it will be appreciated that all characteristics and uses of the polypeptides of SEQ ID NO:32 described throughout the present application also pertain to the polypeptides encoded by the human cDNA included in Clone 119033_105-066-4-0-F10-F. In addition, it will be appreciated that all characteristics and uses of the polynucleotides of SEQ ID NO:31 described throughout the present application also pertain to the nucleic acids comprising the human cDNA in Clone 119033_105-066-4-0-F10-F. A preferred embodiment of the invention is directed toward the compositions of SEQ ID NO:31, SEQ ID NO:32 and Clone 119033_105-066-4-0-F10-F. Also preferred are polypeptide fragments having a biological activity as described herein and the polynucleotides encoding the fragments.

The protein of SEQ ID NO:32, NPIASY, is a novel polymorphic variant of Protein Inhibitor of Activated STAT Protein (PIASY) (accession numbers O75926). The protein of the invention displays a SAP domain: VMSFRVSDLQMLLGFVGRSKSGLKHELVTRALQLV (SEQ ID NO:82). In addition, NPIASY displays a MIZ Zinc finger motif: VSLICPLVKMRLSVPCRAETCAHLQCFDAVFYLQMNEKETCAHLQCFDAVFYLQMNEK (SEQ ID NO:83).

Activation of early response genes by interferons (IFNs) and other cytokines requires tyrosine phosphorylation of a family of transcription factors termed signal transducer and activator of transcripton (STAT) proteins. STAT proteins relay signals from activated cell surface receptors directly to the nucleus and play a critical role in gene induction by a variety of hematopoietic cytokines and hormones,such as the interleukin 6 (IL6) family of cytokines, epidermal growth factor, and leptin. All STAT proteins contain a DNA biding domain, a Src homology 2 domain and a transactivation domain necessary for transcriptional activation of target gene expression. Janus kinases (JAK) are cytoplasmic protein kinases which, upon cytokine signaling, phosphorylate STAT proteins on a specific tyrosine residue. Tyrosine phosphorylated STAT proteins dimerize through specific reciprocal SH2-phosphotyrosine interactions and translocate from the cytoplasm to the nucleus. Once in the nucleus, STAT proteins stimulate the transcription of specific target genes by binding to response elements in their promoters.

The binding of proteins from the Protein Inhibitor of Activated STAT (PAIS) family inhibits the STAT signaling pathway. The PIAS-STAT interaction depends on the tyrosine phosphorylation of STAT proteins.

NPIASY is localized in the nucleus. Upon Interferon stimulation, NPIASY becomes associated with STAT1. An LXXLL coregulator sequence at the NH2-terminus of NPIASY, although not involved in NPIASY-STAT1 interaction, is required for repression of STAT1-mediated gene activation. NPIASY is a transcriptional corepressor of STAT1. Also, NPIASY acts as a potent inhibitor of transcriptional activity of androgen receptor in prostate cancer cells. NPIASY binds to androgen receptor but does not affect the DNA biding activity of androgen receptor. The NH2 terminal LXXLL signature motif of NPIASY, although not required for NPIASY-androgen receptor interaction, is essential for the inhibitory activity of NPIASY. In addition, NPIASY binds to p53 and inhibits p53-mediated transactivation. However, NPIASY does not affect p53-mediated apoptosis. NPIASY regulates p53-mediated functions and directs p53 into a transactivation-independent mode of apoptosis.

An embodiment of the invention is directed to a composition comprising a NPIASY polypeptide sequence of SEQ ID NO:32.

A further embodiment of the invention is directed to a composition comprising a NPIASY polypeptide fragment having a biological activity of binding to STAT, p53, or Androgen Receptor.

A further embodiment of the invention is directed to a composition comprising a polynucleotide sequence of SEQ ID NO:31 encoding a NPIASY polypeptide.

A further embodiment of the invention is directed to a composition comprising a polynucleotide sequence encoding a NPIASY fragment having a biological activity of binding to STAT, p53, or Androgen Receptor.

NPIASY polypeptides bind to STAT, androgen receptor, and p53, which are often associated with cancers including T cell leukemias, breast, prostate, colorectal, pancreatic, lung, and esophageal cancers. A preferred embodiment of the invention is a method comprising the step of binding a NPIASY polypeptide, or fragment thereof with STAT, androgen receptor or p53 molecules under conditions that allow binding of NPIASY polypeptide to said molecules. This method may be directed to in vitro purification and detection methods as well as in vivo methods to inhibit STAT, p53, or Androgen Receptor. Such methods are discussed herein.

In a preferred embodiment, NPIASY polypeptide is used to purify STAT, androgen receptor or p53. In such method, NPIASY polypeptide is preferably covalently or non-covalently attached to a solid matrix and allowed to bind STAT, androgen receptor or p53 using techniques well known in the art. This method comprises the steps of: i) washing the solid matrix to get rid of contaminants, ii) eluting the particle of interest using more stringent conditions. Additional aspects of this embodiment include methods of using NPIASY polypeptide to detect and quantify STAT, androgen receptor, or p53 using techniques common in the art. This method comprises the step of: i) obtaining a biological sample suspected of containing STAT, androgen receptor, or p53; ii) contacting said sample with a NPIASY polypeptide or fragment thereof under conditions suitable for binding of NPIASY; and iii) detecting the presence of STAT, androgen receptor, or p53 by detecting NPIASY. Preferably, NPIASY polypeptide or fragment thereof is covalently attached to a detectable compound. Alternatively, a detectable NPIASY-specific antibody or fragment thereof may be used to detect NPIASY. This embodiment is useful, for example, as a diagnostic tool for detecting risk of p53, STAT, or Androgen Receptor related cancers such as T cell leukemias, breast, prostate, colorectal, pancreatic, lung, and esophageal cancers. In addition, this method may be used to diagnose disorders associated with a low level of the above proteins including muscle atrophy and sexual development defects.

A preferred aspect of the invention is a host cell recombinant for polynucleotides encoding a NPIASY polypeptide or a biologically active fragment thereof. An additional preferred aspect is a host cell recombinant for polynucleotides capable of directing NPIASY expression. Preferably, the polynucleotides capable of directing NPIASY expression are located in the 5' regulatory region of the NPIASY gene. Further preferably, these polynucleotides are located within 500 base pairs of the LIRION coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. NPIASY protein purified from said host cell may be used for in vitro methods of detection and purification, as well as diagnostic and in vivo applications.

An embodiment of the present invention relates to a method of producing compositions comprising NPIASY polypeptides. The method of producing NPIASY polypeptides comprises the steps of: i) transfecting a host cell with a recombinant expression vector comprising a polynucleotide of the present invention, and ii) purifying the produced protein. NPIASY may be purified by any technique known in the art or disclosed herein. Preferably, an antibody directed against NPIASY or part thereof, preferably, an antibody directed against the C-terminal sequence of NPIASY polypeptide, may be bound to a chromatographic support to form an affinity chromatography column. Alternatively, NPIASY polypeptides may be produced by a method comprising the step of: i) transfecting a host cell with a polynucleotide capable of directing NPIASY expression. Preferably, the polynucleotides capable of directing NPIASY expression are located in the 5' regulatory region of the NPIASY gene. Further preferably, these polynucleotides are located within 500 base pairs of the NPIASY coding region. These polynucleotides preferably comprise a promoter sequence, as discussed above.

In another embodiment, the invention is directed to a method of detecting NPIASY polypeptide in a biological sample, said method comprising the steps of: i) contacting a biological sample with an antibody or antibody fragment that specifically binds NPIASY polypeptide; and ii) detecting the antigen-antibody complex formed. The antibody or antibody fragment may be monoclonal or polyclonal. In addition, the antibody or antibody fragment may be primarily or secondarily labeled by a detectable compound common in the art (e.g., radioactive, fluorescent, luminescent, or enzymatic). This method may be applied to diagnosis of NPIASY-related disorders. For example, an abnormally low level of NPIASY may indicate a high risk of p53, STAT, or Androgen Receptor related cancers such as T cell leukemias, breast, prostate, colorectal, pancreatic, lung, and esophageal cancers. An abnormally high level of NPIASY may indicate a risk of growth and cell proliferation defects associated with the above proteins such as incomplete sexual development and muscle atrophy.

In some embodiments, the invention also concerns a diagnostic kit for detecting the presence of NPIASY polypeptide. This kit comprises: i) a polyclonal or monoclonal antibody or fragment thereof that specifically binds a NPISAY polypeptide; and optionally, ii) a reagent allowing the detection of the antigen-antibody complexes formed. Preferably, the antibody, or antibody fragment is detectably labeled. Such labels include fluorescent, luminescent, and radioactive compounds, as well as enzymatic substrates. The optional reagent may provide a detectable signal that either binds to the antibody or reacts with the label on the antibody. NPIASY antibodies may be used to diagnose any of the disorders listed above. To diagnose such disorders, an appropriate biological sample can be tested to determine the level of NPIASY being produced.

In another embodiment, the invention provides methods for regulating an IFN-associated immune response mediated by STAT. The immune response includes an anti-viral or anti-tumor response mediated by IFN secreted by B and/or T cells. This method comprises the step of introducing a polynucleotide construct comprising polynucleotides encoding a NPIASY polypeptide to an IFN-responsive cell. Preferably, the polynucleotide construct comprises an expression control element operably linked to the NPIASY-encoding polynucleotide. Suitable compositions of polypeptides or polynucleotides of the present invention are useful as a method of treatment of IFN-related pathologies such as inflammation.

An embodiment of the invention provides for a method of screening test substances for modulators of NPIASY expression. This method comprises the steps of: i) contacting a cell with a test substance; ii) detecting and quantifying NPIASY expression; and ii) comparing NPIASY expression in the cell after exposure to the test substance to that of an unexposed control cell. NPIASY expression is determined by methods common to the art or included herein, by detecting NPIASY polynucleotides or polypeptides. An example of this method comprises the steps of: i) culturing two equivalent cell samples; ii) adding a test substance to one of the cultures and not the other, iii) harvesting both cultures at a specified time; iv) purifying the mRNA from each sample of cells; v) comparing the level of NPIASY mRNA in each sample by Northern blot, RTPCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) comparing the level of NPIASY polypeptides in each sample by Western blot, immunohistochemistry, or another method common to the art. The invention provides for design and use of specific antibodies and antibody fragments, as discussed herein.

In another embodiment, a NPIASY polypeptide or a fragment thereof, may be used to screen for compounds that activate or inhibit NPIASY activity. This method comprises the steps of: i) contacting a NPIASY polypeptide or fragment thereof with a test substance and ii) monitoring NPIASY activity. NPIASY binds to STAT, androgen receptor, and p53. Thus, NPIASY activity may be monitored upon addition of the test substance by competitive binding assays with either STAT, androgen receptor, or p53. In this aspect of the invention, a NPIASY polypeptide or fragment thereof may be free in solution, affixed to a solid support, recombinantly expressed on or chemically attached to a cell surface, or located intracellularly. The formation of binding complexes between NPIASY polypeptide and the compound being tested, may be measured by methods well known to those skilled in the art, such as the BIAcore (Upsala, Sweden). Another technique provides for high throughput screening of compounds having suitable binding affinity to the protein of the invention as described in published PCT application WO84/03564, and incorporated herein by reference in its entirety. Test substances that decrease NPIASY expression or activity are defined as inhibitors or antagonists of NPIASY. Test substances that increase NPIASY expression or activity are defined as activators or agonists. Antagonists of the polypeptides or polynucleotides of the present invention are used to stimulate, promote, or facilitate progression through the cell cycle, such as in the cellular regeneration of terminally differentiated cardiac myocytes or tissues, e.g., striated muscle myocytes. For example, this could allow restoration of damaged myocardium after cardiac injury, myocardial infarction, myocarditis, cardiomyopathy, trauma, as a consequence of cardial surgery, etc., or repletion of striated muscle exhausted by muscular dystrophy. Agonists of polypeptides or polynucleotides of the present invention are useful in treatment of pathologies such as but not limited to hyperproliferative diseases such as cancer (e.g., leukemia, lymphoma, breast cancer, colon cancer, prostate cancer) coronary artery disease, pulmonary vascular, obstructive disease, either primary or as a feature of Eisenmenger's syndrome, and other disorders of abnormal cellular proliferation. Agents which modulate the expression or activity of NPIASY include, but are not limited to antisense oligonucleotides, ribozymes, and antibodies. These agents may be made and used according to methods well known in the art.

In a further embodiment, expression of the polypeptides encoded by the nucleic acids is expected to prevent, ameliorate, or lessen the cell cycle defect of the host cell, or to restore normal cell cycle progression of the host cell. Whether provided via nucleic acid or polypeptides delivered directly to cells, the therapeutic formulations of the invention can also be used as adjuncts to other forms of therapy, including but not limited to chemotherapy, and radiation therapy.

In another preferred embodiment, the protein of the invention can be used to modulate and/or characterize fertility, including for the treatment or diagnosis of infertility, and for contraception. NPIASY inactivates Androgen receptor which is required for the activation of genes essential for spermatogenesis. Thus, over-expression or activation of NPIASY can be used to repress Androgen receptor transcription activity and thereby inhibit fertility. For example, for contraception, the expression of genes for spermatogenesis can be artificially disrupted, for example by increasing the protein level using polynucleotides encoding the protein, using the protein itself, or using activators of protein expression or activity. Alternatively, for infertility, the protein level can be decreased using inhibitors such as antisense oligonucleotides, antibodies, dominant negative forms of the protein, and using heterologous compounds that inhibit protein expression or activity. Similarly, the cause of infertility in many patients can be detected by detecting the level of expression of the present protein, where an abnormal level of activity or expression of the protein indicates that a cause of infertility involves the NPIASY repression. Such a diagnosis would also point to methods of treating the infertility, e.g. by increasing or decreasing the expression or activation of the present protein.

Another embodiment of the invention relates to composition and methods using polynucleotide sequences encoding the protein of the invention or a fragment thereof to establish transgenic model animals (*D. melanogaster, M. musculus*), by any method familiar to those skilled in the art. By modulating in vivo the expression of the transgene with drugs or modifier genes (activator or suppressor genes), animal models can be developed that mimic human hormone-dependent disorders such as cancers. These animal models would thus allow the identification of potential therapeutic agents for treatment of the disorders. In addition, recombinant cell lines derived from these transgenic animals may be used for similar approaches ex vivo.

Protein of SEQ ID NO:34 (Internal Designation 125402_105-074-4-0-F3-F)

The cDNA of 125402_105-074-4-0-F3-F (SEQ ID NO:33) encodes protein vCRTL-1 of SEQ ID NO:34, comprising the amino acid sequence: MLLLSLTLSLVLLGSSWGCGIPAIKPALSFSQRIVNGENAVLGSWPWQVSLQDSSDFHFCG GSLISQSWVVTAAHCNVSPGRHFVVLGEYDRSSNAEPLQVLSVSRAITHPSWNSTTMNND VTLLKLASPAQYITRISPVCLASSNEALTEGLTCVTTGWGRLSGVGNVTPARLQQVALPL VTVNQCRQYWGSSITDSMICAGGAGASSCQGDSGGPLVCQKGNTWVLIGIVSWGTKNCN VRAPAVYTRVSKFSTWINQVIAYN. Accordingly, it will be appreciated that all characteristics and uses of polypeptides of SEQ ID NO:34 described throughout the present application also pertain to the polypeptides encoded by the human cDNA included in 125402_105-074-4-0-F3-F. In addition, it will be appreciated that all characteristics and uses of the polynucleotides of SEQ ID NO:33 described throughout the present application also pertain to the nucleic acids comprising the human cDNA in 125402_105-074-4-0-F3-F. A preferred embodiment of the invention is directed toward the compositions of SEQ ID NO:33, SEQ ID NO:34, and 125402_105-074-4-0-F3-F. Also preferred are polypeptide fragments having a biological activity as described herein and the polynucleotides encoding the fragments.

The cDNA of SEQ ID NO:33 is a novel polymorphic variant of the human chymotrypsin-like protease CTRL-1 encoded by a gene located on chromosome 16, specifically at position 16q22.1. The 264 amino-acid protein of vCRTL-1 contains a signal peptide (MLLLSLTLSLVLLGSSWG) (SEQ ID NO:84) and a serine protease domain and belongs to the serine protease family.

Proteases are key components in a broad range of biological pathways and can be classified into four groups according to their catalytic mechanisms: the serine, cysteine (thiol), aspartic (carboxyl), and metalloproteases. Chymotrypsins are members of a family of enzymes known as serine proteases, so named because they utilize an activated serine residue in their substrate-binding site to catalyze the hydrolysis of certain peptide bonds. The pancreatic subfamily of proteases comprises trypsins, chymotrypsins, kallikrein, and elastases. Chymotrypsins are the most abundant among the pancreatic proteases and may represent 10-20% of the total protein synthesized by the exocrine pancreas. vCRTL-1 is a digestive enzyme expressed and synthesized by pancreatic acinar cells as an inactive zymogen precursor that must be cleaved to form an active protease. vCRTL-1 displays chymotrypsin- and elastase-2-like activities and hydrolyzes the amide bonds of substrates having tyrosine, phenylalanine, or leucine residues at the P1 position, and preferably a proline in the P2 position. The secretion of vCRTL-1 can be induced by the presence of protease inhibitors in the pancreas or intestinal fluid (in particular duodenal fluid).

An embodiment of the invention is directed to a composition comprising a vCRTL-1 polypeptide sequence of SEQ ID NO:34.

A further embodiment of the invention is directed to a composition comprising a vCRTL-1 polypeptide fragment having a biological activity of protein substrate binding or serine protease activity.

A further embodiment of the invention is directed to a composition comprising a polynucleotide sequence of SEQ ID NO:33 encoding a vCRTL-1 polypeptide.

A further embodiment of the invention is directed to a composition comprising a polynucleotide sequence encoding a vCRTL-1 polypeptide fragment having a biological activity of protein substrate binding or serine protease activity.

A further embodiment of the invention is directed to a composition comprising an antibody directed against the vCRTL-1 polypeptide sequence of SEQ ID NO:34 or a vCRTL-1 polypeptide fragment having a biological activity of protein substrate binding or serine protease activity. Preferably, the antibody specifically binds to vCRTL-1 but not to CTRL-1. Even more preferably, the antibody recognizes the SLQDSSDFHF (SEQ ID NO:85) amino-acid sequence.

An additional preferred embodiment of the invention is a method of binding vCRTL-1 polypeptides with a vCRTL-1-specific antibody or vCRTL-1-binding fragment thereof. This method comprises the step of contacting a vCRTL-1 polypeptide with a vCRTL-1-binding antibody or vCRTL-1-binding fragment thereof under conditions that allow binding. This method may be applied to detection and purification of vCRTL-1. These aspects are discussed in detail herein.

Another embodiment relates to a method of producing a recombinant vCRTL-1 polypeptide comprising the steps of: i) transfecting a host cell with an appropriate expression vector comprising a polynucleotide encoding vCRTL-1 and ii) purifying the produced protein. The host cells are cultured under conditions whereby the nucleic acid sequence coding for this particular protein is expressed. After a suitable amount of time for the product to accumulate, the protein is purified from the host cells or medium surrounding the cells. Introduction of an expression vector incorporating a nucleic acid sequence coding for vCRTL-1 into a host cell can be performed in a variety of ways, such as but not limited to calcium or lithium chloride treatment, electroporation, and lipofection. Also in this embodiment, a milk animal can be used to produce vCRTL-1 in the milk, thereby generating a significant amount of this particular protein after purification. Any type of animal that produces enough milk can be used in this aim such as, but not limited to, sheep, goat, and cow. These animals can be generated with any method of targeting overexpression of vCRTL-1 in the milk. The protein of the invention may be purified using any technique well-known to those skilled in the art including those disclosed in the U.S. Pat. No. 6,268,487, which disclosure is hereby incorporated by reference in its entirety. Preferably, an antibody or antigen-binding fragment directed against vCRTL-1 or a fragment thereof may be bound to a chromatographic support to form an affinity chromatography column. Even more preferably, the antibody binds specifically to vCRTL-1 but not to CTRL-1.

A preferred embodiment of the invention is a method of using vCRTL-1 polypeptide or a biologically active fragment thereof to proteolytically cleave a substrate protein. This method comprises the step of contacting vCRTL-1 with a protein substrate under conditions that allow vCRTL-1 protease activity. This method is directed to both in vitro and in vivo uses of the protein that include biochemical applications and prevention and treatment of vCRTL-1-related disorders such as chronic and acute pancreatits and cystic fibrosis.

In another embodiment, the present invention is to provide a method of effectively inducing vCRTL-1 proteolytic activity to digest a wide range of proteins in a biological sample. This method can be performed either in vitro or in vivo and comprises the step of contacting an effective amount of vCRTL-1 polypeptide or a biologically active fragment thereof with a biological sample under conditions that allow vCRTL-1 proteolytic activity. For example, such a method can be used in vitro for removing proteins in a DNA preparation or for removing enzymes after any enzymatic reaction. Such a composition can be used alone or as a "cocktail" with other proteases. Such protease cocktails are widely used in assays to degrade proteins susceptible of interfering with an assay to be performed.

In another embodiment, vCRTL-1 or fragment thereof can be used in combination with a detergent for the removal of stains having a protein component, similar to the use of proteases described in U.S. Pat. No. 5,599,400, which disclosure is incorporated by reference in its entirety. The composition can contain known detergent constituents such as surfactants, foam enhancers and fillers. vCRTL-1 polypeptides can be included in a detergent composition or can be combined with other constituents at the time of use as an additive. The detergent additive can be formulated as a liquid, powder, granulate or slurry.

A further embodiment of the present invention is directed to substances that increase or decrease vCRTL-1 expression, and to a method of screening for such substances comprising the steps of: i) contacting a cell with a test substance, ii) quantifying and detecting vCRTL-1 expression levels, and iii) comparing vCRTL-1 expression in an exposed cell to that of an unexposed control cell. vCRTL-1 expression may be determined by any specific nucleotide or protein detection techniques common to the art (e.g., Northern or Western blotting) Preferably, vCRTL-1 expression is studied in pancreatic cells. The expression level of vCRTL-1 can be decreased in a biological sample, for example using antisense molecules.

A further embodiment of the present invention is directed to substances that increase or decrease vCRTL-1 activity, and to a method of screening for such substances comprising the steps of: i) contacting a cell with a test substance and ii) detecting vCRTL-1 activity, and iii) comparing vCRTL-1 proteolytic activity in an exposed cell to that of an unexposed control cell. Preferably, vCRTL-1 expression is studied in pancreatic cells. The activity of vCRTL-1 may be inhibited using direct or indirect inhibitor molecules or antagonistic antibodies.

Activators or agonists of vCRTL-1 are substances that increase the activity or expression of vCRTL-1. Inhibitors or antagonists of vCRTL-1 are substances that decrease the activity or expression of vCRTL-1.

The present invention also provides animal models generated by modulating the expression or activity of the present protein in one or more tissues of the animal and preferably in pancreas. Such animals are useful for a number of purposes, because they represent an in vivo assay method for testing candidate molecules potentially useful for the treatment of various pathophysiological aspects of diseases specifically related to the activity of vCRTL-1 such as acute or chronic pancreatitis. Study of the phenotype of such models can also allow the identification of additional human equivalent diseases caused by or linked with vCRTL-1 deficiency. These animals can be generated with any method of targeting overexpression or inactivation of vCRTL-1. Such models are extremely useful, e.g. in the assessment of candidate therapies and drugs for the treatment of such diseases and conditions.

In another embodiment, the current invention is used to diagnose diseases or disorders associated with abnormal vCRTL activity. In particular, it is useful in diagnosing patients with exocrine pancreatic insufficiency which results in a dramatic reduction of vCRTL-1 activity. Examples of such diseases and disorders include, but are not limited to, chronic or acute pancreatits and cystic fibrosis. In addition, vCRTL is associated with metastatic tumor activity, in particular, that of pancreatic tumors. Thus, higher than normal levels of vCRTL may be indicative of metastatic activity. The method includes the steps of: i) contacting a fluid or tissue sample with a compound capable of selectively binding vCRTL-1 polypeptide or polynucleotide and ii) detecting the level of vCRTL-1 polypeptide or polynucleotide in the sample. Preferably, a difference in the level or other property in the sample relative to in a control sample indicates the presence of the disorder or a propensity for developing disorder. Preferably, samples to be analyzed include, but are not limited to, intestinal fluids and in particular duodenal juice, homogenates of pancreatic tissue, urine and plasma. More preferably, the fluid or tissue sample is obtained from an individual suspected of suffering from the disorder, or at risk of developing the disorder. For example, a polyclonal or monoclonal antibody or any antigen binding active fragment thereof or a nucleic acid probe may be used. Preferably, the antibodies used in this embodiment are specifically directed against the variant vCRTL-1 polypeptides and do not recognize CRTL-1 polypeptides. Detection can be carried out directly or indirectly with known immunohistological or immunofluorescent processes. vCRTL-1 binding molecules may be directly labeled with generally known compounds, including, but not limited to, enzymes such as alkaline phosphatase and peroxidase and fluorescent dyes such as FITC, rhodamine, and Texas-Red. However, labeling can also occur indirectly by using secondary reagents. Also in this embodiment, diagnosis may be facilitated by the identification of the variant vCRTL-1 using well known PCR or RT-PCR techniques and in particular in with "real-time" PCR system. Alternatively, using such a method, the present invention provides a tool to correlate modulations in the expression of vCRTL-1 with certain pathologies. Thus, the present invention provides a novel candidate gene for such conditions.

In a further embodiment, the invention includes a test kit useful for the quantification of the amount of vCRTL-1 in a biological sample. The level of vCRTL-1 polypeptide is useful in evaluating the degree of severity of pancreatic disorders that have been clinically ascertained and also represents a useful marker in examining the pathophysiology and possible treatment modalities in the animal model of acute pancreatitis. In addition, vCRTL-1 level may be useful in the estimation of tumor invasiveness and metastasis ability, preferably in the case of pancreatic cancers. In this embodiment, the application of such assays can be used to monitor the progress of therapy administered to treat these or other conditions. Further, the assays can be used as a measure of toxicity, for example, during clinical testing of new drugs to assess the impact on tissue degradation. Thus, the assays may be applied in any situation wherein vCRTL-1 may be used as an index of the condition, treatment, or effect of substances directly administered to the subject. Thus, the condition of a patient can be monitored continuously and the quantified amount of vCRTL-1 in the pathological sample can be compared with the amount quantified in a biological sample of a normal individual or with the previous analysis of the same patient. In this embodiment, this marker can be measured effectively in intestinal fluids and in particular in duodenal juice, homogenates of pancreatic tissue, urine and plasma, by any suitable method, including immunoassays. The kit comprises at least one immunological binding partner (e.g., a monoclonal or polyclonal antibody specific for vCRTL-1) and optionally, a secondary detectable marker. Preferably, the antibody or antigen-binding fragment thereof used in the kit is specifically directed against the variant vCRTL-1 polypeptides and not to CTRL-1 polypeptides.

A further embodiment of the present invention is to provide novel methods and compositions useful for treating individuals at risk of developing or suffering from a disorder associated with insufficient secretion of vCRTL-1. These methods and compositions are useful for the treatment of exocrine pancreatic deficiency charaterized by steatorrhoea such as chronic or acute pancreatits and cystic fibrosis. This method comprises the step of: administering an effective amount of vCRTL-1 polypeptide, a biologically active fragment thereof, or agonist to an individual with or at risk of one of the listed conditions. Preferably, vCRTL-1 or agonist compositions are delivered in combination with a physiologically acceptable carrier, such as a saline solution or other physiologically buffer. The particular amount of the compositions of the invention that will be administered to the individual for any particular condition will depend on the clinical condition of the patient, and other factors such as the weight, age, and route of delivery. Such compositions may be administered by any suitable route including, but not limited to, oral, aerosol, intravenous, intramuscular, intraperitoneal, or subcutaneous routes. These compositions can comprise the protein of the invention, and, optionally, one or more other types of protease, or any other compound of interest. This co-administration may be by simultaneous administration or by separate or sequential administrations. All of these additional components may be either obtained from natural sources or produced by recombinant genetic engineering techniques and/or chemical modification.

A further embodiment of the present invention is to provide novel methods and compositions useful for treating individuals at risk of developing or suffering from a disorder associated with higher than normal levels of vCRTL-1. This method is useful for the treatment of metastatic cell growth, in particular, pancreatic cancers. This method comprises the step of administering an effective amount of a vCRTL-1 antagonist to an individual with or at risk of developing a metastatic cell growth. Preferably, vCRTL-1 antagonist compositions are delivered in combination with a physiologically acceptable carrier, such as a saline solution or other physiologically buffer. The particular amount of the compositions of the invention that will be administered to the individual for any particular condition will depend on the clinical condition of the patient, and other factors such as the weight, age, and route of delivery. Such compositions may be administered by any suitable route including, but not limited to, oral, aerosol, intravenous, intramuscular, intraperitoneal, or subcutaneous routes.

Protein of SEQ ED NO:36 (Internal Designation Clone 107640_105-036-2-0-H3F)

The cDNA of Clone 107640 105-036-2-0-H3-F (SEQ ID NO:35) encodes the 447 amino acid LIRION protein of SEQ ID NO:36 comprising the amino acid sequence: MIPTFTALLCLGLSLGPRTHMQAGPLPKPTLWAEPGSVISWGNSVTIWCQGTLEAREYRLD KEESPAPWDRQNPLEPKNKARFSIPSMTEDYAGRYRC YYRSPVGWSQPSDPLELVMTGAY SKPTLSALPSPLVTSEKSVTLLCQSRSPMDTFLLIKERAAHPLLHLRSEHGAQQHQAEFPMS PVTSVHGGTYRCFSSHGFSHYLLSHPSDPLELIVSGSLE DPRPSPTRSVSTAAGPEDQPLMP TGSVPHSGLRRHWEVLIGVLWSILLLSLLLFLLLQHWRQGKHRTLAQRQADFQRPPGAA EPEPKDGGLQRRSSPAADVQGENFCAAVKDTQPEDGVEM DTRSPHDEDPQAVTYAKVKH SRPRREMASPPSPLSGEFLDTKDRQAEEDRQMDTEAAASEAPQDVTYAQLHSFTLRQKAT EPPPSQEGASPAEPSVYATLAIH. Accordingly, it will be appreciated that all characteristics and uses of polypeptides of SEQ ID NO:36 described throughout the present application also pertain to the polypeptides encoded by the human cDNA included in Clone 107640 105-036-2-0-H3-F. In addition, it will be appreciated that all characteristics and uses of the polynucleotides of SEQ ID NO:35 described throughout the present application also pertain to the nucleic acids comprising the human cDNA in 107640 105-036-2-0-H3-F. Also preferred are fragments having a biological activity as described therein and the polynucleotides encoding the fragments.

LIRION, the protein of SEQ ID NO:36, represents a novel variant form of the ILT-3 receptor precursor (Genbank entry U82979) starting with a 259 amino acid long extracellular domain including a peptide signal sequence (MIPTFTALLCLGLSLGPRTHMQA) (SEQ ID NO:86) and two C2 type immunoglobulin-like-domains, followed by a transmembrane region (VLIGVLVVSILLLSLLLFLLL) (SEQ ID NO:87) and a 167 amino acid long intracellular domain which contains three Immunoreceptor Tyrosine-based Inhibitory Motifs (ITIMs).

Immune system cellular activity is controlled by a complex network of cell surface interactions and associated signaling processes. Upon receptor binding, cellular activity is regulated by a balance between activating and inhibitory signals. Many receptors that mediate positive signaling have cytoplasmic tails containing sites of tyrosine phosphorylation known as Immunoreceptor Tyrosine-based Activation Motifs (ITAMs). The inhibitory pathways involve receptors having ITIMs, which provide binding sites for protein tyrosine phosphatases.

The cytolytic activity of Natural Killer (NK) cells is regulated by a balance between positive signals that initiate cell function and inhibitory signals which prevent the cell activity. Normal cells are protected from NK cells by cell surface expression of MHC class I proteinss that are recognized by inhibitory receptors on the NK cells. These receptors, known as Killer Inhibitory Receptors (KIRs) send a negative signal to the cell upon engagement and down regulate NK cell cytotoxic activity. MHC class I expression is often down-regulated in virally infected and in tumor cells, which renders these cells susceptible to NK cell attack. The KIRs are immunoglobulin superfamily receptors with two ITIMs. These phosphorylated ITIMs recruit tyrosine phosphatases which dephosphorylate molecules in the signal transduction pathway and prevent cell activation.

LIRION, the protein of the invention, is an inhibitory Immunoglobulin-Like Transcript (ILT) receptor. This class of receptor is closely related to the KIRs and functions in the same manner. LIRION is selectively expressed on myeloid antigen presenting cells (APCs), i.e. dendritic cells, monocytes and macrophages and negatively regulates the functional response of APCs triggered by stimulatory receptors. In addition to its inhibitory function, LIRION is involved in antigen uptake and processing.

Preferred LIRION polypeptides for use in the methods described below include the polypeptides comprising the amino sequence of: GPLPKPTLWAEPGSVISWGNSVTI-WCQGTLEAREYRLDKEESPAPWDRQN-PLEPKNKARF SIPSMTEDYAGRYRCYYRSPVG-WSQPSDPLELVMTGAYSKPTLSALPSPLVTSEK SVTLLC QSRSPMDTFLLIKERAAHPLLHLRSEH-GAQQHQAEFPMSPVTSVHGGTYRCFSSHGFSHY LLSHPSDPLELIVSGSLEDPRPSPTRS-VSTAAGPEDQPLMPTGSVPHSGLRRHWEVLIGVL VSILLLSLLLFLLLQHWRQGKHRT-LAQRQADFQRPPGAAEPEIKDGGLQRRSSPAADVQG ENFCAAVKDTQPEDGVEMDTRSPHDED-PQAVTYAKVKIISRPRREMASPPSPLSGEFLDT KDRQAEEDRQMDTEAAASEAPQD-VTYAQLHSFTLRQKATEPPPSQEGASPAEPSVYATL AIH (SEQ ID NO:88);

A polypeptide comprising the amino acid sequence of: GPLPKPTLWAEPGSVISWGNSVTIWC-QGTLEAREYRLDKEESPAPWDRQNPLEPKNKARF SIPSMTEDYAGRYRCYYRSPVGWSQPS-DPLELVMTGAYSRPTLSAIPSPLVTSEKSVTLLC QSR-SPMDTFLLIKERAAHPLLHLRSEH-GAQQHQAEFPMSPVTSVHGGTYRCFSSHGFSHY LLSHPSDPLELIVSGSLEDPRPSPTRS-VSTAAGPEDQPLMPTGSVPHSGLRRHWE (SEQ ID NO:89).

A polypeptide comprising the amino acid sequence of: QHWRQGKHRTLAQRQADFQRPP-GAAEPEPKDGGLQRRSSPAADVQGENFCAAV KDTQPEDGVEMDTRSPHDEDPQAVTY-AKVKHSRPRREMASPPSPLSGEFLDTKDRQAEE DRQMDTEAAASEAPQDVTYAQLHSFTL-RQKATEPPPSQEGASPAEPSVYATLAIH (SEQ ID NO:90).

An embodiment of the invention is directed to a composition comprising a LIRION polypeptide sequence of SEQ ID NO:36.

A further embodiment of the invention is directed to a composition comprising a LIRION polypeptide fragment having biological activity of interacting with SHP-1, MHC I, MHC I-like molecules (such as CD1, MR1, MIC), MHCII, and complement components (such as C1, C2, C3, C4, C5, and factor B).

A further embodiment of the invention is directed to a composition comprising a polynucleotide sequence of SEQ ID NO:35 encoding a LIRION polypeptide.

A further embodiment of the invention is directed to a composition comprising a polynucleotide sequence encoding a LIRION polypeptide fragment having biological activity of interacting with SHP-1, MHC I, MHC I-like molecules (such as CD1, MR1, MIC), MHCII, and complement components (such as C1, C2, C3, C4, C5, and factor B).

A further embodiment of the invention is directed to a method of screening test substances for modulators of LIRION expression comprising the steps of: i) contacting a cell with a substance to be tested; and ii) comparing LIRION expression in the cell after exposure to the test substance to that of an untreated control cell.

A preferred embodiment relates to an antibody that specifically binds to LIRION polypeptides. Further included are LIRION binding antibody fragments. Preferably, the LIRION-specific antibody or LIRION-binding fragment thereof binds LIRION and not ILT3. Monoclonal, polyclonal, heterologous, and detectably labeled antibodies and antigen-binding fragments are included in the invention. Methods of making such antibodies and fragments thereof are common to the art and included herein.

An additional preferred embodiment of the invention is a method of binding LIRION polypeptides with a LIRION-specific antibody or LIRION-binding fragment thereof. This method comprises the step of contacting a LIRION polypeptide with a LIRION-binding antibody or LIRION-binding fragment thereof under conditions that allow binding. This method may be applied to detection and purification of LIRION, as well as targeting LIRION-expressing cells. These aspects are discussed in detail herein.

In one embodiment, a sequence encoding SEQ ID NO:36 bearing G to A, G to A and A to G substitutions at nucleotide positions 447, 705 and 1040 of SEQ ID NO:35 corresponding to positions 137, 223 and 335, and resulting in the substitution of a glycine residue by a glutamic acid at position 137, a glycine by an aspartic acid at position 223 and an asparagine residue by an aspartic acid at position 335, respectively, can be used for DNA genotyping. Genotyping this locus could be of interest, e.g., in DNA fingerprinting for paternity studies or forensic analyses. It could also be used for genetic association studies, especially in pathologies relating to B cell autoimmune disorders (e.g., rheumatoid arthritis and ulcerative colitis) and antigen presentation disorders (such as bare lymphocyte syndrome).

In another embodiment, the polynucleotide sequence of the invention can be used in pharmacogenomic applications in order to aid in the choice of the ideal drug (e.g. an agonist or an antagonist of LIRION), or dosage of a drug, for the treatment of a condition or disease in a patient. For example, in one embodiment, the invention provides a method of genotyping a patient to determine the identity of the nucleotides encoding the amino acids at positions 137, 223 and 335 of LIRION, and administering to the patient a drug or a dosage of the drug that has been established to be preferentially efficacious in those with glutamic acid, aspartic acid and aspartic acid residues at positions 137, 223 and 335 (e.g. because of preferential binding of the drug to the isoform of the protein with glutamic acid, aspartic acid and aspartic acid at these positions). In another embodiment, the patient is genotyped for the nucleotides encoding amino acid positions 137, 223 and 335, a drug is not administered, e.g. because side effects are known to be associated with the administration of the drug to individuals with glutamic acid, aspartic acid and aspartic acid at positions 137, 223 and 335, respectively.

A preferred aspect of the invention is a host cell recombinant for polynucleotides encoding a LIRION polypeptide or a biologically active fragment thereof. An additional preferred aspect is a host cell recombinant for polynucleotides capable of directing LIRION expression. Preferably, the polynucleotides capable of directing LIRION expression are located in the 5' regulatory region of the LIRION gene. Further preferably, these polynucleotides are located within 500 base pairs of the LIRION coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties.

Another embodiment relates to methods of producing LIRION polypeptides. The protein of the invention can be produced in host cells that have been transfected with an appropriate expression vector comprising a nucleic acid sequence coding for LIRION. Introduction of such expression vector to a host can be performed in a variety of ways, including calcium or lithium chloride treatment, electroporation, or lipofection. Any of a wide variety of expression systems can be used to express the recombinant proteins. Suitable expression vehicles include, but are not limited to plasmids, viral particles or baculovirus for insect cells. The expression vehicle can be integrated into the host cell genome. Optionally, an inducible expression vector can be used to achieve controlled expression of the gene in the host cell. The recombinant protein can be recovered from the host cell and purified by any technique well known to those skilled in the art. Preferably, an antibody directed against the protein of the invention or part thereof can be bound to a chromatographic support to form an affinity chromatography column. Alternatively, LIRION or fragments thereof can be chemically synthesized using solid-phase techniques.

In another embodiment, the present protein can be used to purify myeloid APCs from a biological sample or from cells grown in vitro. In one such a method a monoclonal or polyclonal antibody directed against the protein of the invention can be used to immunopurify the cells. Methods used to immunopurify cells are well known in the art. For example, the antibody can be fixed on a sepharose column or linked to a solid support. Alternatively, the antibody is fluorescently labeled and cells are purified by FACS.

In another embodiment, the invention provides compositions and methods for detecting the level of expression of the mRNA encoding the protein of the invention in a mammal, preferably a human. Quantification of mRNA levels of LIRION may be useful for the diagnosis of conditions correlated with abnormal expression of the protein, including autoimmune disorders, or to monitor regulation of LIRION during therapeutic intervention as described herein. Assays for the detection and quantification of mRNA are well known in the art. Preferred method comprises the steps of: isolating RNA from a biological sample, measuring LIRION mRNA level by quantitative RT-PCR, and comparing the expression in the subject sample to that of a control sample. Polynucleotide probes or primers used for the detection of LIRION mRNA by hybridization or PCR amplification may be designed from the polynucleotide of SEQ ID NO:35 by methods well known in the art.

In another embodiment, the invention relates to methods and compositions for detecting LIRION and quantifying its level of expression in a biological sample. These methods may be useful for the diagnosis of conditions characterized by altered or abnormal LIRION expression including autoimmune (e.g., rheumatoid arthritis, multiple sclerosis, and virally-induced autoimmunity), metabolic (e.g., obesity, hypercholesterolemia, insulin-related disorders), and neurological (e.g., schizophrenia) conditions. A method to quantify the expression of LIRION protein comprises the step of: contacting a biological sample with a LIRION-specific antibody or LIRION specific fragment thereof under conditions that allow antibody-antigen binding. Preferably, the antibody or fragment is detectably labeled. Preferred labels include fluorescent labels (e.g., GFP, FITC, and rhodamine) and secondary labels (e.g., biotin and enzymatic substrates). A preferred method comprises contacting an antibody which specifically binds to LIRION with a biological sample from a mammalian subject, and determining the level of LIRION in the subject sample compared to a control level of a healthy subject, wherein abnormal level of LIRION in the subject sample indicates that the subject has the disease or is at an elevated risk of developing the disease. The antibody used can be either monoclonal or polyclonal and can be labeled directly or indirectly for quantification of immune complexes by methods well known to those skilled in the art, for example by ELISA or radioimmunoassays. Preferred specific antibodies directed to LIRION are generated using the polypeptide fragments listed above. Diagnostic assays to detect the protein of the invention may rely on a biological sample of a biopsy or in situ assay of cells from organ or tissue sections. Preferred biological samples include whole cells and cellular extracts from organs, tissues, or blood.

An embodiment of the invention provides for a method of screening test substances for modulators of LIRION expression. This method comprises the steps of: i) contacting a cell with a test substance; ii) detecting expression of LIRION; and iii) comparing LIRION expression in the cell after exposure to the test substance to that of an unexposed control cell. LIRION expression is determined by methods common to the art or included herein, by detecting LIRION polynucleotides or polypeptides. An example of this method comprises the steps of: i) culturing two equivalent cell samples; ii) adding a test substance to one of the cultures and not the other; iii) harvesting both cultures at a specified time; iv) purifying the mRNA from each sample of cells; v) detecting the level of LIRION mRNA in each sample. LIRION mRNA may be detected by Northern blot, RT-PCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) detecting the level of LIRION polypeptides in each sample. LIRION may be detected by enzyme-linked immunoabsorbent assay (ELISA), western blot, radioimmunoassay (RIA), or another method common to the art. The invention provides for design and use of specific antibodies and antibody fragments, as discussed herein.

A preferred embodiment of the invention provides a method of screening for test substances that bind LIRION polypeptides. This method comprises the steps of: i) contacting a test substance with a LIRION polypeptide or fragment thereof under conditions that allow binding; and ii) detecting the binding of the test substance by methods common to the art (e.g., competitive antibody-based methods such as coimmunopreciptation and Western blotting). Included in this method are test substances that are conjugated to an antibody, antibody fragment, cell-type specific ligand or a portion thereof. Substances that bind specifically to LIRION may be used to detect and purify the protein, as well as inhibit or activate its activity.

A further preferred embodiment of the invention provides a method of screening test substances that bind to LIRION for agonists of LIRION activity, comprising: i) contacting a cell with the substance to be tested; and ii) comparing LIRION biological activity after exposure to the test substance to that of an unexposed control cell. Measure of LIRION biological activity may be assessed indirectly by monitoring signalling events following co-engagement with an activating receptor. An example of an assay to measure LIRION activation comprises the steps of culturing monocytes in vitro, contacting the cells with the test substance, an anti-LIRION antibody and an anti-HLA-DR antibody, adding a cross-linking antibody, harvesting the cells, separating cell extracts by SDS-PAGE and detecting protein tyrosine phosphorylation using a specific antiphosphotyrosine antibody. A decrease in tyrosine protein phosphorylation in the test sample compared to the control sample being indicative of an activating effect of the test substance on LIRION. Activation of LIRION can also be assessed by measuring intracellular Ca++ mobilization induced upon receptor co-ligation as described in Cella et al. (1997, Journal of Experimental Medicine; Vol.185, pp 1743-1751, which disclosure is hereby incorporated by reference in its entirety).

A further preferred embodiment of the invention provides a method of screening test substances that bind to LIRION for antagonists of LIRION activity. This method comprises the steps of: i) contacting a cell with a test substance; and ii) comparing LIRION biological activity after exposure to the test substance to that of an unexposed control cell. Detection of LIRION biological activity may be detected by measuring protein dephosphorylation following LIRION stimulation as mentioned above. In this case, an increase in protein phosphorylation in the test sample compared to the control sample is indicative of an inhibitory effect of the test substance on LIRION activity.

Substances that increase LIRION expression or activity (agonists or activators) may be used to decrease APC activity or treat myeloid cancers. Substances that decrease LIRION expression or activity (antagonists or inhibitors) may be used to treat or prevent infectious diseases.

Another embodiment of the invention is also directed to methods to treat or prevent disorders associated with suppressed immune function such as pathogenic infections. This method comprises the step of introducing a LIRION antagonist to a cell. Preferred cells are those that express LIRION, such as APCs.

A preferred embodiment of the invention includes methods of increasing LIRION expression or activity by administering a LIRION agonist or polypeptides encoding LIRION to a cell. These methods may be applied to LIRION-associated conditions, including autoimmune (e.g., osteoarthritis, Crohn's disease, Grave's disease, autoimmune thyroiditis, lupus erythematosus, autoimmune hemolytic anemia, thrombocytopenia, atherosclerosis, osteoporosis, asthma, myasthenia gravis, rheumatoid arthritis, multiple sclerosis, and virally-induced autoimmunity), metabolic (e.g., obesity, hypercholesterolemia, insulin-related disorders), and neurological (e.g., schizophrenia) conditions as well as myeloid cancers. One such method comprises the step of contacting a cell with a LIRION agonist. Preferred agonists include those that affect LIRION expression, such as heterologous promoter sequences. An additional method comprises the step of introducing a polynucleotide encoding a LIRION polypeptide to a cell. One example of this method includes: i) removing a sample of APC cells of an individual; ii) introducing ex vivo a polynucleotide sequence complementary to LIRION polynucleotide sequences to those cells, and iii) reinjecting the recombinant cells into the individual. APCs include monocytes, macrophages and dendritic cells. Expression vectors derived from retroviruses, adenovirus, herpes, or vaccinia viruses may be used for the delivery of the polynucleotide sequences complementary to those of the invention to the targeted cell population. Many methods for introducing vectors into cells or tissues are available and equally suitable for use either in vivo or ex vivo. Delivery by transfection and liposome injections may be achieved using methods which are well known in the art. Pharmaceutical compositions comprising LIRION agonists, antagonists, or oligonucleotides can be administered alone or in combination with at least one other agent, such as stabilizing compound, which may be administered in any sterile biocompatible carrier. They may be administered by any number of routes including, but not limited to, oral, intravenous, intramuscular, intra-arterial, intramedullary, intrathecal, intraventiculary, transdermal, subcutaneous, intranasal, enteral or rectal means. The compositions may be administered to the subject alone or in combination with other agents, or drugs.

It is yet a further object of the invention to provide compositions and methods to deliver into a cell a molecule of interest comprising contacting cells expressing LIRION with a molecule joined to a LIRION antibody. Preferably, these methods are to be applied in vivo. A preferred method comprises joining a molecule of interest with a compound that specifically binds the extracellular portion of LIRION; and contacting the chimeric molecule with a cell that express under conditions that trigger LIRION internalization. The targeted cell populations may be naturally expressing the protein of the invention at their cell surface or may be transfected by LIRION encoding sequences prior to the addition of the chimeric antibody. Antibodies to be used in such methods are directed against the extracellular domain of the mature protein, preferably comprising the epitope VTSEKSVT or a LIRION-specific fragment thereof. Molecules to be delivered into the cells can be fluorescent or radioactive dyes or therapeutically active molecules, including but not limited to chemical drugs, radioactive compounds, peptides or nucleic acids. Methods to link an antibody moiety to a second molecule are well known by those skilled in the art. Alternatively, chimeric proteins with LIRION antibodies may also be obtained by synthesis in vivo. Using these methods would be of particular interest in gene therapy, radioimmunoscintigraphy (RIS) and radioimmunotherapy (RIT) of specific LIRION-expressing cell types such as APCs.

Protein of SEQ ID NO:38 (Internal Designation Clone 588394_160-105-4-0-A11-F)

The cDNA of Clone 588394 160-105-4-0-A11-F (SEQ ID NO:37) encodes the 383 amino acid SLAMP protein of SEQ ID NO:38 comprising the amino acid sequence: MRTYWLHSVWVLGFFLSLFSLQGLPVRSVDFN-RGTDNITVRQGDTAILRCVVEDKNSKV AWLNRSGII-FAGHDKWSLDPRVELEKRHSLEYSLRIQKVDVYD EGSYTCSVQTQHEPKTS QVYLIVQVPPKISNISSD-VTVNEGSNVTLVCMANGRPEPVIT-WRHLTPTGREFEGEEEYLEI LGITREQSGKYECK-AANEVSSADVKQVKVTVNYPPTITESKSNEAT TGRQASLKCEASAV PAPDFEWYRDDTRINSAN-GLEIKSTEGQSSLTVTNVTEEHYGNY-TCVAANKLGVTNASLV LFKRVLPTIPHPIQEIGTTVH-FKQKGIFLSESQRGETMTITLNCGNLFLRNLHPTS DQEPQRL WTLCCLLPRKGQHRIYGQC. Accordingly, it will be appreciated that all characteristics and uses of polypeptides of SEQ ID NO:38 described throughout the present application also pertain to the polypeptides encoded by the human cDNA included in Clone 588394 160-105-4-0-A11-F. In addition, it will be appreciated that all characteristics and uses of the polynucleotides of SEQ ID NO:37 described throughout the present application also pertain to the nucleic acids comprising the human cDNA in 588394 160-105-4-0-A11-F. Also preferred are fragments having a biological activity as described therein and the polynucleotides encoding the fragments.

SLAMP, the protein of SEQ ID NO:38, represents a novel splice variant of the limbic system-associated membrane protein (LAMP; Swissprot entry Q13449). SLAMP has a 22 amino acid signal sequence (MRTYWLHSVWVLGF-FLSLFSLQ) (SEQ ID NO:91), three C2-type immunoglobulin-like-domains, and a unique 80 amino acid carboxy-terminus. The protein belongs to the IgLON family, a group of neuronal glycoproteins which have been isolated from chicken, rat and human. These include the LAMP protein, Neurotrimin/CEPU-1, OBCAM and kilon/Neurotractin polypeptides. Most of the known members of this family are cell-surface adhesion molecules with a glycosyl phosphatidylinositol anchor at their C-terminus which tethers them to the neuronal plasma membrane. SLAMP, however, lacks the GPI anchor and is thus secreted by neurons in cortical and subcortical regions of the limbic system. SLAMP interacts with itself and other IgLON proteins and is involved in cell-cell recognition, contact-dependent regulation of neurite out-growth and axon guidance of specific subset of neurons during brain development. SLAMP interacts with LAMP, Neurotrimin and OBCAM, promotes neurite outgrowth of limbic neurons and inhibits neurite outgrowth of non-limbic neurons both in vivo and in vitro.

Preferred SLAMP polypeptides for uses in the methods described below include the polypeptides comprising the amino sequence of: GLPVRSVDFNRGTDNITVRQGD-TAILRCVVEDKNSKVAWLNRSGIIFAGH-DKWSLDPRVE LEKRHSLEYSLRIQKVDVYDEG-SYTCSVQTQHEPKTSQVYLIVQVPPKISNISSDV TVNEGS NVTLVCMANGRPEPVITWRHLTPT-GREFEGEEEYLEILGITREQSGKYECKAANEVSSADV KQVKVTVNYPPTITESKSNEAT-TGRQASLKCEASAVPAPDFEWYRD-DTRINSANGLEIKST EGQSSLTVTNVTEEHYGNY-TCVAANKLGVTNASLVLFKRVLPTIPHPIQEIGTTV HFKQKG IFLSESQRGETTKITLNCGNLFL-RNLNIPTSDQEPQRLWTLCCLLPRKGQHRIYGQC (SEQ ID NO:92);

A polypeptide comprising the amino acid sequence of: GLPVRSVDFNRGTDNITVRQGDTAIL-RCVVEDKNSKVAWLNRSGIIFAGHDKWSLDPRVE LEKRHSLEYSLRIQKVDVYDEGSYTCS-VQTQHEPKTSQVYLIVQVPPKJSNISSDVTVNEG SNVTLVCMANGRPEPVITWRHLTPT-GREFEGEEEYLEILGITREQSGKYECKAANEVSSAD VKQVKVTVNYPPTITESKSNEAT-TGRQASLKCEASAVPAIDFEWYRD-DTRINSANGLEIKS TEGQSSLTVTNVTEEHYGNY-TCVAANKLGVTNASLVLF (SEQ ID NO:93);

A polypeptide comprising the amino acid sequence of: KRVLPTIPHPIQEIGTTVIJFKQKGI-FLSESQRGETTKITLNCGNLFLRNLHPTSDQEPQRLW TLCCLLPRKGQHRIYGQC (SEQ ID NO:94).

An embodiment of the invention is directed to a composition comprising a SLAMP polypeptide sequence of SEQ ID NO:38.

A further embodiment of the invention is directed to a composition comprising a SLAMP polypeptide fragment having biological activity of binding to any one of the group consisting of LAMP, Neurotrimin, CEPU-1, CEPU-1-Se, OBCAM, kilon, Neurotractin, and GP55-A.

A further embodiment of the invention is directed to a composition comprising a polynucleotide sequence of SEQ ID NO:37 encoding a SLAMP polypeptide.

A further embodiment of the invention is directed to a composition comprising a polynucleotide sequence encoding a SLAMP polypeptide fragment having biological activity of binding to any one of the group consisting of LAMP, Neurotrimin, CEPU-1, CEPU-1-Se, OBCAM, kilon, Neurotractin, and GP55-A.

A further embodiment of the invention is directed to a method of screening test substances for modulators of SLAMP expression comprising the steps of: i) contacting a cell with a substance to be tested; and ii) comparing SLAMP expression in the cell after exposure to the test substance to that of an untreated control cell.

A preferred aspect of the invention is a host cell recombinant for polynucleotides encoding a SLAMP polypeptide or a biologically active fragment thereof. An additional preferred aspect is a host cell recombinant for polynucleotides capable of directing SLAMP expression. Preferably, the polynucleotides capable of directing SLAMP expression are located in the 5' regulatory region of the SLAMP gene. Further preferably, these polynucleotides are located within 500 base pairs of the SLAMP coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties.

One embodiment of the present invention relates to methods of producing SLAMP polypeptides. The protein of the invention can be produced in host cells that have been transfected with an appropriate expression vector comprising a nucleic acid sequence coding for the protein of the invention. Introduction into a host cell of such expression vector for SLAMP can be performed in a variety of ways, including but not limited to calcium or lithium chloride treatment, electroporation, or lipofection. Any of a wide variety of expression systems can be used to provide the recombinant proteins. Suitable expression vehicles include, but are not limited to plasmids, viral particles or baculovirus for insect cells. The expression vehicle can be integrated into the host cell genome. Optionally, an inducible expression vector can be used to achieve tight controlled expression of the gene in the host cell. The recombinant protein can be recovered from the host cell or the cell culture medium and purified by any technique well known to those skilled in the art. Preferably, a SLAMP-specific antibody SLAMP-specific fragment thereof can be bound to a chromatographic support to form an affinity chromatography column. Alternatively, SLAMP or fragments thereof can be chemically synthesized using solid-phase techniques.

In a further embodiment, the invention provides compositions and methods using SLAMP or fragments thereof to label neurons in order to visualize any change in number, topology or morphology of these cells. Preferred neurons are those expressing LAMP, Neurotrimin, CEPU-1, CEPU-1-Se, OBCAM, kilon, Neurotractin, and GP55-A. These changes may be associated with a central nervous system disorder. SLAMP may be rendered easily detectable by labeling or conjugating with a detectable molecule or antibody.

In another embodiment, the present protein can be used to purify neuronal cells from a biological sample such as neurons grown in vitro. This method comprises the steps of: i) contacting a cell sample with SLAMP or a biologically active fragment thereof; ii) removing non-binding contaminants; and iii) eluting the remaining cells. Preferred cell samples are samples comprising neuronal cells. Further preferred are cells expressing LAMP, Neurotrimin, CEPU-1, CEPU-1-Se, OBCAM, kilon, Neurotractin, and GP55-A. Preferably, SLAMP is fixed on a sepharose column or covalently or noncovalently linked to a solid support. Alternatively, the neuronal cells can be preincubated with SLAMP and then a monoclonal or polyclonal antibody directed against SLAMP can be used to immunopurify the cells, for example on a column. Alternatively, the SLAMP-specific antibody is fluorescently labeled and cells are purified by FACS.

In another embodiment, the invention provides compositions and methods for detecting the level of expression of the mRNA encoding the protein of the invention in a mammal, preferably a human. This method comprises the steps of: contacting a SLAMP mRNA or cDNA molecule with a detectable compound under conditions that allow binding. Preferably, the detectable compound is a nucleotide sequence complimentary to SLAMP mRNA. Preferably, SLAMP mRNA is purified from a cell sample. SLAMP cDNA is preferably generated from such an RNA sample. Quantification of mRNA levels of SLAMP may be useful for the diagnosis of diseases or conditions correlated with abnormal expression of the protein, or to monitor regulation of SLAMP during therapeutic intervention as described herein. Assays for the detection and quantification of mRNA are well known in the art. An example of this method comprises the steps of: isolating RNA from a brain sample of a subject, measuring SLAMP mRNA level by quantitative RT-PCR, and comparing the expression in the subject sample to that of a control sample. Polynucleotide probes or primers used for the detection of SLAMP mRNA by hybridization or PCR amplification may be designed from the polynucleotide of SEQ ID NO:37 by methods well known in the art.

In another embodiment, the invention relates to methods and compositions for detecting SLAMP and quantifying its level of expression in a biological sample. These methods may be useful for the diagnosis of conditions or diseases characterized by altered or abnormal expression of the protein of the invention, or in assays to monitor subjects being treated with SLAMP, agonists or antagonists. A preferred method comprises contacting an antibody which specifically binds to SLAMP with a brain sample from a mammalian subject, preferably human, and determining the level of SLAMP in the subject sample compared to a control level representative of a healthy subject, wherein an altered or abnormal level of SLAMP in the subject sample relative to the control level indicates that the subject has the disease or is at an elevated risk of developing the disease. The antibody used can be either monoclonal or polyclonal and can be labeled directly or indirectly for quantification of immune complexes by methods well known to those skilled in the art, for example by ELISA or radioimmunoassays. Preferred specific antibodies directed to SLAMP are generated using the polypeptide fragments listed above. Diagnostic assays to detect the protein of the invention may comprise a biopsy, in situ assay of cells. In addition, assays may be conducted upon cellular extracts.

An embodiment of the invention provides for a method of screening test substances for modulators of SLAMP expression. This method comprises the steps of: i) contacting a cell with a test substance; and ii) comparing SLAMP expression in the cell after exposure to the test substance to that of an unexposed control cell. SLAMP expression is determined by methods common to the art or included herein, by detecting SLAMP polynucleotides or polypeptides. An example of this method comprises the steps of: i) culturing two equivalent cell samples; ii) adding a test substance to one of the cultures and not the other; iii) harvesting both cultures at a specified time; iv) purifying the mRNA from each sample of cells; and v) detecting the level of SLAMP mRNA in each sample. Detection may be accomplished by Northern blot, RT-PCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; and v) detecting the level of SLAMP polypeptides in each sample. Detection may be accomplished by enzyme-linked immunoabsorbent assay (ELISA), western blot, radioimmunoassay (RIA), or another method common to the art. The invention provides for design and use of specific antibodies and antibody fragments, as discussed herein. Substances that increase SLAMP expression or activity (agonists or activators) may be used to treat or prevent neurodegenerative diseases affecting the limbic system or abnormal cell proliferation in the non-limbic region. Substances that decrease SLAMP expression or activity (antagonists or inhibitors) may be used to treat or prevent conditions associated with abnormal cell proliferation in the limbic region or neurodegenerative diseases affecting primarily the non limbic system. Methods utilizing SLAMP agonists and antagonists are included herein.

A preferred embodiment of the invention provides a method of screening for test substances that bind SLAMP polypeptides. This method comprises the steps of: i) contacting a test substance with a SLAMP polypeptide or fragment thereof under conditions that allow binding; and ii) detecting the binding of the test substance by methods common to the art (e.g., competitive antibody-based methods such as coimmunopreciptation and Western blotting). Included in this method are test substances that are conjugated to an antibody, antibody fragment, cell-type specific ligand or a portion thereof. This method may be used for purification and detection of SLAMP polypeptides, as well as for the screening methods discussed below.

A further preferred embodiment of the invention provides a method of screening test substances that bind to SLAMP for agonists of SLAMP activity. This method comprises the steps of: i) contacting a cell with SLAMP and the substance to be tested; and ii) comparing SLAMP biological activity after exposure to the test substance to that of a control exposed only to SLAMP. Measure of SLAMP biological activity may be assessed by monitoring neurite outgrowth. An example of an in vitro assay to measure SLAMP activation comprises the steps of culturing hippocampal neurons in vitro, contacting the cells with SLAMP and the test substance, and measuring neurite number/cell or neurite extension as described by Marg et al. (1999; Journal of Cell Biology, vol.145, pp 865-876, which disclosure is hereby incorporated by reference in its entirety), an increase in the test sample compared to the control sample being indicative of an activating effect of the test substance on SLAMP.

A further preferred embodiment of the invention provides a method of screening test substances that bind to SLAMP for antagonists of SLAMP activity. This method comprises the steps of: i) contacting a cell with SLAMP and a test substance; and ii) comparing SLAMP biological activity after exposure to the test substance to that of an unexposed control. SLAMP activity may be measured as described above, a decrease in SLAMP activity in the test sample compared to the control sample being indicative of an inhibitory effect of the test substance on SLAMP.

Another embodiment of the invention is also directed to methods to treat or prevent a disease state of a mammal, preferably a human, associated with excessive neural growth in the limbic region comprising administering to said mammal antagonistic antibodies, ribozymes or antisense vectors or oligonucleotides. Preferably, the disease state to be treated by such methods is brain cancer. A preferred method comprises injecting into an individual antagonistic antibodies directed against SLAMP. Polynucleotide or oligonucleotide sequences complementary to SLAMP polynucleotide sequences may also be used to decrease or inhibit SLAMP expression by limbic neurons. Expression vectors derived from retroviruses, adenovirus, herpes, or vaccinia viruses may be used for the delivery of the polynucleotide sequences complementary to those of the invention to the targeted cell population. Many methods for introducing vectors into cells or tissues are available and equally suitable for use either in vivo or ex vivo. Delivery by transfection and liposome injections may be achieved using methods which are well known in the art. Alternatively, an antagonist of SLAMP expression or activity isolated as described above can be used, such method comprising the step of administering to a subject an antagonist of SLAMP expression or activity. Preferably, the antagonist is delivered to the limbic neurons of the subject, for example, by conjugating the antagonist to a cell specific targeting moiety (e.g., an antibody fragment). Pharmaceutical compositions comprising SLAMP agonists, antisense vectors or oligonucleotides can be administered alone or in combination with at least one other agent, such as stabilizing compound, which may be administered in any sterile biocompatible carrier. They may be administered by any number of routes including, but not limited to, oral, intravenous, intramuscular, intra-arterial, intramedullary, intrathecal, intraventiculary, transdermal, subcutaneous, intranasal, enteral or rectal means. The compositions may be administered to the subject alone or in combination with other agents, or drugs.

It is another object of the invention to provide methods for treating or preventing neuropathologies in a mammal, preferably human, involving the limbic system. This can be achieved by increasing SLAMP expression or activity in vivo using the protein of the invention or fragments thereof or polynucleotides encoding the present protein. A preferred method comprises introducing in vivo into a subject an effective amount of SLAMP polypeptides with a pharmaceutically acceptable carrier. Increased expression of the protein of the invention may also be achieved by introducing into the cells of a subject the sequences encoding the protein of the invention. A preferred method ex-vivo comprising: i) introducing to neural stem cells a polynucleotide sequence encoding SLAMP, and ii) injecting the recombinant cells into an individual. Alternatively, an agonist of SLAMP expression or activity isolated as described above can be used, such method comprising the step of administering to a subject an agonist of SLAMP expression or activity. SLAMP agonists in a physiologically acceptable solution may be delivered by methods common to the art. Preferably, the SLAMP agonist is delivered in vivo to the limbic neurons of the subject. These method are useful for prevention and treatment of neurodegenerative diseases and neuropathies including, but not limited to, Alzheimer's disease, Parkinson's disease, Huntington's disease, cerebral ischaemia, limbic encephalitis, cerebellar ataxia, schizophrenia, and Tourette syndrome.

Protein of SEQ ID NO:40 (Internal Designation Clone 495718_160-262-0-E12-F)

The cDNA of Clone 495718_160-26-2-0-E12-F (SEQ ID NO: 39) encodes SAP-MU-10 of SEQ ID NO:40, comprising the amino acid sequence: MYALFLLASLLGAALAGP VLGLKECTRGSAVWCQNVKTASDC-GAVKJICLQTVWNKPTVKSLPCDICKDVVTAAGDM LKDNATEEEILVYLEKTCDWLPKPNM-SASCKEIVDSYLPVILDIIKGEMSRPGEVCSALNLC ESLQKHLAELNHQKQLESNKIPELD-MTEVVAPFMANIPLLLYPQDQRSKPQPKDNGDVC QDCIQMVTDIQTAVRTNSTFVQALVEHV-KEECDRLGPGMADICKNYISQYSEIAIQMMMH MQDQQPKEICALVGFCDEVKEMPMQTLV-PAKVASKNVIPAIELVEPIKKHEVPAKSDVYC EVCE-FLVKEVTKLIDNNKTEKEILDAFDKMC-SKLPKSLSEECQEVVDTYGSSILSILLEEVSP ELVCSMLHLCSGTRLPALTVHVTQPKDG-GFCEVCKKLVGYLDRNLEKNSTKQEILAALEK GCS-FLPDPYQKQCDQFVAEYEPVLIEILVEVWILPSCA. Accordingly, it will be appreciated that all characteristics and uses of the polypeptides of SEQ ID NO:40 described throughout the present application also pertain to the polypeptides encoded by the nucleic acids comprising the human cDNA in Clone 495718_160-26-2-0-E12-F. In addition, it will be appreciated that all characteristics and uses of the polynucleotides of SEQ ID NOs:39 described throughout the present application also pertain to the nucleic acids comprising the human cDNA in Clone 495718_160-26-2-0-E12-F. A preferred embodiment of the invention is directed toward the compositions of SEQ ID NO:40, SEQ ID NO:39, and Clone 495718_160-26-2-0-E12-F. Preferred SAP-MU-10 polypeptide fragment for uses in the methods described below include the Sap-D10 polypeptide comprising the amino sequence of: DGGFCEVCKKLVGYLDRN-LEKNSTKQEILAALEKGCSFLPDPYQKQCDQF VAEYEPVLIEILVEVWILPSCA (SEQ ID NO:95). Also preferred are polypeptide fragments comprising the seven C-terminal amino acids, having a biological activity as described herein and the polynucleotides encoding the fragments.

The protein of the invention, SAP-MU-10, is a novel isoform of Saposin (GenBank accession number P07602). Three different isoforms of Saposin have been described. The 472 amino terminal amino acids of SAP-MU-10 are identical to the SAP-MU-9 isoform and the 7 carboxyl-terminal amino-acids are unique to SAP-MU-10.

SAP-MU-10 is a precursor for 4 different proteins, and proteolytic cleavage of SAP-MU-10 gives rise to the Sap-A10, Sap-B10, Sap-C10 and Sap-D10 proteins. The unprocessed SAP-MU-10 precursor binds to sphingolipids and promotes ganglioside transport from liposomes to membrane. The processed proteins are non-enzymatic activators of the hydrolysis of sphingolipids. Sphingolipids are important components of the myelin sheath, a structure that protects and insulates nerve fibers. SAP-MU-10 and Sap-D10 play a major role both in myelination of neurons and in storage of sphingolipids. SAP-MU-10 is expressed and processed in various tissues, being expressed at especially high level in the nervous system. Furthermore, the unprocessed SAP-MU-10 precursor is secreted in the cerebrospinal plasma. The SAP-MU-10 protein binds to sphingolipids and gangliosides, and displays neurotrophic properties. The Sap-D10 protein binds to sphingomyelin and ceramide, and displays a sphingomyelin phosphodiesterase activator activity.

As used herein, SAP-MU-10 refers to the polypeptide sequence of SEQ ID NO:40. As used herein, a SAP-MU-10 polypeptide refers to a fragment of polypeptide sequence of SEQ ID NO:40 having either sphingolipid or ganglioside binding activity, or neurotrophic properties. As used herein, a Sap-D10 polypeptide refers to a polypeptide comprising the Sap-D10 polypeptide described above and having sphingomyelinase phosphodiesterase activator activity.

An embodiment of the invention is directed to a composition comprising a SAP-MU-10 polypeptide sequence of SEQ ID NO:40.

A further embodiment of the invention is directed to a composition comprising a SAP-MU-10 polypeptide fragment having biological activity.

A further embodiment of the invention is directed to a composition comprising a Sap-D10 polypeptide fragment having biological activity.

A further embodiment of the invention is directed to a composition comprising a polynucleotide sequence of SEQ ID NO:39 encoding a SAP-MU-10 polypeptide.

A further embodiment of the invention is directed to a composition comprising a polynucleotide sequence of SEQ ID NO:39 encoding a Sap-D10 polypeptide.

A further embodiment of the invention is directed to a composition comprising an antibody that specifically recognizes a SAP-MU-10 polypeptide. Preferably, the antibody recognizes an epitope comprising one or more of the 7 C-terminal amino acids of SAP-MU-10 and Sap-D10, wherein one or more of the seven C-terminal amino acids is required for antibody binding. Preferably, the antibody binds specifically to SAP-MU-10 and to Sap-D10 but not to other saposin isoforms. Alternatively, the antibody binds specifically to SAP-MU-10 but not to Sap-D10 and other saposin isoforms. Alternatively, the antibody binds specifically to Sap-D10 but not to SAP-MU-10 and other saposin isoforms.

A preferred aspect of the invention is a host cell recombinant for polynucleotides encoding a SAP-MU-10 polypeptide or a biologically active fragment thereof. An additional preferred aspect is a host cell recombinant for polynucleotides capable of directing SAP-MU-10 expression. Preferably, the polynucleotides capable of directing SAP-MU-10 expression are located in the 5' regulatory region of the SAP-MU-10 gene. Further preferably, these polynucleotides are located within 500 base pairs of the SAP-MU-10 coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. SAP-MU-10 protein produced by said host cell may be used for in vitro detection and purification methods as well as diagnosis and in vivo applications.

Another embodiment relates to a method of producing SAP-MU-10 polypeptides comprising the steps of: i) transfecting a mammalian host cell with a recombinant expression vector comprising a polynucleotide of the present invention, and ii) purifying the produced protein. The purification of the protein can be done following any technique well-known to those skilled in the art. Preferably, an antibody directed against SAP-MU-10 or part thereof may be bound to a chromatographic support to form an affinity chromatography column.

An embodiment of the invention is a method comprising the step of binding a SAP-MU-10 polypeptide with a sphingolipid or a ganglioside molecule under conditions that allow binding of a SAP-MU-10 polypeptide to said molecule. In a preferred embodiment, a SAP-MU-10 polypeptide is used to purify sphingolipid or ganglioside molecules. In such method, a SAP-MU-10 polypeptide is preferably covalently or non-covalently attached to a solid matrix and allowed to bind sphingolipids and gangliosides using techniques well-known in the art. This method comprises the steps of: i) contacting SPA-MU-10 with a sphingolipid or ganglioside molecule in solution; ii) washing the solid matrix to remove non-binding contaminants; and iii) eluting the sphingolipid or ganglioside using more stringent conditions. Purifying sphingolipids and gangliosides can for example be useful for confirming deficiency of lysosomal enzyme activity affecting ganglioside breakdown, or for monitoring ganglioside catabolism in cultured fibroblasts loaded with ganglioside.

Additional aspects of this embodiment include methods of using SAP-MU-10 polypeptides to detect and quantify sphingolipids and gangliosides using techniques common in the art. Such methods comprise the steps of: i) obtaining a biological sample suspected of containing sphingolipids or gangliosides; ii) contacting such sample with a SAP-MU-10 polypeptide under conditions allowing binding of SAP-MU-10; and iii) detecting the presence or absence of sphingolipids and gangliosides by detecting SAP-MU-10. Preferably, the SAP-MU-10 polypeptide is covalently attached to a detectable compound (e.g., enzymatic substrates, or fluorescent, luminescent, and radioactive compounds). Alternatively, a detectable SAP-MU-10-specific antibody may be used to detect SAP-MU-10. This embodiment is useful, for example, as a diagnostic tool for quantifying the amount of sphingolipids in cerebrospinal plasma. Such diagnostic tool may be useful to diagnose sphingolipidosis and various lysosomal storage disorders (LSDs) such as, e.g., cystinosis, Gaucher's disease, multiple sulfatase deficiency, Niemann-Pick disease, Pompe's disease and Wolman's disease.

In another embodiment, the invention is directed to a method of detecting SAP-MU-10 polypeptides in a biological sample, said method comprising the steps of: i) contacting a biological sample with an antibody or antigen binding antibody fragment that specifically binds SAP-MU-10 polypeptide; and ii) detecting the antigen-antibody complex formed. The antibody or antigen binding antibody fragment may be monoclonal or polyclonal. In addition, the antibody or antigen binding antibody fragment may be primarily or secondarily labeled by a detectable compound (e.g., radioactive, fluorescent, luminescent, or enzymatic) common in the art.

In some embodiments, the invention also concerns a diagnostic kit for detecting in vitro the presence of a SAP-MU-10 polypeptide. Such kit comprises: i) a polyclonal or monoclonal antibody or fragment thereof that specifically binds a SAP-MU-10 polypeptide; and optionally, ii) a reagent allowing the detection of the antigen-antibody complexes formed. Preferably, the antibody or antibody fragment is detectably labeled. Such labels include fluorescent, luminescent, and radioactive compounds, as well as enzymatic substrates. The optional reagent may provide a detectable signal and either bind to the antibody or react with the label on such antibody. Preferably, the kit containing antibodies for SAP-MU-10 is used to diagnose LSDs such as those listed herein. Alternatively, the kit of the present invention is used for monitoring the condition of a patient receiving treatment for a LSD. To detect such disorders, an appropriate biological sample (blood or cerebrospinal plasma for example) can be tested to determine the level of SAP-MU-10 being produced. A kit for detecting LSDs comprising an anti-SAP-MU-10 antibody may also comprise other antibodies such as those described in PCT application WO00/55632, which disclosure is incorporated by reference in its entirety. Alternatively, an anti-Sap-D10 antibody may be used in such method.

An embodiment of the invention provides for a method of screening test substances for modulators of SAP-MU-10 expression. This method comprises the steps of: i) contacting a cell with a test substance; and ii) comparing SAP-MU-10 expression in the cell after exposure to the test substance to that of an unexposed control cell. SAP-MU-10 expression is determined by methods common to the art or included herein, by detecting SAP-MU-10 polynucleotides or polypeptides. An example of this method comprises the steps of: i) culturing two equivalent cell samples; ii) adding a test substance to one of the cultures and not the other; iii) harvesting both cultures at a specified time; iv) purifying the mRNA from each sample of cells; v) comparing the level of SAP-MU-10 mRNA in each sample by Northern blot, RTPCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) comparing the level of SAP-MU-10 polypeptides in each sample by Western blot, immunohistochemistry, or another method common to the art. The invention provides for design and use of specific antibodies and antibody fragments, as discussed herein.

In another embodiment, a SAP-MU-10 polypeptide or a fragment thereof, may be used to screen for compounds that activate or inhibit SAP-MU-10 activity. This method comprises the steps of: i) contacting a SAP-MU-10 polypeptide or fragment thereof with a test substance, and ii) monitoring SAP-MU-10 activity. SAP-MU-10 activity may be monitored by binding assays with gangliosides as described by Hiraiwa et al. (Proc Natl Acad Sci USA. 89:11254-8 (1992)), which disclosure is incorporated by reference in its entirety.

In another embodiment, a Sap-D10 polypeptide may be used to screen for compounds that activate or inhibit Sap-D10 activity. This method comprises the steps of: i) contacting a Sap-D10 polypeptide or fragment thereof with a test substance, and ii) monitoring Sap-D10 activity. Sap-D10 activity may for example be determined by monitoring sphingomyelinase activity as described by Morimoto et al. (Biochem Biophys Res Commun 156:403-10 (1988)), which disclosure is incorporated by reference in its entirety.

Test substances that decrease SAP-MU-10 expression or activity are defined as inhibitors or antagonists of SAP-MU-10. Test substances that decrease Sap-D10 activity are defined as inhibitors or antagonists of Sap-D10. Test substances that increase SAP-MU-10 expression or activity or that increase Sap-D10 activity are defined as activators or agonists. Agents which modulate the expression or activity of SAP-MU-10 or Sap-D10 activity of the subject invention include, but are not limited to, antisense oligonucleotides, ribozymes, and antibodies. These agents may be made and used according to methods well known in the art.

One embodiment of the present invention relates to a method for increasing myelination, stimulating neural cell outgrowth, or slowing down a process of demyelination or neural degeneration. The method comprises the step of: contacting a cell with a composition comprising a SAP-MU-10 polypeptide or an agonist thereof. Preferred cells are neurons and oligodendrocytes. The cells can be treated in vitro or in vivo by directly administering the composition to the cells. In a preferred embodiment, a composition comprising a SAP-MU-10 polypeptide or an agonist thereof is introduced to an individual suffering from a demyelinating disorder (e.g., multiple sclerosis, virus-induced inflammatory demyelination, leukoencephalopathies and leukodystrophies such as Krabbe's disease, metachromatic leukodistrophy, ALD, Canavan disease and Alexander disease). Preferably, the amount of agonist or polypeptide used is effective to increase myelination in an individual. In another preferred embodiment, a composition comprising a SAP-MU-10 polypeptide or an agonist thereof is introduced to an individual suffering from a neurodegenerative disorder (e.g., retinal neuropathy, Alzheimer's disease, Parkinson's disease, stroke, post-polio syndrome and amyotrophic lateral sclerosis). Preferably, the amount of agonist or polypeptide used is effective to stimulate neural cell outgrowth.

In another embodiment, a Sap-D10 polypeptide or a Sap-D10 agonist is used to activate sphingomyelinase diphosphoesterase in vitro or in vivo. A preferred embodiment is directed to a method comprising the step of: contacting a sphingomyelinase diphosphoesterase with a Sap-D10 polypeptide or a Sap-D10 agonist. Another preferred embodiment is directed to a method comprising the step of: contacting a cell with a composition comprising a Sap-D10 polypeptide or an agonist thereof. Still another preferred embodiment relates to a method comprising the step of: administering a composition comprising a Sap-D10 polypeptide or a Sap-D10 agonist in a physiologically acceptable composition to an individual. Preferably, such a method is directed to treat an individual suffering from Tay-Sachs disease associated with Saposin D deficiency. Preferably, the amount of Sap-D10 agonist or polypeptide used is effective to increase sphingomyelinase phosphodiesterase activity in the individual suffering from Tay-Sachs disease.

The composition of the invention may comprise a pharmaceutically acceptable carrier such as those described herein and may be administered to an individual by any technique known in the art. Preferably, the composition is introduced by injection (e.g., direct intracranial injection, injection to the cerebrospinal fluid, local injection to peripheral neural tissue or systemic injection). Even more preferably, the composition is introduced in a patient by one of the methods described in U.S. Pat. Nos. 5,714,459, and 4,902,505 which disclosure is incorporated by reference in its entirety.

Another embodiment is directed to a method of using SAP-MU-10 polynucleotides comprising the steps of: i) constructing a recombinant molecule comprising a nucleic acid sequence encoding a SAP-MU-10 polypeptide that allows expression of SAP-MU-10 or fragment thereof under suitable physiological conditions, and ii) introducing this recombinant molecules into a cell, a mammal or a human. Preferably, the recombinant molecule is introduced into a neural cell.

Recombinant molecules comprising a nucleic acid sequence encoding a SAP-MU-10 polypeptide may be directly introduced into cells or tissues in vitro using delivery vehicles such as retroviral vectors, adenoviral vectors and DNA virus vectors. They may also be introduced into cells in vivo using physiological techniques such as microinjection and electroporation or chemical methods such as coprecipitation and incorporation of DNA into liposomes.

Recombinant molecules may also be delivered in the form of an aerosol or by lavage. The SAP-MU-10 polynucleotides may also be applied intracellularly such as by direct injection into cells. Methods for carrying out SAP-MU-10 transfer into a cell and grafting in the brain are described in U.S. Pat. No. 5,762,926, which disclosure is hereby incorporated by reference in its entirety. Such a method can be used to treat, e.g., multiple sclerosis, leukoencephalopathies and leukodystrophies.

Another embodiment of the invention relates to transgenic animals and methods of using a SAP-MU-10 polynucleotide sequence or part thereof to establish transgenic animals (*D. melanogaster, M Musculus*), by any method familiar to those skilled in the art. By modulating in vivo the expression of the transgene with drugs or modifier genes (activator or suppressor genes), animal models can be developed that mimic human disorders such as LSDs. These animal models would thus allow the identification of potential therapeutic agents for treatment of the disorders. In addition, recombinant cell lines derived from these transgenic animals may be used for similar approaches ex vivo.

Protein of SEQ ID NO:42 (Internal Designation Clone 612386_187-9-4-0-B2-F)

The cDNA of Clone 612386_187-9-4-0-B2-F (SEQ ID NO: 41) encodes cytogram of SEQ ID NO:42, comprising the amino acid sequence: MELCRSLALLGGSLGLMFC LIALSTDFWFEAVGPTHSAHSGLWPTGH-GDIISGHGPLVSTTAAFAAGKDSGLDWGLASQR IPAEELSHLSCPCPQPSPWWWPWRCT-PASGGTSLHTPRSRPSSPGPSTWAGSQLSSCSVQVP. Accordingly, it will be appreciated that all characteristics and uses of the polypeptides of SEQ ID NO:42 described throughout the present application also pertain to the polypeptides encoded by the nucleic acids comprising the human cDNA in Clone 612386_187-9-4-0-B2-F. In addition, it will be appreciated that all characteristics and uses of the polynucleotides of SEQ ID NOs:41 described throughout the present application also pertain to the nucleic acids included in Clone 612386_187-9-4-0-B2-F. A preferred embodiment of the invention is directed toward the compositions of SEQ ID NO:42, SEQ ID NO:41, and Clone 612386_187-9-4-0-B2-F. Preferred cytogrampolypeptides for uses in the methods described below include the polypeptides comprising the amino sequence of: AHSGL-WPTGHGDIISGHGPLVSTTAAFAAGKDS-GLDWGIASQRIPAEELSHLSCPCPQPSP WWWP-WRCTPASGGTSLHTPRSRPSSPGPSTWAGSQLSS CSVQVP (SEQ ID NO:96). Also preferred are polypeptide fragments having a biological activity as described herein and the polynucleotides encoding the fragments.

The protein of the invention, cytogram, is a splice variant of GMP-17 (or NKG7, GenBank accession number Q16617). CytogramcDNA lacks the second exon of GMP-17 cDNA. Cytogram is a 142 amino-acid long protein, and GMP-17 is 165 amino acid long. The 53 amino-terminal amino acids are identical between the two proteins, and the 89 carboxyl-terminal amino acids are unique to cytogram. Cytogram displays a signal peptide (MELCRSLA-LLGGSLGLMFCLIALSTDFWFEAVGPTHS) (SEQ ID NO:97), a transmembrane domain (GDIISGHGPLVST-TAAFAAGK) (SEQ ID NO:98), and a PEC family methallothionein domain (SCPCPQPSPWWWPWRCTPASG-GTSLHTPRSRPSSPGPSTWAGSQLSSCSV) (SEQ ID NO:99) that binds to zinc ions.

Cytogram is a cytotoxic granule membrane protein that is constitutively and specifically expressed in NK cells (NKs) and cytotoxic T lymphocytes (CTLs). NK and CTL degranulation results in translocation of cytogram from granules to the plasma membrane. Cytogram contributes to the formation of junctions between effector cells and target cells following exocytosis. Furthermore, once located on the plasma membrane, cytogram regulates ion channels required for cytotoxicity of NKs and CTLs and promotes cytolytic effector function.

An embodiment of the invention is directed to a composition comprising a cytogram polypeptide sequence of SEQ ID NO:42.

A further embodiment of the invention is directed to a composition comprising a cytogram polypeptide fragment having biological activity of promoting NK and CTL cytotoxicity.

A further embodiment of the invention is directed to a composition comprising a polynucleotide sequence of SEQ ID NO:41 encoding a cytogram polypeptide.

A further embodiment of the invention is directed to a composition comprising a polynucleotide sequence encoding a cytogram polypeptide fragment having biological activity.

A further embodiment of the invention is directed to a composition comprising an antibody recognizing a cytogram polypeptide sequence of SEQ ID NO:42 or a cytogram polypeptide fragment having biological activity. Preferably, the antibody recognizes a non-linear epitope or an epitope located within the 89 C-terminal amino acids of cytogram. Preferably, the antibody binds to cytogram but not to GMP-17. Preferably, the antibody recognizes the AGKDSGLD (SEQ ID NO:100) amino acid sequence.

A further embodiment of the present invention relates to a method of binding activated NKs and CTLs comprising the step of: contacting activated NKs and CTLs with an antibody that specifically binds to cytogram polypeptides under conditions that allow binding of cytogram polypeptides to the antibody. In a preferred embodiment, antibodies that specifically bind to cytogram polypeptides can be used to purify activated NKs and CTLs. In such method, the antibody is preferably covalently or not covalently attached to a solid matrix and allowed to bind cytogram polypeptides using techniques well known in the art. This method comprises the steps of: i) contacting activated NKs and CTLs with an antibody that specifically binds to cytogram polypeptides under conditions that allow binding of cytogram polypeptides to the antibody, ii) washing the solid matrix to get rid of contaminants, and iii) eluting the cells of interest using more stringent conditions. Such a method can for example be useful for purifying NKs and CTLs from cancer patients prior to in vitro expansion.

A preferred aspect of the invention is a host cell recombinant for polynucleotides encoding a cytogram polypeptide or a biologically active fragment thereof. An additional preferred aspect is a host cell recombinant for polynucleotides capable of directing cytogram expression. Preferably, the polynucleotides capable of directing cytogram expression are located in the 5' regulatory region of the cytogram gene. Further preferably, these polynucleotides are located within 500 base pairs of the cytogram coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. Cytogram protein produced by said host cell may be used for in vitro detection and purification methods as well as diagnosis and in vivo applications.

One embodiment of the present invention is directed to methods of detecting or quantifying activated NKs and CTLs comprising the steps of: i) contacting a body fluid, a tissue sample or a mammalian cell culture with an antibody that specifically binds to cytogram polypeptides, and ii) detecting the antibody in the sample using any detectable signal. Compounds such as, e.g., alkaline phosphatase, peroxidase, FITC, rhodamine, Texas-Red, biotin and digoxigenin can be used to provide a detectable signal. The detection of the signal may be carried out using immunohistological or immunofluorescing processes that are well-known to those skilled in the art. The antibody that specifically binds to cytogram polypeptides may be directly labeled with the compound giving the detectable signal. Alternatively, the antibody that specifically binds to cytogram polypeptides is not labeled and detection of the signal occurs indirectly by using labeled secondary antibodies. In a preferred embodiment, detecting activated NKs and CTLs can be used to measure the effect of a test compound on CTL or NK activity in mammalian cell cultures. In another preferred embodiment, such methods can be used to monitor the effects of a treatment aiming to increase or decrease CTL or NK activity in a patient, or to detect the beginning of a graft rejection reaction in a patient.

An embodiment of the present invention relates to methods of using cytogram or fragment thereof as a marker of cytotoxic granules comprising the steps of: i) contacting a body fluid, a tissue sample or a mammalian cell culture with an antibody that specifically binds to cytogram polypeptides, and ii) detecting the localization of the antibody in the sample using any detectable signal. Compounds such as, e.g., FITC, rhodamine, Texas-Red, [$^{35}$S]methionine, [$^{35}$S] cysteine and bisbenzimide can be used to provide a detectable signal. The detection of the signal may be carried out using immuno-electron microscopy or fluorescence microscopy. The antibody that specifically binds to cytogram polypeptides may be directly labeled with the compound giving the detectable signal. Alternatively, the antibody that specifically binds to cytogram polypeptides is not labeled and detection of the signal occurs indirectly by using labeled secondary antibodies. Such methods of using cytogram or part thereof as a marker of cytotoxic granules include those described by Medley et al.(Proc Natl Acad Sci USA. 93: 685-9 (1996)), which disclosure is incorporated by reference in its entirety. CTLs and NKs form the major defense of higher organisms against virus-infected and transformed cells and a key function of CTLs is to detect and eliminate potentially harmful cells by lysis. Thus, a marker for detecting degranulation of NKs and CTLs is very useful when screening for drugs to treat or monitor the status or progression of, for example, infection with intracellular pathogens, graft versus host disease, susceptibility to transplantable and spontaneous malignancies, lymphoid homeostasis, the tendency to auto-immune diseases or when studying these diseases.

Another embodiment relates to a method of producing cytogram polypeptides comprising the steps of: i) obtaining a cell capable of expressing a cytogrampolypeptide; ii) growing said cell under conditions suitable to produce said polypeptide; and iii) purifying said polypeptide. The purification of the protein can be done following any technique well-known to those skilled in the art. Preferably, an antibody directed against cytogram or part thereof may be bound to a chromatographic support to form an affinity chromatography column. Even more preferably, the antibody binds to cytogram but not to GMP-17. The cell capable of expressing a cytogram polypeptide may be obtained by any of the techniques well-known to those skilled in the art. A host cell may be transfected with a recombinant expression vector comprising a polynucleotide of the present invention. Alternatively, a heterologous promoter may be used. Preferably, the host cell is a mammalian host cell.

Another preferred embodiment relates to a method of screening test substances for modulators of cytogram expression. This method comprises the steps of: i) contacting a cell with a test substance; and ii) comparing cytogram expression in the cell after exposure to the test substance to that of an unexposed control cell. Cytogram expression is determined by methods common to the art or included herein. Methods of determining cytogram expression include but are not limited to methods of quantifying cytogram polynucleotides (e.g., detection of cytogram mRNA by northern blot or RTPCR) or to methods of quantifying cytogram polynucleotides (e.g., detection of cytogram proteins by western bot or immunochemistry). Preferably, the test substance modifies the expression of cytogram in a specific cell type while not in others. Most preferably, the test substance modifies cytogram expression specifically in NKs and CTLs.

A further embodiment of the present invention is directed to test substances for modulators of cytogram activity and to a method of screening for such test substances comprising the steps of: i) contacting a cell with a test substance, ii) determining cytogram activity, and iii) comparing cytogram activity in the cell after exposure to that of an unexposed control cell. Cytogram activity can for example be monitored by studying cytotoxic activity of NKs using the cytotoxic assay described in U.S. Pat. No. 5,229,494, which disclosure is hereby incorporated by reference in its entirety. Preferably, cytogram activity is studied in NKs or CTLs. Most preferably, a substance that modulate cytogram activity is administered to an individual in modulate NK or CTL cytotoxicity.

Test substances that decrease cytogram expression or activity are defined as inhibitors or antagonists of cytogram. Test substances that increase cytogram expression or activity are defined as activators or agonists of cytogram. Tests substances that modulate the expression or activity of cytogram include but are not limited to chemical compounds, oligonucleotides, riboymes and antibodies. These substances may be made and used according to methods well known in the art.

An embodiment of the present invention relates to a method of using the compositions of the present invention to prevent or reduce in severity disorders caused as a result of NK or CTL cytotoxicity. In a preferred embodiment, such a method comprises the step of administering to an individual a cytogram antagonist in a physiologically acceptable composition. Preferably, such methods for reducing NK and CTL activation are directed to treat allergy and asthma, and to prevent on-going immune responses. More particularly, such methods can be used to prevent or reduce in severity graft rejections, graft versus host diseases and autoimmune diseases (e.g., rheumatoid arthritis, systemic lupus, multiple sclerosis, insulin-dependent diabetes, hepatitis, rheumatoid arthritis, Graves disease), and to induce tolerance to graft transplantation (e.g., transplantation of cells, bone marrow, tissue, solid-organ, bone). A preferred cytogram antagonist for use in such method is an antibody that specifically binds to cytogram polypeptides.

In another preferred embodiment, an anti-cytogram antibody may be used as a targeting and delivery mechanism for bringing a pharmaceutical agent to activated NKs and CTLs.

Such a method comprises the steps of: i) conjugating an anti-cytogram antibody to a pharmaceutical agent; and ii) administering a composition comprising said conjugate and a pharmaceutically acceptable carrier to an individual suffering from a disorder caused as a result of NK or CTL cytotoxicity. Preferably, an anti-cytogram antibody is used in an antibody-directed enzyme-prodrug therapy comprising the steps of: i) conjugating an anti-cytogram antibody to an enzyme converting a relatively non-toxic compound into a substantially more toxic compound; and ii) administering said relatively non-toxic compound to a patient after a delay that allowed residual enzyme-antibody conjugate to be cleared from the blood. Such a method may be performed as described by Melton et al. (J. Natl. Cancer Inst. 1996 88:153-65 (1996)), which disclosure is hereby incorporated by reference in its entirety.

An embodiment of the present invention relates to methods of using the compositions of the present invention to enhance NK or CTL cytotoxicity. A preferred method directed to enhance NK or CTL cytotoxicity comprises the step of introducing a cytogram polypeptide or a cytogram agonist in a physiologically acceptable carrier in an individual suffering from diseases and disorders where a boost to the immune system is desirable. More particularly, such treatments can be used in conjunction with a radiation therapy or a chemotherapy when treating a cancer, and can be used to treat neoplastic disorders (e.g., multiple myeloma, colon cancer, hepatoma) viral infections (e.g., HIV, HBV, HCV, hepatitis, measles and herpes viruses infections), and various immune deficiencies. These immune deficiencies may be genetic (e. g. severe combined immunodeficiency (SCID)) or be caused by various bacterial or fungal infections (e.g. infections by mycobacteria, Leishmania spp., malaria spp. and candidiasis).

Physiologically acceptable carriers can be prepared by any method known by those skilled in the art. Physiologically acceptable carriers include but are not limited to those described in Remington's Pharmaceutical Sciences (Mack Publishing Company, Easton, USA 1985), which disclosure is hereby incorporated by reference in its entirety. Pharmaceutical compositions can be for, e.g., intravenous, topical, rectal, local, inhalant or subcutaneous, intradermal, intramuscular, oral and intracerebral use. The compositions can be in liquid (e.g., solutions, suspensions), solid (e.g., pills, tablets, suppositories) or semisolid (e.g., creams, gels) form. Dosages to be administered depend on individual needs, on the desired effect and the chosen route of administration.

Another embodiment is directed to a method of using cytogram polynucleotides comprising the steps of: i) constructing a recombinant molecule comprising a nucleic acid sequence encoding a cytogram polypeptide that allows expression of cytogram or part thereof under given physiological conditions, and ii) introducing this recombinant molecules into a cell, a mammal or a human. Such a method can be used to treat, e.g., the genetic immune deficiencies and neoplastic diseases listed above. Preferably, the recombinant molecule is introduced into NKs or CTLs.

Still another embodiment is directed to a method of using antisense cytogram polynucleotides comprising the steps of: i) constructing a recombinant molecule comprising a nucleic acid sequence encoding a cDNA that is complementary to cytogram polynucleotides, and ii) introducing this recombinant molecules into a cell, a mammal or a human. Such a method can be used to treat autoimmune diseases. Alternatively, such a method can be used to prevent the autoimmune disorders listed above, graft versus host disease or graft rejection when transplanting an organ. The recombinant molecule may be introduced into NKs, CTLs, or graft cells.

Recombinant molecules comprising a nucleic acid sequence encoding a cytogram polypeptide or a nucleic acid sequence that encodes a cDNA that is complementary to cytogram polynucleotides may be directly introduced into cells or tissues in vivo using delivery vehicles such as retroviral vectors, adenoviral vectors and DNA virus vectors. They may also be introduced into cells in vivo using physiological techniques such as microinjection and electroporation or chemical methods such as coprecipitation and incorporation of DNA into liposomes. Recombinant molecules may also be delivered in the form of an aerosol or by lavage. The cytogram polynucleotides may also be applied extracellularly such as by direct injection into cells. Preferably, cytogram polynucleotides are introduced into NKs or CTLs.

Protein of SEQ ID NO:44 (Internal Designation Clone 1000838982_220-20-4-0-C2-F)

The cDNA of Clone 1000838982_220-20-4-0-C2-F (SEQ ID NO: 43) encodes Tetranab of SEQ ID NO:44, comprising the amino acid sequence:

```
MSAQESCLSLIKYFLFVFNLFFFVLGSLIFCFGIWILIDKTSFVSFVGLAFVPLQIWSKVLAIS

GIFTMGIALLGCVGALKELRCLLGLYFGMLLLLFATQITLGILISTQRASWSEACGTS.
```

Accordingly, it will be appreciated that all characteristics and uses of the polypeptides of SEQ ID NO:44 described throughout the present application also pertain to the polypeptides encoded by the human cDNA included in Clone 1000838982_220-20-4-0-C2-F. In addition, it will be appreciated that all characteristics and uses of the polynucleotides of SEQ ID NOs:43 described throughout the present application also pertain to the nucleic acids comprising the human cDNA included in Clone 1000838982_220-20-4-0-C2-F. A preferred embodiment of the invention is directed toward the compositions of SEQ ID NO:44, SEQ ID NO:43, and Clone 1000838982_220-204-0-C2-F. Also preferred are polypeptide fragments having a biological activity as described herein and the polynucleotides encoding the fragments.

The protein of the invention, Tetranab, is a variant of CD37 (GenBank accession number P11049). CD37 is a molecular facilitator that brings together molecular complexes necessary for T-cell dependant B-cell response. CD37 stabilizes molecular interactions, resulting in a more efficient response. Tetranab is a divergent member of the tetraspanin family, which displays one signal anchor (FNLFFFVLGSLIFCFGIWILI) (SEQ ID NO: 101) and two transmembrane domains (VLAISGIFTMGIALLGCVGAL (SEQ ID NO:102) and LYFGMLLLLFATQITLGILIS) (SEQ ID NO:103). Tetranab is specifically expressed on mature B cells. It is not expressed during differentiation of B cells and its expression is down-regulated with activation of B cells. Tetranab acts as a dominant negative inhibitor of CD37-facilitated assembly of functional complexes at B cells surfaces. Thus Tetranab prevents CD37-dependent activation of B cells.

An embodiment of the invention is directed to a composition comprising a Tetranab polypeptide sequence of SEQ ID NO:44.

A further embodiment of the invention is directed to a composition comprising a Tetranab polypeptide fragment having biological activity of preventing T-cell dependant B-cell response.

A further embodiment of the invention is directed to a composition comprising a polynucleotide sequence of SEQ ID NO:43 encoding a Tetranab polypeptide.

A further embodiment of the invention is directed to a composition comprising a polynucleotide sequence encoding a Tetranab polypeptide fragment having biological activity of preventing T-cell dependent B-cell response.

A further embodiment of the invention is directed to a composition comprising an antibody recognizing a Tetranab polypeptide. Preferably, the antibody recognizes an epitope comprising one or more of the 9 C-terminal amino acids of Tetranab, wherein one or more of the 9 C-terminal amino acids is required for antibody binding. Preferably, the antibody binds specifically to Tetranab but not to CD37. As used herein, an anti-Tetranab antibody refers to an Tetranab-specific antibody or an antigen binding fragment thereof.

The present invention also relates to a method of binding such an antibody to a Tetranab polypeptide comprising the step of: contacting a Tetranab polypeptide with said antibody or an antigen-binding fragment thereof under conditions that allow binding to take place. Such conditions are well known to those skilled in the art. Such methods are useful for detecting Tetranab polypeptides or for purifying B cells as further described herein.

An embodiment of the present invention is directed to a method of detecting Tetranab polypeptides in a biological sample, said method comprising the steps of: i) contacting a biological sample with an anti-Tetranab antibody; and ii) detecting the antigen-antibody complex formed. The antibody or antibody fragment may be monoclonal or polyclonal. In addition, the antibody or antibody fragment may be primarily or secondarily labeled by any detectable compound (e.g., radioactive, fluorescent, luminescent, or enzymatic) common in the art. Further preferred is a method of using said anti-Tetranab antibodies or antigen binding fragments in a flow cytometric analysis of Tetranab expression by B cells. Such a method can be used as a diagnostic tool for detecting the presence of a Tetranab polypeptide as further described herein.

Another embodiment of the present the invention is directed to a diagnostic kit for detecting in vitro the presence of a Tetranab polypeptide. Such kit comprises: i) a polyclonal or monoclonal antibody or fragment thereof that specifically binds a Tetranab polypeptide; and optionally, ii) a reagent allowing the detection of the antigen-antibody complexes formed. Preferably, the antibody or antibody fragment is detectably labeled as described above The optional reagent may provide a detectable signal, and either bind to the antibody, or react with the label on said antibody. Preferably, the kit comprising anti-Tetranab antibodies or antigen binding fragments is used for diagnosing non-Hodgkin's lymphomas, or for monitoring the condition of a patient receiving treatment for a non-Hodgkin's lymphoma. Optionally, said kit for diagnosing non-Hodgkin's lymphomas comprises a sample of an individual suffering from lymphoma, as well as a control sample from a normal individual.

Another preferred embodiment relates to a method for detecting in vivo the presence of a Tetranab polypeptide using anti-Tetranab antibodies. Such a method is very useful for imaging of tumor involved sites, and especially for imaging of non-Hodgkin's lymphomas. Preferably, imaging is carried out using $^{111}In$ or $^{131}I$ conjugated to an anti-Tetranab antibody as described by Bunn et al (Lancet 2:1219-21 (1894)), which disclosure is incorporated by reference in its entirety. This embodiment also relates to a kit for use in tumor imaging such as the kit described above.

Still another embodiment of the present invention relates to a method using an anti-Tetranab antibody for immunotherapeutic purposes comprising the step of administering a therapeutic dose of a radioactively labeled anti-Tetranab antibody in a pharmaceutically acceptable carrier. Such a method can be applied to treat non-Hodgkin's lymphomas and post-transplant lymphoproliferative disorders. In such a method, labeling with $^{90}Y$ or $^{131}I$ is preferred. Radioactive isotopes can be attached to the anti-Tetranab antibody by a number of methods well-known to those skilled in the art, e.g., by covalent attachment of a iodine isotope directly to the antibody or by covalent attachment of a chelating moiety to the antibody allowing the chelator to coordinate the metal isotope. Routes of administration may vary widely. Preferred modes of administration are intravenous injection and intralymphatic routes of administration such as subcutaneous and intramuscular injection, or catherization of lymphatic vessels. The radiometric dosage to be applied can vary substantially. Methods of administration and dosage regimen for treating lymphomas can be determined as described in U.S. Pat. No. 5,595,721, which disclosure is hereby incorporated by reference in its entirety.

A preferred aspect of the invention is a host cell recombinant for polynucleotides encoding a Tetranab polypeptide or a biologically active fragment thereof. An additional preferred aspect is a host cell recombinant for polynucleotides capable of directing Tetranab expression. Preferably, the polynucleotides capable of directing Tetranab expression are located in the 5' regulatory region of the Tetranab gene. Further preferably, these polynucleotides are located within 500 base pairs of the Tetranab coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. Tetranab protein produced by said host cell may be used for in vitro detection and purification methods as well as diagnosis and in vivo applications.

An embodiment of the invention provides for a method of screening test substances for modulators of Tetranab expression. This method comprises the steps of: i) contacting a cell with a test substance; and ii) comparing Tetranab expression in the cell after exposure to the test substance to that of an unexposed control cell. Tetranab expression is determined by methods common to the art or included herein, by detecting Tetranab polynucleotides or polypeptides. An example of this method comprises the steps of: i) culturing two equivalent cell samples; ii) adding a test substance to one of the cultures and not the other; iii) harvesting both cultures at a specified time; iv) purifying the mRNA from each sample of cells; v) comparing the level of Tetranab mRNA in each sample by Northern blot, RTPCR, or another method common to the art. An additional example comprises the steps of: i) having two equivalent cultures of cells; ii) adding a test substance to one of the cultures and not the other; iii) harvesting both cultures; iv) purifying the protein from each sample of cells; v) comparing the level of Tetranab polypeptides in each sample by Western blot, immunohistochemistry, or another method common to the art. Preferably, Tetranab expression is measured in B cells.

In another embodiment, a Tetranab polypeptide or a fragment thereof may be used to screen for compounds that modulate Tetranab activity. This method comprises the steps of: i) contacting a Tetranab polypeptide or fragment thereof with a test substance, and ii) monitoring Tetranab activity. Tetranab activity may be determined by monitoring B cell activation. For example, B cell function can be determined by measuring calcium ion flux across the membrane as described in U.S. Pat. No. 4,987,084, which disclosure is incorporated by reference in its entirety.

Test substances that decrease Tetranab expression or activity are defined as inhibitors or antagonists of Tetranab. Test substances that increase Tetranab expression or activity are defined as activators or agonists. Agents that modulate the expression or activity of Tetranab activity of the subject invention include, but are not limited to antisense oligonucleotides, ribozymes, and antibodies. These agents may be made and used according to methods well known in the art.

A further embodiment of the present invention relates to a method of antagonizing CD37 action, thus preventing T-cell dependant B-cell activation. Such a method comprises the step of contacting a B cell with a composition comprising a Tetranab agonist. The B cells can be treated in vitro or in vivo by directly administering the composition of the present invention to the cells. In a preferred embodiment, this invention provides a method of inhibiting B cell activation in an individual comprising the step of administering to the individual an effective inhibiting amount of a pharmaceutical composition comprising a Tetranab agonist and a pharmaceutically acceptable carrier. A method of inhibiting B cell activation is a useful method for inhibiting the immune response of an individual. Preferably, inhibiting the immune response using a method of the present invention is directed to inhibit a graft rejection reaction, to treat an individual suffering from autoimmune disease (e.g., rheumatoid arthritis, Myasthenia gravis, systemic lupus erythematosus, Graves' disease, idiopathic hrombocytopenia purpura, hemolytic anemia, diabetes mellitus and drug-induced autoimmune diseases such as drug-induced lupus), or to reduce allergic responses (e.g., asthma, hay fever and allergy to penicillin).

Another embodiment of the present invention relates to a method of favoring CD37 action, thus stabilizing molecular complexes that are necessary for T cell dependant B cell activation. Such a method comprises the step of contacting a B cell with a composition comprising a Tetranab antagonist. In this aspect of the invention, an effective inhibiting amount of a pharmaceutical composition comprising a Tetranab antagonist and a pharmaceutically acceptable carrier may be administered to an individual in order to enhance B cell activation. Such a method is useful for treating disorders where a boost of the immune system is desirable such as immune deficiencies (e.g., severe combined immunodeficiency), various viral, fungal or bacterial infections (e.g., HBV, HCV, HIV, hepatitis, measles and herpes virus infections, mycobacteria, *Leishmania* spp., malaria spp. and candidiasis infections), and in association with a radiation or chemotherapy.

Compositions comprising a Tetranab agonist or a Tetranab antagonist may be formulated using a variety of acceptable excipients known in the art. Typically, the compositions are administered topically, orally or by injection, either intravenously or intraperitoneally. Methods to accomplish this administration and to determine the dosage regimen are known to those of ordinary skill in the art.

Another embodiment relates to a method of producing Tetranab polypeptides comprising the steps of: i) transfecting a host cell with a recombinant expression vector comprising a polynucleotide of the present invention, and ii) purifying the produced protein. The purification of the protein can be done following any technique well-known to those skilled in the art. Preferably, an antibody directed against Tetranab or part thereof may be bound to a chromatographic support to form an affinity chromatography column. Such a purified Tetranab polypeptide may for example be useful for preparing the pharmaceutical compositions described above.

A preferred aspect of the invention is a host cell recombinant for polynucleotides encoding a Tetranab polypeptide or a biologically active fragment thereof. An additional preferred aspect is a host cell recombinant for polynucleotides capable of directing Tetranab expression. Preferably, the polynucleotides capable of directing Tetranab expression are located in the 5' regulatory region of the Tetranab gene. Further preferably, these polynucleotides are located within 500 base pairs of the Tetranab coding region. These polynucleotides preferably comprise a promoter sequence. Techniques known in the art for introducing polynucleotide sequences to endogenous sequences are described in U.S. Pat. No. 5641670 and PCT WO9629411, which disclosures are hereby incorporated by reference in their entireties. In preferred embodiments, the recombinant molecule is introduced into an *Escherichia coli* cell or into a human B cell. Alternatively, the recombinant molecule is a vector comprising an heterologous promotor that increases Tetranab expression that is introduced into a human cell. In a preferred embodiment, said recombinant molecule is introduced into animals, more particularly mammals. Said recombinant molecule may be introduced into animals in several ways. A preferred method of introducing the recombinant molecule into animals comprises the steps of: i) introducing the recombinant molecule into a host cell by means known in the art such as, e.g., transformation, electroporation, lipofection, microinjection, and transduction, including the use of retroviral vectors, adenoviral vectors and DNA virus vectors; and ii) administering the recombinant cells to an animal. For example, the cells can be administered by infusion. Such a method may be directed to treat, e.g., autoimmune diseases. Alternatively, the recombinant molecule may encode a cDNA that is complementary to SEQ ID NO:43 or part thereof, and the method may be used to treat, e.g., immune deficiencies.

In another preferred embodiment, said recombinant molecule is used to establish transgenic model animals by any method familiar to those skilled in the art. For example, transgenic mice may be established as described by Hogan et al. ("Manipulating the Mouse Embryo: A Laboratory Manual", Cold Spring Harbor Laboratory), which disclosure is incorporated herein by reference. By modulating in vivo the expression of the transgene with drugs or modifier genes (activator or suppressor genes), animal models can be developed that mimic human disorders such as those listed above. These animal models thus allow the identification of potential therapeutic agents for treatment of the disorders. In addition, recombinant cell lines derived from these transgenic animals may be used for similar approaches ex vivo.

Protein of SEQ ID NO:46 (Internal Designation Clone 500720840_205-20-1-0-B7-F)

The cDNA of Clone 500720840_205-20-1-0-B7-F (SEQ ID NO:45) encodes PDI protein of SEQ ID NO:46 comprising the amino acid sequence: MRLRRLALFPGVALLLAAARLAAASDVLELTDDNFESRISDTGSAGLMLVEFFAPWCGHC KRLAPEYEAAATRLKGIVPLAKVDCTANTNTCNKYGVSGYPTLKIFRDGEEAGAYDGPRT ADGIVSHLKKQAGPASVPLRTEEEFKKFISDKDASIVGFFDDSFSEAHSEFLKAA SNLRDNY RFAHTNVESLVNEYDDNGEGIILFRPSHLTNKFEDKTVAYTEQKMTSGKIKKFIQENIFGIC PHMTEDNKDLIQGKDLLIAYYDVDYEKNAKGSNYRRNRVMMVAKKFLDAGHKLNFAV ASRKTFSHELSDFGLESTAGEIPVVAIRTAKGEKFVMQEEFSRDGKALERF LQDYFDGNLK RYLKSEPIPESNDGPVKVVVAENFDENNENKDVLIEFYAPWCGHCKNLEPKYKELGEK LSKDPNWIVIDATANDVPSPYEVRGFPTIYFSPANKKLNPKKYEGGRELSDFISYLQREA TIPPVIQEEKPKKKKKAQEDL. Accordingly, it will be appreciated that all characteristics and uses of the polypeptides of SEQ ID NO:46 described throughout the present application also pertain to the polypeptides encoded by the human cDNA included in Clone 500720840_205-20-1-0-B7-F. In addition, it will be appreciated that all characteristics and uses of the polynucleotides of SEQ ID NO:45 described throughout the present application also pertain to the nucleic acids comprising the human cDNA in Clone 500720840_205-20-1-0-B7-F. A preferred embodiment of the invention is directed toward the compositions of SEQ ID NO:45, SEQ ID NO:46 and Clone 500720840_205-20-1-0-B7-F. Also preferred are polypeptide fragments having a biological activity as described herein and the polynucleotides encoding the fragments.

The protein of SEQ ID NO:46, PDI, is a polymorphism variant of protein disulfide isomerase A3 precursor (accession numbers U42068). The protein of the invention displays two thioredoxin domain: ASDVLELTDDNFESRISDTGSAGLMLVEFFAPWCGHCKRLAPEYEAAATRLKGIVPLAKV DCTANTNTCNKYGVSGYPTLKIFRDGEEAGAYDGPRTADGIVSHLKKQAG (SEQ ID NO:104); and DGPVKVVVAENFDEIVNNENKDVLIEFYAPWCGHCKNLEPKYKELGEKLSKDPNIVIAK MDATANDVPSPYEVRGFPTIYFSPANKKLNPKKYEGGRELSDFISYLQREAT (SEQ ID NO:105). Also, the 505 amino acid protein of PDI displays one membrane-spanning segment: SDTGSAGLMLVEFFAPWCGHC (SEQ ID NO:106).

Thioredoxin family active site proteins are a superfamily of proteins that participate in redox reactions and are distributed among a wide range of living organisms. The reduced form of thioredoxin is known to activate some enzymes by reducing disulfide bridges that control their activity. In addition, thioredoxin is an electron donor in the reactions sequence that reduces ribonucleotides to deoxyribonucleotides catalyzed by ribonucleotide reductase. It has been reported that in humans, thioredoxin and the cellular redox state modified by thioredoxin play a crucial role in arterial neointima formation in atheroscleriosis. Thioredoxin is involved in cellular defense mechanisms against oxidative damage. Thioredoxin has also been implicated in regulating glucocorticoid responsiveness to cellular oxidative stress response pathways. In particular, thioredoxin is capable of sensing and transmitting the redox state of the cell to the glucorticoid receptor by targeting both the ligand- and DNA-binding domains of the receptor. Human thioredoxin has been suggested to act as a free radical scavenger and has been shown to limit the extent of ischemia reperfusion injury. Multiple in vitro substrates for thioredoxin have been identified, including ribonuclease, choriogonadotropins, coagulation factors, glucocorticoid receptor, and insulin.

PDI belongs to the protein disulfide isomerase class of thioredoxin family active site-containing proteins that catalyze the oxidation of thiols, reduction of disulfide bonds, and isomerization of disulfides, depending on the reaction conditions. PDI catalyzes the formation of correct disulfide pairing in nascent proteins. PDI preferentially interacts with peptides that contain cysteine residues but is otherwise undiscriminating. The broad substrate specificity of PDI enables it to speed the folding of diverse disulfide-containing proteins. By shuffling disulfide bonds, PDI enables proteins to quickly find the most thermodynamically stable pairings amongst available cysteine residues. Consequently, PDI is involved in protein processing, protein folding, and protein secretion. PDI is also involved in collagen and collagen-like protein biosynthesis and mutations of PDI cause Ehlers-Danlos syndrome.

An embodiment of the invention is directed to a composition comprising a PDI polypeptide sequence of SEQ ID NO:46.

A further embodiment of the invention is directed to a composition comprising a PDI polypeptide fragment having a biological activity of binding peptides with cysteine residues.

A further embodiment of the invention is directed to a composition comprising a polynucleotide sequence of SEQ ID NO:45 encoding a PDI polypeptide.

A further embodiment of the invention is directed to a composition comprising a polynucleotide sequence encoding a PDI polypeptide fragment having biological activity of binding peptides with cysteine residues.

A preferred aspect of the invention is a host cell recombinant for polynucleotides encoding a PDI polypeptide or a biologically active fragment thereof. An additional preferred aspect is a host cell recombinant for polynucleotides capable of directing PDI expression. Preferably, the polynucleotides capable of directing PDI expression are located in the 5' regulatory region of the PDI gene. Further preferably, these polynucleotides are located within 500 base pairs of the PDI coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. PDI protein produced by said host cell may be used for in vitro detection and purification methods as well as diagnosis and in vivo applications.

A method of oxidating thiols species comprising the step of: contacting a PDI polypeptide with peptides with reduced cysteine residues. Preferably, thiols are oxidized to disulfide bonds. More preferably, the disulfide bonds are correctly isomerized. This method may be applied to recombinant production of protein sequences containing collagen/collagen-like protein sequences.

A preferred aspect of the invention is a host cell recombinant for polynucleotides encoding a PDI polypeptide or a biologically active fragment thereof. An additional preferred aspect is a host cell recombinant for polynucleotides capable of directing PDI expression. Preferably, the polynucleotides capable of directing PDI expression are located in the 5' regulatory region of the PDI gene. Further preferably, these polynucleotides are located within 500 base pairs of the PDI coding region. These polynucleotides preferably comprise a promoter sequence.

An embodiment of the present invention relates to compositions comprising PDI polypeptides. The method of producing PDI polypeptides comprises the steps of: i) transfecting a mammalian host cell with a recombinant expression vector comprising a polynucleotide of the present invention, and ii) purifying the produced protein. The purification of the protein can be done following any technique well known to those skilled in the art. Preferably, an antibody directed against PDI or part thereof, preferably, an antibody directed against the Thioredoxin domain of the polypeptide, may be bound to a chromatographic support to form an affinity chromatography column.

Another embodiment of the invention provides for a method utilizing PDI alone or in combination with a reductant or reduction system to reduce protein intramolecular disulfide bonds. For example, PDI may be used in combination with glutenins or gliadins present in flour or seeds to improve dough strength and baked goods characteristics such as crumb quality, softness, and higher loaf volume as further described in U.S. Pat. No. 6,113,951, which disclosure is hereby incorporated in its entirety.

Further preferred is a method of reducing a toxic protein having one or more intramolecular cystines comprising contacting the toxic protein with an amount of PDI effective for reducing the protein, and maintaining the contact for a time sufficient to reduce one or more disulfide bridge and denature the toxic protein (as further described in U.S. Pat. No. 6,113,951, which disclosure is hereby incorporated in its entirety).

In one embodiment, PDI may be co-expressed with a desired protein or proteins in a host cell which is used to produce the desired protein or proteins. The co-expression of PDI will result in an increase in the amount of correctly folded protein obtained from the host cell. In this method, a first vector expressing PDI and a second vector expressing a desired protein are introduced into a host cell using conventional methods, and following expression, the desired protein is harvested.

In another embodiment, PDI may be added to a protein sample during processing to increase the efficiency of protein processing. Processing of protein will be carried out following expression of at least one desired protein in the host cell and may include purification, renaturation, solubilization or any other steps used to obtain a pure and active form of a desired protein. In this embodiment, PDI may be added during these steps to minimize loss of protein resulting, for example, from protein oxidation, aggregation, or improper folding. The amount of PDI to be added may be determined by one of skill using routine methods, and will be sufficient to reduce the loss of protein.

In another embodiment, the invention provides a method for neutralizing food allergens by PDI as described in U.S. Pat. No. 6,190,723, which disclosure is hereby incorporated by reference in its entirety. A method of decreasing the allergenicity of an allergenic food protein comprises the step of: contacting the protein with and amount of PDI, Nicotinamide adenine dinucleotide phosphate-thioredoxin reductase and NADPH, or an amount of PDI and dithiothreitol effective for decreasing the allergenicity of the protein.

In another embodiment, the invention provides a method for increasing the digestibility of food proteins. This method may be carried out as described in U.S. Pat. No. 5,952,034, which disclosure is hereby incorporated by reference in its entirety. A method of increasing the digestibility of a food protein comprises the step of: treating a food with an amount of PDI, nicotinamide adenine dinucleotide phosphate-thioredoxin reductase (NTR) and NADPH effective for increasing the digestibility of the food.

An embodiment of the invention provides for a method of screening test substances for modulators of PDI expression. This method comprises the steps of: i) contacting a cell with a test substance; and ii) comparing PDI expression in the cell after exposure to the test substance to that of an unexposed control cell. PDI expression is determined by methods common to the art or included herein, by detecting PDI polynucleotides or polypeptides. An example of this method comprises the steps of: i) culturing two equivalent cell samples; ii) adding a test substance to one of the cultures and not the other; iii) harvesting both cultures at a specified time; iv) purifying the mRNA from each sample of cells; v) comparing the level of PDI mRNA in each sample by Northern blot, RTPCR, or another method common to the art. The invention provides for design and use of specific polynucleotide probes and primers, as discussed herein. An additional example comprises the steps of: i) having two equivalent cultures of cells; ii) adding a test substance to one of the cultures and not the other; iii) harvesting both cultures; iv) purifying the protein from each sample of cells; v) comparing the level of PDI polypeptides in each sample by Western blot, immunohistochemistry, or another method common to the art. The invention provides for design and use of specific antibodies and antibody fragments, as discussed herein. This method may be applied to diagnosis of PDI-related disorders. For example, an abnormally high level of PDI indicates presence of primary tumors such as lung, colon, cervical and hepatocellular carcinoma.

Over-expression of PDI plays a role in the development of disease. Increased expression of PDI is associated with Sjogrens' syndrome, increased growth of leukemia and lymphoma cells, and the proliferation of virally transformed cells. A deficiency of PDI is associated with immunological diseases, including, but not limited to, atherosclerosis, stroke, asthma, allergies, Crohns' disease, ulcerative colitis, diabetes, Hermansky-Pudlack syndrome, Alzheimers disease, and damage to tissues caused by trauma, ischemia, hypoxia, radiation and ultraviolet exposure.

In another embodiment, a PDI polypeptide or a fragment thereof, may be used to screen for compounds that activate or inhibit PDI activity. This method comprises the steps of: i) contacting a PDI polypeptide or fragment thereof with a test substance and ii) monitoring PDI activity.

Test substances that decrease PDI expression or activity are defined as inhibitors or antagonists of PDI. Test substances that increase PDI expression or activity are defined as activators or agonists. Inhibitors of PDI include, but are not limited to antisense oligonucleotides, ribozymes, and antibodies. These agents may be made and used according to methods well known in the art. Disorders characterized by aberrant PDI expression is a cardiovascular disorder, e.g. atherosclerosis, ischaemia reperfusion injury, cardiac hypertrophy, hypertension, coronary artery disease, myocardial infarction, arrythmia, cardiomyopathies, and congestive heart failure; a connective tissue disorder, e.g., Ehlers-Danlos Syndrome; or a hepatic disorder, e.g., alcoholic liver disease, liver cirrhosis and liver cancer.

In another embodiment, the protein of the present invention, as well as agents, or modulators which have a stimulatory or inhibitory effect on PDI activity as identified by a screening assay can be administered to individuals to treat (prophylactically or therapeutically) disorders, described herein, associated with aberrant PDI activity.

In another embodiment of the invention, PDI, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between PDI and the agent being tested, may be measured. Another technique for drug screening which may be used provides for high throughput screening of compounds having suitable binding affinity to the protein of interest as described in published PCT application WO84/03564, which disclosure is hereby included in its entirety. In this method, as applied to PDI, large numbers of different small test compounds are synthesized on a solid substrate, such as plastic pins or some other surface. The test compounds are reacted with PDI, or fragments thereof, and washed. Bound PDI is then detected by methods well known in the art. Purified PDI can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PDI specifically compete with a test compound for binding PDI. In this manner, the antibodies can be used to detect the presence of any peptide which shares one or more antigenic determinants with PDI.

In one embodiment, PDI or a biologically active fragment thereof is administered to a subject to treat conditions or diseases associated with a deficiency of PDI. These include, but are not limited to, cancers of the brain, prostate, breast, bladder, and thyroid, and immunological and infectious diseases, including, but not limited to, atherosclerosis, stroke, asthma, allergies, Crohns' disease, ulcerative colitis, diabetes, Hermansky-Pudlack syndrome, Alzheimers disease, and damage to tissues caused by trauma, ischemia, hypoxia, radiation and ultraviolet exposure.

In another embodiment, a vector capable of expressing PDI, or a fragment or a derivative thereof, may also be administered to a subject to treat or prevent diseases or conditions described above.

In one embodiment, agonists of PDI may be administered to a subject to treat or prevent diseases or conditions described above.

In another embodiment, a vector expressing antisense of the polynucleotide encoding PDI may be administered to a subject to treat or prevent conditions or diseases associated with over-expression of PDI. Such conditions or diseases include lymphoma, leukemia, Sjogrens' syndrome, human T-lymphotropic virus, Epstein-Barr virus, human immunodeficiency virus. An example is described in published PCT application WO 99/38963, which disclosure is hereby included in its entirety.

Another embodiment of the invention relates to composition and methods using polynucleotide sequences encoding the protein of the invention or part thereof to establish transgenic model animals (*D. melanogaster, M. musculus*), by any method familiar to those skilled in the art. By modulating in vivo the expression of the transgene with drugs or modifier genes (activator or suppressor genes), animal models can be developed that mimic human hormone-dependent disorders such as cancers. These animal models would thus allow the identification of potential therapeutic agents for treatment of the disorders. In addition, recombinant cell lines derived from these transgenic animals may be used for similar approaches ex vivo.

In another embodiment, an array of oligonucleotides probes comprising the nucleotide sequence of PDI or fragments thereof can be constructed to conduct efficient screening of e.g., genetic mutations or deletion. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents (see for example: Chee, M. et al., Science, 274:610-614 (1996) which disclosure is hereby incorporated by reference in its entirety). For example, mutations of PDI cause Ehlers-Danlos syndrome.

Protein of SEQ ID NO:48 (Internal Designation Clone 146821_106-020-1-0-G3-F)

The cDNA of Clone 146821_106-020-1-0-G3-F (SEQ ID NO:47) encodes NBART protein of SEQ ID NO:48, comprising the amino acid sequence: MLVMYLLAALFGYLTFYGEVEDELLHAYSKVYTLDIPLLMVRLAVLVAVTLTVPIVLFPIR TSVITLLFPKRPFSWIRHFLIAAVLIALNNVLVILVPTIKYIFGFI GASSATMLIFILPAVFYLK LVKKETFRSPQKVGALIFLVVGIFFMIGSMALIIIDWIYDPPNSKHH. Accordingly, it will be appreciated that all characteristics and uses of the polypeptides of SEQ ID NO:48 described throughout the present application also pertain to the polypeptides encoded by the human cDNA included in Clone 146821_106-020-1-0-G3-F. In addition, it will be appreciated that all characteristics and uses of the polynucleotides of SEQ ID NO:47 described throughout the present application also pertain to the nucleic acids comprising the human cDNA in Clone 146821_106-020-1-0-G3-F. A preferred embodiment of the invention is directed toward the compositions of SEQ ID NO:47, SEQ ID NO:48 and Clone 146821_106-020-1-0-G3-F. Also preferred are polypeptide fragments having a biological activity as described herein and the polynucleotides encoding the fragments.

ADP ribosylation factor (ARF) and ARF-like (ARL) proteins comprise the ARF family within the Ras superfamily of regulatory GTPases. Members of this superfamily function as molecular nodes in signaling that can directly activate one or more enzymatic activities or coordinate the recruitment and assembly of more elaborate multi-subunit complexes. ARL2 is a member of a functionally distinct group of ARF-like genes. ARL2 binds GTP rapidly and hydrolyzes it. In the GDP-bound form, ARL2 interacts with the tubulin-specific chaperone cofactor D. This interaction prevents the destruction of tubulin and microtubles by overexpressed cofactor D. The tubulin GTPase activating protein activity of cofactor D is also inhibited by ARL2 binding. This interaction prevents ARL2 contributes to modulating microtubule dynamics. NBART binds specifically to ARL2-GTP with high affinity but does not interact with ARL2-GDP.

An embodiment of the invention is directed to a composition comprising a NBART polypeptide sequence of SEQ ID NO:48.

A further embodiment of the invention is directed to a composition comprising a NBART polypeptide fragment having a biological activity of binding to ARL2.

A further embodiment of the invention is directed to a composition comprising a polynucleotide sequence of SEQ ID NO:47 encoding a NBART polypeptide. A further embodiment of the invention is directed to a composition comprising a polynucleotide sequence encoding a NBART polypeptide fragment having biological activity of binding to ARL2.

A preferred aspect of the invention is a host cell recombinant for polynucleotides encoding a NBART polypeptide or a biologically active fragment thereof. An additional preferred aspect is a host cell recombinant for polynucleotides capable of directing NBART expression. Preferably, the polynucleotides capable of directing NBART expression are located in the 5' regulatory region of the NBART gene. Further preferably, these polynucleotides are located within 500 base pairs of the NBART coding region. These polynucleotides preferably comprise a promoter sequence. Techniques known in the art for introducing polynucleotide sequences to endogenous sequences are described in U.S. Pat. No. 5,641,670 and PCT WO9629411, which disclosures are hereby incorporated by reference in their entireties. NBART protein produced by said host cell may be used for in vitro detection and purification methods as well as diagnosis and in vivo applications.

A preferred embodiment of the invention is a method of using NBART to bind ARL2. This method comprises the step of contacting a NBART polypeptide or active fragment thereof with an ARL2 protein under conditions that allow NBART binding, whereby binding inhibits the activity of ARL2.

A preferred embodiment of the invention is a method of purifying ARL2. This method comprises the steps of: contacting a NBART polypeptide of active fragment thereof with a ARL2 under conditions that allow binding; removing contaminants; and eluting the ARL2 with more stringent conditions. Preferably, the NBART peptide is immobilized on a solid or semi-solid matrix to facilitate washing of sample to remove contaminants.

A preferred embodiment of the inventions is a method of detecting ARL2. This method comprises the step of contacting a NBART polypeptide or active fragment thereof with ARL2 and detecting the presence of said ARL2 by detecting NBART. Preferably, the NBART polypeptide is detectably labeled with, for example, a fluorescent, luminescent, or radioactive compound. Preferably, ARL2 is detected in a biological fluid such as cell culture media and body fluids. This method may be applied to quantifying the level of ARL2 expression in a cell sample or individual. This information may be useful in determination of microtubule-related disorders, such as, but not limited to, cancer, human polycystic kidney disease, Alzheimer disease, and Down syndrome.

An additional preferred aspect is a host cell recombinant for polynucleotides capable of directing NBART expression. Preferably, the polynucleotides capable of directing NBART expression are located in the 5' regulatory region of the NBART gene. Further preferably, these polynucleotides are located within 500 base pairs of the NBART coding region. These polynucleotides preferably comprise a promoter sequence.

A further aspect of the present invention involves the isolation and purification of NBART. An embodiment of the present invention relates to compositions comprising NBART polypeptides. The method of producing NBART polypeptides comprises the steps of: i) transfecting a mammalian host cell with a recombinant expression vector comprising a polynucleotide of the present invention, and ii) purifying the produced protein. NBART may be isolated according to any technique known in the art or disclosed herein. Preferably, an antibody directed against NBART or a fragment thereof, is bound to a chromatographic support to form an affinity chromatography column.

Protein of SEQ ID NO:50 (Internal Designation Clone 644724_181-21-1-0-A12-F)

The cDNA of Clone 644724_181-21-1-0-A12-F (SEQ ID NO:49) encodes NBTG protein of SEQ ID NO:50, comprising the amino acid sequence: MHPFYTRAATMIGEIAAAVSFISKFLRTKGLTSERQLQTFSQSLQELLAEHYKHHWFPEKP CKGSGYRCIRINHPLIGQAAQRIGLSSQELFRLLPSELTLWVD PYEVSYRIGEDGSICV LYEASPAGGSTQNSTNVQMVDSRISCKEELLLGRTSPSKNYNMMTVSS. Accordingly, it will be appreciated that all characteristics and uses of the polypeptides of SEQ ID NO:50 described throughout the present application also pertain to the polypeptides encoded by the human cDNA included in Clone 644724_181-21-1-0-A12-F. In addition, it will be appreciated that all characteristics and uses of the polynucleotides of SEQ ID NO:49 described throughout the present application also pertain to the nucleic acids comprising the human cDNA in Clone 644724_181-21-1-0-A12-F. A preferred embodiment of the invention is directed toward the compositions of SEQ ID NO:49, SEQ ID NO:50 and Clone 644724_181-21-1-0-A12-F. Also preferred are polypeptide fragments having a biological activity as described herein and the polynucleotides encoding the fragments.

NBTG is a novel polymorphism variant of B-cell translocation gene 1 protein (accession numbers P31607). The protein of the invention displays an anti-proliferative domain: IGEIAAAVSFISKFLRTKGLTSERQLQTFSQSLQELLAEHYKHHWFPEKPCKGSGYRCIRIN HKMDPLIGQAAQRJGLSSQELFRLLPSELTLWVDPYEVSYRJGEDGSICVLYEASP AGGST QNSTNVQMVDSRISCKEELLLGRTSPSKNYNMMTVSS (SEQ ID NO: 107). Accordingly, some embodiments of the present invention relate to polypeptides comprising the anti-proliferative domain.

The ability to negatively regulate cell proliferation is a necessity for all living organisms. Unicellular organisms must limit their replication to the time when adequate nutrients and other environmental factors are present, and multicellular organisms must accurately shape and maintain the architecture of their component tissues. The failure in a multicellular organism to provide adequate negative growth control in the developmental period may result in a malformation, which may be lethal. In the postdevelopmental period, such a failure may result in neoplasia. Because negative control is so critical, specific genes have evolved whose role is actively antiproliferative.

NBTG is a member of a family of antiproliferative genes. NBTG is crucial to counteract the growth inducing elements and have the same importance as proto-oncogenes in controlling cell division. Loss of NBTG is associated with irregular cellular differentiation and proliferation or with alteration of embryonic development. NBTG downregulates N1H3T3 cell proliferation when over expressed. NBTG gene is involved in a chromosomal translocation in B-cell chronic lymphocytic leukemia. NBTG is expressed in tissues (lymphoid, liver, plasma) containing non-dividing cells likely to re-enter the cell cycle upon stimuli, however, NBTG is barely detectable in fully differentiated tissues such as brain and muscle.

An embodiment of the invention is directed to a composition comprising a NBTG polypeptide sequence of SEQ ID NO:50.

A further embodiment of the invention is directed to a composition comprising a NBTG polypeptide fragment having a biological activity of inhibiting cell proliferation.

A further embodiment of the invention is directed to a composition comprising a polynucleotide sequence of SEQ ID NO:49 encoding a NBTG polypeptide. A further embodiment of the invention is directed to a composition comprising a polynucleotide sequence encoding a NBTG polypeptide fragment having a biological activity of inhibiting cell proliferation.

A further embodiment of the invention is directed to a composition comprising an antibody directed against the NBTG polypeptide or a NBTG polypeptide fragment having biological activity. Preferably, the antibody recognizes a non-linear epitopes, and specifically binds to the C-terminal sequence of NBTG.

A preferred aspect of the invention is a host cell recombinant for polynucleotides encoding a NBTG polypeptide or a biologically active fragment thereof. An additional preferred aspect is a host cell recombinant for polynucleotides capable of directing NBTG expression. Preferably, the polynucleotides capable of directing NBTG expression are located in the 5' regulatory region of the NBTG gene. Further preferably, these polynucleotides are located within 500 base pairs of the NBTG coding region. These polynucleotides preferably comprise a promoter sequence. Techniques known in the art for introducing polynucleotide sequences to endogenous sequences are described in U.S. Pat. No. 5641670 and PCT WO9629411, which disclosures are hereby incorporated by reference in their entireties. NBTG protein produced by said host cell may be used for in vitro detection and purification methods as well as diagnosis and in vivo applications.

An embodiment of the present invention relates to compositions comprising NBTG polypeptides. The method of producing NBTG polypeptides comprises the steps of: i) transfecting a mammalian host cell with a recombinant expression vector comprising a polynucleotide of the present invention, and ii) purifying the produced protein. The purification of the protein can be done following any technique well known to those skilled in the art. Preferably, an antibody directed against NBTG or part thereof, more preferably, an antibody directed against the C-terminal sequence of NBTG polypeptide, may be bound to a chromatographic support to form an affinity chromatography column.

In another embodiment, the invention provides methods and compositions for detecting the level of expression of NBTG mRNA. Quantification of mRNA levels of NBTG polypeptides is useful for the diagnosis or prognosis of diseases associated with an altered expression of the protein of the invention. Conditions, diseases or disorders associated with altered expression include, but are not limited to, aberrant cellular proliferation, such as cancer, psoriasis, blood vessel proliferative disorders, fibrotic disorders, and actinic lesions. Assays for the detection and quantification of the mRNA of the protein of the invention are well known in the art (see, for example, Maniatis, Fitsch and Sambrook, Molecular Cloning; A Laboratory Manual (1982), or Current Protocols in Molecular Biology, Ausubel, F. M. et al. (Eds), Wiley & Sons, Inc.). For example, the nucleic acid molecule or probe may be labeled by standard methods and added to a biological sample from a patient under conditions of formation of hybridization complexes. After an incubation period, the sample is washed and the amount of label (or signal) associated with hybridization is quantified and compared with a standard value. If the amount of label in the patient sample is significantly altered in comparison to the standard value, then the presence of the associated condition, disease or disorder is indicated. Such assays may also be used to evaluate the efficacy of a particular therapeutic treatment regimen in animal studies and in clinical trial and to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

In another embodiment, the invention relates to methods and compositions for detecting and quantifying the level of NBTG present in a particular biological sample. These methods are useful for the diagnosis or prognosis of diseases associated with altered levels of the protein of the invention. Diagnostic assays to detect NBTG may require cells from a biopsy, in situ assay of cells from organ or tissue sections, or an aspirate of cells from a tumor or normal tissue. In addition, assays may be conducted upon cellular extracts from organs, tissues, cells, urine, or serum or blood or any other body fluid or extract. Detection and quantification of NBTG polypeptides using either specific polyclonal or monoclonal antibodies are known in the art. Examples of such techniques include enzyme-linked immunoabsorbent assays (ELISAs), radioimmunoassays (RIAs), and fluorescence activated cell sorting (FACS).

NBTG has an antiproliferative ability, and thus may be employed to treat diseases or pathological conditions associated with aberrant cellular proliferation and malignant conditions. The polypeptides may be employed to inhibit tumor growth and cell proliferation. NBTG may also be employed to prevent scar formation at the site of wound healing. Restenosis, or re-occlusion of arterial walls after balloon angioplasty, may also be treated with NBTG as arteries re occlude through cell proliferation. Similarly angiogenesis into a tumor may be inhibited.

In one embodiment, NBTG or a biologically active fragment thereof is administered to treat or prevent a condition associated with altered NBTG expression or activity. Examples of such conditions include, but are not limited to, those described above. Most preferably, a composition comprising a NBTG polypeptide is administered to an individual suffering from abnormal or undesirable cell proliferation, such as, e.g., tumor growth, endothelial cell proliferation, and angiogenesis related to tumor growth. Tumors that can be treated with the compositions of the present invention include, but are not limited to, gliomas, amelanotic melanomas, prostate tumors and lung tumors.

In another embodiment, a pharmaceutical composition comprising a substantially purified NBTG polypeptide in conjunction with a pharmaceutical carrier may be administered to a subject to treat or prevent a condition associated with altered expression or activity of the endogenous protein including, but not limited to, those provided above.

In another embodiment, a substance which modulates the activity of NBTG may be administered to a subject to treat or prevent a condition associated with altered lifespan, expression, or activity of NBTG polypeptides including, but not limited to, those listed above. In one aspect, an antibody which specifically binds NBTG may be used as a targeting and delivery mechanism for bringing a pharmaceutical agent to cells or tissue which express NBTG like, but not limited to, the liver cells.

Another embodiment of the subject invention provides compositions and methods of selectively increasing the activity of the protein of the invention. Activation of NBTG allows for the successful treatment and/or management of diseases or biochemical abnormalities associated with NBTG activity. Agonists, able to increase the expression or the activity of the protein of the invention, are useful in the treatment of diseases associated with cell proliferation, like, but not limited to, cancer, psoriasis, blood vessel proliferative disorders, fibrotic disorders, and actinic lesions. Alternatively, antagonist, able to decrease the expression or the activity of NBTG, are useful in the treatment of conditions characterized by insufficient cellular proliferation. The conditions to be treated include, for example, osteoporosis, fragile skin and poor wound healing.

In an additional embodiment, a vector capable of expressing NBTG or a preferred fragment may be administered to a subject to treat or prevent a condition associated with altered lifespan, expression, or activity of the protein of the invention including but not limited to, those listed above. NBTG gene and gene products may also be employed for modulation of cellular growth. Due to their anti-proliferative effect they could be selectively administered or possibly inhibited when it is desirable to have certain cells proliferate. An example would be a disorder related to the underproduction of certain cells, where proliferation and differentiation of theses cells would helps to treat the disorders listed above.

In some embodiments, the invention also concerns a diagnostic kit for detecting in vitro the presence of NBTG polypeptide. This kit comprises: a polyclonal or monoclonal antibody or fragment thereof that specifically binds a NBTG polypeptide; and optionally, ii) a reagent allowing the detection of the antigen-antibody complexes formed. Preferably, the antibody, or antibody fragment is detectably labeled. Such labels include fluorescent luminescent, and radioactive compounds, as well as enzymatic substrates. The optional reagent may provide a detectable signal in either bind to the antibody or react with the label on the antibody. NBTG antibodies may be used to diagnose low proliferative diseases such as osteoporosis, fragile skin and poor wound healing. To diagnose such disorders, an appropriate biological sample can be tested to determine the level of NBTG being produced.

In another embodiment, the current invention provides a method of effectively blocking proliferation or inhibiting the growth of a cell in vivo or in vitro. Preferably, the present invention can be used to stop unrestrained cell proliferation and to eliminate as many tumor cells as possible. The method will be performed by administering an antisense oligonucleotide directed against NBTG to a cell. One strategy for delivering antisense oligonucleotides to targeted cells involves encapsulation or incorporation of the therapeutic bioactive molecules in liposomes, such as cationic liposomes. These liposomes are known to provide a shield against nucleotide degradation in vivo and can be targeted to specific areas of the body at which point they slowly release their contents. Alternatively, a polynucleotide construct comprising plasmid DNA operably linked to the antisense oligonucleotide could be used. The nucleotide sequences are administered in vivo in a suitable buffer or carrier solution known to those skilled in the art.

Another embodiment of the invention relates to composition and methods using polynucleotide sequences encoding the protein of the invention or a fragment thereof to establish transgenic model animals (*D. melanogaster, M. musculus*), by any method familiar to those skilled in the art. By modulating in vivo the expression of the transgene with drugs or modifier genes (activator or suppressor genes), animal models can be developed that mimic human hormone-dependent disorders such as cancers. These animal models would thus allow the identification of potential therapeutic agents for treatment of the disorders. In addition, recombinant cell lines derived from these transgenic animals may be used for similar approaches ex vivo.

Protein of SEQ ID NO:52 (Internal Designation 583702__181-8-4-0-C8-F)

The cDNA of 583702__181-84-0-C8-F (SEQ ID NO:51) encodes protein vITH1 of SEQ ID NO:52, comprising the amino acid sequence:

```
MPLPLPSAFVLSALQPSPTHSSSNTQRLPDRVTGGFSVNGQLIGNKARSPGQHDGTYFGRL
GIANPATDFQLEVTPQNITLNPGFGGPVFSWRDQAVLRQDGVVVTINKKRNLVVSVDDGG
TFEVVLHRVWKGSSVHQDFLGFYVLDSHRMSARTHGLLGQFFHPIGFEVSDIHPGSDPTKP
DATMVVRNRRLTVTRGLQKDYSKDPWHGAEVSCWFIHNNGAGLIDGAYTDYIVPDIF.
```

Accordingly, it will be appreciated that all characteristics and uses of polypeptides of SEQ ID NO:52 described throughout the present application also pertain to the polypeptides encoded by the human cDNA included in Clone 583702__181-84-0-C8-F. In addition, it will be appreciated that all characteristics and uses of the polynucleotides of SEQ ID NO:51 described throughout the present application also pertain to the nucleic acids comprising the human cDNA in Clone 583702__181-8-4-0-C8-F. A preferred embodiment of the invention is directed toward the compositions of SEQ ID NO:51, SEQ ID NO:52, and 583702__181-8-4-0-C8-F. Also preferred are polypeptide fragments having a biological activity as described herein and the polynucleotides encoding the fragments.

The cDNA of SEQ ID NO:51 is a splice variant of the heavy chain 1 of the human inter-alpha-trypsin inhibitor (ITH1), encoding a 239 amino-acid protein of SEQ ID NO:52 named vITH1.

Inter-alpha-trypsin inhibitor belongs to the superfamily of Kunitz-type serine protease inhibitors in mammals. It is a glycosylated protease inhibitor with a polypeptide chain structure composed of two heavy chains (HC1 and HC2) covalently linked to a light chain (bikunin). Bikunin functions as the protease inhibitor. vITH1 polypeptide is a novel splice variant of the heavy chain 1 that lacks the bikunin linkage site. However, ITH1 binds hyaluronic acid (HA) protein. The connective tissues are the main mammalian source of HA but it is also found in the extracellular matrix, cartilage, bone marrow, synovial fluid. After endocytosis, HA is normally catabolized by hyaluronidase digestion in the liver.

An embodiment of the invention is directed to a composition comprising a vITH1 polypeptide sequence of SEQ ID NO:52.

A further embodiment of the invention is directed to a composition comprising a vITH1 polypeptide fragment having a biological HA-binding protein activity.

A further embodiment of the invention is directed to a composition comprising a polynucleotide sequence of SEQ ID NO:51 encoding a vITH1 polypeptide.

A further embodiment of the invention is directed to a composition comprising a polynucleotide sequence encoding a vITH1 polypeptide fragment having a biological HA-binding protein activity.

A further embodiment of the invention is directed to a composition comprising an antibody directed against a vITH1 polypeptide sequence of SEQ ID NO: 52 or a vITH1 polypeptide fragment having a biological HA-binding protein activity. Preferably, the antibody specifically binds to vITH1 but not to ITH1. Preferably, the antibody specifically recognizes an epitope comprising the amino acids: VTGG (SEQ ID NO:108), TGGF (SEQ ID NO:109), GGFS (SEQ ID NO:110), VTGGFS (SEQ ID NO:111), MPLP (SEQ ID NO: 112), PLPL (SEQ ID NO:113), PLPS (SEQ ID NO:114), LPSA (SEQ ID NO:115), or MPLPLPSA (SEQ ID NO:116).

An embodiment of the present invention relates to compositions comprising vITH1 polypeptides. The method of producing vITH1 polypeptides comprises the steps of: i) transfecting a mammalian host cell with a recombinant expression vector comprising a polynucleotide of the present invention, and ii) purifying the produced protein. The purification of the protein can be done following any technique well known to those skilled in the art. Preferably, an antibody directed against vITH1 or fragment thereof, as described above, may be bound to a chromatographic support to form an affinity chromatography column.

In another embodiment, the invention is directed to a method of detecting vITH1 polypeptide in a biological sample, said method comprising the steps of: i) contacting a biological sample with an antibody or antibody fragment that specifically binds vITH1 polypeptide; and ii) detecting the antigen-antibody complex formed. The antibody or antibody fragment may be monoclonal or polyclonal. In addition, the antibody or antibody fragment may be primarily or secondarily labeled by a detectable compound (e.g., radioactive, fluorescent, luminescent, or enzymatic) common in the art.

In a further embodiment, vITH1 polypeptide is used to purify HA. In such method, vITH1 polypeptide is preferably covalently or non-covalently attached to a solid matrix and allowed to bind HA using techniques well known in the art. This method comprises the steps of: i) washing the solid matrix to get rid of contaminants, ii) eluting the particle of interest using more stringent conditions. Additional aspects of this embodiment include methods of using vITH1 polypeptide to detect and quantify HA using techniques common in the art. This method comprises the steps of: i) obtaining a biological sample suspected of containing HA, ii) contacting said sample with a vITH1 polypeptide or fragment thereof under conditions suitable for binding of vITH1 and detecting the presence or absence of HA by detecting vITH1. Preferably, vITH1 polypeptide or fragment thereof is covalently attached to a detectable compound. Alternatively, a detectable vITH1-specific antibody or fragment thereof may be used to detect vITH1. This embodiment is useful, for example, as a diagnostic tool for detecting the presence of HA for individuals at risk of or suffering from a wide range of diseases associated with an abnormal HA storage. For example, it can be applied in the diagnosis of conditions such as, but not limited to, hyaluronidase deficiency also known as type IX mucopolysaccharidosis, disorders of HA metabolism associated with generalized folding and thickening of the skin as described by Ramsden C A et al, J Pediatr January 2000; 136(1):62-68), liver diseases such as cirrhosis, renal failure and several lung diseases, arthritis diseases such as rheumatoid arthritis and osteoarthritis, and certain cancers such as mesothelioma and Wilms' tumors. Such method is also useful to evaluate the severity degree of such diseases. This kit comprises: a polyclonal or monoclonal antibody or fragment thereof that specifically binds a vITH1 polypeptide; and optionally, ii) a reagent allowing the detection of the antigen-antibody complexes formed. Preferably, the antibody or antibody fragment is detectably labeled. Such labels include fluorescent, luminescent, and radioactive compounds, as well as enzymatic substrates. The optional reagent may provide a detectable signal and either bind to the antibody or react with the label on such antibody. To determine the level of HA and diagnose or manage such disorders, preferred appropriate biological samples are serum, urine and synovial fluid in the case of arthritis disorders.

An embodiment of the invention provides for a method of screening test substances for modulators of vITH1 expression. This method comprises the steps of: i) contacting a cell with a test substance, and ii) comparing vITH1 expression in the cell after exposure to the test substance to that of an unexposed control cell. vITH1 expression is determined by methods common to the art or included herein, by detecting vITH1 polynucleotides or polypeptides. An example of this method comprises the steps of: i) culturing two equivalent cell samples, ii) adding a test substance to one of the cultures and not the other, iii) harvesting both cultures at a specified time, iv) purifying the mRNA from each sample of cells, v) comparing the level of vITH1 mRNA in each sample by Northern blot, RTPCR, or another method common to the art. The invention provides for design and use of specific polynucleotide probes and primers, as discussed herein. An additional example comprises the steps of: i) having two equivalent cultures of cells, ii) adding a test substance to one of the cultures and not the other, iii) harvesting both cultures, iv) purifying the protein from each sample of cells, v) comparing the level of vITH1 polypeptides in each sample by Western blot, immunohistochemistry, or another method common to the art. The invention provides for design and use of specific antibodies and antibody fragments, as discussed herein.

In another embodiment, a vITH1 polypeptide or a fragment thereof, may be used to screen for compounds that activate or inhibit vITH1 activity. This method comprises the steps of: i) contacting a vITH1 polypeptide or fragment thereof with a test substance and ii) monitoring vITH1 activity. vITH1 binds to HA. Thus, vITH1 activity may be monitored upon addition of the test substance by competitive binding assays with HA. In this aspect of the invention, a vITH1 polypeptide or fragment thereof may be free in solution, affixed to a solid support, recombinantly expressed on or chemically attached to a cell surface, or located intracellularly. The formation of binding complexes between vITH1 polypeptide and the compound being tested, may be measured by methods well known to those skilled in the art, such as the BIAcore (Upsala, Sweden). Another technique provides for high throughput screening of compounds having suitable binding affinity to the protein of the invention. Test substances that decrease vITH1 expression or activity are defined as inhibitors or antagonists of vITH1. Test substances that increase vITH1 expression or activity are defined as activators or agonists. Agents which modulate the expression or activity of the vITH1 of the subject invention include, but are not limited to antisense oligonucleotides, ribozymes, and antibodies. These agents may be made and used according to methods well known in the art.

In another embodiment of the invention, the vITH1 polypeptide, fragments thereof, or vITH1 agonists are used to bind HA in vivo and remove this molecule from the bloodstream. This method can be used to prevent or treat disorders associated with abnormal storage of HA, including those due to a decrease hepatic clearance, an excessive synthesis or an increased hyaluronidase activity, For example, vITH1 polypeptides, fragments thereof, or vITH1 agonists can be used in a composition delivered to an individual at risk of or suffering from, but not limited to, hyaluronidase deficiency also known as type IX mucopolysaccharidosis, disorders of HA metabolism associated with generalized folding and thickening of the skin as described by Ramsden C A et al, J Pediatr 2000 January; 136(1):62-68), liver diseases such as cirrhosis, renal failure and several lung diseases. In this embodiment, such compositions can also be used in any other conditions associated with elevated serum levels of HA such as arthritis diseases such as rheumatoid arthritis and osteoarthritis, and certain cancers such as, but not limited to, mesothelioma and Wilms' tumors. This method comprises the step of: introducing an effective amount of vITH1 polypeptide, fragment thereof or vITH1 agonist to the bloodstream of an individual. In this embodiment, the vITH1 polypeptide may further be expressed as a fusion protein with a polypeptide signal specifying excretion from the body. A preferred method of delivering vITH1 polypeptides or biologically active fragments thereof to an individual includes direct, intravenous injection of said polypeptides or fragments in a physiologically acceptable solution (e.g., pH-buffered isotonic saline solutions, pH-buffered isotonic saline solutions modified by addition of viscous elements such as glycerol). Alternatively, vITH1 polynucleotides may be introduced to express vITH1 polypeptides in the bloodstream. This method comprises the steps of: i) constructing a recombinant viral vector corresponding to a portion of the genome of an adenovirus capable of infecting a cell operatively linked to the nucleotide sequence of the invention and a regulatory sequence directing its expression; ii) delivery of an effective amount of the recombinant adenoviral vector to an individual with or at risk of suffering diseases or conditions mentioned above.

Another embodiment of the invention relates to animal models generated by modulating the expression or activity of the present protein in one or more tissues of the animal. These animals can be generated with any method of targeting overexpression or inactivation of vITH1, or by modulating the in vivo expression of the transgene with drugs or modifier genes (activator or suppressor genes). Such animals are useful for a number of purposes, because they represent an in vivo assay method for testing therapeutic candidate molecules potentially useful for the treatment of various pathophysiological aspects of diseases specifically related to the activity of vITH1. In addition, recombinant cell lines derived from these transgenic animals may be used for similar approaches ex vivo.

Nested N-Terminal Fragments of Related Proteins Acrp30R1L and Acrp30R1

The cDNA of Accession No. AAB30232 comprising the nucleotide sequence: ggaaaactatgcctggggccgacgctct-gcccggctgctgccgctgaggaaagc-cgggacgcggagccccgccgagagcttctttgctcc ggacgcccctggacgtg-gcgggcagzcgcgagggtaaccaccatgatcccctgggtgctcctggcct gtgccctcccctgtgctgctgac ccactgcttggcgcctttgctcgcagg-gacttccggaaaggctcccctcaactg-gtctgcagcctgcctggcccccagggcccacccggcc ccccaggagc-cccagggccctcaggaatgatgggacgaatgggctttcctggcaaagacg gccaagatggacacgacggcgaccgggg ggacagcggagaggaaggtc-cacctggccggacaggtaaccggg-gaaagccaggaccaaagggcaaagccggggccattgggcggg ctggc-cccgtggccccaagggggtcaacggtacccccgggaagcatggcac accaggcaagaaggggcccaagggcaagaaaggg gagccaggcctcccag-gcccctgcagctgtggcagtggccalac-caagtcagctttctcggtggcagtgaccaagagctacccacgggag cggctgc-ccatcaagtttgacaagattctgatgaacgagggtggccactacaatgctt ccagcggcaagttcgtctgcggcgtgcctgggat ctactacttcacctacgacat-cacgctggccaac aagcacctggccatcggcctggtgca-caacggccagtaccgcatccggacctttgatg ccaacaccggcaaccacgat-gtggcctcaggctccaccatcctggctctcaagcagggtgacgaagtttgg ctgcagatcttctactcagag cagaacgggctcttctatgaccct-tactggacagacagcctctttacgggct-tcctaatctatgccgaccaggatgaccccaacgaggtatag acatgccacggcg-gtcctccaggcagggaacaagcttctggacttgggcftacagagcaagac cccacaactgtaggctgggggtgggg ggtcgagtgagcggttctagcctcag-gctcacctcctccgcctctttttttccccttcattaaatccaaacctttttattca (SEQ ID NO:117) encodes the protein Acrp30R1L comprising the amino acid sequence: MIPWVLLACALPCAADPLLGA-FARRDFRKGSPQLVCSLPGPQGPPGPPGAPGPSGM MGRMGFPGKDGQDGHDGDRGDSGEEGP-PGRTGNRGKPGPKGKAGAIGRAGPRGPKGVN GTPGKHGTPGKKGPKGKKGEPGLPGPC-SCGSGHTKSAYSVAVTKSYPREPIPIKFDMLMN EGGHYNASSGKFVCGVPGIYYFTYDIT-LANKHLAJGLVHNGQYRIRTFDANTGNHDVASGS TILALKQGDEVWLQIFYSEQNGLFYDPY-WTDSLFTGFLIYADQDDPNEV (SEQ ID NO:118).

Accordingly, it will be appreciated that all characteristics and uses of polypeptides of the aforesaid Acrp30R1 amino acid sequence described throughout the present application also pertain to the polypeptides encoded by the nucleic acids included in the aforesaid Acrp30R1 nucleotide sequence. Also preferred are fragments having a biological activity as described therein and the polynucleotides encoding the fragments.

Acrp30R1 is comprised of at least three regions including:

1. an N-terminal putative signal sequence about from amino acids 1-20;
2. a unique region about from amino acids 21-39;
3. a collagen-like region about from amino acids 40-141; and
4. a globular region of C1q homology about from amino acids 149-285.

Acrp30R1L is comprised of several notable putative sites fot proteolytic cleavage including:

1. collagenase matrix metalloproteinase -1 (MMP-1) between amino acids 46-47;
2. plasmin between amino acids 125-126, 126-127, 131-132, and 132-133; and
3. precerebellin processing protease between amino acids 133-134.

The cDNA of Accession No. AAZ45688 comprising the nucleotide sequence gaattcggcacgagggccgcgaggg-laaccaccatgatcccctgggtgctc-ctggcctgtgccctcccctgtgctgctgacccactgcttgg cgcctttgctcg-cagggacttccggaaaggctcccctcaactggtctgcagcctgcctggcccc cagggcctacccggccccccaggagc cccagggccctcaggaatgatgggac-gaatgggctttcctggcaaagacggc-caagatggacacgacggcgaccggggggacagcgg agaggaaggtccac-ctggccggacagtgaccaagagctacccacgggagcggctgcccatcaa gtttgacaagattctgatgaacgagg gtggccactacaatgcttccagcg-gcaagttcgtctgcggcgtgcctgg-gatctactacttcacctacgacatcacgctggccaacaagcac ctggccatcggc-ctggtgcacaacggccagtaccgcatccggacctttgatgccaacaccggca accacgatgtggcctcaggctccacc atcctggctctcaagcagggtgac-gaagtttggctgcagatcttctactca-gagcagaacgggctcttctatgacccttactggacagacagc ctctttacgggct-tcctaatctatgccgaccaggatgaccccaacgaggtatagacatgccacgg cggtcctccaggcagggaacaagcttc tggacttgggcttacagagcaagac-cccacaa ctgtaggctgggggtggggggtcgagt-gagcggtctagcctcaggctcacctcctct gcctcttttttccccttcattaaatc-caaaccttttattcaaaaaaaaaaaaaaaaaa gatgcggccg (SEQ ID NO:119) encodes the protein Acrp30R1 comprising the amino acid sequence MIPWVLLACALPCAADPLLGA-FARRDFRKGSPQLVCSLPGPQGPPGPPGAPGPSGMM GRMGFPGKDGQDGHDGDRGDSGEEGP-PGRTVTKSYPRERLPIKFDKILMNEGGHYNASSGK FVCGVPGIYYFTYDITLANKHLAIGLVH-NGQYRIRTFDANTGNHDVASGSTLLALKQGDEVW LQIFYSEQNGLFYDPYWTDSLFTGFLIYADQDDPNEV (SEQ ID NO:120).

Accordingly, it will be appreciated that all characteristics and uses of polypeptides of the aforesaid Acrp30R1 amino acid sequence described throughout the present application also pertain to the polypeptides encoded by the nucleic acids included in the aforesaid Acrp30R1 nucleotide sequence. Also preferred are fragments having a biological activity as described therein and the polynucleotides encoding the fragments.

1. an N-terminal-putative signal sequence about from amino acids 1-20;
2. a unique region about from amino acids 21-39;
3. a collagen-like region about from amino acids 40-87; and
4. a globular region of C1q homology about from amino acids 88-217.

Acrp30R1 retains the putative site for MMP-1 cleavage present in Acrp30R1L but lacks the putative sites in Acrp30R1L for cleavage by plasmin and precerebellin processing protease.

Acrp30R1L and Acrp30R1 are related proteins resulting from differential splicing of a single gene. Acrp30R1L and Acrp30R1 are comprised of a collagen domain and a C1q homology domain. Acrp30R1 lacks an internal 68 amino acid segment present in Acrp30R1L. The N-terminal fragments of Acrp30R1L and Acrp30R1 generated in vivo by proteolytic cleavage of the full-length protein have unexpected and novel function as described below.

Chemokines are chemotactic cytokines that signal through G protein-coupled receptors (GPCR). Secondary lymphoid-tissue chemokine (SLC) is a polypeptide of 134 amino acids including a putative signal sequence of 23 amino acids (Nagira, M et al., J Biol Chem 272:19518-24 (1997) which disclosure is hereby incorporated by reference in its entirety). SLC is highly expressed by high endothelial venules, specialized vessels involved in the homing of lymphocytes from the blood into lymph nodes and Peyer's patches (Murphy, P M et al., Pharmacological Reviews 52:145-176 (2000); Dieu-Nosjean, M C et al., J Leukoc Biol 66:252-62 (1999) which disclosures are hereby incorporated by reference in their entirety). SLC is chemotactic for T cells, B cells, and mature dendritic cells. SLC functions as an important mediator of physiological lymphocyte recirculation in vivo (Gunn, M D et al, Proc Natl Acad Sci USA 95:258-63 (1998); Gunn, M D et al., J Exp Med 189:451-60 (1999) which disclosures are hereby incorporated by reference in their entirety). Recently it was shown that neurodegenerative stress induces neuronal expression of SLC and that SLC acts on microglia (Biber, K et al., Glia 34:121-33 (2001) which disclosure is hereby incorporated by reference in its entirety).

SLC binds to chemokine receptor CCR7 (Yoshida, R et al., J Biol Chem 273:7118-22 (1998) which disclosure is hereby incorporated by reference in its entirety). EBI1-ligand chemokine (ELC) also binds to CCR7. Recently it was shown that SLC also binds to the recently identified chemokine receptor CCR10 (Gosling, J et al., J Immunol 164:2851-6 (2000) which disclosure is hereby incorporated by reference in its entirety). SLC and ELC bind competitively and only to CCR7 and CCR10.

SLC has been implicated in chronic inflammation, including rheumatoid arthritis (Patel, D D et al., Clin Immunol 99:43-52 (2001) which disclosure is hereby incorporated by reference in its entirety) and prediabetic NOD mice (Hjelmstrom, P et al., Am J Pathol 156:1133-8 (2000) which disclosure is hereby incorporated by reference in its entirety). SLC (and ELC) enhance the replication of HIV-1 in secondary lymphoid tissues (Nagira, M et al., Virology 264:422-6 (1999) which disclosure is hereby incorporated by reference in its entirety). SLC has been shown to suppress proliferation of myeloid progenitor cells (Kim, C H et al., J Leukoc Biol 66:455-61 (1999) which disclosure is hereby incorporated by reference in its entirety). ELC (but not SLC) has been implicated in human atherosclerosis (Reape, T J et al., Am J Pathol 154:365-74 (1999) which disclosure is hereby incorporated by reference in its entirety).

SLC and ELC have been found to facilitate anti-tumor responses in vivo. SLC was found to enhance the anti-tumor response in several mouse models (Kirk, C J et al., Cancer Res 61:2062-70 (2001); Nomura, T et al., Int J Cancer 91:597-606 (2001); Sharma, S et al., J Immunol 164:4558-63 (2000) which disclosures are hereby incorporated by reference in their entirety). ELC was found to mediate tumor rejection of murine breast cancer cells (Braun, S E et al., J Immunol 164:4025-31 (2000) which disclosure is hereby incorporated by reference in its entirety).

Acrp30R1L and Acrp30R1 are characterized by an amino acid motif that is otherwise specific for chemokine SLC, as determined by BLAST analysis of the public protein database. The specificity of this motif for SLC extends across species. The motif, encompassing amino acids 21 to 46 of Acrp30R1L and Acrp30R1 (and therefore N-terminal to the putative protease cleavage sites within Acrp30R1L and Acrp30R1) is: RxxRKxxPxLxCSxP (SEQ ID NO:121) (where "x" is an unassigned amino acid). This specific motif is conserved between human (Accession Nos. AAY12316, 000585, AAG03773, AAW87589), mouse (009006, AAG45834) and pig (AAW50886) SLC (encompassing amino acids 46 to 60 of SLC). This motif is inferred to be important for SLC function, namely for binding to chemokine receptors CCR7 and CCR10 and, as a corollary, for its competitive binding with chemokine ELC to said receptors. N-terminal polypeptide fragments of Acrp30R1L and Acrp30OR1 comprising said motif non-productively bind to CCR7 and CCR10 and in so doing antagonize SLC and ELC function through CCR7 and CCR10.

Thus, the invention is drawn to Acrp30R1L and Acrp30R1 polypeptide fragments, polynucleotides encoding said Acrp30R1L and Acrp30R1 polypeptide fragments, vectors comprising said Acrp30R1L and Acrp30R1 polynucleotides, and cells recombinant for said Acrp30R1L and Acrp30R1 polynucleotides, as well as to pharmaceutical and physiologically acceptable compositions comprising said Acrp30R1L and Acrp30R1 polypeptide fragments and methods of administering said Acrp30R1L and Acrp30R1 pharmaceutical and physiologically acceptable compositions in order to reduce chronic inflammation, reduce atheriosclerosis, reduce HIV replication in secondary lymphoid tissue, increase myelopoiesis, or treat SLC- or ELC-related diseases or disorders. Assays for identifying antagonists of said SLC- or ELC-related activity are also part of the invention.

In a first aspect, the invention features a purified, isolated, or recombinant Acrp30R1L or Acrp30R1 polypeptide fragment that that has significantly greater activity than a full-length Acrp30R1L or Acrp30R1 polypeptide, wherein said activity is selected from but not restricted to antagonism of SLC function or antagonism of ELC function. In preferred embodiments, Acrp30R1L polypeptide fragments having unexpected activity are selected from amino acids 21-46, 21-47, 21-48, 21-49, 21-50, 21-51, 21-52, 21-53, 21-54, 21-55, 21-56, 21-57, 21-58, 21-59, 21-60, 21-61, 21-62, 21-63, 21-64, 21-65, 21-66, 21-67, 21-68, 21-69, 21-70, 21-21-71, 21-73, 21-74, 21-75, 21-76, 21-77, 21-78, 21-79, 21-80, 21-81, 21-82, 21-83, 21-84, 21-85, 21-21-87, 21-88, 21-89, 21-90, 21-91, 21-92, 21-93, 21-94, 21-95, 21-96, 21-97, 21-98, 21-99, 21-100, 21-101, 21-102, 21-103, 21-104, 21-105, 21-106, 21-107, 21-108, 21-109, 21-110, 21-111, 21-112, 21-113, 21-114, 21-115, 21-116, 21-117, 21-118, 21-119, 21-120, 21-121, 21-122, 21-123, 21-124, 21-125, 21-126, 21-127, 21-128, 21-129, 21-130, 21-131, 21-132, or 21-133 of aforesaid Acrp30R1L amino acid sequence and wherein amino acid 21 is taken to be understood to denote the N-terminal amino acid of full-length mature Acrp30R1L polypeptide lacking the signal peptide.

In other preferred embodiments, Acrp30R1 polypeptide fragments having unexpected activity are selected from amino acids 21-46, 21-47, 2148, 21-49, 21-50, 21-51, 21-52, 21-53, 21-54, 21-55, 21-56, 21-57, 21-58, 21-59, 21-60, 21-61, 21-62, 21-63, 21-64, 21-65, 21-66, 21-67, 21-68, 21-69, 21-70, 21-71, 21-72, 21-73, 21-74, 21-75, 21-76, 21-77, 21-78, 21-79, 21-80, 21-81, 21-82, 21-83, 21-84, 21-85, 21-86, or 21-87 of aforesaid Acrp30R1 amino acid sequence and wherein amino acid 21 is taken to be understood to denote the N-terminal amino acid of full-length mature Acrp30R1 polypeptide lacking the signal peptide.

In yet other preferred embodiments, Acrp30R1L polypeptide fragments having unexpected activity are selected from amino acids 21-46, 21-125, 21-126, 21-131, 21-132, and 21-133 of aforesaid Acrp30R1L amino acid sequence and wherein amino acid 21 is taken to be understood to denote the N-terminal amino acid of full-length mature Acrp30R1L polypeptide. In still other preferred embodiments, Acrp30R1 polypeptide fragments having unexpected activity are selected from amino acids 21-46 and 21-87 of aforesaid Acrp30R1 amino acid sequence and wherein amino acid 21 is taken to be understood to denote the N-terminal amino acid of full-length mature Acrp30R1 polypeptide.

In other further preferred embodiments, said polypeptide fragment comprises an amino acid sequence at least 70%, 75%, 80%, 85%, 90%, 91%, 92%, 93%, 94%, 95%, 96%, 97%, 98%, or 99% identical to the corresponding consecutive amino acids of aforesaid Acrp30R1L amino acid sequence or aforesaid Acrp30R1 amino acid sequence.

In other preferred embodiments, said Acrp30R1L polypeptide fragments are made by recombinant means or by proteolytic cleavage of full-length mature Acrp30R1L polypeptide. In other preferred embodiments, said Acrp30R1 polypeptide fragments are made by recombinant means or by proteolytic cleavage of full-length mature Acrp30R1 polypeptide lacking the signal peptide.

Particularly preferred proteolytic fragment of full-length mature Acrp30R1L polypeptide lacking the signal peptide is about amino acids 2146 made by collagenase cleavage of aforesaid Acrp30R1L amino acid sequence at about position 46 and wherein amino acid 21 is taken to be understood to denote the N-terminal amino acid of full-length mature Acrp30R1L polypeptide lacking the signal peptide. Other particularly preferred proteolytic fragment of full-length mature Acrp30R1L polypeptide lacking the signal peptide is about amino acids 2146 made by MMP-1 cleavage of aforesaid Acrp30R1L amino acid sequence at about position 46 and wherein amino acid 21 is taken to be understood to denote the N-terminal amino acid of full-length mature Acrp30R1L polypeptide lacking the signal peptide. Other particularly preferred proteolytic fragment of full-length mature Acrp30R1L polypeptide lacking the signal peptide is about amino acids 21-125 made by plasmin cleavage of aforesaid Acrp30R1L amino acid sequence at about position 125 and wherein amino acid 21 is taken to be understood to denote the N-terminal amino acid of full-length mature Acrp30R1L polypeptide lacking the signal peptide. Other particularly preferred proteolytic fragment of full-length mature Acrp30R1L polypeptide lacking the signal peptide is about amino acids 21-126 made by plasmin cleavage of aforesaid Acrp30R1L amino acid sequence at about position 126 and wherein amino acid 21 is taken to be understood to denote the N-terminal amino acid of full-length mature Acrp30R1L polypeptide lacking the signal peptide. Other particularly preferred is proteolytic fragment of full-length mature Acrp30R1L polypeptide lacking the signal peptide is about amino acids 21-131 made by plasmin cleavage of aforesaid Acrp30R1L amino acid sequence at about position 131. Other particularly preferred proteolytic fragment of full-length mature Acrp30R1L polypeptide lacking the signal peptide is about amino acids 21-132 made by plasmin cleavage of aforesaid Acrp30R1L amino acid sequence at about position 132 and wherein amino acid 21 is taken to be understood to denote the N-terminal amino acid of full-length mature Acrp30R1L polypeptide lacking the signal peptide. Other particularly preferred proteolytic fragment of full-length mature Acrp30R1L polypeptide lacking the signal peptide is about amino acids 21-133 made by precerebellin processing protease cleavage of aforesaid Acrp30R1L amino acid sequence at about position 133 and wherein amino acid 21 is taken to be understood to denote the N-terminal amino acid of full-length mature Acrp30R1L polypeptide lacking the signal peptide.

Particularly preferred proteolytic fragment of full-length mature Acrp30R1 polypeptide lacking the signal peptide is about amino acids 2146 made by collagenase cleavage of aforesaid Acrp30R1 amino acid sequence at about position 46 and wherein amino acid 21 is taken to be understood to denote the N-terminal amino acid of full-length mature Acrp30R1 polypeptide lacking the signal peptide. Other particularly preferred proteolytic fragment of full-length mature Acrp30R1 polypeptide lacking the signal peptide is about amino acids 21-46 made by MMP-1 cleavage of aforesaid Acrp30R1 amino acid sequence at about position 46 and wherein amino acid 21 is taken to be understood to denote the N-terminal amino acid of full-length mature Acrp30R1 polypeptide lacking the signal peptide.

In a second aspect, the invention features a pharmaceutical or physiologically acceptable composition comprising, consisting essentially of, or consisting of, said Acrp30R1L or Acrp30R1 polypeptide fragment described in the first aspect and, alternatively, a pharmaceutical or physiologically acceptable diluent.

In a third aspect, the invention features a method of preventing or treating an immune-related disorder comprising providing or administering to an individual in need of such treatment said pharmaceutical or physiologically acceptable composition described in the second aspect. Preferably, said immune-related disorder is selected from but not restricted to allograft rejection or delayed type hypersensitivity.

In a fourth aspect, the invention features a method of preventing or treating atheriosclerosis comprising providing or administering to an individual in need of such treatment said pharmaceutical or physiologically acceptable composition described in the second aspect.

In a fifth aspect, the invention features a method of preventing or treating the inflammation associated with ischemic neurodegeneration in brain tissue comprising providing or administering to an individual in need of such treatment said pharmaceutical or physiologically acceptable composition described in the second aspect.

In a sixth aspect, the invention features a method of preventing or treating the inflammation associated with stroke comprising providing or administering to an individual in need of such treatment said pharmaceutical or physiologically acceptable composition described in the second aspect.

In a seventh aspect, the invention features a method of preventing or treating the inflammation associated with myocardial infarction comprising providing or administering to an individual in need of such treatment said pharmaceutical or physiologically acceptable composition described in the second aspect.

In an eighth aspect, the invention features a method of preventing or treating the inflammation associated with reperfusion injury comprising providing or administering to an individual in need of such treatment said pharmaceutical or physiologically acceptable composition described in the second aspect.

In a ninth aspect, the invention features a method of preventing or treating HIV infection comprising providing or administering to an individual in need of such treatment said pharmaceutical or physiologically acceptable composition described in the second aspect.

In a tenth aspect, the invention features a method of preventing or treating an inflammation-related disorder comprising providing or administering to an individual in need of such treatment said pharmaceutical or physiologically acceptable composition described in the second aspect. Preferably, said inflammation-related disorder is selected from but not restricted to rheumatoid arthritis, inflammatory bowel disease, insulin dependent diabetes mellitus (Type 1 diabetes), systemic lupus erythematosus, psoriasis, allergic asthma, or septic shock.

In an eleventh aspect, the invention features a method of facilitating engraftment and expansion of infused hematopoietic stem cells or myeloid progenitor cells comprising providing or administering to an individual in need of such treatment said pharmaceutical or physiologically acceptable composition described in the second aspect.

In a twelfth aspect, the invention features a method of facilitating engraftment and expansion within NOD/scid mice of infused human hematopoietic stem cells or myeloid progenitor cells related to the preconditioning regimen comprising a xenogeneic in vivo model of human lymphoid and myeloid leukemia (Dialynas, D P et al., Blood 97:3218-25 (2001) which disclosure is hereby incorporated by reference in its entirety).

In a thirteenth aspect, the invention features a method of using said Acrp30R1L or Acrp30R1 polypeptide fragment described in the first aspect in in vitro cell migration assays as an internal control for intact CCR7 or CCR10 function.

The invention further features a method of using said Acrp30R1L or Acrp30R1 polypeptide fragment described in the first aspect in in vitro cell migration assays as an internal control for an intact T cell, B cell, or mature dendritic cell chemotactic response (Patel, D D et al., Clin Immunol 99:43-52 (2001) which disclosure is hereby incorporated by reference in its entirety).

In a fourteenth aspect, the invention provides for an antibody that specifically binds said preferred polypeptide fragment of mature Acrp30R1L lacking the signal peptide but not to full-length mature Acrp30R1L polypeptide lacking the signal peptide. Further preferred is said antibody that recognizes a non-conformational or conformational epitope of said preferred polypeptide fragment of mature Acrp30R1L lacking the signal peptide. Further preferred is said antibody that neutralizes the capacity of said preferred polypeptide fragment of mature Acrp30R1L lacking the signal peptide to antagonize SLC or ELC chemokine function.

Further preferred is a method wherein a mouse is immunized with said preferred polypeptide fragment of mature Acrp30R1L lacking the signal peptide. Further preferred is a method wherein monoclonal antibodies from said mouse are screened for binding to said preferred polypeptide fragment of mature Acrp30R1L lacking the signal peptide but not to full-length mature Acrp30R1L polypeptide lacking the signal peptide. Further preferred is a method wherein monoclonal antibodies derived from said mouse are screened by enzyme-linked immunosorbent assay (ELISA) for binding to said preferred polypeptide fragment of mature Acrp30R1L but not to mature Acrp30R1L polypeptide lacking the signal peptide. Further preferred is a method wherein said antibody is screened for the capacity to sterically or allosterically neutralize the capacity of said preferred polypeptide fragment of mature Acrp30R1L lacking the signal peptide to antagonize SLC or ELC chemokine function. Further preferred is a method of humanizing said monoclonal antibody. Methods of generating said monoclonal antibody and of establishing specificity by methods including ELISA are well known to those skilled in the art. Methods of screening said antibody for neutralization of the capacity of said preferred polypeptide fragment of mature Acrp30R1L lacking the signal peptide to antagonize SLC or ELC chemokine function are well known to those skilled in the art and include, but are not limited to: contacting the antibody with said preferred polypeptide fragment of mature Acrp30R1L lacking the signal peptide, incubation of said contacted Acrp30R1L polypeptide fragment with radiolabeled SLC or ELC in the presence of CCR7 or CCR10 chemokine receptor, and determination of whether said antibody contact blocks the capacity of said preferred polypeptide fragment of mature Acrp30R1L lacking the signal peptide to competed with SLC or ELC for binding to CCR7 or CCR10 (Gosling, J et al., J Immunol 164:2851-6 (2000) which disclosure is hereby incorporated by reference in its entirety). Methods of humanizing said monoclonal antibody are well known to those skilled in the art.

In a fifteenth aspect, the invention provides for an antibody that specifically binds said preferred polypeptide fragment of Acrp30R1 but not full-length mature Acrp30R1 polypeptide lacking the signal peptide. Further preferred is said antibody that recognizes a non-conformational or conformational epitope of said preferred polypeptide fragment of Acrp30R1. Further preferred is said antibody that neutralizes the capacity of said preferred Acrp30R1 polypeptide fragment to antagonize SLC or ELC chemokine function.

Further preferred is a method wherein a mouse is immunized with said preferred polypeptide fragment of mature Acrp30R1 lacking the signal peptide. Further preferred is a method wherein monoclonal antibodies from said mouse are screened for binding to said preferred polypeptide fragment of mature Acrp30R1 lacking the signal peptide but not to full-length mature Acrp30R1 polypeptide lacking the signal peptide. Further preferred is a method wherein monoclonal antibodies derived from said mouse are screened by enzyme-linked immunosorbent assay (ELISA) for binding to said preferred polypeptide fragment of mature Acrp30R1 but not to mature Acrp30R1 polypeptide lacking the signal peptide. Further preferred is a method wherein said antibody is screened for the capacity to sterically or allosterically neutralize the capacity of said preferred polypeptide fragment of mature Acrp30R1 lacking the signal peptide to antagonize SLC or ELC chemokine function. Further preferred is a method of humanizing said monoclonal antibody. Methods of generating said monoclonal antibody and of establishing specificity by methods including ELISA are well known to those skilled in the art. Methods of screening said antibody for neutralization of the capacity of said preferred polypeptide fragment of mature Acrp30R1 lacking the signal peptide to antagonize SLC or ELC chemokine function are well known to those skilled in the art and include, but are not limited to: contacting the antibody with said preferred polypeptide fragment of mature Acrp30R1 lacking the signal peptide, incubation of said contacted Acrp30R1 polypeptide fragment with radiolabeled SLC or ELC in the presence of CCR7 or CCR10 chemokine receptor, and determination of whether said antibody contact blocks the capacity of said preferred polypeptide fragment of mature Acrp30R1 lacking the signal peptide to competed with SLC or ELC for binding to CCR7 or CCR10 (Gosling, J et al., J Immunol 164:2851-6 (2000) which disclosure is hereby incorporated by reference in its entirety). Methods of humanizing said monoclonal antibody are well known to those skilled in the art.

In a sixteenth aspect, the invention features a pharmaceutical or physiologically acceptable composition comprising, consisting essentially of, or consisting of, said antibody of the fourteenth aspect directed to said preferred Acrp30R1L polypeptide fragment and, alternatively, a pharmaceutical or physiologically acceptable diluent.

In a seventeenth aspect, the invention features a pharmaceutical or physiologically acceptable composition comprising, consisting essentially of, or consisting of, said antibody of the fifteenth aspect directed to said preferred Acrp30R1 polypeptide fragment and, alternatively, a pharmaceutical or physiologically acceptable diluent.

In an eighteenth aspect, the invention features a method of using said antibody specific for said preferred Acrp30R1L or Acrp30R1 polypeptide fragment described in the fourteenth or sixteenth aspect in a method of measuring the amount of said Acrp30R1L or Acrp30R1 polypeptide fragment in a clinical sample for diagnosis of immune dysfunction. Preferably, said clinical sample is selected from the group consisting of blood, serum, plasma, urine, and saliva. Preferably, said immune dysfunction is selected from but not restricted to recurrent infection, innate immunodeficiency, or acquired immunodeficiency. Elevated levels of said Acrp30R1L or Acrp30R1 polypeptide fragment are expected to be contributory to said immune dysfunction.

In a nineteenth aspect, the invention features a method of using said antibody specific for said preferred Acrp30R1L or Acrp30R1 polypeptide fragment described in the fourteenth or sixteenth aspect in a method of measuring the amount of said Acrp30R1L or Acrp30R1 polypeptide fragment in a clinical sample for cancer stratification. Preferably, said clinical sample is selected from but not restricted to blood, serum, plasma, urine, and saliva. Preferably, said cancer is selected from but not restricted to melanoma, squamous cell carcinoma of the skin, breast carcinoma, lung small-cell carcinoma, colon carcinoma, Hodgkin's lymphoma, non-Hodgkin's lymphoma, prostatic carcinoma, pancreatic carcinoma, osteosarcoma, uterine carcinoma, ovarian carcinoma, chondrosarcoma, endometrial cancer, testicular carcinoma, renal carcinoma, hepatic carcinoma, lung non-small-cell carcinoma, T cell acute lymphoblastic leukemia, B cell acute lymphoblastic leukemia, acute myeloid leukemia, chronic lymphocytic leukemia, or multiple myeloma. Elevated levels of said Acrp30R1L or Acrp30R1 are expected to be contributory to an impaired anti-tumor response.

In a twentieth aspect, the invention features a method of treating cancer characterized by diagnostically determined elevated level of said preferred Acrp30R1L or Acrp30R1 polypeptide fragment comprising providing or administering to an individual in need of such treatment said pharmaceutical or physiologically acceptable composition described in the sixteenth or seventeenth aspect wherein the antibody comprising said composition neutralizes the capacity of said preferred Acrp30R1L or Acrp30R1 polypeptide fragment to antagonize SLC or ELC chemokine function. Said neutralization is expected to facilitate the in vivo anti-tumor response. Preferably, said cancer is selected from but not restricted to melanoma, squamous cell carcinoma of the skin, breast carcinoma, lung small-cell carcinoma, colon carcinoma, Hodgkin's lymphoma, non-Hodgkin's lymphoma, prostatic carcinoma, pancreatic carcinoma, osteosarcoma, uterine carcinoma, ovarian carcinoma, chondrosarcoma, endometrial cancer, testicular carcinoma, renal carcinoma, hepatic carcinoma, lung non-small-cell carcinoma, T cell acute lymphoblastic leukemia, B cell acute lymphoblastic leukemia, acute myeloid leukemia, chronic lymphocytic leukemia, or multiple myeloma.

In a twenty-first aspect, the invention provides for a non-antibody compound that specifically binds said preferred polypeptide fragment of mature Acrp30R1L lacking the signal peptide but not to full-length mature Acrp30R1L polypeptide lacking the signal peptide. Preferred said compound is selected from but not restricted to small molecular weight organic or inorganic compound, protein, peptide, carbohydrate, or lipid. Further preferred is said antibody that recognizes a non-conformational or conformational epitope of said preferred polypeptide fragment of mature Acrp30R1L lacking the signal peptide. Further preferred is said antibody that neutralizes the capacity of said preferred polypeptide fragment of mature Acrp30R1L lacking the signal peptide to antagonize SLC or ELC chemokine function.

Further preferred are methods of screening for one or more compounds capable of neutralizing the capacity of said preferred polypeptide fragment of mature Acrp30R1L lacking the signal peptide to antagonize SLC or ELC chemokine function. Said methods are well known to those skilled in the art and include, but are not limited to: contacting the compound with said preferred polypeptide fragment of mature Acrp30R1L lacking the signal peptide, incubation of said contacted Acrp30R1L polypeptide fragment with radiolabeled SLC or ELC in the presence of CCR7 or CCR10 chemokine receptor, and determination of whether said contact with compound blocks the capacity of said preferred polypeptide fragment of mature Acrp30R1L lacking the signal peptide to competed with SLC or ELC for binding to CCR7 or CCR10 (Gosling, J et al., J Immunol 164:2851-6 (2000) which disclosure is hereby incorporated by reference in its entirety).

In a twenty-second aspect, the invention provides for a non-antibody compound that specifically binds said preferred polypeptide fragment of mature Acrp30R1 lacking the signal peptide but not to full-length mature Acrp30R1 polypeptide lacking the signal peptide. Preferred said compound is selected from but not restricted to small molecular weight organic or inorganic compound, protein, peptide, carbohydrate, or lipid. Further preferred is said antibody that recognizes a non-conformational or conformational epitope of said preferred polypeptide fragment of mature Acrp30R1 lacking the signal peptide. Further preferred is said antibody that neutralizes the capacity of said preferred polypeptide fragment of mature Acrp30R1 lacking the signal peptide to antagonize SLC or ELC chemokine function.

Further preferred are methods of screening for one or more compounds capable of neutralizing the capacity of said preferred polypeptide fragment of mature Acrp30R1 lacking the signal peptide to antagonize SLC or ELC chemokine function. Said methods are well known to those skilled in the art and include, but are not limited to: contacting the compound with said preferred polypeptide fragment of mature Acrp30R1 lacking the signal peptide, incubation of said contacted Acrp30R1L polypeptide fragment with radiolabeled SLC or ELC in the presence of CCR7 or CCR10 chemokine receptor, and determination of whether said contact with compound blocks the capacity of said preferred polypeptide fragment of mature Acrp30R1L lacking the signal peptide to competed with SLC or ELC for binding to CCR7 or CCR10 (Gosling, J et al., J Immunol 164:2851-6 (2000) which disclosure is hereby incorporated by reference in its entirety).

In a twenty-third aspect, the invention features a pharmaceutical or physiologically acceptable composition comprising, consisting essentially of, or consisting of, said compound of the twenty-first aspect directed to said preferred Acrp30R1L polypeptide fragment and, alternatively, a pharmaceutical or physiologically acceptable diluent.

In a twenty-fourth aspect, the invention features a pharmaceutical or physiologically acceptable composition comprising, consisting essentially of, or consisting of, said antibody of the twenty-second aspect directed to said preferred Acrp30R1 polypeptide fragment and, alternatively, a pharmaceutical or physiologically acceptable diluent.

In a twenty-fifth aspect, the invention features a method of treating cancer characterized by diagnostically determined elevated level of said preferred Acrp30R1L or Acrp30R1 polypeptide fragment comprising providing or administering to an individual in need of such treatment said pharmaceutical or physiologically acceptable composition described in the twenty-third or twenty-fourth aspect wherein the compound comprising said composition neutralizes the capacity of said preferred Acrp30R1L or Acrp30R1 polypeptide fragment to antagonize SLC or ELC chemokine function. Said neutralization is expected to facilitate the in vivo anti-tumor response. Preferably, said cancer is selected from but not restricted to melanoma, squamous cell carcinoma of the skin, breast carcinoma, lung small-cell carcinoma, colon carcinoma, Hodgkin's lymphoma, non-Hodgkin's lymphoma, prostatic carcinoma, pancreatic carcinoma, osteosarcoma, uterine carcinoma, ovarian carcinoma, chondrosarcoma, endometrial cancer, testicular carcinoma, renal carcinoma, hepatic carcinoma, lung non-small-cell carcinoma, T cell acute lymphoblastic leukemia, B cell acute lymphoblastic leukemia, acute myeloid leukemia, chronic lymphocytic leukemia, or multiple myeloma.

CRPF Polypeptides CRPF-1, CRPF-2A, CRPF-2B, CRPF-2C, and CRPF-3

CRPF polypeptide CRPF-1 comprises the amino acid sequence: SHHH (SEQ ID NO:122). CRPF polypeptide CRPF-2A comprises the amino acid sequence: AANSKVAFSAVRSTNH (SEQ ID NO:123). CRPF polypeptide CRPF-2B comprises the amino acid sequence: AANSKVAFSAVR (SEQ ID NO:124). CRPF polypeptide CRPF-2C comprises the amino acid sequence: STNH (SEQ ID NO:125). CRPF polypeptide CRPF-3 comprises the amino acid sequence: SGSAKVAFSATRSTNH (SEQ ID NO:126). Also preferred are polynucleotides encoding the CRPF polypeptides.

The CRPF polypeptides are related to cerebellin. The CRPF polypeptides have unexpected and novel function as described below.

Cerebellin is a 16 amino acid polypeptide liberated by specific proteolytic cleavage from a precursor polypeptide, precerebellin (Urade, Y et al., Proc Natl Acad Sci USA 88:1069-1073 (1991) which disclosure is hereby incorporated by reference in its entirety). Cerebellin is conserved in sequence from human to chicken. Cerebellin is highly expressed in cerebellum, weakly expressed in other areas of the brain, and possibly also expressed in adrenomedullary tissue (Satoh, F et al., Journal of Endocrinology 154:27-34 (1997) which disclosure is hereby incorporated by reference in its entirety). Cerebellin is also expressed by the tumor tissues of adrenal tumor, ganglioneuroblastoma, and neuroblastoma (Satoh, F et al., Journal of Endocrinology 154:27-34 (1997) which disclosure is hereby incorporated by reference in its entirety). Cerebellin elicits epinephrine and norepinephrine release by human adrenomedullary cells (Albertin, G et al., Neuropeptides 34:7-11 (2000) which disclosure is hereby incorporated by reference in its entirety). Norepinephrine has been shown to up-regulate expression of the proinflammatory cytokine interferon gamma by the Th1 subset of CD4+T lymphocytes (Swanson, M A et al., J Immunol 166:232-240 (2001) which disclosure is hereby incorporated by reference in its entirety). Interferon gamma plays an important role in the development of cytolytic T lymphocytes (CTL). Recently, a precerebellin-like protein was shown to be part of the acute phase response in rainbow trout (Gerwick, L et al., Developmental and Comparative Immunology 24:597-600 (2000) which disclosure is hereby incorporated by reference in its entirety).

The instant invention is based on the discovery that the CRPF polypeptides oppose the proinflammatory action of cerebellin.

Thus, the invention is drawn to CRPF polypeptides, polynucleotides encoding said CRPF polypeptides, vectors comprising said CRPF polynucleotides, and cells recombinant for said CRPF polynucleotides, as well as to pharmaceutical and physiologically acceptable compositions comprising said CRPF polypeptides and methods of administering said CRPF pharmaceutical and physiologically acceptable compositions in order to reduce inflammation or to treat inflammation-related disorders. Assays for identifying antagonists of CRPF polypeptide function are also part of the invention.

In a first aspect, the invention features purified, isolated, artificially synthesized, or recombinant CRPF polypeptide that has anti-inflammatory activity. In preferred embodiment, CRPF polypeptide is CRPF-1 polypeptide comprising the amino acid sequence: SHHH (SEQ ID NO:122). In other preferred embodiment, CRPF polypeptide is CRPF-2A polypeptide comprising the amino acid sequence: AANSKVAFSAVRSTNH (SEQ ID NO:123). In other preferred embodiment, CRPF polypeptide is CRPF-2B polypeptide comprising the amino acid sequence AANSKVAFSAVR (SEQ ID NO:124). In other preferred embodiment, CRPF polypeptide is CRPF-2C polypeptide comprising the amino acid sequence STNH (SEQ ID NO:125). In other preferred embodiment, CRPF polypeptide is CRPF-3 comprising the amino acid sequence SGSAKVAFSATRSTNH (SEQ ID NO:126).

In a second aspect, the invention features a pharmaceutical or physiologically acceptable composition comprising, consisting essentially of, or consisting of said CRPF polypeptides described in the first aspect and, alternatively, a pharmaceutical or physiologically acceptable diluent.

In a third aspect, the invention features a method of reducing inflammation comprising providing or administering to individuals in need of reducing inflammation said pharmaceutical or physiologically acceptable composition described in the second aspect. In preferred embodiment, said administration of said pharmaceutical or physiologically acceptable composition is systemic or local.

In a fourth aspect, the invention features a method of preventing or treating psoriasis comprising providing or administering to an individual in need of such treatment said pharmaceutical or physiologically acceptable composition described in the second aspect.

In a fifth aspect, the invention features a method of preventing or treating atherosclerosis comprising providing or administering to an individual in need of such treatment said pharmaceutical or physiologically acceptable composition described in the second aspect.

In a sixth aspect, the invention features a method of preventing or treating the inflammation associated with ischemic neurodegeneration in brain tissue comprising providing or administering to an individual in need of such treatment said pharmaceutical or physiologically acceptable composition described in the second aspect.

In a seventh aspect, the invention features a method of preventing or treating the inflammation associated with stroke comprising providing or administering to an individual in need of such treatment said pharmaceutical or physiologically acceptable composition described in the second aspect.

In an eighth aspect, the invention features a method of preventing or treating the inflammation associated with myocardial infarction comprising providing or administering to an individual in need of such treatment said pharmaceutical or physiologically acceptable composition described in the second aspect.

In a ninth aspect, the invention features a method of preventing or treating the inflammation associated with reperfusion injury comprising providing or administering to an individual in need of such treatment said pharmaceutical or physiologically acceptable composition described in the second aspect.

In a tenth aspect, the invention features a method of preventing or treating the inflammation associated with rheumatoid arthritis comprising providing or administering to an individual in need of such treatment said pharmaceutical or physiologically acceptable composition described in the second aspect.

In an eleventh aspect, the invention features a method of preventing or treating the inflammation associated with inflammatory bowel disease comprising providing or administering to an individual in need of such treatment said pharmaceutical or physiologically acceptable composition described in the second aspect.

In a twelfth aspect, the invention features a method of preventing or treating the inflammation associated with systemic lupus erythematosus comprising providing or administering to an individual in need of such treatment said pharmaceutical or physiologically acceptable composition described in the second aspect.

In a thirteenth aspect, the invention features a method of preventing or treating the inflammation associated with allergic asthma comprising providing or administering to an individual in need of such treatment said pharmaceutical or physiologically acceptable composition described in the second aspect.

In a fourteenth aspect, the invention features a method of preventing or treating the inflammation associated with insulin dependent diabetes mellitus (Type 1 diabetes) comprising providing or administering to an individual in need of such treatment said pharmaceutical or physiologically acceptable composition described in the second aspect.

In a fifteenth aspect, the invention features a method of preventing or treating the inflammation associated with septic shock comprising providing or administering to an individual in need of such treatment said pharmaceutical or physiologically acceptable composition described in the second aspect.

In a sixteenth aspect, the invention features a method of preventing or treating the inflammation associated with multiple sclerosis comprising providing or administering to an individual in need of such treatment said pharmaceutical or physiologically acceptable composition described in the second aspect.

In a seventeenth aspect, the invention features a method of preventing or treating the inflammation associated with elevated cerebellin level in blood or locally at a site of inflammation or other disorder described herein comprising providing or administering to an individual in need of such treatment said pharmaceutical or physiologically acceptable composition described in the second aspect. Preferably the magnitude of said elevated cerebellin level is at least 10%, 20%, 30%, 35%, 40%, 50%, 75%, 100%, or 500%. Preferably, cerebellin level is elevated at the site where said CRPF polypeptide is administered.

In an eighteenth aspect, the invention features a method of suppressing an in vivo Th1 immune response in an animal model of inflammopathology or immune dysfunction comprising providing or administering to said animal said pharmaceutical or physiologically acceptable composition described in the second aspect. Preferably said animal is a mammal. Most preferably, said animal is a rodent.

In a nineteenth aspect, the invention provides for an antibody that specifically binds to said CRPF polypeptide described in the first aspect. Further preferred is said antibody that neutralizes the capacity of said CRPF polypeptide to reduce inflammation. Further preferred is said antibody that neutralizes the capacity of said CRPF polypeptide to bind to a ligand. Further preferred is said antibody that neutralizes the capacity of said CRPF polypeptide to bind to its receptor.

In a twentieth aspect, the invention features a pharmaceutical or physiologically acceptable composition comprising, consisting essentially of, or consisting of, said neutralizing antibody described in the nineteenth aspect specific for said CRPF polypeptide described in the first aspect and, alternatively, a pharmaceutical or physiologically acceptable diluent.

In a twenty-first aspect, the invention features a method of using said antibody described in the nineteenth aspect specific for said CRPF polypeptide described in the first aspect to measure the amount of said CRPF polypeptide in a clinical sample in order to diagnose or stratify an inflammation-related disorder. Preferably, said clinical sample is selected from the group consisting of blood, serum, plasma, urine, saliva, and lymphoid tissue. Preferably, said inflammation-related disorder is selected from but not restricted to those described herein. Reduced levels of said CRPF polypeptide are expected to be contributory to said inflammation-related disorder.

In a twenty-second aspect, the invention features a method of using said antibody described in the nineteenth aspect specific for said CRPF polypeptide described in the first aspect to measure the amount of said CRPF polypeptide in a clinical sample obtained from a cancer patient for the purpose of characterizing said cancer. Preferably, said clinical sample is selected from but not restricted to blood, serum, plasma, urine, saliva, and cancer tissue. Preferably, said method is selected from but not restricted to ELISA or immunohistochemistry. Preferably, said cancer is selected from but not restricted to adrenal tumor, ganglioneuroblastoma, neuroblastoma, melanoma, squamous cell carcinoma of the skin, breast carcinoma, lung small-cell carcinoma, colon carcinoma, Hodgkin's lymphoma, non-Hodgkin's lymphoma, prostatic carcinoma, pancreatic carcinoma, osteosarcoma, uterine carcinoma, ovarian carcinoma, chondrosarcoma, endometrial cancer, testicular carcinoma, renal carcinoma, hepatic carcinoma, lung non-small-cell carcinoma, T cell acute lymphoblastic leukemia, B cell acute lymphoblastic leukemia, acute myeloid leukemia, chronic lymphocytic leukemia, or multiple myeloma. Elevated levels of said CRPF polypeptide (for example released by the tumor cells) are expected to be contributory to an impaired anti-tumor response.

In a twenty-third aspect, the invention features a method of treating cancer characterized by elevated level of said CRPF polypeptide described in the first aspect comprising providing or administering to an individual in need of such treatment said pharmaceutical or physiologically acceptable composition described in the twentieth aspect. Neutralization of the capacity of said CRPF polypeptide suppress an inflammatory response is expected to facilitate the in vivo anti-tumor response. Preferably, said cancer is selected from but not restricted to adrenal tumor, ganglioneuroblastoma, neuroblastoma, melanoma, squamous cell carcinoma of the skin, breast carcinoma, lung small-cell carcinoma, colon carcinoma, Hodgkin's lymphoma, non-Hodgkin's lymphoma, prostatic carcinoma, pancreatic carcinoma, osteosarcoma, uterine carcinoma, ovarian carcinoma, chondrosarcoma, endometrial cancer, testicular carcinoma, renal carcinoma, hepatic carcinoma, lung non-small-cell carcinoma, T cell acute lymphoblastic leukemia, B cell acute lymphoblastic leukemia, acute myeloid leukemia, chronic lymphocytic leukemia, or multiple myeloma.

In a twenty-fourth aspect, the invention provides for a non-antibody compound that specifically binds said CRPF polypeptide described in the first aspect but not to unrelated polypeptide. Preferred said compound is selected from but not restricted to small molecular weight organic or inorganic compound, protein, peptide, carbohydrate, or lipid. Further preferred is said compound that neutralizes the capacity of said CRPF polypeptide to reduce inflammation.

Further preferred are methods of screening for one or more compounds capable of neutralizing the capacity of said CRPF polypeptide fragment to reduce inflammation. Said methods are well known to those skilled in the art and include, but are not limited to: administering to a mouse model of inflammopathology said CRPF polypeptide in the presence of said antibody; administering to said mouse model said CRPF polypeptide in the absence of said antibody; and determination of whether said antibody abrogates the capacity of said CRPF polypeptide to reduce inflammation in said mouse model.

In a twenty-fifth aspect, the invention features a pharmaceutical or physiologically acceptable composition comprising, consisting essentially of, or consisting of, said neutralizing compound of the twenty-fourth aspect and, alternatively, a pharmaceutical or physiologically acceptable diluent.

In a twenty-sixth aspect, the invention features a method of treating a cancer patient having elevated levels of said CRPF polypeptide described in the first aspect comprising providing or administering to an individual in need of such treatment said pharmaceutical or physiologically acceptable composition described in the twenty-fifth aspect. Preferably, methods for measuring the amount of said CRPF polypeptide fragment include but are not restricted to said methods described in the twenty-second aspect. Neutralization of the capacity of said CRPF polypeptide to suppress an inflammatory response is expected to facilitate the in vivo anti-tumor response. Preferably, said cancer is selected from but not restricted to adrenal tumor, ganglioneuroblastoma, neuroblastoma, melanoma, squamous cell carcinoma of the skin, breast carcinoma, lung small-cell carcinoma, colon carcinoma, Hodgkin's lymphoma, non-Hodgkin's lymphoma, prostatic carcinoma, pancreatic carcinoma, osteosarcoma, uterine carcinoma, ovarian carcinoma, chondrosarcoma, endometrial cancer, testicular carcinoma, renal carcinoma, hepatic carcinoma, lung non-small-cell carcinoma, T cell acute lymphoblastic leukemia, B cell acute lymphoblastic leukemia, acute myeloid leukemia, chronic lymphocytic leukemia, or multiple myeloma.

Uses of Antibodies

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of antigen-bearing substances, including the polypeptides of the present invention, in biological samples (See, e.g., Harlow et al., 1988). The antibodies may also be used in therapeutic compositions for killing cells expressing the protein or reducing the levels of the protein in the body.

The invention further relates to antibodies that act as agonists or antagonists of the polypeptides of the present invention. For example, the present invention includes antibodies that disrupt the receptor/ligand interactions with the polypeptides of the invention either partially or fully. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng et al., (1998) Blood. 92(6):1981-1988; Chen et al., (1998), Cancer Res. 58(16):3668-3678; Harrop et al., (1998), J. Immunol. 161(4):1786-1794; Zhu, et al. (1998), J. Res. 58(15):3209-3214; Yoon, et al. (1998), J. Immunol. 160(7):3170-3179; Prat et al., (1998), J. Cell. Sci. 111(Pt2):237-247; Pitard et al., (1997), J. Immunol. Methods. 205(2):177-190; Liautard et al., (1997), Cytokine. 9(4):233-241; Carlson et al., (1997), J. Biol. Chem. 272(17):11295-11301; Taryman, et al., (1995), Neuron. 14(4):755-762; Muller et al., (1998), Structure. 6(9):1153-1167; Bartunek et al., (1996), Cytokine. 8(1):14-20.

As discussed above, antibodies of the polypeptides of the invention can, in turn, be utilized to generate anti-idiotypic antibodies that "mimic" polypeptides of the invention using techniques well known to those skilled in the art (see, e.g. Greenspan and Bona (1989), FASEB J. 7(5):437-444 and Nissinoff, (1991), J. Immunol. 147(8): 2429-2438). For example, antibodies which bind to and competitively inhibit polypeptide multimerization or binding of a polypeptide of the invention to ligand can be used to generate anti-idiotypes that "mimic" the polypeptide multimerization or binding domain and, as a consequence, bind to and neutralize polypeptide or its ligand. Such neutralization anti-idiotypic antibodies can be used to bind a polypeptide of the invention or to bind its ligands/receptors, and thereby block its biological activity.

Immunoaffinity Chromatography

Antibodies prepared as described herein are coupled to a support. Preferably, the antibodies are monoclonal antibodies, but polyclonal antibodies may also be used. The support may be any of those typically employed in immunoaffinity chromatography, and the antibodies may be coupled to the support using any standard reagent. After coupling the antibody to the support, the support is contacted with a sample which contains a target polypeptide whose isolation, purification or enrichment is desired.

Thereafter, the support is washed with an appropriate wash solution, and the specifically bound target polypeptide is eluted from the support using the high pH or low pH elution solutions typically employed in immunoaffinity chromatography.

Expression of GENSET Gene Products

Evaluation of Expression Levels and Patterns of GENSET Polypeptide-encoding mRNAs The spatial and temporal expression patterns of GENSET polypeptide-encoding mRNAs, as well as their expression levels, may be determined using any suitable method.

In one embodiment, expression levels and patterns of GENSET polypeptide-encoding mRNAs is analyzed by solution hybridization with probes (see, e.g., WO 97/05277). Briefly, an RNA complementary to the mRNA of interest is labeled and derivatized with a capturable moiety, e.g., biotin. After hybridization in solution with mRNA isolated from cells or tissues of interest, unhybridized probe is removed by digestion, and the remaining, hybridized RNA is captured, e.g., on a microtitration plate, and quantified.

In another embodiment, the GENSET polypeptide-encoding cDNAs, or fragments thereof, may also be tagged with nucleotide sequences for the serial analysis of gene expression (SAGE) (see, e.g., UK Patent Application No. 2 305 241 A).

Quantitative analysis of GENSET gene expression may also be performed using arrays. For example, quantitative analysis of gene expression may be performed with GENSET polynucleotides, or fragments thereof in a complementary DNA microarray as described by Schena et al. (1995) Science 270:467-470 and Schena et al. (1996), PNAS, 93(20):10614-10619, Pietu et al, (1996) Genome Research 6:492-503) or using any other microarray technology. Briefly, GENSET polypeptide-encoding cDNAs or fragments thereof are arrayed onto slides, and the arrays are hybridized with probes derived from mRNA of cells or tissues of interest. Following washing, the arrays are scanned using a fluorescence laser scanning device fitted with a custom filter set. Accurate differential expression measurements are obtained by taking the average of the ratios of two independent hybridizations.

Alternatively, expression analysis of GENSET genes can be done through high density nucleotide arrays as described by Lockhart et al., (1996) Nature Biotechnology 14: 1675-1680 and Sosnowski, et al, (1997) PNAS 94:1119-1123. Oligonucleotides of 15-50 nucleotides corresponding to sequences of a GENSET polynucleotide or fragments thereof are synthesized directly on the chip or synthesized and then addressed to the chip. Labeled cDNA probes are synthesized from the appropriate mRNA population and then randomly fragmented to an average size of 50 to 100 nucleotides. The probes are then hybridized to the chip. After washing, the label is detected and quantified. Comparative analysis of the intensity of the signal originating from cDNA probes on the same target oligonucleotide in different cDNA samples indicates a differential expression of the GENSET polypeptide-encoding mRNA.

Uses of GENSET Gene Expression Data

Once the expression levels and patterns of a GENSET polypeptide-encoding mRNA has been determined, this information may be used to design GENSET gene specific markers for detection, identification, screening and diagnostic purposes as well as to design DNA constructs with an expression pattern similar to a GENSET gene expression pattern.

Detection of GENSET Polypeptide Expression and/or Biological Activity

The invention further relates to methods of detection of GENSET polypeptide expression and/or biological activity in a biological sample using the polynucleotide and polypeptide sequences described herein. Such methods can be used, for example, as a screen for normal or abnormal GENSET polypeptide expression and/or biological activity and, thus, can be used diagnostically.

Detection of GENSET Polypeptides

The invention further relates to methods of detection of GENSET polypeptides in a cell or sample. In certain embodiments, the presence of polypeptides in a cell or sample is detected indirectly, by detecting the presence of mRNA encoding the polypeptide. For example, a labeled polynucleotide probe can be used in a method to detect a GENSET polypeptide-encoding mRNA, wherein the presence of the mRNA is indicative of the expression of the GENSET polypeptide-encoding gene.

Consequently, the invention comprises methods for detecting the presence of a polynucleotide of the invention in a sample, the method comprising bringing into contact said sample and a nucleic acid probe or a plurality of nucleic acid probes which hybridize to the polynucleotide, and detecting the hybrid complex formed between said probe or said plurality of probes and said polynucleotide. In certain embodiments, the probe or probes are labeled or are immobilized on a substrate.

In another embodiment, the polynucleotide is detected using an amplification reaction, wherein the sample is contacted with amplification reaction reagents, an amplification reaction is performed to synthesize amplification products containing said region of said selected nucleotide sequence; and the amplification products are detected. In a preferred embodiment, when the polynucleotide to be amplified is a RNA molecule, preliminary reverse transcription and synthesis of a second cDNA strand are first performed in order to provide a DNA template to be amplified.

Alternatively, a method of detecting GENSET polypeptide expression in a test sample can be accomplished using any product which binds to a GENSET polypeptide of the present invention or portion thereof. Such products may be antibodies, binding fragments of antibodies, polypeptides able to bind specifically to GENSET polypeptides or fragments thereof, including GENSET polypeptide agonists and antagonists. Detection of specific binding to the antibody indicates the presence of a GENSET polypeptide in the sample (e.g., ELISA).

Consequently, the invention is also directed to a method for detecting specifically the presence of a GENSET polypeptide in a biological sample, said method comprising bringing into contact the biological sample with a product able to bind to a polypeptide of the invention or fragments thereof; allowing the product to bind to the polypeptide to form a complex; and detecting the complex. In a preferred embodiment, the product is an antibody, e.g., an antibody that is immobilized on a substrate.

The present invention also relates to kits that can be used in the detection of GENSET polypeptide-encoding gene expression products, e.g. containing a compound that specifically binds a GENSET polypeptide (e.g. binding proteins, antibodies or binding fragments thereof (e.g. F(ab')2 fragments) or a GENSET polypeptide-encoding mRNA (e.g. a complementary probe or primer), disposed within a container means. The kit can further comprise ancillary reagents, including buffers and the like.

Detection of GENSET Polypeptide Biological Activity

The invention further includes methods of detecting specifically a GENSET polypeptide biological activity, and to identify compounds capable of modulating the activity of a GENSET polypeptide. Assessing the GENSET polypeptide biological activity may be performed by the detection of a change in any cellular property associated with the GENSET polypeptide, using a variety of techniques, including those described herein. To identify modulators of the polypeptides, a control is preferably used. For example, a control sample includes all of the same reagents but lacks the compound or agent being assessed; it is treated in the same manner as the test sample.

The present invention also relates to kits that can be used in the detection of GENSET polypeptide biological activity, e.g., including substrates for GENSET polypeptides, GENSET-binding compounds, antibodies to GENSET polypeptides, etc., disposed within a container means. The kit can further comprise ancillary reagents, including buffers and the like.

Identification of a Specific Context of GENSET Polypeptide-Encoding Gene Expression When the expression pattern of a GENSET polypeptide-encoding mRNA shows that a GENSET polypeptide-encoding gene is specifically expressed in a given context, probes and primers specific for this gene as well as antibodies binding to the GENSET polypeptide-encoding polynucleotide may then be used as markers for the specific context. Examples of specific contexts are: specific expression in a given tissue/cell or tissue/cell type, expression at a given stage of development of a process such as embryo development or disease development, expression in response to a particular compound or drug, or specific expression in a given organelle. Such primers, probes, and antibodies are useful commercially to identify tissues/cells/organelles of unknown origin, for example, forensic samples, differentiated tumor tissue that has metastasized to foreign bodily sites, or to differentiate different tissue types in a tissue cross-section.

Determination of tissue/cell/organelle identity is based on methods that detect the presence or absence of the mRNA (or corresponding cDNA or protein) in a tissue/cell sample using methods well known in the art (e.g., hybridization, PCR based methods, immunoassays, immunochemistry, ELISA). Therefore, the invention encompasses uses of the polynucleotides, polypeptides, and antibodies of the invention as tissue markers.

Identification of Tissue Types or Cell Species by Means of Labeled Tissue Specific Antibodies Identification of specific tissues is accomplished by the visualization of tissue specific antigens by means of antibody preparations which are conjugated, directly (e.g., green fluorescent protein) or indirectly to a detectable marker. Selected labeled antibody species bind to their specific antigen binding partner in tissue sections, cell suspensions, or in extracts of soluble proteins from a tissue sample to provide a pattern for qualitative or semi-qualitative interpretation.

A. Immunohistochemical Techniques

Purified, high-titer antibodies, prepared as described above, are conjugated to a detectable marker, as described, for example, by Fudenberg, (1980) Chap. 26 in: Basic 503 Clinical Immunology, 3rd Ed. Lange, Los Altos, Calif. or Rose et al., (1980) Chap. 12 in: Methods in Immunodiagnosis, 2d Ed. John Wiley 503 Sons, New York.

Antibodies can be labeled using any suitable method, e.g. fluorescent labels, enzymes (e.g. horseradish peroxidase), ferritin (for detection using EM), or radiolabeling. In one embodiment, cryostat sections of the unknown tissue and known control are mounted and each slide covered with different dilutions of the antibody preparation. Following incubation, excess fluid is blotted away, and the marker detected. The antigen found in the tissues by the above procedure can be quantified by measuring the intensity of color or fluorescence on the tissue section, and calibrating that signal using appropriate standards.

B. Identification of Tissue Specific Soluble Proteins

The visualization of tissue specific proteins and identification of unknown tissues from that procedure is carried out using the labeled antibody reagents and detection strategy as described for immunohistochemistry; however the sample is prepared according to an electrophoretic technique to distribute the proteins extracted from the tissue in an orderly array on the basis of molecular weight for detection, e.g. by western blotting. See, e.g., Davis et al., Basic Methods in Molecular Biology, ed., Elsevier Press, NY (1986), Section 19-3.

Screening and Diagnosis of Abnormal GENSET Polypeptide Expression and/or Biological Activity Moreover, antibodies and/or primers or probes specific for GENSET polypeptide expression may also be used to identify abnormal GENSET polypeptide expression and/or biological activity, and subsequently to screen and/or diagnose disorders associated with abnormal GENSET polypeptide expression. For example, a particular disease may result from lack of expression, over-expression, or under-expression of a GENSET polypeptide-encoding mRNA. By comparing mRNA expression patterns and quantities in samples taken from healthy individuals with those from individuals suffering from a particular disorder, genes responsible for this disorder may be identified.

Screening for Specific Disorders

The present invention also relates to methods and uses of GENSET polypeptides for identifying individuals having elevated or reduced levels of GENSET polypeptides, which individuals are likely to benefit from therapies to suppress or enhance GENSET polypeptide-encoding gene expression, respectively. One example of such methods and uses comprises detecting the presence in a biological sample of a GENSET polypeptide-encoding gene product (mRNA or protein); comparing the amount of the GENSET polypeptide-encoding gene product present in said sample with that of a control sample; and determining whether the sample has a reduced or elevated level of GENSET gene expression compared to the control sample.

A biological sample from a subject affected by, or at risk of developing, any disease or condition associated with a GENSET polypeptide can be screened for the presence of increased or decreased levels of GENSET gene product, relative to a normal population (standard or control), with an increased or decreased level of the GENSET polypeptide relative to the normal population being indicative of predisposition to or a present indication of the disease or condition, or any sympton associated with the disease or condition. Such individuals would be candidates for therapies, e.g., treatment with pharmaceutical compositions comprising the GENSET polypeptide, a polynucleotide encoding the GENSET polypeptide, or any other compound that affects the expression or activity of the GENSET polypeptide. Generally, the identification of elevated levels of the GENSET polypeptide in a patient would be indicative of an individual that would benefit from treatment with agents that suppress GENSET polypeptide expression or activity, and the identification of low levels of the GENSET polypeptide in a patient would be indicative of an individual that would benefit from agents that induce GENSET expression or activity.

Biological samples suitable for use in this method include any biological fluids, including, but not limited to, blood, saliva, milk, and urine, as well as tissue samples such as biopsies. Cell cultures or cell extracts derived, for example, from tissue biopsies can also be used. In preferred embodiments, the biological sample is taken from animals presenting any symptom associated with any disease or condition associated with a GENSET gene product. In accordance with this method, the presence in the sample of altered (e.g. increased or decreased) levels of the GENSET product indicates that the subject is predisposed to the disease or condition.

The diagnostic methodologies described herein are applicable to both humans and non-human mammals.

Detection of GENSET Gene Mutations

The invention also encompasses methods and uses of GENSET polynucleotides to detect mutations in GENSET polynucleotides of the invention. When the mutation was proven to be associated with a disease, the detection of such mutations may be used for screening and diagnosis purposes.

In one embodiment, an oligonucleotide probe matrix may advantageously be used to detect mutations occurring in GENSET genes and preferably in their regulatory regions. For this particular purpose, probes are specifically designed to have a nucleotide sequence allowing their hybridization to the genes that carry known mutations (either by deletion, insertion or substitution of one or several nucleotides). By known mutations, it is meant, mutations on the GENSET genes that have been identified according, for example to the technique used by Huang et al., (1996) Cancer Res 56(5): 1137-1141 or Samson et al., (1996) Nature, 382(6593):722-725.

Another technique that is used to detect mutations in GENSET genes is the use of a high-density DNA array. Each oligonucleotide probe constituting a unit element of the high density DNA array is designed to match a specific subsequence of a GENSET genomic DNA or cDNA. Thus, an array consisting of oligonucleotides complementary to subsequences of the target gene sequence is used to determine the identity of the target sequence with the wild gene sequence, measure its amount, and detect differences between the target sequence and the reference wild gene sequence of the GENSET gene. In one such embodiment, a 4L tiled array is used (see, e.g., Chee et al., (1996) Science. 274:610-614).

Construction of DNA Constructs with a GENSET Gene Expression Pattern

In addition, characterization of the spatial and temporal expression patterns and expression levels of GENSET polypeptide-encoding mRNAs is also useful for constructing expression vectors capable of producing a desired level of gene product in a desired spatial or temporal manner, as discussed below.

DNA Constructs that Direct Temporal and Spatial GENSET Gene Expression in Recombinant Cell Hosts and in Transgenic Animals.

In order to study the physiological and phenotypic consequences of a lack of synthesis of a GENSET polypeptide, both at the cellular level and at the multi-cellular organism level, the invention also encompasses DNA constructs and recombinant vectors enabling a conditional expression of a specific allele of a GENSET polypeptide-encoding genomic sequence or cDNA, including alleles that include substitutions, deletions, or additions of one or more bases within the sequence.

In one embodiment, a DNA construct is used that is based on the tetracycline resistance operon tet from *E. coli* transposon Tn10 for controlling the GENSET gene expression, such as described by Gossen et al., (1992) PNAS 89:5547-5551; Gossen et al., (1995) Science 268:1766-1769; and Furth P. A. et al. (1994) PNAS 91:9302-9306.

In another embodiment, a DNA construct is used that comprises, from 5'-end to 3'-end: a first nucleotide sequence that is found in the GENSET polypeptide-encoding genomic sequence; a nucleotide sequence comprising a positive selection marker (e.g. neo); and a second nucleotide sequence that is found in the GENSET polypeptide-encoding genomic sequence, and is located downstream of the first GENSET nucleotide sequence. In a preferred embodiment, the construct also comprises a negative selection marker (e.g. thymidine kinase, hygromycine beta, hprt, Diphtheria toxin A fragment) located upstream of the first GENSET nucleotide sequence or downstream from the second GENSET nucleotide sequence (see, e.g., Thomas et al. (1986), Cell. 44:419-428; Te Riele et al. (1990), Nature.

348:649-651; Van der Lugt et al. (1991), Gene 105:263-267; Reid et al., (1990) PNAS 87:4299-4303; Nada et al., (1993) Cell 73:1125-1135; Yagi, T., et al. (1990), PNAS 87:9918-992; Thomas et al. (1986; 1987), Mansour et al.(1988) and Koller et al., (1992) Annu. Rev. Immunol. 10:705-730).

In another embodiment, vectors are used that involve the use of the Cre-loxP system (Hoess et al., (1986) Nucleic Acids Res. 14:2287-2300). The Cre-loxP system used in combination with a homologous recombination technique has been described by Gu H. et al., (1993) Cell 73:1155-1164 and Gu H. et al., (1994) Science 265:103-106. Briefly, a nucleotide sequence of interest to be inserted in a targeted location of the genome harbors at least two loxP sites in the same orientation and located at the respective ends of a nucleotide sequence to be excised from the recombinant genome. The excision event requires the presence of the recombinase (Cre) enzyme within the nucleus of the recombinant cell host, which may be supplied in any of a number of ways, e.g., by incubating the recombinant cell hosts in a culture medium containing this enzyme, by injecting the Cre enzyme directly into the desired cell, by lipofection of the enzyme into the cells, or by otherwise transfecting the cell with a Cre coding sequence under the control of an appropriate promoter (see, e.g., Baubonis et al (1993) *Nucleic Acids Res.* 21(9):2025-9); Araki et al., (1995) PNAS 92(1): 160-4; Gu et al. (1993); Sauer et al., (1998) PNAS 85:5166-5170; Gu et al.(1994); Zou, et al, (1994) Curr. Biol. 4:1099-1103 ; Anton and Graham, (1995), J. Virol., 69: 4600-4606; and Kanegae et al., (1995) Nucl. Acids Res. 23:3816-3821).

The DNA constructs described above may be used to introduce a desired nucleotide sequence of the invention, preferably a GENSET genomic sequence or a GENSET cDNA sequence, and most preferably an altered copy of a GENSET genomic or cDNA sequence, within a predetermined location of the targeted genome, leading either to the generation of an altered copy of a targeted gene (knock-out homologous recombination) or to the replacement of a copy of the targeted gene by another copy sufficiently homologous to allow an homologous recombination event to occur (knock-in homologous recombination).

Modifying GENSET Polypeptide Expression and/or Biological Activity

Modifying endogenous GENSET expression and/or biological activity is expressly contemplated by the present invention.

Screening for Compounds that Modulate GENSET Expression and/or Biological Activity The present invention further relates to compounds able to modulate GENSET expression and/or biological activity and methods to use these compounds. Such compounds may interact with the regulatory sequences of GENSET genes or they may interact with GENSET polypeptides directly or indirectly.

Compounds Interacting with GENSET Regulatory Sequences

The present invention also concerns a method for screening substances or molecules that are able to interact with the regulatory sequences of a GENSET gene, such as for example promoter or enhancer sequences in untranscribed regions of the genomic DNA, as determined using any techniques known to those skilled in the art, or such as regulatory sequences located in untranslated regions of GENSET mRNA.

Sequences within untranscribed or untranslated regions of polynucleotides of the invention may be identified by comparison to databases containing known regulatory sequence such as transcription start sites, transcription factor binding sites, promoter sequences, enhancer sequences, 5'UTR and 3'UTR elements (Pesole et al., (2000) Nucleic Acids Res, 28(1): 193-196; http://igs-server.cnrs-mrs.fr/~gauthere/UTR/index.html). Alternatively, the regulatory sequences of interest may be identified through conventional mutagenesis or deletion analyses of reporter plasmids.

Following the identification of potential GENSET regulatory sequences, proteins which interact with these regulatory sequences may be identified as described below.

Any of a number of methods can be used to identify molecules capable of interacting with the regulatory sequence of a GENSET gene, such as gel retardation assays (see, e.g., Fried and Crothers, (1981) Nucleic Acids Res. 9:6505-6525; Garner and Revzin, (1981) Nucleic Acids Res 9:3047-3060 ; and Dent and Latchman (1993) The DNA mobility shift assay. In: Transcription Factors: A Practical Approach (Latchman D S, ed.) pp: 1-26, Oxford: IRL Press). Nucleic acids encoding proteins which are able to interact with the promoter sequence of a GENSET gene may also be identified by using a one-hybrid system (e.g., the Matchmaker One-Hybrid System kit from Clontech (Catalog Ref. no. K1603-1)).

Ligands Interacting with GENSET Polypeptides

For the purpose of the present invention, a ligand means a molecule, such as a protein, a peptide, an antibody or any synthetic chemical compound capable of binding to a GENSET protein or one of its fragments or variants or to modulate the expression of the polynucleotide coding for GENSET or a fragment or variant thereof.

In one embodiment, a biological sample or a defined molecule (e.g. a molecule generated through combinatorial chemistry) to be tested as a putative ligand of a GENSET protein is brought into contact with the purified GENSET protein, in order to determine if a complex is formed between this protein and a component of the sample or the defined molecule. The interaction between such molecules and the protein can be assessed in any way, e.g., using microdialysis coupled to HPLC, using affinity capillary electrophoresis, etc. (see, e.g., Wang, et al. (1997), Chromatographia, 44 : 205-208; Bush et al., (1997), J. Chromatogr., 777: 311-328).

Any type of compound can be tested, using any method, for interaction with a GENSET polypeptide or polynucleotide in the present methods, including, but not limited to, peptides, drugs, fatty acids, lipoproteins, or small molecules, and may be obtained from any source. For example, the molecule to be tested is labeled with a detectable label, such as a fluorescent, radioactive, or enzymatic tag and placed in contact with immobilized GENSET protein, or a fragment thereof under conditions which permit specific binding to occur. After removal of non-specifically bound molecules, bound molecules are detected using appropriate means.

A. Candidate Ligands Obtained from Random Peptide Libraries

In a particular embodiment of the screening method, the putative ligand is the expression product of a DNA insert contained in a phage vector, e.g. from a random peptide phage library comprising peptides of from 8 to 20 amino acids in length (Parmley and Smith (1988) *Gene* 73:305-318; Oldenburg et al (1992) *PNAS* 89:5393-5397; Valadon et al. (1996) *J. Mol. Biol.,* 261:11-22; Lucas (1994) In: Development and Clinical Uses of Haempophilus b Conjugate; Westerink (1995) *PNAS* 92:4021-4025; Felici (1991) *J. Mol. Biol.,* 222:301-310).

Once the ligand library in recombinant phages has been constructed, the phage population is brought into contact with the immobilized GENSET protein, and, following washing, the phages that bind specifically to the GENSET protein are either eluted by a buffer (acid pH) or immunoprecipitated using an antibody specific to the GENSET protein. The isolated phage is subsequently amplified by an over-infection of bacteria (for example *E. coli*). The selection step may be repeated several times, preferably 2-4 times, in order to select the more specific recombinant phage clones.

B. Candidate Ligands Obtained by Competition Experiments.

Alternatively, peptides, drugs or small molecules which bind to polypeptides of the present 35 invention may be identified in competition experiments. In one such assay, a GENSET protein, or a fragment thereof, is immobilized to a surface, such as a plastic plate. Increasing amounts of the peptides, drugs or small molecules are placed in contact with the immobilized GENSET protein, or a fragment thereof, in the presence of a detectable labeled known GENSET protein ligand. For example, the GENSET ligand may be detectably labeled with a fluorescent, radioactive, or enzymatic tag. The ability of the test molecule to bind the GENSET protein, or a fragment thereof, is determined by measuring the amount of detectably labeled known ligand bound in the presence of the test molecule. A decrease in the amount of known ligand bound to the GENSET protein, or a fragment thereof, when the test molecule is present indicated that the test molecule is able to bind to the GENSET protein, or a fragment thereof.

C. Candidate Ligands Obtained by Affinity Chromatography.

Proteins or other molecules interacting with a polypeptide of the present invention can also be found using affinity columns which contain the GENSET protein, or a fragment thereof. The GENSET protein, or a fragment thereof, may be attached to the column using conventional techniques including chemical coupling to a suitable column matrix (e.g. agarose, Affi Gel®, etc.). In some embodiments of this method, the affinity column contains chimeric proteins in which the GENSET protein, or a fragment thereof, is fused to glutathion S transferase (GST). A mixture of cellular proteins or pool of expressed proteins as described above is applied to the affinity column. Proteins or other molecules interacting with the GENSET protein, or a fragment thereof, attached to the column can then be isolated and analyzed, e.g., on 2-D electrophoresis gel as described in Ramunsen et al., (1997), Electrophoresis, 18: 588-598. Alternatively, the proteins retained on the affinity column can be purified by electrophoresis-based methods and sequenced. The same method can be used to isolate antibodies, to screen phage display products, or to screen phage display human antibodies.

D. Candidate Ligands Obtained by Optical Biosensor Methods

Proteins interacting with a polypeptide of the present invention, can also be screened by using an Optical Biosensor (see, e.g., Edwards and Leatherbarrow (1997) Anal. Bioch. 246:1-6; Szabo et al., (1995) Curr Opin Struct Biol 5, 699-705. This technique permits the detection of interactions between molecules in real time, without the need of labeled molecules. This technique is based on the surface plasmon resonance (SPR) phenomenon. In one embodiment, a GENSET polypeptide, or fragment thereof, is attached to a surface (such as a carboxymethyl dextran matrix) comprising one side of a cell through which flows the candidate molecule to be assayed. A light beam is directed towards the side of the surface that does not contain the sample to be tested and is reflected by said surface. The binding of a candidate ligand molecules cause a change in the refraction index on the surface, which change is detected as a change in the SPR signal. This technique may also be performed by immobilizing eukaryotic or prokaryotic cells or lipid vesicles exhibiting an endogenous or a recombinantly expressed GENSET protein at their surface.

E. Candidate Ligands Obtained Through a Two-Hybrid Screening Assay.

The yeast two-hybrid system is designed to study protein-protein interactions in vivo (Fields and Song, 1989; U.S. Pat. Nos. 5,667,973 and 5,283,173), and relies upon the fusion of a bait protein to the DNA binding domain of the yeast Gal4 protein. The general procedure of library screening by the two-hybrid assay may be performed as described by Harper et al., (1993), *Cell* 75:805-816; Cho et al., (1998) *PNAS* 95(7):3752-3757; Fromont-Racine et al., (1997) *Nature Genetics* 16(3):277-282. In typical embodiments, the bait protein comprises a polypeptide of the present invention, and the "prey" comprises a human cDNA library constructed such that the human cDNA insert is fused to a nucleotide sequence in the vector that encodes the transcriptional domain of the GAL4 protein. In another embodiment, interaction between the GENSET polypeptide or a fragment or variant thereof with cellular proteins is assessed using the Matchmaker Two Hybrid System 2 (Catalog No. K1604-1, Clontech).

Compounds Modulating GENSET Biological Activity

Another method of screening for compounds that modulate GENSET expression and/or biological activity is by measuring the effects of test compounds on specific biological activity, e.g. a GENSET biological activity in a host cell or in an in vitro assay. A GENSET biological activity can include any of the activities, functions, or properties described herein for any GENSET polypeptide or polynucleotide. In one embodiment, a nucleic acid construct encoding a GENSET polypeptide is introduced into a host cell, and the host cell is maintained under conditions appropriate for expression of the encoded GENSET polypeptide, whereby the nucleic acid is expressed. The host cell is then contacted with a test agent, wherein a detection of a change in any GENSET polypeptide-associated property in the presence of the agent indicates that the agent alters GENSET biological activity. In a particular embodiment, the invention relates to a method of identifying an agent which is an activator of GENSET biological activity, wherein detection of an increase of any GENSET polypeptide-associated property in the presence of the agent indicates that the agent activates GENSET biological activity. In another particular embodiment, the invention relates to a method of identifying an agent which is an inhibitor of GENSET biological activity, wherein detection of a decrease of any GENSET polypeptide-associated property in the presence of the agent indicates that the agent inhibits GENSET biological activity. In another particular embodiment, a high throughput screen is used to identify agents that activate (enhance) or inhibit GENSET biological activity (see, e.g., WO 98/45438).

Methods of Screening for Compounds Modulating GENSET Gene Expression and/or Activity The present invention also relates to methods of screening compounds for their ability to modulate (e.g. increase or inhibit) the activity or expression of GENSET polypeptides and polynucleotides. More specifically, the present invention relates to methods of testing compounds for their ability either to increase or to decrease expression or activity of GENSET polypeptides and polynucleotides. The assays are performed in vitro or in vivo.

In Vitro Methods

In vitro, cells expressing GENSET polypeptides, or capable of expressing GENSET polypeptides, are incubated in the presence and absence of the test compound. By determining the level of GENSET expression in the presence of the test compound or the level of GENSET biological activity in the presence of the test compound, compounds can be identified that suppress or enhance GENSET expression or activity. Alternatively, constructs comprising a GENSET regulatory sequence operably linked to a reporter gene (e.g. luciferase, chloramphenicol acetyl transferase, LacZ, green fluorescent protein, etc.) can be introduced into host cells and the effect of the test compounds on expression of the reporter gene detected. Consequently, the present invention encompasses a method for screening molecules that modulate the expression of a GENSET gene, said screening method comprising cultivating a prokaryotic or a eukaryotic cell that has been transfected with a nucleotide sequence encoding either a GENSET polypeptide, placed under the control of its own promoter, or a detectable polypeptide, placed under the control of a GENSET 5' regulatory region; bringing into contact the cultivated cell with a molecule to be tested; and quantifying the expression of the GENSET or detectable polypeptide in the presence of the molecule. The method can also be performed using fragments, variants, or derivatives of any of the GENSET polypeptides or 5' regulatory regions.

The quantification of the expression of a GENSET polypeptide may be realized either at the mRNA level (using for example Northen blots, RT-PCR, preferably quantitative RT-PCR with primers and probes specific for the GENSET mRNA of interest) or at the protein level (using polyclonal or monoclonal antibodies in immunoassays such as ELISA or RIA assays, Western blots, or immunochemistry).

In a further embodiment, the GENSET 5' regulatory region includes the 5'UTR region of a GENSET polynucleotide sequence, and/or a promoter sequence which is endogenous or exogenous with respect to the GENSET 5'UTR sequence.

The invention further relates to a method for the production of a pharmaceutical composition comprising identifying a molecule that modulates the expression of a GENSET gene using any of the herein-described methods, and combining the identified molecule with a physiologically acceptable carrier.

Kits for the screening candidate substances for the ability to modulate the expression of a GENSET gene. Preferably, such kits comprise a recombinant vector comprising a GENSET 5' regulatory region or a regulatory active fragment or a variant thereof, operably linked to a polynucleotide encoding a detectable protein or a GENSET protein or a fragment or a variant thereof.

Another object of the present invention comprises methods and kits for the screening of candidate substances that interact with a GENSET polypeptide, fragments or variants thereof. By their capacity to bind covalently or non-covalently to a GENSET protein, fragments or variants thereof, these substances or molecules may be advantageously used both in vitro and in vivo.

In vitro, said interacting molecules may be used as detection means in order to identify the presence of a GENSET protein in a sample, preferably a biological sample.

In one embodiment, a method is provided for the screening of a candidate substance, the method comprising providing a GENSET protein; bringing into contact the protein with the candidate substance; and determining whether a complex is formed between the polypeptide or fragment and the candidate substance.

The invention further relates to a method for the production of a pharmaceutical composition comprising identifying a substance that interacts with a GENSET polypeptide using any of the herein-described methods, fragments or variants thereof and furthermore mixing the identified substance with a physiologically acceptable carrier.

The invention further concerns a kit for the screening of a candidate substance interacting with the GENSET polypeptide, wherein said kit comprises a GENSET polypeptide, and optionally means to detect a complex formed between the polypeptide and the candidate substance. In one embodiment, the detection means comprises a monoclonal or polyclonal antibody binding to said GENSET protein or fragment or variant thereof.

In Vivo Methods

Compounds that suppress or enhance GENSET gene expression can also be identified using in vivo screens. In a typical assay, a test compound is administered (e.g. intravenously, intraperitoneally, intramuscularly, orally, or otherwise) to an animal, at a variety of dose levels, and the effect of the compound on GENSET gene expression is determined by comparing the levels of the mRNA or protein encoded by the gene in tissues known to express the gene of interest, e.g., using Northern blots, immunoassays, PCR, etc. Suitable test animals include, but are not limited to, rodents (e.g., mice and rats), primates, and rabbits. Humanized mice can also be used, that is mice in which the endogenous mouse protein is ablated (knocked out) and the homologous human protein introduced using standard transgenic approaches. Such mice thus express only the human form of a protein. Humanized mice expressing only the human GENSET polypeptide can be used to study in vivo responses to potential agents regulating GENSET protein or mRNA levels. Such transgenic animals are useful for dissecting the biochemical and physiological steps of disease, and for development of therapies for disease intervention (see, e.g., Loring, et al, 1996).

In addition, the detection of any change in any GENSET gene-associated behavior or characteristic of an animal following the administration of a compound can also be used as an indication that the compound modulates the expression or activity of the gene.

Uses for Compounds Modulating GENSET Expression and/or Biological Activity

Using in vivo (or in vitro) systems, it may be possible to identify compounds that exert a tissue specific effect, for example, that increase GENSET expression or activity in one or more particular tissues of interest, such as the adrenal gland, bone marrow, brain, cerebellum, colon, fetal brain, fetal kidney, fetal liver, heart, hypertrophic prostate, kidney, liver, lung, lymph ganglia, lymphocytes, muscle, ovary, pancreas, pituitary gland, placenta, prostate, salivary gland, spinal cord, spleen, stomach, intestine, substantia nigra, testis, thyroid, umbilical cord, or uterus. Screening procedures such as those described above are also useful for identifying agents for their potential use in pharmacological intervention strategies. Agents that enhance GENSET gene expression or stimulate its activity may thus be used to induce any phenotype associated with a GENSET gene, or to treat disorders resulting from a deficiency of a GENSET polypeptide activity or expression. Compounds that suppress GENSET polypeptide expression or inhibit its activity can be used to treat any disease or condition associated with increased or deleterious GENSET polypeptide activity or expression.

Also encompassed by the present invention is an agent which interacts with a GENSET gene or polypeptide directly or indirectly, and inhibits or enhances GENSET polypeptide expression and/or function. In one embodiment, the agent is an inhibitor which interferes with a GENSET polypeptide directly (e.g., by binding the GENSET polypeptide) or indirectly (e.g., by blocking the ability of the GENSET polypeptide to have a GENSET biological activity). In a particular embodiment, an inhibitor of a GENSET protein is an antibody specific for the GENSET protein or a functional portion of the GENSET protein. Alternatively, the inhibitor can be an agent other than an antibody (e.g., small organic molecule, protein or peptide) which binds the GENSET polypeptide and blocks its activity. For example, the inhibitor can be an agent which mimics the GENSET polypeptide structurally, but lacks its function (e.g. a dominant negative form of the protein). Alternatively, it can be an agent which binds to or interacts with a molecule which the GENSET polypeptide normally binds to or interacts with, thus blocking the GENSET polypepetide from doing so and preventing it from exerting the effects it would normally exert.

In another embodiment, the agent is an enhancer (activator) of a GENSET polypeptide which increases the activity of the GENSET polypeptide (increases the effect of a given amount or level of GENSET polypeptide), increases the length of time it is effective (by preventing its degradation or otherwise prolonging the time during which it is active) or both either directly or indirectly. For example, GENSET polynucleotides and polypeptides can be used to identify drugs which increase or decrease the ability of GENSET polypeptides to induce GENSET biological activity, which drugs are useful for the treatment or prevention of any disease or condition associated with a GENSET biological activity.

Thus the present invention relates to a method of inhibiting (partially or completely) a GENSET biological activity in a mammal (e.g., a human), the method comprising administering to the mammal an effective amount of an inhibitor of a GENSET polypeptide or polynucleotide. The invention also relates to a method of enhancing a GENSET biological activity in a mammal, the method comprising administering to the mammal an effective amount of an enhancer of a GENSET polypeptide or polynucleotide.

Inhibiting GENSET Gene Expression

GENSET gene expression can be inhibited, e.g., for therapeutic applications, in any of a large number of ways, including by using an antisense tool or a triple helix tool that inhibits the expression of the corresponding GENSET gene.

Antisense Approach

In antisense approaches, DNA and/or RNA sequences complementary to an mRNA are hybridized to the mRNA intracellularly, thereby blocking the expression of the protein encoded by the mRNA. Preferred methods for using antisense polynucleotide according to the present invention are the procedures described by Sczakiel et al., (1995) Trends Microbiol. 3(6):213-217; Green et al., (1986) Ann. Rev. Biochem. 55:569-597 ; Izant and Weintraub, (1984) Cell 36(4):1007-15; Liu et al. (1994) PNAS 91: 4528-4262 ; Eckner et al., (1991) EMBO J. 10:3513-3522).

Preferably, the antisense tools are chosen among the polynucleotides (15-200 bp long) that are complementary to GENSET mRNA, more preferably to the 5'end (e.g. the translation initiation codon ATG) or to a splicing donor or acceptor site of the GENSET mRNA. In another embodiment, a combination of different antisense polynucleotides complementary to different parts of the desired targeted gene are used. The antisense molecules can be prepared in any way, including by reversing the orientation of a coding region of a GENSET gene in a cell, or by synthesizing an oligonucleotide in vitro and administering it to the cell.

Any antisense sequence complementary to any portion of any of the herein-described polynucleotides can be used, and can involve any number of modifications to the backbone, linkages, or bases, a large number of which are known in the art. Suitable modifications, other forms of antisense molecules, and the preparation thereof, are taught, inter alia, in The Concise Encyclopedia Of Polymer Science And Engineering, pages 858-859, Kroschwitz, J. I., ed. John Wiley & Sons, 1990; Englisch et al., Angewandte Chemie, International Edition (1991), 30, 613; Sanghvi, et al., eds., (1993) Antisense Research and Applications, CRC Press, Boca Raton; U.S. Pat. No. 6,242,590; WO94/23026, WO 96/31523; WO 92/18522; European Patent Application No. 0 572 287 A2; WO 92/19732; Letsinger et al., PNAS (1989) 86: 6553-6556; Manoharan et al., Bioorg. Med. Chem. Let. (1994) 4:1053-1060; Manoharan et al., Ann. N.Y. Acad. Sci. (1992) 660:306-309; Manoharan et al., Bioorg. Med. Chem. Let. (1993) 3:2765-2770; Oberhauser et al., Nucl. Acids Res. (1992) 20:533-538; Saison-Behmoaras et al., EMBO J. (1991) 10:1111-1118; Kabanov et al., FEBS Lett. (1990) 259: 327-330; Svinarchuk et al., Biochimie (1993) 75:49-54; Manoharan et al., Tetrahedron Lett. (1995) 36, 3651-3654; Shea et al., Nucl. Acids Res. (1990) 18:3777-3783; Manoharan et al., Nucleosides & Nucleotides (1995) 14: 969-973; Manoharan et al., Tetrahedron Lett. (1995) 36:3651-3654; Mishra et al., Biochim. Biophys. Acta (1995) 1264:229-237; Crooke et al., J. Pharmacol. Exp. Ther. (1996) 277:923-937; U.S. Pat. No. 6,242,590.

Further included in the present invention is a method of high throughput screening of antisense nucleic acids and modified versions thereof for binding to targeted GENSET polynucleotide sequences or fragments thereof (see, e.g., U.S. Pat. No. 6,022,691).

The appropriate level of antisense nucleic acids required to inhibit gene expression may be determined using in vitro expression analysis. Typically, antisense molecules are introduced onto cell samples at a number of different concentrations preferably between $1\times10^{-10}$M to $1\times10^{-4}$M. Once the minimum concentration that can adequately control gene expression is identified, the optimized dose is translated into a dosage suitable for use in vivo or ex vivo. For example, an inhibiting concentration in culture of $1\times10^{-7}$ translates into a dose of approximately 0.6 mg/kg bodyweight.

An alternative to the antisense technology that is used according to the present invention comprises using ribozymes that will bind to a target sequence via their complementary polynucleotide tail and that will cleave the corresponding RNA by hydrolyzing its target site (see, e.g., Rossi et al, (1991) Pharmacol. Ther. 50:245-254 and Sczakiel et al. (1995)).

Triple Helix Approach

The GENSET genomic DNA may also be used to inhibit the expression of the GENSET gene based on intracellular triple helix formation (see, e.g., Griffin et al., (1989) Science 245:967-971). To carry out gene therapy strategies using the triple helix approach, the sequences of the GENSET genomic DNA are typically first scanned to identify 10-mer to 20-mer homopyrimidine or homopurine stretches which could be used in triple-helix based strategies for inhibiting GENSET gene expression. Following identification of candidate homopyrimidine or homopurine stretches, their efficiency in inhibiting GENSET gene expression is assessed by introducing varying amounts of oligonucleotides containing the candidate sequences into tissue culture cells which express the GENSET gene. The oligonucleotides can be introduced into the cells using a variety of methods known to those skilled in the art, and treated cells are monitored for altered cell function or reduced GENSET gene expression.

The oligonucleotides which are effective in inhibiting gene expression in tissue culture cells may then be introduced in vivo using the techniques and at a dosage calculated based on the in vitro results, as described in the section entitled “Antisense Approach”.

Treating GENSET Gene-Related Disorders

The present invention further relates to methods, uses of GENSET polypeptides and polynucleotides, and uses of modulators of GENSET polypeptides and polynucleotides, for treating diseases/disorders associated with GENSET genes by increasing or decreasing GENSET gene activity and/or expression. These methodologies can be effected using compounds selected using screening protocols such as those described herein and/or by using the gene therapy and antisense approaches described in the art and herein. Gene therapy can be used to effect targeted expression of GENSET genes in any tissue, e.g. a tissue associated with the disease or condition to be treated. The GENSET coding sequence can be cloned into an appropriate expression vector and targeted to a particular cell type(s) to achieve efficient, high level expression. Introduction of the GENSET coding sequence into target cells can be achieved, for example, using particle mediated DNA delivery, (Haynes et al., (1996) J Biotechnol. 44(1-3):37-42 and Maurer et al., (1999) Mol Membr Biol. 16(1):129-40), direct injection of naked DNA (Levy et al., (1996) Gene Ther. 3(3):201-11; and Felgner (1996) Hum Gene Ther. 7(15):1791-3), or viral vector mediated transport (Smith et al., (1996) Antiviral Res. 32(2):99-115, Stone et al., (2000) J Endocrinol. 164(2): 103-18; Wu and Ataai (2000), Curr Opin Biotechnol. 11(2): 205-8). Tissue specific effects can be achieved, for example, in the case of virus mediated transport by using viral vectors that are tissue specific, or by the use of promoters that are tissue specific. For instance, any tissue-specific promoter may be used to achieve specific expression, for example albumin promoters (liver specific; Pinkert et al., 1987 Genes Dev. 1:268-277), lymphoid specific promoters (Calame et al., 1988 Adv. Immunol. 43:235-275), promoters of T-cell receptors (Winoto et al., 1989 EMBO J. 8:729-733) and immunoglobulins (Banedi et al., 1983 Cell 33:729-740; Queen and Baltimore 1983 Cell 33:741-748), neuron-specific promoters (e.g. the neurofilament promoter; Byrne et al., 1989 PNAS 86:5473-5477), pancreas-specific promoters (Edlunch et al., 1985 Science 230:912-916) or mammary gland-specific promoters (milk whey promoter, U.S. Pat. No. 4,873,316 and European Application Publication No. 264, 166). Developmentally-regulated promoters can also be used, such as the murine homeobox promoters (Kessel et al., 1990 Science 249:374-379) or the alpha-fetoprotein promoter (Campes et al., 1989 Genes Dev. 3:537-546).

Combinatorial approaches can also be used to ensure that the GENSET coding sequence is activated in the target tissue (Butt and Karathanasis (1995) Gene Expr. 4(6):319-36; Miller and Whelan, (1997) Hum Gene Ther. 8(7):803-15). Antisense oligonucleotides complementary to GENSET mRNA can be used to selectively diminish or ablate the expression of the protein (Wagner, et al. (1996), Nat Biotechnol. 14(7):840-4)), for example, at sites of inflammation. More specifically, antisense constructs or antisense oligonucleotides can be used to inhibit the production of GENSET in high expressing cells, e.g., by transfecting target cells with an expression vector comprising a GENSET gene sequence, or portion thereof, in an antisense orientation relative to the direction of transcription, or by introducing antisense oligonucleotides directly into target cells. The therapeutic methodologies described herein are applicable to both human and non-human mammals.

Pharmaceutical and Physiologically Acceptable Compositions

The present invention also relates to pharmaceutical or physiologically acceptable compositions comprising, as active agent, the polypeptides, nucleic acids or antibodies of the invention. The invention also relates to compositions comprising, as active agent, compounds selected using the above-described screening protocols. Such compositions include the active agent in combination with a pharmaceutical or physiologically acceptable carriers such as a physiologically acceptable salt, ester, or salt of such esters. In the case of naked DNA, the “carrier” may be gold particles. The amount of active agent in the composition can vary with the agent, the patient and the effect sought. Likewise, the dosing regimen can vary depending on the composition and the disease/disorder to be treated.

Therefore, the invention related to methods for the production of pharmaceutical composition comprising a method for selecting an active agent, compound, substance or molecule using any of the screening method described herein and furthermore mixing the identified active agent, compound, substance or molecule with a physiologically acceptable carrier.

The term “physiologically acceptable salts” refers to physiologically and pharmaceutically acceptable salts of the compounds of the invention: i.e., salts that retain the desired biological activity of the parent compound and do not impart undesired toxicological effects thereto. Physiologically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., “Pharmaceutical Salts,” J. of Pharma Sci. (1977) 66:1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a “pharmaceutical addition salt” includes a physiologically acceptable salt of an acid form of one of the components of the compositions of the invention. These include organic or inorganic acid salts of the amines. Preferred acid salts are the hydrochlorides, acetates, salicylates, nitrates and phosphates. Other suitable physiologically acceptable salts are well known to those skilled in the art and include basic salts of a variety of inorganic and organic acids, such as, hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Physiologically acceptable salts of compounds may also be prepared with a physiologically acceptable cation. Suitable physiologically acceptable cations are well known to those skilled in the art and include alkaline, alkaline earth, ammonium and quaternary ammonium cations. Carbonates or hydrogen carbonates are also possible. For oligonucleotides, preferred examples of physiologically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The pharmaceutical compositions utilized in this invention may be administered by any number of routes including, but not limited to: parenteral, intracranial, intraorbital, intracapsular, intraspinal, intracisternal, intrapulmonary, oral, intravenous, intramuscular, intraarterial, intramedullary, intrathecal, intraventricular, transdermal, subcutaneous, intraperitoneal, intranasal, enteral, topical, sublingual, rectal, intradermal, intravascular. In addition to the active ingredients, these pharmaceutical compositions may contain suitable physiologically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack PublishingCo. Easton, Pa.).

Pharmaceutical compositions for oral administration can be formulated using physiologically acceptable carriers well known in the art in dosages suitable for oral administration. Such carriers enable the pharmaceutical compositions to be formulated as powders, tablets, pills, dragees, capsules, liquids, gels, syrups, slurries, suspensions, and the like, for ingestion by the patient. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Formulations suitable for pulmonary or respiratory delivery include dry powders, liquid solutions or suspensions suitable for nebulization, and propellant formulations suitable for use in metered dose inhalers (MDI's). In typical embodiments, dry powder formulations will have a particle size within a preferred range for deposition within the alveolar region of the lung, typically from 0.5 μm to 5 μm. Respirable powders of pharmaceutical compositions within the preferred size range can be produced by a variety of conventional techniques, such as jet-milling, spray-drying, solvent precipitation, and the like. Dry powders can then be administered to the patient in conventional dry powder inhalers (DPI's) that use the patient's inspiratory breath through the device to disperse the powder or in air-assisted devices that use an external power source to disperse the powder into an aerosol cloud (see, e.g., U.S. Pat. No. 5,458,135).

Liquid formulations for use in nebulizer systems preferably employ slightly acidic buffers (pH 4-6) such as acetate, ascorbate, and citrate, at concentrations of 5 mM to 50 mM. These buffers can act as antioxidants. Physiologically acceptable components to enhance or maintain chemical stability include: antioxidants, chelating agents, protease inhibitors, isotonic modifiers, inert gases, and the like. A preferred type of nebulizer suitable for delivering such liquid formulations is described in U.S. Pat. No. 5,458,135.

For use in MDI's, the pharmaceutical composition will typically be processed into respirable particles as described for the dry powder formulations, and the particles then suspended in a suitable aerosol propellant (such as a CFC or HFC), typically being coated with a surfactant to enhance their dispersion. Such aerosol propellant formulations may further include a lower alcohol, such as ethanol (up to 30% by weight) and other additives to maintain or enhance chemical stability and physiological acceptability (see, e.g., U.S. Pat. No. 6,080,721).

For topical or nasal administration, penetrants appropriate to the particular barrier to be permeated are used in the formulation. Such penetrants are generally known in the art.

Pharmaceutical formulations suitable for parenteral administration may be formulated in aqueous solutions, preferably in physiologically compatible buffers such as Hanks solution, Ringer's solution, or physiologically buffered saline. Aqueous injection suspensions may contain substances which increase the viscosity of the suspension, such as sodium carboxymethylcellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

In one embodiment, the preparation is a lyophilized powder which may contain any or all of the following: 1-50 mM histidine, 0.1%-2% sucrose, and 2-7% mannitol, at a pH range of 4.5 to 5.5, that is combined with buffer prior to use.

After pharmaceutical compositions have been prepared, they can be placed in an appropriate container and labeled for treatment of an indicated condition. For administration of a GENSET polypeptide, such labeling would include, e.g., amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art. For any compound, a therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example a GENSET polypeptide or fragments thereof, antibodies specific to GENSET polypeptides, agonists, antagonists or inhibitors of GENSET polypeptides, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Other factors that may be considered when evaluating the proper dosage include the chemical nature of the compound destined for delivery, the biological responses associated with the compound (both intended and coincidental) and anticipated contraindications. Additionally, the mode of delivery, the duration and frequency of administration (e.g. n doses per hours, n doses per day, n doses per week, cumulative dosage per day, cumulative dosage per week), the biologically effective dose delivered to target site, often indicated by plasma level concentrations, and the rate or efficiency of compound clearance from the body may be considered. Long-acting pharmaceutical compositions may be administered, e.g., every 3 to 4 days, every week, or once every two weeks depending on half-life and clearance rate of the particular formulation.

Normal dosage amounts may vary depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. In general, for a 75 kg individual the normal dosage range are as follows: for a small molecule compound an effective does is usually between 0.3-50 mg/kg; for recombinant polypeptides an effective dose is usually between 0.25-7.5 mg/kg; for compounds used for mediating humoral immune responses (e.g., polyvalent pneumococcal vaccine, R (D) immune globulin, Hepatitis B vaccine, anti-CD20 antigen) the effective dose is usually between 0.0015-1.5 mg/kg; for hormone supplemental compounds (e.g. estradiol, norethindrone) the effective dose is usually between 0.0005-0.5 mg/kg depending upon delivery system utilized (e.g. transdermal, oral, topical).

Transdermal delivery systems (e.g. estradiol transdermal system, transdermal scopolamine system, transfermal nicotine patch) must be calibrated for nominal delivery dosages based upon efficiency of percutaneous delivery for the individual and specific compounds, surface area ($cm^2$) of transdermal system contact, quantity and form of compound integrated into transdermal delivery system and anatomical location of positioned transdermal system. The effective dosage range of compounds admistered in this manner is usually between 0.005-0.5 mg/kg

Uses of GENSET Sequences: Computer-Related Embodiments

It will be appreciated by those skilled in the art that the nucleic acid codes of the invention and polypeptide codes of the invention can be stored, recorded, and manipulated on any medium which can be read and accessed by a computer. As used herein, the words "recorded" and "stored" refer to a process for storing information on a computer medium. A skilled artisan can readily adopt any of the presently known methods for recording information on a computer readable medium to generate manufactures comprising one or more of the nucleic acid codes of the invention, or one or more of the polypeptide codes of the invention. Another aspect of the present invention is a computer readable medium having recorded thereon at least 1, 2, 5, 10, 15, 20, 25, 30, or 50 nucleic acid or polypeptide codes of the invention.

Computer readable media include magnetically readable media, optically readable media, electronically readable media and magnetic/optical media. For example, the computer readable media may be a hard disk, a floppy disk, a magnetic tape, CD-ROM, Digital Versatile Disk (DVD), Random Access Memory (RAM), or Read Only Memory (ROM).

Embodiments of the present invention include systems, particularly computer systems which store and manipulate the sequence information described herein. As used herein, "a computer system" refers to the hardware components, software components, and data storage components used to analyze the nucleotide sequences of the nucleic acid codes of the invention or the amino acid sequences of the polypeptide codes of the invention. The computer system preferably includes a processor for processing, accessing and manipulating the sequence data. The processor can be any well-known type of central processing unit, such as the Pentium III from Intel Corporation, or similar processor from Sun, Motorola, Compaq or International Business Machines. Preferably, the computer system is a general purpose system that comprises the processor and one or more internal data storage components for storing data, and one or more data retrieving devices for retrieving the data stored on the data storage components. A skilled artisan can readily appreciate that any one of the currently available computer systems are suitable.

In some embodiments, the computer system may comprise a sequence comparer for comparing the above-described nucleic acid codes of the invention or the polypeptide codes of the invention stored on a computer readable medium to reference nucleotide or polypeptide sequences stored on a computer readable medium or present in a database. A "sequence comparer" refers to one or more programs which are implemented on the computer system to compare a nucleotide or polypeptide sequence with other nucleotide or polypeptide sequences and/or compounds including but not limited to peptides, peptidomimetics, and chemicals stored within the data storage means. For example, the sequence comparer may compare the nucleotide sequences of nucleic acid codes of the invention or the amino acid sequences of the polypeptide codes of the invention stored on a computer readable medium to reference sequences stored on a computer readable medium to identify homologies, motifs implicated in biological function, or structural motifs. The various sequence comparer programs identified elsewhere in this patent specification are particularly contemplated for use in this aspect of the invention. Alternatively, a nucleotide or amino acid sequence is compared with a database of sequences in order to determine the homology levels between the sequence and the sequences in the database. The database of sequences can be a private database stored within the computer system, or a public database such as GENBANK, PIR OR SWISSPROT that is available, e.g., through the Internet.

Accordingly, one aspect of the present invention is a computer system comprising a processor, a data storage device having stored thereon a nucleic acid code of the invention or a polypeptide code of the invention, a data storage device having retrievably stored thereon reference nucleotide sequences or polypeptide sequences to be compared to the nucleic acid code of the invention or polypeptide code of the invention and a sequence comparer for conducting the comparison.

Alternatively, the computer program may be a computer program which compares the nucleotide sequences of the nucleic acid codes of the present invention, to reference nucleotide sequences in order to determine whether the nucleic acid code of the invention differs from a reference nucleic acid sequence at one or more positions. Optionally such a program records the length and identity of inserted, deleted or substituted nucleotides with respect to the sequence of either the reference polynucleotide or the nucleic acid code of the invention. In one embodiment, the computer program may be a program which determines whether the nucleotide sequences of the nucleic acid codes of the invention contain one or more single nucleotide polymorphisms (SNP) with respect to a reference nucleotide sequence. These single nucleotide polymorphisms may each comprise a single base substitution, insertion, or deletion. The method may also be performed by reading at least 2, 5, 10, 15, 20, 25, 30, or 50 of the nucleic acid codes of the invention and the reference nucleotide sequences through the use of the computer program and identifying differences between the nucleic acid codes and the reference nucleotide sequences with the computer program.

In other embodiments the computer based system may further comprise an identifier for identifying features within the nucleotide sequences of the nucleic acid codes of the invention or the amino acid sequences of the polypeptide codes of the invention. An "identifier" refers to one or more programs which identifies certain features within the above-described nucleotide sequences of the nucleic acid codes of the invention or the amino acid sequences of the polypeptide codes of the invention. In one embodiment, the identifier may comprise a program which identifies an open reading frame in the cDNAs codes of the invention.

In additional embodiments, the present amino acid sequences can be analyzed using any of a number of computer programs to identify structural features of the protein, such as secondary, tertiary, and quaternary structures, to identify potential binding partners, etc. The results of the molecular modeling analysis may then be used, e.g., in rational drug design techniques to identify agents which modulate the activity of the polypeptide codes of the invention.

Accordingly, another aspect of the present invention is a method of identifying a feature within the nucleic acid codes of the invention or the polypeptide codes of the invention comprising reading the nucleic acid code(s) or the polypeptide code(s) through the use of a computer program which identifies features therein and identifying features within the nucleic acid code(s) or polypeptide code(s) with the computer program. The method may be performed by reading a single sequence or at least 2, 5, 10, 15, 20, 25, 30, or 50 of the nucleic acid codes of the invention or the polypeptide codes of the invention through the use of the computer program and identifying features within the nucleic acid codes or polypeptide codes with the computer program.

Motifs which may be detected using the above programs include leucine zippers, helix-turn-helix motifs, glycosylation sites, ubiquitination sites, alpha helices, beta sheets, signal sequences, sequences implicated in transcription regulation such as homeoboxes, acidic stretches, enzymatic active sites, substrate binding sites, and enzymatic cleavage sites.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

Throughout this application, various publications, kit manuals, patents and published patent applications are cited. The entire disclosures of each of these publications, patents, manuals and published patent specifications are hereby incorporated by reference into the present disclosure to more fully describe the state of the art to which this invention pertains.

TABLE I

| SEQ ID NO. | Sequence Type | Clone ID_Clone Name | Name | ATCC Deposit | ATCC Deposit Date |
|---|---|---|---|---|---|
| 1 | DNA | 243525_116-119-1-0-G6-F | PCNAlt | | |
| 2 | Protein | 243525_116-119-1-0-G6-F | PCNAlt | | |
| 3 | DNA | 643144_181-17-2-0-A12-F | Lectir | | |
| 4 | Protein | 643144_181-17-2-0-A12-F | Lectir | | |
| 5 | DNA | 212950.cREC_116-075-2-0-H1-F | vlADAM20 | | |
| 6 | Protein | 212950.cREC_116-075-2-0-H1-F | vlADAM20 | | |
| 7 | DNA | 1000849866_181-44-3-0-A9-F | Lipoglobulin | | |
| 8 | Protein | 1000849866_181-44-3-0-A9-F | Lipoglobulin | | |
| 9 | DNA | 164341_117-001-5-0-E2-F | PBK | | |
| 10 | Protein | 164341_117-001-5-0-E2-F | PBK | | |
| 11 | DNA | 1000837037_228-43-2-0-C3-F | Myeloidin | | |
| 12 | Protein | 1000837037_228-43-2-0-C3-F | Myeloidin | | |
| 13 | DNA | 101005_105-020-4-0-H11-F | vACT | | |
| 14 | Protein | 101005_105-020-4-0-H11-F | vACT | | |
| 15 | DNA | 500743419_188-281-3-0-H5-F | Claudinyn-5 | | |
| 16 | Protein | 500743419_188-281-3-0-H5-F | Claudinyn-5 | | |
| 17 | DNA | 645730_181-16-1-0-G9-F | Benzodiazepine receptor 3 (BZRP-R3) | | |
| 18 | Protein | 645730_181-16-1-0-G9-F | Benzodiazepine receptor 3 (BZRP-R3) | | |
| 19 | DNA | 646762_181-21-2-0-A3-F | Benzodiazepine receptor 4 (BZRP-R4) | | |
| 20 | Protein | 646762_181-21-2-0-A3-F | Benzodiazepine receptor 4 (BZRP-R4) | | |
| 21 | DNA | 420594_145-19-4-0-E7-F | Scolakin | | |
| 22 | Protein | 420594_145-19-4-0-E7-F | Scolakin | | |
| 23 | DNA | 119658_105-067-2-0-H4-F | DOV | | |
| 24 | Protein | 119658_105-067-2-0-H4-F | DOV | | |
| 25 | DNA | 500706437_204-5-2-0-C9-F | Placentalin | | |
| 26 | Protein | 500706437_204-5-2-0-C9-F | Placentalin | | |
| 27 | DNA | 176355_117-005-2-0-H11-F | NAAR | | |
| 28 | Protein | 176355_117-005-2-0-H11-F | NAAR | | |
| 29 | DNA | 222588_116-094-1-0-H2-F | Neurexinal | | |
| 30 | Protein | 222588_116-094-1-0-H2-F | Neurexinal | | |
| 31 | DNA | 119033_105-066-4-0-F10-F | NPAISY | | |
| 32 | Protein | 119033_105-066-4-0-F10-F | NPAISY | | |
| 33 | DNA | 125402_105-074-4-0-F3-F | vCRTL-1 | | |
| 34 | Protein | 125402_105-074-4-0-F3-F | vCRTL-1 | | |
| 35 | DNA | 107640_105-036-2-0-H3 | LIRION | | |
| 36 | Protein | 107640_105-036-2-0-H3 | LIRION | | |
| 37 | DNA | 588394_160-105-40-A11-F | SLAMP | | |
| 38 | Protein | 588394_160-105-40-A11-F | SLAMP | | |
| 39 | DNA | 495718_160-26-2-0-E12-F | SAP-MU-10 | | |
| 40 | Protein | 495718_160-26-2-0-E12-F | SAP-MU-10 | | |
| 41 | DNA | 612386_187-9-4-0-B2-F | Cytogram | | |
| 42 | Protein | 612386_187-9-4-0-B2-F | Cytogram | | |
| 43 | DNA | 1000838982_220-20-4-0-B7-F | Tetranab | | |
| 44 | Protein | 1000838982_220-20-4-0-B7-F | Tetranab | | |
| 45 | DNA | 500720840_205-20-1-0-B7-F | PDI | | |
| 46 | Protein | 500720840_205-20-1-0-B7-F | PDI | | |
| 47 | DNA | 146821_106-020-1-0-G3-F | NBART | | |
| 48 | Protein | 146821_106-020-1-0-G3-F | NBART | | |
| 49 | DNA | 644724_181-21-1-0-A12-F | NBTG | | |
| 50 | Protein | 644724_181-21-1-0-A12-F | NBTG | | |
| 51 | DNA | 583702_181-8-4-0-C8-F | vITH1 | | |
| 52 | Protein | 583702_181-8-4-0-C8-F | vITH1 | | |

TABLE II

| SEQ ID NO: | ORF | Signal Peptide | Mature peptide | Polyadenylation Signal | PolyA tail |
|---|---|---|---|---|---|
| 1 | [225-593] | — | — | [769-774] | [800-850] |
| 3 | [91-777] | — | — | [826-831] | [848-883] |
| 5 | [235-2562] | — | — | — | — |
| 7 | [264-926] | [264-320] | [321-926] | [1404-1409] | [1421-1436] |
| 9 | [93-551] | [93-197] | [198-551] | [2085-2090] | [2117-2132] |
| 11 | [201-986] | [201-269] | [270-986] | [2233-2238] | [2251-2266] |

TABLE II-continued

| SEQ ID NO: | ORF | Signal Peptide | Mature peptide | Polyadenylation Signal | PolyA tail |
|---|---|---|---|---|---|
| 13 | [66-1334] | [66-134] | [135-1334] | [1558-1563] | [1582-1597] |
| 15 | [153-806] | — | — | [1362-1367] | [1382-1397] |
| 17 | [63-572] | — | — | [750-755] | [767-782] |
| 19 | [63-572] | — | — | [750-755] | [774-789] |
| 21 | [86-403] | — | — | [504-509] | [540-555] |
| 23 | [415-1653] | — | — | — | [1688-1726] |
| 25 | [76-339] | [76-147] | [148-339] | [903-908] | [926-941] |
| 27 | [21-1118] | [21-89] | [90-1118] | [1858-1863] | [1879-1894] |
| 29 | [32-559] | — | — | [702-707] | [728-742] |
| 31 | [4-1533] | — | — | [1709-1714] | [1744-1766] |
| 33 | [11-802] | [11-64] | [65-802] | [836-841] | [862-877] |
| 35 | [38-1378] | [38-106] | [107-1378] | [107-1378] | — |
| 37 | [330-1478] | [330-398] | [399-1478] | [1722-1727] | [1742-1757] |
| 39 | [81-1517] | — | — | [2786-2791] | [2804-2818] |
| 41 | [121-546] | [121-231] | [232-546] | [739-744] | [755-770] |
| 43 | [136-501] | — | — | [1232-1237] | [1255-1340] |
| 45 | [118-1632] | [118-189] | [190-1632] | [1937-1942] | [1956-1999] |
| 47 | [154-546] | — | — | — | [722-836] |
| 49 | [196-708] | — | — | — | [847-862] |
| 51 | [62-778] | [62-124] | [125-778] | [912-917] | [932-937] |

TABLE III

| SEQ ID NO: | Positions of immunogenic epitopes |
|---|---|
| 4 | 1 . . . 8: 12 . . . 17: 57 . . . 64: 63 . . . 74: 90 . . . 114: 122 . . . 132: 162 . . . 174: 186 . . . 194: 196 . . . 206: 207 . . . 214 |
| 6 | 3 . . . 19: 20 . . . 28: 79 . . . 89: 100 . . . 107: 150 . . . 164: 209 . . . 221: 333 . . . 343: 368 . . . 373: 398 . . . 406: 418 . . . 432: 430 . . . 439: 447 . . . 453: 513 . . . 521: 524 . . . 539: 553 . . . 565: 569 . . . 583: 582 . . . 593: 635 . . . 648: 684 . . . 692: 694 . . . 733: 770 . . . 775 |
| 8 | 22 . . . 31: 39 . . . 45: 81 . . . 90: 94 . . . 99: 98 . . . 106: 108 . . . 116: 136 . . . 144: 183 . . . 191: 190 . . . 196: 205 . . . 217 |
| 10 | 11 . . . 21: 50 . . . 60: 77 . . . 84: 118 . . . 126 |
| 12 | 81 . . . 88: 142 . . . 150: 180 . . . 186: 194 . . . 203: 219 . . . 227: 251 . . . 261 |
| 14 | 25 . . . 31: 34 . . . 45: 124 . . . 133: 182 . . . 193: 216 . . . 221: 219 . . . 230: 230 . . . 239: 267 . . . 272: 279 . . . 285: 296 . . . 302: 317 . . . 325: 416 . . . 422 |
| 16 | 58 . . . 63: 188 . . . 194: 199 . . . 217 |
| 18 | 22 . . . 36: 151 . . . 156: 161 . . . 169 |
| 20 | 22 . . . 28: 31 . . . 36: 151 . . . 156: 161 . . . 169 |
| 22 | 21 . . . 31: 71 . . . 77: 77 . . . 105 |
| 24 | 1 . . . 14: 20 . . . 44: 50 . . . 59: 82 . . . 99: 101 . . . 113: 153 . . . 162: 163 . . . 169: 175 . . . 194: 254 . . . 259: 291 . . . 298: 326 . . . 331: 353 . . . 361: 368 . . . 378: 381 . . . 386: 394 . . . 406 |
| 26 | 24 . . . 33: 52 . . . 62: 67 . . . 78 |
| 28 | 21 . . . 42: 79 . . . 91: 122 . . . 132: 182 . . . 189: 264 . . . 277: 286 . . . 293: 314 . . . 321: 326 . . . 336: 354 . . . 363 |
| 30 | 1 . . . 17: 22 . . . 28: 30 . . . 42: 48 . . . 55: 93 . . . 101 |
| 32 | 28 . . . 35: 63 . . . 75: 72 . . . 82: 87 . . . 95: 152 . . . 162: 176 . . . 185: 196 . . . 212: 224 . . . 243: 262 . . . 270: 355 . . . 363: 369 . . . 374: 407 . . . 417: 455 . . . 462: 471 . . . 480: 489 . . . 503 |
| 34 | 50 . . . 59: 77 . . . 82: 88 . . . 98: 108 . . . 120: 208 . . . 216: 234 . . . 241 |
| 36 | 16 . . . 22: 63 . . . 83: 87 . . . 112: 145 . . . 151: 168 . . . 174: 189 . . . 195: 221 . . . 232: 236 . . . 244: 281 . . . 291: 290 . . . 307: 304 . . . 320: 334 . . . 341: 344 . . . 355: 361 . . . 373: 418 . . . 433 |
| 38 | 29 . . . 39: 39 . . . 44: 51 . . . 59: 71 . . . 79: 99 . . . 108: 111 . . . 120: 139 . . . 145: 152 . . . 157: 164 . . . 173: 185 . . . 195: 217 . . . 232: 244 . . . 257: 264 . . . 270: 277 . . . 286: 331 . . . 341: 352 . . . 365: 371 . . . 381 |
| 40 | 24 . . . 29: 34 . . . 41: 52 . . . 58: 92 . . . 104: 124 . . . 131: 180 . . . 198: 332 . . . 340: 403 . . . 411: 422 . . . 433: 446 . . . 455 |
| 42 | 66 . . . 73: 91 . . . 102: 113 . . . 130 |
| 46 | 31 . . . 41: 38 . . . 43: 58 . . . 63: 86 . . . 98: 107 . . . 122: 128 . . . 133: 176 . . . 186: 193 . . . 202: 209 . . . 215: 266 . . . 283: 341 . . . 349: 354 . . . 368: 368 . . . 378: 390 . . . 397: 406 . . . 419: 421 . . . 427: 440 . . . 447: 456 . . . 471: 480 . . . 485 |
| 48 | 98 . . . 105: 123 . . . 130 |
| 50 | 30 . . . 40: 53 . . . 68: 114 . . . 119: 128 . . . 139: 157 . . . 166 |
| 52 | 15 . . . 31: 46 . . . 58: 107 . . . 113: 150 . . . 155: 172 . . . 184: 197 . . . 210 |

What is claimed is:

1. A composition of matter comprising an isolated polypeptide comprising:

a) SEQ ID NO: 8;

b) a mature polypeptide consisting of amino acids 1 to 202 of SEQ ID NO: 8; or c) the polypeptide of a) or b) further comprising a physiologically acceptable carrier.

2. The polypeptide of claim 1, wherein said polypeptide belongs to the lipocalin superfamily.

3. The polypeptide of claim 2, wherein said polypeptide is a splice variant of Alpha 1 Microglobulin.

4. The polypeptide of claim 1, wherein said polypeptide is a plasma glycoprotein binding and transporting a small hydrophobic ligand selected from the group consisting of a steroid, a bilin, a retinoid and a lipid.

5. The polypeptide of claim 2, wherein said polypeptide is a plasma glycoprotein binding and transporting a small hydrophobic ligand selected from the group consisting of a steroid, a bilin, a retinoid and a lipid.

6. The polypeptide of claim 3, wherein said polypeptide is a plasma glycoprotein binding and transporting a small hydrophobic ligand selected from the group consisting of a steroid, a bilin, a retinoid and a lipid.

* * * * *

SEQUENCE LISTING

```
<160> NUMBER OF SEQ ID NOS: 52

<210> SEQ ID NO 1
<211> LENGTH: 850
<212> TYPE: DNA
<213> ORGANISM: Homo sapiens
```

-continued

```
<220> FEATURE:
<221> NAME/KEY: 5'UTR
<222> LOCATION: 1..224
<220> FEATURE:
<221> NAME/KEY: CDS
<222> LOCATION: 225..593
<220> FEATURE:
<221> NAME/KEY: 3'UTR
<222> LOCATION: 594..850
<220> FEATURE:
<221> NAME/KEY: polyA_signal
<222> LOCATION: 769..774
<220> FEATURE:
<221> NAME/KEY: polyA_site
<222> LOCATION: 800..850

<400> SEQUENCE: 1

atatagctct ctctaacctg ggattcctgg gctcaagcag tcctcttgcc ttagtctcct     60

aagtggctag gaaggactac gggcctgtcc caccacacct ggctaatttt ttcatttttg    120

tgtgtgggcg tgggggcagt cttgcccagg ctggtctgga actcctggcc tcaagtgatc    180

ctcctccgtc aagatatgaa caggagtaca gctgtgtagt aaag atg cct tct ggt     236
                                                 Met Pro Ser Gly
                                                 1

gaa ttt gca cgt ata tgc cga gat ctc agc cat att gga gat gct gtt      284
Glu Phe Ala Arg Ile Cys Arg Asp Leu Ser His Ile Gly Asp Ala Val
5                   10                  15                  20

gta att tcc tgt gca aaa gac gga gtg aaa ttt tct gca agt gga gaa      332
Val Ile Ser Cys Ala Lys Asp Gly Val Lys Phe Ser Ala Ser Gly Glu
                25                  30                  35

ctt gga aat gga aac att aaa ttg tca cag aca agt aat gtc gat aaa      380
Leu Gly Asn Gly Asn Ile Lys Leu Ser Gln Thr Ser Asn Val Asp Lys
            40                  45                  50

gag gag gaa gct gtt acc ata gag atg aat gaa cca gtt caa cta act      428
Glu Glu Glu Ala Val Thr Ile Glu Met Asn Glu Pro Val Gln Leu Thr
        55                  60                  65

ttt gca ctg agg tac ctg aac ttc ttt aca aaa gcc act cca ctc tct      476
Phe Ala Leu Arg Tyr Leu Asn Phe Phe Thr Lys Ala Thr Pro Leu Ser
    70                  75                  80

tca acg gtg aca ctc agt atg tct gca gat gta ccc ctt gtt gta gag      524
Ser Thr Val Thr Leu Ser Met Ser Ala Asp Val Pro Leu Val Val Glu
85                  90                  95                  100

tat aaa att gcg gat atg gga cac tta aaa tac tac ttg gct ccc aag      572
Tyr Lys Ile Ala Asp Met Gly His Leu Lys Tyr Tyr Leu Ala Pro Lys
                105                 110                 115

atc gag gat gaa gaa gga tct taggcattct taaaattcaa gaaaataaaa         623
Ile Glu Asp Glu Glu Gly Ser
            120

ctaagctctt tgagaactgc ttctaagatg ccagcatata ctgaagtctt ttctgtcacc    683

aaatttgtac ctctaagtac atatgtagat attgttttct gtaaataacc tatttttttc    743

tctattctct gcaatttgtt taaagaataa agtccaaagt cagatctggt ctagttaaaa    803

aaaaaaaaaa aaaaaaaaaa aaaaaaaaaa rgaaaaaaaa aaaaaaa                   850


<210> SEQ ID NO 2
<211> LENGTH: 123
<212> TYPE: PRT
<213> ORGANISM: Homo sapiens

<400> SEQUENCE: 2

Met Pro Ser Gly Glu Phe Ala Arg Ile Cys Arg Asp Leu Ser His Ile
1               5                   10                  15
```

-continued

```
Gly Asp Ala Val Val Ile Ser Cys Ala Lys Asp Gly Val Lys Phe Ser
            20                  25                  30

Ala Ser Gly Glu Leu Gly Asn Gly Asn Ile Lys Leu Ser Gln Thr Ser
        35                  40                  45

Asn Val Asp Lys Glu Glu Glu Ala Val Thr Ile Glu Met Asn Glu Pro
    50                  55                  60

Val Gln Leu Thr Phe Ala Leu Arg Tyr Leu Asn Phe Phe Thr Lys Ala
65                  70                  75                  80

Thr Pro Leu Ser Ser Thr Val Thr Leu Ser Met Ser Ala Asp Val Pro
                85                  90                  95

Leu Val Val Glu Tyr Lys Ile Ala Asp Met Gly His Leu Lys Tyr Tyr
            100                 105                 110

Leu Ala Pro Lys Ile Glu Asp Glu Glu Gly Ser
        115                 120


<210> SEQ ID NO 3
<211> LENGTH: 883
<212> TYPE: DNA
<213> ORGANISM: Homo sapiens
<220> FEATURE:
<221> NAME/KEY: 5'UTR
<222> LOCATION: 1..90
<220> FEATURE:
<221> NAME/KEY: CDS
<222> LOCATION: 91..777
<220> FEATURE:
<221> NAME/KEY: 3'UTR
<222> LOCATION: 778..883
<220> FEATURE:
<221> NAME/KEY: polyA_signal
<222> LOCATION: 826..831
<220> FEATURE:
<221> NAME/KEY: polyA_site
<222> LOCATION: 848..883

<400> SEQUENCE: 3

ataaactgac agatactgaa attgtaaagt tcgaaactac attttgcaaa gtcattgaac      60

tctgagctca gttgcagtac tcgggaagcc atg cag gat gaa gat gga tac atc      114
                                 Met Gln Asp Glu Asp Gly Tyr Ile
                                 1               5

acc tta aat att aaa act cgg aaa cca gct ctc gtc tcc gtt ggc tct      162
Thr Leu Asn Ile Lys Thr Arg Lys Pro Ala Leu Val Ser Val Gly Ser
    10                  15                  20

gca tcc tcc tcc tgg tgg cgt gtg atg gct ttg att ctg ctg atc ctg      210
Ala Ser Ser Ser Trp Trp Arg Val Met Ala Leu Ile Leu Leu Ile Leu
25                  30                  35                  40

tgc gtg ggg atg gtt gtc ggg ctg gtg gct ctg ggg att tgg tct gtc      258
Cys Val Gly Met Val Val Gly Leu Val Ala Leu Gly Ile Trp Ser Val
                45                  50                  55

atg cag cgc aat tac cta caa gat gag aat gaa aat cgc aca gga act      306
Met Gln Arg Asn Tyr Leu Gln Asp Glu Asn Glu Asn Arg Thr Gly Thr
            60                  65                  70

ctg caa caa tta gca aag cgc ttc tgt caa tat gtg gta aaa caa tca      354
Leu Gln Gln Leu Ala Lys Arg Phe Cys Gln Tyr Val Val Lys Gln Ser
        75                  80                  85

gaa cta aag ggc act ttc aaa ggt cat aaa tgc agc ccc tgt gac aca      402
Glu Leu Lys Gly Thr Phe Lys Gly His Lys Cys Ser Pro Cys Asp Thr
    90                  95                  100

aac tgg aga tat tat gga gat agc tgc tat ggg ttc ttc agg cac aac      450
Asn Trp Arg Tyr Tyr Gly Asp Ser Cys Tyr Gly Phe Phe Arg His Asn
105                 110                 115                 120

tta aca tgg gaa gag agt aag cag tac tgc act gac atg aat gct act      498
```

-continued

```
Leu Thr Trp Glu Glu Ser Lys Gln Tyr Cys Thr Asp Met Asn Ala Thr
                125                 130                 135

ctc ctg aag att gac aac cgg aac att gtg gag tac atc aaa gcc agg      546
Leu Leu Lys Ile Asp Asn Arg Asn Ile Val Glu Tyr Ile Lys Ala Arg
            140                 145                 150

act cat tta att cgt tgg gtc gga tta tct cgc cag aag tcg aat gag      594
Thr His Leu Ile Arg Trp Val Gly Leu Ser Arg Gln Lys Ser Asn Glu
        155                 160                 165

gtc tgg aag tgg gag gat ggc tcg gtt atc tca gaa aat atg ttt gag      642
Val Trp Lys Trp Glu Asp Gly Ser Val Ile Ser Glu Asn Met Phe Glu
    170                 175                 180

ttt ttg gaa gat gga aaa gga aat atg aat tgt gct tat ttt cat aat      690
Phe Leu Glu Asp Gly Lys Gly Asn Met Asn Cys Ala Tyr Phe His Asn
185                 190                 195                 200

ggg aaa atg cac cct acc ttc tgt gag aac aaa cat tat tta atg tgt      738
Gly Lys Met His Pro Thr Phe Cys Glu Asn Lys His Tyr Leu Met Cys
                205                 210                 215

gag agg aag gct ggc atg acc aag gtg gac caa cta cct taatgcaaag       787
Glu Arg Lys Ala Gly Met Thr Lys Val Asp Gln Leu Pro
            220                 225

aggtggacag gataacacag ataagggctt tattgtacaa taaaagatat gtatgaatgc    847

aaaaaaaaaa aaaaaaaaat aaaaaaaaaa aaaaaa                              883


<210> SEQ ID NO 4
<211> LENGTH: 229
<212> TYPE: PRT
<213> ORGANISM: Homo sapiens

<400> SEQUENCE: 4

Met Gln Asp Glu Asp Gly Tyr Ile Thr Leu Asn Ile Lys Thr Arg Lys
1               5                   10                  15

Pro Ala Leu Val Ser Val Gly Ser Ala Ser Ser Ser Trp Trp Arg Val
            20                  25                  30

Met Ala Leu Ile Leu Leu Ile Leu Cys Val Gly Met Val Val Gly Leu
        35                  40                  45

Val Ala Leu Gly Ile Trp Ser Val Met Gln Arg Asn Tyr Leu Gln Asp
    50                  55                  60

Glu Asn Glu Asn Arg Thr Gly Thr Leu Gln Gln Leu Ala Lys Arg Phe
65                  70                  75                  80

Cys Gln Tyr Val Val Lys Gln Ser Glu Leu Lys Gly Thr Phe Lys Gly
                85                  90                  95

His Lys Cys Ser Pro Cys Asp Thr Asn Trp Arg Tyr Tyr Gly Asp Ser
            100                 105                 110

Cys Tyr Gly Phe Phe Arg His Asn Leu Thr Trp Glu Glu Ser Lys Gln
        115                 120                 125

Tyr Cys Thr Asp Met Asn Ala Thr Leu Leu Lys Ile Asp Asn Arg Asn
    130                 135                 140

Ile Val Glu Tyr Ile Lys Ala Arg Thr His Leu Ile Arg Trp Val Gly
145                 150                 155                 160

Leu Ser Arg Gln Lys Ser Asn Glu Val Trp Lys Trp Glu Asp Gly Ser
                165                 170                 175

Val Ile Ser Glu Asn Met Phe Glu Phe Leu Glu Asp Gly Lys Gly Asn
            180                 185                 190

Met Asn Cys Ala Tyr Phe His Asn Gly Lys Met His Pro Thr Phe Cys
        195                 200                 205

Glu Asn Lys His Tyr Leu Met Cys Glu Arg Lys Ala Gly Met Thr Lys
```

```
    210                 215                 220

Val Asp Gln Leu Pro
225


<210> SEQ ID NO 5
<211> LENGTH: 3230
<212> TYPE: DNA
<213> ORGANISM: Homo sapiens
<220> FEATURE:
<221> NAME/KEY: 5'UTR
<222> LOCATION: 1..234
<220> FEATURE:
<221> NAME/KEY: CDS
<222> LOCATION: 235..2562
<220> FEATURE:
<221> NAME/KEY: 3'UTR
<222> LOCATION: 2563..3230

<400> SEQUENCE: 5

agtgtgttta agactagggt catgcccaca tcaatctcag attcccattt tatctttctt      60

ttttggtatc actcctagta ccaagtcttg tgtctgtcaa tatcctgtcc aaaaaagaaa     120

aacacaccaa ggaaaattaa tataggaaaa atttaaaaag ttattagagg actgaaaata     180

taaaaatgga acactgaaag acacagagtt tttattttca gcactgcagc tctg atg       237
                                                            Met
                                                            1

gtc cag ctc cac cag gac aca gat ccc cag atc cct aaa ggt cag cca       285
Val Gln Leu His Gln Asp Thr Asp Pro Gln Ile Pro Lys Gly Gln Pro
            5                   10                  15

tgc acc ctg aac agc tca gag gga gga gcc agg cca gca gtg cct cac       333
Cys Thr Leu Asn Ser Ser Glu Gly Gly Ala Arg Pro Ala Val Pro His
        20                  25                  30

acc ttg ttc tct tct gct cta gac aga tgg ctc cat aat gac agc ttc       381
Thr Leu Phe Ser Ser Ala Leu Asp Arg Trp Leu His Asn Asp Ser Phe
    35                  40                  45

ata atg gca gtg ggt gag ccc ctg gtg cac atc agg gtc act ctt ctg       429
Ile Met Ala Val Gly Glu Pro Leu Val His Ile Arg Val Thr Leu Leu
50                  55                  60                  65

ctg ctc tgg ttt gga atg ttt ttg tct att tct ggc cac tct cag gcc       477
Leu Leu Trp Phe Gly Met Phe Leu Ser Ile Ser Gly His Ser Gln Ala
                70                  75                  80

agg ccc tcc cag tat ttc act tct cca gaa gtg gtg atc cct ttg aag       525
Arg Pro Ser Gln Tyr Phe Thr Ser Pro Glu Val Val Ile Pro Leu Lys
            85                  90                  95

gtg atc agc agg ggc aga ggt gca aag gct cct gga tgg ctc tcc tat       573
Val Ile Ser Arg Gly Arg Gly Ala Lys Ala Pro Gly Trp Leu Ser Tyr
        100                 105                 110

agc ctg cgg ttt ggg gga cag aga tac att gtc cac atg agg gta aat       621
Ser Leu Arg Phe Gly Gly Gln Arg Tyr Ile Val His Met Arg Val Asn
    115                 120                 125

aag ctg ttg ttt gct gca cac ctt cct gtg ttc acc tac aca gag cag       669
Lys Leu Leu Phe Ala Ala His Leu Pro Val Phe Thr Tyr Thr Glu Gln
130                 135                 140                 145

cat gcc ctg ctc cag gat cag ccc ttc atc cag gat gac tgc tac tac       717
His Ala Leu Leu Gln Asp Gln Pro Phe Ile Gln Asp Asp Cys Tyr Tyr
                150                 155                 160

cat ggt tat gtg gag ggg gtc cct gag tcc ttg gtt gcc ctt agt acc       765
His Gly Tyr Val Glu Gly Val Pro Glu Ser Leu Val Ala Leu Ser Thr
            165                 170                 175

tgt tct ggg ggc ttt ctt gga atg cta cag ata aat gac ctt gtt tat       813
Cys Ser Gly Gly Phe Leu Gly Met Leu Gln Ile Asn Asp Leu Val Tyr
        180                 185                 190
```

-continued

```
gaa atc aag cca att agt gtt tct gcc aca ttt gaa cac cta gta tat      861
Glu Ile Lys Pro Ile Ser Val Ser Ala Thr Phe Glu His Leu Val Tyr
    195                 200                 205

aag ata gac agt gat gat aca cag ttt cca cct atg aga tgt ggg tta      909
Lys Ile Asp Ser Asp Asp Thr Gln Phe Pro Pro Met Arg Cys Gly Leu
210                 215                 220                 225

aca gaa gag aaa ata gca cac cag atg gag ttg caa ttg tca tat aat      957
Thr Glu Glu Lys Ile Ala His Gln Met Glu Leu Gln Leu Ser Tyr Asn
                230                 235                 240

ttc act ctg aag caa agt tct ttt gtg ggc tgg tgg acc cat cag cgg     1005
Phe Thr Leu Lys Gln Ser Ser Phe Val Gly Trp Trp Thr His Gln Arg
            245                 250                 255

ttt gtt gag ctg gta gtg gtc gtg gat aat att aga tat ctt ttc tct     1053
Phe Val Glu Leu Val Val Val Val Asp Asn Ile Arg Tyr Leu Phe Ser
        260                 265                 270

caa agt aat gca aca aca gtg cag cat gaa gta ttt aac gtt gtc aat     1101
Gln Ser Asn Ala Thr Thr Val Gln His Glu Val Phe Asn Val Val Asn
    275                 280                 285

ata gtg gat tcc ttc tat cat cct ttg gag gtt gat gta att ttg act     1149
Ile Val Asp Ser Phe Tyr His Pro Leu Glu Val Asp Val Ile Leu Thr
290                 295                 300                 305

gga att gat ata tgg act gca tca aat cca ctt cct acc agt gga gac     1197
Gly Ile Asp Ile Trp Thr Ala Ser Asn Pro Leu Pro Thr Ser Gly Asp
                310                 315                 320

cta gat aat gtt tta gag gac ttt tct att tgg aag aat tat aac ctt     1245
Leu Asp Asn Val Leu Glu Asp Phe Ser Ile Trp Lys Asn Tyr Asn Leu
            325                 330                 335

aat aat cga cta caa cat gat gtt gca cat ctt ttc ata aaa gac aca     1293
Asn Asn Arg Leu Gln His Asp Val Ala His Leu Phe Ile Lys Asp Thr
        340                 345                 350

caa ggc atg aag ctt ggt gtt gcc tat gtt aaa gga ata tgc cag aat     1341
Gln Gly Met Lys Leu Gly Val Ala Tyr Val Lys Gly Ile Cys Gln Asn
    355                 360                 365

cct ttt aat act gga gtt gat gtt ttt gaa gac aac agg ttg gtc gtt     1389
Pro Phe Asn Thr Gly Val Asp Val Phe Glu Asp Asn Arg Leu Val Val
370                 375                 380                 385

ttt gca att act ttg ggc cac gag ctt ggt cat aat ttg ggt atg caa     1437
Phe Ala Ile Thr Leu Gly His Glu Leu Gly His Asn Leu Gly Met Gln
                390                 395                 400

cat gac acc cag tgg tgt gtg tgc gag cta cag tgg tgc ata atg cat     1485
His Asp Thr Gln Trp Cys Val Cys Glu Leu Gln Trp Cys Ile Met His
            405                 410                 415

gcc tat aga aag gtg aca act aaa ttt agc aac tgc agt tat gcc caa     1533
Ala Tyr Arg Lys Val Thr Thr Lys Phe Ser Asn Cys Ser Tyr Ala Gln
        420                 425                 430

tat tgg gac agt act atc agt agt gga tta tgt att caa ccg cct cca     1581
Tyr Trp Asp Ser Thr Ile Ser Ser Gly Leu Cys Ile Gln Pro Pro Pro
    435                 440                 445

tat cca ggg aat ata ttt aga ctg aag tac tgt ggg aat cta gtg gtt     1629
Tyr Pro Gly Asn Ile Phe Arg Leu Lys Tyr Cys Gly Asn Leu Val Val
450                 455                 460                 465

gaa gaa ggg gag gaa tgt gac tgt gga acc ata cgg cag tgt gca aaa     1677
Glu Glu Gly Glu Glu Cys Asp Cys Gly Thr Ile Arg Gln Cys Ala Lys
                470                 475                 480

gat ccc tgt tgt ctg tta aac tgt act cta cat cct ggg gct gct tgt     1725
Asp Pro Cys Cys Leu Leu Asn Cys Thr Leu His Pro Gly Ala Ala Cys
            485                 490                 495

gct ttt gga ata tgt tgc aaa gac tgc aaa ttt ctg cca tca gga act     1773
Ala Phe Gly Ile Cys Cys Lys Asp Cys Lys Phe Leu Pro Ser Gly Thr
```

-continued

```
        500                 505                 510

tta tgt aga caa caa gtt ggt gaa tgt gac ctt cca gag tgg tgc aat      1821
Leu Cys Arg Gln Gln Val Gly Glu Cys Asp Leu Pro Glu Trp Cys Asn
    515                 520                 525

ggg aca tcc cat caa tgc cca gat gat gtg tat gtg cag gac ggg atc      1869
Gly Thr Ser His Gln Cys Pro Asp Asp Val Tyr Val Gln Asp Gly Ile
530                 535                 540                 545

tcc tgt aat gtg aat gcc ttc tgc tat gaa aag acg tgt aat aac cat      1917
Ser Cys Asn Val Asn Ala Phe Cys Tyr Glu Lys Thr Cys Asn Asn His
                550                 555                 560

gat ata caa tgt aaa gag att ttt ggc caa gat gca agg agt gca tct      1965
Asp Ile Gln Cys Lys Glu Ile Phe Gly Gln Asp Ala Arg Ser Ala Ser
            565                 570                 575

cag agt tgc tac caa gaa atc aac acc caa gga aac cgt ttc ggt cac      2013
Gln Ser Cys Tyr Gln Glu Ile Asn Thr Gln Gly Asn Arg Phe Gly His
        580                 585                 590

tgt ggt att gta ggc aca aca tat gta aaa tgt tgg acc cct gat atc      2061
Cys Gly Ile Val Gly Thr Thr Tyr Val Lys Cys Trp Thr Pro Asp Ile
    595                 600                 605

atg tgt ggg agg gtt cag tgt gaa aat gtg gga gta att ccc aat ctg      2109
Met Cys Gly Arg Val Gln Cys Glu Asn Val Gly Val Ile Pro Asn Leu
610                 615                 620                 625

ata gag cat tct aca gtg cag cag ttt cac ctc aat gac acc act tgc      2157
Ile Glu His Ser Thr Val Gln Gln Phe His Leu Asn Asp Thr Thr Cys
                630                 635                 640

tgg ggc act gat tat cat tta ggg atg gct ata cct gat att ggt gag      2205
Trp Gly Thr Asp Tyr His Leu Gly Met Ala Ile Pro Asp Ile Gly Glu
            645                 650                 655

gtg aaa gat ggc aca gta tgt ggt cca gaa aag atc tgc atc cgt aag      2253
Val Lys Asp Gly Thr Val Cys Gly Pro Glu Lys Ile Cys Ile Arg Lys
        660                 665                 670

aag tgt gcc agt atg gtt cat ctg tca caa gcc tgt cag cct aag acc      2301
Lys Cys Ala Ser Met Val His Leu Ser Gln Ala Cys Gln Pro Lys Thr
    675                 680                 685

tgc aac atg agg gga atc tgc aac aac aaa caa cac tgt cac tgc aac      2349
Cys Asn Met Arg Gly Ile Cys Asn Asn Lys Gln His Cys His Cys Asn
690                 695                 700                 705

cat gaa tgg gca ccc cca tac tgc aag gac aaa ggc tat gga ggt agt      2397
His Glu Trp Ala Pro Pro Tyr Cys Lys Asp Lys Gly Tyr Gly Gly Ser
                710                 715                 720

gct gat agt ggc cca cct cct aag aac aac atg gaa gga tta aat gtg      2445
Ala Asp Ser Gly Pro Pro Pro Lys Asn Asn Met Glu Gly Leu Asn Val
            725                 730                 735

atg gga aag ttg cgt tac ctg tca cta ttg tgc ctt ctt cct ttg gtt      2493
Met Gly Lys Leu Arg Tyr Leu Ser Leu Leu Cys Leu Leu Pro Leu Val
        740                 745                 750

gct ttt tta tta ttt tgc tta cat gtg ctt ttt aag aaa cgc aca aaa      2541
Ala Phe Leu Leu Phe Cys Leu His Val Leu Phe Lys Lys Arg Thr Lys
    755                 760                 765

agt aaa gaa gat gaa gaa gga taagagaaat gggaaaaaga aggagactaa        2592
Ser Lys Glu Asp Glu Glu Gly
770                 775

actttatact tcatttttaa tatccaattt tttaatagaa aaatatgaag ccatgtctca   2652

ctgtttaaat aaaacttcat ggacatttca tgtcaggatt gcaagcatta gctatcacag   2712

caaaggattc ctagcctatt cttacttact ctacagtgtc ttaagcaata ttaaaggttc   2772

cttttcccag aagttgtgtc tttatgtttc ctgagcaaag gcacagaaaa gatagtttca   2832

agctgttgtc cctcattttt aactctcctc tctctctctc tctttttttt tttttttttg   2892
```

-continued

```
ctgtactatg taatgttcag gatgtgcctg tacacaactc atttctgttt ggcacattca   2952

gctgtgccaa agggggcagt agaagtagcc tggagtgatg atgagggaag aagggagctt   3012

tctttcctgt gtgcttacca tgagtgtcac cattattttg gttggggcca ttcactctgg   3072

caattatatt tggtttcaga ttccagttct gttgtcactt ttagaaccac cctcattttt   3132

ccttagaaat accagcagca gttggacact gacctcctta ggggtccggg agtgagcagg   3192

gttgtggtcc tctgagttct tgaagcagca gcagctgt                            3230


<210> SEQ ID NO 6
<211> LENGTH: 776
<212> TYPE: PRT
<213> ORGANISM: Homo sapiens

<400> SEQUENCE: 6

Met Val Gln Leu His Gln Asp Thr Asp Pro Gln Ile Pro Lys Gly Gln
1               5                   10                  15

Pro Cys Thr Leu Asn Ser Ser Glu Gly Gly Ala Arg Pro Ala Val Pro
            20                  25                  30

His Thr Leu Phe Ser Ser Ala Leu Asp Arg Trp Leu His Asn Asp Ser
        35                  40                  45

Phe Ile Met Ala Val Gly Glu Pro Leu Val His Ile Arg Val Thr Leu
    50                  55                  60

Leu Leu Leu Trp Phe Gly Met Phe Leu Ser Ile Ser Gly His Ser Gln
65                  70                  75                  80

Ala Arg Pro Ser Gln Tyr Phe Thr Ser Pro Glu Val Val Ile Pro Leu
                85                  90                  95

Lys Val Ile Ser Arg Gly Arg Gly Ala Lys Ala Pro Gly Trp Leu Ser
            100                 105                 110

Tyr Ser Leu Arg Phe Gly Gly Gln Arg Tyr Ile Val His Met Arg Val
        115                 120                 125

Asn Lys Leu Leu Phe Ala Ala His Leu Pro Val Phe Thr Tyr Thr Glu
    130                 135                 140

Gln His Ala Leu Leu Gln Asp Gln Pro Phe Ile Gln Asp Asp Cys Tyr
145                 150                 155                 160

Tyr His Gly Tyr Val Glu Gly Val Pro Glu Ser Leu Val Ala Leu Ser
                165                 170                 175

Thr Cys Ser Gly Gly Phe Leu Gly Met Leu Gln Ile Asn Asp Leu Val
            180                 185                 190

Tyr Glu Ile Lys Pro Ile Ser Val Ser Ala Thr Phe Glu His Leu Val
        195                 200                 205

Tyr Lys Ile Asp Ser Asp Asp Thr Gln Phe Pro Pro Met Arg Cys Gly
    210                 215                 220

Leu Thr Glu Glu Lys Ile Ala His Gln Met Glu Leu Gln Leu Ser Tyr
225                 230                 235                 240

Asn Phe Thr Leu Lys Gln Ser Ser Phe Val Gly Trp Trp Thr His Gln
                245                 250                 255

Arg Phe Val Glu Leu Val Val Val Val Asp Asn Ile Arg Tyr Leu Phe
            260                 265                 270

Ser Gln Ser Asn Ala Thr Thr Val Gln His Glu Val Phe Asn Val Val
        275                 280                 285

Asn Ile Val Asp Ser Phe Tyr His Pro Leu Glu Val Asp Val Ile Leu
    290                 295                 300

Thr Gly Ile Asp Ile Trp Thr Ala Ser Asn Pro Leu Pro Thr Ser Gly
```

-continued

```
305                 310                 315                 320

Asp Leu Asp Asn Val Leu Glu Asp Phe Ser Ile Trp Lys Asn Tyr Asn
                325                 330                 335

Leu Asn Asn Arg Leu Gln His Asp Val Ala His Leu Phe Ile Lys Asp
            340                 345                 350

Thr Gln Gly Met Lys Leu Gly Val Ala Tyr Val Lys Gly Ile Cys Gln
        355                 360                 365

Asn Pro Phe Asn Thr Gly Val Asp Val Phe Glu Asp Asn Arg Leu Val
    370                 375                 380

Val Phe Ala Ile Thr Leu Gly His Glu Leu Gly His Asn Leu Gly Met
385                 390                 395                 400

Gln His Asp Thr Gln Trp Cys Val Cys Glu Leu Gln Trp Cys Ile Met
                405                 410                 415

His Ala Tyr Arg Lys Val Thr Thr Lys Phe Ser Asn Cys Ser Tyr Ala
            420                 425                 430

Gln Tyr Trp Asp Ser Thr Ile Ser Ser Gly Leu Cys Ile Gln Pro Pro
        435                 440                 445

Pro Tyr Pro Gly Asn Ile Phe Arg Leu Lys Tyr Cys Gly Asn Leu Val
    450                 455                 460

Val Glu Glu Gly Glu Glu Cys Asp Cys Gly Thr Ile Arg Gln Cys Ala
465                 470                 475                 480

Lys Asp Pro Cys Cys Leu Leu Asn Cys Thr Leu His Pro Gly Ala Ala
                485                 490                 495

Cys Ala Phe Gly Ile Cys Cys Lys Asp Cys Lys Phe Leu Pro Ser Gly
            500                 505                 510

Thr Leu Cys Arg Gln Gln Val Gly Glu Cys Asp Leu Pro Glu Trp Cys
        515                 520                 525

Asn Gly Thr Ser His Gln Cys Pro Asp Asp Val Tyr Val Gln Asp Gly
    530                 535                 540

Ile Ser Cys Asn Val Asn Ala Phe Cys Tyr Glu Lys Thr Cys Asn Asn
545                 550                 555                 560

His Asp Ile Gln Cys Lys Glu Ile Phe Gly Gln Asp Ala Arg Ser Ala
                565                 570                 575

Ser Gln Ser Cys Tyr Gln Glu Ile Asn Thr Gln Gly Asn Arg Phe Gly
            580                 585                 590

His Cys Gly Ile Val Gly Thr Thr Tyr Val Lys Cys Trp Thr Pro Asp
        595                 600                 605

Ile Met Cys Gly Arg Val Gln Cys Glu Asn Val Gly Val Ile Pro Asn
    610                 615                 620

Leu Ile Glu His Ser Thr Val Gln Gln Phe His Leu Asn Asp Thr Thr
625                 630                 635                 640

Cys Trp Gly Thr Asp Tyr His Leu Gly Met Ala Ile Pro Asp Ile Gly
                645                 650                 655

Glu Val Lys Asp Gly Thr Val Cys Gly Pro Glu Lys Ile Cys Ile Arg
            660                 665                 670

Lys Lys Cys Ala Ser Met Val His Leu Ser Gln Ala Cys Gln Pro Lys
        675                 680                 685

Thr Cys Asn Met Arg Gly Ile Cys Asn Asn Lys Gln His Cys His Cys
    690                 695                 700

Asn His Glu Trp Ala Pro Pro Tyr Cys Lys Asp Lys Gly Tyr Gly Gly
705                 710                 715                 720

Ser Ala Asp Ser Gly Pro Pro Pro Lys Asn Asn Met Glu Gly Leu Asn
                725                 730                 735
```

-continued

```
Val Met Gly Lys Leu Arg Tyr Leu Ser Leu Leu Cys Leu Leu Pro Leu
            740                 745                 750

Val Ala Phe Leu Leu Phe Cys Leu His Val Leu Phe Lys Lys Arg Thr
        755                 760                 765

Lys Ser Lys Glu Asp Glu Glu Gly
    770                 775


<210> SEQ ID NO 7
<211> LENGTH: 1436
<212> TYPE: DNA
<213> ORGANISM: Homo sapiens
<220> FEATURE:
<221> NAME/KEY: 5'UTR
<222> LOCATION: 1..263
<220> FEATURE:
<221> NAME/KEY: CDS
<222> LOCATION: 264..926
<220> FEATURE:
<221> NAME/KEY: 3'UTR
<222> LOCATION: 927..1436
<220> FEATURE:
<221> NAME/KEY: polyA_signal
<222> LOCATION: 1404..1409
<220> FEATURE:
<221> NAME/KEY: polyA_site
<222> LOCATION: 1421..1436

<400> SEQUENCE: 7

attgtgcttg gccaatgcct cttctgaagc agccatcccg gcctcttggt actgctgacc     60

ccagccaggc tacagggatc gattggagct gtccttgggg ctgtaattgg ccccagctga    120

gcagggcaaa cactgaggtc aactacaagc cacaggcccc ttccccagcc tcagttcaca    180

gctgccctgt tgcagggagg cggtggccct tctgttgcta gaccgagcct gtgggatata    240

ccaaggcaga ggagcccata gcc atg agg agc ctc ggg gcc ctg ctc ttg ctg    293
                          Met Arg Ser Leu Gly Ala Leu Leu Leu Leu
                                          -15                 -10

ctg agc gcc tgc ctg gcg gtg agc gct ggc cct gtg cca acg ccg ccc      341
Leu Ser Ala Cys Leu Ala Val Ser Ala Gly Pro Val Pro Thr Pro Pro
                -5                  1               5

gac aac atc caa gtg cag gaa aac ttc aat atc tct cgg atc tat ggg      389
Asp Asn Ile Gln Val Gln Glu Asn Phe Asn Ile Ser Arg Ile Tyr Gly
        10                  15                  20

aag tgg tac aac ctg gcc atc ggt tcc acc tgc ccc tgg ctg aag aag      437
Lys Trp Tyr Asn Leu Ala Ile Gly Ser Thr Cys Pro Trp Leu Lys Lys
    25                  30                  35

atc atg gac agg atg aca gtg agc acg ctg gtg ctg gga gag ggc gct      485
Ile Met Asp Arg Met Thr Val Ser Thr Leu Val Leu Gly Glu Gly Ala
40                  45                  50                  55

aca gag gcg gag atc agc atg acc agc act cgt tgg cgg aaa ggt gtc      533
Thr Glu Ala Glu Ile Ser Met Thr Ser Thr Arg Trp Arg Lys Gly Val
                60                  65                  70

tgt gag gag acg tct gga gct tat gag aaa aca gat act gat ggg aag      581
Cys Glu Glu Thr Ser Gly Ala Tyr Glu Lys Thr Asp Thr Asp Gly Lys
            75                  80                  85

ttt ctc tat cac aaa tcc aaa tgg aac ata acc atg gag tcc tat gtg      629
Phe Leu Tyr His Lys Ser Lys Trp Asn Ile Thr Met Glu Ser Tyr Val
        90                  95                  100

gtc cac acc aac tat gat gag tat gcc att ttc ctg acc aag aaa ttc      677
Val His Thr Asn Tyr Asp Glu Tyr Ala Ile Phe Leu Thr Lys Lys Phe
    105                 110                 115

agc cgc cat cat gga ccc acc att act gcc aag ctc tac ggg cgg gcg      725
Ser Arg His His Gly Pro Thr Ile Thr Ala Lys Leu Tyr Gly Arg Ala
```

-continued

```
120                 125                 130                 135

ccg cag ctg agg gaa act ctc ctg cag gac ttc aga gtg gtt gcc cag      773
Pro Gln Leu Arg Glu Thr Leu Leu Gln Asp Phe Arg Val Val Ala Gln
                140                 145                 150

ggt gtg ggc atc cct gag gac tcc atc ttc acc atg gct gac cga ggt      821
Gly Val Gly Ile Pro Glu Asp Ser Ile Phe Thr Met Ala Asp Arg Gly
            155                 160                 165

gaa tgt gtc cct ggg gag cag gaa cca gag ccc atc tta atc ccg aga      869
Glu Cys Val Pro Gly Glu Gln Glu Pro Glu Pro Ile Leu Ile Pro Arg
        170                 175                 180

gtc cgg agg gct gct acc cca aga aga gga agg atc agg ggg tgg gca      917
Val Arg Arg Ala Ala Thr Pro Arg Arg Gly Arg Ile Arg Gly Trp Ala
    185                 190                 195

act ggt aac tgaagtcacc aagaaagaag attcctgcca gctgggctac              966
Thr Gly Asn
200

tcggccggtc cctgcatggg aatgaccagc aggtatttct ataatggtac atccatggcc   1026

tgtgagactt tccagtacgg cggctgcatg ggcaacggta acaacttcgt cacagaaaag   1086

gagtgtctgc agacctgccg aactgtggcg gcctgcaatc tccccatagt ccggggcccc   1146

tgccgagcct tcatccagct ctgggcattt gatgctgtca aggggaagtg cgtcctcttc   1206

ccctacgggg gctgccaggg caacgggaac aagttctact cagagaagga gtgcagagag   1266

tactgcggtg tccctggtga tggtgatgag gagctgctgc gcttctccaa ctgacaactg   1326

gccggtctgc aagtcagagg atggccagtg tctgtcccgg ggtcctgtgg caggcagcgc   1386

caagcaacct gggtccaaat aaaaactaaa ttgcaaaaaa aaaaaaaaaa              1436


<210> SEQ ID NO 8
<211> LENGTH: 221
<212> TYPE: PRT
<213> ORGANISM: Homo sapiens
<220> FEATURE:
<221> NAME/KEY: SIGNAL
<222> LOCATION: 1..19

<400> SEQUENCE: 8

Met Arg Ser Leu Gly Ala Leu Leu Leu Leu Leu Ser Ala Cys Leu Ala
                -15                 -10                 -5

Val Ser Ala Gly Pro Val Pro Thr Pro Pro Asp Asn Ile Gln Val Gln
            1               5                   10

Glu Asn Phe Asn Ile Ser Arg Ile Tyr Gly Lys Trp Tyr Asn Leu Ala
    15                  20                  25

Ile Gly Ser Thr Cys Pro Trp Leu Lys Lys Ile Met Asp Arg Met Thr
30                  35                  40                  45

Val Ser Thr Leu Val Leu Gly Glu Gly Ala Thr Glu Ala Glu Ile Ser
                50                  55                  60

Met Thr Ser Thr Arg Trp Arg Lys Gly Val Cys Glu Glu Thr Ser Gly
            65                  70                  75

Ala Tyr Glu Lys Thr Asp Thr Asp Gly Lys Phe Leu Tyr His Lys Ser
        80                  85                  90

Lys Trp Asn Ile Thr Met Glu Ser Tyr Val Val His Thr Asn Tyr Asp
    95                  100                 105

Glu Tyr Ala Ile Phe Leu Thr Lys Lys Phe Ser Arg His His Gly Pro
110                 115                 120                 125

Thr Ile Thr Ala Lys Leu Tyr Gly Arg Ala Pro Gln Leu Arg Glu Thr
                130                 135                 140
```

-continued

```
Leu Leu Gln Asp Phe Arg Val Val Ala Gln Gly Val Gly Ile Pro Glu
            145                 150                 155

Asp Ser Ile Phe Thr Met Ala Asp Arg Gly Glu Cys Val Pro Gly Glu
        160                 165                 170

Gln Glu Pro Glu Pro Ile Leu Ile Pro Arg Val Arg Arg Ala Ala Thr
    175                 180                 185

Pro Arg Arg Gly Arg Ile Arg Gly Trp Ala Thr Gly Asn
190                 195                 200


<210> SEQ ID NO 9
<211> LENGTH: 2132
<212> TYPE: DNA
<213> ORGANISM: Homo sapiens
<220> FEATURE:
<221> NAME/KEY: 5'UTR
<222> LOCATION: 1..92
<220> FEATURE:
<221> NAME/KEY: CDS
<222> LOCATION: 93..551
<220> FEATURE:
<221> NAME/KEY: 3'UTR
<222> LOCATION: 552..2132
<220> FEATURE:
<221> NAME/KEY: polyA_signal
<222> LOCATION: 2085..2090
<220> FEATURE:
<221> NAME/KEY: polyA_site
<222> LOCATION: 2117..2132

<400> SEQUENCE: 9

gagatgtggt tctgcgcgtg tgcggacggc tgtctgttaa ctccgcggtc agttcccgga      60

ctggtggctg gtctgcaggg ttgacctgcg ca atg cag agg ctg cag gta gtg       113
                                    Met Gln Arg Leu Gln Val Val
                                    -35                 -30

ctg ggc cac ctg agg ggt ccg gcc gat tcc ggc tgg atg ccg cag gcc       161
Leu Gly His Leu Arg Gly Pro Ala Asp Ser Gly Trp Met Pro Gln Ala
            -25                 -20                 -15

gcg cct tgc ctg agc ggt gcc ccg cag gcc tcg gcc gcg gac gtg gtg       209
Ala Pro Cys Leu Ser Gly Ala Pro Gln Ala Ser Ala Ala Asp Val Val
        -10                 -5                  1

gtg gtg cac ggg cgg cgc acg gcc atc tgc cgg gcg ggc cgc ggc ggc       257
Val Val His Gly Arg Arg Thr Ala Ile Cys Arg Ala Gly Arg Gly Gly
5                   10                  15                  20

ttc aag gac acc acc ccc gac gag ctt ctc tcg gca gtc atg acc gcg       305
Phe Lys Asp Thr Thr Pro Asp Glu Leu Leu Ser Ala Val Met Thr Ala
                25                  30                  35

gtt ctc aag gac gtg aat ctg agg ccg gaa cag ctg ggg gac atc tgt       353
Val Leu Lys Asp Val Asn Leu Arg Pro Glu Gln Leu Gly Asp Ile Cys
            40                  45                  50

gtc gga aat gtg ctg cag cct ggg gcc ggg gca atc atg gcc cga atc       401
Val Gly Asn Val Leu Gln Pro Gly Ala Gly Ala Ile Met Ala Arg Ile
        55                  60                  65

gcc cag ttt ctg agt gac atc ccg gag act gtg cct ttg tcc act gtc       449
Ala Gln Phe Leu Ser Asp Ile Pro Glu Thr Val Pro Leu Ser Thr Val
    70                  75                  80

aat aga cag tgt tcg tcg ggg cta cag gca gtg gcc agc ata gca ggg       497
Asn Arg Gln Cys Ser Ser Gly Leu Gln Ala Val Ala Ser Ile Ala Gly
85                  90                  95                  100

tgg agt cca tgt ccc tgg ctg aca gag gga acc ctg gaa ata tta ctt       545
Trp Ser Pro Cys Pro Trp Leu Thr Glu Gly Thr Leu Glu Ile Leu Leu
                105                 110                 115

cgc gct tgatggagaa ggagaaggcc agagattgcc tgattcctat ggggataacc        601
Arg Ala
```

```
tctgagaatg tggctgagcg gtttggcatt tcacgggaga agcaggatac ctttgccctg    661

gcttcccagc agaaggcagc aagagcccag agcaagggct gtttccaagc tgagattgtg    721

cctgtgacca ccacggtcca tgatgacaag ggcaccaaga ggagcatcac tgtgacccag    781

gatgagggta tccgccccag caccaccatg gagggcctgg ccaaactgaa gcctgccttc    841

aagaaagatg gttctaccac agctggtgag actggtccgg ggtaggggta tgagaaagca    901

ggccatggcc atgctgggtg ctgtactctg ggaacctgga atagaccagg cccctctgca    961

aagtagaagt gggagggctg ggatctcctc atccccaccc cgatgccttc ttaccccaac   1021

agtttgcccc taggaaactc tagccaggtg agtgatgggg cagctgccat cctgctggcc   1081

cggaggtcca aggcagaaga gttgggcctt cccatccttg ggtcctgag gtcttatgca    1141

gtggttgggg tcccacctga catcatgggc attggacctg cctatgccat cccagtagct   1201

ttgcaaaaag caggtaaggt ggctccttca tatagtatct gggtcccacc tggatcctgc   1261

agctgccctg catgctgttg ccaggggcat gagggtggtc ctgtgggtgc tgcagagtgg   1321

aggtggggca ggctagtgtc ccatacttca agcccttcct gaccccacag ctgggattgg   1381

ctcacccttc tggaagagac acacaccagg cagcctgtag gcccatggat ggggtgggcc   1441

ccaggggagg cagagggcca gtgtgtcagc tcaggtcttt accttgtctg cagggctgac   1501

agtgagtgac gtggacatct tcgagatcaa tgaggccttt gcaagccagg ctgcctactg   1561

tgtggagaag ctacgactcc cccctgagaa ggtgaacccc ctgggggggtg cagtggcctt   1621

agggcaccca ctgggctgca ctggggcacg acaggtcatc acgctgctca atgagctgaa   1681

gcgccgtggg aagagggcat acggagtggt gtccatgtgc atcgggactg gaatgggagc   1741

cgctgccgtc tttgaatacc ctgggaactg agtgaggtcc caggctggag gcgctacgca   1801

gacagtcctg ctgctctagc agcaaggcag taacaccaca aaagcaaaac cacatgggaa   1861

aactcagcac tggtggtggt ggcagtggac agatcaaggc acttcaactc atttggaaaa   1921

tgtgaacact gatgacatgg tataggagtg ggtggggtgt tgagccaccc atcagaccct   1981

ctttagctgt gcaagataaa agcagcctgg gtcacccagg ccacaaggcc atggttaatt   2041

cttaaggcaa ggcaaatcca tggatgagaa gtgcaatggg catagtaaaa gtgcatgaat   2101

ttatcttaaa aaaagaaaaa aaaaaaaaaa a                                  2132
```

<210> SEQ ID NO 10
<211> LENGTH: 153
<212> TYPE: PRT
<213> ORGANISM: Homo sapiens
<220> FEATURE:
<221> NAME/KEY: SIGNAL
<222> LOCATION: 1..35

<400> SEQUENCE: 10

```
Met Gln Arg Leu Gln Val Val Leu Gly His Leu Arg Gly Pro Ala Asp
-35                 -30                 -25                 -20

Ser Gly Trp Met Pro Gln Ala Ala Pro Cys Leu Ser Gly Ala Pro Gln
                -15                 -10                 -5

Ala Ser Ala Ala Asp Val Val Val Val His Gly Arg Arg Thr Ala Ile
            1               5                   10

Cys Arg Ala Gly Arg Gly Gly Phe Lys Asp Thr Thr Pro Asp Glu Leu
    15                  20                  25

Leu Ser Ala Val Met Thr Ala Val Leu Lys Asp Val Asn Leu Arg Pro
30                  35                  40                  45
```

-continued

```
Glu Gln Leu Gly Asp Ile Cys Val Gly Asn Val Leu Gln Pro Gly Ala
                50                  55                  60

Gly Ala Ile Met Ala Arg Ile Ala Gln Phe Leu Ser Asp Ile Pro Glu
            65                  70                  75

Thr Val Pro Leu Ser Thr Val Asn Arg Gln Cys Ser Ser Gly Leu Gln
        80                  85                  90

Ala Val Ala Ser Ile Ala Gly Trp Ser Pro Cys Pro Trp Leu Thr Glu
    95                  100                 105

Gly Thr Leu Glu Ile Leu Leu Arg Ala
110                 115


<210> SEQ ID NO 11
<211> LENGTH: 2266
<212> TYPE: DNA
<213> ORGANISM: Homo sapiens
<220> FEATURE:
<221> NAME/KEY: 5'UTR
<222> LOCATION: 1..200
<220> FEATURE:
<221> NAME/KEY: CDS
<222> LOCATION: 201..986
<220> FEATURE:
<221> NAME/KEY: 3'UTR
<222> LOCATION: 987..2266
<220> FEATURE:
<221> NAME/KEY: polyA_signal
<222> LOCATION: 2233..2238
<220> FEATURE:
<221> NAME/KEY: polyA_site
<222> LOCATION: 2251..2266

<400> SEQUENCE: 11

aacagagcta gactccgtct caagaagaag aagaaggaga agaaggagaa ggagaaggga      60

aaaaagaatc ctcatcatta atgcaagtgg aaggaaactc ttcaccaaag aattgatcac     120

atcatgaaag gtgaaatcat tacggaattg cttaaatata taatttgaat ctggatttaa     180

aaataataaa tgtgatcagg atg ccc ttc tct cat ctg tct acc tac agc ctg     233
                      Met Pro Phe Ser His Leu Ser Thr Tyr Ser Leu
                                  -20                 -15

gtt tgg gtc atg gca gca gtg gtg ctg tgc aca gca caa gtg caa gtg       281
Val Trp Val Met Ala Ala Val Val Leu Cys Thr Ala Gln Val Gln Val
        -10                 -5                  1

gtg acc cag gat gaa aga gag cag ctg tac aca act gct tcc tta aaa       329
Val Thr Gln Asp Glu Arg Glu Gln Leu Tyr Thr Thr Ala Ser Leu Lys
5                   10                  15                  20

tgc tct ctg caa aat gcc cag gaa gcc ctc att gtg aca tgg cag aaa       377
Cys Ser Leu Gln Asn Ala Gln Glu Ala Leu Ile Val Thr Trp Gln Lys
                25                  30                  35

aag aaa gct gta agc cca gaa aac atg gtc acc ttc agc gag aac cat       425
Lys Lys Ala Val Ser Pro Glu Asn Met Val Thr Phe Ser Glu Asn His
            40                  45                  50

ggg gtg gtg atc cag cct gcc tat aag gac aag ata aac att acc cag       473
Gly Val Val Ile Gln Pro Ala Tyr Lys Asp Lys Ile Asn Ile Thr Gln
        55                  60                  65

ctg gga ctc caa aac tca acc atc acc ttc tgg aat atc acc ctg gag       521
Leu Gly Leu Gln Asn Ser Thr Ile Thr Phe Trp Asn Ile Thr Leu Glu
    70                  75                  80

gat gaa ggg tgt tac atg tgt ctc ttc aat acc ttt ggt ttt ggg aag       569
Asp Glu Gly Cys Tyr Met Cys Leu Phe Asn Thr Phe Gly Phe Gly Lys
85                  90                  95                  100

atc tca gga acg gcc tgc ctc acc gtc tat gta cag ccc ata gta tcc       617
Ile Ser Gly Thr Ala Cys Leu Thr Val Tyr Val Gln Pro Ile Val Ser
                105                 110                 115
```

-continued

```
ctt cac tac aaa ttc tct gaa gac cac cta aat atc act tgc tct gcc      665
Leu His Tyr Lys Phe Ser Glu Asp His Leu Asn Ile Thr Cys Ser Ala
            120                 125                 130

act gcc cgc cca gcc ccc atg gtc ttc tgg aag gtc cct cgg tca ggg      713
Thr Ala Arg Pro Ala Pro Met Val Phe Trp Lys Val Pro Arg Ser Gly
        135                 140                 145

att gaa aat agt aca gtg act ctg tct cac cca aat ggg acc acg tct      761
Ile Glu Asn Ser Thr Val Thr Leu Ser His Pro Asn Gly Thr Thr Ser
    150                 155                 160

gtt acc agc atc ctc cat atc aaa gac cct aag aat cag gtg ggg aag      809
Val Thr Ser Ile Leu His Ile Lys Asp Pro Lys Asn Gln Val Gly Lys
165                 170                 175                 180

gag gtg atc tgc cag gtg ctg cac ctg ggg act gtg acc gac ttt aag      857
Glu Val Ile Cys Gln Val Leu His Leu Gly Thr Val Thr Asp Phe Lys
                185                 190                 195

caa acc gtc aac aaa ggc tat tgg ttt tca gtt ccg cta ttg cta agc      905
Gln Thr Val Asn Lys Gly Tyr Trp Phe Ser Val Pro Leu Leu Leu Ser
            200                 205                 210

att gtt tcc ctg gta att ctt ctc gtc cta atc tca atc tta ctg tac      953
Ile Val Ser Leu Val Ile Leu Leu Val Leu Ile Ser Ile Leu Leu Tyr
        215                 220                 225

tgg aaa cgt cac cgg aat cag gac cga gag ccc taaataagtc acacagcacc   1006
Trp Lys Arg His Arg Asn Gln Asp Arg Glu Pro
    230                 235

ctgaaagtga ttccctggtc tacttgaatt tgacacaaga gaaaagcagg agaaaaaggg   1066

gccattctcc aaaggacctg aaagagcaaa agaggtggga gcgaaagcct taaggatccc   1126

acgacttttt actgccatct gagctactca gtgtttgaat cccaagagga agtcagttta   1186

cctctcaggt ctgttgtagg acttgatttt gtaaagcaat gccatgttat gtggttgaaa   1246

gggcactgga cttagttagt atcaggagca ctgagctcac agactgactt gggctcctac   1306

tggtggggac ctctgttagt cactttacct catccaaagt ataaaggaat tggaccaaat   1366

aatttaccac atagctctaa aacttaattt aaaatgtaat tccagaaaaa aaaagggaat   1426

aagcaaaggg ggaagaattg aaagagagag agaagaaaga atacagagag cttacctttt   1486

gcctttctgt tgatgttaca tctcttcttc ctatgttctt aggtctatga gtctgtttcc   1546

ccatcatttg gtatctagtc cagttcctgc ttactgcttt gctaatagct ggccttgcta   1606

gaatccttgg tttcactgct gttcttcatg tgcttctatg agatttactc caacacaaat   1666

aggactgaat ttattgtgaa gtaacattgg caatcttaac ttattcattt aacttatttt   1726

tatagctaga taaatattgt tagtcttaga caatagctca catttttttga gaagcatgcc  1786

ctccctgtcc atttgtctta taacatgacc cagccctatt ttacgtcatt ctaaattcag   1846

cctcatataa tgaaaataca ttatgaaaac agatgtttag gagatttcct gtatagcagt   1906

cagccaattc atatgctttg tctctgctgg cttctttttc catgcgttaa cttttcccaa   1966

tagcagagga ggcaaatatg agcatacaat ccctttgttc taaagatatt gttccagcta   2026

gtggaatgat gttgaatctt taataaccat aattagttgc tttttcagta tcttctgctt   2086

tgtctgtgtc tatccagtgg cctaggaatt aaagtgtaag ttgttttcgc tgttaaattg   2146

gatatttata tatatatata tagcaagatt ttcatgtgtt atttaattct gtattgtttc   2206

ttatatttgt agtaaaatat tgaacaatta aaagtgttga ctccaaaaaa aaaaaaaaaa   2266
```

<210> SEQ ID NO 12
<211> LENGTH: 262
<212> TYPE: PRT

-continued

```
<213> ORGANISM: Homo sapiens
<220> FEATURE:
<221> NAME/KEY: SIGNAL
<222> LOCATION: 1..23

<400> SEQUENCE: 12

Met Pro Phe Ser His Leu Ser Thr Tyr Ser Leu Val Trp Val Met Ala
            -20                 -15                 -10

Ala Val Val Leu Cys Thr Ala Gln Val Gln Val Val Thr Gln Asp Glu
        -5                  1               5

Arg Glu Gln Leu Tyr Thr Thr Ala Ser Leu Lys Cys Ser Leu Gln Asn
10                  15                  20                  25

Ala Gln Glu Ala Leu Ile Val Thr Trp Gln Lys Lys Lys Ala Val Ser
                30                  35                  40

Pro Glu Asn Met Val Thr Phe Ser Glu Asn His Gly Val Val Ile Gln
            45                  50                  55

Pro Ala Tyr Lys Asp Lys Ile Asn Ile Thr Gln Leu Gly Leu Gln Asn
        60                  65                  70

Ser Thr Ile Thr Phe Trp Asn Ile Thr Leu Glu Asp Glu Gly Cys Tyr
    75                  80                  85

Met Cys Leu Phe Asn Thr Phe Gly Phe Gly Lys Ile Ser Gly Thr Ala
90                  95                  100                 105

Cys Leu Thr Val Tyr Val Gln Pro Ile Val Ser Leu His Tyr Lys Phe
                110                 115                 120

Ser Glu Asp His Leu Asn Ile Thr Cys Ser Ala Thr Ala Arg Pro Ala
            125                 130                 135

Pro Met Val Phe Trp Lys Val Pro Arg Ser Gly Ile Glu Asn Ser Thr
        140                 145                 150

Val Thr Leu Ser His Pro Asn Gly Thr Thr Ser Val Thr Ser Ile Leu
    155                 160                 165

His Ile Lys Asp Pro Lys Asn Gln Val Gly Lys Glu Val Ile Cys Gln
170                 175                 180                 185

Val Leu His Leu Gly Thr Val Thr Asp Phe Lys Gln Thr Val Asn Lys
                190                 195                 200

Gly Tyr Trp Phe Ser Val Pro Leu Leu Leu Ser Ile Val Ser Leu Val
            205                 210                 215

Ile Leu Leu Val Leu Ile Ser Ile Leu Leu Tyr Trp Lys Arg His Arg
        220                 225                 230

Asn Gln Asp Arg Glu Pro
    235


<210> SEQ ID NO 13
<211> LENGTH: 1597
<212> TYPE: DNA
<213> ORGANISM: Homo sapiens
<220> FEATURE:
<221> NAME/KEY: 5'UTR
<222> LOCATION: 1..65
<220> FEATURE:
<221> NAME/KEY: CDS
<222> LOCATION: 66..1334
<220> FEATURE:
<221> NAME/KEY: 3'UTR
<222> LOCATION: 1335..1597
<220> FEATURE:
<221> NAME/KEY: polyA_signal
<222> LOCATION: 1558..1563
<220> FEATURE:
<221> NAME/KEY: polyA_site
<222> LOCATION: 1582..1597
```

-continued

<400> SEQUENCE: 13

```
actactccag acagacggct ttggaatcca ccagctacat ccagctccct gaggcagagt      60

tgaga atg gag aga atg tta cct ctc ctg act ctg ggg ctc ttg gcg gct     110
      Met Glu Arg Met Leu Pro Leu Leu Thr Leu Gly Leu Leu Ala Ala
                  -20                 -15                 -10

ggg ttc tgc cct gct gtc ctc tgc cac cct aac agc cca ctt gac gag       158
Gly Phe Cys Pro Ala Val Leu Cys His Pro Asn Ser Pro Leu Asp Glu
            -5                  1               5

gag aat ctg acc cag gag aac caa gac cga ggg aca cac gtg gac ctc       206
Glu Asn Leu Thr Gln Glu Asn Gln Asp Arg Gly Thr His Val Asp Leu
    10                  15                  20

gga tta gcc tcc gcc aac gtg gac ttc gct ctc agc ctg tac aag cag       254
Gly Leu Ala Ser Ala Asn Val Asp Phe Ala Leu Ser Leu Tyr Lys Gln
25                  30                  35                  40

tta gtc ctg aag gcc cct gat aag aat gtc atc ttc tcc cca ctg agc       302
Leu Val Leu Lys Ala Pro Asp Lys Asn Val Ile Phe Ser Pro Leu Ser
                45                  50                  55

atc tcc acc gcc ttg gcc ttc ctg tct ctg ggg gcc cat aat acc acc       350
Ile Ser Thr Ala Leu Ala Phe Leu Ser Leu Gly Ala His Asn Thr Thr
            60                  65                  70

ctg aca gag att ctc aaa ggc ctc aag ttc aac ctc acg gag act tct       398
Leu Thr Glu Ile Leu Lys Gly Leu Lys Phe Asn Leu Thr Glu Thr Ser
        75                  80                  85

gag gca gaa att cac cag agc ttc cag cac ctc ctg cgc acc ctc aat       446
Glu Ala Glu Ile His Gln Ser Phe Gln His Leu Leu Arg Thr Leu Asn
    90                  95                  100

cag tcc agc gat gag ctg cag ctg agt atg gga aat gcc atg ttt gtc       494
Gln Ser Ser Asp Glu Leu Gln Leu Ser Met Gly Asn Ala Met Phe Val
105                 110                 115                 120

aaa gag caa ctc agt ctg ctg gac agg ttc acg gag gat gcc aag agg       542
Lys Glu Gln Leu Ser Leu Leu Asp Arg Phe Thr Glu Asp Ala Lys Arg
                125                 130                 135

ctg tat ggc tcc gag gcc ttt gcc act gac ttt cag gac tca gct gca       590
Leu Tyr Gly Ser Glu Ala Phe Ala Thr Asp Phe Gln Asp Ser Ala Ala
            140                 145                 150

gct aag aag ctc atc aac gac tac gtg aag aat gga act agg ggg aaa       638
Ala Lys Lys Leu Ile Asn Asp Tyr Val Lys Asn Gly Thr Arg Gly Lys
        155                 160                 165

atc aca gat ctg atc aag gac ctt gac tcg cag aca atg atg gtc ctg       686
Ile Thr Asp Leu Ile Lys Asp Leu Asp Ser Gln Thr Met Met Val Leu
    170                 175                 180

gtg aat tac atc ttc ttt aaa gcc aaa tgg gag atg ccc ttt gac ccc       734
Val Asn Tyr Ile Phe Phe Lys Ala Lys Trp Glu Met Pro Phe Asp Pro
185                 190                 195                 200

caa gat act cat cag tca agg ttc tac ttg agc aag aaa aag tgg gta       782
Gln Asp Thr His Gln Ser Arg Phe Tyr Leu Ser Lys Lys Lys Trp Val
                205                 210                 215

atg gtg ccc atg atg agt ttg cat cac ctg act ata cct tac ttc cgg       830
Met Val Pro Met Met Ser Leu His His Leu Thr Ile Pro Tyr Phe Arg
            220                 225                 230

gac gag gag ctg tcc tgc acc gtg gtg gag ctg aag tac aca ggc aat       878
Asp Glu Glu Leu Ser Cys Thr Val Val Glu Leu Lys Tyr Thr Gly Asn
        235                 240                 245

gcc agc gca ctc ttc atc ctc cct gat caa gac aag atg gag gaa gtg       926
Ala Ser Ala Leu Phe Ile Leu Pro Asp Gln Asp Lys Met Glu Glu Val
    250                 255                 260

gaa gcc atg ctg ctc cca gag acc ctg aag cgg tgg aga gac tct ctg       974
Glu Ala Met Leu Leu Pro Glu Thr Leu Lys Arg Trp Arg Asp Ser Leu
265                 270                 275                 280
```

-continued

```
gag ttc aga gag ata ggt gag ctc tac ctg cca aag ttt tcc atc tcg      1022
Glu Phe Arg Glu Ile Gly Glu Leu Tyr Leu Pro Lys Phe Ser Ile Ser
            285                 290                 295

agg gac tat aac ctg aac gac ata ctt ctc cag ctg ggc att gag gaa      1070
Arg Asp Tyr Asn Leu Asn Asp Ile Leu Leu Gln Leu Gly Ile Glu Glu
            300                 305                 310

gcc ttc acc agc aag gct gac ctg tca ggg atc aca ggg gcc agg aac      1118
Ala Phe Thr Ser Lys Ala Asp Leu Ser Gly Ile Thr Gly Ala Arg Asn
        315                 320                 325

cta gca gtc tcc cag gtg gtc cat aag gct gtg ctt gat gta ttt gag      1166
Leu Ala Val Ser Gln Val Val His Lys Ala Val Leu Asp Val Phe Glu
    330                 335                 340

gag ggc aca gaa gca tct gct gcc aca gca gtc aaa atc acc ctc ctt      1214
Glu Gly Thr Glu Ala Ser Ala Ala Thr Ala Val Lys Ile Thr Leu Leu
345                 350                 355                 360

tct gca tta gtg gag aca agg acc att gtg cgt ttc aac agg ccc ttc      1262
Ser Ala Leu Val Glu Thr Arg Thr Ile Val Arg Phe Asn Arg Pro Phe
            365                 370                 375

ctg atg atc att gtc cct aca gac acc cag aac atc ttc ttc atg agc      1310
Leu Met Ile Ile Val Pro Thr Asp Thr Gln Asn Ile Phe Phe Met Ser
            380                 385                 390

aaa gtc acc aat ccc aag caa gcc tagagcttgc catcaagcag tggggctctc     1364
Lys Val Thr Asn Pro Lys Gln Ala
        395                 400

agtaaggaac ttggaatgca agctggatgc ctgggtctct gggcacagcc tggcccctgt    1424

gcaccgagtg gccatggcat gtgtggccct gtctgcttat ccttggaagg tgacagcgat    1484

tccctgtgta gctctcacat gcacaggggc ccatggactc ttcagtctgg agggtcctgg    1544

gcctcctgac agcaataaat aatttcgttg gacacgcaaa aaaaaaaaaa aaa           1597


<210> SEQ ID NO 14
<211> LENGTH: 423
<212> TYPE: PRT
<213> ORGANISM: Homo sapiens
<220> FEATURE:
<221> NAME/KEY: SIGNAL
<222> LOCATION: 1..23

<400> SEQUENCE: 14

Met Glu Arg Met Leu Pro Leu Leu Thr Leu Gly Leu Leu Ala Ala Gly
            -20                 -15                 -10

Phe Cys Pro Ala Val Leu Cys His Pro Asn Ser Pro Leu Asp Glu Glu
        -5                  1               5

Asn Leu Thr Gln Glu Asn Gln Asp Arg Gly Thr His Val Asp Leu Gly
10                  15                  20                  25

Leu Ala Ser Ala Asn Val Asp Phe Ala Leu Ser Leu Tyr Lys Gln Leu
                30                  35                  40

Val Leu Lys Ala Pro Asp Lys Asn Val Ile Phe Ser Pro Leu Ser Ile
            45                  50                  55

Ser Thr Ala Leu Ala Phe Leu Ser Leu Gly Ala His Asn Thr Thr Leu
        60                  65                  70

Thr Glu Ile Leu Lys Gly Leu Lys Phe Asn Leu Thr Glu Thr Ser Glu
    75                  80                  85

Ala Glu Ile His Gln Ser Phe Gln His Leu Leu Arg Thr Leu Asn Gln
90                  95                  100                 105

Ser Ser Asp Glu Leu Gln Leu Ser Met Gly Asn Ala Met Phe Val Lys
                110                 115                 120
```

-continued

```
Glu Gln Leu Ser Leu Leu Asp Arg Phe Thr Glu Asp Ala Lys Arg Leu
            125                 130                 135

Tyr Gly Ser Glu Ala Phe Ala Thr Asp Phe Gln Asp Ser Ala Ala Ala
        140                 145                 150

Lys Lys Leu Ile Asn Asp Tyr Val Lys Asn Gly Thr Arg Gly Lys Ile
    155                 160                 165

Thr Asp Leu Ile Lys Asp Leu Asp Ser Gln Thr Met Met Val Leu Val
170                 175                 180                 185

Asn Tyr Ile Phe Phe Lys Ala Lys Trp Glu Met Pro Phe Asp Pro Gln
                190                 195                 200

Asp Thr His Gln Ser Arg Phe Tyr Leu Ser Lys Lys Lys Trp Val Met
            205                 210                 215

Val Pro Met Met Ser Leu His His Leu Thr Ile Pro Tyr Phe Arg Asp
        220                 225                 230

Glu Glu Leu Ser Cys Thr Val Val Glu Leu Lys Tyr Thr Gly Asn Ala
    235                 240                 245

Ser Ala Leu Phe Ile Leu Pro Asp Gln Asp Lys Met Glu Glu Val Glu
250                 255                 260                 265

Ala Met Leu Leu Pro Glu Thr Leu Lys Arg Trp Arg Asp Ser Leu Glu
                270                 275                 280

Phe Arg Glu Ile Gly Glu Leu Tyr Leu Pro Lys Phe Ser Ile Ser Arg
            285                 290                 295

Asp Tyr Asn Leu Asn Asp Ile Leu Leu Gln Leu Gly Ile Glu Glu Ala
        300                 305                 310

Phe Thr Ser Lys Ala Asp Leu Ser Gly Ile Thr Gly Ala Arg Asn Leu
    315                 320                 325

Ala Val Ser Gln Val Val His Lys Ala Val Leu Asp Val Phe Glu Glu
330                 335                 340                 345

Gly Thr Glu Ala Ser Ala Ala Thr Ala Val Lys Ile Thr Leu Leu Ser
                350                 355                 360

Ala Leu Val Glu Thr Arg Thr Ile Val Arg Phe Asn Arg Pro Phe Leu
            365                 370                 375

Met Ile Ile Val Pro Thr Asp Thr Gln Asn Ile Phe Phe Met Ser Lys
        380                 385                 390

Val Thr Asn Pro Lys Gln Ala
    395                 400
```

<210> SEQ ID NO 15
<211> LENGTH: 1397
<212> TYPE: DNA
<213> ORGANISM: Homo sapiens
<220> FEATURE:
<221> NAME/KEY: 5'UTR
<222> LOCATION: 1..152
<220> FEATURE:
<221> NAME/KEY: CDS
<222> LOCATION: 153..806
<220> FEATURE:
<221> NAME/KEY: 3'UTR
<222> LOCATION: 807..1397
<220> FEATURE:
<221> NAME/KEY: polyA_signal
<222> LOCATION: 1362..1367
<220> FEATURE:
<221> NAME/KEY: polyA_site
<222> LOCATION: 1382..1397

<400> SEQUENCE: 15
agacctagga ggtgcgacag acccgcgggg caaacggact ggggccaaga gccgggagcg     60

-continued

```
cgggcgcaaa ggcaccaggg cccgcccagg gcgcctcgca gcacggcctt gggggttctg    120

cgggccttcg ggtgcgcgtc tcgcctctag cc atg ggt tcc gca gcg ttg gag      173
                                    Met Gly Ser Ala Ala Leu Glu
                                    1               5

atc ctg ggc ctg gtg ctg tgc ctg gtg ggc tgg ggg ggt ctg atc ctg      221
Ile Leu Gly Leu Val Leu Cys Leu Val Gly Trp Gly Gly Leu Ile Leu
        10                  15                  20

gcg tgc ggg ctg ccc atg tgg cag gtg acc gcc ttc ctg gac cac aac      269
Ala Cys Gly Leu Pro Met Trp Gln Val Thr Ala Phe Leu Asp His Asn
    25                  30                  35

atc gtg acg gcg cag acc acc tgg aag ggg ctg tgg atg tcg tgc gtg      317
Ile Val Thr Ala Gln Thr Thr Trp Lys Gly Leu Trp Met Ser Cys Val
40                  45                  50                  55

gtg cag agc acc ggg cac atg cag tgc aaa gtg tac gac tcg gtg ctg      365
Val Gln Ser Thr Gly His Met Gln Cys Lys Val Tyr Asp Ser Val Leu
                60                  65                  70

gct ctg agc acc gag gtg cag gcg gcg cgg gcg ctc acc gtg agc gcc      413
Ala Leu Ser Thr Glu Val Gln Ala Ala Arg Ala Leu Thr Val Ser Ala
            75                  80                  85

gtg ctg ctg gcg ttc gtt gcg ctc ttc gtg acc ctg gcg ggc gcg cag      461
Val Leu Leu Ala Phe Val Ala Leu Phe Val Thr Leu Ala Gly Ala Gln
        90                  95                  100

tgc acc acc tgc gtg gcc ccg ggc ccg gcc aag gcg cgt gtg gcc ctc      509
Cys Thr Thr Cys Val Ala Pro Gly Pro Ala Lys Ala Arg Val Ala Leu
    105                 110                 115

acg gga ggc gtg ctc tac ctg ttt tgc ggg ctg ctg gcg ctc gtg cca      557
Thr Gly Gly Val Leu Tyr Leu Phe Cys Gly Leu Leu Ala Leu Val Pro
120                 125                 130                 135

ctc tgc tgg ttc gcc aac att gtc gtc cgc gag ttt tac gac ccg tct      605
Leu Cys Trp Phe Ala Asn Ile Val Val Arg Glu Phe Tyr Asp Pro Ser
                140                 145                 150

gtg ccc gtg tcg cag aag tac gag ctg ggc gca gcg ctg tac atc ggc      653
Val Pro Val Ser Gln Lys Tyr Glu Leu Gly Ala Ala Leu Tyr Ile Gly
            155                 160                 165

tgg gcg gcc acc gcg ctg ctc atg gta ggc ggc tgc ctc ttg tgc tgc      701
Trp Ala Ala Thr Ala Leu Leu Met Val Gly Gly Cys Leu Leu Cys Cys
        170                 175                 180

ggc gcc tgg gtc tgc acc ggc cgt ccc gac ctc agc ttc ccc gtg aag      749
Gly Ala Trp Val Cys Thr Gly Arg Pro Asp Leu Ser Phe Pro Val Lys
    185                 190                 195

tac tca gcg ccg cgg cgg ccc acg gcc acc ggc gac aac gac aag aag      797
Tyr Ser Ala Pro Arg Arg Pro Thr Ala Thr Gly Asp Asn Asp Lys Lys
200                 205                 210                 215

aac tac gtc tgagggcgct gggcacggcc gggcccctcc tgccagccac              846
Asn Tyr Val

gcctgcgagg cgttggataa gcctggggag ccccgcatgg accgcggctt ccgccgggta    906

gcgcggcgcg caggcttctc ggaacgtccg gctctgcgcc ccgacgcggc tcctggatcc    966

gctcctgcct gcgcccgcag ctgaccttct cctgccacta gcccggccct gcccttaaca   1026

gacggaatga agtttccttt tctgtgcgcg gcgctgtttc cataggcaga gcgggtgtca   1086

gactgaggat ttcgcttccc ctccaagacg ctgggggtct tggctgctgc cttacttccc   1146

agaggctcct gctgacttcg gaggggcgga tgcagagccc agggccccca ccggaagatg   1206

tgtacagctg gtctttactc catcggcagg gcccgagccc agggaccagt gacttggcct   1266

ggacctcccg gtctcactcc agcatctccc caggcaaggc ttgtgggcac cggagcttga   1326

gagagggcgg gagtgggaag gctaagaatc tgcttagtaa atggtttgaa ctctgaaaaa   1386
```

-continued

```
aaaaaaaaaa a                                                          1397


<210> SEQ ID NO 16
<211> LENGTH: 218
<212> TYPE: PRT
<213> ORGANISM: Homo sapiens

<400> SEQUENCE: 16

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Asp Ser Val Leu Ala Leu Ser Thr Glu Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
        115                 120                 125

Gly Leu Leu Ala Leu Val Pro Leu Cys Trp Phe Ala Asn Ile Val Val
    130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Arg Pro Thr Ala
        195                 200                 205

Thr Gly Asp Asn Asp Lys Lys Asn Tyr Val
    210                 215


<210> SEQ ID NO 17
<211> LENGTH: 782
<212> TYPE: DNA
<213> ORGANISM: Homo sapiens
<220> FEATURE:
<221> NAME/KEY: 5'UTR
<222> LOCATION: 1..62
<220> FEATURE:
<221> NAME/KEY: CDS
<222> LOCATION: 63..572
<220> FEATURE:
<221> NAME/KEY: 3'UTR
<222> LOCATION: 573..782
<220> FEATURE:
<221> NAME/KEY: polyA_signal
<222> LOCATION: 750..755
<220> FEATURE:
<221> NAME/KEY: polyA_site
<222> LOCATION: 767..782

<400> SEQUENCE: 17

atatgtcatc aggccccccg cctgggaggt gtgctgccag agattttgcc tcttcaaggt      60

ga atg cgg ctt caa ggg gct atc ttt gtg ctc ctg ccc cac ctg ggg        107
   Met Arg Leu Gln Gly Ala Ile Phe Val Leu Leu Pro His Leu Gly
```

-continued

```
  1               5                  10                 15

ccc atc ctg gtc tgg ctg ttc act cgt gat cac atg tct ggt tgg tgt      155
Pro Ile Leu Val Trp Leu Phe Thr Arg Asp His Met Ser Gly Trp Cys
                20                  25                  30

gag ggc ccg agg atg ctg tcc tgg tgc cca ttc tac aaa gtc tta ttg      203
Glu Gly Pro Arg Met Leu Ser Trp Cys Pro Phe Tyr Lys Val Leu Leu
            35                  40                  45

ctt gta cag aca gcc atc tac tct gtc gtg ggc tat gcc tcc tac ctg      251
Leu Val Gln Thr Ala Ile Tyr Ser Val Val Gly Tyr Ala Ser Tyr Leu
        50                  55                  60

gtg tgg aag gac ctg gga ggg ggc ttg ggg tgg ccc ctg gcc ctg cct      299
Val Trp Lys Asp Leu Gly Gly Gly Leu Gly Trp Pro Leu Ala Leu Pro
    65                  70                  75

ctt ggc ctc tat gct gat cag ctc acc atc agc tgg act gtc ctg gtt      347
Leu Gly Leu Tyr Ala Asp Gln Leu Thr Ile Ser Trp Thr Val Leu Val
80                  85                  90                  95

ctc ttt ttc aca gtc cac aac cct ggt ctg gcc ctg ctg cac ctg ctg      395
Leu Phe Phe Thr Val His Asn Pro Gly Leu Ala Leu Leu His Leu Leu
                100                 105                 110

ctg ctg tat ggg ctg gtg gtg agc aca gca ctg atc tgg cat ccc atc      443
Leu Leu Tyr Gly Leu Val Val Ser Thr Ala Leu Ile Trp His Pro Ile
            115                 120                 125

aac aaa ctg gct gcc ctg tta ctg ctg ccc tac cta gcc tgg ctc acc      491
Asn Lys Leu Ala Ala Leu Leu Leu Leu Pro Tyr Leu Ala Trp Leu Thr
        130                 135                 140

gtg act tca gcc ctc acc tac cac ctg tgg agg gac agc ctt tgt cca      539
Val Thr Ser Ala Leu Thr Tyr His Leu Trp Arg Asp Ser Leu Cys Pro
    145                 150                 155

gtg cac cag cct cag ccc acg gag aag agt gac tgaggcccta gggcatggga    592
Val His Gln Pro Gln Pro Thr Glu Lys Ser Asp
160                 165                 170

gaggagggac gcccagggtg gggaggaaga gtctgcaagc agggctgtgg agttagggtt    652

caccccaatg ggaccaccct cctgggtccc ctggtgccgt ttttccttag aaatcagaga    712

aatgggaaag ggggggaaac tgattttaca cttaaataat aaaatcctat tagtaaaaaa    772

aaaaaaaaaa                                                           782
```

<210> SEQ ID NO 18
<211> LENGTH: 170
<212> TYPE: PRT
<213> ORGANISM: Homo sapiens

<400> SEQUENCE: 18

```
Met Arg Leu Gln Gly Ala Ile Phe Val Leu Leu Pro His Leu Gly Pro
1               5                   10                  15

Ile Leu Val Trp Leu Phe Thr Arg Asp His Met Ser Gly Trp Cys Glu
            20                  25                  30

Gly Pro Arg Met Leu Ser Trp Cys Pro Phe Tyr Lys Val Leu Leu Leu
        35                  40                  45

Val Gln Thr Ala Ile Tyr Ser Val Val Gly Tyr Ala Ser Tyr Leu Val
    50                  55                  60

Trp Lys Asp Leu Gly Gly Gly Leu Gly Trp Pro Leu Ala Leu Pro Leu
65                  70                  75                  80

Gly Leu Tyr Ala Asp Gln Leu Thr Ile Ser Trp Thr Val Leu Val Leu
                85                  90                  95

Phe Phe Thr Val His Asn Pro Gly Leu Ala Leu Leu His Leu Leu Leu
            100                 105                 110
```

-continued

```
Leu Tyr Gly Leu Val Val Ser Thr Ala Leu Ile Trp His Pro Ile Asn
        115                 120                 125

Lys Leu Ala Ala Leu Leu Leu Leu Pro Tyr Leu Ala Trp Leu Thr Val
    130                 135                 140

Thr Ser Ala Leu Thr Tyr His Leu Trp Arg Asp Ser Leu Cys Pro Val
145                 150                 155                 160

His Gln Pro Gln Pro Thr Glu Lys Ser Asp
                165                 170


<210> SEQ ID NO 19
<211> LENGTH: 789
<212> TYPE: DNA
<213> ORGANISM: Homo sapiens
<220> FEATURE:
<221> NAME/KEY: 5'UTR
<222> LOCATION: 1..62
<220> FEATURE:
<221> NAME/KEY: CDS
<222> LOCATION: 63..572
<220> FEATURE:
<221> NAME/KEY: 3'UTR
<222> LOCATION: 573..789
<220> FEATURE:
<221> NAME/KEY: polyA_signal
<222> LOCATION: 750..755
<220> FEATURE:
<221> NAME/KEY: polyA_site
<222> LOCATION: 774..789

<400> SEQUENCE: 19

atatgtcatc aggccccccg cctgggaggt gtgctgccag agattttgcc tcttcaaggt      60

ga atg cgg ctt caa ggg gct atc ttt gtg ctc ctg ccc cac ctg ggg        107
   Met Arg Leu Gln Gly Ala Ile Phe Val Leu Leu Pro His Leu Gly
   1               5                   10                  15

ccc atc ctg gtc tgg ctg ttc act cgt gat cac atg tct ggt ttg tgt       155
Pro Ile Leu Val Trp Leu Phe Thr Arg Asp His Met Ser Gly Leu Cys
                20                  25                  30

gag ggc ccg agg atg ctg tcc tgg tgc cca ttc tac aaa gtc tta ttg       203
Glu Gly Pro Arg Met Leu Ser Trp Cys Pro Phe Tyr Lys Val Leu Leu
            35                  40                  45

ctt gta cag aca gcc atc tac tct gtc gtg ggc tat gcc tcc tac ctg       251
Leu Val Gln Thr Ala Ile Tyr Ser Val Val Gly Tyr Ala Ser Tyr Leu
        50                  55                  60

gtg tgg aag gac ctg gga ggg ggc ttg ggg tgg ccc ctg gcc ctg cct       299
Val Trp Lys Asp Leu Gly Gly Gly Leu Gly Trp Pro Leu Ala Leu Pro
    65                  70                  75

ctt ggc ctc tat gct gtt cag ctc acc atc agc tgg act gtc ctg gtt       347
Leu Gly Leu Tyr Ala Val Gln Leu Thr Ile Ser Trp Thr Val Leu Val
80                  85                  90                  95

ctc ttt ttc aca gtc cac aac cct ggt ctg gcc ctg ctg cac ctg ctg       395
Leu Phe Phe Thr Val His Asn Pro Gly Leu Ala Leu Leu His Leu Leu
                100                 105                 110

ctg ctg tat ggg ctg gtg gtg agc aca gca ctg atc tgg cat ccc atc       443
Leu Leu Tyr Gly Leu Val Val Ser Thr Ala Leu Ile Trp His Pro Ile
            115                 120                 125

aac aaa ctg gct gcc ctg tta ctg ctg ccc tac cta gcc tgg ctc acc       491
Asn Lys Leu Ala Ala Leu Leu Leu Leu Pro Tyr Leu Ala Trp Leu Thr
        130                 135                 140

gtg act tca gcc ctc acc tac cac ctg tgg agg gac agc ctt tgt cca       539
Val Thr Ser Ala Leu Thr Tyr His Leu Trp Arg Asp Ser Leu Cys Pro
    145                 150                 155

gtg cac cag cct cag ccc acg gag aag agt gac tgaggcccta gggcatggga     592
Val His Gln Pro Gln Pro Thr Glu Lys Ser Asp
```

-continued

```
160                 165                 170

gaggagggac gcccagggtg gggaggaaga gtctgcaagc agggctgtgg agttagggtt    652

caccccaatg ggaccaccct cctgggtccc ctggtgccgt ttttccttag aaatcagaga    712

aatgggaaag ggggggaaac tgattttaca cttaaataat aaaatcctat tagtaactct    772

caaaaaaaaa aaaaaaa                                                    789


<210> SEQ ID NO 20
<211> LENGTH: 170
<212> TYPE: PRT
<213> ORGANISM: Homo sapiens

<400> SEQUENCE: 20

Met Arg Leu Gln Gly Ala Ile Phe Val Leu Leu Pro His Leu Gly Pro
1               5                   10                  15

Ile Leu Val Trp Leu Phe Thr Arg Asp His Met Ser Gly Leu Cys Glu
            20                  25                  30

Gly Pro Arg Met Leu Ser Trp Cys Pro Phe Tyr Lys Val Leu Leu Leu
        35                  40                  45

Val Gln Thr Ala Ile Tyr Ser Val Val Gly Tyr Ala Ser Tyr Leu Val
    50                  55                  60

Trp Lys Asp Leu Gly Gly Gly Leu Gly Trp Pro Leu Ala Leu Pro Leu
65                  70                  75                  80

Gly Leu Tyr Ala Val Gln Leu Thr Ile Ser Trp Thr Val Leu Val Leu
                85                  90                  95

Phe Phe Thr Val His Asn Pro Gly Leu Ala Leu Leu His Leu Leu Leu
            100                 105                 110

Leu Tyr Gly Leu Val Val Ser Thr Ala Leu Ile Trp His Pro Ile Asn
        115                 120                 125

Lys Leu Ala Ala Leu Leu Leu Leu Pro Tyr Leu Ala Trp Leu Thr Val
    130                 135                 140

Thr Ser Ala Leu Thr Tyr His Leu Trp Arg Asp Ser Leu Cys Pro Val
145                 150                 155                 160

His Gln Pro Gln Pro Thr Glu Lys Ser Asp
                165                 170


<210> SEQ ID NO 21
<211> LENGTH: 555
<212> TYPE: DNA
<213> ORGANISM: Homo sapiens
<220> FEATURE:
<221> NAME/KEY: 5'UTR
<222> LOCATION: 1..85
<220> FEATURE:
<221> NAME/KEY: CDS
<222> LOCATION: 86..403
<220> FEATURE:
<221> NAME/KEY: 3'UTR
<222> LOCATION: 404..555
<220> FEATURE:
<221> NAME/KEY: polyA_signal
<222> LOCATION: 504..509
<220> FEATURE:
<221> NAME/KEY: polyA_site
<222> LOCATION: 540..555

<400> SEQUENCE: 21

aaaaacttta cggcaggcgt ccgcgtcgct agctagtcgt tctgaagcgg cggccagaga     60

agagtcaagg gcacgagcat cggcc atg cct ttc ttg gac atc cag aaa agg      112
                            Met Pro Phe Leu Asp Ile Gln Lys Arg
                            1               5
```

```
ttc ggc ctt aac ata gat cga tgg ttg aca atc cag agt tgt gaa cag      160
Phe Gly Leu Asn Ile Asp Arg Trp Leu Thr Ile Gln Ser Cys Glu Gln
10                  15                  20                  25

ccc tac aag atg gct ggt cga tgc cat gct ttt gaa aaa gaa tgg ata      208
Pro Tyr Lys Met Ala Gly Arg Cys His Ala Phe Glu Lys Glu Trp Ile
                30                  35                  40

gaa tgt gca cat gga atc ggt tat act cgg gca gag aaa gag tgc aag      256
Glu Cys Ala His Gly Ile Gly Tyr Thr Arg Ala Glu Lys Glu Cys Lys
            45                  50                  55

ata gaa tat gat gat ttc gta gag tgt ttg ctt cgg cag aaa acg atg      304
Ile Glu Tyr Asp Asp Phe Val Glu Cys Leu Leu Arg Gln Lys Thr Met
        60                  65                  70

aga cgt gca ggt acc atc agg aag cag cgg gat aag ctg ata aag gaa      352
Arg Arg Ala Gly Thr Ile Arg Lys Gln Arg Asp Lys Leu Ile Lys Glu
    75                  80                  85

gga aag tac acc cct cca cct cac cac att ggc aag ggg gag cct tgg      400
Gly Lys Tyr Thr Pro Pro Pro His His Ile Gly Lys Gly Glu Pro Trp
90                  95                  100                 105

ccc tgaacagagc agctgctgat gtctggaggc tgattttcct gttctctgtt           453
Pro

ctccactgga aaggttgttt acgacaaacc tccttgtcaa agtgtgtaaa aataaaggat    513

tgctccatcc tatttgttct attttcaaaa aaaaaaaaaa aa                       555


<210> SEQ ID NO 22
<211> LENGTH: 106
<212> TYPE: PRT
<213> ORGANISM: Homo sapiens

<400> SEQUENCE: 22

Met Pro Phe Leu Asp Ile Gln Lys Arg Phe Gly Leu Asn Ile Asp Arg
1               5                   10                  15

Trp Leu Thr Ile Gln Ser Cys Glu Gln Pro Tyr Lys Met Ala Gly Arg
            20                  25                  30

Cys His Ala Phe Glu Lys Glu Trp Ile Glu Cys Ala His Gly Ile Gly
        35                  40                  45

Tyr Thr Arg Ala Glu Lys Glu Cys Lys Ile Glu Tyr Asp Asp Phe Val
    50                  55                  60

Glu Cys Leu Leu Arg Gln Lys Thr Met Arg Arg Ala Gly Thr Ile Arg
65                  70                  75                  80

Lys Gln Arg Asp Lys Leu Ile Lys Glu Gly Lys Tyr Thr Pro Pro Pro
                85                  90                  95

His His Ile Gly Lys Gly Glu Pro Trp Pro
            100                 105


<210> SEQ ID NO 23
<211> LENGTH: 1726
<212> TYPE: DNA
<213> ORGANISM: Homo sapiens
<220> FEATURE:
<221> NAME/KEY: 5'UTR
<222> LOCATION: 1..414
<220> FEATURE:
<221> NAME/KEY: CDS
<222> LOCATION: 415..1653
<220> FEATURE:
<221> NAME/KEY: 3'UTR
<222> LOCATION: 1654..1726
<220> FEATURE:
<221> NAME/KEY: polyA_site
<222> LOCATION: 1688..1726
```

-continued

<400> SEQUENCE: 23

```
ctctccgcgc gccccctgca gccctggacg cagcacctcc gtttgggacg ccctacgccc      60

accttaactt gaggctccca tccacgcagc ctctgcaagc ctcaccgcaa ccgtgctagg     120

cgcgtcgggt ggggcgggaa taaagttttt ccaacccagt ttggggagag ggctggatgg     180

gaaggaccct ccctgctgca gacttcatgg caggctgcac tgtgtcccct cggctccacg     240

gctgccccgg gggcgctgct ttcgggtttt ctttctagaa tctctggtct gctgctgtgc     300

agatggacct gccggcactg ctgtcagaag tgctacgagt ccagctgttg ccagtcaagt     360

gaggatgaag ttgaaattct gggacctttc cctgctcaga cccctccctg gctg atg       417
                                                            Met
                                                            1

gcc agc cgg agc agt gac aag gat ggt gac tct gtc cac acg gcc agc       465
Ala Ser Arg Ser Ser Asp Lys Asp Gly Asp Ser Val His Thr Ala Ser
            5                   10                  15

gaa gtc ccg ctg acc cca cgg acc aat tcc ccg gat gga aga cgc tcg       513
Glu Val Pro Leu Thr Pro Arg Thr Asn Ser Pro Asp Gly Arg Arg Ser
        20                  25                  30

tcc tca gac aca tcc aag tct aca tac agc ctg acg cgg agg att tcg       561
Ser Ser Asp Thr Ser Lys Ser Thr Tyr Ser Leu Thr Arg Arg Ile Ser
    35                  40                  45

agt ctt gag tca aga cgt ccc agc tct cca ctc atc gat att aaa ccc       609
Ser Leu Glu Ser Arg Arg Pro Ser Ser Pro Leu Ile Asp Ile Lys Pro
50                  55                  60                  65

atc gag ttt ggc gtt ctc agc gcc aag aag gag ccc atc caa cct tcg       657
Ile Glu Phe Gly Val Leu Ser Ala Lys Lys Glu Pro Ile Gln Pro Ser
                70                  75                  80

gtg ctc aga cgg acc tat aac ccc gac gac tat ttc agg aag ttc gaa       705
Val Leu Arg Arg Thr Tyr Asn Pro Asp Asp Tyr Phe Arg Lys Phe Glu
            85                  90                  95

ccc cac ctg tac tcc ctc gac tcc aac agc gac gat gtg gac tct ctg       753
Pro His Leu Tyr Ser Leu Asp Ser Asn Ser Asp Asp Val Asp Ser Leu
        100                 105                 110

aca gac gag gag atc ctg tcc aag tac cag ctg ggc atg cag cac ttc       801
Thr Asp Glu Glu Ile Leu Ser Lys Tyr Gln Leu Gly Met Gln His Phe
    115                 120                 125

agc act cag tac gac ctg ctg cac aac cac ctc acc gtg cgc gtg atc       849
Ser Thr Gln Tyr Asp Leu Leu His Asn His Leu Thr Val Arg Val Ile
130                 135                 140                 145

gag gcc agg gac ctg cca cct ccc atc tcc cac gat ggc tcg cgc cag       897
Glu Ala Arg Asp Leu Pro Pro Pro Ile Ser His Asp Gly Ser Arg Gln
                150                 155                 160

gac atg gcg cac tcc aac ccc tac gtc aag atc tgt ctc ctg cca gac       945
Asp Met Ala His Ser Asn Pro Tyr Val Lys Ile Cys Leu Leu Pro Asp
            165                 170                 175

cag aag aac tca aag cag acc ggg gtc aaa cgc aag acc cag aag ccc       993
Gln Lys Asn Ser Lys Gln Thr Gly Val Lys Arg Lys Thr Gln Lys Pro
        180                 185                 190

gtg ttt gag gag cgc tac acc ttc gag atc ccc ttc ctg gag gcc cag      1041
Val Phe Glu Glu Arg Tyr Thr Phe Glu Ile Pro Phe Leu Glu Ala Gln
    195                 200                 205

agg agg acc ctg ctc ctg acc gtg gtg gat ttt gat aag ttc tcc cgc      1089
Arg Arg Thr Leu Leu Leu Thr Val Val Asp Phe Asp Lys Phe Ser Arg
210                 215                 220                 225

cac tgt gtc att ggg aaa gtt tct gtg cct ttg tgt gaa gtt gac ctg      1137
His Cys Val Ile Gly Lys Val Ser Val Pro Leu Cys Glu Val Asp Leu
                230                 235                 240

gtc aag ggc ggg cac tgg tgg aag gcg ctg att ccc agt tct cag aat      1185
```

-continued

```
Val Lys Gly Gly His Trp Trp Lys Ala Leu Ile Pro Ser Ser Gln Asn
            245                 250                 255

gaa gtg gag ctg ggg gag ctg ctt ctg tca ctg aat tat ctc cca agt     1233
Glu Val Glu Leu Gly Glu Leu Leu Leu Ser Leu Asn Tyr Leu Pro Ser
        260                 265                 270

gct ggc aga ctg aat gtt gat gtc att cga gcc aag caa ctt ctt cag     1281
Ala Gly Arg Leu Asn Val Asp Val Ile Arg Ala Lys Gln Leu Leu Gln
    275                 280                 285

aca gat gtg agc caa ggt tca gac ccc ttt gtg aaa atc cag ctg gtg     1329
Thr Asp Val Ser Gln Gly Ser Asp Pro Phe Val Lys Ile Gln Leu Val
290                 295                 300                 305

cat gga ctc aaa ctt gtg aaa acc aag aag acg tcc ttc tta agg ggc     1377
His Gly Leu Lys Leu Val Lys Thr Lys Lys Thr Ser Phe Leu Arg Gly
                310                 315                 320

aca att gat cct ttc tac aat gaa tcc ttc agc ttc aaa gtt ccc caa     1425
Thr Ile Asp Pro Phe Tyr Asn Glu Ser Phe Ser Phe Lys Val Pro Gln
            325                 330                 335

gaa gaa ctg gaa aat gcc agc cta gtg ttt aca gtt ttc ggc cac aac     1473
Glu Glu Leu Glu Asn Ala Ser Leu Val Phe Thr Val Phe Gly His Asn
        340                 345                 350

atg aag agc agc aat gac ttc atc ggg agg atc gtc att ggc cag tac     1521
Met Lys Ser Ser Asn Asp Phe Ile Gly Arg Ile Val Ile Gly Gln Tyr
    355                 360                 365

tct tca ggc ccc tct gag acc aac cac tgg agg cgc atg ctc aac acg     1569
Ser Ser Gly Pro Ser Glu Thr Asn His Trp Arg Arg Met Leu Asn Thr
370                 375                 380                 385

cac cgc aca gcc gtg gag cag tgg cat agc ctg agg tcc cga gct gag     1617
His Arg Thr Ala Val Glu Gln Trp His Ser Leu Arg Ser Arg Ala Glu
                390                 395                 400

tgt gac cgc gtg tct cct gcc tcc ctg gag gtg acc tgagggctgc          1663
Cys Asp Arg Val Ser Pro Ala Ser Leu Glu Val Thr
            405                 410

agggaaggca gctttcattt gtttaaaaaa aaaaaaaaaa aaagacgaaa aaaaaaaaaa   1723

aaa                                                                 1726


<210> SEQ ID NO 24
<211> LENGTH: 413
<212> TYPE: PRT
<213> ORGANISM: Homo sapiens

<400> SEQUENCE: 24

Met Ala Ser Arg Ser Ser Asp Lys Asp Gly Asp Ser Val His Thr Ala
1               5                   10                  15

Ser Glu Val Pro Leu Thr Pro Arg Thr Asn Ser Pro Asp Gly Arg Arg
            20                  25                  30

Ser Ser Ser Asp Thr Ser Lys Ser Thr Tyr Ser Leu Thr Arg Arg Ile
        35                  40                  45

Ser Ser Leu Glu Ser Arg Arg Pro Ser Ser Pro Leu Ile Asp Ile Lys
    50                  55                  60

Pro Ile Glu Phe Gly Val Leu Ser Ala Lys Lys Glu Pro Ile Gln Pro
65                  70                  75                  80

Ser Val Leu Arg Arg Thr Tyr Asn Pro Asp Asp Tyr Phe Arg Lys Phe
                85                  90                  95

Glu Pro His Leu Tyr Ser Leu Asp Ser Asn Ser Asp Asp Val Asp Ser
            100                 105                 110

Leu Thr Asp Glu Glu Ile Leu Ser Lys Tyr Gln Leu Gly Met Gln His
        115                 120                 125
```

-continued

Phe Ser Thr Gln Tyr Asp Leu Leu His Asn His Leu Thr Val Arg Val
130 135 140

Ile Glu Ala Arg Asp Leu Pro Pro Pro Ile Ser His Asp Gly Ser Arg
145 150 155 160

Gln Asp Met Ala His Ser Asn Pro Tyr Val Lys Ile Cys Leu Leu Pro
165 170 175

Asp Gln Lys Asn Ser Lys Gln Thr Gly Val Lys Arg Lys Thr Gln Lys
180 185 190

Pro Val Phe Glu Glu Arg Tyr Thr Phe Glu Ile Pro Phe Leu Glu Ala
195 200 205

Gln Arg Arg Thr Leu Leu Leu Thr Val Val Asp Phe Asp Lys Phe Ser
210 215 220

Arg His Cys Val Ile Gly Lys Val Ser Val Pro Leu Cys Glu Val Asp
225 230 235 240

Leu Val Lys Gly Gly His Trp Trp Lys Ala Leu Ile Pro Ser Ser Gln
245 250 255

Asn Glu Val Glu Leu Gly Glu Leu Leu Leu Ser Leu Asn Tyr Leu Pro
260 265 270

Ser Ala Gly Arg Leu Asn Val Asp Val Ile Arg Ala Lys Gln Leu Leu
275 280 285

Gln Thr Asp Val Ser Gln Gly Ser Asp Pro Phe Val Lys Ile Gln Leu
290 295 300

Val His Gly Leu Lys Leu Val Lys Thr Lys Lys Thr Ser Phe Leu Arg
305 310 315 320

Gly Thr Ile Asp Pro Phe Tyr Asn Glu Ser Phe Ser Phe Lys Val Pro
325 330 335

Gln Glu Glu Leu Glu Asn Ala Ser Leu Val Phe Thr Val Phe Gly His
340 345 350

Asn Met Lys Ser Ser Asn Asp Phe Ile Gly Arg Ile Val Ile Gly Gln
355 360 365

Tyr Ser Ser Gly Pro Ser Glu Thr Asn His Trp Arg Arg Met Leu Asn
370 375 380

Thr His Arg Thr Ala Val Glu Gln Trp His Ser Leu Arg Ser Arg Ala
385 390 395 400

Glu Cys Asp Arg Val Ser Pro Ala Ser Leu Glu Val Thr
405 410

<210> SEQ ID NO 25
<211> LENGTH: 941
<212> TYPE: DNA
<213> ORGANISM: Homo sapiens
<220> FEATURE:
<221> NAME/KEY: 5'UTR
<222> LOCATION: 1..75
<220> FEATURE:
<221> NAME/KEY: CDS
<222> LOCATION: 76..339
<220> FEATURE:
<221> NAME/KEY: 3'UTR
<222> LOCATION: 340..941
<220> FEATURE:
<221> NAME/KEY: polyA_signal
<222> LOCATION: 903..908
<220> FEATURE:
<221> NAME/KEY: polyA_site
<222> LOCATION: 926..941

<400> SEQUENCE: 25
agaaagccgc gcacctcctc ccgccaggcg ctttctcgga cgccttgccc agcgggccgc 60

-continued

```
ccgaccccct gcacc atg gac ccc gct cgc ccc ctg ggg ctg tcg att ctg      111
                 Met Asp Pro Ala Arg Pro Leu Gly Leu Ser Ile Leu
                                 -20                 -15

ctg ctt ttc ctg acg gag gct gca ctg ggc gat gct gct cag gag cca       159
Leu Leu Phe Leu Thr Glu Ala Ala Leu Gly Asp Ala Ala Gln Glu Pro
        -10                 -5                  1

aca gga aat aac gcg gag atc tgt ctc ctg ccc cta gac tac gga ccc       207
Thr Gly Asn Asn Ala Glu Ile Cys Leu Leu Pro Leu Asp Tyr Gly Pro
5                   10                  15                  20

tgc cgg gcc cta ctt ctc cgt tac tac tac gac agg tac acg cag agc       255
Cys Arg Ala Leu Leu Leu Arg Tyr Tyr Tyr Asp Arg Tyr Thr Gln Ser
                25                  30                  35

tgc cgc cag ttc ctg tac ggg ggc tgc gag ggc aac gcc aac aat ttc       303
Cys Arg Gln Phe Leu Tyr Gly Gly Cys Glu Gly Asn Ala Asn Asn Phe
            40                  45                  50

tac acc tgg gag gct tgc gac gat ctt gct gga gga tagaaaaagt            349
Tyr Thr Trp Glu Ala Cys Asp Asp Leu Ala Gly Gly
        55                  60

tcccaaagtt tgccggctgc aagtgagtgt ggacgaccag tgtgaggggt ccacagaaaa    409

gtatttcttt aatctaagtt ccatgacatg tgaaaaattc ttttccggtg ggtgtcaccg    469

gaaccggatt gagaacaggt ttccagatga agctacttgt atgggcttct gcgcaccaaa    529

gaaaattcca tcattttgct acagtccaaa agatggggac tgtgctctgc caatgtgact    589

cgctattatt ttaatccaag atacagaacc tgtgatgctt tcacctatac tggctgtgga    649

gggaatgaca ataactttgt tagcagggag gattgcaaac gtgcatgtgc aaaagctttg    709

aaaaagaaaa agaagatgcc aaagcttcgc tttgccagta gaatccggaa aattcggaag    769

aagcaatttt aaacattctt aatatgtcat cttgtttgtc tttatggctt atttgccttt    829

atggttgtat ctgaagaata atatgacagc atgaggaaac aaatcattgg tgatttattc    889

accagttttt attaatacaa gtcacttttt aaaaataaaa aaaaaaaaaa aa            941
```

<210> SEQ ID NO 26
<211> LENGTH: 88
<212> TYPE: PRT
<213> ORGANISM: Homo sapiens
<220> FEATURE:
<221> NAME/KEY: SIGNAL
<222> LOCATION: 1..24

<400> SEQUENCE: 26

```
Met Asp Pro Ala Arg Pro Leu Gly Leu Ser Ile Leu Leu Leu Phe Leu
                -20                 -15                 -10

Thr Glu Ala Ala Leu Gly Asp Ala Ala Gln Glu Pro Thr Gly Asn Asn
            -5                  1               5

Ala Glu Ile Cys Leu Leu Pro Leu Asp Tyr Gly Pro Cys Arg Ala Leu
    10                  15                  20

Leu Leu Arg Tyr Tyr Tyr Asp Arg Tyr Thr Gln Ser Cys Arg Gln Phe
25                  30                  35                  40

Leu Tyr Gly Gly Cys Glu Gly Asn Ala Asn Asn Phe Tyr Thr Trp Glu
                45                  50                  55

Ala Cys Asp Asp Leu Ala Gly Gly
            60
```

<210> SEQ ID NO 27
<211> LENGTH: 1894
<212> TYPE: DNA
<213> ORGANISM: Homo sapiens
<220> FEATURE:

-continued

```
<221> NAME/KEY: 5'UTR
<222> LOCATION: 1..20
<220> FEATURE:
<221> NAME/KEY: CDS
<222> LOCATION: 21..1118
<220> FEATURE:
<221> NAME/KEY: 3'UTR
<222> LOCATION: 1119..1894
<220> FEATURE:
<221> NAME/KEY: polyA_signal
<222> LOCATION: 1858..1863
<220> FEATURE:
<221> NAME/KEY: polyA_site
<222> LOCATION: 1879..1894

<400> SEQUENCE: 27

agacgtgagc agagcagata atg gca agc atg gct gcc gtg ctc acc tgg gct      53
                      Met Ala Ser Met Ala Ala Val Leu Thr Trp Ala
                                  -20                 -15

ctg gct ctt ctt tca gcg ttt tcg gcc acc cag gca cgg aaa ggc ttc       101
Leu Ala Leu Leu Ser Ala Phe Ser Ala Thr Gln Ala Arg Lys Gly Phe
    -10                 -5                  1

tgg gac tac ttc agc cag acc agc ggg gac aaa ggc agg gtg gag cag       149
Trp Asp Tyr Phe Ser Gln Thr Ser Gly Asp Lys Gly Arg Val Glu Gln
5                   10                  15                  20

atc cat cag cag aag atg gct cgc gag ccc gcg acc ctg aaa gac agc       197
Ile His Gln Gln Lys Met Ala Arg Glu Pro Ala Thr Leu Lys Asp Ser
                25                  30                  35

ctt gag caa gac ctc aac aat atg aac aag ttc ctg gaa aag ctg agg       245
Leu Glu Gln Asp Leu Asn Asn Met Asn Lys Phe Leu Glu Lys Leu Arg
            40                  45                  50

cct ctg agt ggg agc gag gct cct cgg ctc cca cag gac ccg gtg ggc       293
Pro Leu Ser Gly Ser Glu Ala Pro Arg Leu Pro Gln Asp Pro Val Gly
        55                  60                  65

atg cgg cgg cag ctg cag gag gag ttg gag gag gtg aag gct cgc ctc       341
Met Arg Arg Gln Leu Gln Glu Glu Leu Glu Glu Val Lys Ala Arg Leu
    70                  75                  80

cag ccc tac atg gca gag gcg cac gag ctg gtg ggc tgg aat ttg gag       389
Gln Pro Tyr Met Ala Glu Ala His Glu Leu Val Gly Trp Asn Leu Glu
85                  90                  95                  100

ggc ttg cgg cag caa ctg aag ccc tac acg atg gat ctg atg gag cag       437
Gly Leu Arg Gln Gln Leu Lys Pro Tyr Thr Met Asp Leu Met Glu Gln
                105                 110                 115

gtg gcc ctg cgc gtg cag gag ctg cag gag cag ttg cgc gtg gtg ggg       485
Val Ala Leu Arg Val Gln Glu Leu Gln Glu Gln Leu Arg Val Val Gly
            120                 125                 130

gaa gac acc aag gcc cag ttg ctg ggg ggc gtg gac gag gct tgg gct       533
Glu Asp Thr Lys Ala Gln Leu Leu Gly Gly Val Asp Glu Ala Trp Ala
        135                 140                 145

ttg ctg cag gga ctg cag agc cgc gtg gtg cac cac acc ggc cgc ttc       581
Leu Leu Gln Gly Leu Gln Ser Arg Val Val His His Thr Gly Arg Phe
    150                 155                 160

aaa gag ctc ttc cac cca tac gcc gag agc ctg gtg agc ggc atc ggg       629
Lys Glu Leu Phe His Pro Tyr Ala Glu Ser Leu Val Ser Gly Ile Gly
165                 170                 175                 180

cgc cac gtg cag gag ctg cac cgc agt gtg gct ccg cac gcc ccc gcc       677
Arg His Val Gln Glu Leu His Arg Ser Val Ala Pro His Ala Pro Ala
                185                 190                 195

agc ccc gcg cgc ctc agt cgc tgc gtg cag gtg ctc tcc cgg aag ctc       725
Ser Pro Ala Arg Leu Ser Arg Cys Val Gln Val Leu Ser Arg Lys Leu
            200                 205                 210

acg ctc aag gcc aag gcc ctg cac gca cgc atc cag cag aac ctg gac       773
Thr Leu Lys Ala Lys Ala Leu His Ala Arg Ile Gln Gln Asn Leu Asp
```

-continued

```
        215                 220                 225

cag ctg cgc gaa gag ctc agc aga gcc ttt gca ggc act ggg act gag      821
Gln Leu Arg Glu Glu Leu Ser Arg Ala Phe Ala Gly Thr Gly Thr Glu
    230                 235                 240

gaa ggg gcc ggc ccg gac ccc cag atg ctc tcc gag gag gtg cgc cag      869
Glu Gly Ala Gly Pro Asp Pro Gln Met Leu Ser Glu Glu Val Arg Gln
245                 250                 255                 260

cga ctt cag gct ttc cgc cag gac acc tac ctg cag ata gct gcc ttc      917
Arg Leu Gln Ala Phe Arg Gln Asp Thr Tyr Leu Gln Ile Ala Ala Phe
                265                 270                 275

act cgc gcc atc gac cag gag act gag gag gtc cag cag cag ctg gcg      965
Thr Arg Ala Ile Asp Gln Glu Thr Glu Glu Val Gln Gln Gln Leu Ala
            280                 285                 290

cca cct cca cca ggc cac agt gcc ttc gcc cca gag ttt caa caa aca     1013
Pro Pro Pro Pro Gly His Ser Ala Phe Ala Pro Glu Phe Gln Gln Thr
        295                 300                 305

gac agt ggc aag gtt ctg agc aag ctg cag gcc cgt ctg gat gac ctg     1061
Asp Ser Gly Lys Val Leu Ser Lys Leu Gln Ala Arg Leu Asp Asp Leu
    310                 315                 320

tgg gaa gac atc act cac agc ctt cat gac cag ggc cac agc cat ctg     1109
Trp Glu Asp Ile Thr His Ser Leu His Asp Gln Gly His Ser His Leu
325                 330                 335                 340

ggg gac ccc tgaggatcta cctgcccagg cccattccca gcttcttgtc             1158
Gly Asp Pro

tggggagcct tggctctgag cctctagcat ggttcagtcc ttgaaagtgg cctgttgggt   1218

ggagggtgga aggtcctgtg caggacaggg aggccaccaa aggggctgct gtctcctgca   1278

tatccagcct cctgcgactc cccaatctgg atgcattaca ttcaccaggc tttgcaaacc   1338

cagcctccca gtgctcattt gggaatgctc atgagttact ccattcaagg gtgagggagt   1398

agggagggag aggcaccatg catgtgggtg attatctgca agcctgtttg ccgtgatgct   1458

ggaagcctgt gccactacat cctggagttt ggctctagtc acttctggct gcctggtggc   1518

cactgctaca gctggtccac agagaggagc acttgtctcc ccagggctgc catggcagct   1578

atcaggggaa tagaagggag aaagagaata tcatggggag aacatgtgat ggtgtgtgaa   1638

tatccctgct ggctctgatg ctggtgggta cgaaaggtgt gggctgtgat aggagagggc   1698

agagcccatg tttcctgaca tagctctaca cctaaataag ggactgaacc ctcccaactg   1758

tgggagctcc ttaaaccctc tggggagcat actgtgtgct ctccccatct ccagcccctc   1818

cctctgggtt cccaagttga agcctagact tctggctcaa atgaaataga tgtttatgat   1878

aaaaaaaaaa aaaaaa                                                   1894


<210> SEQ ID NO 28
<211> LENGTH: 366
<212> TYPE: PRT
<213> ORGANISM: Homo sapiens
<220> FEATURE:
<221> NAME/KEY: SIGNAL
<222> LOCATION: 1..23

<400> SEQUENCE: 28

Met Ala Ser Met Ala Ala Val Leu Thr Trp Ala Leu Ala Leu Leu Ser
            -20                 -15                 -10

Ala Phe Ser Ala Thr Gln Ala Arg Lys Gly Phe Trp Asp Tyr Phe Ser
        -5                  1               5

Gln Thr Ser Gly Asp Lys Gly Arg Val Glu Gln Ile His Gln Gln Lys
10                  15                  20                  25
```

-continued

```
Met Ala Arg Glu Pro Ala Thr Leu Lys Asp Ser Leu Glu Gln Asp Leu
                30                  35                  40

Asn Asn Met Asn Lys Phe Leu Glu Lys Leu Arg Pro Leu Ser Gly Ser
            45                  50                  55

Glu Ala Pro Arg Leu Pro Gln Asp Pro Val Gly Met Arg Arg Gln Leu
        60                  65                  70

Gln Glu Glu Leu Glu Glu Val Lys Ala Arg Leu Gln Pro Tyr Met Ala
    75                  80                  85

Glu Ala His Glu Leu Val Gly Trp Asn Leu Glu Gly Leu Arg Gln Gln
90                  95                  100                 105

Leu Lys Pro Tyr Thr Met Asp Leu Met Glu Gln Val Ala Leu Arg Val
                110                 115                 120

Gln Glu Leu Gln Glu Gln Leu Arg Val Val Gly Glu Asp Thr Lys Ala
            125                 130                 135

Gln Leu Leu Gly Gly Val Asp Glu Ala Trp Ala Leu Leu Gln Gly Leu
        140                 145                 150

Gln Ser Arg Val Val His His Thr Gly Arg Phe Lys Glu Leu Phe His
    155                 160                 165

Pro Tyr Ala Glu Ser Leu Val Ser Gly Ile Gly Arg His Val Gln Glu
170                 175                 180                 185

Leu His Arg Ser Val Ala Pro His Ala Pro Ala Ser Pro Ala Arg Leu
                190                 195                 200

Ser Arg Cys Val Gln Val Leu Ser Arg Lys Leu Thr Leu Lys Ala Lys
            205                 210                 215

Ala Leu His Ala Arg Ile Gln Gln Asn Leu Asp Gln Leu Arg Glu Glu
        220                 225                 230

Leu Ser Arg Ala Phe Ala Gly Thr Gly Thr Glu Glu Gly Ala Gly Pro
    235                 240                 245

Asp Pro Gln Met Leu Ser Glu Glu Val Arg Gln Arg Leu Gln Ala Phe
250                 255                 260                 265

Arg Gln Asp Thr Tyr Leu Gln Ile Ala Ala Phe Thr Arg Ala Ile Asp
                270                 275                 280

Gln Glu Thr Glu Glu Val Gln Gln Gln Leu Ala Pro Pro Pro Pro Gly
            285                 290                 295

His Ser Ala Phe Ala Pro Glu Phe Gln Gln Thr Asp Ser Gly Lys Val
        300                 305                 310

Leu Ser Lys Leu Gln Ala Arg Leu Asp Asp Leu Trp Glu Asp Ile Thr
    315                 320                 325

His Ser Leu His Asp Gln Gly His Ser His Leu Gly Asp Pro
330                 335                 340
```

<210> SEQ ID NO 29
<211> LENGTH: 742
<212> TYPE: DNA
<213> ORGANISM: Homo sapiens
<220> FEATURE:
<221> NAME/KEY: 5'UTR
<222> LOCATION: 1..31
<220> FEATURE:
<221> NAME/KEY: CDS
<222> LOCATION: 32..559
<220> FEATURE:
<221> NAME/KEY: 3'UTR
<222> LOCATION: 560..742
<220> FEATURE:
<221> NAME/KEY: polyA_signal
<222> LOCATION: 702..707
<220> FEATURE:
<221> NAME/KEY: polyA_site

```
<222> LOCATION: 728..742

<400> SEQUENCE: 29

aattttttttg tgacttcttc agaccacttt c atg act tct gga agc aaa tgt        52
                                    Met Thr Ser Gly Ser Lys Cys
                                    1               5

cct agt aca gac tca gga aaa gaa gaa tat att gcc acg ttc aaa gga       100
Pro Ser Thr Asp Ser Gly Lys Glu Glu Tyr Ile Ala Thr Phe Lys Gly
        10                  15                  20

tct gaa tac ttc tgc tac gac ttg tct caa aac ccc att caa agc agc       148
Ser Glu Tyr Phe Cys Tyr Asp Leu Ser Gln Asn Pro Ile Gln Ser Ser
    25                  30                  35

agt gat gaa ata act ctg tca ttt aaa acc ctt cag agg aat gga ctg       196
Ser Asp Glu Ile Thr Leu Ser Phe Lys Thr Leu Gln Arg Asn Gly Leu
40                  45                  50                  55

atg ctt cac act ggg aaa tcg gct gat tat gtc aat ctt gcc ctg aaa       244
Met Leu His Thr Gly Lys Ser Ala Asp Tyr Val Asn Leu Ala Leu Lys
                60                  65                  70

aat gga gct gtc tct ctg gtc att aat ttg gga tca ggg gcc ttt gaa       292
Asn Gly Ala Val Ser Leu Val Ile Asn Leu Gly Ser Gly Ala Phe Glu
            75                  80                  85

gca cta gtg gag cct gtg aat gga aag ttt aat gat aat gcc tgg cat       340
Ala Leu Val Glu Pro Val Asn Gly Lys Phe Asn Asp Asn Ala Trp His
        90                  95                  100

gat gtg aaa gtc acc agg aat ctg cgt cag gtg aca ata tca gtg gat       388
Asp Val Lys Val Thr Arg Asn Leu Arg Gln Val Thr Ile Ser Val Asp
    105                 110                 115

ggg att ctt acc aca acg ggc tac acg caa gaa gat tat acc atg ctg       436
Gly Ile Leu Thr Thr Thr Gly Tyr Thr Gln Glu Asp Tyr Thr Met Leu
120                 125                 130                 135

ggg tct gat gac ttt ttc tat gtt gga ggc agt ccc agc aca gcc gac       484
Gly Ser Asp Asp Phe Phe Tyr Val Gly Gly Ser Pro Ser Thr Ala Asp
                140                 145                 150

ctt cca ggg tca cca atc cag cat gaa agc acc ttt gct gaa gac ccg       532
Leu Pro Gly Ser Pro Ile Gln His Glu Ser Thr Phe Ala Glu Asp Pro
            155                 160                 165

atg ttc cag agt caa acg gca caa ctt taaattcaat attctactat             579
Met Phe Gln Ser Gln Thr Ala Gln Leu
        170                 175

tgtttatgta ggattggggg agggaaacag ctcatagatc attatgaagg aattaggttc    639

ctcttcttta ttagtctgta agtaatttac atttgagatt tgtgtggaca gttgatatta    699

gctataaaag aaagtcaaac aaaaagagaa aaaaaaaaaa aaa                      742


<210> SEQ ID NO 30
<211> LENGTH: 176
<212> TYPE: PRT
<213> ORGANISM: Homo sapiens

<400> SEQUENCE: 30

Met Thr Ser Gly Ser Lys Cys Pro Ser Thr Asp Ser Gly Lys Glu Glu
1               5                   10                  15

Tyr Ile Ala Thr Phe Lys Gly Ser Glu Tyr Phe Cys Tyr Asp Leu Ser
            20                  25                  30

Gln Asn Pro Ile Gln Ser Ser Ser Asp Glu Ile Thr Leu Ser Phe Lys
        35                  40                  45

Thr Leu Gln Arg Asn Gly Leu Met Leu His Thr Gly Lys Ser Ala Asp
    50                  55                  60

Tyr Val Asn Leu Ala Leu Lys Asn Gly Ala Val Ser Leu Val Ile Asn
```

-continued

```
65                  70                  75                  80

Leu Gly Ser Gly Ala Phe Glu Ala Leu Val Glu Pro Val Asn Gly Lys
                85                  90                  95

Phe Asn Asp Asn Ala Trp His Asp Val Lys Val Thr Arg Asn Leu Arg
            100                 105                 110

Gln Val Thr Ile Ser Val Asp Gly Ile Leu Thr Thr Thr Gly Tyr Thr
        115                 120                 125

Gln Glu Asp Tyr Thr Met Leu Gly Ser Asp Asp Phe Phe Tyr Val Gly
    130                 135                 140

Gly Ser Pro Ser Thr Ala Asp Leu Pro Gly Ser Pro Ile Gln His Glu
145                 150                 155                 160

Ser Thr Phe Ala Glu Asp Pro Met Phe Gln Ser Gln Thr Ala Gln Leu
                165                 170                 175


<210> SEQ ID NO 31
<211> LENGTH: 1766
<212> TYPE: DNA
<213> ORGANISM: Homo sapiens
<220> FEATURE:
<221> NAME/KEY: 5'UTR
<222> LOCATION: 1..3
<220> FEATURE:
<221> NAME/KEY: CDS
<222> LOCATION: 4..1533
<220> FEATURE:
<221> NAME/KEY: 3'UTR
<222> LOCATION: 1534..1766
<220> FEATURE:
<221> NAME/KEY: polyA_signal
<222> LOCATION: 1709..1714
<220> FEATURE:
<221> NAME/KEY: polyA_site
<222> LOCATION: 1744..1766

<400> SEQUENCE: 31

aag atg gcg gcg gag ctg gtg gag gcc aaa aac atg gtg atg agt ttt       48
    Met Ala Ala Glu Leu Val Glu Ala Lys Asn Met Val Met Ser Phe
    1               5                   10                  15

cga gtc tcc gac ctt cag atg ctc ctg ggt ttc gtg ggc cgg agt aag       96
Arg Val Ser Asp Leu Gln Met Leu Leu Gly Phe Val Gly Arg Ser Lys
                20                  25                  30

agt gga ctg aag cac gag ctc gtc acc agg gcc ctc cag ctg gtg cag      144
Ser Gly Leu Lys His Glu Leu Val Thr Arg Ala Leu Gln Leu Val Gln
            35                  40                  45

ttt gac tgt acc cct gag ctg ttc aag aag atc aag gag ctg tac gag      192
Phe Asp Cys Thr Pro Glu Leu Phe Lys Lys Ile Lys Glu Leu Tyr Glu
        50                  55                  60

acc cgc tac gcc aag aag aac tcg gag cct gcc cca cag ccg cac cgg      240
Thr Arg Tyr Ala Lys Lys Asn Ser Glu Pro Ala Pro Gln Pro His Arg
    65                  70                  75

ccc ctg gac ccc ctg acc atg cac tcc acc tac gac cgg gcc ggc gct      288
Pro Leu Asp Pro Leu Thr Met His Ser Thr Tyr Asp Arg Ala Gly Ala
80                  85                  90                  95

gtg ccc agg act ccg ctg gca ggc ccc aat att gac tac ccc gtg ctc      336
Val Pro Arg Thr Pro Leu Ala Gly Pro Asn Ile Asp Tyr Pro Val Leu
                100                 105                 110

tac gga aag tac tta aac gga ctg gga cgg ttg ccc gcc aag acc ctc      384
Tyr Gly Lys Tyr Leu Asn Gly Leu Gly Arg Leu Pro Ala Lys Thr Leu
            115                 120                 125

aag cca gaa gtc cgc ctg gtg aag ctg ccg ttc ttt aat atg ctg gac      432
Lys Pro Glu Val Arg Leu Val Lys Leu Pro Phe Phe Asn Met Leu Asp
        130                 135                 140
```

-continued

```
gag ctg ctg aag ccc acc gaa tta gtc cca cag aac aac gag aag ctt      480
Glu Leu Leu Lys Pro Thr Glu Leu Val Pro Gln Asn Asn Glu Lys Leu
    145                 150                 155

cag gag agc ccg tgc atc ttc gca ttg acg cca aga cag gtg gag ttg      528
Gln Glu Ser Pro Cys Ile Phe Ala Leu Thr Pro Arg Gln Val Glu Leu
160                 165                 170                 175

atc cgg aac tcc agg gaa ctg cag ccc gga gtt aaa gcc gtg cag gtc      576
Ile Arg Asn Ser Arg Glu Leu Gln Pro Gly Val Lys Ala Val Gln Val
                180                 185                 190

gtc ctg aga atc tgt tac tca gac acc agc tgc cct cag gag gac cag      624
Val Leu Arg Ile Cys Tyr Ser Asp Thr Ser Cys Pro Gln Glu Asp Gln
            195                 200                 205

tac ccg ccc aac atc gct gtg aag gtc aac cac agc tac tgc tcc gtc      672
Tyr Pro Pro Asn Ile Ala Val Lys Val Asn His Ser Tyr Cys Ser Val
        210                 215                 220

ccg ggc tac tac ccc tcc aat aag ccc ggg gtg gag ccc aag agg ccg      720
Pro Gly Tyr Tyr Pro Ser Asn Lys Pro Gly Val Glu Pro Lys Arg Pro
    225                 230                 235

tgc cgc ccc atc aac ctc acc cac ctc atg tac ctt tcc tcg gcc acc      768
Cys Arg Pro Ile Asn Leu Thr His Leu Met Tyr Leu Ser Ser Ala Thr
240                 245                 250                 255

aac cgc atc act gtc acc tgg ggg aac tac ggc aag agc tac tcg gtg      816
Asn Arg Ile Thr Val Thr Trp Gly Asn Tyr Gly Lys Ser Tyr Ser Val
                260                 265                 270

gcc ctg tac ctg gtg cgg cag ctg acc tca tcg gag ctg ctg cag agg      864
Ala Leu Tyr Leu Val Arg Gln Leu Thr Ser Ser Glu Leu Leu Gln Arg
            275                 280                 285

ctg aag acc att ggg gta aag cac ccg gag ctg tgc aag gca ctg gtc      912
Leu Lys Thr Ile Gly Val Lys His Pro Glu Leu Cys Lys Ala Leu Val
        290                 295                 300

aag gag aag ctg cgc ctt gat cct gac agc gag atc gcc acc acc ggt      960
Lys Glu Lys Leu Arg Leu Asp Pro Asp Ser Glu Ile Ala Thr Thr Gly
    305                 310                 315

gtg cgg gtg tcc ctc atc tgt ccg ctg gtg aag atg cgg ctc tcc gtg     1008
Val Arg Val Ser Leu Ile Cys Pro Leu Val Lys Met Arg Leu Ser Val
320                 325                 330                 335

ccc tgc cgg gca gag acc tgc gcc cac ctg cag tgc ttc gac gcc gtc     1056
Pro Cys Arg Ala Glu Thr Cys Ala His Leu Gln Cys Phe Asp Ala Val
                340                 345                 350

ttc tac ctg cag atg aac gag aag aag ccc acc tgg atg tgc ccc gtg     1104
Phe Tyr Leu Gln Met Asn Glu Lys Lys Pro Thr Trp Met Cys Pro Val
            355                 360                 365

tgc gac aag cca gcc ccc tac gac cag ctc atc atc gac ggg ctc ctc     1152
Cys Asp Lys Pro Ala Pro Tyr Asp Gln Leu Ile Ile Asp Gly Leu Leu
        370                 375                 380

tcg aag atc ctg agc gag tgt gag gac gcc gac gag atc gag tac ctg     1200
Ser Lys Ile Leu Ser Glu Cys Glu Asp Ala Asp Glu Ile Glu Tyr Leu
    385                 390                 395

gtg gac ggc tcg tgg tgc ccg atc cgc gcc gaa aag gag ctc agc tgc     1248
Val Asp Gly Ser Trp Cys Pro Ile Arg Ala Glu Lys Glu Leu Ser Cys
400                 405                 410                 415

agc ccg cag ggc gcc atc ctc gtg ctg ggc ccc tcg gac gcc aat ggg     1296
Ser Pro Gln Gly Ala Ile Leu Val Leu Gly Pro Ser Asp Ala Asn Gly
                420                 425                 430

ctc ctg ccc gcc ccc agc gtc aac ggg agc ggt gcc ctg ggc agc acg     1344
Leu Leu Pro Ala Pro Ser Val Asn Gly Ser Gly Ala Leu Gly Ser Thr
            435                 440                 445

ggt ggc ggc ggc ccg gtg ggc agc atg gag aat ggg aag ccg ggc gcc     1392
Gly Gly Gly Gly Pro Val Gly Ser Met Glu Asn Gly Lys Pro Gly Ala
        450                 455                 460
```

-continued

```
gat gtg gtg gac ctc acg ctg gac agc tca tcg tcc tcg gag gat gag     1440
Asp Val Val Asp Leu Thr Leu Asp Ser Ser Ser Ser Ser Glu Asp Glu
    465                 470                 475

gag gag gag gaa gag gag gag gaa gac gag gac gaa gag ggg ccc cgg     1488
Glu Glu Glu Glu Glu Glu Glu Glu Asp Glu Asp Glu Glu Gly Pro Arg
480                 485                 490                 495

ccc aag cgc cgc tgc ccc ttc cag aag ggc ctg gtg ccg gcc tgc         1533
Pro Lys Arg Arg Cys Pro Phe Gln Lys Gly Leu Val Pro Ala Cys
                500                 505                 510

tgaccccggc cgcacacttg actttcctgg tgctcaccac gcagaggggc acgggccagc   1593

ctcgggcgca gagggaggag tgacctttct ttttcctttt attgtcgttc gttttgtttt   1653

tccacccttt tgcctggctc ctggcacctg tacctctgga ctctcctatc gggggattaa   1713

aaaaaaaagt aaaatgacaa aaaaagatac aaaaaagaaa aaaaaaaaaa aaa          1766


<210> SEQ ID NO 32
<211> LENGTH: 510
<212> TYPE: PRT
<213> ORGANISM: Homo sapiens

<400> SEQUENCE: 32

Met Ala Ala Glu Leu Val Glu Ala Lys Asn Met Val Met Ser Phe Arg
1               5                   10                  15

Val Ser Asp Leu Gln Met Leu Leu Gly Phe Val Gly Arg Ser Lys Ser
            20                  25                  30

Gly Leu Lys His Glu Leu Val Thr Arg Ala Leu Gln Leu Val Gln Phe
        35                  40                  45

Asp Cys Thr Pro Glu Leu Phe Lys Lys Ile Lys Glu Leu Tyr Glu Thr
    50                  55                  60

Arg Tyr Ala Lys Lys Asn Ser Glu Pro Ala Pro Gln Pro His Arg Pro
65                  70                  75                  80

Leu Asp Pro Leu Thr Met His Ser Thr Tyr Asp Arg Ala Gly Ala Val
                85                  90                  95

Pro Arg Thr Pro Leu Ala Gly Pro Asn Ile Asp Tyr Pro Val Leu Tyr
            100                 105                 110

Gly Lys Tyr Leu Asn Gly Leu Gly Arg Leu Pro Ala Lys Thr Leu Lys
        115                 120                 125

Pro Glu Val Arg Leu Val Lys Leu Pro Phe Phe Asn Met Leu Asp Glu
    130                 135                 140

Leu Leu Lys Pro Thr Glu Leu Val Pro Gln Asn Asn Glu Lys Leu Gln
145                 150                 155                 160

Glu Ser Pro Cys Ile Phe Ala Leu Thr Pro Arg Gln Val Glu Leu Ile
                165                 170                 175

Arg Asn Ser Arg Glu Leu Gln Pro Gly Val Lys Ala Val Gln Val Val
            180                 185                 190

Leu Arg Ile Cys Tyr Ser Asp Thr Ser Cys Pro Gln Glu Asp Gln Tyr
        195                 200                 205

Pro Pro Asn Ile Ala Val Lys Val Asn His Ser Tyr Cys Ser Val Pro
    210                 215                 220

Gly Tyr Tyr Pro Ser Asn Lys Pro Gly Val Glu Pro Lys Arg Pro Cys
225                 230                 235                 240

Arg Pro Ile Asn Leu Thr His Leu Met Tyr Leu Ser Ser Ala Thr Asn
                245                 250                 255

Arg Ile Thr Val Thr Trp Gly Asn Tyr Gly Lys Ser Tyr Ser Val Ala
            260                 265                 270
```

-continued

```
Leu Tyr Leu Val Arg Gln Leu Thr Ser Ser Glu Leu Leu Gln Arg Leu
        275                 280                 285

Lys Thr Ile Gly Val Lys His Pro Glu Leu Cys Lys Ala Leu Val Lys
    290                 295                 300

Glu Lys Leu Arg Leu Asp Pro Asp Ser Glu Ile Ala Thr Thr Gly Val
305                 310                 315                 320

Arg Val Ser Leu Ile Cys Pro Leu Val Lys Met Arg Leu Ser Val Pro
                325                 330                 335

Cys Arg Ala Glu Thr Cys Ala His Leu Gln Cys Phe Asp Ala Val Phe
            340                 345                 350

Tyr Leu Gln Met Asn Glu Lys Lys Pro Thr Trp Met Cys Pro Val Cys
        355                 360                 365

Asp Lys Pro Ala Pro Tyr Asp Gln Leu Ile Ile Asp Gly Leu Leu Ser
    370                 375                 380

Lys Ile Leu Ser Glu Cys Glu Asp Ala Asp Glu Ile Glu Tyr Leu Val
385                 390                 395                 400

Asp Gly Ser Trp Cys Pro Ile Arg Ala Glu Lys Glu Leu Ser Cys Ser
                405                 410                 415

Pro Gln Gly Ala Ile Leu Val Leu Gly Pro Ser Asp Ala Asn Gly Leu
            420                 425                 430

Leu Pro Ala Pro Ser Val Asn Gly Ser Gly Ala Leu Gly Ser Thr Gly
        435                 440                 445

Gly Gly Gly Pro Val Gly Ser Met Glu Asn Gly Lys Pro Gly Ala Asp
    450                 455                 460

Val Val Asp Leu Thr Leu Asp Ser Ser Ser Ser Ser Glu Asp Glu Glu
465                 470                 475                 480

Glu Glu Glu Glu Glu Glu Glu Asp Glu Asp Glu Glu Gly Pro Arg Pro
                485                 490                 495

Lys Arg Arg Cys Pro Phe Gln Lys Gly Leu Val Pro Ala Cys
            500                 505                 510


<210> SEQ ID NO 33
<211> LENGTH: 877
<212> TYPE: DNA
<213> ORGANISM: Homo sapiens
<220> FEATURE:
<221> NAME/KEY: 5'UTR
<222> LOCATION: 1..10
<220> FEATURE:
<221> NAME/KEY: CDS
<222> LOCATION: 11..802
<220> FEATURE:
<221> NAME/KEY: 3'UTR
<222> LOCATION: 803..877
<220> FEATURE:
<221> NAME/KEY: polyA_signal
<222> LOCATION: 836..841
<220> FEATURE:
<221> NAME/KEY: polyA_site
<222> LOCATION: 862..877

<400> SEQUENCE: 33

atctgccacg atg ttg ctg ctc agc ctg acc cta agc ctg gtt ctc ctc        49
           Met Leu Leu Leu Ser Leu Thr Leu Ser Leu Val Leu Leu
                       -15                 -10

ggc tcc tcc tgg ggc tgc ggc att cct gcc atc aaa ccg gca ctg agc       97
Gly Ser Ser Trp Gly Cys Gly Ile Pro Ala Ile Lys Pro Ala Leu Ser
-5                  1               5                   10

ttc agc cag agg att gtc aac ggg gag aat gca gtg ttg ggc tcc tgg      145
Phe Ser Gln Arg Ile Val Asn Gly Glu Asn Ala Val Leu Gly Ser Trp
```

-continued

```
            15                  20                  25

ccc tgg cag gtg tcc ctg cag gac agc agc gac ttc cac ttc tgc ggt        193
Pro Trp Gln Val Ser Leu Gln Asp Ser Ser Asp Phe His Phe Cys Gly
        30                  35                  40

ggt tct ctc atc agc cag tcc tgg gtg gtc act gct gcc cac tgc aat        241
Gly Ser Leu Ile Ser Gln Ser Trp Val Val Thr Ala Ala His Cys Asn
    45                  50                  55

gtc agc cct ggc cgc cat ttt gtt gtc ctg ggc gag tat gac cga tca        289
Val Ser Pro Gly Arg His Phe Val Val Leu Gly Glu Tyr Asp Arg Ser
60                  65                  70                  75

tca aac gca gag ccc ttg cag gtt ctg tcc gtc tct cgg gcc att aca        337
Ser Asn Ala Glu Pro Leu Gln Val Leu Ser Val Ser Arg Ala Ile Thr
                80                  85                  90

cac cct agc tgg aac tct acc acc atg aac aat gac gtg acg ctg ctg        385
His Pro Ser Trp Asn Ser Thr Thr Met Asn Asn Asp Val Thr Leu Leu
            95                  100                 105

aag ctc gcc tcg cca gcc cag tac aca aca cgc atc tcg cca gtt tgc        433
Lys Leu Ala Ser Pro Ala Gln Tyr Thr Thr Arg Ile Ser Pro Val Cys
        110                 115                 120

ctg gca tcc tca aac gag gct ctg act gaa ggc ctc acg tgt gtc acc        481
Leu Ala Ser Ser Asn Glu Ala Leu Thr Glu Gly Leu Thr Cys Val Thr
    125                 130                 135

acc ggc tgg ggt cgc ctc agt ggc gtg ggc aat gtg aca cca gca cgt        529
Thr Gly Trp Gly Arg Leu Ser Gly Val Gly Asn Val Thr Pro Ala Arg
140                 145                 150                 155

ctg cag cag gtg gct ttg ccc ctg gtc act gtg aat cag tgc cgg cag        577
Leu Gln Gln Val Ala Leu Pro Leu Val Thr Val Asn Gln Cys Arg Gln
                160                 165                 170

tac tgg ggc tca agt atc act gac tcc atg atc tgt gca ggt ggc gca        625
Tyr Trp Gly Ser Ser Ile Thr Asp Ser Met Ile Cys Ala Gly Gly Ala
            175                 180                 185

ggt gcc tcc tcg tgc cag ggt gac tcc gga ggc cct ctt gtc tgc cag        673
Gly Ala Ser Ser Cys Gln Gly Asp Ser Gly Gly Pro Leu Val Cys Gln
        190                 195                 200

aag gga aac aca tgg gtg ctt att ggt att gtc tcc tgg ggc acc aaa        721
Lys Gly Asn Thr Trp Val Leu Ile Gly Ile Val Ser Trp Gly Thr Lys
    205                 210                 215

aac tgc aat gtg cgc gca cct gct gtg tat act cga gtt agc aag ttc        769
Asn Cys Asn Val Arg Ala Pro Ala Val Tyr Thr Arg Val Ser Lys Phe
220                 225                 230                 235

agc acc tgg atc aac cag gtc ata gcc tac aac tgagctcacc acaggccctc      822
Ser Thr Trp Ile Asn Gln Val Ile Ala Tyr Asn
                240                 245

cccagctcaa cccattaaag acccaggccc tgtcccatca aaaaaaaaaa aaaaa           877


<210> SEQ ID NO 34
<211> LENGTH: 264
<212> TYPE: PRT
<213> ORGANISM: Homo sapiens
<220> FEATURE:
<221> NAME/KEY: SIGNAL
<222> LOCATION: 1..18

<400> SEQUENCE: 34

Met Leu Leu Leu Ser Leu Thr Leu Ser Leu Val Leu Leu Gly Ser Ser
            -15                 -10                 -5

Trp Gly Cys Gly Ile Pro Ala Ile Lys Pro Ala Leu Ser Phe Ser Gln
        1               5                   10

Arg Ile Val Asn Gly Glu Asn Ala Val Leu Gly Ser Trp Pro Trp Gln
15                  20                  25                  30
```

-continued

```
Val Ser Leu Gln Asp Ser Ser Asp Phe His Phe Cys Gly Gly Ser Leu
                35                  40                  45

Ile Ser Gln Ser Trp Val Val Thr Ala Ala His Cys Asn Val Ser Pro
            50                  55                  60

Gly Arg His Phe Val Val Leu Gly Glu Tyr Asp Arg Ser Ser Asn Ala
        65                  70                  75

Glu Pro Leu Gln Val Leu Ser Val Ser Arg Ala Ile Thr His Pro Ser
    80                  85                  90

Trp Asn Ser Thr Thr Met Asn Asn Asp Val Thr Leu Leu Lys Leu Ala
95                  100                 105                 110

Ser Pro Ala Gln Tyr Thr Thr Arg Ile Ser Pro Val Cys Leu Ala Ser
                115                 120                 125

Ser Asn Glu Ala Leu Thr Glu Gly Leu Thr Cys Val Thr Thr Gly Trp
            130                 135                 140

Gly Arg Leu Ser Gly Val Gly Asn Val Thr Pro Ala Arg Leu Gln Gln
        145                 150                 155

Val Ala Leu Pro Leu Val Thr Val Asn Gln Cys Arg Gln Tyr Trp Gly
    160                 165                 170

Ser Ser Ile Thr Asp Ser Met Ile Cys Ala Gly Gly Ala Gly Ala Ser
175                 180                 185                 190

Ser Cys Gln Gly Asp Ser Gly Gly Pro Leu Val Cys Gln Lys Gly Asn
                195                 200                 205

Thr Trp Val Leu Ile Gly Ile Val Ser Trp Gly Thr Lys Asn Cys Asn
            210                 215                 220

Val Arg Ala Pro Ala Val Tyr Thr Arg Val Ser Lys Phe Ser Thr Trp
        225                 230                 235

Ile Asn Gln Val Ile Ala Tyr Asn
    240                 245
```

```
<210> SEQ ID NO 35
<211> LENGTH: 1728
<212> TYPE: DNA
<213> ORGANISM: Homo sapiens
<220> FEATURE:
<221> NAME/KEY: 5'UTR
<222> LOCATION: 1..37
<220> FEATURE:
<221> NAME/KEY: CDS
<222> LOCATION: 38..1378
<220> FEATURE:
<221> NAME/KEY: 3'UTR
<222> LOCATION: 1379..1728
<220> FEATURE:
<221> NAME/KEY: polyA_site
<222> LOCATION: 1713..1728

<400> SEQUENCE: 35

atcatctgca cagctggggc ccctgggagg agacgcc atg atc ccc acc ttc acg       55
                                         Met Ile Pro Thr Phe Thr
                                                     -20

gct ctg ctc tgc ctc ggg ctg agt ctg ggc ccc agg acc cac atg cag      103
Ala Leu Leu Cys Leu Gly Leu Ser Leu Gly Pro Arg Thr His Met Gln
        -15                 -10                 -5

gca ggg ccc ctc ccc aaa ccc acc ctc tgg gct gag cca ggc tct gtg      151
Ala Gly Pro Leu Pro Lys Pro Thr Leu Trp Ala Glu Pro Gly Ser Val
    1               5                   10                  15

atc agc tgg ggg aac tct gtg acc atc tgg tgt cag ggg acc ctg gag      199
Ile Ser Trp Gly Asn Ser Val Thr Ile Trp Cys Gln Gly Thr Leu Glu
                20                  25                  30
```

-continued

```
gct cgg gag tac cgt ctg gat aaa gag gaa agc cca gca ccc tgg gac      247
Ala Arg Glu Tyr Arg Leu Asp Lys Glu Glu Ser Pro Ala Pro Trp Asp
            35                  40                  45

aga cag aac cca ctg gag ccc aag aac aag gcc aga ttc tcc atc cca      295
Arg Gln Asn Pro Leu Glu Pro Lys Asn Lys Ala Arg Phe Ser Ile Pro
        50                  55                  60

tcc atg aca gag gac tat gca ggg aga tac cgc tgt tac tat cgc agc      343
Ser Met Thr Glu Asp Tyr Ala Gly Arg Tyr Arg Cys Tyr Tyr Arg Ser
    65                  70                  75

cct gta ggc tgg tca cag ccc agt gac ccc ctg gag ctg gtg atg aca      391
Pro Val Gly Trp Ser Gln Pro Ser Asp Pro Leu Glu Leu Val Met Thr
80                  85                  90                  95

gga gcc tac agt aaa ccc acc ctt tca gcc ctg ccg agt cct ctt gtg      439
Gly Ala Tyr Ser Lys Pro Thr Leu Ser Ala Leu Pro Ser Pro Leu Val
                100                 105                 110

acc tca gaa aag agc gtg acc ctg ctg tgt cag tca cgg agc cca atg      487
Thr Ser Glu Lys Ser Val Thr Leu Leu Cys Gln Ser Arg Ser Pro Met
            115                 120                 125

gac act ttc ctt ctg atc aag gag cgg gca gcc cat ccc cta ctg cat      535
Asp Thr Phe Leu Leu Ile Lys Glu Arg Ala Ala His Pro Leu Leu His
        130                 135                 140

ctg aga tca gag cac gga gct cag cag cac cag gct gaa ttc ccc atg      583
Leu Arg Ser Glu His Gly Ala Gln Gln His Gln Ala Glu Phe Pro Met
    145                 150                 155

agt cct gtg acc tca gtg cac ggg ggg acc tac agg tgc ttc agc tca      631
Ser Pro Val Thr Ser Val His Gly Gly Thr Tyr Arg Cys Phe Ser Ser
160                 165                 170                 175

cac ggc ttc tcc cac tac ctg ctg tca cac ccc agt gac ccc ctg gag      679
His Gly Phe Ser His Tyr Leu Leu Ser His Pro Ser Asp Pro Leu Glu
                180                 185                 190

ctc ata gtc tca gga tcc ttg gag gat ccc agg ccc tca ccc aca agg      727
Leu Ile Val Ser Gly Ser Leu Glu Asp Pro Arg Pro Ser Pro Thr Arg
            195                 200                 205

tcc gtc tca aca gct gca ggc cct gag gac cag ccc ctc atg cct aca      775
Ser Val Ser Thr Ala Ala Gly Pro Glu Asp Gln Pro Leu Met Pro Thr
        210                 215                 220

ggg tca gtc ccc cac agt ggt ctg aga agg cac tgg gag gta ctg atc      823
Gly Ser Val Pro His Ser Gly Leu Arg Arg His Trp Glu Val Leu Ile
    225                 230                 235

ggg gtc ttg gtg gtc tcc atc ctg ctt ctc tcc ctc ctc ctc ttc ctc      871
Gly Val Leu Val Val Ser Ile Leu Leu Leu Ser Leu Leu Leu Phe Leu
240                 245                 250                 255

ctc ctc caa cac tgg cgt cag gga aaa cac agg aca ttg gcc cag aga      919
Leu Leu Gln His Trp Arg Gln Gly Lys His Arg Thr Leu Ala Gln Arg
                260                 265                 270

cag gct gat ttc caa cgt cct cca ggg gct gcc gag cca gag ccc aag      967
Gln Ala Asp Phe Gln Arg Pro Pro Gly Ala Ala Glu Pro Glu Pro Lys
            275                 280                 285

gac ggg ggc cta cag agg agg tcc agc cca gct gct gac gtc cag gga     1015
Asp Gly Gly Leu Gln Arg Arg Ser Ser Pro Ala Ala Asp Val Gln Gly
        290                 295                 300

gaa aac ttc tgt gct gcc gtg aag gac aca cag cct gag gac ggg gtg     1063
Glu Asn Phe Cys Ala Ala Val Lys Asp Thr Gln Pro Glu Asp Gly Val
    305                 310                 315

gaa atg gac act cgg agc cca cac gat gaa gac ccc cag gca gtg acg     1111
Glu Met Asp Thr Arg Ser Pro His Asp Glu Asp Pro Gln Ala Val Thr
320                 325                 330                 335

tat gcc aag gtg aaa cac tcc aga cct agg aga gaa atg gcc tct cct     1159
Tyr Ala Lys Val Lys His Ser Arg Pro Arg Arg Glu Met Ala Ser Pro
                340                 345                 350
```

-continued

```
ccc tcc cca ctg tct ggg gaa ttc ctg gac aca aag gac aga cag gca      1207
Pro Ser Pro Leu Ser Gly Glu Phe Leu Asp Thr Lys Asp Arg Gln Ala
            355                 360                 365

gaa gag gac aga cag atg gac act gag gct gct gca tct gaa gcc ccc      1255
Glu Glu Asp Arg Gln Met Asp Thr Glu Ala Ala Ala Ser Glu Ala Pro
        370                 375                 380

cag gat gtg acc tac gcc cag ctg cac agc ttt acc ctc aga cag aag      1303
Gln Asp Val Thr Tyr Ala Gln Leu His Ser Phe Thr Leu Arg Gln Lys
    385                 390                 395

gca act gag cct cct cca tcc cag gaa ggg gcc tct cca gct gag ccc      1351
Ala Thr Glu Pro Pro Pro Ser Gln Glu Gly Ala Ser Pro Ala Glu Pro
400                 405                 410                 415

agt gtc tat gcc act ctg gcc atc cac taatccaggg gggacccaga            1398
Ser Val Tyr Ala Thr Leu Ala Ile His
                420

ccccacaagc catggagact caggacccca gaaggcatgg aagctgcctc cagtagacat   1458

cactgaaccc cagccagccc agacccctga cacagaccac tagaagattc cgggaacgtt   1518

gggagtcacc tgattctgca aagataaata atatccctgc attatcaaaa taaagtagca   1578

gacctctcaa ttcacaatga gttaactgat aaaacaaaac agaagtcaga caatgtttta   1638

aattgaatga tcatgtaaat attacacatc aaaccaatga catgggaaaa tgggagcttc   1698

taatgaggac aaacaaaaaa aaaaaaaaaa                                     1728


<210> SEQ ID NO 36
<211> LENGTH: 447
<212> TYPE: PRT
<213> ORGANISM: Homo sapiens
<220> FEATURE:
<221> NAME/KEY: SIGNAL
<222> LOCATION: 1..23

<400> SEQUENCE: 36

Met Ile Pro Thr Phe Thr Ala Leu Leu Cys Leu Gly Leu Ser Leu Gly
            -20                 -15                 -10

Pro Arg Thr His Met Gln Ala Gly Pro Leu Pro Lys Pro Thr Leu Trp
        -5                  1               5

Ala Glu Pro Gly Ser Val Ile Ser Trp Gly Asn Ser Val Thr Ile Trp
10                  15                  20                  25

Cys Gln Gly Thr Leu Glu Ala Arg Glu Tyr Arg Leu Asp Lys Glu Glu
                30                  35                  40

Ser Pro Ala Pro Trp Asp Arg Gln Asn Pro Leu Glu Pro Lys Asn Lys
            45                  50                  55

Ala Arg Phe Ser Ile Pro Ser Met Thr Glu Asp Tyr Ala Gly Arg Tyr
        60                  65                  70

Arg Cys Tyr Tyr Arg Ser Pro Val Gly Trp Ser Gln Pro Ser Asp Pro
    75                  80                  85

Leu Glu Leu Val Met Thr Gly Ala Tyr Ser Lys Pro Thr Leu Ser Ala
90                  95                  100                 105

Leu Pro Ser Pro Leu Val Thr Ser Glu Lys Ser Val Thr Leu Leu Cys
                110                 115                 120

Gln Ser Arg Ser Pro Met Asp Thr Phe Leu Leu Ile Lys Glu Arg Ala
            125                 130                 135

Ala His Pro Leu Leu His Leu Arg Ser Glu His Gly Ala Gln Gln His
        140                 145                 150

Gln Ala Glu Phe Pro Met Ser Pro Val Thr Ser Val His Gly Gly Thr
    155                 160                 165
```

-continued

```
Tyr Arg Cys Phe Ser Ser His Gly Phe Ser His Tyr Leu Leu Ser His
170                 175                 180                 185

Pro Ser Asp Pro Leu Glu Leu Ile Val Ser Gly Ser Leu Glu Asp Pro
                190                 195                 200

Arg Pro Ser Pro Thr Arg Ser Val Ser Thr Ala Ala Gly Pro Glu Asp
            205                 210                 215

Gln Pro Leu Met Pro Thr Gly Ser Val Pro His Ser Gly Leu Arg Arg
        220                 225                 230

His Trp Glu Val Leu Ile Gly Val Leu Val Val Ser Ile Leu Leu Leu
    235                 240                 245

Ser Leu Leu Leu Phe Leu Leu Leu Gln His Trp Arg Gln Gly Lys His
250                 255                 260                 265

Arg Thr Leu Ala Gln Arg Gln Ala Asp Phe Gln Arg Pro Pro Gly Ala
                270                 275                 280

Ala Glu Pro Glu Pro Lys Asp Gly Gly Leu Gln Arg Arg Ser Ser Pro
            285                 290                 295

Ala Ala Asp Val Gln Gly Glu Asn Phe Cys Ala Ala Val Lys Asp Thr
        300                 305                 310

Gln Pro Glu Asp Gly Val Glu Met Asp Thr Arg Ser Pro His Asp Glu
    315                 320                 325

Asp Pro Gln Ala Val Thr Tyr Ala Lys Val Lys His Ser Arg Pro Arg
330                 335                 340                 345

Arg Glu Met Ala Ser Pro Pro Ser Pro Leu Ser Gly Glu Phe Leu Asp
                350                 355                 360

Thr Lys Asp Arg Gln Ala Glu Glu Asp Arg Gln Met Asp Thr Glu Ala
            365                 370                 375

Ala Ala Ser Glu Ala Pro Gln Asp Val Thr Tyr Ala Gln Leu His Ser
        380                 385                 390

Phe Thr Leu Arg Gln Lys Ala Thr Glu Pro Pro Pro Ser Gln Glu Gly
    395                 400                 405

Ala Ser Pro Ala Glu Pro Ser Val Tyr Ala Thr Leu Ala Ile His
410                 415                 420
```

<210> SEQ ID NO 37
<211> LENGTH: 1757
<212> TYPE: DNA
<213> ORGANISM: Homo sapiens
<220> FEATURE:
<221> NAME/KEY: 5'UTR
<222> LOCATION: 1..329
<220> FEATURE:
<221> NAME/KEY: CDS
<222> LOCATION: 330..1478
<220> FEATURE:
<221> NAME/KEY: 3'UTR
<222> LOCATION: 1479..1757
<220> FEATURE:
<221> NAME/KEY: polyA_signal
<222> LOCATION: 1722..1727
<220> FEATURE:
<221> NAME/KEY: polyA_site
<222> LOCATION: 1742..1757

<400> SEQUENCE: 37

```
atttagttga agctgcaggg gagtgaggga gaggaggata ggaagcagga aagcgggaga     60

gctcgaggga caagggggct cggtgtgttt acaccaggca cgggctacga gcgtccatcc    120

cggcccctgg cttgcgctcc cgaagaggag agcaaggctg ttctgggatc cggccgtcgt    180

gcggcaagag gcttgtctgt ccgggttgcc ggaaccagga gaacccagag ggaaaccgag    240
```

-continued

```
gcaaaggagc ggcgcgtttt actagagaga gcgcgagcgg aagaggcgag agcaggagcg    300

cgcgagggag catcgagcgc agcggagac atg agg acc tac tgg ctg cac agc     353
                                Met Arg Thr Tyr Trp Leu His Ser
                                            -20

gtc tgg gtg ctg ggc ttt ttc ctg tcc ctc ttc tca ttg caa gga ctg      401
Val Trp Val Leu Gly Phe Phe Leu Ser Leu Phe Ser Leu Gln Gly Leu
-15                 -10                 -5                  1

cct gtt cgc agc gtg gat ttt aac cga ggc acg gac aac atc acc gtg      449
Pro Val Arg Ser Val Asp Phe Asn Arg Gly Thr Asp Asn Ile Thr Val
            5                   10                  15

agg cag ggg gac aca gcc atc ctc agg tgc gtt gta gaa gac aag aac      497
Arg Gln Gly Asp Thr Ala Ile Leu Arg Cys Val Val Glu Asp Lys Asn
        20                  25                  30

tca aag gtg gcc tgg ttg aac cgt tct ggc atc att ttt gct gga cat      545
Ser Lys Val Ala Trp Leu Asn Arg Ser Gly Ile Ile Phe Ala Gly His
    35                  40                  45

gac aag tgg tct ctg gac cca cgg gtt gag ctg gag aaa cgc cat tct      593
Asp Lys Trp Ser Leu Asp Pro Arg Val Glu Leu Glu Lys Arg His Ser
50                  55                  60                  65

ctg gaa tac agc ctc cga atc cag aag gtg gat gtc tat gat gag ggt      641
Leu Glu Tyr Ser Leu Arg Ile Gln Lys Val Asp Val Tyr Asp Glu Gly
                70                  75                  80

tcc tac act tgc tca gtt cag aca cag cat gag ccc aag acc tcc caa      689
Ser Tyr Thr Cys Ser Val Gln Thr Gln His Glu Pro Lys Thr Ser Gln
            85                  90                  95

gtt tac ttg atc gta caa gtc cca cca aag atc tcc aat atc tcc tcg      737
Val Tyr Leu Ile Val Gln Val Pro Pro Lys Ile Ser Asn Ile Ser Ser
        100                 105                 110

gat gtc act gtg aat gag ggc agc aac gtg act ctg gtc tgc atg gcc      785
Asp Val Thr Val Asn Glu Gly Ser Asn Val Thr Leu Val Cys Met Ala
    115                 120                 125

aat ggc cgt cct gaa cct gtt atc acc tgg aga cac ctt aca cca act      833
Asn Gly Arg Pro Glu Pro Val Ile Thr Trp Arg His Leu Thr Pro Thr
130                 135                 140                 145

gga agg gaa ttt gaa gga gaa gaa gaa tat ctg gag atc ctt ggc atc      881
Gly Arg Glu Phe Glu Gly Glu Glu Glu Tyr Leu Glu Ile Leu Gly Ile
                150                 155                 160

acc agg gag cag tca ggc aaa tat gag tgc aaa gct gcc aac gag gtc      929
Thr Arg Glu Gln Ser Gly Lys Tyr Glu Cys Lys Ala Ala Asn Glu Val
            165                 170                 175

tcc tcg gcg gat gtc aaa caa gtc aag gtc act gtg aac tat cct ccc      977
Ser Ser Ala Asp Val Lys Gln Val Lys Val Thr Val Asn Tyr Pro Pro
        180                 185                 190

act atc aca gaa tcc aag agc aat gaa gcc acc aca gga cga caa gct     1025
Thr Ile Thr Glu Ser Lys Ser Asn Glu Ala Thr Thr Gly Arg Gln Ala
    195                 200                 205

tca ctc aaa tgt gag gcc tcg gca gtg cct gca cct gac ttt gag tgg     1073
Ser Leu Lys Cys Glu Ala Ser Ala Val Pro Ala Pro Asp Phe Glu Trp
210                 215                 220                 225

tac cgg gat gac act agg ata aat agt gcc aat ggc ctt gag att aag     1121
Tyr Arg Asp Asp Thr Arg Ile Asn Ser Ala Asn Gly Leu Glu Ile Lys
                230                 235                 240

agc acg gag ggc cag tct tcc ctg acg gtg acc aac gtc act gag gag     1169
Ser Thr Glu Gly Gln Ser Ser Leu Thr Val Thr Asn Val Thr Glu Glu
            245                 250                 255

cac tac ggc aac tac acc tgt gtg gct gcc aac aag ctg ggg gtc acc     1217
His Tyr Gly Asn Tyr Thr Cys Val Ala Ala Asn Lys Leu Gly Val Thr
        260                 265                 270
```

-continued

```
aat gcc agc cta gtc ctt ttc aaa cgt gtt tta ccc aca atc ccc cac      1265
Asn Ala Ser Leu Val Leu Phe Lys Arg Val Leu Pro Thr Ile Pro His
    275                 280                 285

ccc att caa gaa att ggt acc acc gtg cac ttc aag caa aaa ggc atc      1313
Pro Ile Gln Glu Ile Gly Thr Thr Val His Phe Lys Gln Lys Gly Ile
290                 295                 300                 305

ttc ctc tct gag tct cag agg ggt gag aca acc aag atc act ctc aac      1361
Phe Leu Ser Glu Ser Gln Arg Gly Glu Thr Thr Lys Ile Thr Leu Asn
                310                 315                 320

tgt gga aat cta ttc ttg cgg aac tta cat ccc acc agt gat caa gag      1409
Cys Gly Asn Leu Phe Leu Arg Asn Leu His Pro Thr Ser Asp Gln Glu
            325                 330                 335

cca cag aga tta tgg aca ctt tgt tgc tta ctc cca aga aag ggc cag      1457
Pro Gln Arg Leu Trp Thr Leu Cys Cys Leu Leu Pro Arg Lys Gly Gln
        340                 345                 350

cac cgt att tat ggc cag tgc tagaaggtcc tcactgaagg caacagggaa        1508
His Arg Ile Tyr Gly Gln Cys
    355                 360

gaggcagcca tgaatatata cttggaaaca ggatcatttg aggccttcaa gaaggcataa   1568

aatattgtcc ctttcagcct ttcttttctt ctcaatgcca cgattaccaa ttatgtttta   1628

atcttaagtg gctagtgtta tatgtgatac attatgcctt tgatatgtgg ttgaaaaaat   1688

aaggcatagc attgtttttt atttcaaaga caaaataaac tgccagtgtc accaaaaaaa   1748

aaaaaaaaa                                                           1757


<210> SEQ ID NO 38
<211> LENGTH: 383
<212> TYPE: PRT
<213> ORGANISM: Homo sapiens
<220> FEATURE:
<221> NAME/KEY: SIGNAL
<222> LOCATION: 1..23

<400> SEQUENCE: 38

Met Arg Thr Tyr Trp Leu His Ser Val Trp Val Leu Gly Phe Phe Leu
            -20                 -15                 -10

Ser Leu Phe Ser Leu Gln Gly Leu Pro Val Arg Ser Val Asp Phe Asn
        -5                  1               5

Arg Gly Thr Asp Asn Ile Thr Val Arg Gln Gly Asp Thr Ala Ile Leu
10                  15                  20                  25

Arg Cys Val Val Glu Asp Lys Asn Ser Lys Val Ala Trp Leu Asn Arg
                30                  35                  40

Ser Gly Ile Ile Phe Ala Gly His Asp Lys Trp Ser Leu Asp Pro Arg
            45                  50                  55

Val Glu Leu Glu Lys Arg His Ser Leu Glu Tyr Ser Leu Arg Ile Gln
        60                  65                  70

Lys Val Asp Val Tyr Asp Glu Gly Ser Tyr Thr Cys Ser Val Gln Thr
    75                  80                  85

Gln His Glu Pro Lys Thr Ser Gln Val Tyr Leu Ile Val Gln Val Pro
90                  95                  100                 105

Pro Lys Ile Ser Asn Ile Ser Ser Asp Val Thr Val Asn Glu Gly Ser
                110                 115                 120

Asn Val Thr Leu Val Cys Met Ala Asn Gly Arg Pro Glu Pro Val Ile
            125                 130                 135

Thr Trp Arg His Leu Thr Pro Thr Gly Arg Glu Phe Glu Gly Glu Glu
        140                 145                 150

Glu Tyr Leu Glu Ile Leu Gly Ile Thr Arg Glu Gln Ser Gly Lys Tyr
```

-continued

```
    155                 160                 165

Glu Cys Lys Ala Ala Asn Glu Val Ser Ser Ala Asp Val Lys Gln Val
170                 175                 180                 185

Lys Val Thr Val Asn Tyr Pro Pro Thr Ile Thr Glu Ser Lys Ser Asn
                190                 195                 200

Glu Ala Thr Thr Gly Arg Gln Ala Ser Leu Lys Cys Glu Ala Ser Ala
            205                 210                 215

Val Pro Ala Pro Asp Phe Glu Trp Tyr Arg Asp Asp Thr Arg Ile Asn
        220                 225                 230

Ser Ala Asn Gly Leu Glu Ile Lys Ser Thr Glu Gly Gln Ser Ser Leu
    235                 240                 245

Thr Val Thr Asn Val Thr Glu Glu His Tyr Gly Asn Tyr Thr Cys Val
250                 255                 260                 265

Ala Ala Asn Lys Leu Gly Val Thr Asn Ala Ser Leu Val Leu Phe Lys
                270                 275                 280

Arg Val Leu Pro Thr Ile Pro His Pro Ile Gln Glu Ile Gly Thr Thr
            285                 290                 295

Val His Phe Lys Gln Lys Gly Ile Phe Leu Ser Glu Ser Gln Arg Gly
        300                 305                 310

Glu Thr Thr Lys Ile Thr Leu Asn Cys Gly Asn Leu Phe Leu Arg Asn
    315                 320                 325

Leu His Pro Thr Ser Asp Gln Glu Pro Gln Arg Leu Trp Thr Leu Cys
330                 335                 340                 345

Cys Leu Leu Pro Arg Lys Gly Gln His Arg Ile Tyr Gly Gln Cys
                350                 355                 360


<210> SEQ ID NO 39
<211> LENGTH: 2818
<212> TYPE: DNA
<213> ORGANISM: Homo sapiens
<220> FEATURE:
<221> NAME/KEY: 5'UTR
<222> LOCATION: 1..80
<220> FEATURE:
<221> NAME/KEY: CDS
<222> LOCATION: 81..1517
<220> FEATURE:
<221> NAME/KEY: 3'UTR
<222> LOCATION: 1518..2818
<220> FEATURE:
<221> NAME/KEY: polyA_signal
<222> LOCATION: 2786..2791
<220> FEATURE:
<221> NAME/KEY: polyA_site
<222> LOCATION: 2804..2818

<400> SEQUENCE: 39

ggctttgggg cagggcagat ttatatctgc gggggatcag ctgacgctcc gcattgcaga      60

ctgcggagtc agacggcgct atg tac gcc ctc ttc ctc ctg gcc agc ctc ctg     113
                      Met Tyr Ala Leu Phe Leu Leu Ala Ser Leu Leu
                      1               5                   10

ggc gcg gct cta gcc ggc ccg gtc ctt gga ctg aaa gaa tgc acc agg       161
Gly Ala Ala Leu Ala Gly Pro Val Leu Gly Leu Lys Glu Cys Thr Arg
            15                  20                  25

ggc tcg gca gtg tgg tgc cag aat gtg aag acg gcg tcc gac tgc ggg       209
Gly Ser Ala Val Trp Cys Gln Asn Val Lys Thr Ala Ser Asp Cys Gly
        30                  35                  40

gca gtg aag cac tgc ctg cag acc gtt tgg aac aag cca aca gtg aaa       257
Ala Val Lys His Cys Leu Gln Thr Val Trp Asn Lys Pro Thr Val Lys
    45                  50                  55
```

-continued

```
tcc ctt ccc tgc gac ata tgc aaa gac gtt gtc acc gca gct ggt gat       305
Ser Leu Pro Cys Asp Ile Cys Lys Asp Val Val Thr Ala Ala Gly Asp
60                  65                  70                  75

atg ctg aag gac aat gcc act gag gag gag atc ctt gtt tac ttg gag       353
Met Leu Lys Asp Asn Ala Thr Glu Glu Glu Ile Leu Val Tyr Leu Glu
                80                  85                  90

aag acc tgt gac tgg ctt ccg aaa ccg aac atg tct gct tca tgc aag       401
Lys Thr Cys Asp Trp Leu Pro Lys Pro Asn Met Ser Ala Ser Cys Lys
            95                  100                 105

gag ata gtg gac tcc tac ctc cct gtc atc ctg gac atc att aaa gga       449
Glu Ile Val Asp Ser Tyr Leu Pro Val Ile Leu Asp Ile Ile Lys Gly
        110                 115                 120

gaa atg agc cgt cct ggg gag gtg tgc tct gct ctc aac ctc tgc gag       497
Glu Met Ser Arg Pro Gly Glu Val Cys Ser Ala Leu Asn Leu Cys Glu
    125                 130                 135

tct ctc cag aag cac cta gca gag ctg aat cac cag aag cag ctg gag       545
Ser Leu Gln Lys His Leu Ala Glu Leu Asn His Gln Lys Gln Leu Glu
140                 145                 150                 155

tcc aat aag atc cca gag ctg gac atg act gag gtg gtg gcc ccc ttc       593
Ser Asn Lys Ile Pro Glu Leu Asp Met Thr Glu Val Val Ala Pro Phe
                160                 165                 170

atg gcc aac atc cct ctc ctc ctc tac cct cag gac ggc ccc cgc agc       641
Met Ala Asn Ile Pro Leu Leu Leu Tyr Pro Gln Asp Gly Pro Arg Ser
            175                 180                 185

aag ccc cag cca aag gat aat ggg gac gtt tgc cag gac tgc att cag       689
Lys Pro Gln Pro Lys Asp Asn Gly Asp Val Cys Gln Asp Cys Ile Gln
        190                 195                 200

atg gtg act gac atc cag act gct gta cgg acc aac tcc acc ttt gtc       737
Met Val Thr Asp Ile Gln Thr Ala Val Arg Thr Asn Ser Thr Phe Val
    205                 210                 215

cag gcc ttg gtg gaa cat gtc aag gag gag tgt gac cgc ctg ggc cct       785
Gln Ala Leu Val Glu His Val Lys Glu Glu Cys Asp Arg Leu Gly Pro
220                 225                 230                 235

ggc atg gcc gac ata tgc aag aac tat atc agc cag tat tct gaa att       833
Gly Met Ala Asp Ile Cys Lys Asn Tyr Ile Ser Gln Tyr Ser Glu Ile
                240                 245                 250

gct atc cag atg atg atg cac atg cag gat cag caa ccc aag gag atc       881
Ala Ile Gln Met Met Met His Met Gln Asp Gln Gln Pro Lys Glu Ile
            255                 260                 265

tgt gcg ctg gtt ggg ttc tgt gat gag gtg aaa gag atg ccc atg cag       929
Cys Ala Leu Val Gly Phe Cys Asp Glu Val Lys Glu Met Pro Met Gln
        270                 275                 280

act ctg gtc ccc gcc aaa gtg gcc tcc aag aat gtc atc cct gcc ctg       977
Thr Leu Val Pro Ala Lys Val Ala Ser Lys Asn Val Ile Pro Ala Leu
    285                 290                 295

gaa ctg gtg gag ccc att aag aag cac gag gtc cca gca aag tct gat      1025
Glu Leu Val Glu Pro Ile Lys Lys His Glu Val Pro Ala Lys Ser Asp
300                 305                 310                 315

gtt tac tgt gag gtg tgt gaa ttc ctg gtg aag gag gtg acc aag ctg      1073
Val Tyr Cys Glu Val Cys Glu Phe Leu Val Lys Glu Val Thr Lys Leu
                320                 325                 330

att gac aac aac aag act gag aaa gaa ata ctc gac gct ttt gac aaa      1121
Ile Asp Asn Asn Lys Thr Glu Lys Glu Ile Leu Asp Ala Phe Asp Lys
            335                 340                 345

atg tgc tcg aag ctg ccg aag tcc ctg tcg gaa gag tgc cag gag gtg      1169
Met Cys Ser Lys Leu Pro Lys Ser Leu Ser Glu Glu Cys Gln Glu Val
        350                 355                 360

gtg gac acg tac ggc agc tcc atc ctg tcc atc ctg ctg gag gag gtc      1217
Val Asp Thr Tyr Gly Ser Ser Ile Leu Ser Ile Leu Leu Glu Glu Val
    365                 370                 375
```

-continued

```
agc cct gag ctg gtg tgc agc atg ctg cac ctc tgc tct ggc acg cgg     1265
Ser Pro Glu Leu Val Cys Ser Met Leu His Leu Cys Ser Gly Thr Arg
380                 385                 390                 395

ctg cct gca ctg acc gtt cac gtg act cag cca aag gac ggt ggc ttc     1313
Leu Pro Ala Leu Thr Val His Val Thr Gln Pro Lys Asp Gly Gly Phe
                400                 405                 410

tgc gaa gtg tgc aag aag ctg gtg ggt tat ttg gat cgc aac ctg gag     1361
Cys Glu Val Cys Lys Lys Leu Val Gly Tyr Leu Asp Arg Asn Leu Glu
            415                 420                 425

aaa aac agc acc aag cag gag atc ctg gct gct ctt gag aaa ggc tgc     1409
Lys Asn Ser Thr Lys Gln Glu Ile Leu Ala Ala Leu Glu Lys Gly Cys
        430                 435                 440

agc ttc ctg cca gac cct tac cag aag cag tgt gat cag ttt gtg gca     1457
Ser Phe Leu Pro Asp Pro Tyr Gln Lys Gln Cys Asp Gln Phe Val Ala
    445                 450                 455

gag tac gag ccc gtg ctg atc gag atc ctg gtg gag gta tgg atc ctt     1505
Glu Tyr Glu Pro Val Leu Ile Glu Ile Leu Val Glu Val Trp Ile Leu
460                 465                 470                 475

cct tcg tgt gct tgaaaattgg agcctgcccc tcggcccata agcccttgtt         1557
Pro Ser Cys Ala

gggaactgag aagtgtatat ggggcccaag ctactggtgc cagaacacag agacagcagc   1617

ccagtgcaat gctgtcgagc attgcaaacg ccatgtgtgg aactaggagg aggaatattc   1677

catcttggca gaaaccacag cattggtttt tttctacttg tgtgtctggg ggaatgaacg   1737

cacagatctg tttgactttg ttataaaaat agggctcccc cacctccccc atttctgtgt   1797

cctttattgt agcattgctg tctgcaaggg agcccctagc ccctggcaga catagctgct   1857

tcagtgcccc ttttctctct gctagatgga tgttgatgca ctggaggtct tttagcctgc   1917

ccttgcatgg cgcctgctgg aggaggagag agctctgctg gcatgagcca cagtttcttg   1977

actggaggcc atcaaccctc ttggttgagg ccttgttctg agccctgaca tgtgcttggg   2037

cactggtggg cctgggcttc tgaggtggcc tcctgccctg atcagggacc ctccccgctt   2097

tcctgggcct ctcagttgaa caaagcagca aaacaaaggc agttttatat gaaagattag   2157

aagcctggaa taatcaggct ttttaaatga tgtaattccc actgtaatag catagggatt   2217

ttggaagcag ctgctggtgg cttgggacat cagtggggcc aagggttctc tgtccctggt   2277

tcaactgtga tttggctttc ccgtgtcttt cctggtgatg ccttgtttgg ggttctgtgg   2337

gtttgggtgg gaagagggcc atctgcctga atgtaacctg ctagctctcc gaaggccctg   2397

cgggcctggc ttgtgtgagc gtgtggacag tggtggccgc gctgtgcctg ctcgtgttgc   2457

ctacatgtcc ctggctgttg aggcgctgct tcagcctgca cccctccctt gtctcataga   2517

tgctcctttt gaccttttca aataaatatg gatggcgagc tcctaggcct ctggcttcct   2577

ggtagagggc ggcatgccga agggtctgct gggtgtggat tggatgctgg ggtgtggggg   2637

ttggaagctg tctgtggccc acttgggcac ccacgcttct gtccacttct ggttgccagg   2697

agacagcaag caaagccagc aggacatgaa gttgctatta aatggacttc gtgatttttg   2757

ttttgcacta aagtttctgt gatttaacaa taaaattctg ttagccaaaa aaaaaaaaaa   2817

a                                                                   2818
```

<210> SEQ ID NO 40
<211> LENGTH: 479
<212> TYPE: PRT
<213> ORGANISM: Homo sapiens

<400> SEQUENCE: 40

-continued

```
Met Tyr Ala Leu Phe Leu Leu Ala Ser Leu Leu Gly Ala Ala Leu Ala
1               5                   10                  15

Gly Pro Val Leu Gly Leu Lys Glu Cys Thr Arg Gly Ser Ala Val Trp
            20                  25                  30

Cys Gln Asn Val Lys Thr Ala Ser Asp Cys Gly Ala Val Lys His Cys
        35                  40                  45

Leu Gln Thr Val Trp Asn Lys Pro Thr Val Lys Ser Leu Pro Cys Asp
    50                  55                  60

Ile Cys Lys Asp Val Val Thr Ala Ala Gly Asp Met Leu Lys Asp Asn
65                  70                  75                  80

Ala Thr Glu Glu Glu Ile Leu Val Tyr Leu Glu Lys Thr Cys Asp Trp
                85                  90                  95

Leu Pro Lys Pro Asn Met Ser Ala Ser Cys Lys Glu Ile Val Asp Ser
            100                 105                 110

Tyr Leu Pro Val Ile Leu Asp Ile Ile Lys Gly Glu Met Ser Arg Pro
        115                 120                 125

Gly Glu Val Cys Ser Ala Leu Asn Leu Cys Glu Ser Leu Gln Lys His
    130                 135                 140

Leu Ala Glu Leu Asn His Gln Lys Gln Leu Glu Ser Asn Lys Ile Pro
145                 150                 155                 160

Glu Leu Asp Met Thr Glu Val Val Ala Pro Phe Met Ala Asn Ile Pro
                165                 170                 175

Leu Leu Leu Tyr Pro Gln Asp Gly Pro Arg Ser Lys Pro Gln Pro Lys
            180                 185                 190

Asp Asn Gly Asp Val Cys Gln Asp Cys Ile Gln Met Val Thr Asp Ile
        195                 200                 205

Gln Thr Ala Val Arg Thr Asn Ser Thr Phe Val Gln Ala Leu Val Glu
    210                 215                 220

His Val Lys Glu Glu Cys Asp Arg Leu Gly Pro Gly Met Ala Asp Ile
225                 230                 235                 240

Cys Lys Asn Tyr Ile Ser Gln Tyr Ser Glu Ile Ala Ile Gln Met Met
                245                 250                 255

Met His Met Gln Asp Gln Gln Pro Lys Glu Ile Cys Ala Leu Val Gly
            260                 265                 270

Phe Cys Asp Glu Val Lys Glu Met Pro Met Gln Thr Leu Val Pro Ala
        275                 280                 285

Lys Val Ala Ser Lys Asn Val Ile Pro Ala Leu Glu Leu Val Glu Pro
    290                 295                 300

Ile Lys Lys His Glu Val Pro Ala Lys Ser Asp Val Tyr Cys Glu Val
305                 310                 315                 320

Cys Glu Phe Leu Val Lys Glu Val Thr Lys Leu Ile Asp Asn Asn Lys
                325                 330                 335

Thr Glu Lys Glu Ile Leu Asp Ala Phe Asp Lys Met Cys Ser Lys Leu
            340                 345                 350

Pro Lys Ser Leu Ser Glu Glu Cys Gln Glu Val Val Asp Thr Tyr Gly
        355                 360                 365

Ser Ser Ile Leu Ser Ile Leu Leu Glu Glu Val Ser Pro Glu Leu Val
    370                 375                 380

Cys Ser Met Leu His Leu Cys Ser Gly Thr Arg Leu Pro Ala Leu Thr
385                 390                 395                 400

Val His Val Thr Gln Pro Lys Asp Gly Gly Phe Cys Glu Val Cys Lys
                405                 410                 415
```

-continued

```
Lys Leu Val Gly Tyr Leu Asp Arg Asn Leu Glu Lys Asn Ser Thr Lys
            420                 425                 430

Gln Glu Ile Leu Ala Ala Leu Glu Lys Gly Cys Ser Phe Leu Pro Asp
        435                 440                 445

Pro Tyr Gln Lys Gln Cys Asp Gln Phe Val Ala Glu Tyr Glu Pro Val
    450                 455                 460

Leu Ile Glu Ile Leu Val Glu Val Trp Ile Leu Pro Ser Cys Ala
465                 470                 475


<210> SEQ ID NO 41
<211> LENGTH: 770
<212> TYPE: DNA
<213> ORGANISM: Homo sapiens
<220> FEATURE:
<221> NAME/KEY: 5'UTR
<222> LOCATION: 1..120
<220> FEATURE:
<221> NAME/KEY: CDS
<222> LOCATION: 121..546
<220> FEATURE:
<221> NAME/KEY: 3'UTR
<222> LOCATION: 547..770
<220> FEATURE:
<221> NAME/KEY: polyA_signal
<222> LOCATION: 739..744
<220> FEATURE:
<221> NAME/KEY: polyA_site
<222> LOCATION: 755..770

<400> SEQUENCE: 41

cttttcttgg gctctaagga cccaggagtc tgggtgcaca gcctccttct ctctgagatt      60

caagagtctg atcagcagcc tcttcctcct ccaggaccca gaagccctga gcttatcccc     120

atg gag ctc tgc cgg tcc ctg gcc ctg ctg ggg ggc tcc ctg ggc ctg       168
Met Glu Leu Cys Arg Ser Leu Ala Leu Leu Gly Gly Ser Leu Gly Leu
        -35                 -30                 -25

atg ttc tgc ctg att gct ttg agc acc gat ttc tgg ttt gag gct gtg       216
Met Phe Cys Leu Ile Ala Leu Ser Thr Asp Phe Trp Phe Glu Ala Val
    -20                 -15                 -10

ggt ccc acc cac tca gct cac tcg ggc ctc tgg cca aca ggg cat ggg       264
Gly Pro Thr His Ser Ala His Ser Gly Leu Trp Pro Thr Gly His Gly
-5                  1               5                   10

gac atc ata tca ggc cac ggc ccg ctt gtc tca acc acc gca gcc ttt       312
Asp Ile Ile Ser Gly His Gly Pro Leu Val Ser Thr Thr Ala Ala Phe
            15                  20                  25

gct gca ggt aag gac tct gga ctg gac tgg ggc atc gcg agc cag cga       360
Ala Ala Gly Lys Asp Ser Gly Leu Asp Trp Gly Ile Ala Ser Gln Arg
        30                  35                  40

att cct gcc gag gag ctg agc cat ctc tct tgt cct tgt ccc cag cca       408
Ile Pro Ala Glu Glu Leu Ser His Leu Ser Cys Pro Cys Pro Gln Pro
    45                  50                  55

tct cca tgg tgg tgg cca tgg cgg tgt aca cca gcg agc ggt ggg acc       456
Ser Pro Trp Trp Trp Pro Trp Arg Cys Thr Pro Ala Ser Gly Gly Thr
60                  65                  70                  75

agc ctc cac acc ccc aga tcc aga cct tct tct cct ggt cct tct acc       504
Ser Leu His Thr Pro Arg Ser Arg Pro Ser Ser Pro Gly Pro Ser Thr
                80                  85                  90

tgg gct ggg tct cag cta tcc tct tgc tct gta cag gtg ccc               546
Trp Ala Gly Ser Gln Leu Ser Ser Cys Ser Val Gln Val Pro
            95                  100                 105

tgagcctggg tgctcactgt ggcggtcccc gtcctggcta tgaaaccttg tgagcagaag     606

gcaagagcgg caagatgagt tttgagcgtt gtattccaaa ggcctcatct ggagcctcgg     666
```

-continued

```
gaaagtctgg tcccacatct gcccgccctt ccagcccttc cccagcccct cctcttgttt    726

cttcattcat tcaacaaaat ttggctggaa aaaaaaaaaa aaaa                     770


<210> SEQ ID NO 42
<211> LENGTH: 142
<212> TYPE: PRT
<213> ORGANISM: Homo sapiens
<220> FEATURE:
<221> NAME/KEY: SIGNAL
<222> LOCATION: 1..37

<400> SEQUENCE: 42

Met Glu Leu Cys Arg Ser Leu Ala Leu Leu Gly Gly Ser Leu Gly Leu
        -35                 -30                 -25

Met Phe Cys Leu Ile Ala Leu Ser Thr Asp Phe Trp Phe Glu Ala Val
    -20                 -15                 -10

Gly Pro Thr His Ser Ala His Ser Gly Leu Trp Pro Thr Gly His Gly
-5                  1               5                   10

Asp Ile Ile Ser Gly His Gly Pro Leu Val Ser Thr Thr Ala Ala Phe
            15                  20                  25

Ala Ala Gly Lys Asp Ser Gly Leu Asp Trp Gly Ile Ala Ser Gln Arg
        30                  35                  40

Ile Pro Ala Glu Glu Leu Ser His Leu Ser Cys Pro Cys Pro Gln Pro
    45                  50                  55

Ser Pro Trp Trp Trp Pro Trp Arg Cys Thr Pro Ala Ser Gly Gly Thr
60                  65                  70                  75

Ser Leu His Thr Pro Arg Ser Arg Pro Ser Ser Pro Gly Pro Ser Thr
                80                  85                  90

Trp Ala Gly Ser Gln Leu Ser Ser Cys Ser Val Gln Val Pro
            95                  100                 105


<210> SEQ ID NO 43
<211> LENGTH: 1340
<212> TYPE: DNA
<213> ORGANISM: Homo sapiens
<220> FEATURE:
<221> NAME/KEY: 5'UTR
<222> LOCATION: 1..135
<220> FEATURE:
<221> NAME/KEY: CDS
<222> LOCATION: 136..501
<220> FEATURE:
<221> NAME/KEY: 3'UTR
<222> LOCATION: 502..1340
<220> FEATURE:
<221> NAME/KEY: polyA_signal
<222> LOCATION: 1232..1237
<220> FEATURE:
<221> NAME/KEY: polyA_site
<222> LOCATION: 1255..1340

<400> SEQUENCE: 43

ctcttttggg gttcttcctt tctctctcag ctctccgtct ctctttctct ctcagcctct     60

ttctttctcc ctgtctcccc cactgtcagc acctcttctg tgtggtgagt ggaccgctta    120

ccccactagg tgaag atg tca gcc cag gag agc tgc ctc agc ctc atc aag     171
                 Met Ser Ala Gln Glu Ser Cys Leu Ser Leu Ile Lys
                 1               5                   10

tac ttc ctc ttc gtt ttc aac ctc ttc ttc ttc gtc ctc ggc agc ctg      219
Tyr Phe Leu Phe Val Phe Asn Leu Phe Phe Phe Val Leu Gly Ser Leu
        15                  20                  25

atc ttc tgc ttc ggc atc tgg atc ctc att gac aag acc agc ttc gtg      267
Ile Phe Cys Phe Gly Ile Trp Ile Leu Ile Asp Lys Thr Ser Phe Val
```

-continued

```
    30                  35                  40

tcc ttt gtg ggc ttg gcc ttc gtg cct ctg cag atc tgg tcc aaa gtc      315
Ser Phe Val Gly Leu Ala Phe Val Pro Leu Gln Ile Trp Ser Lys Val
45                  50                  55                  60

ctg gcc atc tca gga atc ttc acc atg ggc atc gcc ctc ctg ggt tgt      363
Leu Ala Ile Ser Gly Ile Phe Thr Met Gly Ile Ala Leu Leu Gly Cys
                65                  70                  75

gtg ggg gcc ctc aag gag ctc cgc tgc ctc ctg ggc ctg tat ttt ggg      411
Val Gly Ala Leu Lys Glu Leu Arg Cys Leu Leu Gly Leu Tyr Phe Gly
            80                  85                  90

atg ctg ctg ctc ctg ttt gcc aca cag atc acc ctg gga atc ctc atc      459
Met Leu Leu Leu Leu Phe Ala Thr Gln Ile Thr Leu Gly Ile Leu Ile
        95                  100                 105

tcc act cag cgg gcc agc tgg agc gaa gct tgc ggg acg tcg              501
Ser Thr Gln Arg Ala Ser Trp Ser Glu Ala Cys Gly Thr Ser
    110                 115                 120

tagagaaaac catccaaaag tacggcacca accccgagga gaccgcggcc gaggagagct    561

gggactatgt gcagttccag ctgcgctgct gcggctggca ctacccgcag gactggttcc    621

aagtcctcat cctgagaggt aacgggtcgg aggcgcaccg cgtgccctgc tcctgctaca    681

acttgtcggc gaccaacgac tccacaatcc tagataaggt gatcttgccc cagctcagca    741

ggcttggaca cctggcgcgg tccagacaca gtgcagacat ctgcgctgtc cctgcagaga    801

gccacatcta ccgcgagggc tgcgcgcagg gcctccagaa gtggctgcac aacaacctta    861

tttccatagt gggcatttgc ctgggcgtcg gcctactcga gctcgggttc atgacgctct    921

cgatattcct gtgcagaaac ctggaccacg tctacaaccg gctcgctcga taccgttagg    981

ccccgccctc cccaaagtcc cgccccgccc ccgtcacgtg cgctgggcac ttccctgctg   1041

cctgtaaata tttgtttaat ccccagttcg cctggagccc tcctccttca cattcccctg   1101

gggacccacg tggctgcgtg cccctgctgc tgtcacctct cccacgggac ctggggcttt   1161

cgtccacagc ttcctgtccc catctgtcgg cctaccacca cccacaagat tatttttcac   1221

ccaaacctca aataaatccc ctgcgttttt ggtaaaaaaa aaaaaaaaaa aaaaaaaaaa   1281

aaaaaaaaaa aaaaaaaaaa aaaaaaaaaa aaaaaaaaaa amcaaaaaaa aaaaaaaaa    1340


<210> SEQ ID NO 44
<211> LENGTH: 122
<212> TYPE: PRT
<213> ORGANISM: Homo sapiens

<400> SEQUENCE: 44

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110
```

-continued

```
Ala Ser Trp Ser Glu Ala Cys Gly Thr Ser
        115                 120


<210> SEQ ID NO 45
<211> LENGTH: 1999
<212> TYPE: DNA
<213> ORGANISM: Homo sapiens
<220> FEATURE:
<221> NAME/KEY: 5'UTR
<222> LOCATION: 1..117
<220> FEATURE:
<221> NAME/KEY: CDS
<222> LOCATION: 118..1632
<220> FEATURE:
<221> NAME/KEY: 3'UTR
<222> LOCATION: 1633..1999
<220> FEATURE:
<221> NAME/KEY: polyA_signal
<222> LOCATION: 1937..1942
<220> FEATURE:
<221> NAME/KEY: polyA_site
<222> LOCATION: 1956..1999

<400> SEQUENCE: 45

aggtccgcct gggccagacg cgcgagcgca agcagcgggt tagtggtcgc gcgcccgacc      60

tccgcagtcc cagccgagcc gcgacccttc cggccgtccc caccccacct cgccgcc        117

atg cgc ctc cgc cgc cta gcg ctg ttc ccg ggt gtg gcg ctg ctt ctt       165
Met Arg Leu Arg Arg Leu Ala Leu Phe Pro Gly Val Ala Leu Leu Leu
                -20                 -15                 -10

gcc gcg gcc cgc ctc gcc gct gcc tcc gac gtg cta gaa ctc acg gac       213
Ala Ala Ala Arg Leu Ala Ala Ala Ser Asp Val Leu Glu Leu Thr Asp
            -5                  1               5

gac aac ttc gag agt cgc atc tcc gac acg ggc tct gcg ggc ctc atg       261
Asp Asn Phe Glu Ser Arg Ile Ser Asp Thr Gly Ser Ala Gly Leu Met
    10                  15                  20

ctc gtc gag ttc ttc gct ccc tgg tgt gga cac tgc aag aga ctt gca       309
Leu Val Glu Phe Phe Ala Pro Trp Cys Gly His Cys Lys Arg Leu Ala
25                  30                  35                  40

cct gag tat gaa gct gca gct acc aga tta aaa gga ata gtc cca tta       357
Pro Glu Tyr Glu Ala Ala Ala Thr Arg Leu Lys Gly Ile Val Pro Leu
                45                  50                  55

gca aag gtt gat tgc act gcc aac act aac acc tgt aat aaa tat gga       405
Ala Lys Val Asp Cys Thr Ala Asn Thr Asn Thr Cys Asn Lys Tyr Gly
            60                  65                  70

gtc agt gga tat cca acc ctg aag ata ttt aga gat ggt gaa gaa gca       453
Val Ser Gly Tyr Pro Thr Leu Lys Ile Phe Arg Asp Gly Glu Glu Ala
        75                  80                  85

ggt gct tat gat gga cct agg act gct gat gga att gtc agc cac ttg       501
Gly Ala Tyr Asp Gly Pro Arg Thr Ala Asp Gly Ile Val Ser His Leu
    90                  95                  100

aag aag cag gca gga cca gct tca gtg cct ctc agg act gag gaa gaa       549
Lys Lys Gln Ala Gly Pro Ala Ser Val Pro Leu Arg Thr Glu Glu Glu
105                 110                 115                 120

ttt aag aaa ttc att agt gat aaa gat gcc tct ata gta ggt ttt ttc       597
Phe Lys Lys Phe Ile Ser Asp Lys Asp Ala Ser Ile Val Gly Phe Phe
                125                 130                 135

gat gat tca ttc agt gag gct cac tcc gag ttc cta aaa gca gcc agc       645
Asp Asp Ser Phe Ser Glu Ala His Ser Glu Phe Leu Lys Ala Ala Ser
            140                 145                 150

aac ttg agg gat aac tac cga ttt gca cat acg aat gtt gag tct ctg       693
Asn Leu Arg Asp Asn Tyr Arg Phe Ala His Thr Asn Val Glu Ser Leu
        155                 160                 165

gtg aac gag tat gat gat aat gga gag ggt atc atc tta ttt cgt cct       741
```

-continued

```
Val Asn Glu Tyr Asp Asp Asn Gly Glu Gly Ile Ile Leu Phe Arg Pro
    170                 175                 180

tca cat ctc act aac aag ttt gag gac aag act gtg gca tat aca gag      789
Ser His Leu Thr Asn Lys Phe Glu Asp Lys Thr Val Ala Tyr Thr Glu
185                 190                 195                 200

caa aaa atg acc agt ggc aaa att aaa aag ttt atc cag gaa aac att      837
Gln Lys Met Thr Ser Gly Lys Ile Lys Lys Phe Ile Gln Glu Asn Ile
                205                 210                 215

ttt ggt atc tgc cct cac atg aca gaa gac aat aaa gat ttg ata cag      885
Phe Gly Ile Cys Pro His Met Thr Glu Asp Asn Lys Asp Leu Ile Gln
            220                 225                 230

ggc aag gac tta ctt att gct tac tat gat gtg gac tat gaa aag aac      933
Gly Lys Asp Leu Leu Ile Ala Tyr Tyr Asp Val Asp Tyr Glu Lys Asn
        235                 240                 245

gct aaa ggt tcc aac tac agg aga aac agg gta atg atg gtg gca aag      981
Ala Lys Gly Ser Asn Tyr Arg Arg Asn Arg Val Met Met Val Ala Lys
    250                 255                 260

aaa ttc ctg gat gct ggg cac aaa ctc aac ttt gct gta gct agc cgc     1029
Lys Phe Leu Asp Ala Gly His Lys Leu Asn Phe Ala Val Ala Ser Arg
265                 270                 275                 280

aaa acc ttt agc cat gaa ctt tct gat ttt ggc ttg gag agc act gct     1077
Lys Thr Phe Ser His Glu Leu Ser Asp Phe Gly Leu Glu Ser Thr Ala
                285                 290                 295

gga gag att cct gtt gtt gct atc aga act gct aaa gga gag aag ttt     1125
Gly Glu Ile Pro Val Val Ala Ile Arg Thr Ala Lys Gly Glu Lys Phe
            300                 305                 310

gtc atg cag gag gag ttc tcg cgt gat ggg aag gct ctg gag agg ttc     1173
Val Met Gln Glu Glu Phe Ser Arg Asp Gly Lys Ala Leu Glu Arg Phe
        315                 320                 325

ctg cag gat tac ttt gat ggc aat ctg aag aga tac ctg aag tct gaa     1221
Leu Gln Asp Tyr Phe Asp Gly Asn Leu Lys Arg Tyr Leu Lys Ser Glu
    330                 335                 340

cct atc cca gag agc aat gat ggg cct gtg aag gta gtg gta gca gag     1269
Pro Ile Pro Glu Ser Asn Asp Gly Pro Val Lys Val Val Val Ala Glu
345                 350                 355                 360

aat ttt gat gaa ata gtg aat aat gaa aat aaa gat gtg ctg att gaa     1317
Asn Phe Asp Glu Ile Val Asn Asn Glu Asn Lys Asp Val Leu Ile Glu
                365                 370                 375

ttt tat gcc cct tgg tgt ggt cat tgt aag aac ctg gag ccc aag tat     1365
Phe Tyr Ala Pro Trp Cys Gly His Cys Lys Asn Leu Glu Pro Lys Tyr
            380                 385                 390

aaa gaa ctt ggc gag aag ctc agc aaa gac cca aat atc gtc ata gcc     1413
Lys Glu Leu Gly Glu Lys Leu Ser Lys Asp Pro Asn Ile Val Ile Ala
        395                 400                 405

aag atg gat gcc aca gcc aat gat gtg cct tct cca tat gaa gtc aga     1461
Lys Met Asp Ala Thr Ala Asn Asp Val Pro Ser Pro Tyr Glu Val Arg
    410                 415                 420

ggt ttt cct acc ata tac ttc tct cca gcc aac aag aag cta aat cca     1509
Gly Phe Pro Thr Ile Tyr Phe Ser Pro Ala Asn Lys Lys Leu Asn Pro
425                 430                 435                 440

aag aaa tat gaa ggt ggc cgt gaa tta agt gat ttt att agc tat cta     1557
Lys Lys Tyr Glu Gly Gly Arg Glu Leu Ser Asp Phe Ile Ser Tyr Leu
                445                 450                 455

caa aga gaa gct aca atc ccc cct gta att caa gaa gaa aaa ccc aag     1605
Gln Arg Glu Ala Thr Ile Pro Pro Val Ile Gln Glu Glu Lys Pro Lys
            460                 465                 470

aag aag aag aag gca cag gag gat ctc taaagcagta gccaaacacc           1652
Lys Lys Lys Lys Ala Gln Glu Asp Leu
        475                 480
```

-continued

```
actttgtaaa aggactcttc catcagagat gggaaaacca ttggggagga ctaggaccca   1712

tatgggaatt attacctctc agggccgaga ggacagaatg gatataatct gaatcctgtt   1772

aaattttctc taaactgttt cttagctgca ctgtttatgg aaataccagg accagtttat   1832

gtttgtggtt ttgggaaaaa ttatttgtgt tgggggaaat gttgtggggg tggggttgag   1892

ttgggggtat tttctaattt tttttgtaca tttggaacag tgacaataaa tgagacccct   1952

tttaaaaaaa aaaaaaaaaa aaaaaaaaaa aaaaawaaaa aaaaaaa                 1999
```

<210> SEQ ID NO 46
<211> LENGTH: 505
<212> TYPE: PRT
<213> ORGANISM: Homo sapiens
<220> FEATURE:
<221> NAME/KEY: SIGNAL
<222> LOCATION: 1..24

<400> SEQUENCE: 46

```
Met Arg Leu Arg Arg Leu Ala Leu Phe Pro Gly Val Ala Leu Leu Leu
                -20                 -15                 -10

Ala Ala Ala Arg Leu Ala Ala Ala Ser Asp Val Leu Glu Leu Thr Asp
            -5                  1               5

Asp Asn Phe Glu Ser Arg Ile Ser Asp Thr Gly Ser Ala Gly Leu Met
    10                  15                  20

Leu Val Glu Phe Phe Ala Pro Trp Cys Gly His Cys Lys Arg Leu Ala
25                  30                  35                  40

Pro Glu Tyr Glu Ala Ala Ala Thr Arg Leu Lys Gly Ile Val Pro Leu
                45                  50                  55

Ala Lys Val Asp Cys Thr Ala Asn Thr Asn Thr Cys Asn Lys Tyr Gly
            60                  65                  70

Val Ser Gly Tyr Pro Thr Leu Lys Ile Phe Arg Asp Gly Glu Glu Ala
        75                  80                  85

Gly Ala Tyr Asp Gly Pro Arg Thr Ala Asp Gly Ile Val Ser His Leu
    90                  95                  100

Lys Lys Gln Ala Gly Pro Ala Ser Val Pro Leu Arg Thr Glu Glu Glu
105                 110                 115                 120

Phe Lys Lys Phe Ile Ser Asp Lys Asp Ala Ser Ile Val Gly Phe Phe
                125                 130                 135

Asp Asp Ser Phe Ser Glu Ala His Ser Glu Phe Leu Lys Ala Ala Ser
            140                 145                 150

Asn Leu Arg Asp Asn Tyr Arg Phe Ala His Thr Asn Val Glu Ser Leu
        155                 160                 165

Val Asn Glu Tyr Asp Asp Asn Gly Glu Gly Ile Ile Leu Phe Arg Pro
    170                 175                 180

Ser His Leu Thr Asn Lys Phe Glu Asp Lys Thr Val Ala Tyr Thr Glu
185                 190                 195                 200

Gln Lys Met Thr Ser Gly Lys Ile Lys Lys Phe Ile Gln Glu Asn Ile
                205                 210                 215

Phe Gly Ile Cys Pro His Met Thr Glu Asp Asn Lys Asp Leu Ile Gln
            220                 225                 230

Gly Lys Asp Leu Leu Ile Ala Tyr Tyr Asp Val Asp Tyr Glu Lys Asn
        235                 240                 245

Ala Lys Gly Ser Asn Tyr Arg Arg Asn Arg Val Met Met Val Ala Lys
    250                 255                 260

Lys Phe Leu Asp Ala Gly His Lys Leu Asn Phe Ala Val Ala Ser Arg
265                 270                 275                 280
```

-continued

```
Lys Thr Phe Ser His Glu Leu Ser Asp Phe Gly Leu Glu Ser Thr Ala
                285                 290                 295

Gly Glu Ile Pro Val Val Ala Ile Arg Thr Ala Lys Gly Glu Lys Phe
            300                 305                 310

Val Met Gln Glu Glu Phe Ser Arg Asp Gly Lys Ala Leu Glu Arg Phe
        315                 320                 325

Leu Gln Asp Tyr Phe Asp Gly Asn Leu Lys Arg Tyr Leu Lys Ser Glu
    330                 335                 340

Pro Ile Pro Glu Ser Asn Asp Gly Pro Val Lys Val Val Val Ala Glu
345                 350                 355                 360

Asn Phe Asp Glu Ile Val Asn Asn Glu Asn Lys Asp Val Leu Ile Glu
                365                 370                 375

Phe Tyr Ala Pro Trp Cys Gly His Cys Lys Asn Leu Glu Pro Lys Tyr
            380                 385                 390

Lys Glu Leu Gly Glu Lys Leu Ser Lys Asp Pro Asn Ile Val Ile Ala
        395                 400                 405

Lys Met Asp Ala Thr Ala Asn Asp Val Pro Ser Pro Tyr Glu Val Arg
    410                 415                 420

Gly Phe Pro Thr Ile Tyr Phe Ser Pro Ala Asn Lys Lys Leu Asn Pro
425                 430                 435                 440

Lys Lys Tyr Glu Gly Gly Arg Glu Leu Ser Asp Phe Ile Ser Tyr Leu
                445                 450                 455

Gln Arg Glu Ala Thr Ile Pro Pro Val Ile Gln Glu Glu Lys Pro Lys
            460                 465                 470

Lys Lys Lys Lys Ala Gln Glu Asp Leu
        475                 480


<210> SEQ ID NO 47
<211> LENGTH: 836
<212> TYPE: DNA
<213> ORGANISM: Homo sapiens
<220> FEATURE:
<221> NAME/KEY: 5'UTR
<222> LOCATION: 1..153
<220> FEATURE:
<221> NAME/KEY: CDS
<222> LOCATION: 154..546
<220> FEATURE:
<221> NAME/KEY: 3'UTR
<222> LOCATION: 547..836
<220> FEATURE:
<221> NAME/KEY: polyA_site
<222> LOCATION: 722..836

<400> SEQUENCE: 47

acccctccct ggcccccgcc tcccggactc ctgaccaaat gacccccccc ggcaggtgtt      60

tcgcccgtgc cgggttcatg ctcacaagca gacagctcct ccgcctctga tgcagaattt     120

gatgctgtgg ttggatattt agaggacatt atc atg gat gac gag ttc cag tta      174
                                     Met Asp Asp Glu Phe Gln Leu
                                     1               5

tta cag aga aat ttc atg gac aag tac tac ctg gag ttt gaa gac aca       222
Leu Gln Arg Asn Phe Met Asp Lys Tyr Tyr Leu Glu Phe Glu Asp Thr
        10                  15                  20

gaa gag aat aaa ctc atc tac aca cct att ttt aat gaa tac att tct       270
Glu Glu Asn Lys Leu Ile Tyr Thr Pro Ile Phe Asn Glu Tyr Ile Ser
    25                  30                  35

ttg gta gaa aaa tac att gaa gaa cag ctg ctg cag cgg att cct gag       318
Leu Val Glu Lys Tyr Ile Glu Glu Gln Leu Leu Gln Arg Ile Pro Glu
40                  45                  50                  55
```

-continued

```
ttc aac atg gca gcc ttc acc aca aca tta cag cac cat aag gat gaa      366
Phe Asn Met Ala Ala Phe Thr Thr Thr Leu Gln His His Lys Asp Glu
                60                  65                  70

gtg gct ggt gac ata ttc gac atg ctg ctc acc ttc aca gat ttt ctg      414
Val Ala Gly Asp Ile Phe Asp Met Leu Leu Thr Phe Thr Asp Phe Leu
            75                  80                  85

gct ttt aaa gaa atg ttt ttg gac tac aga gca gaa aaa gaa ggc cga      462
Ala Phe Lys Glu Met Phe Leu Asp Tyr Arg Ala Glu Lys Glu Gly Arg
        90                  95                  100

gga ctg gac tta agc agt ggc tta gtg gtg act tca ttg tgc aaa tca      510
Gly Leu Asp Leu Ser Ser Gly Leu Val Val Thr Ser Leu Cys Lys Ser
    105                 110                 115

tct tct ctg cca gct tcc cag aac aat ctg cgg cac taggtcctac           556
Ser Ser Leu Pro Ala Ser Gln Asn Asn Leu Arg His
120                 125                 130

ctccagccaa tgaatgggat cattctggat gtcaccagcc caataggctc agctcatgat    616

gacagaacac atcttggaaa gactgactct gttatgtaac tcttcattta tgttaagtat    676

taataggtca aaaccaaaat gacctaaccc tcctggacct atttcaaaaa aaaaaaaaaa    736

aaaaaaaaaa aaaaaaaaaa aaaaaaaaaa aaaaaaaaaa aaaaaaaaaa aaaaaaaaaa    796

aaaaaaaaaa aaaaaaaaaa aaaagaaaaa aaaaaaaaat                          836


<210> SEQ ID NO 48
<211> LENGTH: 131
<212> TYPE: PRT
<213> ORGANISM: Homo sapiens

<400> SEQUENCE: 48

Met Asp Asp Glu Phe Gln Leu Leu Gln Arg Asn Phe Met Asp Lys Tyr
1               5                   10                  15

Tyr Leu Glu Phe Glu Asp Thr Glu Glu Asn Lys Leu Ile Tyr Thr Pro
            20                  25                  30

Ile Phe Asn Glu Tyr Ile Ser Leu Val Glu Lys Tyr Ile Glu Glu Gln
        35                  40                  45

Leu Leu Gln Arg Ile Pro Glu Phe Asn Met Ala Ala Phe Thr Thr Thr
    50                  55                  60

Leu Gln His His Lys Asp Glu Val Ala Gly Asp Ile Phe Asp Met Leu
65                  70                  75                  80

Leu Thr Phe Thr Asp Phe Leu Ala Phe Lys Glu Met Phe Leu Asp Tyr
                85                  90                  95

Arg Ala Glu Lys Glu Gly Arg Gly Leu Asp Leu Ser Ser Gly Leu Val
            100                 105                 110

Val Thr Ser Leu Cys Lys Ser Ser Ser Leu Pro Ala Ser Gln Asn Asn
        115                 120                 125

Leu Arg His
    130


<210> SEQ ID NO 49
<211> LENGTH: 862
<212> TYPE: DNA
<213> ORGANISM: Homo sapiens
<220> FEATURE:
<221> NAME/KEY: 5'UTR
<222> LOCATION: 1..195
<220> FEATURE:
<221> NAME/KEY: CDS
<222> LOCATION: 196..708
<220> FEATURE:
<221> NAME/KEY: 3'UTR
```

-continued

```
<222> LOCATION: 709..862
<220> FEATURE:
<221> NAME/KEY: polyA_site
<222> LOCATION: 847..862

<400> SEQUENCE: 49

ttcgcccctc ggagctggaa atgcagctat tgagatcttc gaatgctgcg gagctggagg     60

cggaggcagc tggggaggtc cgagcgatgt gaccaggccg ccatcgctcg tctcttcctc    120

tctcctgccg cctcctgtct cgtaaataac ttttttactc taaagaaaga aagacaaaag    180

tagtcgtccg ccccc atg cat ccc ttc tac acc cgg gcc gcc acc atg ata     231
                 Met His Pro Phe Tyr Thr Arg Ala Ala Thr Met Ile
                 1               5                   10

ggc gag atc gcc gcc gcc gtg tcc ttc atc tcc aag ttt ctc cgc acc      279
Gly Glu Ile Ala Ala Ala Val Ser Phe Ile Ser Lys Phe Leu Arg Thr
        15                  20                  25

aag ggg ctc acg agc gag cga cag ctg cag acc ttc agc cag agc ctg      327
Lys Gly Leu Thr Ser Glu Arg Gln Leu Gln Thr Phe Ser Gln Ser Leu
    30                  35                  40

cag gag ctg ctg gca gaa cat tat aaa cat cac tgg ttc cca gaa aag      375
Gln Glu Leu Leu Ala Glu His Tyr Lys His His Trp Phe Pro Glu Lys
45                  50                  55                  60

cca tgc aag gga tcg ggt tac cgt tgt att cgc atc aac cat aaa atg      423
Pro Cys Lys Gly Ser Gly Tyr Arg Cys Ile Arg Ile Asn His Lys Met
                65                  70                  75

gat cct ctg att gga cag gca gca cag cgg att gga ctg agc agt cag      471
Asp Pro Leu Ile Gly Gln Ala Ala Gln Arg Ile Gly Leu Ser Ser Gln
            80                  85                  90

gag ctg ttc agg ctt ctc cca agt gaa ctc aca ctc tgg gtt gac ccc      519
Glu Leu Phe Arg Leu Leu Pro Ser Glu Leu Thr Leu Trp Val Asp Pro
        95                  100                 105

tat gaa gtg tcc tac aga att gga gag gat ggc tcc atc tgt gtg ctg      567
Tyr Glu Val Ser Tyr Arg Ile Gly Glu Asp Gly Ser Ile Cys Val Leu
    110                 115                 120

tat gaa gcc tca cca gca gga ggt agc act caa aac agc acc aac gtg      615
Tyr Glu Ala Ser Pro Ala Gly Gly Ser Thr Gln Asn Ser Thr Asn Val
125                 130                 135                 140

caa atg gta gac agc cga atc agc tgt aag gag gaa ctt ctc ttg ggc      663
Gln Met Val Asp Ser Arg Ile Ser Cys Lys Glu Glu Leu Leu Leu Gly
                145                 150                 155

aga acg agc cct tcc aaa aac tac aat atg atg act gta tca agt          708
Arg Thr Ser Pro Ser Lys Asn Tyr Asn Met Met Thr Val Ser Ser
            160                 165                 170

taagatatag tctgtggatg gatcatctga tgatgatgga taaatttgat ttttgctttg    768

ggtgggctcc tcttggggat ggattatgga atttaaacca tgtcacagct gtgaagatct    828

ggcacaagat agaatggcaa aaaaaaaaaa aaaa                                862


<210> SEQ ID NO 50
<211> LENGTH: 171
<212> TYPE: PRT
<213> ORGANISM: Homo sapiens

<400> SEQUENCE: 50

Met His Pro Phe Tyr Thr Arg Ala Ala Thr Met Ile Gly Glu Ile Ala
1               5                   10                  15

Ala Ala Val Ser Phe Ile Ser Lys Phe Leu Arg Thr Lys Gly Leu Thr
            20                  25                  30

Ser Glu Arg Gln Leu Gln Thr Phe Ser Gln Ser Leu Gln Glu Leu Leu
        35                  40                  45
```

```
Ala Glu His Tyr Lys His His Trp Phe Pro Glu Lys Pro Cys Lys Gly
    50                  55                  60

Ser Gly Tyr Arg Cys Ile Arg Ile Asn His Lys Met Asp Pro Leu Ile
65                  70                  75                  80

Gly Gln Ala Ala Gln Arg Ile Gly Leu Ser Ser Gln Glu Leu Phe Arg
                85                  90                  95

Leu Leu Pro Ser Glu Leu Thr Leu Trp Val Asp Pro Tyr Glu Val Ser
            100                 105                 110

Tyr Arg Ile Gly Glu Asp Gly Ser Ile Cys Val Leu Tyr Glu Ala Ser
        115                 120                 125

Pro Ala Gly Gly Ser Thr Gln Asn Ser Thr Asn Val Gln Met Val Asp
    130                 135                 140

Ser Arg Ile Ser Cys Lys Glu Glu Leu Leu Leu Gly Arg Thr Ser Pro
145                 150                 155                 160

Ser Lys Asn Tyr Asn Met Met Thr Val Ser Ser
                165                 170


<210> SEQ ID NO 51
<211> LENGTH: 947
<212> TYPE: DNA
<213> ORGANISM: Homo sapiens
<220> FEATURE:
<221> NAME/KEY: 5'UTR
<222> LOCATION: 1..61
<220> FEATURE:
<221> NAME/KEY: CDS
<222> LOCATION: 62..778
<220> FEATURE:
<221> NAME/KEY: 3'UTR
<222> LOCATION: 779..947
<220> FEATURE:
<221> NAME/KEY: polyA_signal
<222> LOCATION: 912..917
<220> FEATURE:
<221> NAME/KEY: polyA_site
<222> LOCATION: 932..947

<400> SEQUENCE: 51

gaggaaagag tcatcagagg gatcagcagc tccagggaag gcctggctgc cccgcttcta      60

a atg cca ctc ccc ctc cca tca gcg ttc gtg ctg tca gcc ttg cag cct     109
  Met Pro Leu Pro Leu Pro Ser Ala Phe Val Leu Ser Ala Leu Gln Pro
      -20                 -15                 -10

tct cct act cat tcc agc tcc aat acc cag cgg ctg cca gac cga gtg       157
Ser Pro Thr His Ser Ser Ser Asn Thr Gln Arg Leu Pro Asp Arg Val
-5                  1               5                   10

acc ggc ggc ttc tca gtg aat gga cag ctc att ggc aac aag gcc agg       205
Thr Gly Gly Phe Ser Val Asn Gly Gln Leu Ile Gly Asn Lys Ala Arg
            15                  20                  25

agc cct ggg cag cat gac ggc acg tac ttc ggg cgg ctg gga atc gca       253
Ser Pro Gly Gln His Asp Gly Thr Tyr Phe Gly Arg Leu Gly Ile Ala
        30                  35                  40

aac cct gcc acg gac ttt cag ttg gaa gtg act cct cag aac att acg       301
Asn Pro Ala Thr Asp Phe Gln Leu Glu Val Thr Pro Gln Asn Ile Thr
    45                  50                  55

ctg aac ccc ggc ttt ggt ggg cct gtg ttt tcc tgg agg gac caa gct       349
Leu Asn Pro Gly Phe Gly Gly Pro Val Phe Ser Trp Arg Asp Gln Ala
60                  65                  70                  75

gtg ctg cgg cag gac ggg gtg gtg gtg acc atc aac aag aag agg aac       397
Val Leu Arg Gln Asp Gly Val Val Val Thr Ile Asn Lys Lys Arg Asn
                80                  85                  90

ctg gtg gtg tct gtg gac gac ggt ggc acc ttt gag gtt gtt ttg cac       445
```

-continued

```
Leu Val Val Ser Val Asp Asp Gly Gly Thr Phe Glu Val Val Leu His
            95                  100                 105

cga gtg tgg aag ggg agc tcg gtc cac cag gac ttc ctg ggc ttc tat      493
Arg Val Trp Lys Gly Ser Ser Val His Gln Asp Phe Leu Gly Phe Tyr
        110                 115                 120

gtg ctg gac agt cat cgg atg tca gcc cgg acg cac ggg ctg ctg ggg      541
Val Leu Asp Ser His Arg Met Ser Ala Arg Thr His Gly Leu Leu Gly
    125                 130                 135

caa ttt ttc cac ccc atc ggt ttt gaa gtg tct gac atc cac cca ggc      589
Gln Phe Phe His Pro Ile Gly Phe Glu Val Ser Asp Ile His Pro Gly
140                 145                 150                 155

tct gac ccc aca aag cca gat gcc acg atg gtg gtg agg aac cgc cgg      637
Ser Asp Pro Thr Lys Pro Asp Ala Thr Met Val Val Arg Asn Arg Arg
                160                 165                 170

ctc acg gtc acc agg ggt ttg caa aaa gac tac agc aag gac ccg tgg      685
Leu Thr Val Thr Arg Gly Leu Gln Lys Asp Tyr Ser Lys Asp Pro Trp
            175                 180                 185

cat ggg gcc gag gtg tcc tgc tgg ttc att cac aac aat ggg gct gga      733
His Gly Ala Glu Val Ser Cys Trp Phe Ile His Asn Asn Gly Ala Gly
        190                 195                 200

ctc atc gat ggt gcc tac act gat tat atc gtc ccc gac atc ttc          778
Leu Ile Asp Gly Ala Tyr Thr Asp Tyr Ile Val Pro Asp Ile Phe
    205                 210                 215

tgagccctct ggccagcacg cctgtcctcc cccggggcca aggcagagga ggaggacgac    838

atcctgacct gctgctgagg ctgtacctcc ttgactaagc tggttccttg tgtcaaagca    898

cctcatgcct tccattaaag agaggccgtg tccaaaaaaa aaaaaaaaa                947


<210> SEQ ID NO 52
<211> LENGTH: 239
<212> TYPE: PRT
<213> ORGANISM: Homo sapiens
<220> FEATURE:
<221> NAME/KEY: SIGNAL
<222> LOCATION: 1..21

<400> SEQUENCE: 52

Met Pro Leu Pro Leu Pro Ser Ala Phe Val Leu Ser Ala Leu Gln Pro
    -20                 -15                 -10

Ser Pro Thr His Ser Ser Ser Asn Thr Gln Arg Leu Pro Asp Arg Val
-5                  1               5                   10

Thr Gly Gly Phe Ser Val Asn Gly Gln Leu Ile Gly Asn Lys Ala Arg
            15                  20                  25

Ser Pro Gly Gln His Asp Gly Thr Tyr Phe Gly Arg Leu Gly Ile Ala
        30                  35                  40

Asn Pro Ala Thr Asp Phe Gln Leu Glu Val Thr Pro Gln Asn Ile Thr
    45                  50                  55

Leu Asn Pro Gly Phe Gly Gly Pro Val Phe Ser Trp Arg Asp Gln Ala
60                  65                  70                  75

Val Leu Arg Gln Asp Gly Val Val Val Thr Ile Asn Lys Lys Arg Asn
                80                  85                  90

Leu Val Val Ser Val Asp Asp Gly Gly Thr Phe Glu Val Val Leu His
            95                  100                 105

Arg Val Trp Lys Gly Ser Ser Val His Gln Asp Phe Leu Gly Phe Tyr
        110                 115                 120

Val Leu Asp Ser His Arg Met Ser Ala Arg Thr His Gly Leu Leu Gly
    125                 130                 135

Gln Phe Phe His Pro Ile Gly Phe Glu Val Ser Asp Ile His Pro Gly
```

-continued

```
140                 145                 150                 155

Ser Asp Pro Thr Lys Pro Asp Ala Thr Met Val Val Arg Asn Arg Arg
                160                 165                 170

Leu Thr Val Thr Arg Gly Leu Gln Lys Asp Tyr Ser Lys Asp Pro Trp
            175                 180                 185

His Gly Ala Glu Val Ser Cys Trp Phe Ile His Asn Asn Gly Ala Gly
        190                 195                 200

Leu Ile Asp Gly Ala Tyr Thr Asp Tyr Ile Val Pro Asp Ile Phe
    205                 210                 215
```